(12) United States Patent
Aharoni et al.

(10) Patent No.: US 11,932,887 B2
(45) Date of Patent: Mar. 19, 2024

(54) CYP76AD1-BETA CLADE POLYNUCLEOTIDES, POLYPEPTIDES, AND USES THEREOF

(71) Applicant: YEDA RESEARCH AND DEVELOPMENT CO. LTD., Rehovot (IL)

(72) Inventors: Asaph Aharoni, Tel Aviv (IL); Guy Polturak, Rehovot, IL (US)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 180 days.

(21) Appl. No.: 16/940,666

(22) Filed: Jul. 28, 2020

(65) Prior Publication Data
US 2020/0354759 A1   Nov. 12, 2020

Related U.S. Application Data

(63) Continuation of application No. 15/758,372, filed as application No. PCT/IL2016/051010 on Sep. 11, 2016, now Pat. No. 10,767,201.

(30) Foreign Application Priority Data

Sep. 10, 2015  (IL) .......................................... 241462

(51) Int. Cl.
| | |
|---|---|
| C12P 13/22 | (2006.01) |
| A23L 3/3463 | (2006.01) |
| A23L 3/3526 | (2006.01) |
| A23L 3/3544 | (2006.01) |
| A23L 5/46 | (2016.01) |
| C07K 14/415 | (2006.01) |
| C12N 9/02 | (2006.01) |
| C12N 9/12 | (2006.01) |
| C12P 13/04 | (2006.01) |
| C12P 17/12 | (2006.01) |
| C12P 19/02 | (2006.01) |

(52) U.S. Cl.
CPC .......... *C12P 13/225* (2013.01); *A23L 3/3463* (2013.01); *A23L 3/3526* (2013.01); *A23L 3/3544* (2013.01); *A23L 5/46* (2016.08); *C07K 14/415* (2013.01); *C12N 9/0083* (2013.01); *C12N 9/1205* (2013.01); *C12P 13/04* (2013.01); *C12P 17/12* (2013.01); *C12P 19/02* (2013.01); *C12Y 207/01095* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,015,580 A | 5/1991 | Christou et al. | |
| 5,464,764 A | 11/1995 | Capecchi et al. | |
| 5,487,992 A | 1/1996 | Capecchi et al. | |
| 5,538,880 A | 7/1996 | Lundquist et al. | |
| 5,550,318 A | 8/1996 | Adams et al. | |
| 5,591,616 A | 1/1997 | Hiei et al. | |
| 5,635,055 A | 6/1997 | Sweet et al. | |
| 5,661,017 A | 8/1997 | Dunahay et al. | |
| 5,824,877 A | 10/1998 | Hinchee et al. | |
| 5,932,447 A | 8/1999 | Siegall | |
| 5,981,840 A | 11/1999 | Zhao et al. | |
| 6,160,208 A | 12/2000 | Lundquist et al. | |
| 6,384,301 B1 | 5/2002 | Mariinell et al. | |
| 6,399,861 B1 | 6/2002 | Anderson et al. | |
| 6,403,865 B1 | 6/2002 | Koziel et al. | |
| 7,001,772 B2 | 2/2006 | Roessler et al. | |
| 8,802,925 B2 | 8/2014 | Luo et al. | |
| 10,167,482 B2 | 1/2019 | Coffin | |
| 10,457,918 B2 * | 10/2019 | Martin | .......... C12Y 114/16002 |
| 10,767,201 B2 * | 9/2020 | Aharoni | .................. C12P 19/02 |

(Continued)

FOREIGN PATENT DOCUMENTS

| | | |
|---|---|---|
| JP | 2015192669 A | 11/2015 |
| JP | 2016182044 A | 10/2016 |

(Continued)

OTHER PUBLICATIONS

Harris et al., "Betalain production is possible" in anthocyanin-producing plant species given the presence of DOPA-dioxygenase and L-DOPA, BMC Plant Biology, Mar. 12, 2012, vol. 12, No. 1, pp. 1-12.

(Continued)

*Primary Examiner* — Hope A Robinson
(74) *Attorney, Agent, or Firm* — The Roy Gross Law Firm, LLC; Roy Gross

(57) ABSTRACT

The invention provides recombinant polynucleotides comprising a nucleic acid encoding a CYP76AD6 or related gene and their use for producing L-DOPA from tyrosine. The invention also provides recombinant polynucleotides comprising a nucleic acid encoding a CYP76AD1 and/or CYP76AD6, a nucleic acid encoding a DOPA 4,5-dioxygenase (DOD) enzyme, such as *Beta vulgaris* DODA1, and, in some cases, a nucleic acid encoding betalain related glucosyltransferase, such as *Mirabilis. jalapa* gene cyclo-DOPA 5-O-glucosyltransferase (cDOPA5GT), and their use for producing betalains. Finally, the invention provides chimeric polypeptides, expression vectors, cells, compositions, and organisms, including plants, and their uses in various methods of the invention.

8 Claims, 46 Drawing Sheets
(26 of 46 Drawing Sheet(s) Filed in Color)

Specification includes a Sequence Listing.

(56) References Cited

U.S. PATENT DOCUMENTS

| | | |
|---|---|---|
| 2001/0031724 A1 | 10/2001 | Roemer et al. |
| 2003/0028913 A1 | 2/2003 | Hein et al. |
| 2003/0049785 A1 | 3/2003 | Schreier et al. |
| 2003/0196219 A1 | 10/2003 | Zhang |
| 2004/0133937 A1 | 7/2004 | Boudreau et al. |
| 2005/0158861 A1 | 7/2005 | Song |
| 2007/0026506 A1 | 2/2007 | Miele et al. |
| 2007/0079396 A1 | 4/2007 | Malvar et al. |
| 2007/0264716 A1 | 11/2007 | Boergel et al. |
| 2008/0194029 A1 | 8/2008 | Hegerrnann et al. |
| 2008/0307541 A1 | 12/2008 | Hsieh |
| 2009/0264320 A1 | 10/2009 | Hsieh et al. |
| 2009/0325247 A1 | 12/2009 | Kodama et al. |
| 2010/0159545 A1 | 6/2010 | Kim et al. |
| 2010/0190223 A1 | 7/2010 | Saito et al. |
| 2010/0199371 A1 | 8/2010 | Castle et al. |
| 2011/0113514 A1 | 5/2011 | Malvar et al. |
| 2011/0209247 A1 | 8/2011 | Aharoni et al. |
| 2011/0251408 A1 | 10/2011 | Mathews et al. |
| 2011/0300633 A1 | 12/2011 | Adachi et al. |
| 2012/0034698 A1 | 2/2012 | Maor |
| 2012/0094385 A1 | 4/2012 | Kuehnle et al. |
| 2013/0130389 A1 | 5/2013 | Adachi et al. |
| 2014/0051135 A1 | 2/2014 | Mathews et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0234972 A1 | 8/2014 | Zhang |
| 2014/0248702 A1 | 9/2014 | Zhang et al. |
| 2014/0283166 A1 | 9/2014 | Chomet et al. |
| 2015/0004704 A1 | 1/2015 | Maor |
| 2015/0011008 A1 | 1/2015 | Fukuzawa et al. |
| 2015/0082478 A1 | 3/2015 | Cigan et al. |
| 2015/0184139 A1 | 7/2015 | Zhang et al. |
| 2015/0356239 A1 | 12/2015 | Zhang et al. |
| 2016/0074535 A1 | 3/2016 | Ranganathan et al. |
| 2016/0177304 A1 | 6/2016 | Collingwood |
| 2016/0243251 A1 | 8/2016 | Blainey et al. |
| 2016/0251648 A1 | 9/2016 | Wang et al. |
| 2020/0354759 A1* | 11/2020 | Aharoni ............... A23L 3/3526 |

FOREIGN PATENT DOCUMENTS

| | | |
|---|---|---|
| JP | 2018057354 A | 4/2018 |
| WO | 2003/104451 A2 | 12/2003 |
| WO | 2014/013056 A1 | 1/2014 |
| WO | 2014/104878 A1 | 7/2014 |
| WO | 2014/194190 A1 | 12/2014 |
| WO | 2015/048707 A2 | 4/2015 |
| WO | 2015/131101 A1 | 9/2015 |
| WO | 2016/033230 A1 | 3/2016 |
| WO | 2016/049364 A2 | 3/2016 |
| WO | 2017/034971 A1 | 3/2017 |
| WO | 2017/122178 A1 | 7/2017 |
| WO | 2017/222779 A1 | 12/2017 |

OTHER PUBLICATIONS

Abuchowski et al. "Reduction of plasma urate levels in the cockerel with polyethylene glycol-uricase" Journal of Pharmacology and Experimental Therapeutics. Nov. 1, 1981;219(2):352-4.

Alberti et al. "A suite of Gateway@ cloning vectors for high-througllput genetic analysis in *Saccharomyces cerevisiae*" Yeast Oct. 2007;24('10):913-9.

An G. "High efficiency transformation of cultured tobacco cells" Plant physiology. Oct. 1, 1985 ;79(2):568-70.

Azeredo, H.M.C. "Betalains: properties, sources, applications. and stability—a review" 2009, International Journal of Food Science & Technology, vol. 44, pp. 2365-2376.

Bak et al. "Cytochromes P450" The *Arabidopsis* Book, American Society of Plant Biologists. Oct. 6, 2011 (DOI'10.1199/Tab.0144).

Baltes et al., "DNA Replicons for Plant Genome Engineering" Jan. 2014, The Plant Celi, vol. 26, pp. 151-163.

Bates GW. "Plant transformation via protoplast electroporation" in Plant Cell Culture Protocols 1999 (pp. 359-366). Humana Press.

Beaudoin et al. "Benzylisoquinoline alkaloid biosynthesis in opium poppy" Planta. Jul. 1, 2014:240(1):19-32.

Behera et al., "Analyses of Ca 2+ dynamics using a ubiquitin-10 promoter-driven Yellow Cameleon 3.6 indicator reveal reliable transgene expression and differences in cytoplasmic Ca 2+ responses in *Arabidopis* and rice (*Oryza saliva*) roots", New Phytologist, vol. 206, No. 2, Jan. 5, 2015, pp. 751-760.

Belhaj et al., "Plant genome editing made easy: targeted mutagenesis in model and crop plants using the CRISPR/Cas system", 2013, Plant Methods, 9:39.

"Beta subsp. Vulgaris geraniol 8-hydroxylase-like (LOC104904803}, mRNA", Dec. 10, 2014, URL: https://www.ncbi.nlm.nih.gov/protein/731359838.

Bitter et al. "Expression and secretion vectors for yeast" In Methods in enzymology Jan. 1, 1987 (vol. 153, pp. 516-544). Academic Press.

Booth et al. "The use of a 'universal' yeast expression vector to produce an antigenic protein of Mycobacterium leprae" Immunology letters. Sep. 1, 1988 ;19(1):65-9.

Brisson et al "Expression of a bacterial gene in plants by using a viral vector" Nature. Aug. 1984;310(5977):511.

Brockington et al, "Lineage-specific gene radiations underlie the evolution of novel betalain pigmentation in Caryophyllales" 2015, New Phytologist vol. 207, Issue 4, pp. "1170-1180.

Broglie et al. "Light-regulated expression of a pea ribuiose-1, 5-bisphosphate carboxylase small subunit gene in transfomled plant cells" Science. May 25, 1984;224:838-44.

Buchwald et al. "Long-term, continuous intravenous heparin administration by an implantable infusion pump in ambulatory patients with recurrent venous H1rombosis" Surgery. Oct. 1, 1980 ;88(4):507-16.

Christinet et al. "Characterization and functional identification of a novel plant 4, 5- extradiol dioxygenase involved in betalain pigment biosynthesis" in Portulaca grandiflora. Plant Physiology. Jan. 1, 2004; 134(1): 265-74.

Clemente T. "Nicotiana (*Nicotiana tobaccum, Nicotiana bentharniana*)" In Agrobacterium protocols 2006 (pp. 143-154). Humana Press.

Brockington et al. "Complex pigment evolution in the Caryophllales" New Phytologist. Jun. 2011:190(4):854-64.

Clifford et al. "The potential benefits of red beetroot supplementation in health and disease" Nutrients. Apr. 2015:7(4):2801-22.

Conesa et al. "Blast2GO: a universal tool for annotation, visualization and analysis in functional genomics research". Bioinformatics. Aug. 4, 2005;21 (18):3674-6.

Conner et al. Transformation and regeneration of Petunia In Petunia 2009 (pp. 395-409). Springer, New York, NY.

Coruzzi et al. "Tissue-specific and light-regulated expression of a pea nuclear gene encoding the small subunit of ribulose-1, 5-bisphosphate carboxylase" The EMBO journal. Aug. 1, 1984 ;3(8): 1671-9.

Database, "Cloning vector PNIGEL 16, complete sequence.", retrieved from Database EMBL [Online], Apr. 7, 2009.

Deloache et al. "An enzyme-coupled biosensor enables (S)-reticuline production in yeast from glucose", 2015, Nat Chem Biol, vol. 11, pp. 465-471.

Dohm et al. "The genome of the recently domesticated crop plant sugar beet (*Beta vulgaris*)" Nature. Jan. 2014;505(7484):546.

Enfissi et al., The regulation of carotenoid formation in tomato fruit 2016, Plant J., vol. 89, pp. 774-788.

Esatbeyoglu et al "Betanin—A food colorant with biological activity" Molecular nutrition & food research Jan. 2015;59(i):36-47.

Finer et al. "Particle bombardment mediated transformation" In Plant Biotechnology 2000 (pp. 59-80). Springer, Berlin, Heidelberg.

Gandia-Herrero et al. "Biosynthesis of betalains: yellow and violet plant pigments" 2013, Trends in Plant Science, vol. 18, pp. 334-343.

Gandia-Herrero et al. "Characterization of recombinant Beta vulgaris 4,5-DOPA- extradiol-dioxygenase active in the biosynthesis of betalains" 2012, Planta, vol. 236, pp. 91-100.

(56) References Cited

OTHER PUBLICATIONS

Gandia-Herrero et al. "Beiaxanthins as pigments responsible for visible fluorescence in flowers" Planta. Nov. 1, 2005 :222(4):586-93.
Gandia-Herrero et al. "Purification and characterization of a latent polyphenol oxidase from beet root (*Beta vulgaris* L.)" Journal of Agricultural and Food Chemistry. Feb. 11, 2004 ;52(:3):609-15.
Gandia-Herrero et al. "Biological activities of plant pigments betalains" Critical reviews in food science and nutrition. Apr. 25, 2016;56(6):937-45.
Garbarino et al., "Expression of stress-responsive ubiquitin genes in potato tubers", Plant Molecular Biology, Springer, Dordrecht, NL, vol. 20, Jan. 1, 1992, pp. 235-244.
Gardella et aL "Expression of human parathyroid hormone-(1-84) in *Escherichia coli* as a factor X-cleavabie fusion protein" Journal of Biological Chemistry. Sep. 15, 1990;265(26): 15854-9.
GenBank Accession No. AKI33834.1 (Version 1), Sep. 9, 2015.
GenBank Accession No. AKI33838.1 (Version 1), Sep. 9, 2015.
GenBank Accession No. AKI33835.1 (Version 1), Sep. 9, 2015.
GenBank Accession No. AKI33831.1 (Version 1), Sep. 9, 2015.
GenBank Accession No. AET43289.1 (Version 1), Jun. 3, 2012.
GenBank Accession No. AET43291.1 (Version 1), Jun. 3, 2012.
GenBank Accession No. AET43292.1 (Version 1), Jun. 3, 2012.
GenBank Accession No. AGI78466.1 (Version 1), Apr. 14, 2013.
GenBank Accession No. JC233128.1 (Version 1), Feb. 3, 2014.
GenBank Accession No. HQ003815.1 (Version 1), Dec. 5, 2010.
GenBank Accession No. AJ580598.1 (Version 1), Feb. 3, 2011.
GenBank Accession No. AB435372.1 (Version 1), May 20, 2009.
GenBank Accession No. A8435373.1 (Version 1), May 20, 2009.
GenBank Accession No. P87064.1 (Version 1), Nov. 24, 2017.
GenBank Accession No. AB182643.1 (Version 1), Aug. 9, 2006.
GenBank Accession No. HQ656027.1 (Version 1), Jun. 3, 2012.
GenBank Accession No. HQ656023.1 (Version 1), Jun. 3, 2012.
GenBank Accession No. KT962274.1 (Version 1), Mar. 29, 2016.
Gengatharan et al. "Betalains: Natural plant pigments with potential application in functional foods" LWT—Food Science and Technology. Dec. 1, 2015 :64(2):645-9.
Gilboa E. "Transfer and expression of cloned genes using retroviral vectors" BioTechniques. 1986;4:504-12.
Girod et al. "Biogenesis of betalains: purification and partial characterization of DOPA 4, 5-dioxygenase from Amanita muscaria" Phytochemistry. Jan. 1, 1991; 30(1):169-74.
Grefen et al, "A ubiquitin-10 promoter-based vector set for fluorescent protein tagging facilitates temporal stability and native protein distribution in transient and stable expression studies", 2010, The Plant Journal, vol. 64, pp. 355-365.
Grotewold E. "The genetics and biochernistry of floral pigments" / Annu. Rev. Plant Biol. Jun. 2, 2006;57:761-80.
Gurley et ai. "Upstream sequences required for effecient expression of a soybean heal shock gene" Molecular and cellular biology. HI86 Feb. 1;6(2):559-65.
Haas et al. "De novo transcript sequence reconstruction from RNA-seq using the Trinity platfom1 for reference generation and analysis" Nature protocols. Aug. 2013:8(8):1494.
Hallmann A., "Algal Transgenic and Biotechnology" Apr. 2007, Transgenic Plant Journal, vol. 1 (1), pp. 81-98.
Harris et al., "Betalain production is possible" in anthocyanin-producing plant species given the presence of DOPA-dioxygenase and L-DOPA, BMC Plant Biology, Mar. 12, 2016, vol. 12, No. 1, pp. 1-12.
Hatlestad et al., "The beet R locus encodes a new cytochrome P450 required for red betalain production", Nature Genetics, Jun. 3, 2012, vol. 44, No. 7, pp. 816-820.
Hatlestad et al. "The beet Y locus encodes an anthocyanin MYB-like protein that activates the betalain red pigment pathway" Nature Genetics. Jan. 20-15;47(1):92.
Heid et al., "Real Time Quantitative PCR", 1996 Genome Research, vol. 6, pp. 986-994.

Herbach et al. "Betalain stability and degradation-structural and chromatic aspects" Journal of food science. May 2006:71(4):R41-50.
Horsch et al., "Leaf disc transformation" 1988, Plant Molecular Biology Manual AS, pp. 1-9, Kluwer Academic Publishers, Dordrecht.
Horsch et al. "A simple and general method for transferring genes into plants" Science. 1985;227(4691):1229-31.
International Search Report dated Nov. 27, 2016 for PCT/IL2016/051010 dated Sep. 11, 2016.
Isaacson et al, "Cloning of tangerine from Tomato Reveals a Carotenoid Isomerase Essential for the Production of B Carotene and Xanthophylls in Plants", 2002, Plant Ceil vol. 14, pp. 333-342.
Jain et. al., "Betalain induction by L-DOPA application confers photoprotection to saline-exposed leaves of Disphyma austral" 2015, New Phytologist, vol. 207, pp. 1075-1083.
Jiang et al "Virus-induced gene silencing in ornamental plants" In RNAi and plant gene function analysis 2011 (pp. 81-96). Humana Press.
Katre et al. "Chemical modification of recombinant interleukin 2 by polyethylene glycol increases its potency in the murine Meth A sarcoma model" Proceedings or the National Academy or Sciences. Mar. 1, 1987 ;84(6):1487-91.
Khan et al "Plant betalains: Chemistry and biochemistry" Phytochemistry. Sep. 1, 2015;117:267-95.
Khan Mi. "Plant betalains: Safety, antioxidant activity, clinical efficacy, and bioavailability" Comprehensive Reviews in Food Science and Food Safety. Mar. 2016; 15(2):316-30.
Killan et al., "High-efficiency homologous recombination in the oil-producing alga Nannochloropsis sp." PNAS 2011, 108(52), pp. 21265-21269.
Komari et al. ", advances in cereal gene transfer" Current opinion in plant biology, Apr. 1, 1998 :1 (2):m1-5.
Kyoungseon et al., "Overview on the biotechnological production of L-DOPA" 2015, Appl Microbial Biotechnol, vol. 99, pp. 575-584.
Liu et al. "Virus-induced gene silencing in tomato" The Plant Journal. Sep. 2002;31 (6):777-86.
Livak et al "Analysis of relative gene expression data using real-time quantitative PCR and the Delta Delta CT method" Methods 25. Dec. 1, 2001;25(4):402-8.
Lu et al. Virus-induced gene silencing in plants Methods 30. Aug. 1, 2003;30(4):296-303.
Martinez-Parra et al "Characterization of betacyanin oxidation catalyzed by a peroxidase from Beta vulgaris L. roots" Journal of agricultural and food chemistry. Aug. 20, 2001;49(8):4064-8.
McCormick S. "Transformation of tomato with Agrobacteriumn tumefaciens" In Plant tissue culture manual—1991 (pp. 311-319). Springer. Dordrecht.
Meissner et al. "A new model system for tomato genetics", 1997, Plant J., vol. 12, pp. 1465-1472.
Min et al., "Overview on the biotechnological production or L-DOPA" 2015, Appl Microbial Biotectrnol, vol. 99, pp. 575-584.
Misra et al., "Extraction of bioactive principles from Mucuna pruriens seeds" 2007, Indian Journal of Biochemistry & Biophysics, vol. 44, pp. 56-60.
Moreno et al. "Betalains in the era of global agri-food science, technology and nutritional health" Phytochemistry Reviews. Jul. 1, 2008;7(2):261-80.
Mozo et al. "Factors affecting the rate of T-DNA transfer from Agrobacterium tumefaciens to Nicotiana glauca plant cells" Plant molecular biology. Sep. 1, 1992;19(6):1019-30.
Nagatsu et al. "L-dopa therapy for Parkinson's disease: past, present, and future" Parkinsonism & related disorders. Jan. 2009; 15:83-8.
Nakatsu Ka et al. "Genetic engineering of yellow betalain pigments beyond the species barrier" Scientific reports. Jun. 12, 2013:3: 1970.
Perl et al. "Regulation of lysine synthesis in transgenic potato plants expressing a bacterial dihydrodipicolinate synthase in their chloroplasts" Plant molecular biology—Aug. 1, 1992;19(5):815-23.
Podevin et al., "Site-directed nucleases: a paradigm shift in predictable, knowledge-base plant breeding", Apr. 17, 2013, Trends in Biotechnology, Elsevier Publications, Cambridge, GB, vol. 31, No. 6, pp. 375-383.

(56) References Cited

OTHER PUBLICATIONS

Polturak et al. "Elucidation of the first committed step in betalain biosynthesis enables the heterologous engineering of betalain pigments in plants" New Phytologist. Apr. 1, 2016:210(1):269-83.
Porta et al. "Use of viral replicons for tile expression of genes in plants" Molecular Biotechnology. Jun. 1, 1996;5(3):209.
Potrykus L, "Gene Transfer to Plants: Assessment of Published Approaches and Results" 1991, Annual Review Plant Physiol, Plant Mol. Biol, vol. 42, pp. 205-225.
Pribat et al., "Nonflowering plants possess a unique folate-dependent phenylalanine hydroxylase that is localized in chloroplasts" The Plant Cell. Oct. 1, 2010:22(10):34 10-22.
Qi et al, "Chapter 3: High efficient genome modification by designed zinc finger nuclease", Jan. 1, 2015, Advances in New Technology for Targeted Modification of Plant Genomes, Springer, pp. 39-53.
Qingzhu et al Transcriptomic analysis reveals key genes related to betalain biosynthesis in pulp coloration of Hylocernus polyrhizus. Frontiers in plant science. Jan. 5, 2016;6:1179.
Radakovits et al., "Genetic Engineering of Algae for Enhanced Biofuel Production Eukaryotic Cell", Apr. 2010, vol. 9(4), pp. 486-501.
Radakovits et al., "Draft genome sequence and genetic transformation of the oleaginous alga Nannochloropsis gaditana", Feb. 21, 2012, Nat Commun., 3: 686.
Ramsden "Quantitative Drug Design", Chapter 17.2, F. Choplin Pergamon Press (1990).
Sambrook, Joseph et al. "Molecular cloning: a laboratory manual." Cold Spring Harbor Laboratory Press, Cold Spring Harbor, New York 2 (2001).
Sarrion-Perdigones et al., "Design and construction of multigenic constructs for plant biotechnology using the GoldenBraid cloning strategy" 2014, Methods Mol. Biol., vol. 1116, pp. 133-151.
Sarrion-Perdigones et al., "GoldenBraid 2.0: A Comprehensive DNA Assembly Framework for Plant Synthetic Biology" 2013, Plant Physiology, vol. 162, pp. 1618-1631.
Sasaki et al., "Isolation and characterization of cDNAs encoding an enzyme with glucosyltransferase activity for cyclo-DOPA from four o'clocks and feather cockscombs" 2005, Plant and Cell Physiology, vol. 46, pp. 666-670.
Sasaki et al. "Detection of DOPA 4. 5-cHoxygenase (DOD} activity using recombinant protein prepared from *Eschericilia coli* cells harboring cDNA encoding DOD from Mirabilis jalapa" Plant and cell physiology. Apr. 13, 2009:50(5): 1012-6.
Saudek et al., "A preliminary trial of the programmable implantable medication system for insulin delivery" New England Journal of Medicine. Aug. 31, 1989 ;321 (9):574-9.
Schiml et al., "The CRISPR/Cas system can be used as nuclease for in planta gene targeting and as paired nickases for directed mutagenesis in *Arabidopsis* resulting in heritable progeny", Nov. 11, 2014, The Plant Journal, vol. 80, No. 6, pp. 1139-1150.
Sefton CR (1987) "Critical Review" in Biomedical Engineering, vol. 14. Issue.3:201-40.
Sekiguchi et al., "In Vitro Synthesis of Betaxanthins Using Recombinant DOPA 4,5-Dioxygenase and Evaluation of Their Radical Scavenging Activities" 2010, Journal of Agricultural and Food Chemistry, vol. 58, pp. 12504-12509.
Sepulveda-Jimenez et al. "A red beet (*Beta vulgaris*) UDP-9lucosyltransferase gene induced by wounding, bacterial infiltration and oxidative stress" Journal of experimental botany. Dec. 6, 2004;56(412):605-11.
Shdema et al., "Targeted recombination between homologous chromosomes for precise breeding in tomato", May 26, 2017, Nature Communications, vol. 8, p. 15605.
Shimamoto et al., "Fertile transgenic rice plants regenerated from transformed protoplasts" Mar. 16, 1989, Nature, vol. 338, pp. 274-276.
Singh et al., Co-silencing of the Mirabilis antiviral protein (MAP) permits virus- induced gene silencing (VIGS) of other genes in Four O'Clock plants (*Mirabilis jalapa* The Journal of Horticulture Science and Biotechnology. Jan. 1, 2012, 87(4):334-40.

Soares et al., "The role of L-DOPA in plants" Plant signaling & behavior. Apr. 2014 i ;9(4): pp. e28275-1-e28275-7.
Solomon et al., "Multicopper oxidases and oxygenases" 1996, Chemical Reviews, vol. 96, pp. 2563-2605.
Sparkes et al. "Rapid, transient expression of fluorescent fusion proteins in tobacco planis and generation of stably transformed plants" Nature protocols. Nov. 2006; 1(4):2019.
Steiner et al. Tyrosinase involved in betalain biosynthesis of higher plants Planta. Mar. 1, 1999 ;208(1):114-24.
Steiner et al. "Assay for tyrosine hydroxylation activity or tyrosinase from betalain-forming plants and cell cultures" Analytical biochemistry. Jun. 15, 1996;238(1):72-5.
Stintzing et al. "Betalains-emerging prospects for food scientists." Trends in Food Science & Technology. Oct. 1, 2007 ;18(10):514-25.
Stintzing et al. "Analysis of betalains. Food colorants: Chemical and functional properties" 2008:507-20.
Stintzing et al. "Evaluation of colour properties and chemical quality parameters of cactus juices" European Food Research and Technology—Apr. 1, 2003 ;216(4):303-11.
Stintzing et al. "Functional properties of anthocyanins and betalains in plants, food, and in human nutrition" Trends in food science & technology. Jan. 1, 2004:15(1):19-38.
Strack et al. "Recent advances in betalain research" Phytochemistry. Feb. 1, 2003,62(3):247-69.
Sunnadeniya et al, Tyrosine Hydroxylation in Betalain Pigment Biosynthesis is Performed by Cytochrome P450 Enzymes in Beets (*Beta vulgaris*) Feb. 18, 2016, PloS One, 11 (2).
Supplementary European Search Report for European Application No. 16884828.1 dated Jan. 9, 2019.
Suzuki et al. "Transposon-mediated mutation of CYP76AD3 affects betalain synthesis and produces variegated flowers in four o'clock (*Mirabilis jalapa*)" Journal of plant physiology. Nov. 1, 20-14:171(17): 1586-90.
Takamatsu et al.—Expression of bacterial chloramphenicol acelyltransferase gene in tobacco plants mediated by TMV-RNA The EMBO journal. Feb. 1, 1987;6(2):307-11.
Tamura et al. "MEGA6: molecular evolutionary genetics analysis version 6.0" Molecular biology and evolution. Oct. 16, 2013;30(12):2725-9.
Tanaka et al. "Biosynthesis of plant pigments: anthocyanins, betalains and carotenoids" The Plant Journal. May 2008;54(4):733-49.
Trenchard el al., "De novo production of the key branch point benzylisoquinoline alkaloid reticuline in yeast" 2015, ELSEVIER Metabolic Engineering, vol. 31, pp. 74-83.
Tzin et al. "Expression of a bacterial feedtback-insensitive 3-deoxy-d-arabino-heptulosonate 7-phosphate synthase of the shikimate pathway in *Arabidopsis* elucidates potential metabolic bottlenecks between primary and secondary metabolism" New Phytologist. Apr. 1, 2012;194(2):430-9.
Van Eck et al. "Eggplant (*Solanum melongena* L)" in Agrobacterium Protocols 2006 (pp. 439-448). Humana Press.
Vogt T. "Substrate specificity and sequence analysis define a polyphyletic origin of betanidin 5-and 6-O-glucosyltransferase from Dorotheanthus bellidiformis" Planta. Jan. 1, 2002 ;214(3):492-5.
Vogt et al. "Cloning and expression of a cDNA encoding betanidin 5-O-glucosyltransferase, a betanidin-and flavonoid-specific enzyme with high homology to inducible glucosyltransferases from the Solanaceae" The Plant Journal Sep. 1999;19(5):509-19.
Von Elbe et al. "Oxygen involvement in betaine degradation—Measurement of active oxygen species and oxidation reduction potentials" Food chemistry. Jan. 1, 1985;16(1):49-67.
Weissbach and Weissbach, "Methods for Plant Molecular Biology" (Eds.), Chapters 23 and 24 pp. 355-401, 1988 Academic Press, inc., San Diego, California, article by Potrykus L et al., "Protoplasts: isolation, Culture, Plant Regeneration".
Weissbach and Weissbach, "Methods for Plant Molecular Biology." Selected Methods in Enzymology (USA) Section Viii: 421-463 (1988).
Williamson et al. "Botrytis cinerea: the cause of grey mould disease" Molecular plant pathology. Sep. 2007;8(5):561-80.
Yamamoto et al. "Isolation and purification of tyrosine hydroxyiase from callus cultures of Portulaca grandiflora" Plant and Cell Physiology. Sep. 15, 2001;42(9):969-75.

(56) References Cited

OTHER PUBLICATIONS

Zhang et al., "Anthocyanins Double the Shelf Life of Tomatoes by Delaying Over-ripening and Reducing Susceptibility to Gray Mold." 2013, Current Biology, vol. 23, pp. 1094-1100.

Zhong et al. "High-throughput illumina strand-specific RNA sequencing library preparation" Cold spring harbor protocols. 20-1 •1 Aug. 1, 2011 (8):pdb-rot5652.

Studier FW. ; Use of T7 RNA polymerase to direct expression of cloned genes Methods Enzymol.. 1990:185:60-89.

Georgiev et al. "Betalain production in plant in vitro systems" Acta Physiologiae Planlarurn. Sep. 2008;30(5):581-93.

Brockington, S. F. et al. Beta vulgaris subsp. maritima isolate FVXD@8922 cytochrome P450 76AD1-like protein mRNA, partial cds, KR376381.1, GenBank, 1-2, 2015.

\* cited by examiner

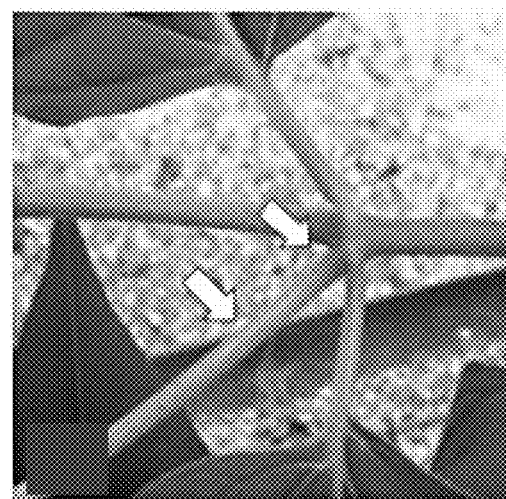
Figure 2C
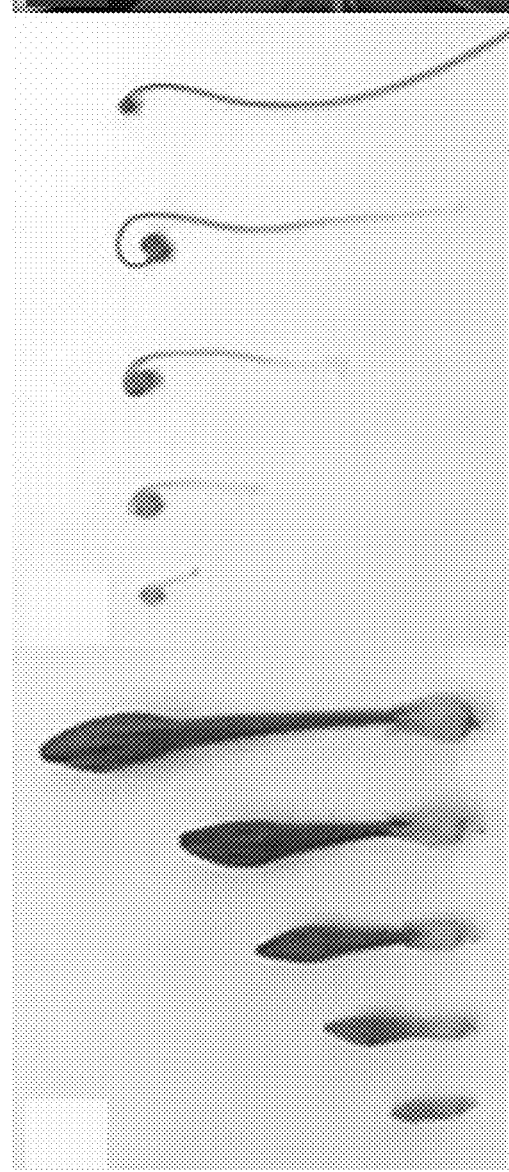
Figure 2A  Figure 2B
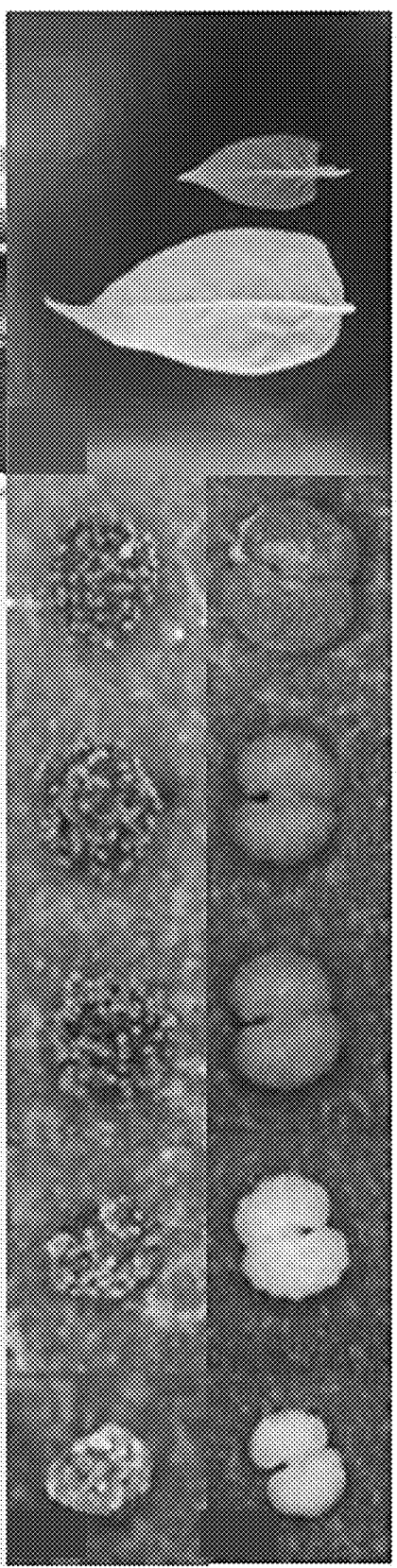
Figure 2F
Figure 2D
Figure 2E

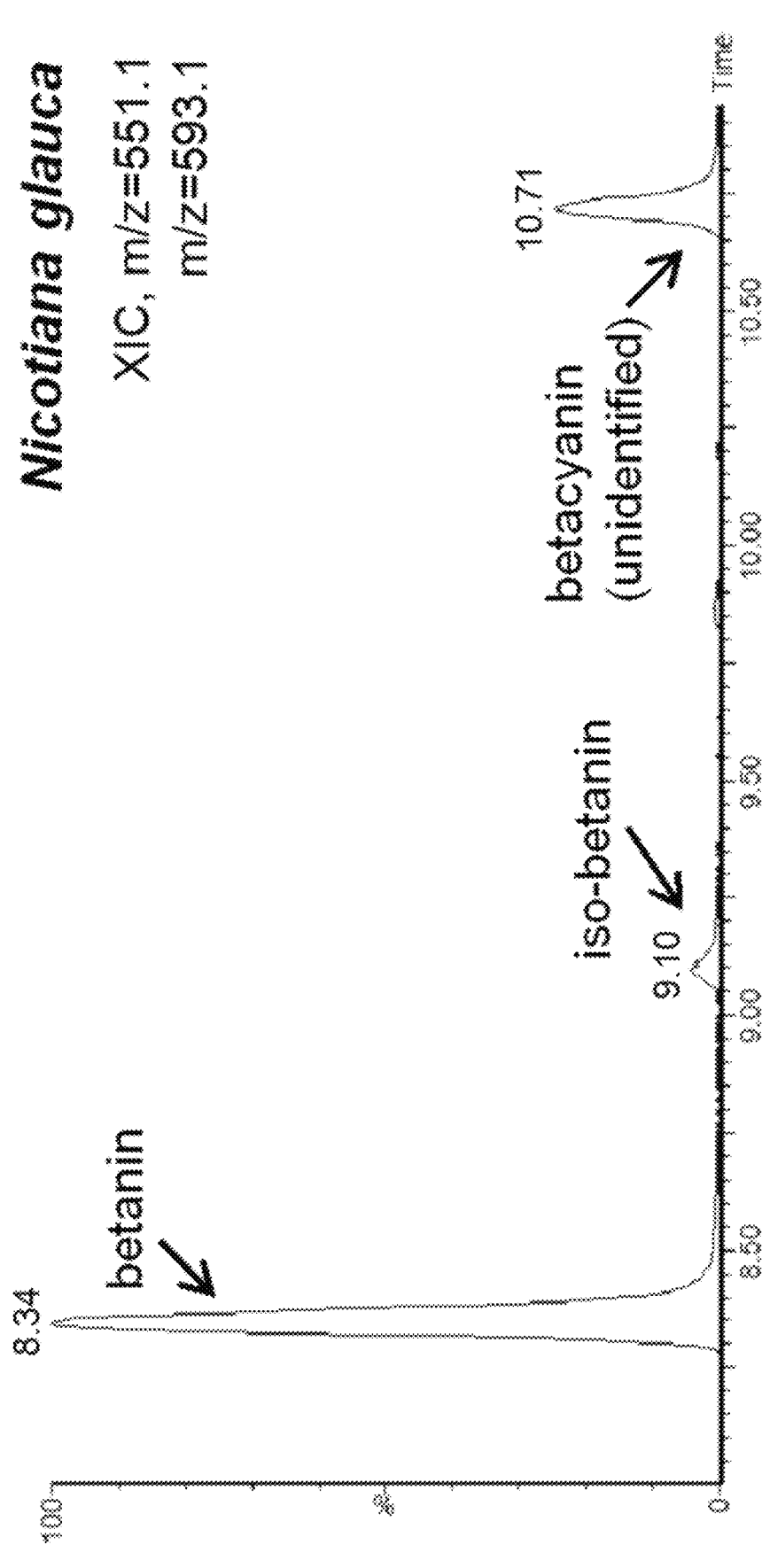
Figure 11B1

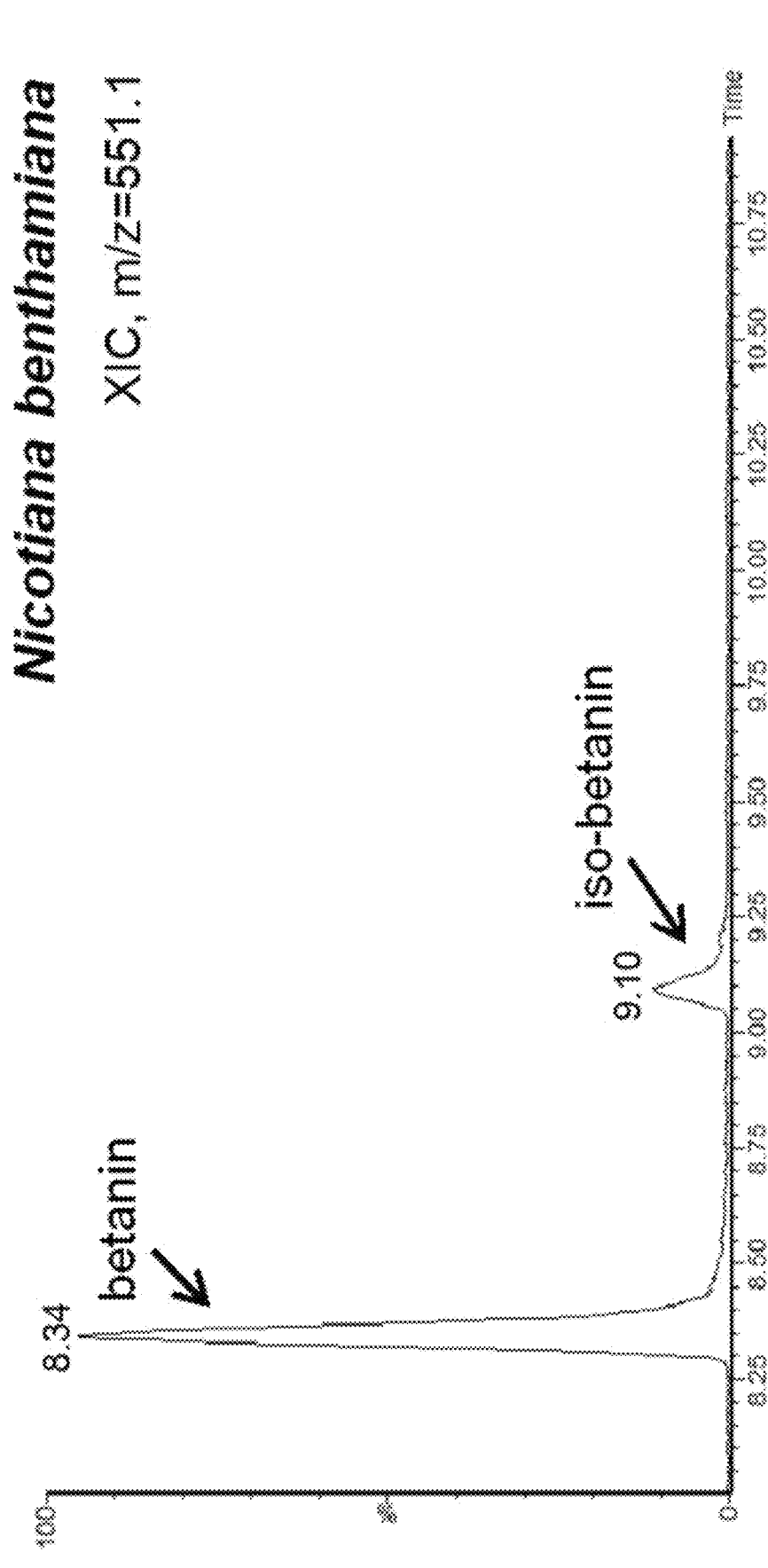
Figure 11B2

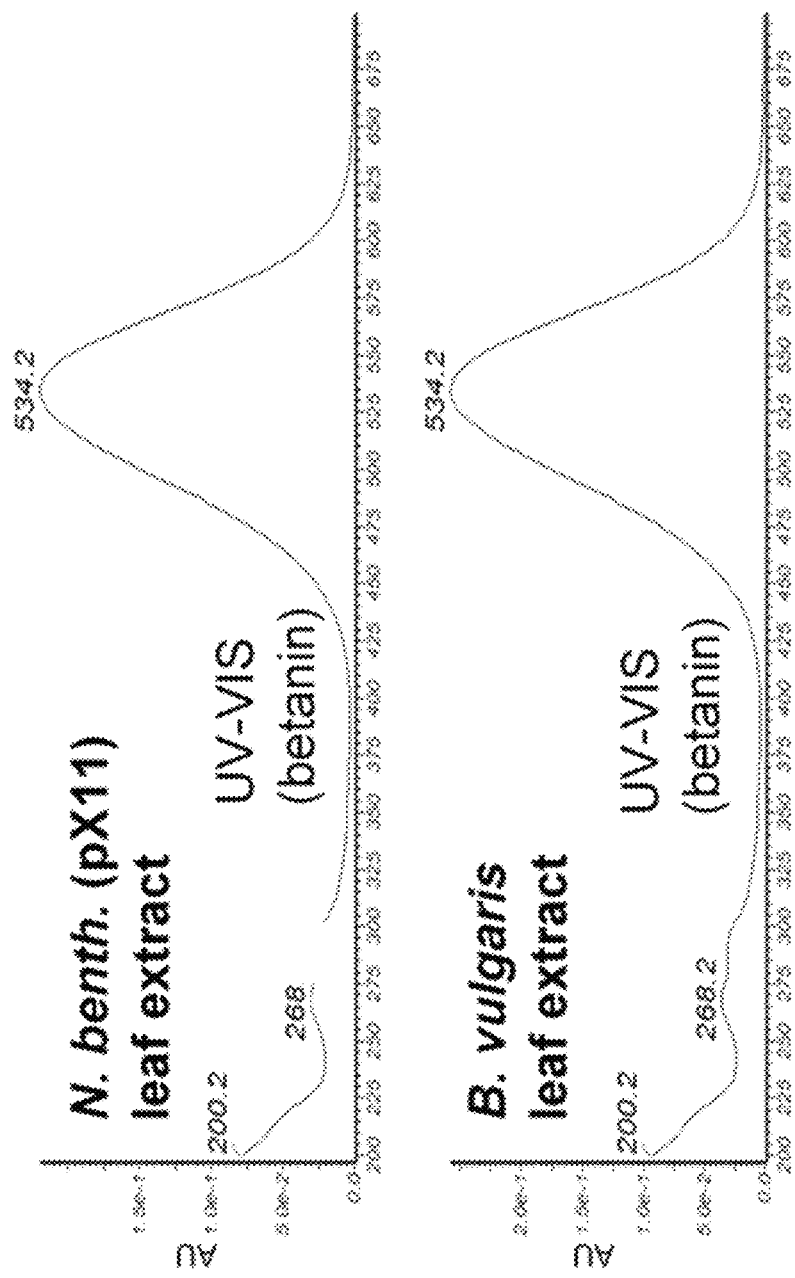
Figure 12A1

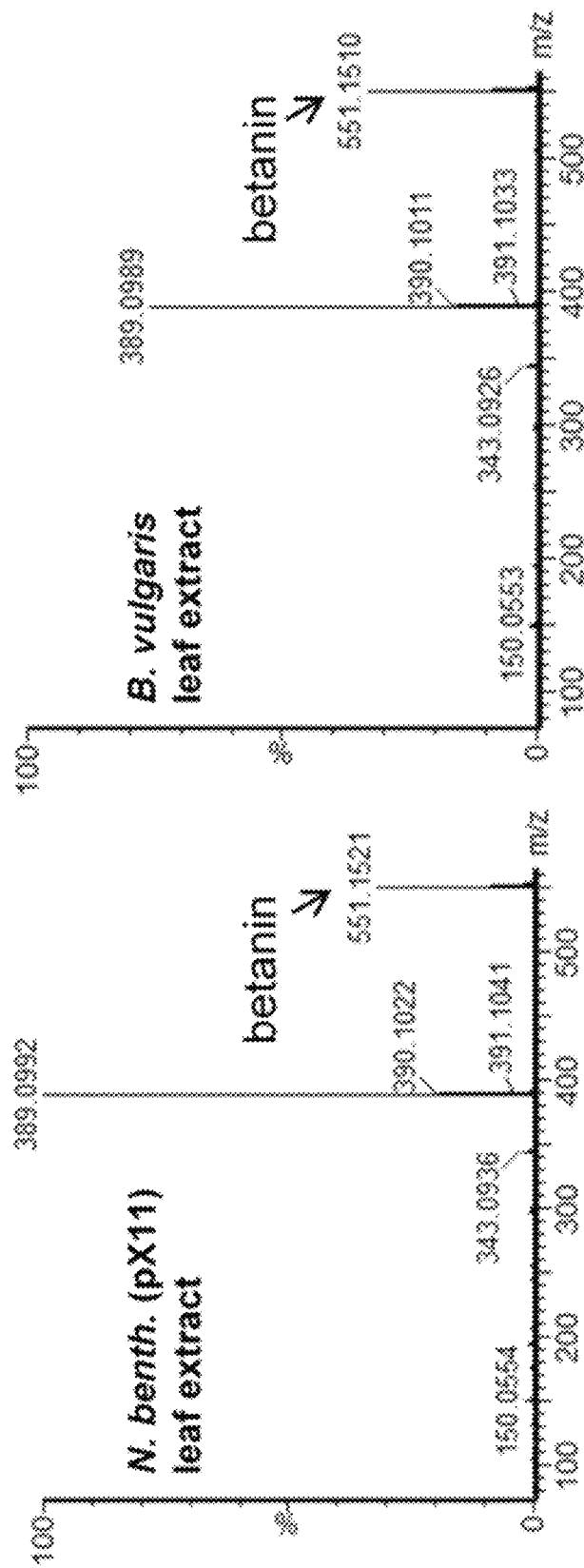
Figure 12A2

Figure 16A
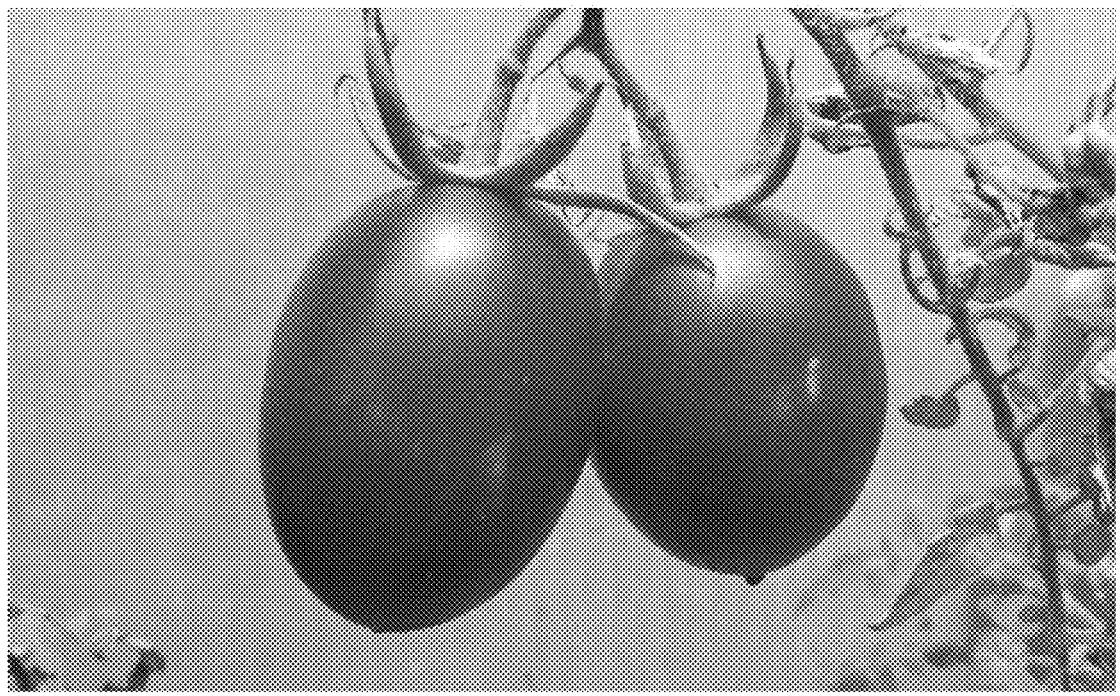
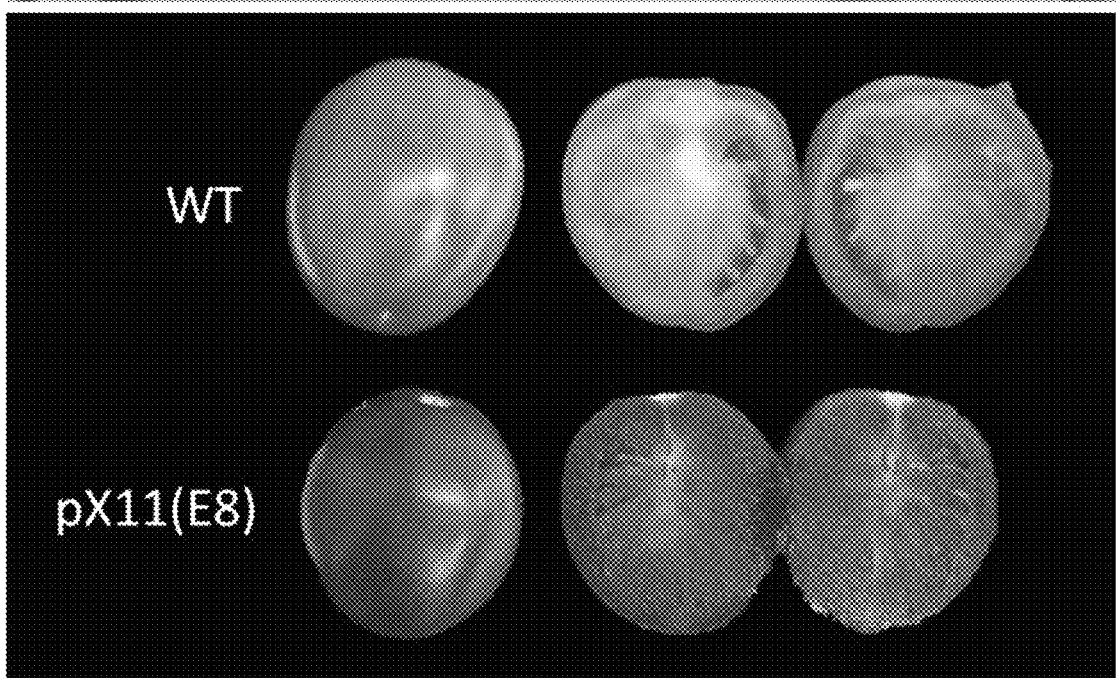
Figure 16B

B

CYP76AD1-BETA CLADE POLYNUCLEOTIDES, POLYPEPTIDES, AND USES THEREOF

CROSS REFERENCE TO RELATED APPLICATIONS

This application is a continuation of U.S. Pat. No. 10,767,201 filed on Mar. 8, 2018, which is a National Phase of PCT Patent Application No. PCT/IL2016/051010 having an International filing date of Sep. 11, 2016, which claims the benefit of priority under 35 U.S.C. § 119(e) of Israel Patent Application No. 241462, filed on Sep. 10, 2015. The contents of the above applications are all incorporated by reference as if fully set forth herein in their entirety.

REFERENCE TO AN ELECTRONIC SEQUENCE LISTING

The contents of the electronic sequence listing (PHYT-P-001-US1_SQL corrected.txt; Size: 293,941 bytes; and Date of Creation: Mar. 1, 2023) is herein incorporated by reference in its entirety. No new matter is added by this incorporation.

FIELD OF THE INVENTION

The invention provides recombinant polynucleotides comprising a nucleic acid encoding a CYP76AD6 or related gene and their use for producing L-DOPA from tyrosine and treating dopamine-responsive disorders, such as Parkinson's Disease. The invention also provides recombinant polynucleotides comprising a nucleic acid encoding a CYP76AD1 and/or CYP76AD6, a nucleic acid encoding a DOPA 4,5-dioxygenase (DOD) enzyme, such as *Beta vulgaris* DODA1, and, in some cases, a nucleic acid encoding betalain related glucosyltransferase, such as *M. jalapa* gene cyclo-DOPA 5-O-glucosyltransferase (cDOPA5GT), and their use for producing betalains. Finally, the invention provides chimeric polypeptides, expression vectors, cells, compositions, and organisms, including plants, and their uses in various methods of the invention.

BACKGROUND OF THE INVENTION

Betalains are tyrosine-derived, red-violet and yellow plant pigments found in only one group of angiosperms, the Caryophyllales order, in which they occur in a mutually exclusive fashion with the chemically distinct and widespread anthocyanin pigments. The betalain class contains a wide array of compounds, which are generally classified into two groups; the red-violet betacyanins, and the yellow betaxanthins.

A key enzyme in betalain biosynthesis, DOPA 4,5-dioxygenase (DOD) converts L-DOPA to betalamic acid, which constitutes the basic backbone of all betalains (FIG. 1). Spontaneous conjugation of betalamic acid with amines or with L-DOPA derivatives, results in the formation of yellow betaxanthins or red-violet betacyanins, respectively. Betalain related glucosyltransferase have also been characterized in several Caryophyllales plant species, catalyzing 5-O glucosylation of cyclo-DOPA or alternatively 5-O or 6-O glucosylation of betanidin. The enzyme catalyzing the formation of L-DOPA from tyrosine is unknown.

Due to their high stability, pH independence and antioxidative properties, betalains may be used as natural food colorants and dietary supplements.

While potential edible plant sources of anthocyanins are numerous, betalains are found in very few edible plants, with red beet being the only major source for betalain extraction in commercial use today. Despite its high betacyanin content, red beet extract has several drawbacks as a source of food colorants; it mainly produces betanin and thus has limited color variability, it carries adverse earthy flavors due to the occurrence of geosmin and various pyrazines, and it holds the risk of carry-over of soil-borne microbes. There are currently no natural sources in large-scale use for betaxanthins as food dyes. Yellow beet, for example, is not used likely due to co-occurring phenolics that are easily oxidized and mask the yellow hue of betaxanthins. Evidently, it is of interest to develop alternative sources for betalains, particularly betaxanthins, as there are currently no natural yellow, water-soluble pigments available for commercial use in the food industry. Heterologous production of betalains may provide numerous new viable sources for these pigments, such as plants, plant cell cultures, algae and yeast.

A betalain pathway intermediate, L-3,4-dihydroxyphenylalanine (L-DOPA), is also a commercially valuable metabolite that is widely used for treatment of Parkinson's disease.

Parkinson's disease is a progressive disorder of the nervous system primarily affecting the motor system of the body. It is the second most common neurodegenerative disorder and the most common movement disorder, affecting an estimate of 5 million people worldwide. A major feature of Parkinson's disease is the reduced levels of dopamine, an important signaling molecule in the nervous system. The most effective therapy for Parkinson's disease is the administration L-DOPA (3,4-dihydroxyphenylalanine), which is converted to dopamine in the brain. L-DOPA is the most effective drug for the treatment of Parkinson's disease, since dopamine fails to pass through the blood brain barrier.

L-DOPA is also widely marketed as a dietary supplement and is a precursor of additional high-value metabolites, which include among others catecholeamines (e.g. dopamine, epinephrine), benzilisoquinoline alkaloids (e.g. morphine and other opiates), betalain pigments and melanin.

Although L-DOPA is produced in many plants and animal species, it rarely accumulates in substantial quantities. This is partially due to the fact that L-DOPA is universally formed by the enzyme tyrosinase, which catalyzes the hydroxylation of tyrosine to L-DOPA but also immediately converts it to its oxidized form, dopaquinone.

L-DOPA for the pharma industry is currently produced using one of several methods, all of which have severe limitations, as chemical synthesis can only be achieved in a costly process that involves many chemical reactions and requires the use of expensive substrates and harsh production conditions. Biotechnological production of L-DOPA via the use of tyrosinase enzymes (also called polyphenol oxidase—PPO) has also been explored. The dual reaction of tyrosinase described above is highly problematic for the commercial production of L-DOPA, as the product of interest is directly metabolized to the commercially useless dopaquinone, and is therefore a major bottleneck for its use in enzymatic biosynthesis for large-scale production of L-DOPA from tyrosine. Thus, there is an unmet need for a more efficient and less expensive method for preparing L-DOPA.

Betalain biosynthesis has remained poorly understood in comparison to the other major classes of plant pigments, namely anthocyanins and carotenoids, especially in regard to the enzyme that catalyzes the conversion of tyrosine to L-DOPA in the betalain synthetic pathway in Caryophyllales.

SUMMARY OF THE INVENTION

In one embodiment, the present invention provides a recombinant polynucleotide comprising a nucleic acid encoding a CYP76AD6 gene, a nucleic acid encoding CYP76AD15 gene, or a nucleic acid encoding a combination thereof under the control of a promoter. In one embodiment, the polynucleotide further comprises a nucleic acid encoding a DOPA 4,5-dioxygenase (DOD) enzyme.

In another embodiment, the present invention provides a recombinant polynucleotide comprising a nucleic acid encoding CYP76AD1, a nucleic acid encoding a DOPA 4,5-dioxygenase (DOD) enzyme, and a nucleic acid encoding betalain related glucosyltransferase, wherein said nucleic acids are inserted into the polynucleotide in frame. In one embodiment, the polynucleotide further comprises a nucleic acid encoding CYP76AD6.

In another embodiment, the present invention provides a composition comprising a recombinant polynucleotide as described hereinabove.

In another embodiment, the present invention provides an expression vector comprising a recombinant polynucleotide as described hereinabove.

In another embodiment, the present invention provides a cell comprising the expression vector as described hereinabove.

In another embodiment, the present invention provides a chimeric polypeptide encoded by a recombinant polynucleotide as described hereinabove.

In another embodiment, the present invention provides a method of producing L-DOPA in a cell comprising the step of contacting said cell with a recombinant polynucleotide comprising a nucleic acid encoding a CYP76AD6 gene, a nucleic acid encoding CYP76AD15 gene, or a nucleic acid encoding a combination thereof under the control of a promoter, under conditions sufficient to produce L-DOPA, thereby producing L-DOPA.

In another embodiment, the present invention provides a method of producing L-DOPA from tyrosine comprising the step of combining CYP76AD6, CYP76AD15, or a combination thereof, and tyrosine under conditions sufficient to produce L-DOPA, thereby producing L-DOPA.

In another embodiment, the present invention provides a use of a CYP76AD1-β clade gene or one or more cells from an organism comprising high levels of said CYP76AD1-β clade gene in the preparation of a composition for treating or suppressing a dopamine-responsive disorder in a subject.

In another embodiment, the present invention provides a method of betalain production comprising the step of contacting a recombinant polynucleotide comprising a nucleic acid encoding a CYP76AD6 gene, a nucleic acid encoding CYP76AD15 gene, or a nucleic acid encoding a combination thereof under the control of a promoter; a nucleic acid encoding a DOPA 4,5-dioxygenase (DOD) enzyme; and a nucleic acid encoding CYP76AD1, wherein said nucleic acids are inserted into the polynucleotide in frame, with one or more cells, under conditions sufficient to produce betalains, thereby producing betalains.

In another embodiment, the present invention provides a method of producing betaxanthins comprising the step of contacting a recombinant polynucleotide comprising a nucleic acid encoding a CYP76AD6 gene, a nucleic acid encoding CYP76AD15 gene, or a nucleic acid encoding a combination thereof under the control of a promoter; and a nucleic acid encoding a DOPA 4,5-dioxygenase (DOD) enzyme, wherein said nucleic acids are inserted into the polynucleotide in frame, with one or more cells, under conditions sufficient to produce betaxanthins, thereby producing betaxanthins.

In another embodiment, the present invention provides a method of increasing the resistance of a plant or plant part to one or more biotic or abiotic stress factors comprising the step of contacting one or more cells of said plant or plant part with a nucleic acid encoding CYP76AD6, a nucleic acid encoding CYP76AD15, a nucleic acid encoding CYP76AD1, or a combination thereof; a nucleic acid encoding a DOPA 4,5-dioxygenase (DOD) enzyme; and, optionally a nucleic acid encoding a betalain related glucosyltransferase, under conditions sufficient to produce betalains, thereby producing betalains and increasing the resistance of said plant or plant part to said one or more stress factors.

In another embodiment, the present invention provides a method of increasing the resistance of a plant or plant part to one or more fungal diseases comprising the step of contacting one or more cells of a plant or plant part with a nucleic acid encoding CYP76AD6, a nucleic acid encoding CYP76AD15, a nucleic acid encoding CYP76AD1, or a combination thereof, a nucleic acid encoding a DOPA 4,5-dioxygenase (DOD) enzyme; and, optionally a nucleic acid encoding a betalain related glucosyltransferase, under conditions sufficient to produce betalains, thereby producing betalains and increasing the resistance of said plant or plant part to said one or more fungal diseases.

In another embodiment, the present invention provides a method of increasing the levels of one or more betalains in an organism or in a part of an organism comprising causing or allowing within at least one part of the organism the expression of a DOPA 4,5-dioxygenase (DOD) enzyme and CYP76AD6, CYP76AD1, or a combination thereof, wherein if said organism expresses CYP76AD1 and DOD and not CYP76AD6 or CYP76AD15, said organism also expresses a betalain related glucosyltransferase, thereby increasing the levels of one or more betalains in said organism or in said part of an organism.

In another embodiment, the present invention provides an organism or part thereof comprising a recombinant nucleic acid sequence encoding a CYP76AD1-α clade gene, a nucleic acid sequence encoding a CYP76AD1-β clade gene, or a nucleic acid sequence encoding a combination thereof, and a nucleic acid sequence encoding a DOPA 4,5-dioxygenase (DOD) enzyme.

In another embodiment, the present invention provides a method of betalain production from tyrosine comprising the step of contacting a composition comprising CYP76AD1, a DOPA 4,5-dioxygenase (DOD) enzyme with tyrosine, and CYP76AD6, CYP76AD15, or a combination thereof, under conditions sufficient to produce betalains, thereby producing betalains.

In another embodiment, the present invention provides a method of producing betaxanthins from tyrosine comprising the step of contacting a composition comprising CYP76AD6, CYP76AD15, or a combination thereof, and a DOPA 4,5-dioxygenase (DOD) enzyme with tyrosine, under conditions sufficient to produce betaxanthins, thereby producing betaxanthins.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 2A-2G. Identification of MjCYP76 (SEQ ID NO: 1) as a betalain-related candidate gene. Gene expression in Mirabilis jalapa was analyzed in a transcriptome dataset derived from 24 tissues, including four floral organ types in five developmental stages, red or green stem epidermis, and red or green leaves. FIG. 2A: Petals. FIG. 2B: Stamen filaments. FIG. 2C: Stem epidermis from node or internode. FIG. 2D: Stigmas. FIG. 2E: Anthers. FIG. 2F: Red-young or mature-green leaf FIG. 2G: Betalain-related genes cyclo-dopa-5-O-glucosyltransferase (cDOPA5GT; SEQ ID NO: 2), DOPA 4,5-dioxygenase (MjDOD; SEQ ID NO: 3) and the cytochrome P450 CYP76AD3 (Genbank Accession No. HQ656026.1; SEQ ID NO: 4) exhibit expression patterns which parallel pigment accumulation. The cytochrome P450 gene MjCYP76 (SEQ ID NO: 1) is highly co-expressed with cDOPA5GT (Pearson correlation r value=0.90) and to a lesser extent with MjDOD (r value=0.67).

In FIG. 5A, whole-plant images, 3.5 weeks post infiltration are presented; in FIG. 5B, single-leaf images, bright field and in FIG. 5C, single-leaf images, blue light are shown.

FIG. 7A: Co-infiltration of agrobacteria harboring plasmids for expression of CYP76AD1 with cDOPA5GT (pAD1-GT) and BvDODA1 (pDODA) in Nicotiana benthamiana leaves causes red pigmentation. FIG. 7B: LC-MS analysis of red-pigmented tissue shows occurrence of betanin and iso-betanin. FIG. 7C: Co-infiltration of the CYP76AD6 expression vector (pAD6) and pDODA in N. benthamiana leaves causes yellow pigmentation. FIG. 7D: Infiltration of pAD1-GT in N. benthamiana leaves enables production of L-DOPA. L-DOPA was not detected in control experiment, where YFP is expressed (pYFP). FIG. 7E: Analysis of yellow-pigmented tissue allows the identification of several betaxanthin compounds, including indicaxanthin. FIG. 7F: Infiltration of pAD6 in N. benthamiana leaves enables production of L-DOPA. L-DOPA was not detected in control experiment (pDODA+pYFP). XIC, extracted ion chromatogram.

FIG. 8A: Recombinant expression of CYP76AD1, CYP76AD6 and BvDODA1 in yeast cells. The image presented is of media in which yeast were grown following overnight galactose induction. Each yeast clone was transformed with three vectors, for expression of CYP76AD1, CYP76AD6, BvDODA1 and beta-glucoronidase (GUS) in different combinations, and grown in standard SD media without L-DOPA supplementation. Combined expression of BvDODA1 and CYP76AD1 resulted in red-violet pigmentation of the culture media, whereas expression of BvDODA1 together with CYP76AD6 led to formation of yellow pigmentation, indicative of the distinction in catalytic activity between CYP76AD1 and CYP76AD6. Expression of BvDODA1 with both cytochrome P450S resulted in orange-red pigmentation of the media. No pigmentation was observed when each of the cytochrome P450s or BvDODA1 was expressed alone.

FIG. 8B: Multiple sequence alignment of CYP76AD1-like protein sequences from betalain-producing Caryophyllales plants was processed into a maximum-likelihood phylogenetic tree, resulting in the formation of two separate clades, previously named alpha and beta clades (Brockington et al., 2015). CYP76AD6 falls in the β clade, while CYP76AD1 is positioned in the α clade. In the CYP76AD1-β clade: B. vulgaris, Beta vulgaris (CYP76AD6; GenBank accession KT962274; SEQ ID NO: 30); Bv. maritima, Beta vulgaris ssp. maritima (accession AKI33834.1; SEQ ID NO: 10); F. latifolia, Froelichia latifolia (accession AKI33838.1; SEQ ID NO: 11); A. caracasana, Alternanthera caracasana (accession AKI33835.1; SEQ ID NO: 12); A. ficoidea, Alternanthera ficoidea (accession AKI33831.1; SEQ ID NO: 13). In the CYP76AD1-α clade: B. vulgaris, Beta vulgaris (CYP76AD1; accession AET43289.1; SEQ ID NO: 14); A. cruentus, Amaranthus cruentus (CYP76AD2; accession AET43291.1; SEQ ID NO: 15); M. jalapa, Mirabilis jalapa (CYP76AD3; accession AET43292.1; SEQ ID NO: 16); C. cristata, Celosia cristata (CYP76AD4; accession AGI78466.1; SEQ ID NO: 17).

FIG. 8C: Liquid chromatography-mass spectrometry (LC-MS) analysis of pigmented yeast media revealed the occurrence of the betalamic acid chromophore when either CYP76AD1, CYP76AD6 or both were expressed with BvDODA1, in addition to several betaxanthins, including glutamine-betaxanthin and valinebetaxanthin (Table 2; not shown in chromatogram). Occurrence of the betacyanins betanidin and iso-betanidin was observed only where CYP76AD1 was expressed. No peaks corresponding to betalain compounds were found where BvDODA1 was not expressed. The y-axes (peak intensity) of all six chromatograms are linked. XIC, extracted ion chromatograms of masses corresponding to betalamic acid [M+H=212.05] and betanidin isomers [M+H=389.10]. Time, retention time (min).

FIGS. 11A-11B. Production of betalains in multiple naturally-non-producing plant species.

FIG. 11A: Agrobacteria-mediated transformation of the pX11 vector, overexpressing cytochrome P450 CYP76AD1, DOPA 4,5-dioxygenase (BvDODA1) and cyclo-dopa 5-O-glucosyltransferase (cDOPA5GT), causes development of red-violet calli or shoots in a variety of Solanaceous plant species, typically observed within 1-2wk of cultivation in tissue culture: Solanum lycopersicum (tomato), Solanum tuberosum (potato), Solanum melongena (eggplant), Nicotiana tabacum (tobacco), Nicotiana glauca (tree tobacco), Solanum nigrum (European black nightshade), Petunia x hybrida (Petunia), Nicotiana benthamiana.

FIGS. 11B1-11B2: Nicotiana glauca (FIG. 11B1) and Nicotiana benthamiana (FIG. 11B2) calli were sampled and analyzed with liquid chromatography-mass spectrometry (LC-MS), allowing the identification of the betacyanins betanin and isobetaninin in both species, in addition to a novel unidentified betacyanin compound, found only in the N. glauca tissue (betacyanin III; Table 2). XIC, extracted ion chromatograms of masses corresponding to the novel betacyanin [M+H=593.10] and betanin isomers [M+H=551.10]. Time, retention time (min).

FIGS. 12A-12C. Betacyanin identification and quantification in engineered and naturally-producing species.

FIG. 12A1-12A2: LC-MS analysis of Nicotiana benthamiana leaves agroinfiltrated with the pX11 vector enabled the identification of betanin, which exhibits the same accurate mass, retention time, fragmentation patterns and UV-VIS absorption spectra as betanin from red beet (Beta vulgaris) leaf extract.

FIG. 12B: Agroinfiltration of agrobacteria harbouring the pX11 vector into N. benthamiana leaves leads to intense red pigmentation in infiltrated area, typically observed within 2-3 days.

FIG. 12C: Betacyanin content of pX11-agroinfiltrated N. benthamiana and pX11-transformed Nicotiana tabacum was assessed in comparison to several betalain-producing species. Betacyanin content was assessed spectrophotometrically by light absorption measurements at 535 nm and 600 nm. Values indicate the mean±SE of the mean of four biological replicates, each consisting of 100 mg tissue (fresh weight).

FIG. 13A: Left, wild-type tobacco; right, pX11-transformed tobacco. FIG. 13B: Top row, wild-type tobacco flower; bottom row, pX11 flower. Pigment accumulation was also evident in pX11 roots (FIG. 13C), stem epidermis section, x20 magnified (FIG. 13D) and leaf glandular trichomes, x20 magnified (FIG. 13E).

FIG. 14A: Transformation of the pX11 vector results in formation of red-pigmented plants in potato (Solanum tuberosum var. Désirée-top left panels), eggplant (Solanum melongena line DR2—bottom left panels) and tomato (Solanum lycopersicum var. MicroTom—right panels).

FIG. 14B: Betanin and isobetanin were identified as the major betacyanins in potato tuber, tomato fruit and eggplant fruit by LC-MS analysis. Extracted ion chromatogram (XIC) of betanin/isobetanin-corresponding mass [M+H=551.1] and UV-VIS absorption of betanin peak is shown for all three tissues.

FIGS. 16A-16B. Fruit-specific accumulation of betalains in tomato.

FIG. 16A: Introduction of the pX11(E8) vector into tomato (*Solanum lycopersicum* var. M-82) results in betalain pigmentation that is restricted to ripening and ripe fruit.

FIG. 16B: Whole fruit and cross-section of wildtype and pX11(E8) tomato fruit.

FIG. 17A: Introduction of pX11, pX12 or pX13 vectors into tobacco results in formation of different colored flowers. Viewed from top (top row) or magnified and viewed under bright-field (middle row) or blue light (bottom row), in which betaxanthins are typically fluorescent.

FIG. 17B: LC-MS analysis of pX11, pX12 and pX13 tobacco petals. Extracted ion chromatograms (XIC) of masses [M+H=309.1, 331.1, 340.1, 551.1], respectively corresponding to proline-betaxanthin, tyramine-betaxanthin, glutamine-betaxanthin, and betanin/isobetanin. Vertical axes are linked.

FIG. 18A: Introduction of pX11 or pX13 into cells of tobacco BY2 line results in red-violet or yellow-orange pigmentation, respectively.

FIG. 18B: LC-MS analysis of pX11 and pX13 BY2 cells. Extracted ion chromatograms (XIC) of masses [M+H=283.1, 340.1, 551.1], respectively corresponding to alanine-betaxanthin, glutamine-betaxanthin, and betanin/isobetanin. Vertical axes are linked.

FIG. 20A: Identification of L-DOPA in leaf extracts of pDOPA1 and pDOPA3-expressing tobacco plants by LC-MS analysis. FIG. 20B: pDOPA2 and pDOPA4 expression in BY2 cells causes blackening of calli in varying degrees, after several weeks of cultivation. FIG. 20C: L-DOPA relative quantification in pDOPA2, pDOPA4 and wildtype BY2 cells by LC-MS analysis.

FIG. 21A: Wildtype and pX11 tobacco seedlings grown under high salinity stress conditions (150 mM NaCl) and control conditions (MS) were photographed and scored for seed germination rates. FIG. 21B: Wildtype and pX11 tobacco seedlings grown under osmotic stress conditions (400 mM mannitol) and control conditions (MS) were photographed and scored for seed germination rates.

FIG. 22A: Leaves of wildtype and pX11 tobacco plants were infected with droplets of *B. cinerea* suspension and photographed 5 days post infection. FIG. 22B: Wildtype and pX11 plants infected with a total of approximately 500 *B. cinerea* spores per plant were scored for lesion size. Average lesion areas are shown of approximately 30 plants per genotype. FIG. 22C: Infected leaves of wildtype tobacco plants showed increased signs of necrosis versus leaves of pX11 plants.

FIG. 23A: Co-infiltration of agrobacteria harboring plasmids for expression of CYP76AD15 and BvDODAlin *Nicotiana benthamiana* leaves causes yellow pigmentation in infiltrated area. FIG. 23B: LC-MS analysis of yellow-pigmented tissue shows occurrence of several betaxanthins, including dopamine-betaxanthin [M+H=347.1] and valine-betaxanthin [M+H=311.1]. XIC, extracted ion chromatogram. FIG. 23C: UV-VIS absorption of peaks representing dopamine-betaxanthin and valine-betaxanthin in analyzed tissue. FIG. 23D: Mass-spectra of L-DOPA peak identified in leaf tissue of *N. benthamiana* expressing CYP76AD15 shows typical L-DOPA fragments [M+H=181.05, 152.07] and molecular ion [M+H=198.07].

DETAILED DESCRIPTION OF THE PRESENT INVENTION

Figure 1:
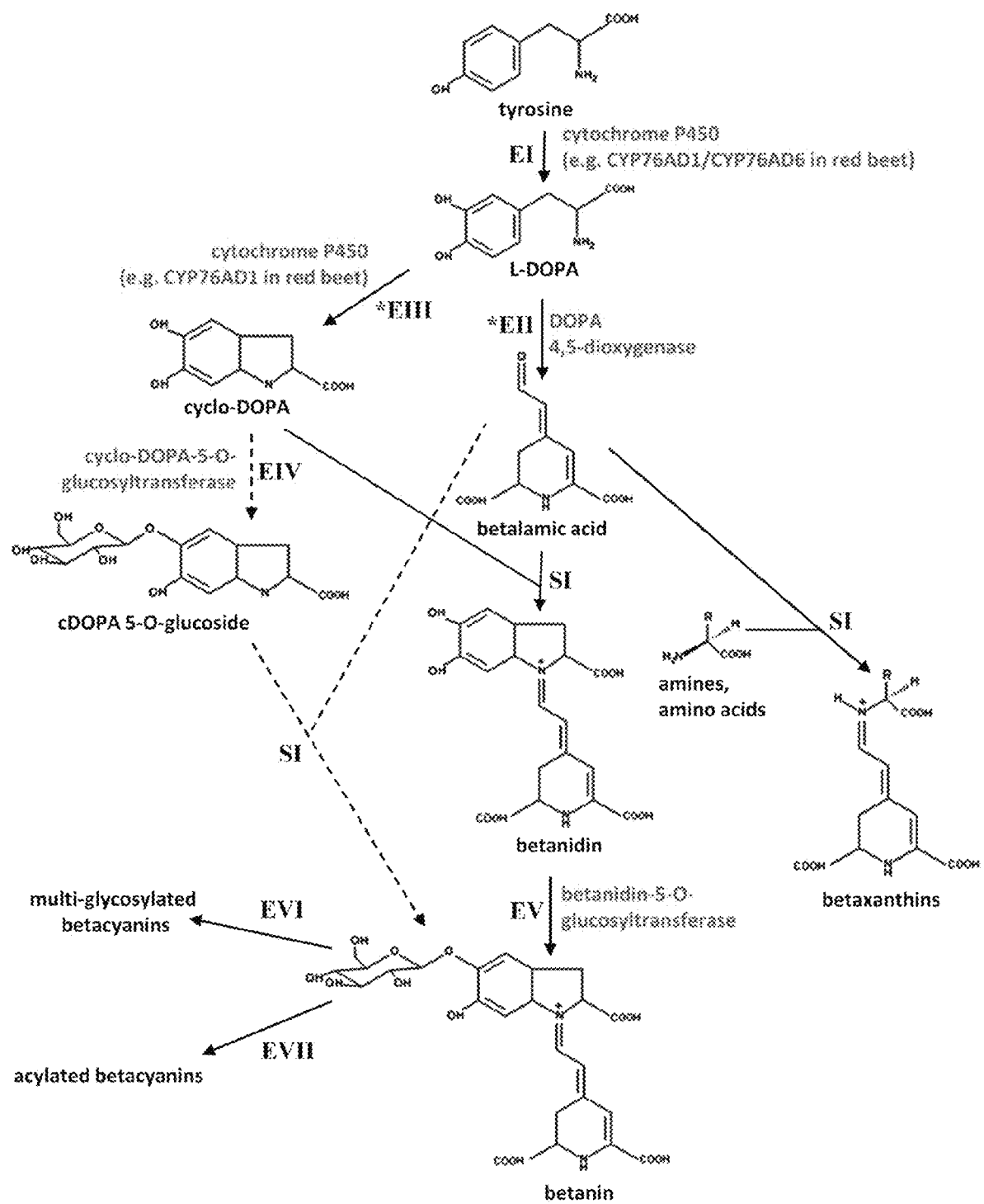
FIG. 1. The betalain biosynthetic pathway. Genes taking part in the pathway are shown in magenta. Enzymatic reactions: EI, hydroxylation of tyrosine; EII, DOPA-4,5 dioxygenase; EIII, oxidation of DOPA; EIV, glucosylation of cyclo-DOPA; EV, glucosylation of betanidin; EVI, additional glucosylation of betacyanins; EVII, acylation of betacyanins. Predicted spontaneous reactions: SI, condensation (aldimine formation). Enzymatic reactions EII and EIII are followed by a spontaneous cyclization reaction and are therefore marked with an asterisk. EV can alternatively be catalyzed by a betanidin-6-O-glucosyltransferase, leading to formation of gomphrenin instead of betanin. Dashed lines designate reactions of an alternative pathway, which was shown to occur in Mirabilis jalapa, in which cyclo-DOPA is first glycosylated and then condensates with betalamic acid to form betanin.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, the present invention provides compositions comprising an enzyme that catalyzes the first step in betalain synthesis in Caryophyllales and uses of the enzyme in genetic engineering of plants and for the production of L-DOPA from tyrosine. In general, tyrosinases are substrate promiscuous oxygenases that exhibit unwanted catechol oxidase activity. A prior study demonstrated that the plant cytochrome P450 CYP76AD1 exhibited this characteristic promiscuity and despite a screening strategy to identify mutations that increased the enzyme's substrate specificity and activity, still produced undesired side products (DeLoache et al., 2015; Nat Chem Biol. 2015 July; 11(7):465-71, incorporated herein by reference in its entirety). It was therefore not expected that a different plant cytochrome P450 would be specific to tyrosine and would catalyze only the reaction to L-DOPA, thereby avoiding the accumulation of undesired end products.

CYP76AD6

The present invention provides a novel gene (belonging to the Cytochrome P450 gene family) which catalyzes tyrosine hydroxylation, to form L-DOPA. This enzyme potentially holds a significant advantage over the tyrosinase enzyme which is being used today for production of L-DOPA; while tyrosinase catalyzes the formation of L-DOPA from tyrosine, and immediately oxidizes it to the unusable metobolite dopaquinone, the novel P450 enzyme only catalyzes the formation of L-DOPA without its oxidation. This P450 enzyme can therefore be used for a more efficient method for L-DOPA production than the use of a tyrosinase enzyme.

Thus, in one embodiment, the present invention provides a novel enzyme which can be used for the biosynthetic production of L-DOPA, a pharmaceutical used for treatment of Parkinson's disease, and a precursor for the economically important drugs benzylisoquinoline alkaloids (e.g. morphine). This enzyme can potentially be used for the commercial production of L-DOPA in several ways; its encoding gene can be expressed in plants or microorganisms to induce production of L-DOPA in vivo, or alternatively it can be recombinantly expressed and used for in vitro enzymatic catalysis.

Methods for L-DOPA and Betalain Production
Production from Proteins

In one embodiment, the methods of the present invention are performed in vitro, such that the tyrosine and enzymes required to produce L-DOPA or betalains are provided in vitro.

In one embodiment, the present invention provides a method of producing L-DOPA from tyrosine comprising the step of combining a CYP76AD1-β clade protein and tyrosine under conditions sufficient to produce L-DOPA, thereby producing L-DOPA.

In one embodiment, the present invention provides a method of producing L-DOPA from tyrosine comprising the step of combining CYP76AD6, CYP76AD15, or a combination thereof, and tyrosine under conditions sufficient to produce L-DOPA, thereby producing L-DOPA.

In another embodiment, the present invention provides a method of producing L-DOPA from tyrosine in vitro comprising the step of combining CYP76AD6, CYP76AD15, or a combination thereof, and tyrosine under conditions sufficient to produce L-DOPA, thereby producing L-DOPA.

In another embodiment, the present invention provides a method of betalain production from tyrosine comprising the step of contacting tyrosine with CYP76AD6, CYP76AD1, or a combination thereof, under conditions sufficient to produce betalains, thereby producing betalains. In one embodiment, the method further comprises the step of contacting the tyrosine and CYP76AD6, CYP76AD15, or a combination thereof, CYP76AD1, or a combination thereof with a DOPA 4,5-dioxygenase (DOD) enzyme.

In another embodiment, the present invention provides a method of betalain production from tyrosine comprising the step of contacting tyrosine with a CYP76AD1-β clade protein and a DOPA 4,5-dioxygenase (DOD) enzyme and, optionally, CYP76AD1, under conditions sufficient to produce betalains, thereby producing betalains.

In another embodiment, the present invention provides a method of betalain production from tyrosine comprising the step of contacting tyrosine with CYP76AD6, CYP76AD15, or a combination thereof, and a DOPA 4,5-dioxygenase (DOD) enzyme and, optionally, CYP76AD1, under conditions sufficient to produce betalains, thereby producing betalains.

In another embodiment, the present invention provides a method of producing a mixture of betalains comprising the step of contacting tyrosine with CYP76AD6, CYP76AD15, or a combination thereof, CYP76AD1, a DOPA 4,5-dioxygenase (DOD) enzyme and a betalain related glucosyltransferase, under conditions sufficient to produce a combination of betacyanin and betaxanthin, thereby producing a mixture of betalains.

In one embodiment, the betalain production described in the present invention is performed without provision of L-DOPA, which had never before been accomplished. In one embodiment, betalains comprise betacyanin and betaxanthin. In one embodiment, betalains, betacyanin, and betaxanthin may be used as food coloring or other dyes.

In one embodiment, betacyanins produce a red-violet color. In one embodiment, betaxanthins produce a yellow color. In one embodiment, a combination of betacyanin and betaxanthin produce an orange color. In one embodiment, a combination of betacyanin and betaxanthin produce an orange-pink color.

In another embodiment, the present invention provides a method of producing an orange dye comprising the step of contacting tyrosine with CYP76AD6, CYP76AD15, or a combination thereof, CYP76AD1, a DOPA 4,5-dioxygenase (DOD) enzyme and a betalain related glucosyltransferase, under conditions sufficient to produce a combination of betacyanin and betaxanthin, thereby producing an orange dye.

In another embodiment, the present invention provides a method of producing betaxanthins from tyrosine comprising the step of contacting tyrosine with CYP76AD6, CYP76AD15, or a combination thereof, and a DOPA 4,5-dioxygenase (DOD) enzyme, under conditions sufficient to produce betaxanthins, thereby producing betaxanthins.

In another embodiment, the present invention provides a method of producing a yellow dye comprising the step of contacting tyrosine with CYP76AD6, CYP76AD15, or a combination thereof and a DOPA 4,5-dioxygenase (DOD) enzyme under conditions sufficient to produce betaxanthins, thereby producing a yellow dye. In one embodiment, said yellow dye is a food coloring.

In one embodiment, the methods of the present invention produce one or more betaxanthins. In one embodiment, the betaxanthin comprises Vulgaxanthin I (glutamine-betaxanthin). In another embodiment, the betaxanthin comprises Indicaxanthin (proline-betaxanthin). In another embodiment, the betaxanthin comprises Dopaxanthin-hexoside. In another embodiment, the betaxanthin comprises Betaxanthin I (unknown), as described in Table 2 herein below. In another embodiment, the betaxanthin comprises histamine-betaxanthin. In another embodiment, the betaxanthin comprises alanine-betaxanthin. In another embodiment, the betaxanthin comprises dopamine-betaxanthin. In another embodiment, the betaxanthin comprises valine-betaxanthin.

In another embodiment, the present invention provides a method of producing betacyanins from tyrosine comprising the step of contacting tyrosine with CYP76AD1, a DOPA 4,5-dioxygenase (DOD) enzyme, and a betalain related glucosyltransferase under conditions sufficient to produce betacyanins, thereby producing betacyanins.

In another embodiment, the present invention provides a method of producing red-violet dye comprising the step of contacting tyrosine with CYP76AD1, a DOPA 4,5-dioxygenase (DOD) enzyme, and a betalain related glucosyltransferase under conditions sufficient to produce betacyanins, thereby producing a red-violet dye. In one embodiment, said red-violet dye is a food coloring.

In one embodiment, the method as described herein provides a glycosylated betalain (betanin) rather than an aglycone (betanidin). In one embodiment, there is a substantial advantage in that betanin is more stable than betanidin. Betanidin is a highly labile compound and ascorbic acid must be added to prevent its degradation. Betanidin is much more susceptible to both enzymatic and non-enzymatic oxidative degradation. The betalain extract used for food coloration comprises betanin. Betanidin would not be usable for food coloration, because of its instability.

In another embodiment, the methods of the present invention produce one or more betacyanins. In one embodiment, the betacyanins comprise betanin. In another embodiment, the betacyanins comprise iso-betanin. In another embodiment, the betacyanins comprise betacyanin I (unknown) or betacyanin II (unknown), as described in Table 2 herein below. In another embodiment, the methods of the present invention produce one or more betacyanin fragments, where, in one embodiment, the betacyanin fragment is betanidin.

In another embodiment, the present invention provides a method of producing a pigment or dye comprising the step of contacting tyrosine with CYP76AD6, CYP76AD15, or a combination thereof, and a DOPA 4,5-dioxygenase (DOD) enzyme and, optionally, CYP76AD1, under conditions sufficient to produce betalains, thereby producing betalains, thereby producing a pigment or dye.

In another embodiment, the present invention provides a method of increasing the levels of one or more betalains in an organism, plant or in a plant part comprising causing or allowing the expression of a DOPA 4,5-dioxygenase (DOD) enzyme, a betalain related glucosyltransferase, and CYP76AD6, CYP76AD15, or a combination thereof, CYP76AD1, or a combination thereof, within said organism, plant or plant part, thereby increasing the levels of one or more betalains in said organism, plant or plant part. In one embodiment, said plant is an ornamental plant. In another embodiment, said plant is a food crop. In one embodiment, the organism or plant does not naturally produce detectable levels of betalains.

Production from Nucleic Acids

In another embodiment, the methods of the present invention are performed in vivo. In one embodiment, the tyrosine is endogenous to the cell. In another embodiment, the tyrosine is provided to the cell. In another embodiment, the cell is transformed with a gene that enhances tyrosine availability. In one embodiment, the gene is AroG175 (Tzin et al., 2012 New Phytologist 194: 430-439; Genbank Accession No. JC233128.1, SEQ ID NO: 28), aromatic amino acid hydroxylase (AAH) (Pribat et al., 2010 Plant Cell 22: 3410-3422; Genbank Accession No. HQ003815.1, SEQ ID NO. 29), or a combination thereof. In one embodiment, the enzymes required to produce betalains are provided to a cell via transfer of a polynucleotide encoding the enzymes.

In one embodiment, the present invention provides a method of L-DOPA production comprising the step of contacting an organism with a nucleic acid encoding a CYP76AD1-β clade gene under conditions sufficient to produce L-DOPA, thereby producing L-DOPA.

In another embodiment, the present invention provides a method of L-DOPA production comprising the step of contacting an organism with a nucleic acid encoding CYP76AD6, CYP76AD15, or a combination thereof, under conditions sufficient to produce L-DOPA, thereby producing L-DOPA.

In another embodiment, the present invention provides a method of L-DOPA production comprising the step of contacting an organism with a nucleic acid encoding CYP76AD6, CYP76AD15, or a combination thereof, under conditions sufficient to produce L-DOPA, thereby producing L-DOPA.

In one embodiment, the organism is a plant. In one embodiment, the plant is a tobacco plant.

In another embodiment, the present invention provides a method of betalain production comprising the step of contacting an organism with a nucleic acid encoding a CYP76AD1-β clade gene, a nucleic acid encoding a CYP76AD1-α clade gene, or a combination thereof, under conditions sufficient to produce betalains, thereby producing betalains.

In another embodiment, the present invention provides a method of betalain production comprising the step of contacting an organism with a nucleic acid encoding CYP76AD6, CYP76AD15, or a combination thereof, a nucleic acid encoding CYP76AD1, or a combination thereof, under conditions sufficient to produce betalains, thereby producing betalains.

In one embodiment, the method further comprises the step of contacting the organism comprising tyrosine with a nucleic acid encoding a DOPA 4,5-dioxygenase (DOD) enzyme.

In one embodiment, the nucleic acid encoding genes disclosed in the present invention, including, inter alia, CYP76AD6, CYP76AD15, or a combination thereof, CYP76AD1, and DOD are present together on a single recombinant polynucleotide, as described in more detail herein below.

In another embodiment, the present invention provides a method of betalain production comprising the step of contacting an organism with a nucleic acid encoding CYP76AD6, CYP76AD15, or a combination thereof, a nucleic acid encoding CYP76AD1, a nucleic acid encoding a DOPA 4,5-dioxygenase (DOD) enzyme, and a nucleic acid encoding a betalain related glucosyltransferase under conditions sufficient to produce betalains, thereby producing betalains.

In another embodiment, the present invention provides a method of producing orange dye comprising the step of contacting an organism comprising tyrosine with a nucleic acid encoding CYP76AD6, CYP76AD15, or a combination thereof, a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betalains, thereby producing orange dye.

In another embodiment, the betalain production described in the present invention is performed without substrate feeding.

In another embodiment, the present invention provides a method of producing betaxanthins comprising the step of contacting an organism comprising tyrosine with a nucleic acid encoding CYP76AD6, CYP76AD15, or a combination thereof, a nucleic acid encoding a DOPA 4,5-dioxygenase (DOD) enzyme, and a nucleic acid encoding a betalain related glucosyltransferase under conditions sufficient to produce betaxanthins, thereby producing betaxanthins.

In another embodiment, the present invention provides a method of producing yellow dye comprising the step of contacting an organism comprising tyrosine with a nucleic acid encoding CYP76AD6, CYP76AD15, or a combination thereof, a nucleic acid encoding a DOPA 4,5-dioxygenase (DOD) enzyme under conditions sufficient to produce betaxanthins, thereby producing yellow dye.

In another embodiment, the present invention provides a method of producing betacyanins comprising the step of contacting an organism comprising tyrosine with a nucleic acid encoding CYP76AD1, a nucleic acid encoding a DOPA 4,5-dioxygenase (DOD) enzyme, and a nucleic acid encoding a betalain related glucosyltransferase under conditions sufficient to produce betacyanins, thereby producing betacyanins. In one embodiment, the method of producing betacyanins is a method of producing predominantly betacyanins.

In another embodiment, the present invention provides a method of producing red-violet dye comprising the step of contacting an organism comprising tyrosine with a nucleic acid encoding CYP76AD1, a nucleic acid encoding a DOPA 4,5-dioxygenase (DOD) enzyme, and a nucleic acid encoding a betalain related glucosyltransferase under conditions sufficient to produce betacyanins, thereby producing red-violet dye.

In one embodiment, the methods described hereinabove provide methods of producing a natural red-violet dye. In another embodiment, the methods described hereinabove provide methods of producing a natural yellow dye. In another embodiment, the methods described hereinabove provide methods of producing a natural orange dye. In one embodiment, the dyes may be used for textiles.

In one embodiment, the organism is a plant. In another embodiment, the organism is yeast. In another embodiment, the organism is a bacterium. In another embodiment, the organism is an alga.

In one embodiment, the methods of the present invention are conducted in planta. In one embodiment, the color of the pigment in the plant is dependent upon other natural or engineered pigments expressed in the plant. Thus, in one embodiment, the method of the present invention produce a red pigment, a yellow pigment, an orange pigment, a brown pigment, and the like, or any of the pigment colors that are known in the art.

It is also to be understood that by varying the ratio of CYP76AD6, CYP76AD15, or a combination thereof, and/or CYP76AD1 expression, it is possible to change the pigment color as well.

In another embodiment, the present invention provides a method of betalain production from tyrosine comprising the step of contacting tyrosine with a nucleic acid encoding CYP76AD6, CYP76AD15, or a combination thereof, a nucleic acid encoding a DOPA 4,5-dioxygenase (DOD) enzyme, and, optionally, a nucleic acid encoding CYP76AD1, under conditions sufficient to produce betalains, thereby producing betalains.

In another embodiment, the present invention provides a method of producing orange dye comprising the step of contacting tyrosine with a nucleic acid encoding CYP76AD1, a nucleic acid encoding CYP76AD6, CYP76AD15, or a combination thereof, and a nucleic acid encoding a DOPA 4,5-dioxygenase (DOD) enzyme, under conditions sufficient to produce betalains, thereby producing orange dye.

In another embodiment, the present invention provides a method of producing betaxanthins from tyrosine comprising the step of contacting tyrosine with a nucleic acid encoding CYP76AD6, CYP76AD15, or a combination thereof, and a nucleic acid encoding a DOPA 4,5-dioxygenase (DOD) enzyme, under conditions sufficient to produce betaxanthins, thereby producing betaxanthins.

In another embodiment, the present invention provides a method of producing yellow dye comprising the step of contacting tyrosine with a nucleic acid encoding CYP76AD6, CYP76AD15, or a combination thereof, and a nucleic acid encoding a DOPA 4,5-dioxygenase (DOD) enzyme under conditions sufficient to produce betaxanthins, thereby producing yellow dye.

In another embodiment, the present invention provides a method of producing betacyanins from tyrosine comprising the step of contacting tyrosine with a nucleic acid encoding CYP76AD1 and a nucleic acid encoding a DOPA 4,5-dioxygenase (DOD) enzyme, under conditions sufficient to produce betacyanins, thereby producing betacyanins.

In another embodiment, the present invention provides a method of producing red-violet dye comprising the step of contacting tyrosine with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betacyanins, thereby producing red-violet dye.

In one embodiment, a dye of the present invention is food coloring. In one embodiment, methods of the present invention for producing dyes may be applied to producing pigments, and the like.

In one embodiment, the present invention provides a food coloring, dye, or pigment produced by the methods of the present invention or comprising the compositions of the present invention.

In another embodiment, the present invention provides a method of producing L-DOPA in a cell comprising the step of contacting said cell with a polynucleotide comprising a nucleic acid encoding CYP76AD6, CYP76AD15, or a combination thereof, under conditions sufficient to produce L-DOPA, thereby producing L-DOPA.

In another embodiment, the present invention provides a method of producing betalains, orange dye, or a combination thereof in a cell comprising the step of contacting said cell with a nucleic acid encoding CYP76AD6, CYP76AD15, or a combination thereof, a nucleic acid encoding CYP76AD1, or a combination thereof, under conditions sufficient to produce betalains, thereby producing betalains, orange dye, or a combination thereof.

In another embodiment, the present invention provides a method of producing betaxanthins, yellow dye, or a combination thereof in a cell comprising the step of contacting said cell with a nucleic acid encoding CYP76AD6, CYP76AD15, or a combination thereof, and a nucleic acid encoding a DOPA 4,5-dioxygenase (DOD) enzyme, under conditions sufficient to produce betaxanthins, thereby producing betaxanthins, yellow dye, or a combination thereof.

In another embodiment, the present invention provides a method of producing betacyanins, red-violet dye, or a combination thereof in a cell comprising the step of contacting said cell with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betacyanins, thereby producing betacyanins, red-violet dye, or a combination thereof.

In one embodiment, the cell described hereinabove is part of a cell line.

In one embodiment, betalains obtained by the methods of the present invention, including betaxanthins, betacyanins, or a combination thereof, are produced in a cell line. In one embodiment, the cell line is a plant cell line. In one embodiment, the plant cell line is tobacco BY2 or *arabidopsis* T87.

In another embodiment, L-DOPA obtained by the methods of the present invention is produced in a cell line. In one embodiment, the cell line is a tobacco cell line. In one embodiment, the tobacco cell line is BY2.

In another embodiment, the present invention provides a method of producing a metabolite of L-DOPA comprising the step of producing L-DOPA by contacting a cell with a nucleic acid encoding CYP76AD6, CYP76AD15, or a combination thereof, under conditions sufficient to produce L-DOPA, and either allowing formation of the L-DOPA metabolite or further contacting said cell with a nucleic acid encoding an enzyme that metabolizes L-DOPA, thereby producing a metabolite of L-DOPA. In one embodiment, the L-DOPA metabolite is a catecholeamine, benzilisoquinoline alkaloid, betalain, melanin, or a combination thereof. In one embodiment, the catecholeamine is dopamine, norepinephrine, or a combination thereof. In one embodiment, the benzilisoquinoline alkaloid is an opiate, which in one embodiment is morphine.

In one embodiment, the enzyme that metabolizes L-DOPA is a DOPA 4,5-dioxygenase (DOD). In another embodiment, the enzyme is CYP76AD1. In another embodiment, the enzyme is a glucosyltransferase. In one embodiment, the glucosyltransferase is cyclo-DOPA 5-O-glucosyltransferase or betanidin-5-O-glucosyltransferase. In one embodiment, the cyclo-DOPA 5-O-glucosyltransferase is *M. jalapa* gene cyclo-DOPA 5-O-glucosyltransferase (cDOPA5GT).

In another embodiment, the enzyme that metabolizes L-DOPA is DOPA decarboxylase. In another embodiment, the enzyme that metabolizes L-DOPA is dopamine beta-hydroxylase. In another embodiment, the enzyme that metabolizes L-DOPA is aromatic L-amino acid decarboxylase. In another embodiment, the enzyme that metabolizes L-DOPA is catechol-O-methyl transferase. In another embodiment, the enzyme that metabolizes L-DOPA is phenylethanolamine N-methyltransferase.

In another embodiment, the enzyme that metabolizes L-DOPA is norcoclaurine synthetase (NCS). In another embodiment, the enzyme that metabolizes L-DOPA is norcoclaurine 6-O-methyltransferase (6OMT). In another embodiment, the enzyme that metabolizes L-DOPA is coclaurine-N-methyltransferase (CNMT). In another embodiment, the enzyme that metabolizes L-DOPA is 3'-hydroxy-N-methylcoclaurine 4'-O-methyltransferase (4'OMT).

Methods of Genetic Transformation

In one embodiment, the present invention provides methods comprising the step of "contacting" a cell with a polynucleotide or expression vector as described herein.

In one embodiment, contacting comprises transforming a cell with the nucleic acid molecule or construct of the invention. Methods for transforming a plant cell with nucleic acids sequences are well known in the art. As used herein the term "transformation" or "transforming" may refer to a process by which a foreign DNA, such as a DNA construct, including expression vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait.

In one embodiment, the present invention provides a transgenic plant. In one embodiment, a transgenic plant of the present invention is genetically modified with foreign or heterologous genes. In one embodiment, transgenic plants of the present invention are used for biofuel. In another embodiment, transgenic plants of the present invention are food crop plants.

In another embodiment, the present invention provides a cisgenic plant. In one embodiment, a cisgenic plant of the present invention is genetically modified, but contains no foreign or heterologous genes. According to this aspect and in one embodiment, betalain enzymes may be overexpressed in plants already comprising betalain enzymes, thereby changing the ratio between betacyanins and betaxanthins. In one embodiment, food crops of the present invention are cisgenic.

Any method or delivery system may be used for the delivery and/or transformation (plant cells)/transfection (algae cells) of the nucleic acid vectors encoding CYP76AD6 and homologs, paralogs, etc. in the host cell, e.g., plant protoplast. The vectors may be delivered to the host cell either alone, or in combination with other agents. Transient expression systems may also be used. Homologous recombination may also be used.

In one embodiment, polynucleotides as described herein are provided to a cell of the present invention via transformation. Transformation may be accomplished by a wide variety of means, as is known to those of ordinary skill in the art. Such methods include, but are not limited to, particle bombardment mediated transformation (e.g., Finer et al., 1999, Curr. Top. Microbiol. Immunol., 240:59), protoplast electroporation (e.g., Bates, 1999, Methods Mol. Biol., 111:359), viral infection (e.g., Porta and Lomonossoff, 1996, Mol. Biotechnol. 5:209), microinjection, and liposome injection. Other exemplary delivery systems that can be used to facilitate uptake by a cell of the nucleic acid include calcium phosphate and other chemical mediators of intracellular transport, microinjection compositions, and homologous recombination compositions (e.g., for integrating a gene into a preselected location within the chromosome of the cell). Alternative methods may involve, for example, the use of liposomes, electroporation, or chemicals that increase free (or "naked") DNA uptake, transformation using viruses or pollen and the use of microprojection. Standard molecular biology techniques are common in the art (e.g., Sambrook et al., 1989, Molecular Cloning: A Laboratory Manual, 2nd ed., Cold Spring Harbor Laboratory Press, New York).

Plant Transformation

There are various methods of introducing foreign genes into both monocotyledonous and dicotyledonous plants (See Potrykus I 1991. Annu Rev Plant Physiol Plant Mol Biol 42, 205-225; Shimamoto K. et al., 1989. Nature 338, 274-276). Transformation methods may include, for example, but are not limited to, the use of liposomes, electroporation, chemicals that increase free DNA uptake, injection of the DNA directly into the plant, particle gun bombardment, transformation using viruses and microprojection.

In one embodiment, polynucleotides as described herein are provided to a cell via agroinfiltration, in one embodiment, via *Agrobacterium*-mediated transformation (e.g., Komari et al., 1998, Curr. Opin. Plant Biol., 1:161), including floral dip transformation. In one embodiment agroinfiltration induces transient expression of genes in a plant to produce a desired protein, by injected a suspension of *Agrobacterium tumefaciens* containing the desired gene or genes into a plant leaf. In one embodiment, the transformation can be performed by an *Agrobacterium*-mediated gene transfer. The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. The transformation can be performed with any suitable tissue explant that provides a good source for initiation of whole-plant differentiation (See Horsch et al., 1988. Plant Molecular Biology Manual A5, 1-9, Kluwer Academic Publishers, Dordrecht).

Plant transformation methods are fully described in U.S. Patent Application Publications US 20110209247; US 20110113514; US 20100199371; US 20070079396; US 20080307541; US 20030028913; and US20030196219; and U.S. Pat. Nos. 5,015,580; 5,550,318; 5,538,880; 6,160,208; 6,399,861; 6,403,865; 5,635,055; 5,824,877; 5,591,616; 5,981,840 and 6,384,301, which are incorporated by reference herein in their entirety.

For the *Agrobacterium tumefaciens*-based plant transformation system, additional elements present on transformation constructs will, in one embodiment, include T-DNA left and right border sequences to facilitate incorporation of the recombinant polynucleotide into the plant genome.

In one embodiment, the transformation can be performed by a direct DNA uptake. There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

In another embodiment, polynucleotides as described herein are provided to a cell via viral transformation (transduction) using a suitable plant virus, using gene gun techniques or electroporation.

In one embodiment, the heterologous genes of the polynucleotide of the present invention are integrated into the plant chromosome. In another embodiment, the heterologous genes of the polynucleotide of the present invention remain extrachromosomal. In one embodiment, the heterologous genes are in a plasmid within the cell. Plasmids useful for either application are known to one skilled in the art.

In one embodiment, DNA is inserted randomly, i.e. at a non-specific location, in the genome of a target plant line. In another embodiment, DNA insertion is targeted in order to achieve site-specific integration, e.g. to replace an existing gene in the genome, to use an existing promoter in the plant genome, or to insert a recombinant polynucleotide at a predetermined site known to be active for gene expression. Several site specific recombination systems exist which are known to function in plants including cre-lox and FLP-FRT.

In one embodiment, transformation methods of this invention are practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making genetically modified plants of this invention, e.g. various media and recipient target cells, transformation of immature embryos and subsequent regeneration of fertile genetically modified plants are known in the art.

In another embodiment in which polynucleotides are introduced into plant cells, the betalains may be expressed or detected in any plant organ, including leaves, stems, roots, flowers, seeds, tuber, or fruit, or a combination thereof.

In another embodiment, the methods of the present invention may be performed in a whole plant, such that the whole plant expresses the betalains as described herein. In addition and in one embodiment, the compositions of the present invention may describe a whole plant that has been genetically modified to express a polynucleotide or polypeptide of the present invention.

Algae Transformation

In one embodiment, the method of transformation of algae comprises any of the methods as described hereinabove. In one embodiment, transformation of algae is accomplished using glass bead-assisted transformation, particle gun-mediated (biolistic) transformation, treatment with cellulolytic enzymes to weaken their cell walls, or homologous recombination.

In another aspect, the nucleic acids of the present invention can be transformed into algae. In one embodiment, the alga is a single cell alga. In another embodiment, the alga is a multi-cellular alga. In one embodiment, the alga is a cyanobacterium, diatom, *chlamydomonas, Dunaliella*, or hematococus. The genes can be over expressed in algae. Betalain, DOPA, or a combination thereof can be produced through such transgenic algae. Method for algae transformation are well known in the art and fully described in U.S. Patent Application Publications US 20150011008; US 20150004704; US 20130130389; US 20120094385; US 20120034698; US 20110300633; and US 20040133937, which are incorporated by reference herein in their entirety.

In one embodiment, the genetically modified algae of the present invention may be used in biofuel production.

Yeast Transformation

In another aspect, the nucleic acids of the present invention can be transformed into yeast. The genes can be over expressed in yeast. Betalain, DOPA, or a combination thereof can be produced through such transgenic yeast. Method for yeast transformation are described herein below and are well known in the art and fully described in U.S. Patent Application Publications US 20090264320; US 20010031724; US 20030049785; US 20050158861; US 20070264716; US 20090325247; and US 20100190223, which are incorporated by reference herein in their entirety.

Viral Transformation

In another embodiment, the nucleic acids of the present invention can be transformed into a virus. In another embodiment, the nucleic acids may be over-expressed in a virus. Betalain, dyes, pigments, DOPA, or a combination thereof can be produced through such viral over expression.

Markers of Genetic Transformation

In one embodiment, DNA is introduced into only a small percentage of target cells in any one experiment.

In one embodiment, cells comprising the transferred exogenous DNA may be identified by color, as described in Example 6 for yeast. In one embodiment, cells expressing CYP76AD1 and DODA are red-violet. In one embodiment, cells expressing CYP76AD6, CYP76AD15, or a combination thereof, and DODA are yellow. In one embodiment, cells expressing CYP76AD1, CYP76AD6, CYP76AD15, or a combination thereof, and DODA are orange or orange-red.

In another embodiment, marker genes are used to provide an efficient system for identification of those cells that are stably transformed by receiving and integrating a genetically modified DNA construct into their genomes.

In another embodiment, selection genes provide selective markers that confer resistance to a selective agent, such as an antibiotic or herbicide. Potentially transformed cells are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

Useful selective marker genes include those conferring resistance to antibiotics such as kanamycin (nptII), hygromycin B (aph IV), nptII, hpt, aad4 and gentamycin (aac3 and aacC4) or resistance to herbicides such as glufosinate (bar or pat) and glyphosate (EPSPS). In another embodiment, the selection gene is an antinetabolite. In one embodiment, the antimetabolite is dhf.

Screenable markers which provide an ability to visually identify transformants can also be employed, e.g., a gene expressing a colored or fluorescent protein such as a cat, lacZ, uidA, luciferase or green fluorescent protein (GFP) or a gene expressing a beta-glucuronidase or uidA gene (GUS) for which various chromogenic substrates are known. It is also contemplated that combinations of screenable and selectable markers will be useful for identification of transformed cells.

In one embodiment, the selection gene is a positive selectable marker gene that is conditional on non-toxic agents that may be substrates for growth or that induce growth and differentiation of the transformed tissues.

In one embodiment, cells that survive exposure to the selective agent, or cells that have been scored positive in a screening assay, may be cultured in regeneration media and allowed to mature into plants. Developing plantlets can be transferred to soil less plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are preferably matured either in a growth chamber or greenhouse. Plants are regenerated from about 6 weeks to 10 months after a transformant is identified, depending on the initial tissue. During regeneration, cells are grown to plants on solid media at about 19 to 28° C. After regenerating plants have reached the stage of shoot and root development, they may be transferred to a greenhouse for further growth and testing. Plants may be pollinated using conventional plant breeding methods known to those of skill in the art and seed produced.

Progeny may be recovered from transformed plants and tested for expression of the exogenous recombinant polynucleotide. Useful assays include, for example, "molecular biological" assays, such as Southern and Northern blotting and PCR; "biochemical" assays, such as detecting the presence of RNA, e.g. double stranded RNA, or a protein product, e.g., by immunological means (ELISAs and Western blots) or by enzymatic function; plant part assays, such as leaf or root assays; and also, by analyzing the phenotype of the whole regenerated plant.

One of skill in the art will be able to select an appropriate vector for introducing the encoding nucleic acid sequence in a relatively intact state. Thus, any vector which will produce a host cell, e.g., plant protoplast, carrying the introduced encoding nucleic acid should be sufficient. The selection of the vector, or whether to use a vector, is typically guided by the method of transformation selected.

Promoters

In another aspect, cell, tissue, or organ specific promoters can be used to transform the genes of the invention and make them express in a specific cell, tissue, or organ. For example, fruit specific promoter can be used to transform the genes of the invention into a plant (e.g., tomato) or plant cell in order to produce betalains in fruits (e.g., tomato fruits).

In one embodiment, a recombinant polynucleotide of the present invention comprises at least one promoter. In one embodiment, a recombinant polynucleotide of the present invention comprises a single promoter controlling the expression of the tandem nucleic acids that are in the same reading frame. In another embodiment, each nucleic acid in the recombinant polynucleotide of the present invention is under the control of a separate promoter.

In one embodiment, the promoter is a constitutive promoter. In one embodiment, the constitutive promoter is the CaMV 35S promoter. In another embodiment, the constitutive promoter is an opine promoter. In another embodiment, the constitutive promoter is a monocot promoter. In another embodiment, the constitutive promoter is a Plant ubiquitin promoter (Ubi). In another embodiment, the constitutive promoter is the *Arabidopsis* ubiquitin-10 promoter. In another embodiment, the constitutive promoter is the *Solanum lycopersicum* ubiquitin 10 promoter (SlUb10). In another embodiment, the constitutive promoter is Rice actin 1 promoter (Act-1). In another embodiment, the constitutive promoter is Maize alcohol dehydrogenase 1 promoter (Adh-1).

In another embodiment, the promoter is an inducible promoter. In one embodiment, the inducible promoter is a galactose-inducible promoter. In another embodiment, the inducible promoter is selected from AlcR/AlcA (ethanol inducible); GR fusions, GVG, and pOp/LhGR (dexamethasone inducible); XVE/OlexA (beta-estradiol inducible); and heat shock induction. In another embodiment, the inducible promoter is selected from tetracycline, dexamethasone, copper, salicyclic acid and herbicide inducible promoters. In another embodiment, mGal4:VP16/UAS or pOp/LhG4 may be used for transactivation, and the alc-switch, GVE/VGE, and XVE systems may be used for chemical induction. These methods are known in the art.

In another embodiment, the promoter is a tissue-specific or a development-stage-specific promoter. In another embodiment, the promoter is a synthetic promoter, which is produced by bringing together the primary elements of a promoter region from diverse origins.

In some embodiments, a fruit specific promoter can be used to transform the genes of the invention in combination with one or more other genes (e.g. anthocyanin genes) into a plant (e.g., tomato) or plant cell in order to produce betalains in fruits (e.g., tomato fruits). In one embodiment, the genes of the invention can be transformed into a transgenic plant (e.g., transgenic tomato plant already transformed with recombinant anthocyanin genes) or plant cell in order to produce betalains in fruits (e.g., tomato fruits).

Thus, in one embodiment, a promoter for any of the polynucleotides described herein, may be a fruit-specific promoter. In one embodiment, the fruit-specific promoter is the E8 promoter. In another embodiment, the promoter may be a flower-specific promoter. In one embodiment, the flower-specific promoter is a chalcone synthase (CHS) promoter. In one embodiment, the CHS promoter is a *Petunia* x *hybrida* CHS promoter. In another embodiment, the promoter may be a root-specific promoter. In another embodiment, the promoter may be a stem-specific promoter. In another embodiment, the promoter may be a leaf-specific promoter. In another embodiment, the promoter may be a seed-specific promoter. In another embodiment, the promoter may be a tuber-specific promoter.

In one embodiment, the promoter may be specific to a part of the tissue. For example and in one embodiment, a promoter may be specific to the petal, stamen, anther, stigma, or a combination thereof.

In another embodiment, the same nucleic acid may be expressed under different non-constitutive promoter sequences to engineer an organism that exhibits two colors of pigmentation and/or expresses both betacyanins and betaxanthins in different organs or in different parts of the same organ. For example, in one embodiment, CYP76AD6 or CYP76AD15 or a homolog thereof may be expressed under a flower-specific promoter and CYP76AD1 may be expressed under a fruit-specific promoter so that the fruit is red-purple due to the presence of both betacyanins and betaxanthins, and the flower is yellow due to the presence of betaxanthins only. In addition, inducible promoters may be used to engineer an organism that exhibits two colors of pigmentation and/or expresses both betacyanins and betaxanthins in different organs or in different parts of the same organ.

In another embodiment, the promoter may be specific to a developmental stage. For example and in one embodiment, a promoter may be specific to Stage 1, which, in one embodiment, is when the flower length is approximately 1 cm. In another embodiment, the developmental stage is Stage 2, which, in one embodiment, is when the flower length is approximately 2 cm. In another embodiment, the developmental stage is Stage 3, which, in one embodiment, is when the flower length is approximately 3 cm. In another embodiment, the developmental stage is Stage 4, which, in one embodiment, is when the flower length is approximately 4 cm. In another embodiment, the developmental stage is Stage 5, which, in one embodiment, is when the flower length is approximately 5-6 cm.

In one embodiment, the promoter may be specific to a tissue and a developmental stage. In one embodiment, the fruit specific E8 promoter is expressed in ripening and ripe fruit. In another embodiment, the flower-specific CHS promoter is expressed in petals during flower maturation.

Gene Silencing Applications

In one embodiment, the present invention provides a method of treating or suppressing a dopamine-responsive disorder in a subject comprising the step of administering a food crop, cell, or cell line comprising high levels of a CYP76AD1-β clade polypeptide, thereby providing said subject with L-DOPA, thereby treating or inhibiting said dopamine-responsive disorder in said subject. In one embodiment, said food crop, cell, or cell line endogenously produces betalains. In one embodiment, the expression of DOPA 4,5-dioxygenase, cyclo-DOPA 5-O-glucosyltransferase, and a CYP76AD1-alpha clade gene in said food crop, cell, or cell line has been suppressed.

In one embodiment, the present invention provides a method of producing yellow plant parts in a plant comprising betalains, comprising silencing CYP76AD1 gene expression.

In one embodiment, the present invention provides a method of producing green plant parts in a plant comprising betalains, comprising silencing CYP76AD1 and CYP76AD6, CYP76AD15, or a combination thereof, gene expression.

In one embodiment, the plant parts comprise leaves, stems, roots, flowers, tuber, fruit, seeds, or a combination thereof.

In one embodiment, gene silencing is gene knockdown, which in one embodiment, is a reduced expression of the gene. In one embodiment, virus induced gene silencing is used to silence the genes encoding CYP76AD1 and/or CYP76AD6. In one embodiment, virus-induced gene silencing (VIGS) is a technology that exploits an RNA-mediated antiviral defense mechanism. In plants infected with unmodified viruses the mechanism is specifically targeted against the viral genome. However, with virus vectors carrying inserts derived from host genes the process can be additionally targeted against the corresponding mRNAs. Such methods are exemplified herein below in Examples 1 and 3.

Other methods of gene silencing that may be used in the present invention include gene silencing with antisense oligonucleotides, ribozymes, RNA interference, three prime untranslated regions/microRNAs. Such methods are well known in the art as well as being described in Example 1 herein below.

In another embodiment, the genes encoding CYP76AD1 and/or CYP76AD6, CYP76AD15, or a combination thereof, are knocked out using methods known in the art.

In one embodiment, the plant comprises betalains, which in one embodiment, is a betacyanin, and in another embodiment, is a betaxanthin.

In one embodiment, methods of gene silencing are performed in plants comprising betalains. In one embodiment, plants comprising betalains are from the Caryophyllales plant order.

In one embodiment, methods of gene silencing are performed in Caryophyllales which comprises cacti, carnations, amaranths, ice plants, beets, and many carnivorous plants. In another embodiment, the plant is from the Caryophyllineae suborder. In another embodiment, the plant is from the Polygonineae suborder. In another embodiment, the plant is from a family selected from one of the following families of the Caryophyllales plant order: Achatocarpaceae; Aizoaceae; Amaranthaceae; Anacampserotaceae; Ancistrocladaceae; Asteropeiaceae; Barbeuiaceae; Basellaceae; Cactaceae; Caryophyllaceae; Didiereaceae; Dioncophyllaceae; Droseraceae; Drosophyllaceae; Frankeniaceae; Gisekiaceae; Halophytaceae; Kewaceae; Limeaceae; Lophiocarpaceae; Macarthuriaceae; Microteaceae; Molluginaceae; Montiaceae; Nepenthaceae; Nyctaginaceae; Physenaceae; Phytolaccaceae; Plumbaginaceae; Polygonaceae; Portulacaceae; Rhabdodendraceae; Sarcobataceae; Simmondsiaceae; Stegnospermataceae; Talinaceae; and Tamaricaceae.

In some embodiments, polynucleotides of the present invention are prepared using PCR techniques using procedures and methods known to one skilled in the art. In some embodiments, the procedure involves the legation of two different DNA sequences (See, for example, "Current Protocols in Molecular Biology", eds. Ausubel et al., John Wiley & Sons, 1992).

Polynucleotides

In one embodiment, the present invention provides a recombinant polynucleotide comprising a nucleic acid encoding CYP76AD6. In one embodiment, the nucleic acid sequence encoding CYP76AD6 comprises:

```
                                         (SEQ ID NO: 30)
tcgatgtgttttcaagaagagcttgagcctacattctacaacaatatatt gttcctctcttgcgcaattaagcccttaaacctgcaattatcttagaatt tttgggtttctaatttattactcctttaattagctagatatagattattc atattttccagcattttcaaacaatggataacgcaacacttgctgtgat cattccatttgtttgtgttttaccacattttcaaatcctattcaccaat tatcatacgtaggatcctcctggtcccaaacccgtgccaattttggcaa cattttcgatcttggcgaaaagcctcatcgatctgccaatctatctaaaa ttcacggccattgattagcctaaagttaggaagtgtaacaactattgttg tttcctcggcctagtggccgaggaaatgttccttaaaaatgaccaagcac ttgctaaccgaaccattcctgactcggttagggctggtgaccacgacaaa ttatccatgtcgtggttgcctgtttcccaaaaatggagaaatatgagaaa aataccgctgtccaattactaccaaccaaaaacttgatgctagtcaacct cttagacaagctaaggtgaaacaacttttatcatacgtacaagtttgttc cgaaaaaatgcaacccgtcgatattggacgggccgcatttacaacgtcac ttaatttattatcaaacacattttctcaatcgaattagcaagtcatgaa tctagtgatcccaagagtttaaacaactcatgtggaatattatggaggaa attggaaggcctaattatgctgattttttccctattcttggttacattga tccattggtataagacgtcgtttggctggttactttgataaactcattga
```

-continued
tgattccaagacattattcgtgaaagacaaaagatcgatcttctaattct tccggcgcaaaacaaacaaatgacattcttgatactatcttaaactccat gaagataatgagttgagtatgcctgaaattaatccacttctcgtggatat ctttgacgccggaacagacacaacagcaagcacattagaatgggcgatgg ccgaacttgtgaaaaacccggaaatgatgactaaagttcaaattgaaatc gaacaagctcttggaaaagattgcttagacatacaagaatccgacatctc aaaactaccttatttacaagccattataaaagaaacgttacgtttacacc ctcctactgtgttttgctgcctcgaaaggcagacaatgacgtagagtta tatggctacgttgtaccaagaatgctcaagtccttgtcaatctttgggc aattggtcgtgatccaaaggtatggaaaaatccggaagtattttacctga aaggtttttagattgcaatatcgattataaaggacgagatttcgaactttt taccattggtgctggtagaaggatatgccaggacttactttggcatatag aatgttgaacttgatgttggctactatcttcaaaactacaattggaaact tgaagatggtatcaatcctaaggatttagacatggatgagaaatttggga ttacattgcaaaaggttaaacctcttcaagttattccagttcccagaaac tagctagtgggttgtgccgttgtgggctgtgggctgattgtgcactgttt cctctaattgttgttgcaaacttctctagaagggtattatcttttgtata aataaagcgaaagctacatgtcctattattaaattagtgtatactatatt aagtaagtatgagcatatagtatccattattgatttggttgaatcgtatt aaactgataaatcaagtaaatgtctccaacctaagcattcaattattctg ttagtcataacatatgtagagggtaagtatgaagaattaataacggcgtg atcatcctta.

In another embodiment, the coding sequence of CYP76AD6 comprises the following sequence:

(SEQ ID NO: 31)
atggataacgcaacacttgctgtgatcattccattttgtttgtgttttac cacattttcaaatcctttttcaccaattcttcatctcgtaggcttcctcc tggtcccaaacccgtgccaattttttggcaacattttcgatatggcgaaaa gcctcatcgatatttgccaatctatctaaaattcacggccctttgattag cctaaagttaggaagtgtaacaactattgttgtttcctcggcctagtggc cgaggaaatgttccttaaaaatgaccaagcacttgctaaccgaaccattc ctgactcggttagggctggtgaccacgacaaattatccatgtcgtggttg cctgtttcccaaaaatggagaaatatgagaaaaatctccgctgtccaatt actaccaaccaaaaacttgatgctagtcaacctatagacaagctaaggtg aaacaactttatcatacgtacaagtttgttccgaaaaaatgcaacccgt cgatattggacgggccgcatttacaacgtcacttaatttattatcaaaca catttttctcaatcgaattagcaagtcatgaatctagtgatcccaagagt ttaaacaactcatgtggaatattatggaggaaattggaaggcctaattat gctgattttttcctattatggttacattgatccattggtataagacgtc gtttggctggttactttgataaactcattgatgttttccaagacattatt cgtgaaagacaaaagatcgatcttctaattcttccggcgcaaaacaaaca aatgacattcttgatactcttcttaaactccatgaagataatgagttgag tatgcctgaaattaatccacttctcgtggatatctttgacgccggaacag acacaacagcaagcacattagaatgggcaatggccgaacttgtgaaaaac ccggaaatgatgactaaagttcaaattgaaatcgaacaagctatggaaaa gattgatagacatacaagaatccgacatacaaaactaccttatttacaag ccattataaaagaaacgttacgtttacaccctcctactgtgttttttgctg cctcgaaaggcagacaatgacgtagagttatatggctacgttgtaccaaa gaatgctcaagtccttgtcaatattgggcaattggtcgtgatccaaaggt atggaaaaatccggaagtattttacctgaaaggtttttagattgcaatat cgattataaaggacgagatttcgaacttttaccattggtgctggtagaag gatatgccaggacttactttggcatatagaatgttgaacttgatgttggc tactatcttcaaaactacaattggaaacttgaagatggtatcaatcctaa ggatttagacatggatgagaaatttgggattacattgcaaaaggttaaac ctatcaagttattccagttcccagaaactag.

Figure 19:
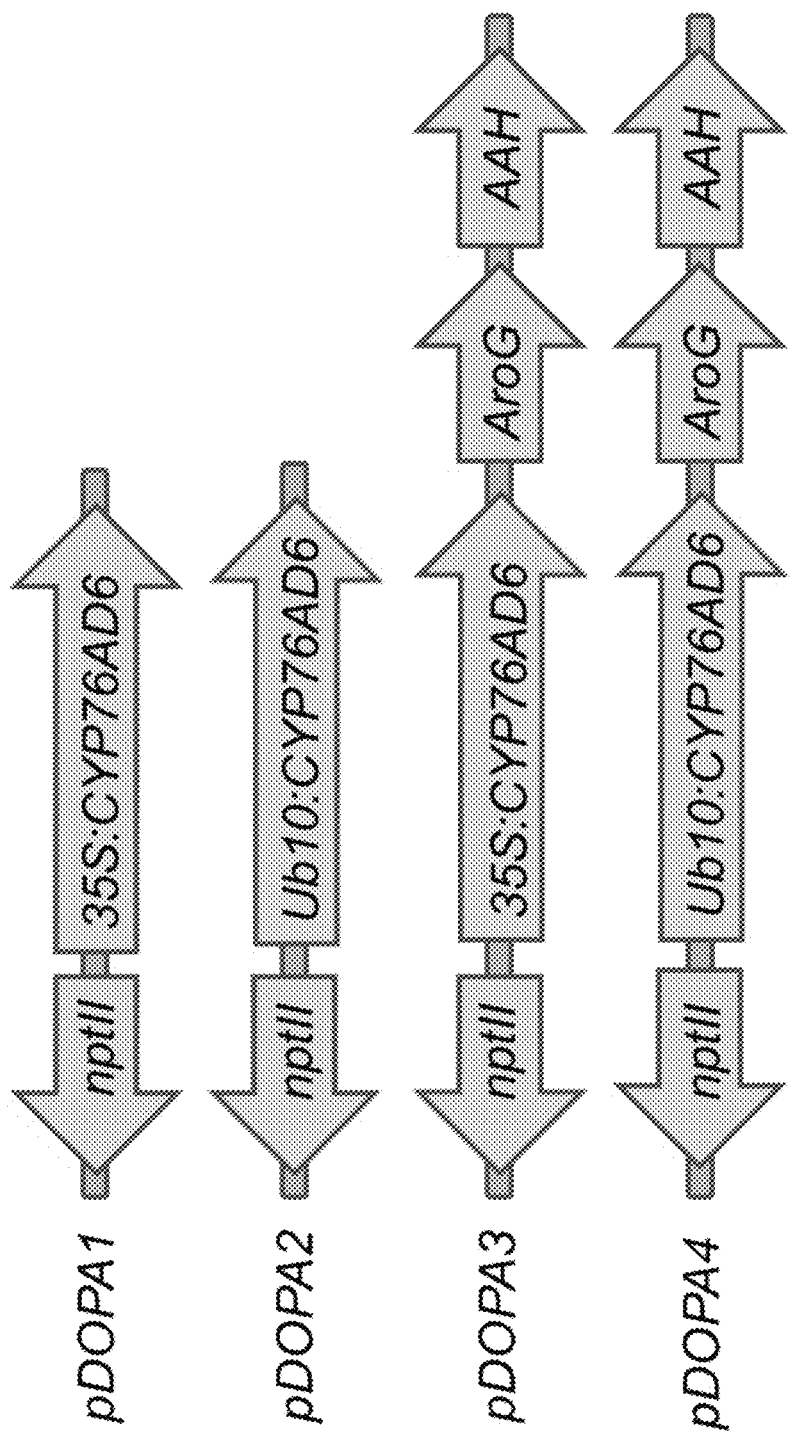
FIG. 19. Schematic of the pDOPA1-pDOPA4 (SEQ ID NOs: 24-27) overexpression vectors. nptII, kanamycin resistance-conferring gene neomycin phosphotransferase II; CYP76AD6, *B. vulgaris* cytochrome P450; AroG, *E. coli* AroG175 (DAHPS) mutant; AAH, *Physcomitrella patens* aromatic amino acid hydroxylase; 35S, CaMV 35S promoter/terminator; Ub10, *Solanum lycopersicum* ubiquitin 10 promoter.

In one embodiment, the nucleic acid encoding CYP76AD6 is driven by the CaMV 35S promoter (pDOPA1; FIG. 19). In another embodiment, the nucleic acid encoding CYP76AD6 is driven by the *Solanum lycopersicum* ubiquitin 10 promoter (SlUb10) (pDOPA2; FIG. 19).

In one embodiment, the nucleic acid encoding CYP76AD6, CYP76AD15, or a combination thereof, is expressed together with AroG175 and aromatic amino acid hydroxylase (AAH).

In one embodiment, the polynucleotide comprising the nucleic acid encoding CYP76AD6, CYP76AD15, or a combination thereof, also comprises the neomycin phosphotransferase II (nptII) gene, which in one embodiment, confers kanamycin resistance.

In another embodiment, the present invention provides a recombinant polynucleotide comprising a nucleic acid encoding a CYP76AD1-α clade gene. In one embodiment, the CYP76AD1-α clade gene comprises CYP76AD1. In one embodiment, the nucleic acid sequence encoding CYP76AD1 comprises:

(SEQ ID NO: 32)
tactaatgtgcaaatgcataaatttaatttcagatactcttattataaat attattatactgtgcattatttaacccaaaaaaaaaactgtcttaataca ccatttaattcctttctctaggatccactatcacatgtagtatataaata taatcctatacagttcacgttatcaaacaccaaagcatcaaaagccttcc acacttgtattattttggggtagttgatttgttagcgtgttatttgtgag atcatcatggatcatgcaacattagcaatgatactagccatttggttcat ttcttttcatttcataaaattacttttagccaacaaactaccaaacttc ttcctcctggtccaaaaccattgccaataattggtaacatcttagaagtt ggtaaaaaaccccatcgttcatttgctaatcttgctaaaattcacggccc tttaatatcgttacgtctaggaagtgtaacaactattgttgtatcatcag cagatgtagctaaagaaatgttcttaaaaaaagaccaccctattctaacc -continued
```
gtactattcctaattctgtcacggccggtgaccaccataaactcaccatg tcgtggttgcccgtttcgccgaaatggcggaattttcgtaagattacagc cgtccatttgattctcctcaaagacttgatgatgccaaacctttcgccat gccaaggtgcaacagctttatgaatatgtacaagaatgtgcacaaaaagg ccaagctgttgatattggcaaagctgcatttactacctcccttaatttgt tatctaaactattcttttcagtggaattagcccaccataaatcacacact tacaagagtttaaggaactaatatggaacattatggaagatattgggaaa cctaattatgctgattattttcctattttaggctgtgttgatccatcagg tattcgtcgaagattagcatgtagttttgacaagttgattgcagttttc agggtataatatgtgaaaggcttgcgcctgattatcaactacaacaacaa cgacgactgatgatgtgctagacgttatcttcagacttcaaacaaaatga gacactatgggcgagattaaccatttgacgtcgacattttttgatgctgga acagacactacatcaagtacttttgagtgggtcatgacagagttaattag gaatcctgaaatgatggaaaaggctcaagaagaaattaagcaagtattgg gcaaagataaacaaattcaggaatcagacattattaacctaccttactta caagccattatcaaagaaactttgcgactacatccaccaactgtatttct tttgcctcgtaaagccgacactgatgttgaactatatggttatattgtgc ctaaagatgcacaaatacttgttaacttatgggctattggaagagatcct aatgcatggcaaaatgctgatatttttcgcccgaaagatttataggtg tgaaattgatgtcaaaggaagagattttggactcttacctttggagccg gaagaaggatatgtcctgggatgaatttggccattagaatgttaactttg atgctagctactttacttcaattcttcaattggaagcttgaaggagacat aagtccaaaagacttagacatggatgagaaatttgggattgcgttacaaa agacaaagcctttaaaacttattccaatacctaggtattgaaatttgtta gacttacgtacaacaattattattgtttgtggttggttttgggttagctt cctgttcatgtttgtttgatgtgacgattgaatttactacaaatcaacga actccaattatatcttgtcaacttggagtaatggcttgggtttctcatct gtcatctcttttggttggctgtgcaagggagtgagcttgcagcttagcat ccttcaagaagatttaattaataatatgtgtatgtgtatgtgtatgtgtg gattgtatacgtcattcattttgcttgttgtaatgattttagttaattat tgtaattataaaggatttgatcctcattgtgttgaaattatatatataat gtgtagcacgacaataaagtgacagataacttatataatcttattttcta tgaaatgttacagacttgattgtgttttaaaaaaa.
```

In another embodiment, the CYP76AD1-α clade gene comprises *A. cruentus*, *Amaranthus cruentus* (CYP76AD2, accession AET43291.1; SEQ ID NO: 15); *M. jalapa*, *Mirabilis jalapa* (CYP76AD3, accession AET43292.1; SEQ ID NO: 16); *C. cristata*, *Celosia cristata* (CYP76AD4, accession AGI78466.1; SEQ ID NO: 17); or a combination thereof.

In one embodiment, the present invention provides a recombinant polynucleotide comprising a nucleic acid encoding a DOPA 4,5-dioxygenase (DOD) enzyme. In one embodiment, the DOD is *Beta vulgaris* DODA1 (BvDODA1). In one embodiment, the nucleic acid sequence encoding BvDODA1 comprises: aaaacaagaagaaacaaaaca-

```
acctttatataactagaaagcaacaaaaaaaaaagaatgaaaatgatgaatggt-
gaagatgctaatgatca aatgatcaaagaaagcttcttcataacacatggaaacc-
caatattaacagtagaagacacacatccattaagacctttctttgaaacttg-
gagagag     aaaatettttetaagaaacetaaggcaattettattatttetggte-
attgggaaaetgttaaacetactgttaatgetgtecatateaatgatactatecat gat-
tttgatgactatectgetgetatgtaceagttcaagtateeagetectggggaac-
cagaattggcaagaaaagtagaggaaattctgaaaaaat     cggttcgaa-
acggcggaaactgatcaaaaacgtgggcttgatcatggtgcatgggtacct-
ctaatgctaatgtatectgaggetgatataccag tatgtcagetetcagttcagccg-
catttagatggaacataccattacaactaggacgagcattggcteccttgaaaa-
acgacggcgtattaatcatt ggttcaggaagtgcaactcacccttggatgaaac-
tcctcattattttgatggagttgcaccttgggcagetgcetttgatcatggettcgt-
aaagct ctcattaatggaaggtttgaagaagtgaatatatatgaaagcaaagcac-
caaattggaaattagcacatcetttcccagaacatttttatccattgcat gttgttctt-
ggegetgetggtgaaaaatggaaggcagagcttattcatagcagttgggatcat-
ggcaccttgtgtcatggctectacaagttcacttc agcetagttttactttaaacac-
tatgtetacagtatatgttatgtatttggtaatttggatgtggtgttgttttgttttatte-
ttttgagttattgtacttggta tttggtgttgttttcatttggtgcataatettttagteta-
tatattgetattettttgaatgaggaataaategegagetegatgtaatagtttgttt-
attgttte aaatctatcattatatatatatatatattaaaaaaaaattattgtgttacte-
gcaaaaaaa (SEQ ID NO: 33). In one embodiment, the DOD
is not *Mirabilis jalapa* DOD.
```

In one embodiment, the present invention provides a recombinant polynucleotide comprising a nucleic acid encoding a betalain related glucosyltransferase. In one embodiment, the nucleic acid sequence encoding the betalain related glucosyltransferase is the nucleic acid sequence encoding cyclo-DOPA 5-O-glucosyltransferase (cDOPA5GT). In one embodiment, cDOPA5GT is from *Mirabilis jalapa*. In one embodiment, the nucleic acid sequence encoding cDOPA5GT comprises:

```
                                        (SEQ ID NO: 2)
cctcacctccataacaaagaaatgaccgccattaaaatgaacaccaatgg tgaaggtgaaacacaacatatactaatgatacctttcatggcgcaagggc atttacgtccttttccttgagcttgctatgtttctatataaacgaagtcat gttatcattactcttcttactaccccgctcaatgcgggtttcctacgaca tctccttcaccaccatagctattctagctcggggatcagaattgtcgagt tacctttcaactcaaccaatcatggtcttccacctggcattgaaaacact gataaacttacactcccacttgtagtatcactattcattcaaccatttct cttgaccctcaccttagagattatatttcccgccatttctccctgcgcg ccctcctctgtgtgtcatacatgatgtgttccttggttgggttgatcaag ttgctaaagacgtgggctcaactggtgttgttttactacgggtggcgcg tatggtacaagcgcatatgtgtccatttggaatgatctgcctcaccagaa ttactctgatgatcaagagttccgcttcctggttccgggagaatcata aattccgacgttctcaacttcatcggtttctgaggtatgccgatggatca gatgattggtcgaaatatttccaaccgcaattgaggcaatcaatgaagag ttttggatggctatgtaattcagttgaggaaatcgaaacacttgggttta gtatcctcaggaactacactaaactacccattgggtattggaccgttg atagcttcacctgtacaacattcatcatctgataataacagtactggtgc cgagtttgttcaatggttgagcttgaaagaaccagattctgtattataca
```

-continued
```
tctcatttggatcacagaacacaatttcaccaacccagatgatggaacta gcagccggtttggagtcaagtgagaagccgtattgtgggtgattcgagca ccatttgggttcgatatcaatgaggaaatgagaccagaatggctaccaga gggattcgaggagcgaatgaaggtgaaaaaacaaggaaagttggtgtata agttgggaccacagttggagatacttaaccatgagtcaatcggagggttc ttaactcattgtgggtggaattcgatccttgagtcacttcgagaaggtgt gcctatgttagggtggccattggcagccgaacaagcttataatttgaagt atttggaggacgaaatgggggttgcagtcgagttagcgaggggattggaa ggagagataagtaaagagaaagtgaagagaattgtggagatgattttaga gagaaatgaaggaagtaaaggatgggaaatgaaaaatagagcagtagaaa tggggaagaaacttaaagacgctgtcaatgaggagaaggaactgaagggt tcttctgttaaggcaatagatgatttcttagatgcggtcatgcaagctaa gttggaaccttctcttcaataataagatcgatagtttatctcgtctcaga gactcaaacaattgactactaggatgatcagaaagagagttatgttcagt gttctgttattatgcaagacttcaataataacagaaaaattcgtgattag attcataactt.
```

In one embodiment, several nucleic acids are combined into a single recombinant polynucleotide as described herein. In one embodiment, the present invention provides a recombinant polynucleotide comprising a nucleic acid encoding CYP76AD6, CYP76AD15, or a combination thereof, and a nucleic acid encoding DOD. In another embodiment, the present invention provides a recombinant polynucleotide comprising a nucleic acid encoding CYP76AD1 and a nucleic acid encoding DOD. In another embodiment, the present invention provides a recombinant polynucleotide comprising a nucleic acid encoding CYP76AD1 and a nucleic acid encoding CYP76AD6. In another embodiment, the present invention provides a recombinant polynucleotide comprising a nucleic acid encoding CYP76AD1, a nucleic acid encoding CYP76AD6, CYP76AD15, or a combination thereof, and a nucleic acid encoding DOD.

In another embodiment, several nucleic acids are incorporated into a cell, but each nucleic acid is a separate polynucleotide as described herein.

In one embodiment, a polynucleotide of the present invention comprises a nucleic acid sequence encoding CYP76AD6, CYP76AD15, or a combination thereof, and a nucleic acid sequence encoding CYP76AD1. In another embodiment, a polynucleotide of the present invention comprises a nucleic acid sequence encoding CYP76AD6, CYP76AD15, or a combination thereof, and a nucleic acid sequence encoding a DOD enzyme. In another embodiment, a polynucleotide of the present invention comprises a nucleic acid sequence encoding CYP76AD1 and a nucleic acid sequence encoding a DOD enzyme. In another embodiment, a polynucleotide of the present invention comprises a nucleic acid sequence encoding CYP76AD6, CYP76AD15, or a combination thereof, a nucleic acid sequence encoding CYP76AD1, and a nucleic acid sequence encoding a DOD enzyme. In another embodiment, a polynucleotide of the present invention comprises a nucleic acid sequence encoding CYP76AD6, CYP76AD15, or a combination thereof, a nucleic acid sequence encoding CYP76AD1, and a nucleic acid sequence encoding a betalain related glucosyltransferase. In another embodiment, a polynucleotide of the present invention comprises a nucleic acid sequence encoding CYP76AD6, CYP76AD15, or a combination thereof, a nucleic acid sequence encoding a DOD enzyme and a nucleic acid sequence encoding a betalain related glucosyltransferase. In another embodiment, a polynucleotide of the present invention comprises a nucleic acid sequence encoding CYP76AD1, a nucleic acid sequence encoding a DOD enzyme and a nucleic acid sequence encoding a betalain related glucosyltransferase. In another embodiment, a polynucleotide of the present invention comprises a nucleic acid sequence encoding CYP76AD6, CYP76AD15, or a combination thereof, a nucleic acid sequence encoding CYP76AD1, a nucleic acid sequence encoding a DOD enzyme and a nucleic acid sequence encoding a betalain related glucosyltransferase.

In another embodiment, any of the recombinant polynucleotides described hereinabove further comprises a betalain related glucosyltransferase. In one embodiment, the betalain related glucosyltransferase is cyclo-DOPA 5-O-glucosyltransferase or betanidin-5-O-glucosyltransferase. In one embodiment, the cyclo-DOPA 5-O-glucosyltransferase is *M. jalapa* gene cyclo-DOPA 5-O-glucosyltransferase (cDOPA5GT) (SEQ ID NO: 2).

In another embodiment, the present invention provides a recombinant polynucleotide comprising a nucleic acid encoding CYP76AD1, a nucleic acid encoding CYP76AD6, CYP76AD15, or a combination thereof, a nucleic acid encoding a DOPA 4,5-dioxygenase (DOD) enzyme, and a nucleic acid sequence encoding a betalain related glucosyltransferase, wherein said nucleic acids are in the same reading frame.

In another embodiment, the present invention provides a recombinant polynucleotide comprising a nucleic acid encoding CYP76AD1, a nucleic acid encoding a DOPA 4,5-dioxygenase (DOD) enzyme, and a nucleic acid sequence encoding a betalain related glucosyltransferase, wherein said nucleic acids are in the same reading frame.

In another embodiment, the present invention provides a recombinant polynucleotide comprising a nucleic acid encoding CYP76AD6, CYP76AD15, or a combination thereof and a nucleic acid encoding a DOPA 4,5-dioxygenase (DOD) enzyme expressed in tandem.

In another embodiment, the present invention provides a recombinant polynucleotide comprising a nucleic acid encoding CYP76AD1, CYP76AD6, CYP76AD15, or a combination thereof, or a combination thereof, a nucleic acid encoding a DOPA 4,5-dioxygenase (DOD) enzyme, and a nucleic acid sequence encoding a betalain related glucosyltransferase, expressed in tandem.

In one embodiment, the polynucleotides as described herein comprise multiple nucleic acid sequences that are in the same reading frame. In one embodiment, the polynucleotides as described herein comprise multiple nucleic acid sequences that are expressed in tandem.

In one embodiment, a polynucleotide of the present invention comprises a nucleic acid encoding CYP76AD1, a nucleic acid encoding a DOPA 4,5-dioxygenase (DOD) enzyme, and a nucleic acid sequence encoding a betalain related glucosyltransferase, wherein said nucleic acids are in the same reading frame. In one embodiment, the DOD gene is under a CaMV 35S promoter. In one embodiment, the CYP76AD1 gene is under a CaMV 35S promoter. In one embodiment, the betalain related glucosyltransferase gene is under an *Arabidopsis* Ubiquitin-10 promoter. In one embodiment, the polynucleotide further comprises a kanamycin resistance gene. In one embodiment, the polynucleotide is the pX11 vector, as described in Example 8, hereinbelow. In one embodiment, the nucleic acid sequence of the pX11 vector comprises (SEQ ID NO: 19).

Figure 15:
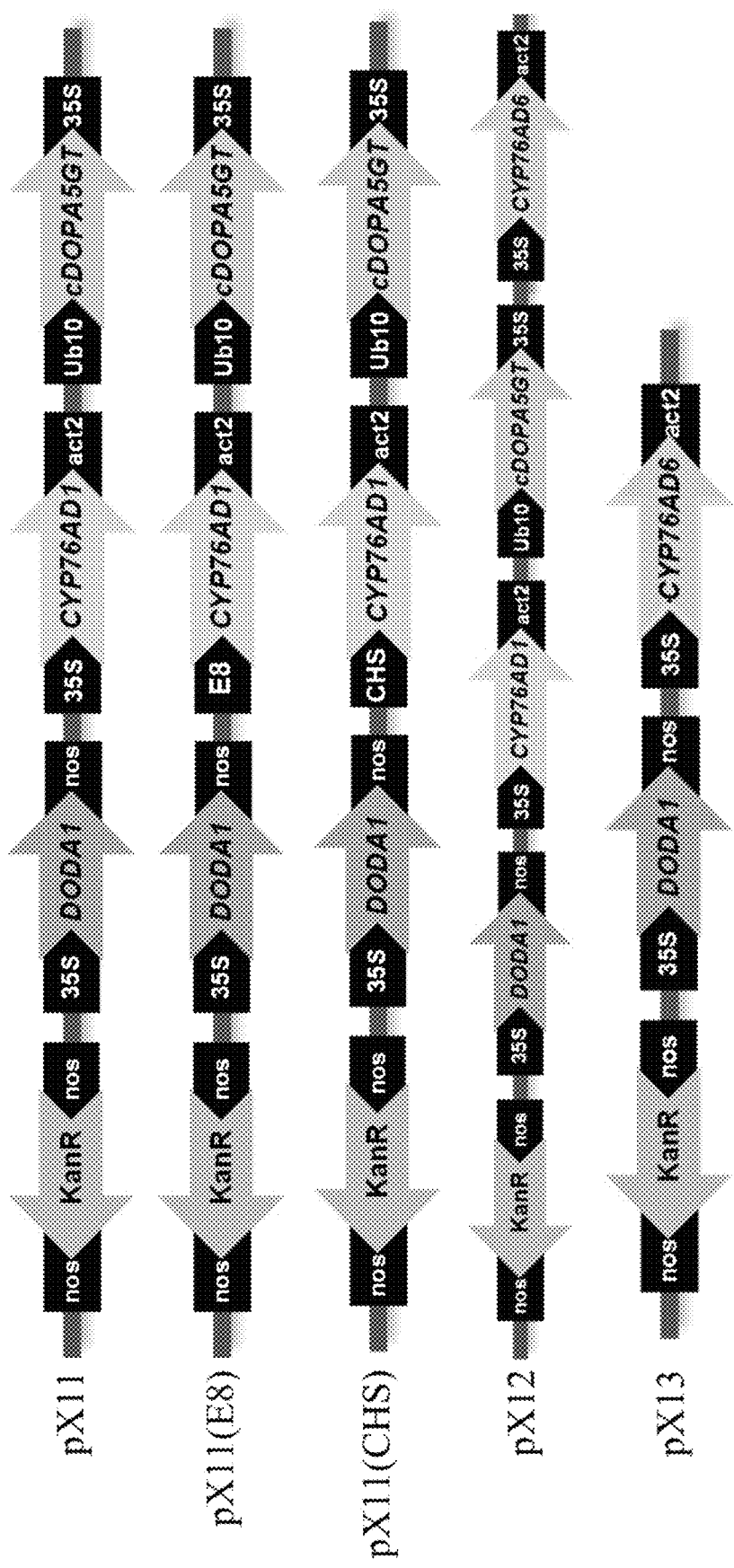
FIG. 15. Schematic of the pX11 (SEQ ID NO: 19), pX11(E8)(SEQ ID NO: 20), pX11(CHS) (SEQ ID NO: 21), pX12 (SEQ ID NO: 22), and pX13 (SEQ ID NO: 23) overexpression vectors. KanR, kanamycin resistance-conferring gene nptII; DODA1, B. vulgaris DOPA 4,5-dioxygenase; CYP76AD1/CYP76AD6, B. vulgaris cytochrome P450; cDOPA5GT, M. jalapa cyclo-DOPA-5-O-glucosyltransferase; nos, nopaline synthase promoter/terminator; 35S, CaMV 35S promoter/terminator; Act2, Arabidopsis actin 2 terminator; Ub10, Arabidopsis ubiquitin 10 promoter; E8, S. lycopersicum E8 promoter; CHS, Petunia x hybrida chalcone synthase promoter.

In another embodiment, the CYP76AD1 gene is under an E8 promoter (pX11(E8), SEQ ID NO: 20; FIG. 15). In another embodiment, the CYP76AD1 gene is under a CHS promoter (pX11(CHS) SEQ ID NO: 21; FIG. 15).

In another embodiment, a polynucleotide of the present invention comprises a nucleic acid encoding CYP76AD6, CYP76AD15, or a combination thereof, a nucleic acid encoding a DOPA 4,5-dioxygenase (DOD) enzyme, and a nucleic acid sequence encoding a betalain related glucosyltransferase, wherein said nucleic acids are in the same reading frame. In one embodiment, the DOD gene is under a CaMV 35S promoter. In one embodiment, the CYP76AD6, CYP76AD15, or a combination thereof, gene is under a CaMV 35S promoter. In one embodiment, the betalain related glucosyltransferase gene is under an *Arabidopsis* Ubiquitin-10 promoter. In one embodiment, the polynucleotide further comprises a kanamycin resistance gene. In one embodiment, the polynucleotide is the pX13 vector, as described in Example 14, hereinbelow.

In another embodiment, the CYP76AD6, CYP76AD15, or a combination thereof, gene is under an E8 promoter. In another embodiment, the CYP76AD6, CYP76AD15, or a combination thereof, gene is under a CHS promoter.

In another embodiment, a polynucleotide of the present invention comprises a nucleic acid encoding CYP76AD6, CYP76AD15, or a combination thereof, a nucleic acid encoding CYP76AD1, a nucleic acid encoding a DOPA 4,5-dioxygenase (DOD) enzyme, and a nucleic acid sequence encoding a betalain related glucosyltransferase, wherein said nucleic acids are in the same reading frame. In one embodiment, the DOD gene is under a CaMV 35S promoter. In one embodiment, the CYP76AD6, CYP76AD15, or a combination thereof, gene is under a CaMV 35S promoter. In one embodiment, the CYP76AD1 gene is under a CaMV 35S promoter. In one embodiment, the betalain related glucosyltransferase gene is under an *Arabidopsis* Ubiquitin-10 promoter. In one embodiment, the polynucleotide further comprises a kanamycin resistance gene. In one embodiment, the polynucleotide is the pX12 vector, as described in Example 14, hereinbelow.

In another embodiment, the CYP76AD6, CYP76AD15, or a combination thereof, gene is under an E8 promoter. In another embodiment, the CYP76AD6, CYP76AD15, or a combination thereof, gene is under a CHS promoter. In another embodiment, the CYP76AD1 gene is under an E8 promoter. In another embodiment, the CYP76AD1 gene is under a CHS promoter.

In one embodiment, the present invention provides a comprising a nucleic acid encoding a CYP76AD1-β clade gene under the control of a promoter. In one embodiment, the CYP76AD1-β clade gene is CYP76AD6. In another embodiment, the CYP76AD1-β clade gene is CYP76AD15.

In one embodiment, the present invention provides a recombinant nucleic acid comprising a CYP76AD1-β clade gene from red beet. In one embodiment, the present invention provides a recombinant nucleic acid comprising a CYP76AD1-β clade gene that is not from sugar beet. In one embodiment, the present invention provides a recombinant nucleic acid comprising a CYP76AD1-β clade gene but excluding the nucleic acid sequence of the CYP76AD1 paralogs from sugar beet (DeLoache et al., 2015), which do not produce betaxanthin when transformed into yeast with DOD. In one embodiment, the present invention provides a recombinant nucleic acid comprising a CYP76AD1-β clade gene but excluding the nucleic acid encoding SEQ ID NO: 34.

In another embodiment, the CYP76AD1-β clade gene is a CYP76AD1-β clade gene as set forth in Brockington et al. 2015 (New Phytol. 2015 September; 207(4):1170-80), which is incorporated herein by reference in its entirety). In one embodiment, the CYP76AD1-β clade gene is a CYP76AD1-β clade gene as set forth in Supplemental FIG. 2 of Brockington et al. 2015.

In one embodiment, the present invention provides a recombinant polynucleotide comprising a nucleic acid encoding a CYP76AD6 gene, a CYP76AD15 gene, or a combination thereof under the control of a promoter.

In one embodiment, the present invention provides a recombinant polynucleotide comprising a nucleic acid encoding a CYP76AD1-β clade gene and a nucleic acid encoding a DOPA 4,5-dioxygenase (DOD) enzyme, wherein said nucleic acids are inserted into the polynucleotide in frame. In one embodiment, the polynucleotide further comprises a nucleic acid encoding betalain related glucosyltransferase.

In one embodiment, the nucleic acid encoding a CYP76AD1-β clade gene is Bv. *maritima*, *Beta vulgaris* ssp. *maritima* (GenBank accession AKI33834.1; SEQ ID NO: 10); *F. latifolia*, *Froelichia latifolia* (accession AKI33838.1; SEQ ID NO: 11); *A. caracasana*, *Alternanthera caracasana* (accession AKI33835.1; SEQ ID NO: 12); *A. ficoidea*, *Alternanthera ficoidea* (accession AKI33831.1; SEQ ID NO: 13), or a combination thereof.

In one embodiment, the present invention provides a recombinant polynucleotide comprising a nucleic acid encoding a CYP76AD6 gene, a CYP76AD15 gene, or a combination thereof and a nucleic acid encoding a DOPA 4,5-dioxygenase (DOD) enzyme, wherein said nucleic acids are inserted into the polynucleotide in frame. In one embodiment, the polynucleotide further comprises a nucleic acid encoding betalain related glucosyltransferase.

In another embodiment, the present invention comprises additional nucleic acids encoding polypeptides that modify betalain structure. In one embodiment, the polypeptide is a glycosylating enzyme. In another embodiment, the polypeptide is an acylating enzyme. In another embodiment, additional nucleic acids encode polypeptides involved in subcellular transport. In another embodiment, additional nucleic acids encode polypeptides involved in detoxification.

Homologs and Variants

In another embodiment, a recombinant polynucleotide or polypeptide of the present invention is homologous to a sequence set forth herein, either expressly or by reference to a GenBank entry. The terms "homology," "homologous," etc, when in reference to any amino acid or nucleic acid sequence, refer, in one embodiment, to a percentage of amino acids or nucleotides, respectively, in the candidate sequence that are identical with the residues of a corresponding native polypeptide or polynucleotide, after aligning the sequences and introducing gaps, if necessary, to achieve the maximum percent homology, and not considering any conservative substitutions as part of the sequence identity. Methods and computer programs for the alignment are well known in the art such as, for example, the BLAST, DOMAIN, BEAUTY (BLAST Enhanced Alignment Utility), GENPEPT and TREMBL packages.

In one embodiment, a homolog of CYP76AD1 may be used instead of CYP76AD1 in accordance with the compositions and methods of the present invention.

In another embodiment, a homolog of CYP76AD6 may be used instead of CYP76AD6, in accordance with the compositions and methods of the present invention.

In another embodiment, a homolog of DOPA 4,5-dioxygenase (DOD) enzyme may be used instead of DOPA 4,5-dioxygenase (DOD) enzyme, in accordance with the compositions and methods of the present invention.

Homology may be at the nucleotide sequence and/or encoded amino acid sequence level. In one embodiment, the nucleic acid and/or amino acid sequence shares at least about 50%, or 60%, or 70%, or 80% homology. In another embodiment, the nucleic acid and/or amino acid sequence shares at least about 90%, 95%, 96%, 97%, 98% or 99% homology with a sequence of the present invention. Homology may be at the nucleotide sequence and/or encoded amino acid sequence level. In one embodiment, the nucleic acid and/or amino acid sequence shares at least about 72% homology. In one embodiment, the nucleic acid and/or amino acid sequence shares at least about 75% homology.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y).

In one embodiment, the homolog is isolated from another Caryophyllales plant. In one embodiment, the homolog is isolated from a cactus, a carnation, an amaranth, an ice plant, a beet, a carnivorous plant, or a combination thereof. In one embodiment, the carnivorous plant is a Dionocophyllaceae such as *Triphyophyllum*, a Droseraceae, such as *Aldrovanda* (Waterwheel Plant), *Dionaea* (Venus Flytrap), *Drosera* (Sundew), a Drosophyllaceae such as a *Drosophyllum* (Dewy Pine or Portugese Sundew), or a *Nepenthaceae* such as Tropical Pitcher Plant or Monkey Cup.

In one embodiment, the homolog is isolated based on temporal expression. In one embodiment, the homolog is isolated based on developmental stage. In one embodiment, the developmental stage is Stage 1, which, in one embodiment, is when the flower length is approximately 1 cm. In another embodiment, the developmental stage is Stage 2, which, in one embodiment, is when the flower length is approximately 2 cm. In another embodiment, the developmental stage is Stage 3, which, in one embodiment, is when the flower length is approximately 3 cm. In another embodiment, the developmental stage is Stage 4, which, in one embodiment, is when the flower length is approximately 4 cm. In another embodiment, the developmental stage is Stage 5, which, in one embodiment, is when the flower length is approximately 5-6 cm.

In another embodiment, the homolog is isolated based on tissue expression. In one embodiment, the tissue expression of a CYP76AD1, CYP76AD6, CYP76AD15, or a combination thereof, or DOD homolog is in a floral tissue. In one embodiment, the floral tissue is a petal. In another embodiment, the floral tissue is a stamen. In another embodiment, the floral tissue is an anther. In another embodiment, the floral tissue is a stigma.

In another embodiment, a recombinant polynucleotide or polypeptide of the present invention is a variant of a sequence set forth herein. In another embodiment, a recombinant polynucleotide or polypeptide of the present invention is an isoform of a sequence set forth herein. In another embodiment, a recombinant polynucleotide or polypeptide of the present invention is a fragment of a sequence set forth herein. In one embodiment, a recombinant polynucleotide or polypeptide of the present invention is a functional variant of a sequence set forth herein. In another embodiment, a recombinant polynucleotide or polypeptide of the present invention is a functional isoform of a sequence set forth herein. In another embodiment, a recombinant polynucleotide or polypeptide of the present invention is a functional fragment of a sequence set forth herein. In another embodiment, a recombinant polynucleotide or polypeptide of the present invention is a functional homologue of a sequence set forth herein.

In another embodiment, the present invention provides a recombinant polynucleotide comprising a nucleic acid encoding a polypeptide as described herein.

In one embodiment, the nucleic acid sequence encoding CYP76AD6 is as set forth in SEQ ID NO: 30. In another embodiment a polynucleotide of the present invention optionally comprises a nucleic acid sequence encoding CYP76AD6. In one embodiment, the nucleic acid sequence of CYP76AD6 is as set forth in SEQ ID NO: 30. In another embodiment, the CYP76AD6 utilized in methods and compositions of the present invention is a homologue of SEQ ID NO: 30. In another embodiment, the CYP76AD6 utilized in methods and compositions of the present invention is a variant of SEQ ID NO: 30. In another embodiment, the CYP76AD6 utilized in methods and compositions of the present invention is a fragment of SEQ ID NO: 30. In another embodiment, the CYP76AD6 utilized in methods and compositions of the present invention is an isoform of SEQ ID NO: 30. In another embodiment, the CYP76AD6 utilized in methods and compositions of the present invention is a functional homologue, functional variant, functional fragment, or functional isoform of SEQ ID NO: 30.

As demonstrated in Example 19, CYP76AD15, an ortholog of CYP76AD6 in *Mirabilis jalapa*, had the same activity as CYP76AD6 during transient expression in *Nicotiana benthamiana*. In another embodiment, CYP76AD15 or a homologue, isoform, or variant thereof, may be used in place of CYP76AD6 in the compositions and methods of the present invention. In one embodiment, the CYP76AD15 gene product from *Mirabilis jalapa* has a similar function as the CYP76AD6 gene product from *Beta vulgaris*. In one embodiment, CYP76AD15 from *Mirabilis jalapa* is the gene encoding an enzyme involved in converting tyrosine to L-DOPA.

In one embodiment, the present invention provides a recombinant polynucleotide comprising a nucleic acid encoding CYP76AD15. In one embodiment, the nucleic acid sequence encoding CYP76AD15 comprises:

(SEQ ID NO: 35)
```
tttgtctattattggctcaaaatccactactatcttttgtaaaagaaaa tagttgttcaacttagggaattattgatatttcattatggaaaacacaat gttaggtgttatcctagcaaccattttcctcactttcacataatgaaga tgttatttagtccttccaaggttaaactaccccgggtccgagaccattg ccaattattggtaatattctcgagcttggggataaaccacatcgttattt gcaaaccttgcgaaaattcacggtcctttagttactttgaaactcgggag tgtaaccactattgtggtttcctcttctgaagttgctaaagaaatgtttt tgaaaaatgaccaacctttggcaaatcgtaccatacctgactcagtaaga
```

-continued
```
gcaggtaaccatgacaaactatcaatgtcgtggttgcctgtatcacccaa
atggcgaaatcttagaaagatttcagccgtccaattgactcaactcaacg
acttgatgcaagtcaagctcatagacaagctaaaatcaaacaacttattg
agtacgtaaaaaaatgcagtaaaatcggccaatacgtcgatattggccaa
gttgcattcactacatcacttaatttactatcaaacacattcttttcaaa
agaactagcatcatttgattcagataatgcacaagagttcaaacaactaa
tgtggtgcattatggaagaaattggtaggcctaattatgccgattatttt
cctatcttgggttatgtcgatccattcggtgctagacgtcgactttacgt
tacttcgatcaactaattgaagtatttcaagtgattattcgtgagagact
tacacatgataataatattgtgggtaataacaatgatgttttagctacgt
tgctcgatattataaacaaaacgagttaactatggatgaaatcaaccatt
tactagtggacattttttgatgctggtacggatacaacagcaagtacacta
gaatgggcaatgtcagagctcataaaaaatccacacataatggccaaagc
tcaagaggaggtccggcgagccaccatgtctcacggcggagctacggtgg
cggaaatacaagaatcggatatcaataatcttccatacatacaatctatt
attaaagaaacacttcgtttacacccaccaactgtgtttttacttcctag
aaaagctgacgtggatgtccaattattcggctatgtggtccccaaaaatg
ctcaagtcctagtcaatttatgggccattggtcgtgacccaaatgtgtgg
cccgacccggaagttttttagtcccgaaagatttatggattgtgagattga
tgtcaagggtcgtgattttgagctattgcctttcggggcgggtcgtcgga
tttgtccggattgtattggcttatcggatgcttaatttgatgttggcta
atatggtacattatttgattggaaattaccggtgttgaaaatggatccg
ggtcggaaatggatagtttggatatggatgagaaatttggtatcactttg
caaaaggttcaacccct taaggttattcctgtctcaaggaaatagatgga
agatcgatggttgggagataatcatattgttttttaattattgttggtgta
ttttattgttattattggggacaattttataataaaagatataaataagt
tcctaattgtgatttatattgtgaattttctagttaatataaatacatat
gaatatttatgatgaaaaaaaaaaaaaaaaaaaagg.
```

In another embodiment, a polynucleotide of the present invention comprises a nucleic acid sequence encoding BvCYP76new, as described in Example 3. In another embodiment, a polynucleotide of the present invention comprises a nucleic acid sequence encoding MjCYP76 from *M. jalapa* (SEQ ID NO: 1). In one embodiment, CYP76AD15, BvCYP76new or MjCYP76 may be used in the compositions and methods of the present invention. In another embodiment, other cytochrome P450-encoding genes co-expressed with one or more of the known betalain related genes used as baits may be used in the compositions and methods of the present invention. In one embodiment, CYP82G1-like (SEQ ID NO: 36), CYP78A9-like (SEQ ID NO: 37), CYP86B1-like (SEQ ID NO: 38), or a combination thereof may be used in the compositions and methods of the present invention. In one embodiment, may be used in place of CYP76AD6.

In one embodiment a polynucleotide of the present invention comprises a nucleic acid sequence encoding CYP76AD1. In one embodiment a polynucleotide of the present invention optionally comprises a nucleic acid sequence encoding CYP76AD1. In one embodiment, the nucleic acid sequence of CYP76AD1 is as set forth in SEQ ID NO: 32. In another embodiment, the CYP76AD1 utilized in methods and compositions of the present invention is a homologue of SEQ ID NO: 32. In another embodiment, the CYP76AD1 utilized in methods and compositions of the present invention is a variant of SEQ ID NO: 32. In another embodiment, the CYP76AD1 utilized in methods and compositions of the present invention is a fragment of SEQ ID NO: 32. In another embodiment, the CYP76AD1 utilized in methods and compositions of the present invention is an isoform of SEQ ID NO: 32. In another embodiment, the CYP76AD1 utilized in methods and compositions of the present invention is a functional homologue, functional variant, functional fragment, or functional isoform of SEQ ID NO: 32.

In another embodiment, a polynucleotide of the present invention comprises a nucleic acid sequence encoding CYP76AD3 (SEQ ID NO: 4), as described in Example 9. In one embodiment, CYP76AD3 may be used instead of CYP76AD1 in the compositions and methods of the present invention.

In one embodiment a polynucleotide of the present invention comprises a nucleic acid sequence encoding *Beta vulgaris* DODA1 (BvDODA1). In one embodiment a polynucleotide of the present invention optionally comprises a nucleic acid sequence encoding BvDODA1. In one embodiment, the nucleic acid sequence of BvDODA1 is as set forth in SEQ ID NO: 33. In another embodiment, the BVDODA1 utilized in methods and compositions of the present invention is a homologue of SEQ ID NO: 33. In another embodiment, the BVDODA1 utilized in methods and compositions of the present invention is a variant of SEQ ID NO: 33. In another embodiment, the BVDODA1 utilized in methods and compositions of the present invention is a fragment of SEQ ID NO: 33. In another embodiment, the BVDODA1 utilized in methods and compositions of the present invention is an isoform of SEQ ID NO: 33. In another embodiment, the BVDODA1 utilized in methods and compositions of the present invention is a functional homologue, functional variant, functional fragment, or functional isoform of SEQ ID NO: 33.

In another embodiment, the DOD enzyme is PgDOD from *Portulaca grandiflora* (Accession No. AJ580598; SEQ ID NO: 39), MjDOD from *Mirabilis jalapa* (Accession No. AB435372; SEQ ID NO: 3), BgDOD from *Bougainvillea glabra* (Accession No. AB435373; SEQ ID NO: 40), or AmDOD from *Amanita muscaria* (Accession No. P87064; SEQ ID NO: 41).

In one embodiment, a polynucleotide of the present invention comprises a nucleic acid sequence encoding cyclo-DOPA 5-O-glucosyltransferase (cDOPA5GT). In one embodiment, a polynucleotide of the present invention optionally comprises a nucleic acid sequence encoding cDOPA5GT. In one embodiment, the nucleic acid sequence of cDOPA5GT is as set forth in SEQ ID NO: 2. In another embodiment, the cDOPA5GT utilized in methods and compositions of the present invention is a homologue of SEQ ID NO: 2. In another embodiment, the cDOPA5GT utilized in methods and compositions of the present invention is a variant of SEQ ID NO: 2. In another embodiment, the cDOPA5GT utilized in methods and compositions of the present invention is a fragment of SEQ ID NO: 2. In another embodiment, the cDOPA5GT utilized in methods and compositions of the present invention is an isoform of SEQ ID NO: 2. In another embodiment, the cDOPA5GT utilized in methods and compositions of the present invention is a functional homologue, functional variant, functional fragment, or functional isoform of SEQ ID NO: 2.

In one embodiment, "variant" refers to an amino acid or nucleic acid sequence (or in other embodiments, an organism or tissue) that is different from the majority of the population but is still sufficiently similar to the common mode to be considered to be one of them, for example splice variants. In one embodiment, the variant may a sequence conservative variant, while in another embodiment, the variant may be a functional conservative variant. In one embodiment, a variant may comprise an addition, deletion or substitution of 1 amino acid. In one embodiment, a variant may comprise an addition, deletion, substitution, or combination thereof of 2 amino acids. In one embodiment, a variant may comprise an addition, deletion or substitution, or combination thereof of 3 amino acids. In one embodiment, a variant may comprise an addition, deletion or substitution, or combination thereof of 4 amino acids. In one embodiment, a variant may comprise an addition, deletion or substitution, or combination thereof of 5 amino acids. In one embodiment, a variant may comprise an addition, deletion or substitution, or combination thereof of 7 amino acids. In one embodiment, a variant may comprise an addition, deletion or substitution, or combination thereof of 10 amino acids. In one embodiment, a variant may comprise an addition, deletion or substitution, or combination thereof of 2-15 amino acids. In one embodiment, a variant may comprise an addition, deletion or substitution, or combination thereof of 3-20 amino acids. In one embodiment, a variant may comprise an addition, deletion or substitution, or combination thereof of 4-25 amino acids.

In one embodiment, the term "fragment" is used herein to refer to a protein or polypeptide that is shorter or comprises fewer amino acids than the full length protein or polypeptide. In another embodiment, fragment refers to a nucleic acid that is shorter or comprises fewer nucleotides than the full length nucleic acid. In another embodiment, the fragment is an N-terminal fragment. In another embodiment, the fragment is a C-terminal fragment. In one embodiment, the fragment is an intrasequential section of the protein, peptide, or nucleic acid. In another embodiment, the fragment is a functional section within the protein, peptide or nucleic acid.

In one embodiment, "isoform" refers to a protein isoform or a gene isoform. In one embodiment, a protein isoform is a different form of a protein coded from the same gene, or a protein from a different gene with amino acid sequence and functional similarities. In one embodiment, a gene isoform is an mRNA that is produced from the same locus but has different transcription start sites (TSSs), protein coding DNA sequences (CDSs) and/or untranslated regions (UTRs). In one embodiment, the gene isoform has altered activity, while in another embodiment, the gene isoform does not have altered activity. Thus, in one embodiment, an isoform is an alternate version of a molecule, for example, a protein, that has the same function as the first molecule but which may have small differences in its structure or sequence. In one embodiment, isoforms may be produced from different but related genes, or in another embodiment, may arise from the same gene by alternative splicing. In another embodiment, isoforms are caused by single nucleotide polymorphisms.

In one embodiment, "functional" within the meaning of the invention, is used herein to refer to the innate ability of a protein, peptide, nucleic acid, fragment or a variant thereof to exhibit a biological activity or function. In one embodiment, such a biological function is its binding property to an interaction partner, e.g., a membrane-associated receptor, and in another embodiment, its trimerization property. In the case of functional fragments and the functional variants of the invention, these biological functions may in fact be changed, e.g., with respect to their specificity or selectivity, but with retention of the basic biological function.

Numerous methods for measuring the biological activity of a protein, polypeptide, or molecule are known from the related art, for example, protein assays, which use labeled substrates, substrate analyses by chromatographic methods, such as HPLC or thin-layer chromatography, spectrophotometric methods, etc. (see, e.g., Maniatis et al. (2001) Molecular Cloning: A Laboratory Manual, Cold Spring Harbor Laboratory Press, Cold Spring Harbor, N.Y.).

Expression Vectors

In another embodiment, the present invention provides an expression vector comprising any of the polynucleotides of the present invention as described herein.

In another embodiment, the present invention provides an expression vector comprising a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame.

In another embodiment, the present invention provides an expression vector comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In another embodiment, the present invention provides an expression vector comprising a recombinant polynucleotide comprising a nucleic acid encoding CYP76AD1, CYP76AD6, CYP76AD15, or a combination thereof, a nucleic acid encoding a DOPA 4,5-dioxygenase (DOD) enzyme, and, optionally, a nucleic acid sequence encoding a betalain related glucosyltransferase, expressed in tandem.

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancer) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In one embodiment, viral vectors of the present invention overexpress the pathway genes described herein. In another embodiment, viral infection of cells expressing the pathway genes described herein induces the cells to overexpress the pathway genes.

In some embodiments, non-bacterial expression systems are used (e.g. mammalian expression systems such as CHO cells) to express the polypeptide of the present invention. In one embodiment, the expression vector used to express polynucleotides of the present invention in mammalian cells is pCI-DHFR vector comprising a CMV promoter and a neomycin resistance gene.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of E. coli expression vectors (Studier et al., Methods in Enzymol. 185:60-89 1990).

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods include, for example, stable or transient transfection, lipofection, electroporation and infection with recombinant viral vectors.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in *E. coli*; or retained on the outer surface of a cell or viral membrane.

Compositions

In another embodiment, the present invention provides a composition comprising one or more recombinant polynucleotides as described herein. In another embodiment, the present invention provides a composition comprising recombinant nucleic acids as described herein.

In one embodiment, the present invention provides a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame, wherein said nucleic acids are in the same reading frame.

In another embodiment, the present invention provides a composition comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In another embodiment, the present invention provides an expression vector comprising a recombinant polynucleotide as described herein.

In another embodiment, the present invention provides a composition comprising an expression vector comprising a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame, wherein said nucleic acids are in the same reading frame.

In another embodiment, the present invention provides a composition comprising an expression vector comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In one embodiment, provides a composition comprising a recombinant polynucleotide or a chimeric polypeptide of the present invention. In one embodiment, the polypeptides and polynucleotides of the present invention can be provided to the individual per se.

In another embodiment, the present invention provides a cell comprising an expression vector or a recombinant polynucleotide as described herein. In another embodiment, the present invention provides a composition comprising a cell as described herein.

Cells

In another embodiment, the present invention provides a cell comprising a recombinant polynucleotide as described herein. In another embodiment, the present invention provides a cell comprising an expression vector as described herein.

In another embodiment, the present invention provides a cell comprising a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame.

In another embodiment, the present invention provides a cell comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In another embodiment, the present invention provides a cell comprising a recombinant polynucleotide comprising a nucleic acid encoding CYP76AD1, CYP76AD6, CYP76AD15, or a combination thereof, a nucleic acid encoding a DOPA 4,5-dioxygenase (DOD) enzyme, and, optionally, a nucleic acid sequence encoding a betalain related glucosyltransferase, expressed in tandem.

In another embodiment, the present invention provides a cell comprising an expression vector comprising a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame.

In another embodiment, the present invention provides a cell comprising an expression vector comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In another embodiment, the present invention provides a cell comprising an expression vector comprising a recombinant polynucleotide comprising a nucleic acid encoding CYP76AD1, CYP76AD6, CYP76AD15, or a combination thereof, a nucleic acid encoding a DOPA 4,5-dioxygenase (DOD) enzyme, and, optionally, a nucleic acid sequence encoding a betalain related glucosyltransferase, expressed in tandem.

In one embodiment, when the genes of the invention can be transformed into a plant cell, a plant cell suspension culture may be produced. In one embodiment, the plant cell is a plant stem cell. Betalain, L-DOPA, or a combination thereof can be isolated from plant suspension culture. Method for making plant cell suspension culture are well known in the art and fully described in U.S. Patent Application Publications US 2014/0051135; US 2011/0251408; US 2010/0159545; and US 2007/0026506, which are incorporated by reference herein in their entirety.

In one embodiment, the plant cells are selected from tobacco (*Nicotiana tabacum*), tomato (*Solanum lycopersicum*), potato (*Solanum tuberosum*), eggplant (*Solanum melongena*), tree tobacco (*Nicotiana glauca*), European black nightshade (*Solanum nigrum*), *Petunia* (*Petunia* x *hybrida*) and *Nicotiana benthamiana* cells. In another embodiment, the plant cells are from any of the plants described hereinbelow.

In one embodiment in which polynucleotides are introduced into plant cells, the plant cells may be derived from any plant organ of interest, as described hereinbelow. In one embodiment, the polynucleotide is introduced into a portion of a plant organ. In one embodiment, the polynucleotide is introduced into a portion of a flower. In one embodiment, the portion of the flower is the petal, stamen, anther, stigma, or a combination thereof.

This invention also provides methods for manufacturing transgenic seed that can be used to produce a crop of transgenic plants with an enhanced trait resulting from expression of a stably-integrated recombinant DNA construct.

In another embodiment, cells of the present invention are cells from a micro-organism. In another embodiment, the cell is a yeast cell. In one embodiment, the yeast cell is a *Saccharomyces cerevisiae* cell. In another embodiment, the cell of the present invention is a bacterial cell. In one embodiment, the bacterial cell is an *Escherichia coli* cell. In another embodiment, the cell is an *Acremonium rutilum, Aspergillus oryzae, Yarrowia ijpolytica, Bacillus* sp. JPJ, *Brevundimonas* sp. SGJ, *E. herbicola, Citrobacter freundii, Symbiobacterium,* or *Pseudomonas aeruginosa* cell. In another embodiment, the bacterial cell is from a bacterium involved in fermentation of dairy products. In one embodiment, the bacterium is *Streptococcus lactis*. In another embodiment, the bacterium is a *Lactobacillus*. In one embodiment, the *Lactobacillus* is *Lactobacillus bulgaricus*. In another embodiment, the bacterium is a *Lactococcus* or a *Leuconostoc*.

Plants and Plant Parts

In another embodiment, the present invention provides a plant or part thereof produced by a method of increasing the levels of one or more betalains or L-DOPA in a plant or in a plant part comprising causing or allowing the expression of a DOPA 4,5-dioxygenase (DOD) enzyme, CYP76AD6, CYP76AD15, or a combination thereof, CYP76AD1, or a combination thereof, within said plant or plant part. In one embodiment, a plant expressing DOD and CYP76AD1 and not CYP76AD6 or CYP76AD15, also expresses a betalain related glucosyltransferase.

In one embodiment, the plant does not naturally produce betalains. In another embodiment, the plant produces low levels of betalains. In another embodiment, the plant does not naturally produce detectable levels of betalains.

In another embodiment, plants or plant parts as described herein naturally produce betalains; however, the genetically modified plant or plant parts have an altered level of betalains or of a particular betalain, thereby altering the color and/or properties of the genetically modified plant. In one embodiment, altered levels of betalains are increased levels. In another embodiment, altered levels of betalains are decreased levels.

In another embodiment, the present invention provides a plant or part thereof comprising a nucleic acid sequence encoding CYP76AD1, a nucleic acid sequence encoding CYP76AD6, CYP76AD15, or a combination thereof, a nucleic acid sequence encoding DOPA 4,5-dioxygenase (DOD) enzyme, or a combination thereof.

In another embodiment, betalains or L-DOPA are produced as described herein in a whole plant. In one embodiment, a seed is genetically modified such that betalains or L-DOPA are produced in a whole plant. In another embodiment, betalains or L-DOPA are produced in a particular organ of a plant. In another embodiment, betalains or L-DOPA are produced in a section of an organ of a plant. For example, betalains or L-DOPA may be produced in some plant cells in the leaf or other organ of a plant.

In another embodiment, the present invention provides an ornamental plant produced by a method of increasing the levels of one or more betalains in a plant or in a plant part thereof comprising causing or allowing the expression of a DOPA 4,5-dioxygenase (DOD) enzyme and CYP76AD6, CYP76AD15, or a combination thereof, CYP76AD1, or a combination thereof, within said plant or plant part. In one embodiment, if the ornamental plant expresses CYP76AD1 and DOD and not CYP76AD6 or CYP76AD15, it further expresses a betalain related glucosyltransferase.

In another embodiment, the present invention provides an ornamental plant comprising a nucleic acid sequence encoding CYP76AD1, CYP76AD6, CYP76AD15, or a combination thereof, and a nucleic acid sequence encoding DOPA 4,5-dioxygenase (DOD) enzyme.

In one embodiment, different parts or organs of an organism of the present invention comprise different pigmentation due to the expression of multiple cytochrome P450s (e.g., CYP76AD6, CYP76AD1) under different, non-constitutive promoter sequences (e.g. fruit-specific, flower-specific or inducible promoters). In one embodiment, the organism is a plant and the different pigmentation are in different parts of the plant. In one embodiment, the plant is an ornamental plant.

In another embodiment, the present invention provides a food crop produced by a method of increasing the levels of one or more betalains in a plant or part thereof that serves as a food crop comprising causing or allowing the expression of a DOPA 4,5-dioxygenase (DOD) enzyme and CYP76AD6, CYP76AD15, or a combination thereof, CYP76AD1, or a combination thereof, within said plant or part thereof. In one embodiment, if the food crop expresses CYP76AD1 and DOD and not CYP76AD6 or CYP76AD15, it further expresses a betalain related glucosyltransferase.

In another embodiment, the present invention provides plant or part thereof that serves as a food crop comprising a nucleic acid sequence encoding CYP76AD1, CYP76AD6, CYP76AD15, or a combination thereof, and a nucleic acid sequence encoding DOPA 4,5-dioxygenase (DOD) enzyme.

In one embodiment, the compositions and method of the present invention comprise one or more plant parts. In one embodiment, a plant part as described herein is a plant organ. In one embodiment, the plant part is a leaf, stem, root, flower, seed, tuber, or fruit. In one embodiment, the plant part is the edible portion of the plant. In one embodiment, the compositions and method of the present invention comprise one or more portions of one or more plant parts. In one embodiment, the portion of the plant part is a portion of a flower. In one embodiment, the portion of the flower is the petal, stamen, anther, or stigma.

In one embodiment, CYP76AD6, CYP76AD15, or a combination thereof, and other genes of the invention described herein can be transformed into a plant or a plant cell. The term "plant," as used herein may relate to any monocot or dicot plant. Examples of monocot plants include, but are not limited to, corn, wheat, rice, sugar cane, and banana. Examples of dicot plants include, but are not limited to, soybean, beans, peas, lentils, peanuts, tomatoes, potatoes, cotton, and perennial fruit trees including grapes, apple, and orange.

In one embodiment, the plant is tobacco (*Nicotiana tabacum*), tomato (*Solanum lycopersicum*), potato (*Solanum tuberosum*), eggplant (*Solanum melongena*), tree tobacco (*Nicotiana glauca*), European black nightshade (*Solanum nigrum*), Petunia (*Petunia* x *hybrida*) or *Nicotiana benthamiana*. In another embodiment, the plant is *B. vulgaris*. In another embodiment, the plant is *Mirabilis jalapa*.

In one embodiment, a plant of the present invention is a crop plant. In one embodiment, the crop plant is *Solanum tuberosum* (Potato). In another embodiment, the crop plant is *Zea mays* (Maize). In another embodiment, the crop plant is *Oryza sativa* (Rice). In another embodiment, the crop plant is *Manihot esculenta* (Cassava). In another embodiment, the crop plant is *Hordeum vulgare* (Barley). In another embodiment, the crop plant is *Triticum aestivum* (Wheat). In another embodiment, the crop plant is *Sorghum bicolor*. In another embodiment, the crop plant is *Brassica napus* (Rapeseed). In another embodiment, the crop plant is *Ricinus communis* (Castor). In another embodiment, the crop plant is *Phaseolus vulgaris* (Bean). In another embodiment, the crop plant is *Gossypium histrum* (Cotton). In another embodiment, the crop plant is *Glycine max* (Soybean). In another embodiment, the crop plant is *Beta vulgaris* (Beet). In another embodiment, the crop plant is Musa acuminate (Banana). In another embodiment, the crop plant is *Capsicum annuum* (Sweet and Chili Peppers). In another embodiment, the crop plant is *Cicer arietinum* (Chick pea). In another embodiment, the crop plant is *Solanum lycopersicum* (Tomato). In another embodiment, the crop plant is *Elaeis guineensis* (African oilpalm). In another embodiment, the crop plant is *Setaria italic* (Foxtail millet).

In another embodiment, a plant of the present invention is a bamboo, which in one embodiment is river cane (*Arundinaria gigantea*) and switch cane (*Arundinaria tecta*). In another embodiment, the plant is a *Lemna*.

In another embodiment, a plant of the present invention is a moss. In one embodiment, the moss is a Sphagnum. In one embodiment, the Sphagnum species is *cristatum* or *subnitens*. In one embodiment, the moss is used for peat. In one embodiment, peat is used for fuel, as a horticultural soil additive, and in smoking malt in the production of Scotch whisky. In another embodiment, the moss is used for decorative purposes, such as in gardens and in the florist trade. In another embodiment, the moss is used as insulation. In another embodiment, the moss is used as an absorber of liquids. In another embodiment, moss is used for first-aid dressings, for diapers or napkins. In another embodiment, the moss is a *Physcomitrella patens*. In another embodiment, the moss is a *Fontinalis antipyretica* which, in one embodiment, is used to subdue fires.

Plants included in the invention are any plants amenable to transformation techniques, including gymnosperms and angiosperms, both monocotyledons and dicotyledons.

Examples of monocotyledonous angiosperms include, but are not limited to, asparagus, field and sweet corn, barley, wheat, rice, sorghum, onion, pearl millet, rye and oats and other cereal grains.

Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

In another embodiment, any species of woody, ornamental or decorative, crop or cereal, fruit or vegetable plant, and algae (e.g., *Chlamydomonas reinhardtii*) may be used in the compositions and methods provided herein. Non-limiting examples of plants include plants from the genus *Arabidopsis* or the genus *Oryza*. Other examples include plants from the genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Peryea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

Examples of woody species include poplar, pine, sequoia, cedar, oak, etc.

In certain embodiments, plants of the present invention are crop plants (for example, cereals and pulses, maize, wheat, potatoes, tapioca, rice, sorghum, millet, cassava, barley, pea, and other root, tuber, or seed crops). Exemplary cereal crops used in the compositions and methods of the invention include, but are not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). Grain plants that provide seeds of interest include oil-seed plants and leguminous plants. Other seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Other important seed crops are oil-seed rape, sugar beet, maize, sunflower, soybean, and sorghum. Leguminous plants include beans and peas. Beans include guar, locust bean, fenugreek, soybean, garden beans, cowpea, mungbean, lima bean, fava bean, lentils, chickpea, etc.

Horticultural plants to which the present invention may be applied may include lettuce, endive, and vegetable brassicas including cabbage, broccoli, and cauliflower, and carnations and geraniums. The present invention may also be applied to tobacco, cucurbits, carrot, strawberry, sunflower, tomato, pepper, *chrysanthemum*, poplar, *eucalyptus*, and pine.

The present invention may be used for transformation of other plant species, including, but not limited to, canola (*Brassica napus, Brassica rapa* ssp.), alfalfa (*Medicago sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), tree tobacco (*Nicotiana glauca*), peanuts (*Arachis hypogaea*), cotton (*Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), tomato (*Solanum lycopersicum*), eggplant (*Solanum melongena*), European black nightshade (*Solanum nigrum*), *Petunia* (*Petunia* x *hybrida*), oats, barley, millet, fruit, vegetables, ornamentals, turfgrass, and conifers.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant. Plant extracts and derivatives are also provided.

Throughout this application a plant, plant part, seed or plant cell transformed with—or interchangeably transformed by—a construct or transformed with or by a nucleic acid is to be understood as meaning a plant, plant part, seed or plant cell that carries said construct or said nucleic acid as a transgene due the result of an introduction of said construct or said nucleic acid by biotechnological means. The plant, plant part, seed or plant cell therefore comprises said recombinant construct or said recombinant nucleic acid. Any plant, plant part, seed or plant cell that no longer contains said recombinant construct or said recombinant nucleic acid after introduction in the past, is termed null-segregant, nullizygote or null control, but is not considered a plant, plant part, seed or plant cell transformed with said construct or with said nucleic acid within the meaning of this application.

In one embodiment, tyrosine is endogenous to an organism or part of an organism of the present invention. In another embodiment, an organism or part of an organism of the present invention synthesizes tyrosine. In another embodiment, an organism or part of an organism of the present invention is genetically modified to produce tyrosine. In another embodiment, an organism or part of an organism of the present invention is provided or fed with tyrosine. In another embodiment, an organism or part of an organism that comprises endogenous tyrosine is genetically modified as described herein in order to produce larger amounts of tyrosine, thereby increasing L-DOPA or betalain production. In another embodiment, an organism or part of an organism that comprises endogenous tyrosine is fed tyrosine in order to have larger amounts of available tyrosine, thereby increasing L-DOPA or betalain production.

Methods of Extracting L-DOPA and Betalains

In one embodiment, methods of the present invention further provide methods of extracting L-DOPA or betalains as described hereinbelow in Example 1 as well as using other L-DOPA or betalain extraction methods known in the art, such as, for example, Misra and Wagner (Indian J Biochem Biophys. 2007 February; 44(1):56-60), which is incorporated by reference herein in its entirety.

In another embodiment, L-DOPA or betalains are extracted from algae, yeast or bacterial culture using methods known in the art.

In another embodiment, the present invention provides a method of harvesting L-DOPA or betalains comprising the steps of producing L-DOPA or betalains as described herein and further comprising the step of extracting said L-DOPA or said betalain from the plant, plant part, colony, organ, tissue or cells that produce said L-DOPA or said betalain. In one embodiment, the plant part is a leaf, stem, root, flower, seed, tuber, or fruit.

In one embodiment, the L-DOPA or betalain is extracted from the root of a plant. In one embodiment, L-DOPA or betalain is secreted through the roots of a plant to a liquid or other medium and then harvested from the liquid or other medium. In another embodiment, the L-DOPA or betalain is extracted from the medium of a plant cell suspension, such as BY2 tobacco.

In another embodiment, L-DOPA or betalain is extracted from a water plant. In one embodiment, the water plant is a *Lemna*. In one embodiment, the *Lemna* is *Lemna aequinoctialis*; *Lemna perpusilla*; *Lemna*; *Lemna gibba*; *Lemna minor*; *Lemna trisulcaUninerves*; *Lemna minuta*; *Lemna valdiviana*; *Lemna japonica*; *Lemna obscura*; *Lemna tenera*; *Lemna turionfera*; *Lemna yungensis*, or a combination thereof.

Polypeptides

In one embodiment, the present invention provides a chimeric polypeptide encoded by a recombinant polynucleotide comprising a nucleic acid encoding CYP76AD6. In one embodiment, the amino acid sequence encoding CYP76AD6 comprises:

(SEQ ID NO: 18)
MDNATLAVILSILFVFYHIFKSFFTNSSSRRLPPGPKPVPIFGNIFDLGE

KPHRSFANLSKIHGPLISLKLGSVTTIVVSSASVAEEMFLKNDQALANRT

IPDSVRAGDHDKLSMSWLPVSQKWRNMRKISAVQLLSNQKLDASQPLRQA

KVKQLLSYVQVCSEKMQPVDIGRAAFTTSLNLLSNTFFSIELASHESSAS

QEFKQLMWNIMEEIGRPNYADFFPILGYIDPFGIRRRLAGYFDKLIDVFQ

DIIRERQKLRSSNSSGAKQTNDILDTLLKLHEDNELSMPEINHLLVDIFD

AGTDTTASTLEWAMAELVKNPEMMTKVQIEIEQALGKDCLDIQESDISKL

PYLQAIIKETLRLHPPTVFLLPRKADNDVELYGYVVPKNAQVLVNLWAIG

RDPKVWKNPEVFSPERFLDCNIDYKGRDFELLPFGAGRRICPGLTLAYRM

LNLMLATLLQNYNWKLEDGINPKDLDMDEKFGITLQKVKPLQVIPVPRN.

In another embodiment, the present invention provides a chimeric polypeptide encoded by a recombinant polynucleotide comprising a nucleic acid encoding CYP76ADL. In one embodiment, the amino acid sequence encoding CYP76AD1 comprises:

(SEQ ID NO: 14)
MDHATLAMILAIWFISFHFIKLLFSQQTTKLLPPGPKPLPIIGNILEVGK

KPHRSFANLAKIHGPLISLRLGSVTTIVVSSADVAKEMFLKKDHPLSNRT

IPNSVTAGDHHKLTMSWLPVSPKWRNFRKITAVHLLSPQRLDACQTFRHA

KVQQLYEYVQECAQKGQAVDIGKAAFTTSLNLLSKLFFSVELAHHKSHTS

QEFKELIWNEVIEDIGKPNYADYFPILGCVDPSGIRRRLACSFDKLIAVF

QGIICERLAPDSSTTTTTTDDVLDVLLQLFKQNELTMGEINHLLVDIFD

AGTDTTSSTFEWVMTELIRNPEMMEKAQEEIKQVLGKDKQIQESDIINLP

YLQAIIKETLRLHPPTVFLLPRKADTDVELYGYIVPKDAQILVNLWAIGR

-continued

DPNAWQNADIFSPERFIGCEIDVKGRDFGLLPFGAGRRICPGMNLAIRML

TLMLATLLQFFNWKLEGDISPKDLDMDEKFGIALQKTKPLKLIPIPRY.

In another embodiment, the present invention provides a chimeric polypeptide encoded by a recombinant polynucleotide comprising a nucleic acid encoding a DOPA 4,5-dioxygenase (DOD) enzyme. In one embodiment, the DOD enzyme is *Beta vulgaris* DODA1 (BvDODA1). In one embodiment, the amino acid sequence encoding BvDODA1 comprises:

(SEQ ID NO: 42)
MKMMNGEDANDQMIKESFFITHGNPILTVEDTHPLRPFFETWREKIFSKK

PKAILIISGHWETVKPTVNAVHINDTIHDFDDYPAAMYQFKYPAPGEPEL

ARKVEEILKKSGFETAETDQKRGLDHGAWVPLMLMYPEADIPVCQLSVQP

HLDGTYHYNLGRALAPLKNDGVLIIGSGSATHPLDETPHYFDGVAPWAAA

FDSWLRKALINGRFEEVNIYESKAPNWKLAHPFPEHFYPLHVVLGAAGEK

WKAELIHSSWDHGTLCHGSYKFTSA.

In one embodiment, the present invention provides a chimeric polypeptide encoded by a recombinant polynucleotide comprising a nucleic acid encoding cyclo-DOPA 5-O-glucosyltransferase (cDOPA5GT). In one embodiment, the amino acid sequence encoding cDOPA5GT comprises:

(SEQ ID NO: 43)
MTAIKMNTNGEGETQHILMIPFMAQGHLRPFLELAMFLYKRSHVIITLLT

TPLNAGFLRHLLHHHSYSSSGIRIVELPFNSTNHGLPPGIENTDKLTLPL

VVSLFHSTISLDPHLRDYISRHFSPARPPLCVIHDVFLGWVDQVAKDVGS

TGVVFTTGGAYGTSAYVSIWNDLPHQNYSDDQEFPLPGFPENHKFRRSQL

HRFLRYADGSDDWSKYFQPQLRQSMKSFGWLCNSVEEIETLGFSILRNYT

KLPIWGIGPLIASPVQHSSSDNNSTGAEFVQWLSLKEPDSVLYISFGSQN

TISPTQMMELAAGLESSEKPFLWVIRAPFGFDINEEMRPEWLPEGFEERM

KVKKQGKLVYKLGPQLEILNHESIGGFLTHCGWNSILESLREGVPMLGWP

LAAEQAYNLKYLEDEMGVAVELARGLEGEISKEKVKRIVEMILERNEGSK

GWEMKNRAVEMGKKLKDAVNEEKELKGSSVKAIDDFLDAVMQAKLEPSL

Q.

In one embodiment, a polypeptide of the present invention comprises an amino acid sequence encoding CYP76AD6, CYP76AD15, or a combination thereof, and an amino acid sequence encoding CYP76AD1. In another embodiment, a polypeptide of the present invention comprises an amino acid sequence encoding CYP76AD6, CYP76AD15, or a combination thereof, and an amino acid sequence encoding a DOD enzyme. In another embodiment, a polypeptide of the present invention comprises an amino acid sequence encoding CYP76AD1 and an amino acid sequence encoding a DOD enzyme. In another embodiment, a polypeptide of the present invention comprises an amino acid sequence encoding CYP76AD6, CYP76AD15, or a combination thereof, an amino acid sequence encoding CYP76AD1, and an amino acid sequence encoding a DOD enzyme. In another embodiment, a polypeptide of the present invention comprises an amino acid sequence encoding CYP76AD6, CYP76AD15, or a combination thereof, an amino acid sequence encoding CYP76AD1, and an amino acid sequence encoding a betalain related glucosyltransferase. In another embodiment, a polypeptide of the present invention comprises an amino acid sequence encoding CYP76AD6, CYP76AD15, or a combination thereof, an amino acid sequence encoding a DOD enzyme and an amino acid sequence encoding a betalain related glucosyltransferase. In another embodiment, a polypeptide of the present invention comprises an amino acid sequence encoding CYP76AD1, an amino acid sequence encoding a DOD enzyme and an amino acid sequence encoding a betalain related glucosyltransferase. In another embodiment, a polypeptide of the present invention comprises an amino acid sequence encoding CYP76AD6, CYP76AD15, or a combination thereof, an amino acid sequence encoding CYP76AD1, an amino acid sequence encoding a DOD enzyme and an amino acid sequence encoding a betalain related glucosyltransferase.

In another embodiment, any of the polypeptides described hereinabove further comprises a betalain related glucosyltransferase. In one embodiment, the betalain related glucosyltransferase is cyclo-DOPA 5-O-glucosyltransferase or betanidin-5-O-glucosyltransferase. In one embodiment, the cyclo-DOPA 5-O-glucosyltransferase is *M. jalapa* gene cyclo-DOPA 5-O-glucosyltransferase (cDOPA5GT) (SEQ ID NO: 43).

In one embodiment, the present invention provides a chimeric polypeptide encoded by a recombinant polynucleotide as described herein.

In another embodiment, the present invention provides a chimeric polypeptide comprising CYP76AD6, CYP76AD15, or a combination thereof, CYP76AD1, a DOPA 4,5-dioxygenase (DOD) enzyme, a betalain related glucosyltransferase, or a combination thereof, wherein said proteins are expressed in tandem.

In another embodiment, the present invention provides a chimeric polypeptide comprising CYP76AD1, a DOPA 4,5-dioxygenase (DOD) enzyme, and, optionally, a betalain related glucosyltransferase, wherein said proteins are expressed in tandem.

In another embodiment, the present invention provides a chimeric polypeptide comprising CYP76AD6, CYP76AD15, or a combination thereof, and a DOPA 4,5-dioxygenase (DOD) enzyme, wherein said proteins are expressed in tandem.

In another embodiment, the present invention provides a chimeric polypeptide comprising CYP76AD6, CYP76AD15, or a combination thereof, CYP76AD1, or a combination thereof, a DOPA 4,5-dioxygenase (DOD) enzyme, and, optionally a betalain related glucosyltransferase, wherein said proteins are expressed in tandem.

In one embodiment, a "chimeric" or "fusion" polypeptide or protein is a polypeptide or protein created through the joining of two or more genes that originally coded for separate proteins.

It is to be understood that according to the present invention, CYP76AD6 and CYP76AD6-like polypeptides from plants other than *Beta vulgaris* can be used in place of CYP76AD6 from *Beta vulgaris* in the compositions and methods described herein. In one embodiment, the CYP76AD6-like polypeptide is from Caryophyllales. In one embodiment, the CYP76AD6-like polypeptide is a homologue within the CYP76AD1-beta clade, as described in Brockington et al. (2015) (New Phytol. 2015 September; 207(4):1170-80), which is incorporated herein by reference in its entirety.

In one embodiment, CYP76AD15 or a homologue, isoform, or variant thereof, may be used in place of CYP76AD6 in the compositions and methods of the present invention. CYP76AD15 from *Mirabilis jalapa* has a similar function as CYP76AD6 from *Beta vulgaris*. In one embodiment, CYP76AD15 is an enzyme involved in converting tyrosine to L-DOPA. In one embodiment the amino acid sequence of CYP76AD15 comprises:

```
                                          (SEQ ID NO: 44)
MENTMLGVILATIFLTFHIMKMLFSPSKVKLPPGPRPLPIIGNILELG

DKPHRSFANLAKIHGPLVTLKLGSVTTIVVSSSEVAKEMFLKNDQPLA

NRTIPDSVRAGNHDKLSMSWLPVSPKWRNLRKISAVQLLSTQRLDASQ

AHRQAKIKQLIEYVKKCSKIGQYVDIGQVAFTTSLNLLSNTFFSKELA

SFDSDNAQEFKQLMWCIIVIEEIGRPNYADYFPILGYVDPFGARRRLS

RYFDQLIEVFQVIIRERLTHDNNIVGNNNDVLATLLDLYKQNELTMDE

INHLLVDIFDAGTDTTASTLEWAMSELIKNPHIMAKAQEEVRRATMSH

GGATVAEIQESDINNLPYIQSIIKETLRLHPPTVFLLPRKADVDVQLF

GYVVPKNAQVLVNLWAIGRDPNVWPDPEVFSPERFMDCEIDVKGRDFE

LLPFGAGRRICPGLSLAYRMLNLMLANMVHSFDWKLPGVENGSGSEMD

SLDMDEKFGITLQKVQPLKVIPVSRK.
```

In one embodiment, the present invention provides an isolated polypeptide comprising an amino acid sequence encoding CYP76AD6, CYP76AD15, or a combination thereof, or another polypeptide described herein. In another embodiment, the present invention provides a non-naturally occurring polypeptide comprising an amino acid sequence encoding CYP76AD6, CYP76AD15, or a combination thereof, or another polypeptide described herein. In one embodiment, the CYP76AD6, CYP76AD15, or a combination thereof, sequence is a modified sequence. In one embodiment, it is an enhanced sequence. In one embodiment, it is an optimized sequence.

In one embodiment a polypeptide of the present invention optionally comprises CYP76AD6. In one embodiment, the amino acid sequence of CYP76AD6 is as set forth in SEQ ID NO: 18. In another embodiment, the CYP76AD6 utilized in methods and compositions of the present invention is a homologue of SEQ ID NO: 18. In another embodiment, the CYP76AD6 utilized in methods and compositions of the present invention is a variant of SEQ ID NO: 18. In another embodiment, the CYP76AD6 utilized in methods and compositions of the present invention is a fragment of SEQ ID NO: 18. In another embodiment, the CYP76AD6 utilized in methods and compositions of the present invention is an isoform of SEQ ID NO: 18. In another embodiment, the CYP76AD6 utilized in methods and compositions of the present invention is a functional homologue, functional variant, functional fragment, or functional isoform of SEQ ID NO: 18.

In one embodiment a polypeptide of the present invention optionally comprises CYP76AD15. In one embodiment, the amino acid sequence of CYP76AD15 is as set forth in SEQ ID NO: 44. In another embodiment, the CYP76AD15 utilized in methods and compositions of the present invention is a homologue of SEQ ID NO: 44. In another embodiment, the CYP76AD15 utilized in methods and compositions of the present invention is a variant of SEQ ID NO: 44. In another embodiment, the CYP76AD15 utilized in methods and compositions of the present invention is a fragment of SEQ ID NO: 44. In another embodiment, the CYP76AD15 utilized in methods and compositions of the present invention is an isoform of SEQ ID NO: 44.

In another embodiment, the CYP76AD15 utilized in methods and compositions of the present invention is a functional homologue, functional variant, functional fragment, or functional isoform SEQ ID NO: 44.

In one embodiment a polypeptide of the present invention optionally comprises CYP76AD1. In one embodiment, the amino acid sequence of CYP76AD1 is as set forth in SEQ ID NO: 14. In another embodiment, the CYP76AD1 utilized in methods and compositions of the present invention is a homologue of SEQ ID NO: 14. In another embodiment, the CYP76AD1 utilized in methods and compositions of the present invention is a variant of SEQ ID NO: 14. In another embodiment, the CYP76AD1 utilized in methods and compositions of the present invention is a fragment of SEQ ID NO: 14. In another embodiment, the CYP76AD1 utilized in methods and compositions of the present invention is an isoform of SEQ ID NO: 14.

In another embodiment, the CYP76AD1 utilized in methods and compositions of the present invention is a functional homologue, functional variant, functional fragment, or functional isoform of SEQ ID NO: 14.

In one embodiment a polypeptide of the present invention optionally comprises BvDODA1. In one embodiment, the amino acid sequence of BvDODA1 is as set forth in SEQ ID NO: 42. In another embodiment, the BVDODA1 utilized in methods and compositions of the present invention is a homologue of SEQ ID NO: 42. In another embodiment, the BVDODA1 utilized in methods and compositions of the present invention is a variant of SEQ ID NO: 42. In another embodiment, the BVDODA1 utilized in methods and compositions of the present invention is a fragment of SEQ ID NO: 42. In another embodiment, the BVDODA1 utilized in methods and compositions of the present invention is an isoform of SEQ ID NO: 42.

In another embodiment, the BVDODA1 utilized in methods and compositions of the present invention is a functional homologue, functional variant, functional fragment, or functional isoform of SEQ ID NO: 42.

In one embodiment, a polypeptide of the present invention optionally comprises cDOPA5GT. In one embodiment, the amino acid sequence of cDOPA5GT is as set forth in SEQ ID NO: 43. In another embodiment, the cDOPA5GT utilized in methods and compositions of the present invention is a homologue of SEQ ID NO: 43. In another embodiment, the cDOPA5GT utilized in methods and compositions of the present invention is a variant of SEQ ID NO: 43. In another embodiment, the cDOPA5GT utilized in methods and compositions of the present invention is a fragment of SEQ ID NO: 43. In another embodiment, the cDOPA5GT utilized in methods and compositions of the present invention is an isoform of SEQ ID NO: 43.

In another embodiment, the cDOPA5GT utilized in methods and compositions of the present invention is a functional homologue, functional variant, functional fragment, or functional isoform of SEQ ID NO: 43.

In some embodiments, "polypeptide", "engineered polypeptide", or "protein" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides even more stable while in a body or more capable of penetrating into cells.

In some embodiments, modifications include, but are limited to C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)—CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (~CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and in one embodiment at several (2-3 bonds) at the same time.

In some embodiments, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid sequence" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acids.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the engineered polypeptide of the present invention is utilized in a linear form, although it will be appreciated by one skilled in the art that in cases where cyclicization does not severely interfere with engineered polypeptides characteristics, cyclic forms of the engineered polypeptides can also be utilized.

In some embodiments, the engineered polypeptides of the present invention are biochemically synthesized such as by using standard solid phase techniques. In some embodiments, these biochemical methods include exclusive solid phase synthesis, partial solid phase synthesis, fragment condensation, or classical solution synthesis.

In some embodiments, recombinant protein techniques are used to generate the engineered polypeptides of the present invention. In some embodiments, recombinant protein techniques are used for the generation of relatively long polypeptides (e.g., longer than 18-25 amino acids). In some embodiments, recombinant protein techniques are used for the generation of large amounts of the engineered polypeptides of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463, which are incorporated herein by reference in their entirety.

In one embodiment, the present invention provides a chimeric polypeptide comprising a CYP76AD1-β clade polypeptide. In one embodiment, the CYP76AD1-β clade polypeptide is CYP76AD6. In another embodiment, the CYP76AD1-β clade polypeptide is CYP76AD15. In one embodiment, the present invention provides a chimeric polypeptide comprising a CYP76AD1-β clade polypeptide but excluding the amino acid sequence of the CYP76AD1 paralogs from sugar beet known as Bv9_228610_ygeq or Bv9_228860_ickx, which do not produce betaxanthin when transformed into yeast with DOD. In one embodiment, the present invention provides a chimeric polypeptide comprising a CYP76AD1-β clade polypeptide but excluding the following amino acid sequence:

```
                                        (SEQ ID NO: 34)
MDNATLAVILSILFVFYHIFKSFFTNSSSRRLPPGPKPVPIFGNIFDL

GEKPHRSFANLSKIHGPLISLKLGSVTTIVVSSASVAEEMFLKNDQAL

ANRTIPDSVRAGDHDKLSMSWLPVSQKWRNMRKISAVQLLSNQKLDAS

QPLRQTKVKQLLSYVQDCSKKMQPVDIGRAAFTTSLNLLSNTFFSIEL

ASHESSASQEFKQLMWNIMEEIGRPNYADFFPILGYIDPFGIRRRLAG

YFDKLIDVFQDIIRERQKLRSSNSSGAKQTNDILDTLLKLHEDNELSM

PEINHLLVDIFDAGTDTTASTLEWAMAELVKNPEMMTKVQIEIEQALG

KDCLDIQESDISKLPYLQGIIKETLRLHPPTVFLLPRKADNDVELYGY

VVPKNAQVLVNLWAIGRDPKVWKNPEVFSPERFLDCNIDYKGRDFELL

PFGAGRRICPGLTLAYRMLNLMLATLLQNYNWKLEDGINPKDLDMDEK

FGITLQKVKPLQVIPVPRN.
```

In one embodiment, the present invention provides methods comprising the step of "contacting" tyrosine with one or more polypeptides as described herein. In one embodiment, said contacting step is conducted in vitro under conditions which allow the production of L-DOPA or betalains, as described herein.

Polypeptide Recovery

In one embodiment, methods of the present invention further provide methods of extracting betalains or L-DOPA from plants as described hereinbelow in Example 1 as well as using other betalain extraction methods known in the art. In another embodiment, betalains are extracted from algae, yeast or bacterial culture using methods known in the art. In one embodiment, the algae, yeast or bacterial culture are genetically modified to express betalains or L-DOPA.

In one embodiment, following a predetermined time in culture, recovery of a polypeptide is affected.

In one embodiment, the phrase "recovering the polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

Methods of producing betaxanthins in vitro using a DOD enzyme with its substrate L-DOPA and adding amino acids was described in Sekiguchi et al. (2010) (Journal of Agricultural and Food Chemistry 58, 12504-12509), which is incorporated herein by reference in its entirety. In one embodiment, the present method of in vitro synthesis of betalains is as described in Sekiguchi et al. but with the added step of synthesizing L-DOPA from tyrosine rather than providing L-DOPA as described in Sekiguchi et al.

In one embodiment, in vitro production of red-violet betalains (betacyanins) is performed using the same or similar conditions as for the production of betaxanthins, except that the CYP76AD1 enzyme is provided together with the DOD enzyme, and the substrate could be either tyrosine or L-DOPA. In one embodiment, the co-factor NADPH may be added to activate the CYP76AD1 enzyme.

In some embodiments, the recombinant polypeptides are synthesized and purified; their therapeutic efficacy can be assayed in vivo or in vitro.

Pharmaceutical Compositions

In another embodiment, provides a pharmaceutical composition comprising a recombinant polynucleotide or a chimeric polypeptide of the present invention. In one embodiment, the polypeptides and polynucleotides of the present invention can be provided to the individual as part of a pharmaceutical composition where it is mixed with a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the recombinant polynucleotide or the chimeric polypeptide, which is accountable for the biological or biochemical effect.

In other embodiments, the composition comprises additional components. In one embodiment, such additional components may comprise carriers or diluents including, but not limited to, a gum, a starch (e.g. corn starch, pregeletanized starch), a sugar (e.g. lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g. Tris-HCl., acetate, phosphate) of various pH and ionic strength, additives such as albumin or gelatin to prevent absorption to surfaces, detergents (e.g. Tween 20, Tween 80, Pluronic F68, bile acid salts), protease inhibitors, surfactants (e.g. sodium lauryl sulfate), permeation enhancers, solubilizing agents (e.g. glycerol, polyethylene glycerol), anti-oxidants (e.g. ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g. Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g. poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e., compositions in which the antigen is released over a period of time after administration. Controlled- or sustained-release compositions include formulation in lipophilic depots (e.g. fatty acids, waxes, oils). In another embodiment, the composition is an immediate-release composition, i.e., a composition in which all the antigen is released immediately after administration.

In another embodiment, the pharmaceutical composition is delivered in a controlled release system. In another embodiment, the agent is administered using intravenous infusion, an implantable osmotic pump, a transdermal patch, liposomes, or other modes of administration. In another embodiment, a pump is used (see Langer, supra; Sefton, CRC Crit. Ref Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant.

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Each of the above additives, excipients, formulations and methods of administration represents a separate embodiment of the present invention.

In one embodiment, methods of the present invention comprise administering a polynucleotide or polypeptide of the present invention in a pharmaceutically acceptable carrier.

The pharmaceutical compositions containing the polypeptide can be, in another embodiment, administered to a subject by any method known to a person skilled in the art, such as parenterally, transmucosally, transdermally, intramuscularly, intravenously, intra-dermally, intra-nasally, subcutaneously, intra-peritonealy, intra-ventricularly, intra-cranially, or intra-vaginally. In another embodiment, compositions of the instant invention are administered via epidermal injection, in another embodiment, intramuscular injection, in another embodiment, subcutaneous injection, and in another embodiment, intra-respiratory mucosal injection.

In another embodiment, of methods and compositions of the present invention, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment, of the present invention, the composition is formulated in a capsule. In another embodiment, compositions of the present invention comprise a hard gelating capsule.

In another embodiment, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of antigen agent over a period of time.

In another embodiment, the pharmaceutical composition is delivered in a vesicle, e.g. a liposome.

Plant Regeneration

In one embodiment, a transgenic plant of the present invention is grown under conditions suitable for the expression of the recombinant DNA construct or constructs. The regeneration, development and cultivation of plants from single plant protoplast transformants or from various transformed explants is well known in the art (See Weissbach and Weissbach, In.: Methods for Plant Molecular Biology, (Eds.), 1988 Academic Press, Inc., San Diego, Calif). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

Following transformation, plant cells transformed with a plant expression vector may be regenerated, e.g., from single cells, callus tissue or leaf discs according to standard plant tissue culture techniques. Almost any plant can be entirely regenerated from cells, tissues, and organs of the plant using methods that are known in the art.

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

In one embodiment, a plant cell is regenerated to obtain a whole plant from the transformation process. The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension. In one embodiment, the culture media will contain various amino acids and hormones, necessary for growth and regeneration. Examples of hormones utilized include auxins and cytokinins. Efficient regeneration will depend on the medium, on the genotype, and on the history of the culture. If these variables are controlled, regeneration is reproducible. Regeneration also occurs from plant callus, explants, organs or parts.

In vegetatively propagated crops, the mature genetically modified plants are propagated by utilizing cuttings or tissue culture techniques to produce multiple identical plants. Selection of desirable genetically modified plants is made and new varieties are obtained and propagated vegetatively for commercial use.

In seed propagated crops, mature genetically modified plants can be self-crossed to produce a homozygous inbred plant. The resulting inbred plant produces seed containing the genetic mutation. These seeds can be grown to produce plants that would produce the selected phenotype, e.g., increased lateral root growth, uptake of nutrients, overall plant growth and/or vegetative or reproductive yields.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences. In one embodiment, genetically modified plants expressing a selectable marker can be screened for transmission of the nucleic acid of the present invention by, for example, standard immunoblot and DNA detection techniques. In another embodiment, genetically modified plant cells may be evaluated on levels of expression of the genetically modified nucleic acid. Expression at the RNA level can be determined initially to identify and quantitate expression-positive plants. Standard techniques for RNA analysis can be employed and include PCR amplification assays using oligonucleotide primers designed to amplify only the genetically modified RNA templates and solution hybridization assays using genetically modified nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be performed using genetically modified nucleic acid specific polynucleotide probes and antibodies, respectively, to localize sites of expression within genetically modified tissue. In one embodiment, a number of genetically modified lines are screened for the incorporated nucleic acid to identify and select plants with the most appropriate expression profiles.

In one embodiment, the present invention provides a genetically modified plant that is homozygous for the introduced nucleic acid; i.e., a genetically modified plant that contains two added nucleic acid sequences, one gene at the same locus on each chromosome of a chromosome pair. A homozygous genetically modified plant can be obtained by sexually mating (selfing) a heterozygous genetically modified plant that contains a single added genetically modified nucleic acid, germinating some of the seed produced and analyzing the resulting plants produced for altered expression of a polynucleotide of the present invention relative to a control plant (i.e., native, non-genetically modified). Backcrossing to a parental plant and out-crossing with a non-genetically modified plant are also contemplated.

Transformed plant cells which are derived by any of the above transformation techniques can be cultured to regenerate a whole plant which possesses the transformed genotype. In one such, regeneration techniques rely on manipulation of certain phytohormones in a tissue culture growth medium.

The regenerated plants containing the foreign, exogenous gene that encodes a protein of interest can then be further propagated as is well known in the art. The particular method of propagation will depend on the starting plant tissue and the particular plant species to be propagated.

In one embodiment, the generated transformed plants are clonally propagated. In another embodiment, the generated transformed plants are propagated by classical breeding techniques. In a particular embodiment, the regenerated plants are self-pollinated to provide homozygous transgenic plants. Otherwise, pollen obtained from the regenerated plants is crossed to seed-grown plants of agronomically important lines, or pollen from plants of these important lines is used to pollinate regenerated plants. A transgenic plant of the present invention containing a desired polypeptide is cultivated using methods well known to one of skill in the art.

Products of Genetically Modified Plants

In one embodiment, the present invention provides a food crop comprising betalains. In one embodiment, the food crop does not endogenously comprise betalains. In another embodiment, the food crop does endogenously comprise betalains and the methods of the present invention serve to increase or enhance the amount of betalains present in the food crop.

In one embodiment, a food crop comprising betalains or enhanced amounts of betalains is nutritionally enhanced. In one embodiment, a food crop comprising betalains or enhanced amounts of betalains comprises anti-oxidative properties. In one embodiment, consumption of a food crop comprising betalains or enhanced amounts of betalains protects a subject from degenerative diseases or conditions. In one embodiment, consumption of betalains or food crops containing betalains may protect a subject from cancer (e.g. skin, lung, cervical, ovarian and bladder), cardiopathy, or neurodegenerative diseases. Betalains may also inhibit lipid peroxidation and heme decomposition; prevent oxidative hemolysis of red blood cells; and bind to human low-density lipoproteins increasing their resistance to oxidation.

In one embodiment, the present invention provides fruit comprising betalains of the present invention. In another embodiment, the present invention provides vegetables comprising betalains of the present invention. In another embodiment, the present invention provides underground organs, such as potatoes, comprising betalains of the present invention. In another embodiment, the present invention provides juices derived from fruits or vegetables comprising betalains of the present invention.

In one embodiment, the plant organs or derivatives thereof (such as juice) comprise, in addition to betalains of the present invention, natural or engineered anthocyanins, carotenes, or a combination thereof.

In another embodiment, the present invention provides a dietary supplement comprising a betalain produced by the methods as described herein or a plant or plant part as described herein.

In another embodiment, the present invention provides an allelochemical comprising L-DOPA produced by the methods as described herein or a plant or plant part as described herein.

Additional Uses

The heterologous production of betalains enables the biofortification and enhancement of nutritional qualities of essential foods, as well as the development of new varieties of ornamental plants. The simple biosynthetic pathway of these pigments, which starts from the ubiquitous precursor tyrosine and requires expression of two to three genes, allows for the production of these pigments in numerous plant species or other species.

In another embodiment, the present invention provides a method of producing an ornamental plant, comprising the step of: contacting a plant cell with a nucleic acid sequence encoding CYP76AD1, CYP76AD6, CYP76AD15, or a combination thereof, and a nucleic acid sequence encoding DOPA 4,5-dioxygenase (DOD) enzyme and under conditions sufficient to produce betalains, wherein if said cell is contacted with a nucleic acid sequence encoding CYP76AD1 and DOD and not a nucleic acid sequence encoding CYP76AD6 or CYP76AD15, then said cell is contacted with a nucleic acid sequence encoding a betalain related glucosyltransferase, thereby producing an ornamental plant. In one embodiment, the plant is not a naturally betalain-expressing plant. In one embodiment, the plant is not a Cafyophyllales plant. In one embodiment, the species of plant is: *Syngonium Podophyllum, Nephrolepis Exaltata 'Bostoniensis', Phoenix Canariensis, Aglaonema, Asplenium Nidus, Rhapis Excelsa, Aspidistra Elatior, Nertera Granadensis, Pteris Cretica, Dieffenbachia Amoena, Chamaerops Humilis, Epipremnum Aureum, Codiaeum Variegatum, Alocasia Amazonica,* Fiddle Leaf Fig—*Ficus Lyrata, Alocasia Micholitziana, Philodendron Scandens, Dracaena Braunii, Adiantum Raddianum, Chamaedorea Elegans, Howea Forsteriana, Dracaena Marginata, Pachira Aquatica, Calathea Makoyana, Davallia Fejeensis, Calathea Roseopicta, Cycas Revoluta, Dracaena Reflexa, Calathea Lancifolia, Ficus Elastica, Howea Belmoreana,* Spider Plant-*Chlorophytum Comosum, Dionaea Muscipula, Peperomia Argyela, Aphelandra Squarrosa, Zamioculcas Zamiifolia, Tradescantia, Ficus Benjamina, Calathea Zebrina,* or a Cactus.

In one embodiment, changing the color of a plant, and in particular the color of a flower of a plant, will affect the pollination of the plant. In one embodiment, methods of the present invention will increase or enhance the pollination of a plant. In another embodiment, methods of the present invention will decrease the pollination of a plant. In another embodiment, methods of the present invention will change the organisms that are attracted to the plant, thereby changing the pollination of a plant. In one embodiment, the present invention provides a method of increasing the pollination of a plant comprising the step of inserting a recombinant polynucleotide or one or more nucleic acids of the present invention into at least one cell of said plant.

In another embodiment, the present invention provides a method of increasing the pollination of a plant, comprising the step of: contacting a plant with a nucleic acid sequence encoding CYP76AD1, CYP76AD6, CYP76AD15, or a combination thereof, and, optionally, a nucleic acid sequence encoding DOPA 4,5-dioxygenase (DOD) enzyme and under conditions sufficient to produce betalains, thereby changing the color of the plant, thereby increasing the pollination of a plant. In one embodiment, the plant is not a naturally betalain-expressing plant. In one embodiment, the plant is not a Caryophyllales plant.

In another embodiment, the methods of the present invention provide methods of changing the color of an organism. In one embodiment, the organism is a fish.

In another embodiment, the methods of the present invention provide a method of producing an organism in which one or more parts of said organism is red-violet comprising the step of contacting one or more cells of said organism with a recombinant polynucleotide comprising a nucleic acid encoding a CYP76AD1, a nucleic acid encoding a DOPA 4,5-dioxygenase (DOD) enzyme, and a nucleic acid encoding betalain related glucosyltransferase, wherein said nucleic acids are inserted into the polynucleotide in frame.

In another embodiment, the methods of the present invention provide a method of producing an organism in which one or more parts of said organism is yellow comprising the step of contacting one or more cells of said organism with a recombinant polynucleotide comprising a nucleic acid encoding a CYP76AD6 and a nucleic acid encoding a DOPA 4,5-dioxygenase (DOD) enzyme, wherein said nucleic acids are inserted into the polynucleotide in frame.

In another embodiment, the methods of the present invention provide a method of producing an organism in which one or more parts of said organism is orange, comprising the step of contacting one or more cells of said organism with a recombinant polynucleotide comprising a nucleic acid encoding a CYP76AD6, a nucleic acid encoding CYP76AD1, a nucleic acid encoding a DOPA 4,5-dioxygenase (DOD) enzyme, and a nucleic acid encoding betalain related glucosyltransferase, wherein said nucleic acids are inserted into the polynucleotide in frame.

In one embodiment, the organism is a fish. In one embodiment, the fish is an ornamental fish.

In one embodiment, the present invention provides a method of producing an ornamental fish comprising contacting a cell of a fish with a polynucleotide encoding a nucleic acid encoding a DOPA 4,5-dioxygenase (DOD) enzyme and a nucleic acid encoding CYP76AD6, a nucleic acid encoding CYP76AD15, a nucleic acid encoding CYP76AD1, or a combination thereof, wherein if said cell is contacted with a nucleic acid encoding CYP76AD1 and a nucleic acid encoding DOD and not a nucleic acid encoding CYP76AD6 or a nucleic acid encoding CYP76AD15, said cell is also contacted with a nucleic acid encoding a betalain related glucosyltransferase.

In another embodiment, the present invention provides a method of producing a plant expressing a betalain, comprising the step of: contacting one or more cells of said plant with a nucleic acid sequence encoding CYP76AD1, CYP76AD6, CYP76AD15, or a combination thereof, and a nucleic acid sequence encoding DOPA 4,5-dioxygenase (DOD) enzyme, screening said one or more cells to identify cells comprising said nucleic acid sequences, and regenerating plants or plant parts from said cells, thereby producing a plant expressing a betalain.

In one embodiment, the plant does not naturally express a betalain. In another embodiment, the plant expresses a betalain and the methods of the present invention are used to increase the amount of one or more betalains that are expressed by the plant.

In another embodiment, the present invention provides a method of producing a food crop expressing a betalain, comprising the step of: contacting one or more cells of a food crop plant with a nucleic acid sequence encoding CYP76AD1, CYP76AD6, CYP76AD15, or a combination thereof, and a nucleic acid sequence encoding DOPA 4,5-dioxygenase (DOD) enzyme, screening said one or more cells to identify cells comprising said nucleic acid sequences, and regenerating plants or plant parts from said cells, thereby producing a food crop expressing a betalain.

In one embodiment, a "food crop" or an "agricultural crop" is a plant intentionally grown with the primary purpose of being eaten by humans or animals. In one embodiment, the food crop is plantains, yams, sorghum, sweet potatos, soybeans, cassava, rice, wheat, or corn. In another embodiment, the food crop is aubergines, peppers, broccoli, calabrese, buckwheat, maize, barley, grapes, berries, tomatoes, cucumbers, artichoke, onion, rhubarb, blackberries, blueberries, zucchini, radishes, carrots, brussel sprouts, lettuce, melons, beans, peas, grains, peanuts, sugarcane, watermelon, papaya, apple, pear, peach, cherry, strawberry or squash.

In one embodiment, the strong antioxidant activity of betalains is beneficial for human health.

They have been extensively studied for their potential health-promoting properties, including anti-cancer, hypo-lipidemic, anti-inflammatory, hepatoprotective and anti-diabetic activities. Thus, in one embodiment, the present invention provides a method of treating or suppressing cancer, hyperlipidemia, inflammation, liver disease, and diabetes comprising the step of feeding to a subject in need a plant or plant part of the present invention, which expresses betalains, betacyanins, and/or betaxanthins, thereby treating or suppressing cancer, hyperlipidemia, inflammation, liver disease, or diabetes in said subject.

In one embodiment, ingestion by a subject of a food crop of the present invention comprising betalains or enhanced amounts of betalains protect subjects against Inflammatory-Immune Injury (including, but not limited to glomerulonephritis, vasculitis, autoimmune disease, adult respiratory distress syndrome, rheumatoid arthritis, inflammatory bowel disease, pancreatitis); cancer (including, but not limited to radiation induced cancer, cervical carcinoma, hepatocellular carcinoma, promotors of carcinogenesis, cancer in inflammatory bowel disease); ischemia/reoxygenation (including, but not limited to stroke, myocardial infraction, organ transplantation (heart, lung, skin, cornea, kidney), organ preservation, reattachment of severed limbs, frostbite, Dupuytren's contracture, hemorrhagic shock, endotoxic shock, crush injury); metal overload (including, but not limited to hemochromatosis, thalassemia, kwashlorkor, chemotherapy for leukemias, fulminant hepatic failure, Wilson's disease, alcohol induced iron overload, nickel induced carcinogenesis, lead poisoning); toxins (including, but not limited to hemolytic drugs, lead, halogenated hydrocarbons, ozone, oxides of nitrogen, asbestos, other mineral dusts, sulfur dioxid, paraquat, aluminum, cigarette smoke, diabetogenic drugs, fava beans (hemolytic agents), anthracyclines (cardiotoxicity), heavy metals (nephrotoxicity), photosensitizing drugs, contact dermatitis); eye disorders (including, but not limited to cataract development, deterioration after ocular hemorrhage, photochemical retinal damage, retinopathy of prematurity (retrolental fibroplasia)); inborn disease (including, but not limited to porphyrias, sickle cell anemia, Fanconi's anemia, neuronal ceroid lipofuscinoses, thalassemia); insufficient antioxidant protection (including, but not limited to Keshan disease (severe selenuim deficiency), hemolytic disease of prematurity, retinopathy of prematurity, bronchopulmonary dysplasia, intracranial hemorrhage, neurological degeneration due to severe vitamin E deficiency (in inborn errors affecting intestinal fat absorption), acquired immunodeficiency syndrome); brain and central nervous system disorders (including, but not limited to stroke, trauma, neurotoxicities (e.g., of aluminum), effects of hyperbaric oxygen, Parkinson's disease, potentiation of traumatic injury, cerebral malaria).

In another embodiment, the present invention provides new ways of producing betalains in non-naturally betalain-expressing species, in which betalains may be used as a natural food colorant. Therefore, the present invention also provides a natural food colorant comprising betalains produced as described herein. In one embodiment, betalains are extracted from plants expressing betalain as described herein. In another embodiment, betalains are produced in vitro in a cell line. The heterologous production of betalains enables the biofortification and enhancement of nutritional qualities of essential foods.

In another embodiment, the methods of present invention may be used to enhance the aesthetic quality of a food crop or produce by changing its color by genetically engineering a plant to express one or more betalains.

Thus, in one embodiment, the present invention provides methods of treating or suppressing the diseases, disorders, and conditions mentioned hereinabove comprising the step of providing a subject with a food crop that has been genetically modified to express betalains, as described herein. In another embodiment, the present invention provides uses of polynucleotides, nucleic acids and other compositions described herein in the preparation of a composition for treating or suppressing the diseases, disorders, and conditions mentioned hereinabove. In one embodiment, the composition is a pharmaceutical composition. In another embodiment, the present invention provides polynucleotides, nucleic acids and other compositions described herein for use in treating or suppressing the diseases, disorders, and conditions mentioned hereinabove.

In another embodiment, a food crop comprising betalains or enhanced amounts of betalains has an increased shelf life compared to the same food crop lacking betalains or having lower level of betalains. In another embodiment, a food crop comprising betalains or enhanced amounts of betalains has increased resistance to fungal diseases compared to the same food crop lacking betalains or having lower level of betalains.

In another embodiment, betalains produced by the methods described herein may be used for food preservation.

Therefore, in one embodiment, the present invention provides methods of increasing the shelf life of a food crop comprising the step of contacting one or more cells of a food crop plant comprising tyrosine with a nucleic acid encoding CYP76AD6, CYP76AD15, or a combination thereof, a nucleic acid encoding CYP76AD1, or a combination thereof, under conditions sufficient to produce betalains, thereby producing betalains and increasing the shelf life of said food crop.

Within the plant kingdom, betalains are found in only one group of angiosperms, the Caryophyllales. In this order, betalains and anthocyanins occur in a mutually exclusive fashion, i.e. no plant species produces both types of pigments. One of the most prominent features of the Caryophyllales order is its dominance in arid and semi-arid regions, and habitation of saline and alkaline soils. While some families within the Caryophyllales are distributed worldwide in a variety of habitats, members of several families are particularly adapted to arid or saline regions, including the Aizoaceae (ice-plant family), Portulacaceae (purslane family) and most notably, the Cactaceae (cactus family; www.britannica.com/plant/Caryophyllales). Heterologous betalain production in plants was used hereinbelow for studying the roles for these pigments in conferring tolerance to different a-biotic stress cues that are associated with arid regions such as drought, high UV radiation, excess light and high salinity and as plant defense compounds, acting against pathogenic fungi.

In another embodiment, the present invention provides methods of increasing the resistance of an organism or part of an organism to one or more stress factors comprising the step of contacting one or more cells of said organism with a nucleic acid encoding CYP76AD6, CYP76AD15, or a combination thereof, a nucleic acid encoding CYP76AD1, or a combination thereof, under conditions sufficient to produce betalains, thereby producing betalains and increasing the resistance of said organism or said part of an organism to said one or more stress factors. In one embodiment, the organism is a plant. In one embodiment, the organism comprises tyrosine. In one embodiment, the stress factor is an abiotic stress factor. In another embodiment, the stress factor is high osmotic pressure, high salinity condition, or a combination thereof. In another embodiment, the stress factor is drought. In another embodiment, the stress factor is excess light. In one embodiment, the plant part is a seed. In one embodiment, the plant is a food crop.

In one embodiment, the method comprises the step of contacting one or more cells of a plant or plant part with a nucleic acid encoding CYP76AD1, a nucleic acid encoding a DOPA 4,5-dioxygenase (DOD) enzyme, and a nucleic acid encoding a betalain related glucosyltransferase.

In another embodiment, the present invention provides methods of increasing the resistance of a plant or plant part to high osmotic pressure comprising the step of contacting one or more cells of a plant or plant part comprising tyrosine with a nucleic acid encoding CYP76AD6, CYP76AD15, or a combination thereof, a nucleic acid encoding CYP76AD1, or a combination thereof, under conditions sufficient to produce betalains, thereby producing betalains and increasing the resistance of said plant or plant part to high osmotic pressure.

In another embodiment, the present invention provides methods of increasing the resistance of a plant or plant part to high salinity conditions comprising the step of contacting one or more cells of a plant or plant part comprising tyrosine with a nucleic acid encoding CYP76AD6, CYP76AD15, or a combination thereof, a nucleic acid encoding CYP76AD1, or a combination thereof, under conditions sufficient to produce betalains, thereby producing betalains and increasing the resistance of said plant or plant part to high salinity conditions.

In another embodiment, the present invention provides a method of increasing seed germination rates in a plant comprising the step of contacting one or more cells of a plant or plant part with a polynucleotide comprising a nucleic acid encoding CYP76AD1, a nucleic acid encoding DODA1 and a nucleic acid encoding cDOPA5GT, under conditions sufficient to produce betalains, thereby increasing seed germination rates in said plant.

In another embodiment, the present invention provides methods of increasing the resistance of an organism or part of an organism to one or more fungal diseases comprising the step of contacting one or more cells of said organism with a nucleic acid encoding CYP76AD6, CYP76AD15, or a combination thereof, a nucleic acid encoding CYP76AD1, or a combination thereof, under conditions sufficient to produce betalains, thereby producing betalains and increasing the resistance of said organism or said part of an organism to said one or more fungal diseases. In one embodiment, the organism comprises tyrosine. In one embodiment, the organism is a plant. In one embodiment, the plant is a food crop.

In one embodiment, the fungus causing said fungal disease is a phytopathogenic fungus. In one embodiment, the fungus causing said fungal disease is *Botrytis cinerea*. In one embodiment, the plant is a tobacco plant. In one embodiment, the plant part is the leaf.

In another embodiment, the present invention provides methods of increasing the resistance of a plant or plant part to one or more fungal diseases comprising the step of contacting one or more cells of a plant or plant part with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betalains, thereby producing betalains and increasing the resistance of said plant or plant part to one or more fungal diseases. In one embodiment, the plant is a food crop.

In another embodiment, the present invention provides methods of decreasing the lesion area due to a fungal disease in a plant or plant part comprising the step of contacting one or more cells of said plant or plant part with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betalains, thereby producing betalains and thereby decreasing said lesion area due to a fungal disease in said plant or plant part.

In another embodiment, the present invention provides methods of decreasing necrosis due to a fungal disease in a plant or plant part comprising the step of contacting one or more cells of said plant or plant part with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betalains, thereby producing betalains and thereby decreasing necrosis due to a fungal disease in said plant or plant part.

In another embodiment, the present invention provides methods of inhibiting growth of plant species near to a first plant or plant part comprising the step of contacting one or more cells of said first plant or plant part with a nucleic acid encoding a CYP76AD1-β clade gene, under conditions sufficient to produce and secrete L-DOPA, thereby inhibiting growth of plants species near to said first plant or plant part. In one embodiment, the plant species is a heterologous plant species to the first plant.

In another embodiment, the present invention provides methods of allelopathic growth of an organism comprising the step of contacting one or more cells of an organism or part thereof with a nucleic acid encoding a CYP76AD1-β clade gene, under conditions sufficient for said organism or part thereof to produce and secrete L-DOPA, thereby allowing allelopathic growth of said organism.

In one embodiment, allelopathy is a biological phenomenon by which an organism produces one or more biochemicals that influence the germination, growth, survival, and reproduction of other organisms.

In another embodiment, the present invention provides methods of weed control comprising the step of contacting one or more cells of a plant or plant part with a nucleic acid encoding a CYP76AD1-β clade gene, under conditions sufficient for said plant or plant part to produce and secrete L-DOPA, thereby inhibiting the growth of weeds near to said plant or plant part.

In one embodiment, the step of contacting one or more cells of a plant or plant part with a nucleic acid encoding CYP76AD6, CYP76AD15, or a combination thereof, a nucleic acid encoding CYP76AD1, or a combination thereof, under conditions sufficient to produce betalains comprises contacting said one or more cells with a nucleic acid encoding CYP76AD1, a nucleic acid encoding a a DOPA 4,5-dioxygenase (DOD) enzyme, and a nucleic acid encoding a betalain related glucosyltransferase. In one embodiment, the DOD is *Beta vulgaris* DODA1. In one embodiment, the betalain related glucosyltransferase is cyclo-DOPA 5-O-glucosyltransferase or betanidin-5-O-glucosyltransferase. In one embodiment, the cyclo-DOPA 5-O-glucosyltransferase is *M. jalapa* gene cyclo-DOPA 5-O-glucosyltransferase (cDOPA5GT).

In one embodiment, a polynucleotide comprises the nucleic acids. In one embodiment, the polynucleotide is pX11. In another embodiment, the polynucleotide is pX12. In another embodiment, the polynucleotide is pX13.

In one embodiment, pX11-expressing species exhibited a predominantly red-violet color due to the production of higher amounts of betacyanins than betaxanthins.

The invention described herein has numerous applications in various diverse industries, including, for example, but not limited to, agriculture, food and beverages, pharmaceuticals, cosmetics, textiles, and consumer products.

In one embodiment, applications of the present invention include production of betalains and/or L-DOPA for fish feed. In another embodiment, production of betalains and/or L-DOPA is for inclusion in a food supplement. In one embodiment, the food supplement is for humans. In another embodiment, the food supplement is for non-human animals. In another embodiment, the food supplement is for veterinary use. In another embodiment, the food supplement is for aquaculture. In another embodiment, the food supplement is in the form of a vitamin. In another embodiment, the food supplement is added to milk or other dairy products.

In another embodiment, the present invention provides a method of increasing one or more betalains in a dairy product comprising the steps of a) contacting a bacterial cell with a polynucleotide encoding a nucleic acid encoding a DOPA 4,5-dioxygenase (DOD) enzyme and a nucleic acid encoding CYP76AD6, a nucleic acid encoding CYP76AD15, a nucleic acid encoding CYP76AD1, or a combination thereof, wherein if said cell is contacted with a nucleic acid encoding CYP76AD1 and a nucleic acid encoding DOD and not a nucleic acid encoding CYP76AD6 or a nucleic acid encoding CYP76AD15, said cell is also contacted with a nucleic acid encoding a betalain related glucosyltransferase, and b) fermenting a dairy product with bacteria grown from said cell, thereby increasing one or more betalains in said dairy product. In one embodiment, the bacteria is a bacteria used in fermentation for preparation of dairy products. In one embodiment, the bacteria is a *Lactobacillus*.

In another aspect, the genes of the invention can be transformed into a plant or a plant cell in order to protect against one or more biotic stresses such as, for example, but not limited to, fungi, bacteria, and virus and/or one or more abiotic stresses such as, for example, but not limited to, heat, cold, salt, drought, and ultraviolet exposure.

In one embodiment, a plant organ expressing a polynucleotide or polypeptide of the present invention may serve as a food coloring, dye, or pigment. In another embodiment, a derivative product of a plant organ expressing a polynucleotide or polypeptide of the present invention may serve as a food coloring, dye, or pigment.

In another embodiment, juice from transformed fruit can be extracted from such fruit for making beverages. In another embodiment, the juice or other extract from a plant organ expressing a polynucleotide or polypeptide of the present invention may serve as a food coloring, dye, or pigment. In one embodiment, such juice may be used to dye yogurt, sweet, chewing gum, ice cream and the like. Such dye or coloring agent can also be used in textile industry to dye clothes.

In another embodiment, an extract of a transgenic plant or plant cell as described herein may be sprayed on vulnerable plants to protect them from biotic and abiotic stresses, as described hereinabove. Thus, the present invention includes both an extract of a plant or food crop as described herein as well as a method of protecting a plant from biotic stress, abiotic stress, or a combination thereof comprising contacting said plant with a plant or plant extract produced by the methods of the present invention as described herein.

In another embodiment, production of betalains and/or L-DOPA is for cosmetic uses. In one embodiment, production of betalains and/or L-DOPA is for inclusion in sunscreens. In another embodiment, betalains and/or L-DOPA for use in sunscreens is produced in yeast.

In another embodiment, the present invention provides a method of treating, inhibiting, suppressing, or preventing a dopamine-responsive disorder in a subject comprising the step of administering a food crop, cell, or cell line comprising high levels of a CYP76AD1-β clade polypeptide, thereby providing said subject with L-DOPA, thereby treating, inhibiting, suppressing, or preventing dopamine-responsive disorder in said subject.

In another embodiment, the present invention provides a use of a CYP76AD1-β clade gene or a food crop, cell, or cell line comprising high levels of said CYP76AD1-β clade gene in the preparation of a composition for treating or inhibiting a dopamine-responsive disorder in a subject.

In another embodiment, the present invention provides a CYP76AD1-β clade gene or a food crop, cell, or cell line comprising high levels of said CYP76AD1-β clade gene for treating or inhibiting a dopamine-responsive disorder in a subject.

In one embodiment, the CYP76AD1-β clade polypeptide is CYP76AD6, CYP76AD15, or a combination thereof. In one embodiment, said dopamine-responsive disorder is Parkinson's Disease, Dopamine-responsive Dystonia, or a combination thereof.

In another embodiment, the present invention provides a method of treating, inhibiting, suppressing, or preventing Parkinson's Disease or Dopamine-responsive Dystonia in a subject, comprising providing said subject with a tyrosine-expressing plant or plant part genetically modified to express CYP76AD6, CYP76AD15, or a combination thereof, thereby providing said subject with L-DOPA, thereby treating, inhibiting, suppressing, or preventing Parkinson's Disease or Dopamine-responsive Dystonia in said subject.

In another embodiment, the present invention provides a method of treating, inhibiting, suppressing, or preventing Parkinson's Disease or Dopamine-responsive Dystonia in a subject, comprising administering a CYP76AD6, CYP76AD15, or a combination thereof, enzyme to said subject, optionally with phenylalanine or tyrosine, thereby producing L-DOPA from tyrosine, thereby treating, inhibiting, suppressing, or preventing Parkinson's Disease or Dopamine-responsive Dystonia in said subject.

In another embodiment, the present invention provides a method of suppressing the symptoms, stabilizing symptoms, delaying the onset, and/or slowing the progression, Parkinson's Disease or Dopamine-responsive Dystonia in a subject, comprising providing said subject with a tyrosine-expressing plant or plant part genetically modified to express CYP76AD6, CYP76AD15, or a combination thereof, thereby providing said subject with L-DOPA, thereby suppressing the symptoms, stabilizing symptoms, delaying the onset, and/or slowing the progression, Parkinson's Disease or Dopamine-responsive Dystonia in said subject.

In another embodiment, the present invention provides a method of suppressing the symptoms, stabilizing symptoms, delaying the onset, and/or slowing the progression, Parkinson's Disease or Dopamine-responsive Dystonia in a subject, comprising administering a CYP76AD6, CYP76AD15, or a combination thereof, enzyme to said subject, optionally with phenylalanine or tyrosine, thereby producing L-DOPA from tyrosine, thereby suppressing the symptoms, stabilizing symptoms, delaying the onset, and/or slowing the progression, Parkinson's Disease or Dopamine-responsive Dystonia in said subject.

In one embodiment, the Parkinson's Disease is idiopathic Parkinson's disease, postencephalitic parkinsonism, or symptomatic parkinsonism.

In one embodiment, the subject is additionally administered a peripheral DOPA decarboxylase inhibitor (DDCI). In one embodiment, the DDCI is carbidopa, a benserazide, or a combination thereof.

In another embodiment, the subject is additionally administered pyridoxine.

In one embodiment, administration of CYP76AD6, CYP76AD15, or a combination thereof, enzyme and/or the L-DOPA produced by the CYP76AD6, CYP76AD15, or a combination thereof, enzyme as described herein is via oral administration. In another embodiment, administration is via a catheter. In another embodiment, the enzyme is administered epidurally, intracerebrally, or intracerebroventricularly. Other suitable methods of administration are described hereinbelow.

According to any of the methods of the present invention and in one embodiment, the subject is human. In another embodiment, the subject is murine, which in one embodiment, is a mouse, and, in another embodiment, is a rat. In another embodiment, the subject is canine, feline, bovine, ovine, or porcine. In another embodiment, the subject is mammalian. In another embodiment, the subject is any organism susceptible to Parkinson's Disease.

In one embodiment, the methods of the present invention are employed in veterinary medicine. In one embodiment, the present invention provides treatment of domesticated mammals which are maintained as human companions (e.g., dogs, cats, horses), which have significant commercial value (e.g., dairy cows. beef cattle, sporting animals), which have significant scientific value (e.g., captive or free specimens of endangered species), or which otherwise have value.

In one embodiment, methods of the present invention include use of the compositions for treating and/or preventing a disease, disorder, or condition. In one embodiment, methods of the present invention include both therapeutic treatment or prophylactic or preventative measures, wherein the object is to prevent or lessen the targeted pathologic condition or disorder as described hereinabove. Thus, in one embodiment, methods of the present invention may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of the disease, disorder, or condition, while in one embodiment, "secondary" refers to a symptom that is derived from or consequent to a primary cause. In one embodiment, the polynucleotides, polypeptides, compositions, cells and their use in the present invention treat or inhibit primary or secondary symptoms or secondary complications related to Parkinson's Disease.

In another embodiment, "symptoms" may be any manifestation of Parkinson's Disease, comprising tremors, bradykinesia, rigid muscles, impaired posture and balance, loss of automatic movements, speech changes, writing changes, or a combination thereof.

In another embodiment, the present invention provides a method of marking a genetic transformation comprising the step of contacting a cell with a polynucleotide comprising a nucleic acid sequence encoding a) CYP76AD1, CYP76AD6, CYP76AD15, or a combination thereof, b) a nucleic acid sequence encoding DOPA 4,5-dioxygenase (DOD) enzyme; and c) an additional nucleic acid sequence of interest, under conditions sufficient to produce betalains in said cell, wherein the color produced by betalain production in said cell thereby marks said genetic transformation in said cell. In one embodiment, the contacting step further comprises contacting a betalain related glucosyltransferase.

In one embodiment, the method further comprises contacting a growth medium with ascorbic acid as a reducing agent to prevent spontaneous betanidin oxidation, which causes the pigment to polymerize and lose its violet color.

In another embodiment, the present invention provides a method of identifying betalain related genes in an organism comprising the step of searching a plant genome database for genes with expression patterns that highly correlate to those of the betalain related genes described herein. In one embodiment, the gene is MjDOD, cDOPA5GT CYP76AD3, or a combination thereof. In another embodiment, the gene is CYP76AD1, CYP76AD6, CYP76AD15, or a combination thereof.

Combinations

In one embodiment, betalains produced using the compositions and methods of the present invention may be administered or provided by themselves. In another embodiment, betalains produced using the compositions and methods of the present invention may be administered or provided together with an additional dietary supplement. In another embodiment, betalains produced using the compositions and methods of the present invention may be administered or provided together with a terpene, which in one embodiment, is an astaxanthin. In another embodiment, betalains produced using the compositions and methods of the present invention may be administered or provided together with anthocyanins, carotenoids, or a combination thereof.

In another embodiment, betalains produced using the compositions and methods of the present invention may be produced together with an additional component, which in one embodiment, may serve as a dietary supplement. In another embodiment, betalains produced using the compositions and methods of the present invention may be produced together with a terpene, which in one embodiment, is an astaxanthin. In another embodiment, betalains produced using the compositions and methods of the present invention may be produced together with anthocyanins, carotenoids, or a combination thereof.

In another embodiment, the present invention provides a food crop comprising a polynucleotide of the present invention. In one embodiment, the food crop comprising a polynucleotide of the present invention further comprises anthocyanin, carotene, or a combination thereof. In one embodiment, the food crop comprising a polynucleotide of the present invention is genetically modified to comprise anthocyanin, carotene, or a combination thereof. In one embodiment, the food crop is purple anthocyanin tomatoes.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Example 1

Materials and Methods (1)

Plant Material and Growth Conditions

*Mirabilis jalapa* plants were soil-grown in a greenhouse with long-day light conditions (25° C.). *Beta vulgaris* and *Nicotiana benthamiana* plants were soil-grown in climate rooms (22° C.; 70% humidity; 18/6 hours of light/dark). Plant material for *M. jalapa* RNA-sequencing was collected from red flowers in five developmental stages (stage 1—flower length approx. 1 cm; stage 2-2 cm; stage 3-3 cm; stage 4-4 cm; stage 5-5-6 cm), red-young or green-mature leaves, and epidermis from stem node (red) or internode (green) areas. Plant material for *B. vulgaris* RNA-sequencing was collected from hypocotyls of 10 day old seedlings of three varieties (Red beet, Burpees Golden beet and Chioggia 'striped' beet). Collected tissue was immediately frozen in liquid nitrogen and maintained at −80° C. until processing.

Transcriptome Sequencing, Assembly and Analysis

*M. jalapa* and *B. vulgaris* libraries for Illumina high-throughput strand-specific RNA-Seq were prepared as follows: total RNA was extracted from sampled tissues with the TRIzol method based on the TRI reagent user manual (Sigma-Aldrich). Five μg of total RNA from each sample was used for preparation of RNA-seq libraries using methods known in the art with minor modifications. Briefly: poly(A) RNA was isolated from total RNA using Dynabeads Oligo (dT)25 (Invitrogen), fragmented at 94° C. for 5 minutes and eluted. First-strand cDNA was synthesized using reverse transcriptase SuperScript III (Invitrogen) with random primers and dNTPs, and second-strand cDNA was generated using DNA polymerase I (Enzymatics) and dUTPs. After end-repair (Enzymatics), dA-tailing with Klenow 3'-5' (Enzymatics) and adapter ligation (Quick T4 DNA Ligase, NEB), the dUTP-containing second-strand was digested by uracil DNA glycosylase (Enzymatics). The resulting first-strand adaptor-ligated cDNA was used for 13-15 cycles of PCR enrichment with NEBNext High-Fidelity PCR Master Mix (NEB). Indexed libraries were pooled and sequenced with an Illumina HiSeq2000 instrument. De-novo assembly and calculation of normalized count values for the *M. jalapa* dataset were done with Trinity software version Trinityrnaseq_r2013-02-25, following standard procedure. Contig annotations were assigned using Blast2GO. De-novo, genome-guided assembly of the *B. vulgaris* dataset was done with Trinity version Trinityrnaseq_r2014-07-17, using the *B. vulgaris* (sugar beet) genome resource as reference (bvseq.molgen.mpg.de). Gene annotation was obtained with the inclusive Trinotate module.

Generation of DNA Constructs

Gene sequences used in this study; cDOPA5GT (GenBank accession AB182643.1; SEQ ID NO: 2), DODA1 (accession HQ656027.1; SEQ ID NO: 33), CYP76AD1 (accession HQ656023.1; SEQ ID NO: 32). Other sequences are provided in Materials and Methods. CYP76AD6 was named by Dr. David R. Nelson, University of Tennessee, Memphis USA, to maintain consistency in nomenclature. *M. jalapa* cDOPA5GT and *B. vulgaris* CYP76AD1, BvDODA1, BvCYP76new and CYP76AD6 transcripts were amplified from *M. jalapa* red petal and *B. vulgaris* red hypocotyl cDNA libraries, which were prepared using a High-Capacity cDNA Reverse Transcription Kit (Life technologies). PCR amplification was done using 'Phusion' DNA polymerase (Finnzyme) and oligonucleotides specified in Table 1. For VIGS assay, all gene fragments were cloned into a pTRV2 vector using XhoI and SacI restriction. Vectors for co-silencing were constructed by cloning a CYP76AD1 fragment into pTRV2: BvCYP76new and pTRV2: CYP76AD6 using EcoRI and BamHI restriction. DNA constructs used for *N. benthamiana* agroinfiltration and for agrobacteria-mediated plant transformation were constructed with Goldenbraid cloning. CYP76AD1, BvDODA1, CYP76AD6 and cDOPA5GT were cloned into a pUPD vector using oligonucleotides specified in Table 1. pDODA, pAD1-GT, pYFP, pAD6 and pX11 are respectively 2α2, 2Ω2, 2α1, 2α1 and 3α1 vectors, all of which are based on a pCAMBIA backbone.

TABLE 1

Oligonucleotides used in this study

| SEQ ID NO: | Oligonucleotide name | Sequence (5' to 3') |
|---|---|---|
| | Quantitative real-time PCR | |
| 45 | CYP76AD1 qPCR Fwd | TGTGCTAGACGTTCTTCTTCAGCT |
| 46 | CYP76AD1 qPCR Rev | AAAATGTCGACGAGCAAATG |
| 47 | CYP76AD6 qPCR Fwd | CTTCATCTCGTAGGCTTCCTCC |
| 48 | CYP76AD6 qPCR Rev | GATGAGGCTTTTCGCCAAGA |
| 49 | Bv15885 qPCR Fwd | CCTGTATCGGCTAAATGGCG |
| 50 | Bv15885 qPCR Rev | CAATTGCACAGCGGAGATTTT |
| 51 | Bv20048 qPCR Fwd | TTGATGCTGTTTGCGCAGTC |
| 52 | Bv20048 qPCR Rev | TGCGAAGATTTCGCCATTTT |
| 53 | BvGAPDH qPCR Fwd | TGGTGCTGATTTTCGTCGTAGAG |
| 54 | BvGAPDH qPCR Rev | TGGCACCACCCTTCAAGTG |
| 55 | Bv10427 qPCR Fwd | TAAAGCTCCCTCCTGGTCCA |
| 56 | Bv10427 qPCR Rev | CCGCAGAACGATGAGGTTTG |
| 57 | BvCYP76new qPCR Fwd | TCAAACTCGGAAGCATCACTACA |
| 58 | BvCYP76new qPCR Rev | GGGCTAAGTCGTGCTCGAGG |
| | pTRV2 cloning | |
| 59 | BvDODA1 Fwd + XhoI | AAAAACTCGAGGTTAAACCTACTGTTAATGCTGTC |
| 60 | BvDODA1 Rev + SacI | AAAAAGAGCTCGCTGCCCAAGGTGCAACTCC |
| 61 | CYP76AD1 Fwd + XhoI | AAAAACTCGAGGCTAATCTTGCTAAAATTCACGG |
| 62 | CYP76AD1 Rev + SacI | AAAAAGAGCTCTTATGGTGGGCTAATTCCACTG |
| 63 | CYP76AD1 Fwd + BamHI | AAAAAGGATCCGCTAATCTTGCTAAAATTCACGG |
| 64 | CYP76AD1 Rev + EcoRI | AAAAAGAATTCTTATGGTGGGCTAATTCCACTG |
| 65 | BvCYP76new Fwd + XhoI | AAAAACTCGAGCTGCAAGAGTCAATGATCTCA |
| 66 | BvCYP76new Rev + SacI | AAAAAGAGCTCTCATCTGGGAATTGGAATTGCT |
| 67 | CYP76AD6 Fwd + XhoI | AAAAACTCGAGCACAACAGCAAGCACATTAGA |
| 68 | CYP76AD6 Rev + SacI | AAAAAGAGCTCAGTCCAGGGCATATCCTTCTAC |
| | Goldenbraid cloning | |
| 69 | BvDODA1 Fwd | GCGCCGTCTCGCTCGAATGAAAATGATGAATGGTGAAGATG |

TABLE 1-continued

Oligonucleotides used in this study

| SEQ ID NO: | Oligonucleotide name | Sequence (5' to 3') |
|---|---|---|
| 70 | BvDODA1 Rev | GCGCCGTCTCGCTCGAAGCCTAGGCTGAAGTGAACTTGTA |
| 71 | CYP76AD1 Fwd | GCGCCGTCTCGCTCGAATGGATCATGCAACATTAGCAATG |
| 72 | CYP76AD1 Rev | GCGCCGTCTCGCTCGAAGCTCAATACCTAGGTATTGGAATAAG |
| 73 | CYP76AD6 Fwd1 | GCGCCGTCTCGCTCGAATGGATAACGCAACACTTGCT |
| 74 | CYP76AD6 Rev1 | GCGCCGTCTCGTTGCCCATTCTAATGTGCTTG |
| 75 | CYP76AD6 Fwd2 | GCGCCGTCTCGGCAATGGCCGAACTTGTGAA |
| 76 | CYP76AD6 Rev2 | GCGCCGTCTCGCTCGAAGCCTAGTTTCTGGGAACTGGAAT |
| 77 | cDOPA5GT Fwd1 | GCGCCGTCTCGCTCGAATGACCGCCATTAAAATGAACAC |
| 78 | cDOPA5GT Rev1 | GCGCCGTCTCGGCCTCATTTCCTCATTGATATC |
| 79 | cDOPA5GT Fwd2 | GCGCCGTCTCGAGGCCAGAATGGCTACCAGA |
| 80 | cDOPA5GT Rev2 | GCGCCGTCTCGCTCGAAGCTTATTGAAGAGAAGGTTCCAACTT |
| | Gateway cloning for yeast expression | |
| 81 | BvDODA1 Fwd | ggggacaagtttgtacaaaaaagcaggatcATGAAAATGATGAATGGTGAAGAT |
| 82 | BvDODA1 Rev | ggggaccactttgtacaagaaagctgggtcCTAGGCTGAAGTGAACTTGTAGGAG |
| 83 | CYP76AD1 Fwd | ggggacaagtttgtacaaaaaagcaggatcATGGATCATGCAACATTAGCAA |
| 84 | CYP76AD1 Rev | ggggaccactttgtacaagaaagctgggtcTCAATACCTAGGTATTGGAATAAGTTT |
| 85 | CYP76AD6 Fwd | ggggacaagtttgtacaaaaaagcaggatcATGGATAACGCAACACTTGCTGTGATCC |
| 86 | CYP76AD6 Rev | ggggaccactttgtacaagaaagagggtcCTAGTTTCTGGGAACTGGAATAACTTGAAGAG |

Virus-Induced Gene Silencing in *Beta vulgaris*

Fragments of BvDODA1 (407 bp), CYP76AD1 (418 bp), BvCYP76new (471 bp), and CYP76AD6 (420 bp) were cloned into a pTRV2 vector, transformed to agrobacteria strain GV3101 and introduced to *B. vulgaris* 'Bull's Blood' variety 10 day old seedlings using the previously described vacuum infiltration method. Agrobacteria were brought to O.D.600 2.0 in VIGS infiltration buffer (10 mM MES, 10 mM MgCl2, 200 µM acetosyringone), incubated at room temperature for 3 hours and mixed in a 1:1 ratio with pTRV1-carrying agrobacteria before infiltration. For each experiment, 48 seedlings were infected. In experiments resulting in visible phenotypes, depigmentation patches were typically observed in over half of the infected seedlings within 2-3 weeks. Tissues for spectrophotometric analysis were sampled 3.5 weeks post infection.

Quantitative Real-Time PCR (qRT-PCR) Analysis qRT-PCR analysis was carried out on VIGS-infected red beet plants. Three biological replicates from each experiment were analyzed, each replicate consisting of leaf tissue from two to three plants, sampled 3.5 wk post infection. RNA was extracted with the TRIzol method (according to the Sigma-Aldrich user manual for the TRI reagent), DNase-treated and reverse-transcribed to cDNA with a High Capacity cDNA Reverse Transcription kit (Applied Biosystems, Foster City, CA, USA), according to the manufacturer's instructions. All oligonucleotides were designed using PRIMEREXPRESS software (Applied Biosystems) (Table 1). qRT-PCR was performed with Fast SYBR Green reagent and a StepOnePlus instrument (Applied Biosystems) in the following conditions: initial step in the thermal cycler for 20 s at 95° C., followed by PCR amplification for 40 cycles of 3 s at 95° C. and 30 s at 59° C., and finally dissociation analysis to confirm the specificity of PCR products. Each reaction consisted of 10 µl total volume, containing 2.5 µM of each primer. Relative transcript levels were calculated according to the ΔΔCt method (Livak & Schmittgen, 2001), using the 'housekeeping' gene GAPDH for reference.

Transient Expression in *Nicotiana benthamiana*

Transient gene expression assays in *N. benthamiana* with the pDODA, pAD1-GT, pYFP, pAD6 and pX11 vectors were based on a previously described agroinfiltration method. All constructs were transformed to *Agrobacterium tumefaciens* GV3101 strain, excluding pX11 which was transformed to *A. tumefaciens* EHA105 strain. In all cases, agrobacteria were grown overnight in LB media and brought to a final O.D.600 0.2 in infiltration buffer. When co-infiltrated, agrobacteria carrying separate constructs were each brought to O.D.600 0.2 and mixed in a 1:1 ratio before infiltration. Tissues used for subsequent LC-MS analysis were sampled from leaves 7 days post infiltration. For LC-MS analysis of L-DOPA and betalains, 3-4 biological replicates for each experiment were sampled, each consisting of infiltrated tissues from 2-3 different leaves.

Metabolite Extraction and Analysis

For betalain analysis, extraction solution (80% ethanol and 0.1% formic acid in DDW) was added to frozen, ground plant tissue (0.1-0.25 g) in a ratio of 200 µL 0.1 g-1 tissue. Samples were incubated at room temperature for 30 min. followed by 5 min. sonication, 5 min. centrifugation and filtration through 0.22 µm PVDF filters (Millipore). Samples diluted 3 fold in DDW were analyzed using a high resolution UPLC/PDA-qTOF system comprised of a UPLC (Waters Acquity) connected on-line to an Acquity PDA detector (200-700 nm) and a qTOF detector (tandem quadrupole/time-of-flight mass spectrometer, XEVO, Waters) equipped with an electrospray ionization (ESI) source. ESI was used in positive ionization mode at the m/z range from 50 to 1600 Da. The following settings were used: capillary—1 kV, cone—27V, collision energy—6 eV. For MS/MS or MSE runs, collision energy ramp from 15 to 40 eV was used. Separation of compounds was performed on a UPLC HSS T3 column (Waters Acquity, 1.8 µm, 2.1×100 mm) using eluents A (1% acetonitrile, 0.1% formic acid) and B (100% acetonitrile, 0.1% formic acid) as follows: the first 3 min.—isocratic elution at 100% A; 3.0-22.0 min—a linear gradient to 75% A, 22.0-22.5 min—a linear gradient to 100% B, 22.5-25.5 min—washing at 100% B, 25.5-26.0 min—return to 100% A and 26.0-28.0 min—equilibration at 100% A. Column temperature was set to 35° C., flow—0.3 ml/min. Betanin and iso-betanin were assigned using red beet leaf extract as reference. Other betalain compounds were putatively identified based on accurate mass, UV-VIS spectra, and MS/MS or MSE fragmentation (detailed in Table 2).

TABLE 2

Betalain compounds identified by LC-MS analysis.

| No. | Name | Elemental composition | [M + H]+, Da | Mass error, ppm | Rt, min | MS fragments | UV/VIS, nm |
|---|---|---|---|---|---|---|---|
| | | | | | | Betacyanins | |
| 1 | Betanin[a, c, d, e, f] | C24H26N2O13 | 551.1513 | 0 | 8.31 | 389.10 [M + H—Hex] 345.11 [M + H—Hex—COO]- 343.0 [M + H—Hex—H2COO] 297.09 [M + H—Hex—2H2COO] 194.05 150.1 [M + H—Hex—H2COO—C9H7NO4] | 534 |
| 2 | Iso-betanin[a, c, d, e, f] | C24H26N2O13 | 551.1502 | 2 | 9.06 | 389.10 [M + H—Hex] 343.0 [M + H—Hex—H2COO] 150.1 [M + H—Hex—H2COO—C9H7NO4] | 534 |
| 3 | Betacyanin I[c] (unknown) | C31H31N3O14 | 670.189 | 0.9 | 12.67 | 626.20 [M + H—COO] 582.21 [M + H—2xCOO] 538.22 [M + H—3xCOO] 389.10 [M + H-281.0902 (C13H15NO6)] 345.11 [M + H-281-COO] 301.11 [M + H-281-2xCOO] 282.09 [M + H-389.10 (Betanidin)] 264.09 [M + H-389.1 (Betanidin)-H2O] 257.13 [M + H-281-3xCOO] 247.08 180.10 138.06 | 532 |
| 4 | Betacyanin II[c] (unknown) | C31H30N2O14 | 655.1771 | 0.8 ppm | 15.68 | 389.10 [M + H-266.0790 (C13H14O6)] 345.10 [M + H-266-COO] 343.10 [M + H-266-H2COO] 301.12 [M + H-266-2xCOO] 299.10 [M + H-266-H2COO—COO] 196.06 [M + H—C9H7NO4] 194.04 [M + H—C9H9NO4] 150.05 [M + H-266.0790-H2COO—C9H7NO4] | 533 |

TABLE 2-continued

Betalain compounds identified by LC-MS analysis.

| No. | Name | Elemental composition | [M + H]+, Da | Mass error, ppm | Rt, min | MS fragments | UV/VIS, nm |
|---|---|---|---|---|---|---|---|
| 5 | Betanidin[g, i] | C18H16N2O8 | 389.0991 | 1.5 | 9.89 | 343.09 [M + H—H2CO2]<br>297.09 [M + H—2H2CO2]<br>255.1 [M + H—2H2CO2—CO2]<br>253.08 [M + H—3H2CO2]<br>150.05 [M + H—Hex—H2CO2—C9H7NO4] | 539 |
| 6 | Iso-betanidin[g, i] | C18H16N2O8 | 389.0988 | 0.8 | 10.83 | 343.09 [M + H—H2CO2]<br>297.09 [M + H—2H2CO2]<br>255.1 [M + H—2H2CO2—CO2]<br>253.08 [M + H—3H2CO2]<br>150.05 [M + H—Hex—H2CO2—C9H7NO4] | 539 |
| 7 | Betacyanin III[e] (unknown) | C26H28N2O14 | 593.1618 | 0.2 | 10.72 | 547.11 [M + H—H2COO]<br>511.17 [M + H—2xH2O]<br>389.09 [M + H—C8H12O6]<br>345.11 [M + H—C8H12O6—COO]<br>325.07 [M + H—C8H12O6—H2COO—H2O]<br>301.11 [M + H—C8H12O6—2—COO]<br>299.10 [M + H—C8H12O6—H2COO—COO]<br>297.08 [M + H—C8H12O6—2xH2COO]<br>194.04 [M + H—C8H12O6—C9H9NO4]<br>178.05 [M + H—C8H12O6—C9H7NO4—H2O]<br>176.03 [M + H—C8H12O6—C9H9NO4—H2O]<br>150.05 [M + H—C8H12O6—H2CO2—C9H7NO4] | 534 |
| Betaxanthins |
| 1 | Vulgaxanthin I[f, g, h, i] (glutamine-betaxanthin) | C14H17N3O7 | 340.1147 | 0.6 | 2.21 | 323.08 [M + H—NH3]<br>277.08 [M + H—NH3—H2CO2]<br>231.07 [M + H—NH3—2xH2CO2]<br>194.04<br>185.07 [M + H—3H2CO2—NH3]<br>157.06 [M + H—3H2CO2—NH3—CO]<br>150.05 [M + H—COO—C5H10N2O3]<br>148.05 [M + H—H2CO2—C5H10N2O3]<br>132.10<br>86.1 | 476 |
| 2 | Indicaxanthin[b, c] (proline-betaxanthin) | C14H16N2O6 | 309.1090 | 1.0 | 7.69 | 263.10 [M + H—H2COO]<br>217.10 [M + H—2xH2COO]<br>219.11 [M + H—COO—H2COO]<br>189.10<br>175.12 [M + H—H2COO—2COO]<br>173.11 [M + H—2xH2COO—COO]<br>150.05 [M + H—COO—C5H9NO2]<br>145.07<br>106.07 [M + H—2COO—C5H9NO2] | 478 |
| 3 | Dopaxanthin-hexoside[b] | C24H28N2O13 | 553.1667 | 0.5 | 7.97 | 391.11 (C18H19N2O8) [M + H—Hex]<br>357.13 [M + H—Hex—2xOH]<br>347.13 [M + H—Hex—COO]<br>345.11 [M + H—Hex—H2COO]<br>303.13 [M + H—Hex—2xCOO]<br>299.10 [M + H—Hex—2xH2COO]<br>255.11 [M + H—Hex—COO—2xH2COO]<br>211.07 [M + H—Hex—C9H8O4]<br>208.05<br>194.04<br>181.05 [M + H—C9H10N2O4]<br>165.05 [M + H—Hex—C9H8O4—H2COO]<br>150.05 [M + H—Hex—H2COO—C9H9NO4]<br>106.06 [M + H—Hex—H2COO—COO—C9H9NO4] | 478 |
| 4 | Betaxanthin I[b] (unknown) | C18H19N3O4 | 342.1445 | 2.6 | 6.67 | 298.15 [M + H—COO]<br>254.16 [M + H—2xCOO]<br>252.15 [M + H—H2COO—COO]<br>237.14 [M + H—2xCOO—NH3]<br>225.14<br>196.10<br>159.09<br>132.08<br>117.05<br>106.06 | 476 |

TABLE 2-continued

Betalain compounds identified by LC-MS analysis.

| No. | Name | Elemental composition | [M + H]+, Da | Mass error, ppm | Rt, min | MS fragments | UV/VIS, nm |
|---|---|---|---|---|---|---|---|
| 5 | Valine-betaxanthin[g, h, i] | C14H18N2O6 | 311.1245 | 0.6 | 10.69 | 267.11 [M + H—COO]<br>265.11 [M + H—H2COO]<br>221.13 [M + H—COO—H2COO]<br>219.13 [M + H—2xH2COO]<br>193.13<br>175.12 [M + H—COO—2xH2COO]<br>166.05<br>150.05 [M + H—H2CO2—C5H9NO2]<br>132.05 [M + H—H2CO2—C5H9NO2—H2O]<br>119.06<br>104.05 [M + H—2xH2CO2—C5H9NO2]<br>94.05 | 469 |
| 6 | Betalamic acid[g, h, i] | C9H9NO5 | 212.0558 | 0.5 | 8.79 | 166.05 [M + H—H2COO]<br>148.04 [M + H—H2COO—H2O]<br>138.05 [M + H—H2COO—CO]<br>120.05 [M + H—2x(H2COO)]<br>92.05 [M + H—2x(H2COO)—CO]<br>65.04 | 408 |

Betalain compounds identified by LC-MS analysis in *N. benthamiana* agroinfiltration experiments of [a]pAD1-GT+pDODA1, [b]pAD6+pDODA1 and [c]pX11, d[N]. *benthamiana* callus, [e]*N. glauca* callus, [f]pX11-transformed *N. tabacum*, yeast expression experiments of [g]CYP76AD1+DODA1, [h]CYP76AD6+DODA1 and [i]CYP76AD1/AD6+DODA1. All fragments were obtained in the MS/MS mode excluding betanidin and iso-betanidin, for which fragments were determined in the MS[(E)] mode. Rt, retention time; MS fragments, masses of fragments obtained in positive ionization mode; UV/VIS, absorption maxima at UV/visible range; Hex, Hexose.

For L-DOPA analysis, samples were extracted as described above and analyzed using a UPLC/PDA-MSMS instrument, where a UPLC separation module (Waters Acquity) was connected to a photodiode array detector (Waters Acquity 2996, 190-800 nm), and (on-line) to a triple quadrupole MS detector (Waters Xevo TQ MS), equipped with an ESI source. Compounds were separated with a Phenomenex Luna column (2×150 mm, 3 µm) using a following gradient: the first 1 min.—linear gradient from 100 until 90% A, 1-4 min.—90-75% A, 4-5 min.—75-0% A, 5-9.5 min. —washing at 100% B, 9.5-10 min.—return to 100% A, and 10-12 min.—equilibration at 100% A, where A is 0.1% formic acid in water, and B is 0.1% formic acid in acetonitrile. Column temperature was set to 35° C., flow—0.25 ml/min. Samples were analyzed in positive ionization mode, using the following settings: capillary—2 kV, cone—26 eV, with two transitions 198.1>152.1 (collision—15 eV) and 198.1>181.1 (collision—10 eV) used for compound assignment. L-DOPA was identified by comparison with an L-DOPA commercial standard (Sigma-Aldrich), dissolved in DDW (5 µM) and injected with the same LC-MS conditions.

For relative quantification of betaxanthins in VIGS-silenced beet leaves by spectrophotometry, samples were extracted using the same procedure as detailed above, except 80% methanol was used instead of 80% ethanol. Extracts were diluted 4 fold in extraction solution, placed on a 96 well plate and analyzed with a Biotek Synergy HT Microplate Reader. Relative betaxanthin content of each sample was assessed by measuring absorption at 475 nm and subtracting the value of absorption at 600 nm.

For estimation of betacyanin content by spectrophotometry, the same extraction method was used as above. Samples were diluted in DDW to obtain solutions of O.D.535<2.0. Betacyanin quantification was based on absorption measurements at 535 nm and 600 nm, and calculated using a previously described method.

Recombinant Expression in Yeast

Figure 8A:
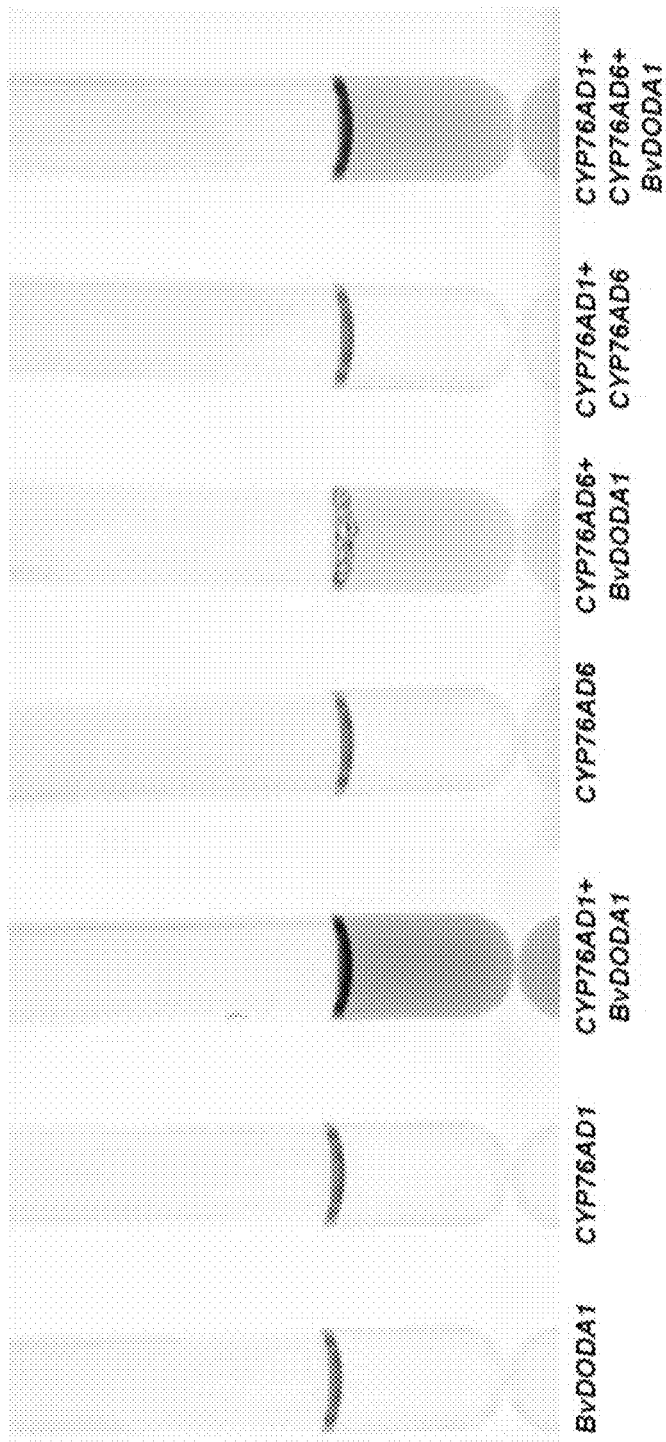
FIGS. 8A-8C. Cytochrome P450s CYP76AD1 and CYP76AD6 differ in activity and phylogeny.
Figure 8B:
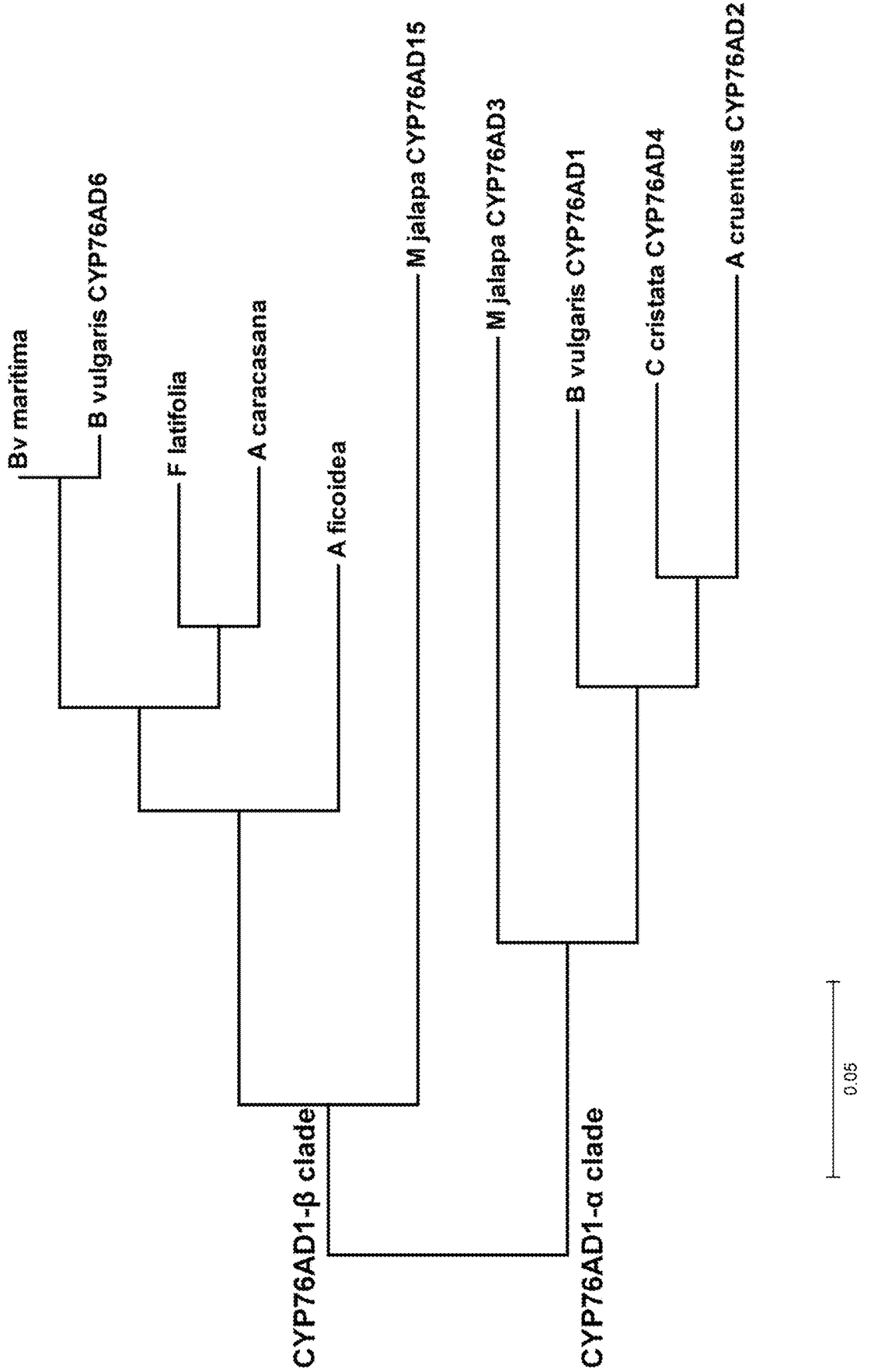
Figure 8C:
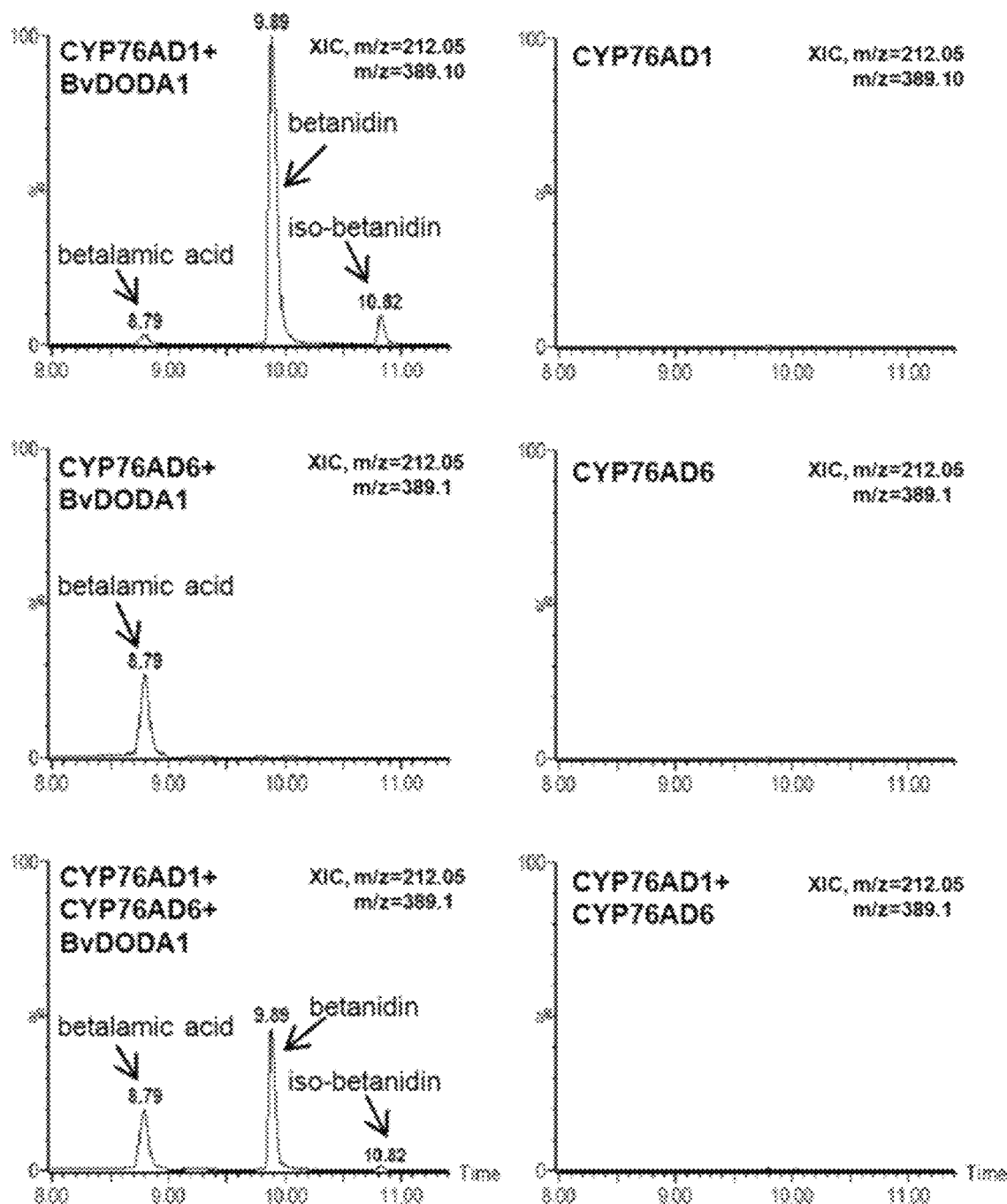

CYP76AD1, CYP76AD6 and BvDODA1 coding sequences were PCR-amplified and cloned to BP sites of a pDONR207 vector using Gateway cloning (Life technologies, Invitrogen) according to manufacturer's manual, and were next recombined to the LR sites of pAG423GAL-ccdB (for CYP76AD6), pAG425GAL (for BvDODA1), and pYES-DEST52 (for CYP76AD1, Invitrogen) vectors. In addition, the beta-glucoronidase (GUS) coding sequence was introduced to these vectors for control assays. The destination vectors were transformed using the PEG/LiAc method to *S. cerevisiae* strain BY4742, in sequential transformation. Each yeast clone was eventually transformed with the three destination vectors, expressing different combinations of CYP76AD1, CYP76AD6, BvDODA1 and GUS. Yeast strains were grown in standard SD medium overnight, containing 2% glucose and lacking histidine, leucine and uracil. The yeast were pelleted, re-suspended to O.D.600 1.0 in 2 ml SD media with 2 mM ascorbate, 1% raffinose and 2% galactose, lacking histidine, leucine and uracil, and grown overnight. Images in FIG. 8 are of media in which yeast were grown, following overnight galactose induction. For LC-MS analysis, 1 ml of liquid medium was dried in an evaporator and re-suspended in 100 µl of DDW.

Bioinformatic Analyses

For co-expression analysis, contigs corresponding to DOPA 4,5-dioxygenase (MjDOD), cyclo-DOPA-5-O-glucosyltransferase (cDOPA5GT) and CYP76AD3 were separately used as 'baits'. Genes co-expressing with either of the 'baits' were identified by using an R script to calculate Pearson correlation values, based on normalized count values of each gene across all 24 libraries.

For generation of the phylogenetic tree of CYP76AD1-like proteins, CYP76AD6 protein sequence was first used for a BLASTp query of the NCBI nr database. BLASTp top four hits with highest sequence identity and full protein sequence were selected for multiple sequence alignment, together with the CYP76AD1 protein and its previously described orthologs CYP76AD2, CYP76AD3 and CYP76AD4. Multiple sequence alignment was performed with Clustal Omega and processed into a neighbor-joining phylogenetic tree with MEGA software version 6.06. Bootstrapping of 100 iterations was used for validation. CYP76AD6 and CYP76AD1 pairwise alignment was done with Clustal Omega using default parameters and edited with GeneDoc software.

Plant Transformation and Regeneration

Agrobacteria-mediated plant transformation and regeneration was done in tobacco leaf discs, eggplant, *N. benthamiana*, tomato, potato, *Petunia, Nicotiana glauca* according to methods known in the art. A protocol used for *Solanum nigrum* transformation is provided in hereinbelow. All plant species were transformed using agrobacteria GV3101 strain. Plant tissue culture was carried out in a climate rooms (22° C.; 70% humidity; 16/8 hours of light/dark, 2500 Lux light intensity).

Sequences of Genes Used in this Study

Sequences provided are contig sequences obtained from de-novo assembly of *Beta vulgaris* and *Mirabilis jalapa* transcriptome (RNA-seq) data. All sequences are presented in the 5'→-3' direction.

>MjCYP76 from *M. jalapa*
(SEQ ID NO: 1)
CTTCAAATCCTCCCACGTATATATCAACAAAAACCAAAAACATCATCT

CATTACAATAATGGAGTATCATCTTCTCTTCCTTCTCCTCCTGCCGAT

CATCCTTATCTTCGTGTTCCTCAATCACAAGCCCAAGCAAACCAAACT

CGAACCACCAGGACCACGTCCATGGCCCATCATAGGCCACACCAACCT

CGTCGGCTCCAAACCTCATCAGTCCATTGCCAAACTAGCTCATATTTA

CGGTCCCATAATGTCACTTAAGCTAGGGAGAATCACTACTATTGTCAT

ATCTTCCCCTGAAGCAGCCAAAGACTTGTTCCTGAAACATGACCTTAC

TTTCTCAAGTAGGCAAGTTCCTCACGCTTCAACCGCTACAAACCATGA

CAAACTATCCATGGTTTGGCTCCCTGTATGTCCCAAATGGCGCTATCT

TAGAAAGATCGCGGCCATCCAACTATTCACCAACCAACAACTTGATGG

TGGTCAGGTACTAAGGCGTAAGAAAGTGGACGAGTTGATCCAATTTGT

GACTCGTTGTAGTAAACAAGGGCAAGTCATTGATATTGGAGAGGCTGT

TTTTATTACTACTCTTAACTTAATGTCAAATACCTTTTTTTCCAAGGA

TTTGTGTAGTTATGGTTTGGCCGAATCACGAGAGTTTAAGGATCTATT

TTGGGAGTTCATGAAAGTGCTAGCGAGTCCTAATGTTTCTGATTATTT

TCCATGGTTAAGATGGTTGGATTTGCAAGGCATCAAGAGAAGAAGCGA

GGGTTGTTATCGCAAGATGTTGGGTTTTTTTGGGGAGATTATTGATCA

GAGATTGAGAGATCCAATGTCATGTAAGAACGATGTATTGGACACTCT

ACTCAAACTTGTCGACCAAAAAGAGTTGAGCTTTGAGGATGTCAAACA

TATGCTTGTGGATTTGTTTGTTGCAGGGACGGATACAACTTCGAACAC

ATTGGAATGGACAATGGTAGAACTTTTACGCCACCCTAACATATTGAC

TAAAGCACAAACTGAACTCAGCCAAGTCATAGGCAAGGACAAGTTAGT

CCAAGAATCATGTATCACCAAGTTGCCATATCTTCAATCAATATTGAA

AGAAACATTCAGGTTGCACCCACCGACTCCTTTTTTACTTCCACACAA

AGCAATCGAGAACGTTGAACTATGCAACTATCACATACCTAAAGGTGC

TCAAGTTTGGGTGAATGTGTGGTCTATTGGCCGCGATCCCAACATTTG

GTCAAGCCCGGACTTATTTTCCCCAGAGAGATTTTTAGGTACCGACAT

TGATATAAAAGGTAACCATTTCGAGCTCATACCATTCGGAGCAGGAAG

AAGGATTTGCCCCGGGTTGTCACTAGCTTACAGGATGCTTCATTTGAT

TTTGGCCACTCTCCTTCATTCATTCAATTGGAACCTTCCTAATGACGT

ATGTCCGGAAAATATGGATATTGAAGAAAAATTTGGGATTACACTTCA

AAAGATCATGCCACTCAAAGTCATACCAAGCTCTAGGTGTCTGGATCA

CGACAACTAACTGGTGTTAATCTTTTACAACATATTGAATGATATATA

TCACGTTAAGGTACATGCGTCTAGATGCAGAAACTTGCATACGTTTCC

TTTTCAATAAAGTCTTGCATATGTATGGTTTATAGGGTGATGTAATTT

CTTGTTTGTTTTTACTTAAGTTTATAAGACATTTTTTTTTTTTTTA

TCGATGCTCTTACTCATTAAAATATTGGAACATATACAAAATTTTATA

TGTTTTAGATAAAATTATACAGGTTTTAATTTTAGGAACTTACCACTT

GTTCACACTGCGAGACTTAAATAGTCAAAATAGAAAATACACACTATT

AAAAAGTACTCACTATTTATCAAATTTAT.

>BvCYP76new from *Beta vulgaris*
(SEQ ID NO: 9)
CAGTCATTTAAAATCCTGTAAATTACTCACATACATAACCAAATTAAA

GTTGCCGCCGTACTGATTTCCAAAGGTCCTACATCTATCAATGGAGTA

TTACACCATAACGCTATTATTCATCATCTTCACAATATCAATATTCGG

TACAAAAATTTTGAGCAAGTCCAAACTTCCTCCAGGACCAACACCATG

GCCTATCATAGGCAACATCCTCGAGCTAGGCAAGTTACCTCATCAGGC

AGTTGACAAGCTCTCAAAAACCTATGGCCCTATATTATCTCTCAAACT

CGGAAGCATCACTACAATAGTAATATCATCCCCTGAAATCGTTAAAGA

AATGTTCCTCGAGCACGACTTAGCCCTTTCTAGTAGGCCTTCCCCGGA

TGCTTCGAGGGTGGGAAACCATAACAAATTTTCCATTGTTTGGCTCCC

AGTGTCCCCCAAATGGCGGGACCTTAGAAAAATTGCTACTATCCAATT

GTTTACTACTCAACGCCTAGATTCTAGCCAAGAACTACGGCAGATCAA

GGTGAACGAGCTGGTTGATTATGTACGACAGTGTTGTGAAAAGGGTCT

ACCTGTTGATGTTGGTAAAGCCGGGTTTACTACCACGTTAAATATGTT

GTCTAACACGTTTTTCTCCATGGATTTGGCTAGCCATGCTTCTTCGAA

TTCGCAAGAGTTCAAGGATCTTGTTTGGAGTCTTTTGGAAGAGGGTGC

AAAGCCTAATGTGTCGGATTTTTTCCCGATAGTTAGAGAATTGGATTT

GCAGGGAGTATCGAAAAATAGAAGGGTGCACATGAAGAAGCTAATGGG

AATTTTCGAGGAAATCATTGATGGAAGGTTGACAAAGTTAAAGGATGT

GAAGGATGATGTTCTAAGTACTTTACTCAAACTTGTTAAGGATGAAGA

ATTGAACCTTGACGACGTCAAACATATGCTCATGGATTTATTTTTAGC

GGGAACAGATACAACCTCTATCACATTGGAGTGGGCGATGACAGAATT

ACTTCGCAATCCAGAAAAGATGGAAAAGGTTCAAATTGAGTTGGACAA

AGTACTTGGCAAGGATAGTTCTCTGCAAGAGTCAATGATCTCAAAATT

ACCATATATTCAAGCAATAGTGAAAGAAACATTAAGATTACACCCACC

-continued

AACTCCTTTCTTGATTCCTCACAAAGCAGAAAAAGATGTATTGTTATG

CAACTATTTAGTGCCCAAAAACTCAATTATTTGGGTTAATTTATGGTC

GATCGCTCGTAGTCCAAGTGTGTGGCCAAATCCAGAATCATTTTCTCC

TGAAAGGTTTTTGGAGATGGAAATTGATATTAAAGGACGAGATTTCAA

ACTCATACCCTTTGGATCAGGAAGAAGAATGTGTCCTGGAATGCCACT

TGCTTATAGGATGACACATATGTTGTTGGCTACTCTTCTTCATTCATT

TAACTGGAAGTATGGTGAGGCAAGTCCAAAAGATATAGACATGAAAGA

AAAGTTTGGGTTGACGTTGCAAAAGGCTCAGCCACTTCAAGCAATTCC

AATTCCCAGATGATCAATCTCTTTTGAGGAGTTAGACGATTTCTTTGT

GTCAACCAACTAGTACTTATCGGAACATTTATTGTTAAATGTGTCTGT

TAGATGTACATATGATGTTGTTATACTAAGAAATAACGGTGTTTAAGT

GCAACATGGGACAAGAGGATTATGTAAAGTATCCTAGATTTTATTAGG

TGCTCCTACACCTATGTATTGGTGCATTTGCACCAAGTCGTCTGTAGA

AAACTTGAGACTTGGGAGGCAAGAACTTTACCTCTGTAAAAAAAACGC

GTTTTTTGCATTCTCCTTGTATCTTTTGCAAGAGATTGTACGCATTCA

CAAAACATCAAATACATTTGTGTTTACACAATAAGAATCGCCAACACT

GA.

>CYP82G1-like from *M. jalapa*
(SEQ ID NO: 36)
TACGTCTATTCTTGCCTCCCATTTCCTCCCTGCAAAAAGGAAGAAAAT

GGAAATACCCTTTAATTTGCAACCTATTTTTCTAATTATTGTACTATC

TACCTTCATTCTAACCCACCTAATAACAAAAAACACAAGAAAGTTCAA

CCAATGCAAATCAAAAACCAAGCCAATACCAAAACCACCTGGCTCACT

ACCCATAATAGGTCACTTGCACCTCCTAAGAGGTCATGGAACCACCCT

AGGTCGCACCCTCGGAGCCATGGCCGACAAGTCCGGACCCATTTTCGG

CCTCAAGCTAGGCCAACACAAGGCTATAGTCATTAGTAACTGGGAGAT

AGTCAAGGATTGTTTCACCAATAATGACATGAACCTTGCAACTAGACC

TAGCATGGCTATTAGCAAATATATTGGTTATGACTTTGCCTCTTTCTC

TATCTCACCTTATGGCCGATATTGGCGTGAGATTCGTAAGATCTCTAC

TGTTGAGCTCTTGTCAAACAAACGCCTTGAGAAAATGAAGCATGTTCG

AACTTTTGAGGTGAACTCTTGCCTTCAAATCTTCTATGAAAAATGTGT

CAAATCAGAGGATAATGAAAGTAATAAAGTAGCAAAAATTTGTCTTAA

AAAGTGGTTAGAATATATTGGTTTTAATATCGCACTATCTATGATAGT

TGGCAAGAGATTCTCCTACGACCAGTATTATAAAAAAAATACTGTTGC

ATCGAGATTTATGAAGGCAATAGAAAGAGCAACCCACTTAGCAGGACT

TCCTATACCCTCGGATTTTTTACCATGGGTTGAATGGATGGATTTGGT

GGGTTACATTGGTGCTATGAAGGAAACTCATAAGGAAATTGATGTGAT

TATTGGACATTGGCTTGATGAGCATATTCAAAAGAGGAAAGAGACGTT

AGAAAGGCGAGGTACAAGCATTGATGATAGTGACTTCATGGATGTAAT

GTTATCTAACATTACTGAACAATTTGCCAAGTCAACCTACTCTAAAAA

CACCATCATTAAAGCAACAGCTTTGACACTACTTCTAACAGGTTCAGA

-continued

AAGCACCTCAATCACACTAACATGGGCCATATCACTACTTCTAAACAA

CCCTACGGCCCAAAATTTGGCCCAACAAGAAATGGACAAACAAGTTGG

TAAACAAAGATGGGTTGAAGAATCTGACATCACCAATCTACCATACCT

CCAAGCCATCATAAAGGAAACTTTACGTTTGTATCCACCAAGCCCATT

AGCAGGCCCAAGAGTGGCCCAAGAAGACTGCCAAATCAATGGACATTG

TATCACAAAAGGAACCCGGGTGATTGTTAACATATGGAAGTTGCATCG

TGATCCGATGGTTTGGTCCGACCCAGATAAGTTCCGACCCGAAAGGTT

TATTGGGGAGCATAAGGATATTGATTTTAAGGGTCAATACTTTGGGTA

TATACCTTTTAGCTTGGGTAGGAGGGGTTGTCCTGGGATGAATTTTGG

GCTACAAGTGGTCCATTTGATGTTAGCTCGTTTGGTCCAAGGGTTCGA

TATTTGGGCTCAAAATGGTGGCCTAATTGATTTGAAGGAAGGGTTGGG

CTTGGCTTTGCCCAAGGCTGGTCCATTGGATGTCATTCTTGCACCACG

TTTGTCCAGTGAGCTTTATGGAGCTTTATCAAAGGTGAATGTTACTTA

TGGTCGGGCAATGAATGAACTAGCTTTGTATTTATAATTTTACAAATA

ATTTGTAAGATATGAACTGTTTATCTAGTCACTTTTCCGCGTCTTAGA

ATATCAATAAGCAAAAAGTTTTATGTAATAATATGTATTAGTGTGTTA

TTGTATCATGATTCGTCGGTATACTGAAAATATTTTACGTCTAGGAGA

ATGTGCACACATTTAATCTTATTTGCTTATAAGTATTATATACATAAA

ATTTTCTACTTTATAAATTTAGGTATATTGAGCTTTCGACCAAAACCCA

AAAACTAAAGAAGTTTTTTTTAAAACATACAAGTTGGTATTGTTTAGA

TTTTTATTTATTTTTATTATCTCTTTTATTTGTACTTAGTGGGTGTGT

TAATAATGTAAAGAAGTATTAAATATTTATAGAGTTGGAAAAACCCAA

TATTTTACATTGGAAAAA.

>CYP78A9-like from *M. jalapa*
(SEQ ID NO: 37)
TACGTCTCTAACCTCCTTCTCCTCACCATCATCATCTTATTTCTCTCT

CTAACTTCCTATTTCTCTCTCTAGAATGGTCTCAACTAGTGACTCACT

CTGGCTTTTCACCTACTTAGCTTCAAAATATGATCATTTTACGACCCC

TAACTTTATTTATTCTTTGTTTTGTTTCGTAATATTTTTTATTTTGAT

TCATCTACTGTACTGGTCCCACCCAGGTGGTCCGGCATGGGGGAAGTA

TTCATGGACTCATCTCTCGGGATGGGCCGGGAAGCCCATCCCGGGCCC

AAGAAGTTGGCCCATTATAGGTGGTTTGGACCTGAAGATGGGACTGGC

TCATCGGAAGTTAGCCACAATGGCTGAGAAATACGGGACCATGGCTAA

GAGGCTCATGGCTTTTAGCCTAGGAGAAACACGCGTGATTGTCACGTG

CAATCCCGACGTGGCGAAAGAAATACTAAATAGCCCGGTTTTCTTGGA

CCGACCCGACCAGGAGTCGGCTTATGGGTTGATGTTTAACCGGTCTAT

AGGGGTTCGCACCCTATGGGACCTACTGGCGAACCCTAAGGAAAATAAC

ATCAACCCATTTATTAAGCCCTAAACACGTAAAAGAATATGAGAACCT

ACGTAGGGAAATAATGGAACAAATGGTTGACTCGATATCGAACCAAGC

CGGACCGGTTCGGGTCCGGGAAATACTAAGGAGGGCTTCATTGGATAA

TATGATGGGGTCAGTGTTTGGTGGGCCCCACAAGGAGGTCGTTGAACA

GTTGATAGAAATGGTTGGTGAAGGGTATGACTTATTGGGTGTCCTTAA

-continued

TTTGGGGGACCATCTATCTTGGCTAGCCGAGTTTGACTTTCAAAAGGT

TCGGTTCAGGTGCTCTCAACTTGTTCCAAAAGTCAACCGGTTCGTTGG

TGAAATTATCGATGAACATCGGTCTAGTTCGGGTCAAATTATGAACCG

GGACTTTGTTGATGTTTTGTTGACTCTACCACAACATGAACAACTTTC

TCATTCTGACATGGTCGCTGTTCTTTGGGAGATGATATTTAGAGGAAC

AGATGCAACAGCAGTATTAATAGAATGGACATTAGCACGATTAGTAAT

TCATAAAGATATTCAATCAAAGGTCCAAAATGAGTTAGACCAAGTAGT

TGGAACATCACGAGCCGTTGAAGAGTCTGACCTATCATCACTGATATA

TCTAACGGCTGTGATTAAAGAAGTATTGCGGGTCCACCCACCTGGGCC

CCTCCTATCGTGGTCTCGCCTTTCAATTCAAGATACTACTATAGATGG

TTGTCATGTGCCAAAAGGTACTACTGCTATGGTTAACATGTGGGCTAT

TGCTAGAGATCCTAATGTGTGGGCCAACCCAGATGAATTTGACCCGGA

TAGATTTTTAATCGGTGGGTCCGAGTTTGAGTTCTCTGTTCTTGGGTC

GGATCTTAGACTTGCCCCTTTCGGGTCGGGTCGTAGGTCATGTCCTGG

GAAGGTCTTAGGTTTGACCACAGTCAGTTTTTGGGTTGCTTCACTCTT

GCATGAGTTTGAGTGGGTGACATCACCTAACGCTGACGTGGATTTGAG

TGAAGTGCTTAAGCTTTCGTGTGAGATGGCTCATCCTCTTACCGTGGA

AGCTAGGCCGCGACGTCATTAATTTTACAAAAGACGATATTCTCATAC

ACAGATTATTGTCAACTTTATCAATATATACGGGTGATAGTTTGACAT

TGTTATAGTATTCGGAAAAATATTTTCTAGAGATAAGTAAATTTATAA

TAATCTAAAAAACTGAATGTATAATTATATTAATTAATGTACTAATGT

TATTATAATGTTTATAAATGATTGTGAAATATATATGGTTAACATTAT

ATGTAATGAGAAATGGTTTGCTTGGCAAAAA.

>CYP86B1-like from M. jalapa  
(SEQ ID NO: 38)  
GCTAGCTGCCTTGTTCATTTCAAGAACAATATACACTAGTCAATCCAT

TTCAAATGGCCTACTTAGAAATTGTCATATTCTTCATTTTTCTCATCG

TAATTTGTTTTTCTTTTCGTGACAAAAATGGTCTCCCAACAAATTGGC

CGATTGTTGGGATGCTACCAGCTGTTCTAATCAATCTTCATAGAATTA

ATGACTATTTTGCTGAACTTGTTGCTAAATCAAATTTAACATTCTCAT

TTAAGGGTCCTTGGTTTAGCAACATGCGAATTTTAGCGACAGTTGATC

CAGCAAATGTGCACCATATAATGAGTAAGAATTTTAACAATTATCCTA

AGGGTGCTAAGTTTTACGACATCTTTGATATACTTGGAGATGGTATTT

TTAACACCGACTTTAATATATGGCAATACCATCGGAAAATGGCTCAGT

CATATATTGGTGACTCAAGATTTCAACAATTTTTGTTGAAGAAGTTG

GGGAAAAGATTGAAGGTGGATTAATTCCTATCCTTGATCATGTTGCCA

TGCAAGGGTTACAAGTTGATTTACAAGATTTATTTGAAAGGTTTACTT

TTGATACTATTTGTTCACTTATTATGAACTATGATCCTATGTCTTTGT

CCATTGATTTTCCTGATGTTCCATCATCTAAGGCTCTAGATGTTGCTG

AAGAAGTCATACTTCTTCGTCATTTAGTACCTACAAGTGTTTGGAAGT

TTCAAAGATGGTTAGGTGTAGGGATGGAAAAGAAGCATAAGATAGCTT

-continued

GGCAAGTACTTGATGATTTCATTTATGAGTGCATATCAAGGAAAAGAG

AAGAGATGAGAGATAGTTTGTCCTATGAGAATAAGGACAATGAGATGG

GTGTTGATTTAATGACATTGTATATGAATGAAATCAAAAGTAATGAAC

TTGTCAAGGATGATCCTAACAAGTTTTTGAGGGATACTATTCTTAACT

TTTTTATTGCAGGTCGAGATACAACTAGTACTGCTTTATCGTGGTTTT

TCTATCTACTATCCAAGAATCCACAAGTGGTAGAAAAGATTAGACAAG

AGTTATCTTGGATCGTTTCACAAGAAAAAACTAAAAATTATGCTAATT

TGATTGATAAACTTGTTTATCTTCATGCCGCATTATGTGAAGCTTTAA

GATTATATCCTCCGGTGGTATTTGAAGCAAAGTCTCCGATTGAATCGG

ACACTTTACCAAGTGGTCATAAGATTGATCCTGACACACAAATAATCT

TAAATATGTACGCAATGGCGAGGATGAAAACAATATGGGCGATGATT

GCGATCAATTTAAACCTGAGAGGTGGATATCATCAACAACAGGAAAGA

TTAAGCATGAACCTTCGTACAAGTTCTTGGCTTTTAATGCAGGACCAA

GAACTTGTGTAGGAAAAAATATGGCTTTTACTCAAATGAAAGCAATAG

CAATAGCTATATTACAAAACTATCATATACATGGTATTGATGGACAAG

TTATTGAACCTGATCTATCCATAATTCTCCATATGAAGAATGGATTCA

GAGTAACTGTTTCACCGTGTAACGTTTCTATATAACCATCGAGAGAAC

CAAGTTTCCTCGATCTCTTTTAAACATTGTAATGTTTAATTATCAACT

AAAAAATCGTATATTCTCTTCGTTTCATTTTTTCTTTTTCTTTTTAT

CAAAGATCAAGGTAACGTCGGAAATAACCATATTGTTTTCTTTGGTTA

AATGAAAGACAATGTAAGTTGTAAAAGTATGTAAGTGTAAAAATAAA

TTTAAAAAATTGTGTGAAAATAAGTTGTAATAAATAAAGAATAATGTT

GGTATTTTATTGTTTACTATTTTGATAAACAGAAAAAATAAAATAAAA

CTGTTTAAAAATAAAAGTGAGAAGAAAAAAAAATAAAAGAAAAT.

Hypocotyl Transformation of *Solanum nigrum*

Media

Liquid Jones (pH5.2)

Basal media (pH to 5.8 with NaOH before adding the agar)

MS with vitamins (cat M0222)=4.41 g/L

Sucrose 3%=30 g/L

Agarose (plant agar) 0.6%=6 g/L

TABLE 3

| | IND1 (first callus induction medium) | | | |
|---|---|---|---|---|
| | Stock solution | Final conc. in medium | Amt. to add to 1 L of basal media | Amt. to add to 800 ml of basal media |
| IAA | 0.2 mg/ml | 0.02 mg/L | 100 µl | 80 µl |
| BAP | 1 g/L | 1 mg/L | 1000 µl | 800 µl |

TABLE 4

IND2 (second callus induction medium)

| | Stock solution | Final conc. in medium | Amt. to add to 1 L of basal media | Amt. to add to 800 ml of basal media |
|---|---|---|---|---|
| IAA | 0.2 mg/ml | 0.02 mg/L | 100 µl | 80 µl |
| BAP | 1 g/L | 1 mg/L | 1000 µl | 800 µl |
| Kan* | 100 mg/ml | 75 mg/L | 750 µl | 600 µl |
| Tic | 100 mg/ml | 100 mg/L | 1000 µl | 800 µl |

*Make media without Kan for controls

TABLE 5

SHOOT (shoot induction medium)

| | Stock solution | Final conc. in medium | Amt. to add to 1 L of basal media | Amt. to add to 800 ml of basal media |
|---|---|---|---|---|
| BAP | 1 g/L | 0.5 mg/L | 500 µl | 400 µl |
| Kan* | 100 mg/ml | 25 mg/L | 250 µl | 200 µl |
| Tic | 100 mg/ml | 100 mg/L | 1000 µl | 800 µl |

*Make media without Kan for controls

TABLE 6

MAT (maturation medium)

| | Stock solution | Final conc. in medium | Amt. to add to 1 L of basal media | Amt. to add to 800 ml of basal media |
|---|---|---|---|---|
| Kan* | 100 mg/ml | 25 mg/L | 250 µl | 200 µl |
| Tic | 100 mg/ml | 100 mg/L | 1000 µl | 800 µl |

*Make media without Kan for controls

TABLE 7

ROOT (rooting medium in magenta)

| | Stock solution | Final conc. in medium | Amt. to add to 1 L of basal media | Amt. to add to 800 ml of basal media |
|---|---|---|---|---|
| Kan* | 100 mg/ml | | | |
| Tic | 100 mg/ml | | | |
| IBA | 2 mg/ml | | | |

*Make media without Kan for controls

Procedure
*Always work in a flow hood, close to a flame
*Use forceps & scalpel sterilised with EtOH & flamed
*Seal plates with parafilm before removing from the flow hood
Prepare the *Agrobacterium:*
Pick a colony from a fresh transformation into *Agrobacterium* GV3101 & inoculate 7.5 ml LB buffer in a 50 ml falcon tube
Grow, shaking at 28° C. o/n
Add liquid Jones (pH5.2) up to a total volume of 25 ml
Handling of the Explant:
Using seedlings that have expanded cotyledons, but no true leaves—remove individual seedlings using sterilised forceps & place onto a sterile Petri dish (approx. 30 hypocotyls per plate).
Cut the hypocotyl using a sterile scalpel, dipping the scalpel into the *Agrobacterium* mix before each incision.
For the control, dip the scalpel into liquid Jones before each incision.
Place all of the explants onto IND1 plates & place in the growth room in the dark for 3 days (wrap in foil).
Subsequent Sub-Culturing:
Move the explants onto IND2 plates (spacing them out more ~20 per plate) & place in the growth room with light/dark cycling
*Check the plates every couple of days for contamination & transfer healthy explants to fresh media sooner if contamination is visible.
After 2-3 weeks, calli will form at the ends of the explants (where they were cut). Cut the calli away from the rest of the tissue & transfer to SHOOT media.
If calli have not formed—move to fresh IND2 media.
After 1-2 weeks, green shoots will start to develop from the calli. Transfer these calli to MAT media.
If shoots have not formed—move to fresh SHOOT media.
After 1-2 weeks, the shoots should be big enough to be cut away from the callus and transferred to ROOT media (in magentas).
If shoots are still small—move to fresh MAT media.
Move the plantlets to fresh ROOT media every 2-3 weeks until they have enough roots to move to soil.

Example 2

Transcriptome Profiling and Co-Expression Analysis in *Mirabilis Jalapa* Suggests the Involvement of a CYP76AD1 Subfamily Member in Betalain Biosynthesis The primary goal of this study was to elucidate the first committed step in biosynthesis of betalains in plants, which commences with the aromatic amino acid tyrosine. Achieving this would close the gap in our current knowledge with respect to the plant enzymes and genes acting in the core betalain pathway (FIG. 1). Since genome and transcriptome sequence data from betalain-producing plants is currently very limited, we generated a comprehensive transcriptome dataset from the betalain pigmented *Mirabilis jalapa* (i.e. four o'clocks) plant. Libraries of 24 *M. jalapa* tissues were sequenced, including both betalain producing and non-producing ones. The selected set of tissues provided a temporal and spatial representation of betalain synthesis, as four different floral parts (i.e. petals, stamen, anthers and stigmas) were sampled in five developmental stages, each exhibiting increasing pigmentation during development (FIG. 2 A to F).

Figure 2G:
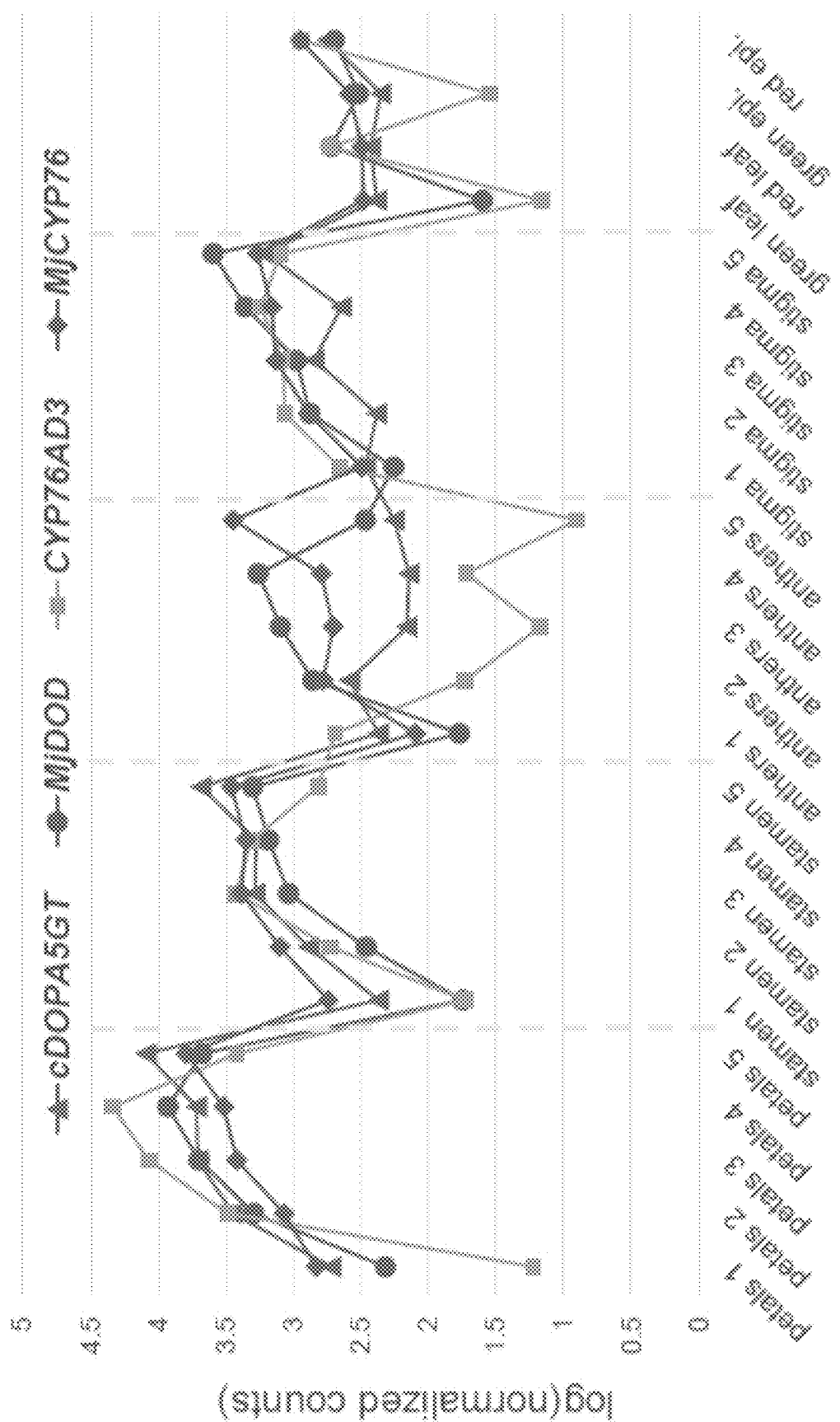

The transcriptome data was first analyzed by examination of gene expression patterns of the previously identified betalain-related genes in *M. jalapa*, namely DOPA 4,5-dioxygenase (MjDOD), cyclo-DOPA-5-O-glucosyltransferase (cDOPA5GT) and the cytochrome P450 CYP76AD3. These three genes were found to exhibit expression patterns which parallel pigment accumulation (i.e. increasing expression during flower development, and higher expression in red vs. green tissues) (FIG. 2G). Additional betalain related genes could thus potentially be found by co-expression analysis, searching for genes with expression patterns which highly correlate to those of MjDOD, cDOPA5GT or CYP76AD3.

Figure 3:
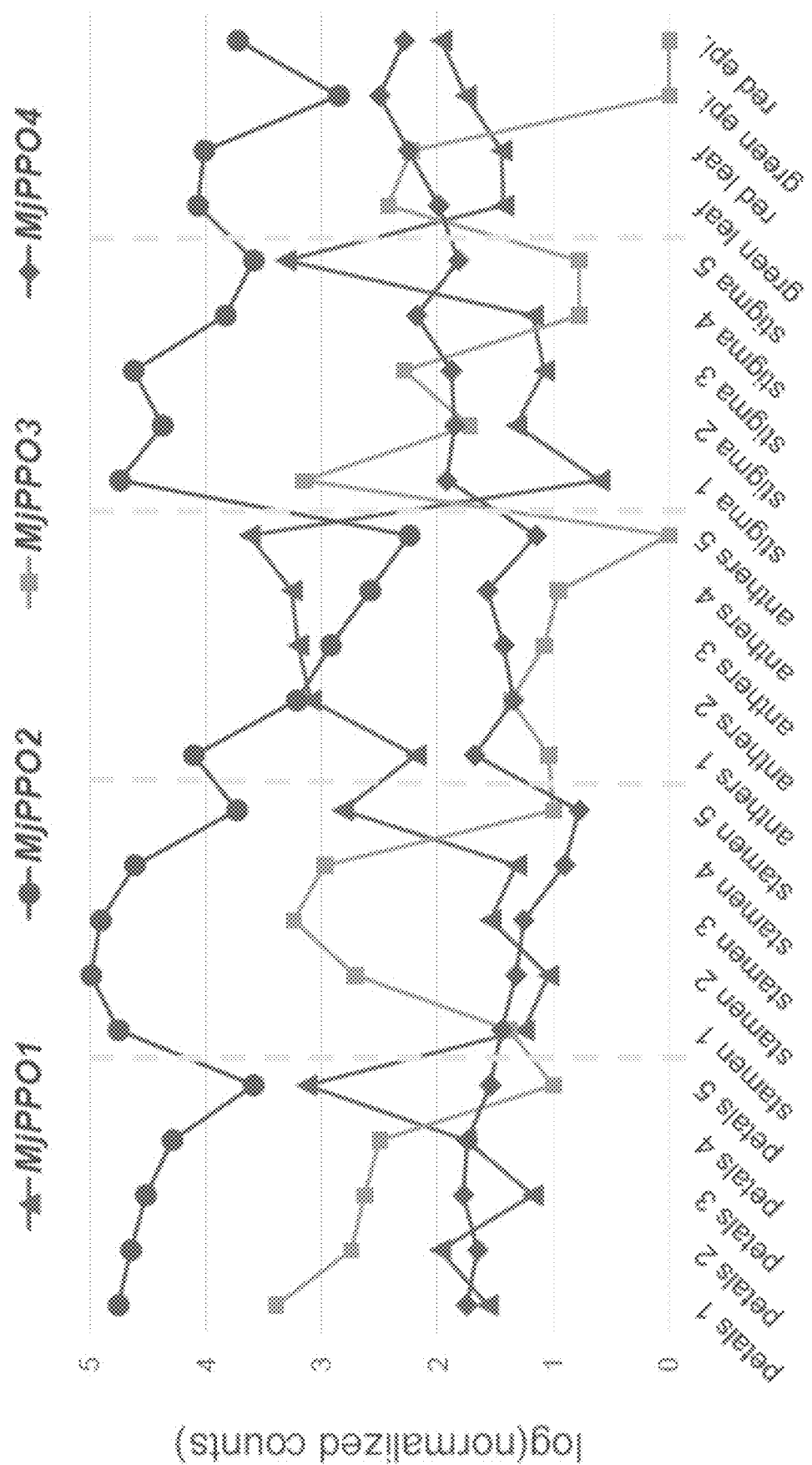
FIG. 3. Gene expression patterns of putative polyphenol oxidase-encoding genes MjPPO1 (SEQ ID NO: 5); MJPPO2 (SEQ ID NO: 6); MJPPO3 (SEQ ID NO: 7); and MJPPO4 (SEQ ID NO: 8) in the Mirabilis jalapa RNA-seq dataset.

Tyrosine hydroxylation in betalain-producing plants is commonly thought to be catalyzed by a tyrosinase (polyphenol oxidase) enzyme. We therefore initially searched for a tyrosinase-encoding gene that is co-expressed with either MjDOD, cDOPA5GT or CYP76AD3, however none was found. A polyphenol oxidase expressed in a pattern which parallels betalain accumulation could neither be detected by manual examination of genes annotated as polyphenol oxidases in the *M. jalapa* dataset (FIG. 3). Alternatively, L-DOPA formation could in theory be catalyzed in *M. jalapa* by a cytochrome P450-type enzyme. Four cytochrome P450-encoding genes were found to be co-expressed with one or more of the known betalain related genes used as baits, namely CYP82G1-like (SEQ ID NO: 36), CYP78A9-like (SEQ ID NO: 37), CYP86B1-like (SEQ ID NO: 38) and CYP76AD1-like (SEQ ID NO: 1). The latter, hereinafter named MjCYP76, stood out as a promising candidate, exhibiting high expression values throughout the dataset, in a pattern which highly correlated with betalain accumulation (FIG. 2G).

Example 3

CYP76AD1 and CYP76AD6 Co-Silencing Inhibits Betalain Production in *Beta vulgaris*

In order to examine whether MjCYP76 is indeed involved in betalain biosynthesis, a gene silencing assay was required. Since a robust and stable transformation procedure is not available for any betalain-producing plant we decided to apply Virus Induced Gene Silencing (VIGS), a widely used method for transient gene silencing in plants that is highly suitable for tracking pigmentation phenotypes. However, gene silencing with the VIGS method was previously shown to be particularly challenging in *M. jalapa*, most likely due to the inhibitory activity of the *Mirabilis* Antiviral Protein (MAP), and could only be achieved when the MAP gene is co-silenced with the gene of interest. Attempts for gene silencing in *M. jalapa* using VIGS were unsuccessful in our hands, including the attempted silencing of cDOPA5GT, which should result in partial loss of betalain pigmentation in the plant. We therefore proceeded to try and identify an MJCYP76 ortholog in a different betalain-producing plant species, in which gene silencing assays may be effectively implemented. An efficient VIGS method using vacuum infiltration was previously described in red beet, which was successfully used for silencing betalain related genes. Identification of an MJCYP76 ortholog in red beet could thus aid in assessment of the relevance of this gene to betalain biosynthesis.

Figure 4A:
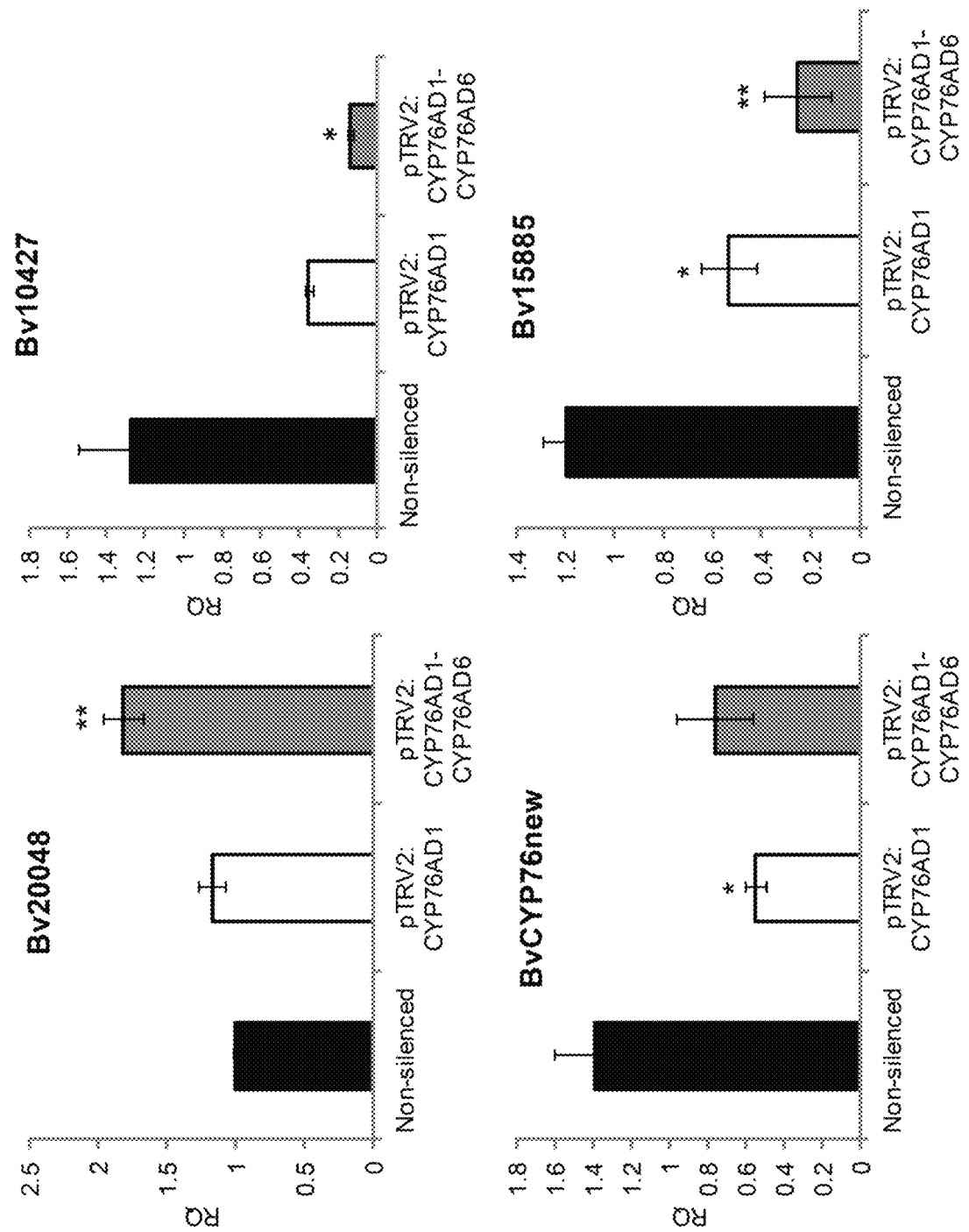
FIG. 4A. qRT-PCR analysis of four CYP76AD paralogs shows partial downregulation following infection with pTRV2:CYP76AD1 or pTRV2:CYP76AD1-CYP76AD6 vectors, suggesting off-target silencing. Upregulation of Bv20048 was observed in tissues infected with pTRV2:CYP76AD1-CYP76AD6. Relative quantification (RQ) values indicate means of three biological replicates ±SE. Asterisks denote statistical significance of differential expression in comparison with non-silenced tissue. *, P<0.05; **, P<0.01.
Figure 4B:
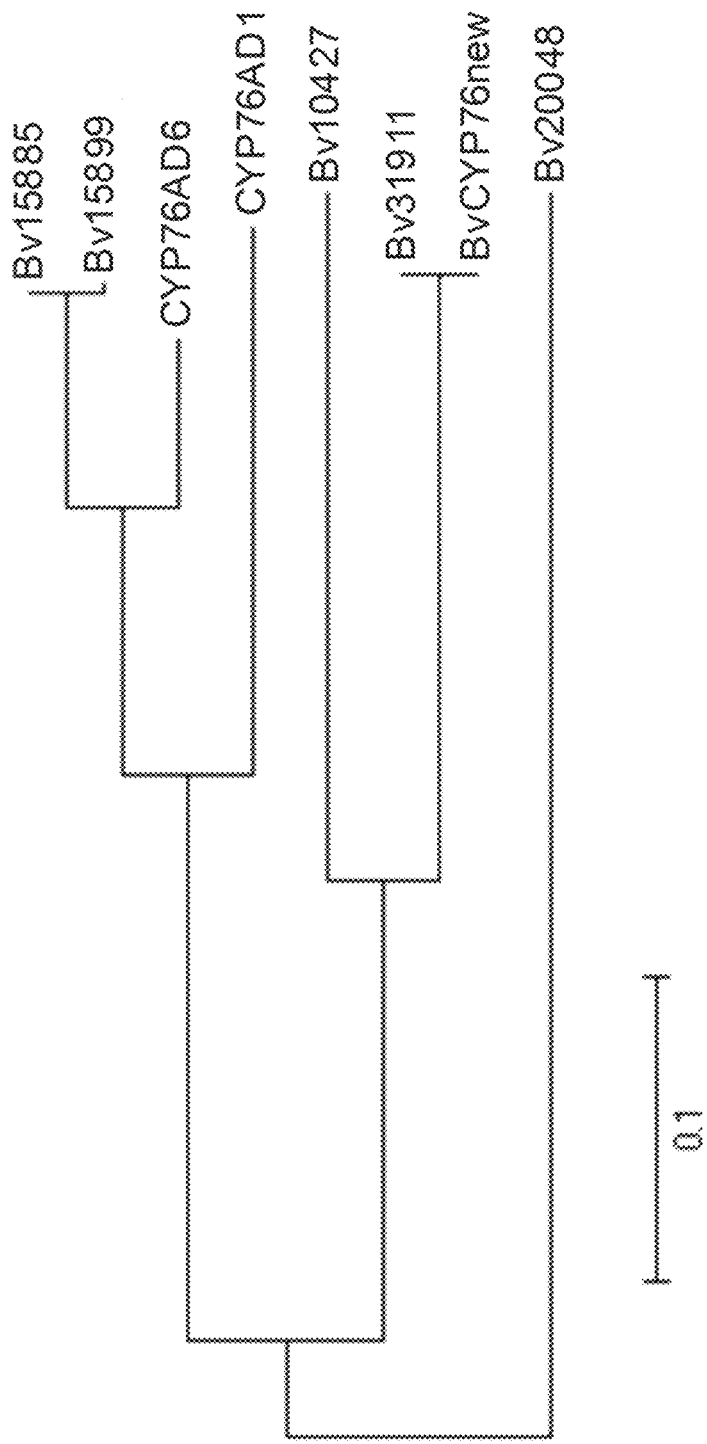
FIG. 4B. Maximum-likelihood phylogenetic tree of CYP76AD paralogs in B. vulgaris. CYP76AD6 (GenBank accession KT962274; SEQ ID NO: 30); CYP76AD1 (accession AET43289.1; SEQ ID NO: 14); BvCYP76new (accession KU041699; SEQ ID NO: 9); Bv20048 (accession KU041700); Bv10427 (accession KU041701); Bv31911 (accession KU041702); Bv15899 (accession KU041703); Bv15885 (accession KU041704).

To this end, we sequenced the transcriptomes of hypocotyl tissues of three varieties of beet; a 'golden beet' variety which produces solely yellow betaxanthins, as well as a red beet and a 'striped beet' variety, both of which have red-pigmented hypocotyls. An MjCYP76 ortholog in beet, which would putatively play a key role in betalain biosynthesis, was expected to be highly expressed in all three tissues. Homologs were identified by tBLASTx querying of the beet trasncriptome dataset with the MjCYP76 coding sequence. Contigs representing eight different cytochrome P450 genes with high sequence homology to MJCYP76 (over 50% identity on the protein level) were found, including the previously characterized CYP76AD1 (FIG. 4A). The highest scoring gene, BvCYP76new, was selected as a potential candidate to be a functional ortholog of MjCYP76 in beet. An additional gene within this group, hereinafter named CYP76AD6, which holds a 60% identity with MJCYP76 on the nucleotide level and 53% on the amino acid level, exhibited markedly higher expression values compared to the other paralogs and was therefore also selected for subsequent analysis.

Fragments from BvCYP76new and CYP76AD6 were cloned into the VIGS vector pTRV2 and introduced into seedlings of the 'Bull's Blood' red beet variety, which produces plants with highly pigmented dark red leaves and is therefore particularly compatible for gene silencing assays for betalain related genes. Since the tyrosine hydroxylase reaction to form L-DOPA is essential for formation of all betalain compounds, including both red betacyanins and yellow betaxanthins, silencing of either BvCYP76new or CYP76AD6 was expected to produce plants exhibiting green patches, due to lack of betalain pigmentation. pTRV2: BvDODA1 and pTRV2:CYP76AD1 were also introduced to beet seedlings and served as positive controls for the assay. Silencing of BvCYP76new or CYP76AD6 did not result in any visible phenotype (data not shown), while the silencing of BvDODA1 and CYP76AD1 produced patches of green or yellow color, respectively, as was previously reported. One possible explanation for a lack of visible phenotype when silencing a gene putatively encoding the enzyme responsible for L-DOPA production, was that this enzyme may be redundant with another enzyme or enzymes that also catalyze the same reaction. One such candidate is CYP76AD1, which could possibly catalyze the tyrosine hydroxylation step in addition to its experimentally demonstrated activity of conversion of L-DOPA to cyclo-DOPA. CYP76AD1 would have to be acting redundantly with another enzyme, since the silencing of CYP76AD1 does not prevent the formation of betaxanthins, for which L-DOPA is an essential precursor (FIG. 1). This hypothesis could be examined by co-silencing of BvCYP76new or CYP76AD6 together with CYP76AD1.

Figures 5A, 5B, 5C:
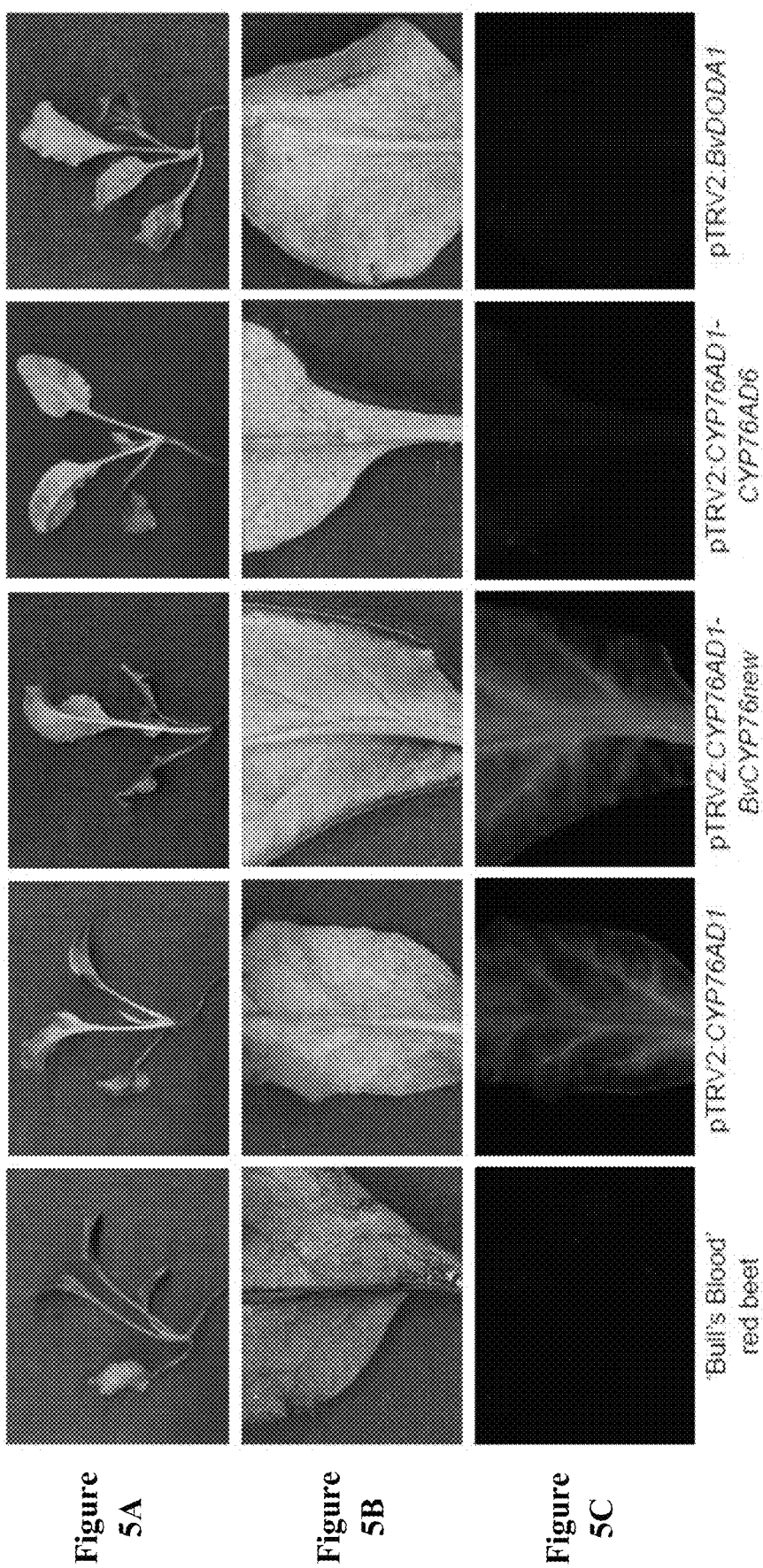
FIGS. 5A-5C. Co-silencing of CYP76AD1 and CYP76AD6 inhibits betalain production. Virus Induced Gene Silencing (VIGS) assays in red beet were used for silencing of BvDODA1 or CYP76AD1. CYP76AD1 was additionally co-silenced with each of the two new candidates BvCYP76new (SEQ ID NO: 9) and CYP76AD6. While silencing of CYP76AD1 alone or co-silencing with BvCYP76new blocks formation of betacyanins but not of betaxanthins, co-silencing of CYP76AD1 and CYP76AD6 prevents production of both types of pigments, resulting in a phenotype similar to the one obtained by silencing of BvDODA1. Reduction of betaxanthin levels is observed by a visible decrease in yellow color and lack of fluorescence under blue light, typical for betaxanthins.
Figure 6A:
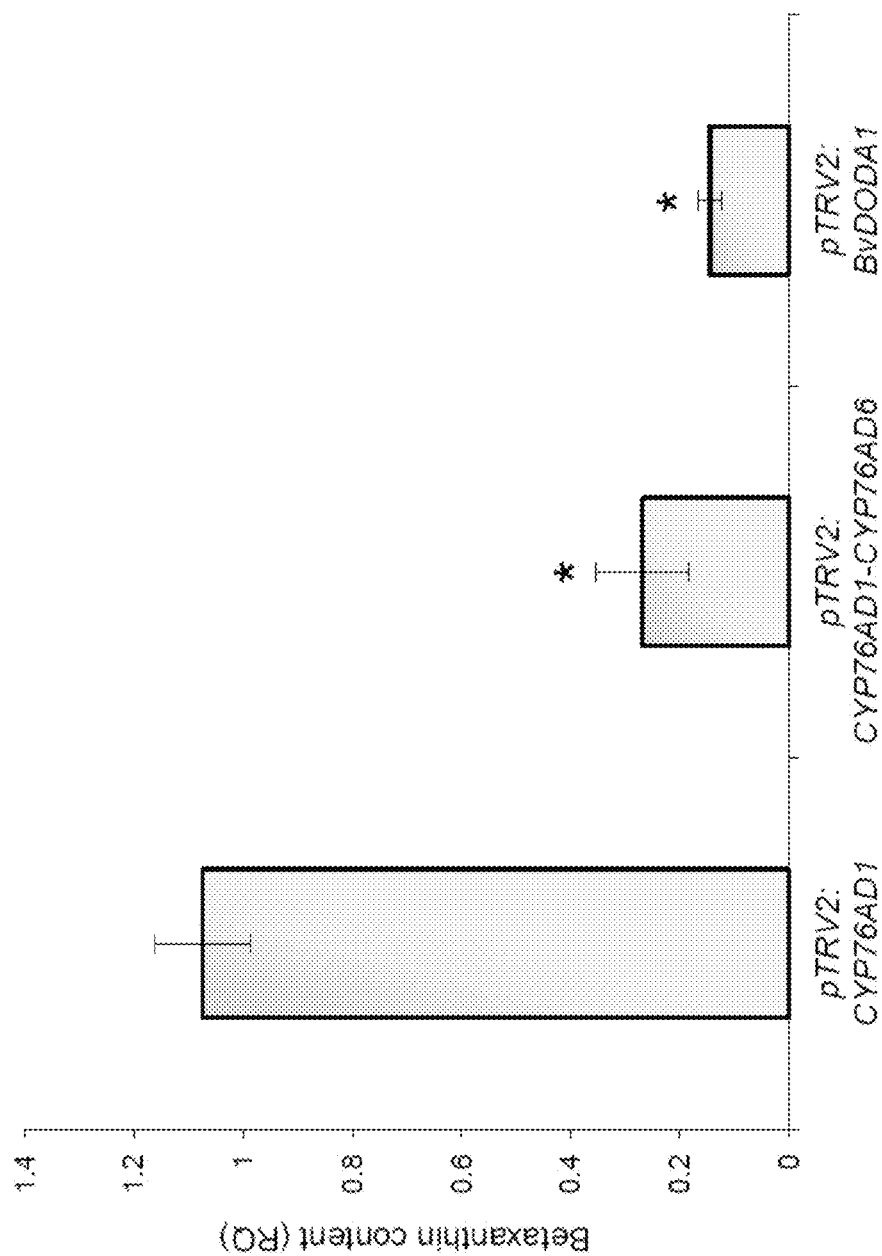
FIG. 6A. Relative quantification of betaxanthin in VIGS-silenced beet leaves. Relative betaxanthin content was assessed spectrophotometrically by light absorption measurements at 475 nm and 600 nm. Values indicate the mean±SEM of four biological replicates, each consisting of gene-silenced tissue from two to three plants. Asterisks denote statistically significant difference from pTRV2:CYP76AD1. **, P value<0.01. RQ, relative quantification.
Figure 6B:
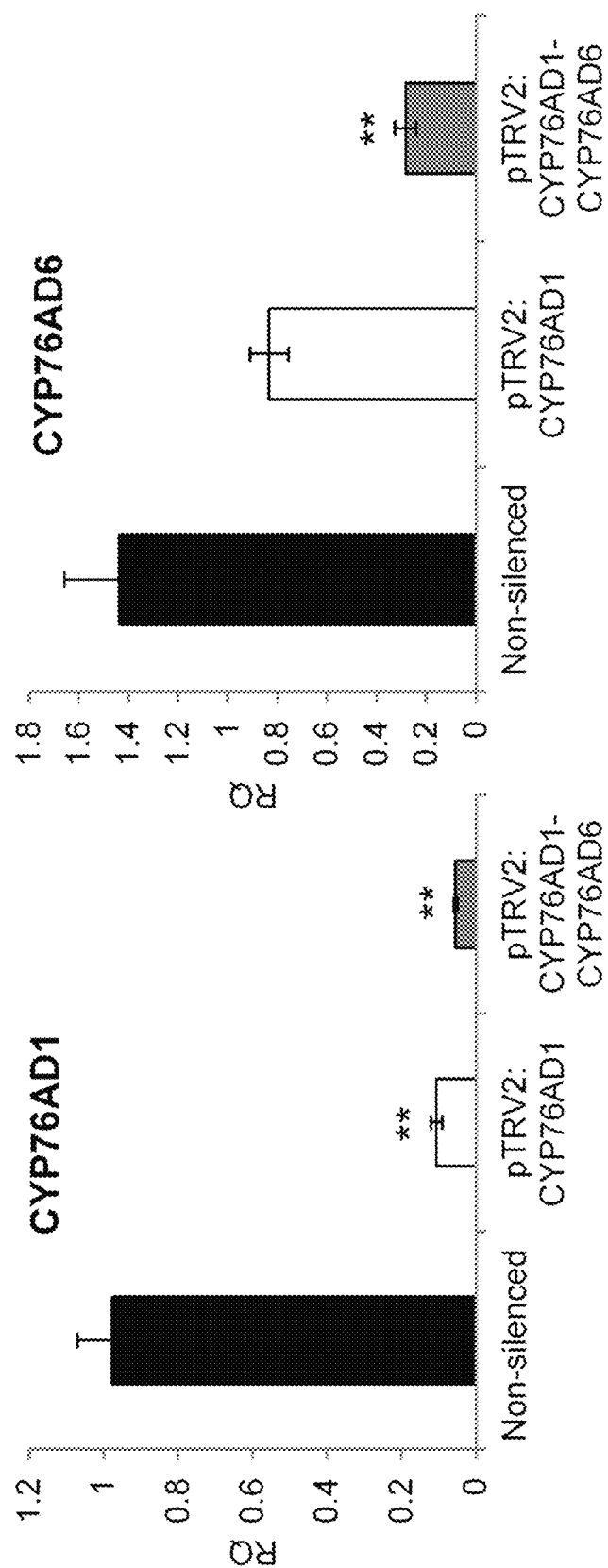
FIG. 6B. Quantitative real-time PCR (qRT-PCR) analysis of CYP76AD1 and CYP76AD6. CYP76AD1 is down-regulated in tissues infected with pTRV2:CYP76AD1 or pTRV2:CYP76AD1-CYP76AD6. CYP76AD6 is significantly down-regulated following infection with pTRV2:CYP76AD1-CYP76AD6. Relative quantification (RQ) values indicate means of three biological replicates ±SE. Asterisks denote statistical significance of differential expression in comparison with noninfected plants. **, P-value<0.01.

We therefore constructed pTRV2 vectors which harbor fragments of CYP76AD1 with either of the BvCYP76new or CYP76AD6 candidates, in tandem. A subsequent experiment was carried out for silencing of BvDODA1, CYP76AD1, BvCYP76new or CYP76AD6, as was done in the aforementioned VIGS experiment, in addition to co-silencing of CYP76AD1 with each of the CYP76 candidates. Plants in which CYP76AD1 and BvCYP76new were co-silenced produced yellow patches in leaves, similarly to plants in which only CYP76AD1 was silenced. However, co-silencing of CYP76AD1 and CYP76AD6 caused a clearly evident phenotype of green patches, which lack both betacyanins and betaxanthins, similarly to the phenotype obtained by BvDODA1 silencing (FIG. 5A, B). Differences in betaxanthin accumulation levels could also be observed by blue light imaging (FIG. 5C), under which betaxanthins typically exhibit strong fluorescence. Reduced betaxanthin accumulation in CYP76AD1-CYP76AD6 co-silenced tissue versus CYP76AD1 silenced tissue was further demonstrated by spectrophotometric analysis (FIG. 6A). These findings supported the notion of redundancy in the tyrosine hydroxylation step of betalain biosynthesis in red beet, by which this step may be catalyzed by either CYP76AD1 or CYP76AD6. Additionally, the fact that silencing of CYP76AD1 alone blocks production of betacyanins but not of betaxanthins, suggested that CYP76AD6 does not catalyze the conversion of L-DOPA to cyclo-DOPA, but only the formation of L-DOPA from tyrosine.

qRT-PCR analysis was performed in order to examine expression of CYP76AD1 and CYP76AD6 in plants infected with the pTRV2:CYP76AD1 or pTRV2: CYP76AD1-CYP76AD6 vectors. CYP76AD1 was found to be down-regulated upon infection with both vectors, while CYP76AD6 only showed down-regulation following infection with pTRV2:CYP76AD1-CYP76AD6 (FIG. 6B). Expression of four CYP76AD1 and CYP76AD6 paralogs was also examined. Three of the four paralogs examined showed down-regulation in tissues infected with at least one of the pTRV2:CYP76AD1 or pTRV2:CYP76AD1-

CYP76AD6 vectors (FIG. 4A). Thus, the possible involvement of one or more of these paralogs in betalain biosynthesis cannot be ruled out at present. However, irrelevance of one of the three paralogs, BvCYP76new, to betalain biosynthesis may be inferred from results of the silencing experiments, as silencing of BvCYP76new alone caused no visible change in phenotype, and silencing of this gene together with CYP76AD1 produced the same phenotype as observed when CYP76AD1 was silenced alone.

Example 4

Figure 7A:
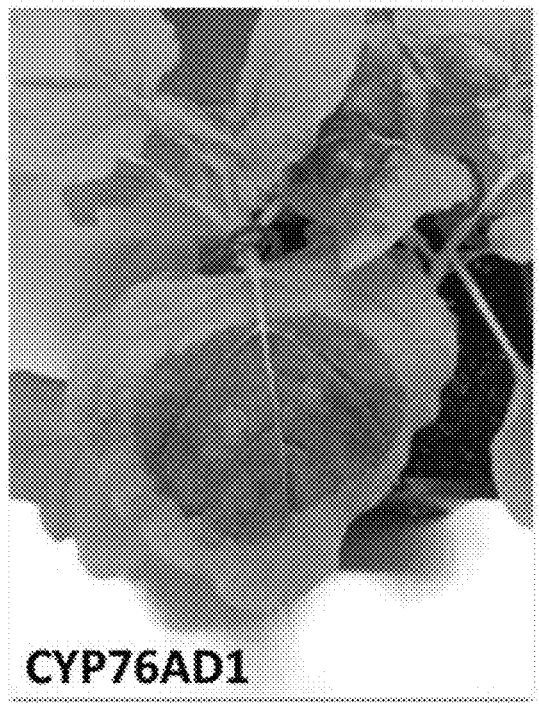
FIGS. 7A-7F. Recombinant expression of CYP76AD1 or CYP76AD6 in Nicotiana benthamiana leaves enables L-DOPA and betalain production.
Figure 7B:
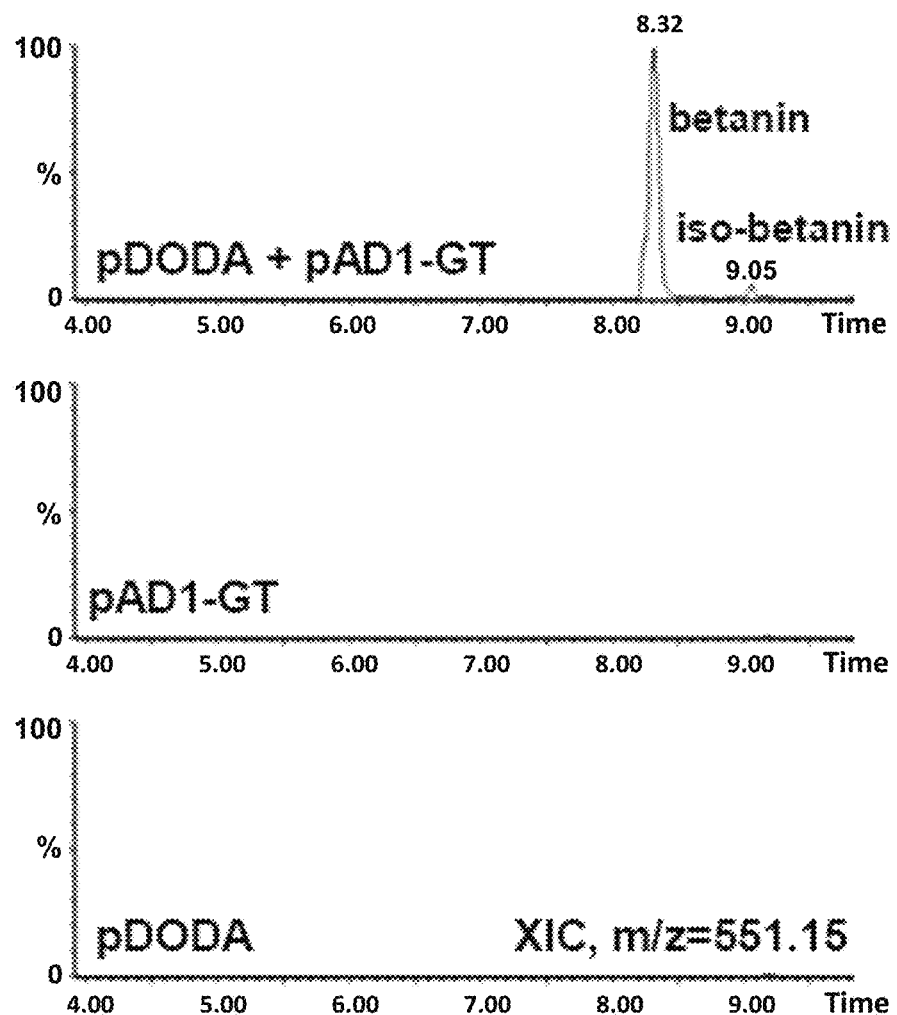

Transient Expression of CYP76AD1 in N. Benthamiana Enables Production of L-Dopa and Betacyanins If CYP76AD1 indeed catalyzes both the formation of L-DOPA and its conversion to cyclo-DOPA, then heterologous expression of CYP76AD1 together with a DOD enzyme and a betalain related glucosyltransferase (e.g. cyclo-DOPA 5-O-glucosyltransferase or betanidin-5-O-glucosyltransferase) should be sufficient for biosynthesis of the widely common glucosylated betacyanin, betanin. To test this, we generated overexpression constructs for the beet BvDODA1 and CYP76AD1 genes and the *M. jalapa* gene cyclo-DOPA 5-O-glucosyltransferase (cDOPA5GT), to be used for transient, agroinfiltration-mediated overexpression in *Nicotiana benthamiana* leaves. Two vectors were made for this purpose; one for overexpression of BvDODA1 under the CaMV 35S promoter (pDODA) and another vector for the tandem expression of CYP76AD1 and cDOPA5GT, driven by the CaMV 35S and *Arabidopsis* ubiquitin-10 promoters, respectively (pAD1-GT). Co-infiltration of agrobacteria (*Agrobacterium tumefaciens*) harboring the pDODA and pAD1-GT vectors into *N. benthamiana* leaves caused the appearance of dark red pigmentation in infiltrated areas within 2-3 days post infiltration (FIG. 7A). Liquid chromatography-mass spectrometry (LC-MS) analysis revealed that the pigmented leaf tissue contained high levels of betanin, as well as the betanin isomer iso-betanin (FIG. 7B; Table 2). This result provided a first proof of concept for the possibility of engineering betalain production in-planta without substrate feeding. Additionally, the formation of betacyanins without the need for L-DOPA feeding or overexpression of a tyrosine hydroxylating enzyme (e.g. tyrosinase) indicated that CYP76AD1 catalyzes the formation of L-DOPA in addition to its previously known activity of converting L-DOPA to cyclo-DOPA.

Figure 7C:
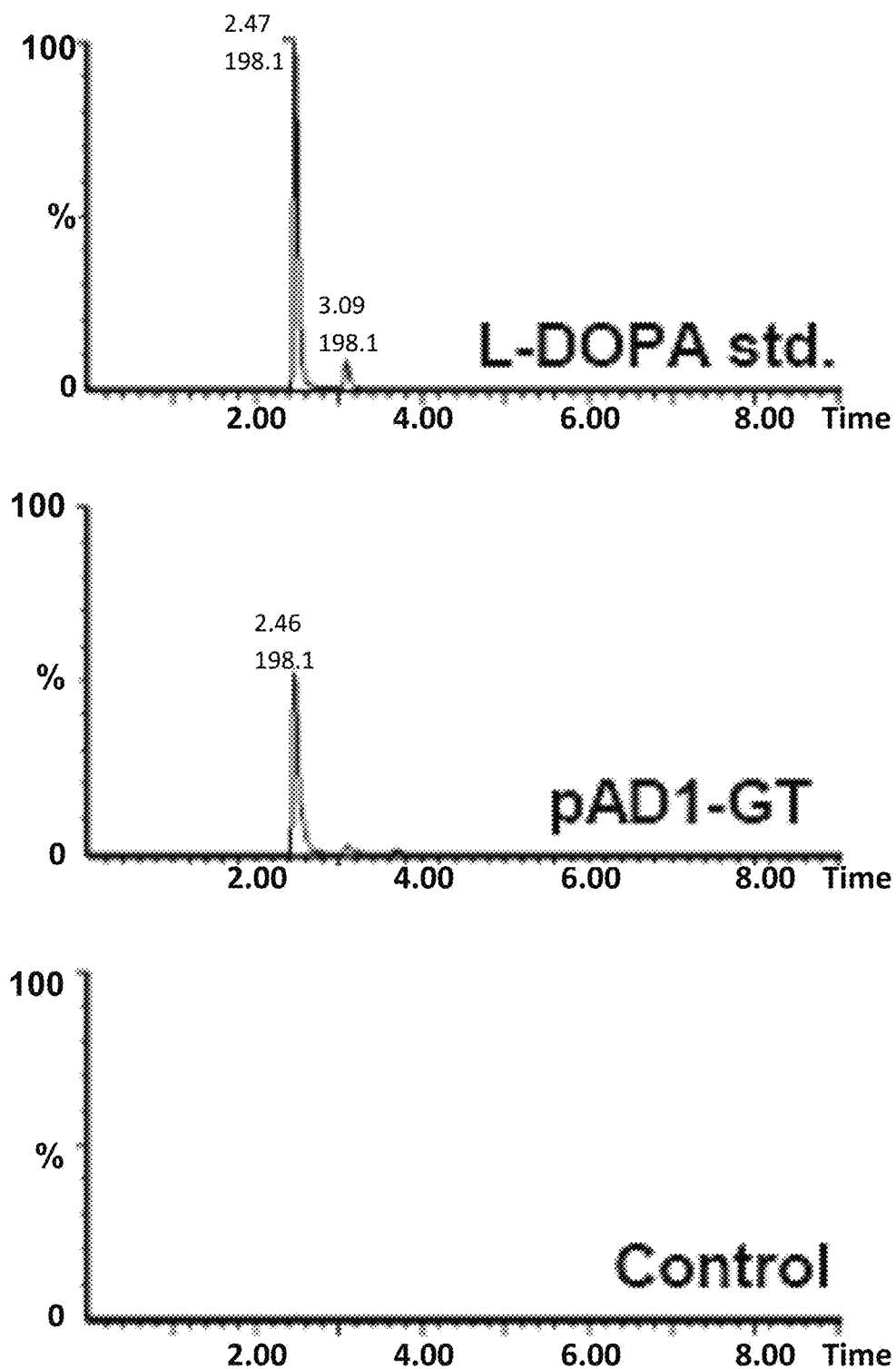

However, the production of betalains may have alternatively been possible due to occurrence of L-DOPA in *N. benthamiana* leaves as a result of tyrosine hydroxylase activity by an endogenous enzyme. To examine whether L-DOPA production was enabled due to the expression of CYP76AD1, pAD1-GT was infiltrated into *N. benthamiana* leaves without pDODA. Introduction of a vector overexpressing YFP protein (pYFP) was used as a control for this experiment. LC-MS analysis confirmed the presence of L-DOPA in pAD1-GT infiltrated tissues but not in pYFP infiltrated tissues (FIG. 7C).

Example 5

Figure 7D:
Figure 7E:
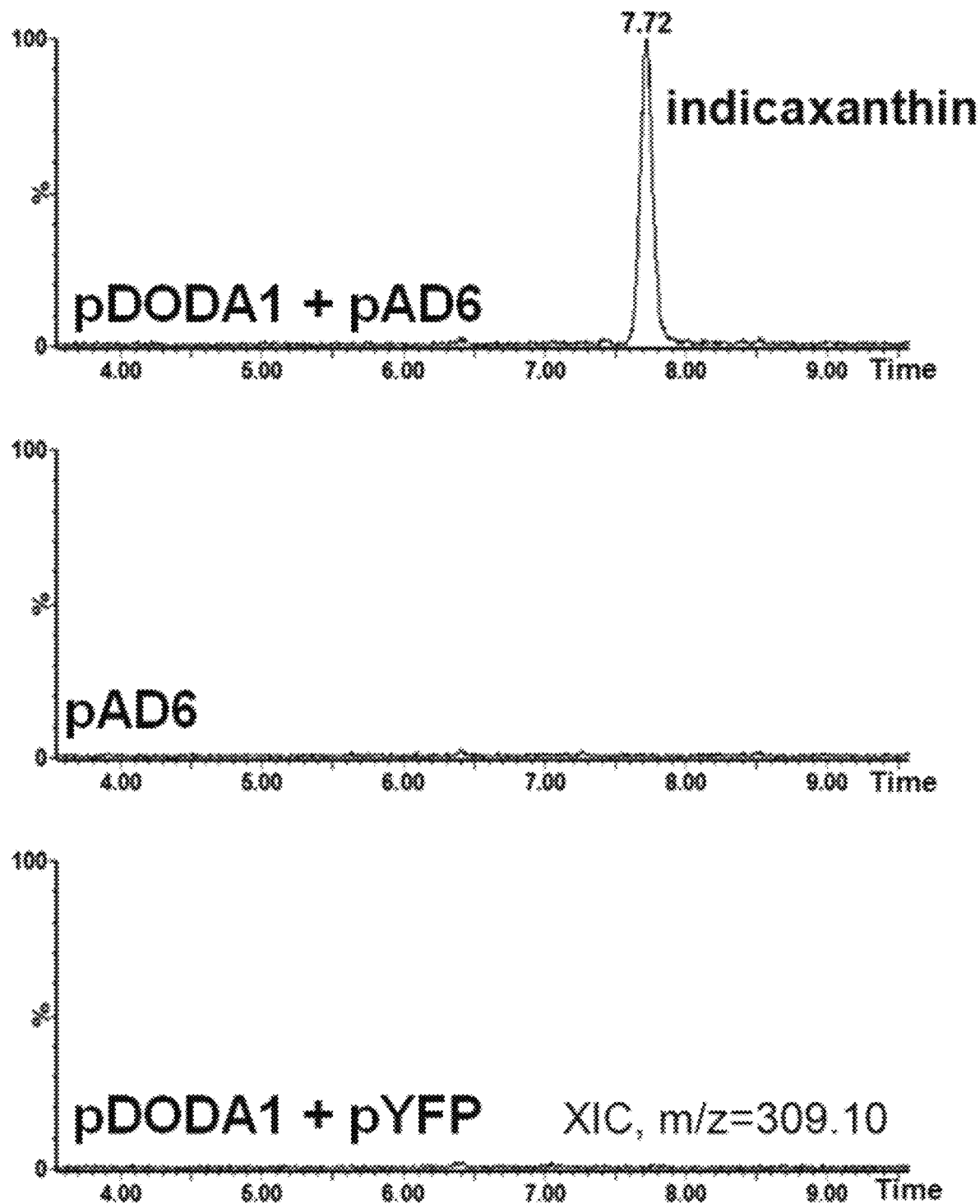
Figure 7F:
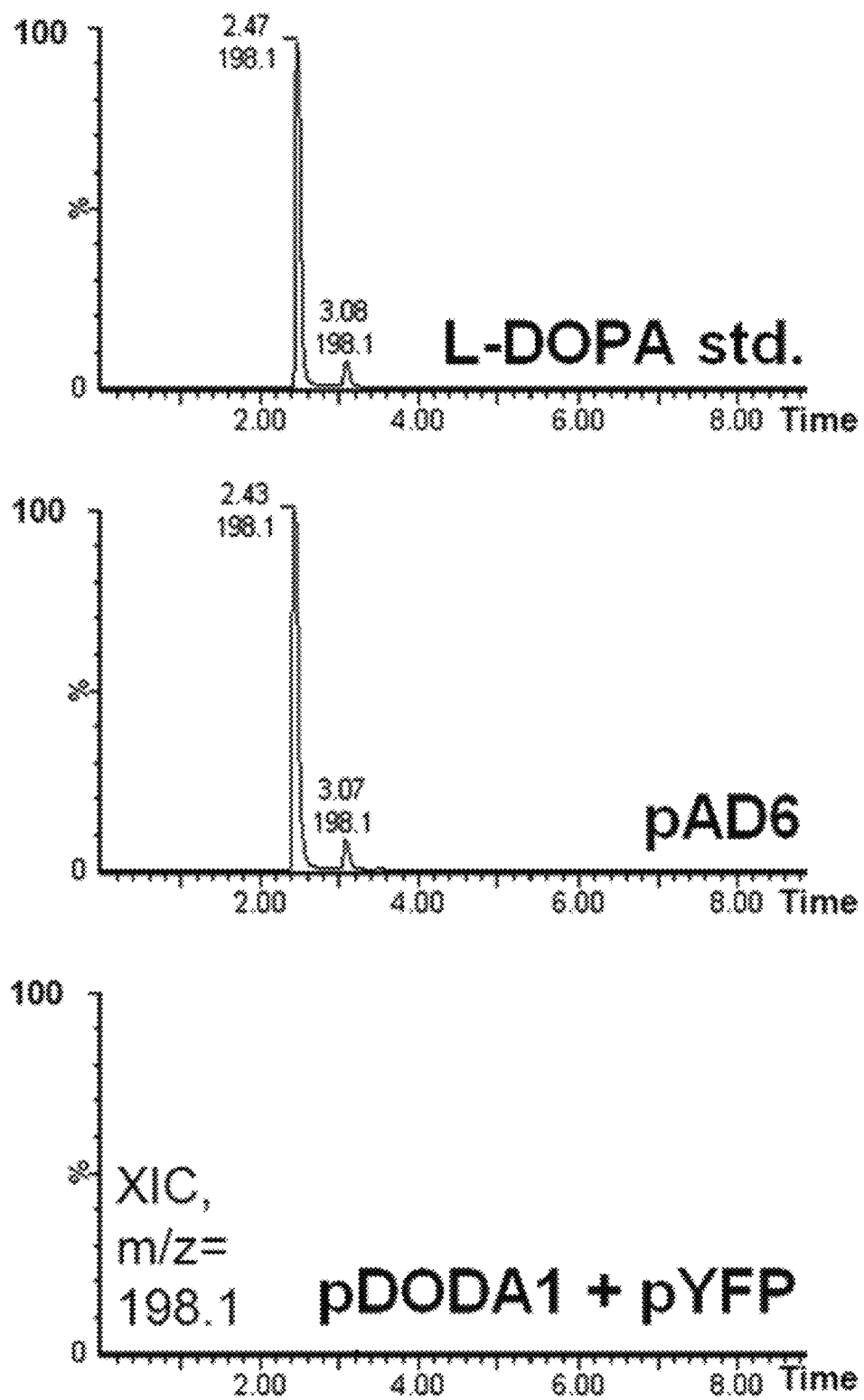

Transient Expression of CYP76AD6 in *N. benthamiana* Enables Production of L-DOPA and Betaxanthins Tyrosine hydroxylase activity of CYP76AD6 was also assessed by transient overexpression in *N. benthamiana* leaves. An overexpression vector for CYP76AD6 under the CaMV 35S promoter (pAD6) was constructed and inserted to agrobacteria. Co-infiltration of pAD6 and pDODA resulted in the appearance of yellow pigmentation in infiltrated areas, visible within several days post infiltration. (FIG. 7D). LC-MS analysis of the yellow-pigmented tissue revealed the occurrence of one major betaxanthin compound, identified as indicaxanthin (proline-betaxanthin) (FIG. 7E). Two additional compounds were found to exhibit typical betaxanthin light absorption spectra, one of which was putatively identified as a dopaxanthin-hexoside, based on accurate mass and fragmentation (Table 2). Notably, glycosylated-betaxanthins do not occur, to the best of our knowledge, in natural betalain-producing species. The fact that co-infiltration of CYP76AD6 and BvDODA1 induced the production of betaxanthins but not of betacyanins coincides with the data obtained in the aforementioned gene silencing assays, confirming that CYP76AD6 catalyzes only the single step of L-DOPA formation and not its subsequent conversion to cyclo-DOPA. Agroinfiltration of the pAD6 vector alone resulted in production of L-DOPA in *N. benthamiana* leaves, verified by LC-MS (FIG. 7F).

Example 6

Recombinant Expression of CYP76AD1 and CYP76AD6 Allows Betalain Synthesis in Yeast CYP76AD1 and CYP76AD6 activity was further evaluated by recombinant expression of each of the two enzymes in yeast, together with BvDODA1. To this end, full coding sequences of BvDODA1, CYP76AD1 and CYP76AD6 were cloned into galactose-inducible yeast overexpression vectors and transformed into *Saccharomyces cerevisiae* cells. Yeast were subsequently grown in standard SD media, with no L-DOPA supplementation. Similarly to the *N. benthamiana* transient expression assays discussed above, red-violet pigmentation was observed in media of yeast expressing CYP76AD1 and BvDODA1, while yellow pigmentation was evident in media of yeast expressing CYP76AD6 and BvDODA1. Expression of each of the cytochrome P450 enzymes without BvDODA1 or expression of BvDODA1 alone did not result in formation of red or yellow pigments. Additionally, expression of CYP76AD1, CYP76AD6, and BvDODA1 together, resulted in formation of orange pigmentation in the media (FIG. 8A). LC-MS analysis was used to verify the occurrence of betalains in the yellow, red-violet and orange-pigmented media (FIG. 7C; Table 2).

Example 7

Figure 9:
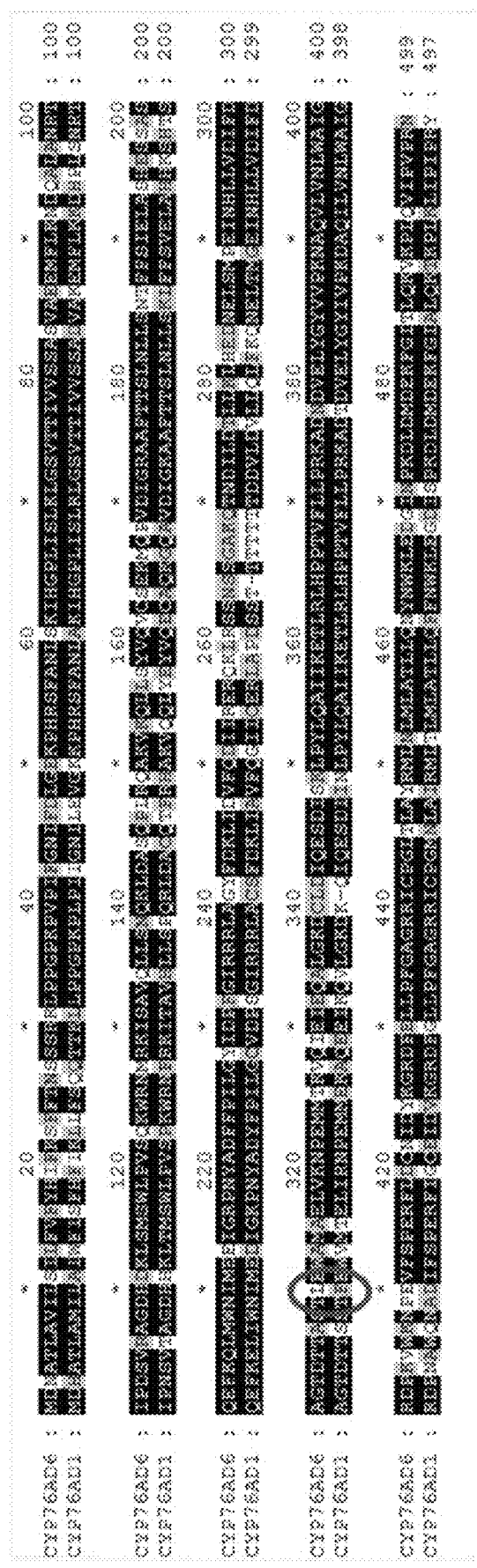
FIG. 9. Alignment of the CYP76AD1 (SEQ ID NO: 14) and CYP76AD6 (SEQ ID NO: 18) protein sequences shows a 72 percent identity between them.

CYP76AD6 Belongs to a Phylogenetic Clade that was Not Previously Associated With Betalain Biosynthesis In a recently published study, large-scale phylogenetic analyses of Caryophyllales plants suggested the occurrence of several gene duplication events of the CYP76AD1 locus early in Caryophyllales evolutionary history. These events were suggested to give rise to three clades within the CYP76AD1 lineage, named CYP76AD1-α, CYP76AD1-β and CYP76AD1-γ. The inventors deduced that the CYP76AD1-α clade is directly associated with betalain biosynthesis as it includes, among others, the functionally characterized *B. vulgaris* CYP76AD1 gene and its *M. jalapa* ortholog CYP76AD3, which has also been implicated to play a similar role in betalain biosynthesis. However, nothing is currently known with respect to the function of genes belonging to the CYP76AD1-β and CYP76AD1-γ clades. Interestingly, the CYP76AD6 gene reported here [accession 'Bv9_228610_ygeq.t1' in the *B. vulgaris* genome] is positioned in the CYP76AD1-α clade, as demonstrated in the phylogenetic analyses presented by Brockington and co-workers, and further presented here in a maximum-likelihood phylogenetic tree (FIG. 8B). Pairwise alignment of the CYP76AD6 and CYP76AD1 protein sequences showed a 72% percent identity (FIG. 9). Their corresponding genes exhibit 70% sequence identity at the nucleotide level.

Example 8

Figure 10:
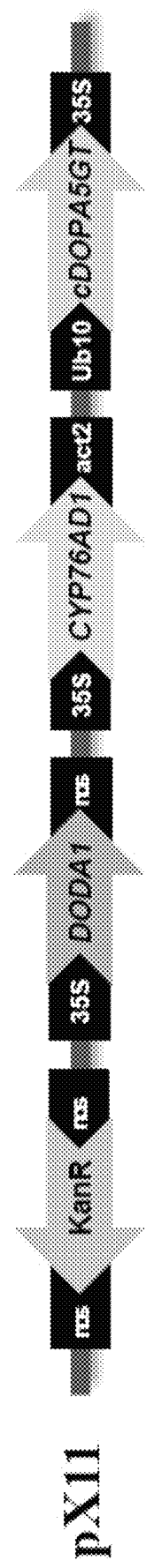
FIG. 10. Schematic of the pX11 overexpression vector (SEQ ID NO: 19). KanR, kanamycin resistance-conferring gene nptII; DODA1, B. vulgaris DOPA 4,5-dioxygenase; CYP76AD1, B. vulgaris cytochrome P450; cDOPA5GT, M. jalapa cyclo-DOPA-5-O-glucosyltransferase; nos, nopaline synthase promoter/terminator; 35S, CaMV 35S promoter/terminator; Act2, Arabidopsis actin 2 terminator; Ub10, Arabidopsis ubiquitin 10 promoter.
Figure 11A:
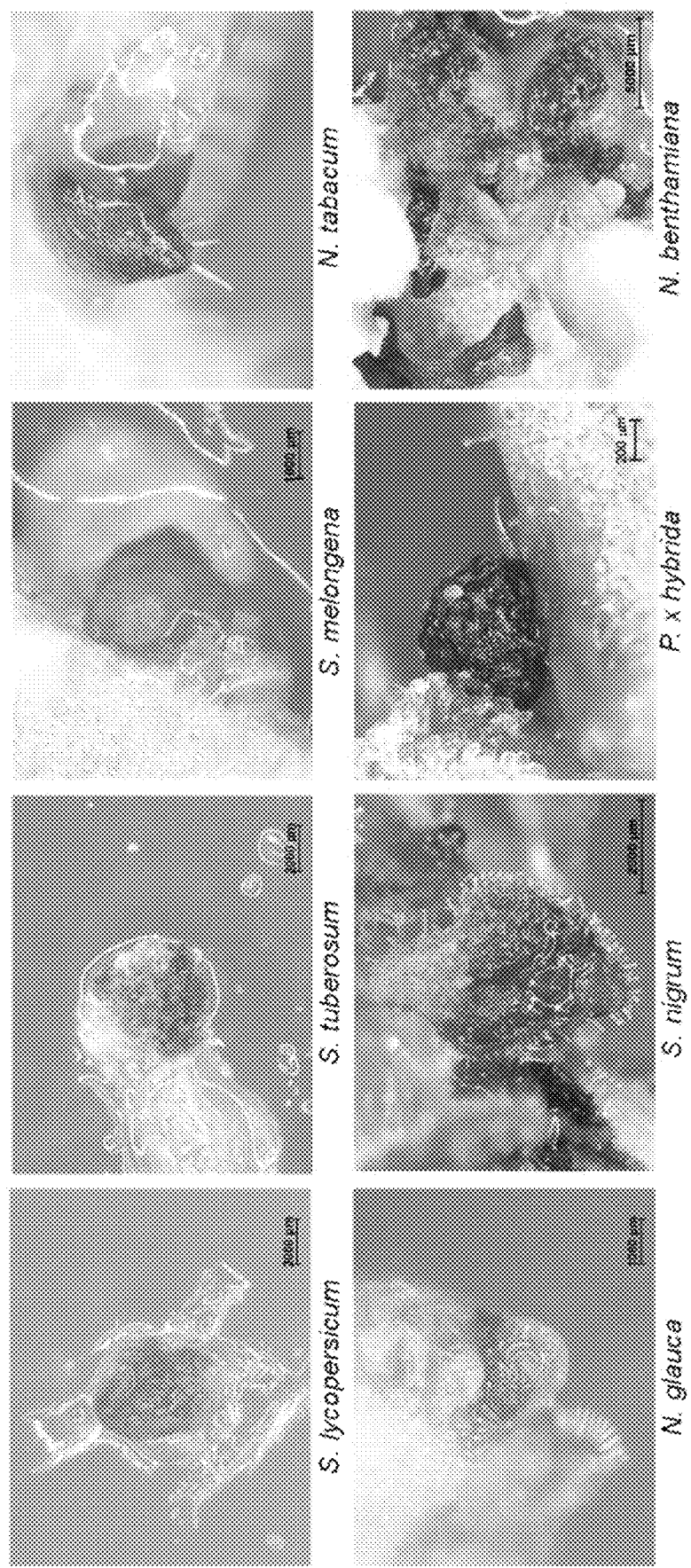
Figures 12B, 12C:
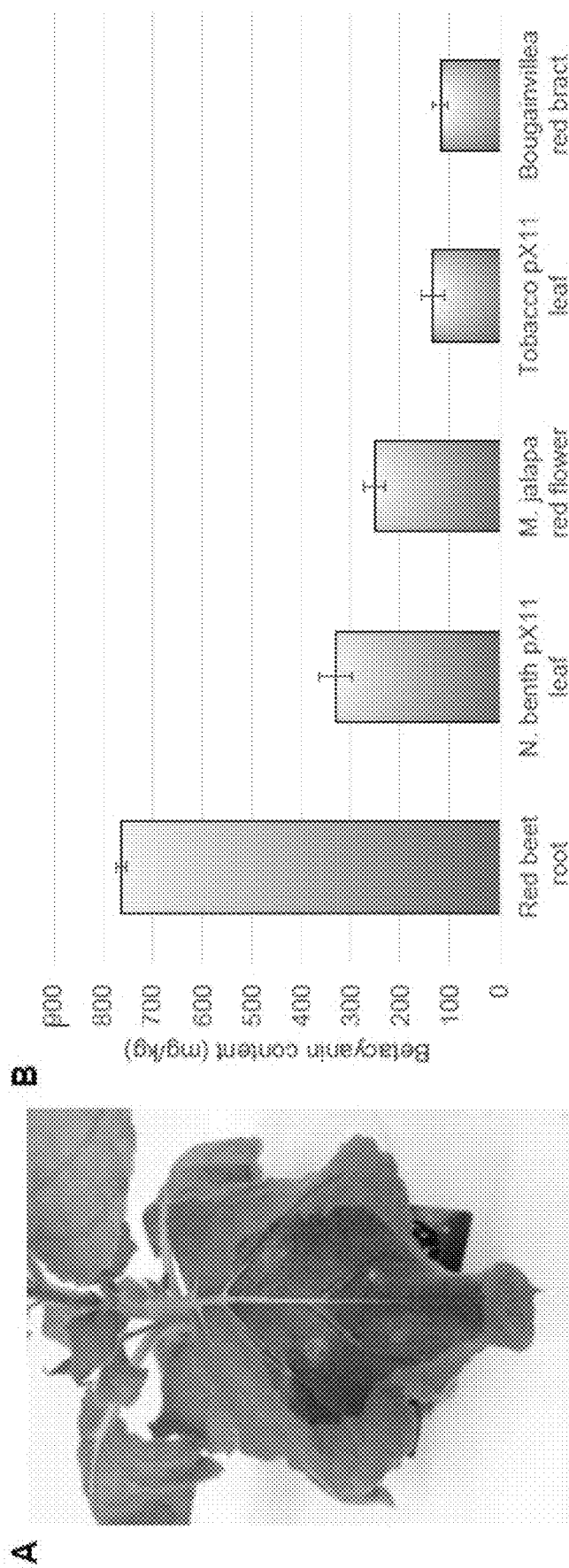

Metabolic Engineering of Red Betalain Pigments in Transgenic Plants Requires Heterologous Expression of Three Biosynthetic Genes As discussed above, we were able to generate both red betacyanins and yellow betaxanthins through transient gene overexpression in *N. benthamiana* leaves. We subsequently attempted to engineer betalain production in naturally non-producing plant species through stable transformation. To this end, Goldenbraid cloning was used to generate a four-gene construct (termed hereafter pX11), in which CYP76AD1, BvDODA1 and cDOPA5GT are expressed in tandem and driven by constitutive promoters, in addition to a kanamycin resistance gene for transgene selection (FIG. 10). The pX11 vector was initially tested by agroinfiltration into *N. benthamiana*. Similarly to the co-infiltration of pDODA and pAD1-GT, introduction of pX11 resulted in red pigmentation of the infiltrated tissue (FIG. 12B). LC-MS analysis of pX11-infiltrated tissue was conducted in order to determine betalain composition. Peaks corresponding to betanin and iso-betanin were found, as previously observed by the co-infiltration of pDODA and pAD1-GT overexpression vectors (FIG. 11A). Also identified was the betaxanthin compound indicaxanthin (proline-betaxanthin), indicating some level of flux towards betaxanthin formation. Two additional metabolites were recognized as betacyanins, based on light absorption spectra and fragmentation, which included the nearly ubiquitous betacyanin fragment, betanidin (m/z=389; Table 2). The pX11-infiltrated leaf tissue appeared intensely red-pigmented, seemingly producing betacyanins in high quantities (FIG. 12B). Infiltrated tissue was therefore assessed for total betacyanin content by spectrophotometric analysis, and was found to contain an estimate of 330 mg kg-1, higher than red bracts of *Bougainvillea glabra* and red petals of *M. jalapa*, containing 120 mg kg-1 and 250 mg kg-1 betacyanins, respectively, and 2.3 fold lower than red beet root, which was estimated to contain 760 mg kg-1 (FIG. 12C).

The pX11 vector was next used for stable transformation of several plant species, including tobacco (*Nicotiana tabacum*), tomato (*Solanum lycopersicum*), potato (*Solanum tuberosum*), eggplant (*Solanum melongena*), tree tobacco (*Nicotiana glauca*), European black nightshade (*Solanum nigrum*), Petunia (*Petunia* x *hybrida*) and *Nicotiana benthamiana*. Explants of the different species were co-cultivated with agrobacteria and placed on selective media. In *N. benthamiana, N. glauca*, Petunia and tomato, small patches of red-violet pigmentation were visible on the explant surface within two days of co-cultivation with agrobacteria. In all species transformed, introduction of pX11 caused the formation of red-violet calli, which generally appeared within 1-2 weeks of culture (FIG. 11A). Pigmented *N. benthamiana* and *N. glauca* callus tissues were found to contain betanin and iso-betanin with LC-MS. Additionally, a novel unidentified betacyanin compound was found in the *N. glauca* callus (FIG. 10B, Table 2).

Figure 13B:
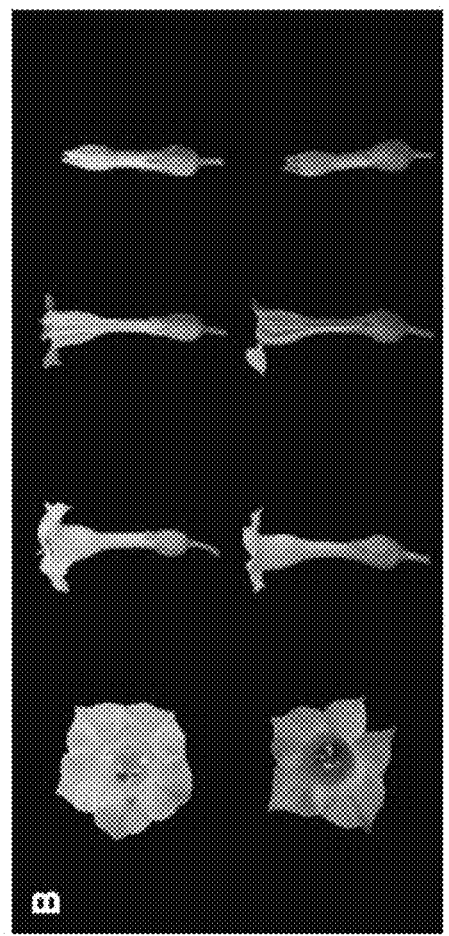
FIGS. 13A-13E. Pigmentation phenotypes observed in transgenic tobacco plants engineered for betalain production. Three betalain pathway genes, namely, CYP76AD1, BvDODA1 and cDOPA5GT (in the pX11 binary vector) were heterologously expressed in Nicotiana tabacum, resulting in red pigmentation in different plant organs, including leaves, stems, roots and flowers.
Figures 13C, 13D, 13E:
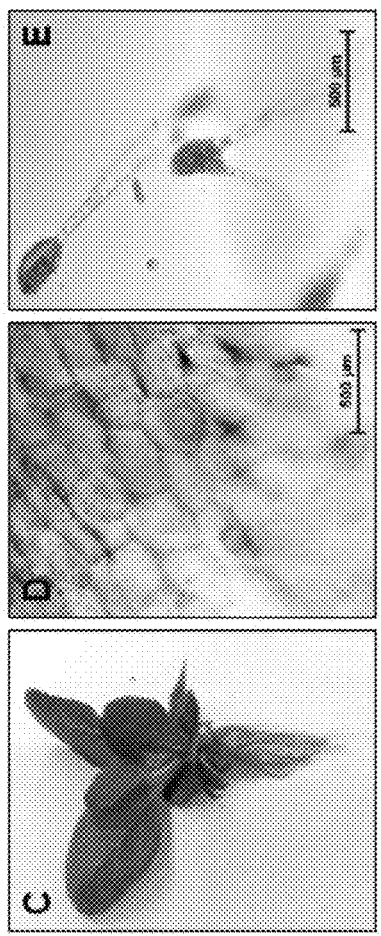
Figure 13A:
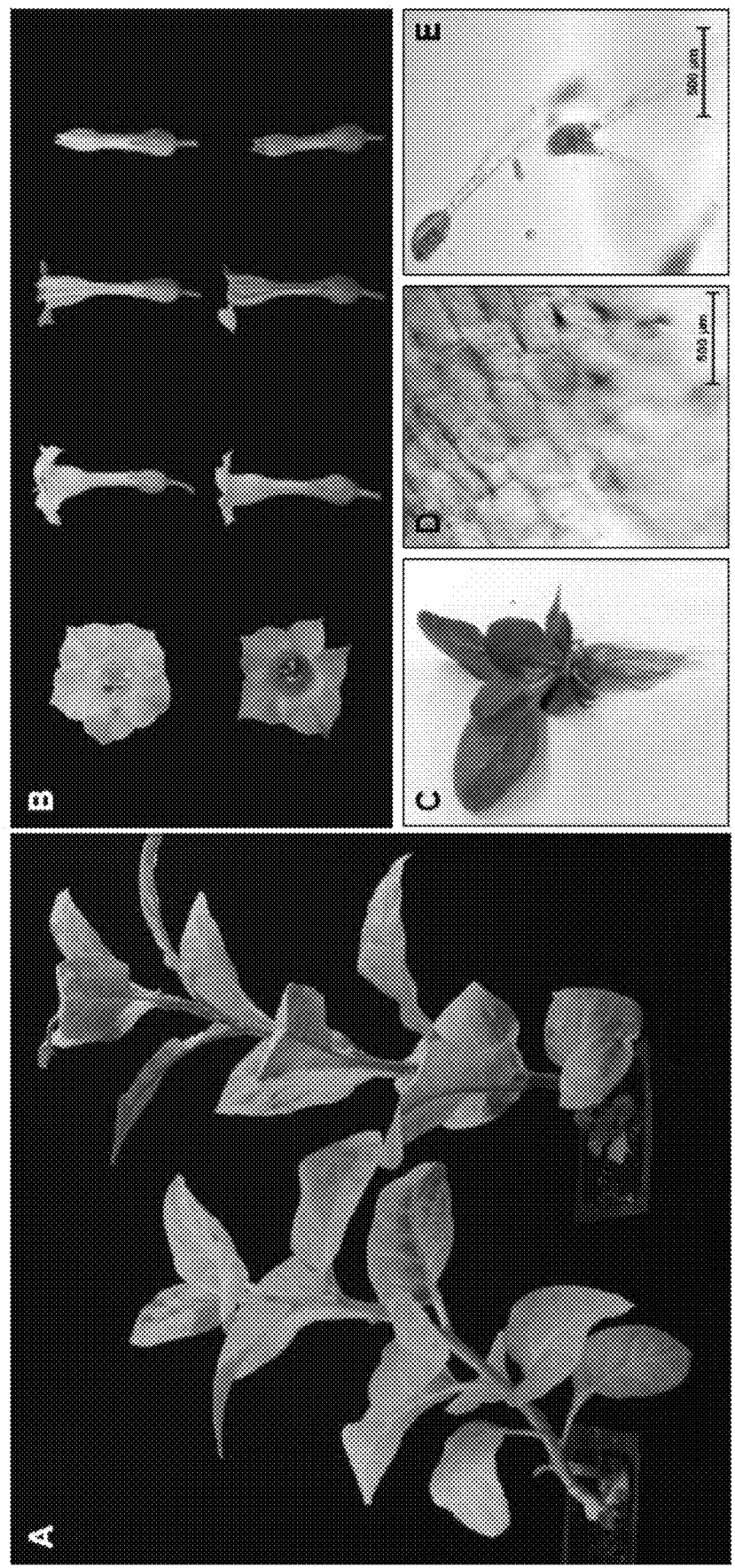

Tissue culture of pX11-transformed tobacco (*Nicotiana tabacum* L. cv. Samsun-NN) eventually led to the generation of mature, intensely red-pigmented plants that displayed betalain accumulation in all major plant organs including stems, leaves, roots, and flowers (FIG. 13). LC-MS analysis of transgenic pX11-tobacco leaves validated the occurrence of the betacyanins, betanin, and iso-betanin as well as the betaxanthin compound vulgaxanthin I (glutamine-betaxanthin) (Table 2). Betacyanin content of pX11-tobacco leaves was additionally measured spectrophotometrically to be 135 mg kg-1 (FIG. 12C).

Example 9

Discussion

CYP76AD1 and CYP76AD6 Redundantly Catalyze Tyrosine Hydroxylation, the First Committed Step in Betalain Biosynthesis in Plants In this study we have demonstrated the involvement of CYP76AD1 in tyrosine hydroxylation to L-DOPA in red beet, apart from its previously reported role in catalyzing the subsequent reaction leading to cyclo-DOPA formation. Furthermore, we identified an additional beet cytochrome P450 enzyme, CYP76AD6, which catalyzes the first hydroxylation step in redundancy with CYP76AD1 (FIG. 1). A CYP76AD6 ortholog, MjCYP76, was primarily identified in *Mirabilis jalapa*, exhibiting an expression pattern which parallels betalain accumulation. It is likely that MjCYP76 and the previously identified CYP76AD3, respectively, serve the same functions in *M. jalapa* as CYP76AD6 and CYP76AD1 do in red beet, although this remains to be conclusively verified by functional analyses, mostly gene silencing assays in *M. jalapa*.

CYP76AD6 involvement in the formation of L-DOPA was initially demonstrated by gene silencing assays; while silencing CYP76AD1 by itself inhibits formation of betacyanins but not betaxanthins, silencing CYP76AD1 and CYP76AD6 in parallel blocks the formation of both betalain groups. Silencing of CYP76AD6 alone produces no visible phenotype, since both L-DOPA and cyclo-DOPA formation continue to be catalyzed by CYP76AD1. This lack of visible phenotype may partially explain why CYP76AD6 and the tyrosine hydroxylation step remained last to be discovered within the core betalain biosynthesis pathway. While DOD and CYP76AD1-like genes could be identified in betalain-producing species by naturally occurring or artificially induced mutations that cause clearly visible phenotypes, CYP76AD6 could not, due do its functional redundancy with CYP76AD1. The suggested roles of CYP76AD1 and CYP76AD6 in betalain biosynthesis were further corroborated by recombinant expression in *N. benthamiana* and yeast cells, which led to the formation of betacyanins or betaxanthins, respectively, when coupled to BvDODA1 expression. Additionally, formation of L-DOPA in *N. benthamiana* was detected when either CYP76AD1 or CYP76AD6 were overexpressed without BvDODA1.

CYP76AD1 and CYP76AD6 belong to two separate clades within the CYP76AD1 subfamily, named CYP76AD1-α and CYP76AD1-β clades. It is conceivable that the two cytochrome P450 enzymes would share some degree of structural relatedness, as they redundantly catalyze an identical enzymatic reaction. Moreover, it was reported previously that cytochrome P450s belonging to a single subfamily catalyze subsequent steps in the same biosynthetic pathway. It is plausible that while the CYP76AD1-α clade may be comprised of enzymes which possess dual activity of L-DOPA and cyclo-DOPA formation, the CYP76AD1-0 may include enzymes which catalyze only L-DOPA formation. However, functional analyses of corresponding genes from additional betalain-producing species will be needed to support this hypothesis.

Tyrosinase enzymes catalyze both the ortho-hydroxylation of monophenols and the oxidation of o-diphenols to o-quinones, thus directly converting tyrosine to the oxidized form of L-DOPA, dopaquinone. CYP76AD1, in a currently unknown reaction mechanism, also catalyzes both tyrosine hydroxylation and L-DOPA conversion to cyclo-DOPA. Our experimental results suggest that CYP76AD6 is unique in that it catalyzes the ortho-hydroxylation of tyrosine but not the conversion of L-DOPA to dopaquinone or cyclo-DOPA. The unique activity of the CYP76AD6 enzyme can be harnessed for high-scale production of L-DOPA that is highly advantageous and unexpected compared to current production methods. CYP76AD6 directly forms L-DOPA from the substrate tyrosine. The ubiquitous nature of tyrosine enables the possibility of expression of CYP76D6 in a variety of biological platforms including plants and microbes.

The discovery of a new class of tyrosine hydroxylating enzymes might also facilitate the identification of additional cytochrome P450 genes that may catalyze L-DOPA formation in biosynthesis of other L-DOPA derived metabolites. For example, the gene responsible for tyrosine hydroxylation in the biosynthesis of benzylisoquinoline alkaloids (BIAs) remains unknown to date, in an otherwise well-characterized pathway. It is possible that in BIA producing plants, L-DOPA is also catalyzed by a cytochrome P450 similar to CYP76AD1 and CYP76AD6.

Uncovering of the roles of CYP76AD1 and CYP76AD6 in L-DOPA formation advances our understanding of betalain biosynthesis in plants and essentially completes the identification of genes and enzymes that make the core betalain structures. Yet, the betalain pathway remains relatively poorly understood with regards to betalain structure modification through 'decorating' enzymes (e.g. glycosylating and acylating enzymes), subcellular transport and detoxification. Further characterization of the genes and regulatory factors involved in the biosynthesis of these pigments will hopefully be facilitated by the elucidation of the core pathway and through increasing availability of sequence data from betalain producing plants.

Metabolic Engineering of Betalain Production in Plants

While anthocyanins and carotenoids are prevalent throughout the plant kingdom, betalains are pigments specific to the Caryophyllales plant order, in which they are produced in a phylogenetically ordered, mutually exclusive fashion with anthocyanins. Their enigmatic evolutionary history, as well as their nutritionally beneficial qualities and economical value as natural food colorants, have led to increasing interest in these pigments in recent years, including the prospect of synthesizing them in microorganisms and plants.

In this study, we have demonstrated for the first time the engineering of betalain production in plants, without substrate feeding, by both transient gene expression and stable transformation. This was made possible by identification of the additional tyrosine hydroxylase activity of CYP76AD1. Expression of CYP76AD1, in combination with BvDODA1 and cDOPA5GT, was therefore found to be sufficient for biosynthesis of betanin, without the need for an exogenous supply of L-DOPA. The use of the pX11 vector that includes the CYP76AD1, BvDODA1 and cDOPA5GT genes was first demonstrated by transient, agroinfiltrated-mediated expression in N. benthamiana, which resulted in the production of betalains in high quantity, visible within two days post infiltration. Attempts for the stable transformation of pX11 into plants and their subsequent cultivation in tissue culture, resulted in pigmentation of explants and the formation of red-violet calli and shoots in a variety of plant species within several days, demonstrating the potential use of betalains as visible genetic transformation markers. Stable transformation of tobacco plants with pX11 ultimately led to the generation of fully pigmented mature plants. LC-MS analysis of the betalain producing tobacco plants confirmed the occurrence of betanin as the major betalain produced.

The findings in this study therefore open the way for heterologous production of betalains in additional plant species, potentially resulting in the development of nutritionally enhanced food crops as well as new varieties of ornamentals. Apart from engineering red-pigmented betacyanin-producing plants, betalain production could principally be modified to be limited to betaxanthins by expressing CYP76AD6 instead of CYP76AD1, as exemplified by the transient expression experiments in N. benthamiana. Engineering of plants which exhibit both red and yellow pigmentation might also hypothetically be achieved by expressing both cytochrome P450s under different, non-constitutive promoter sequences (e.g. fruit-specific, flower-specific or inducible promoters). The engineered betalain producing plants will also serve as an exceptional genetic resource to examine the pigment-based attraction of pollinators to flowers and frugivores to fruit, as well as the role of pigments in assisting plant organs to resist abiotic and biotic cues.

Example 10

Materials and Methods (2)

Generation of DNA Constructs

Gene sequences used in this study; cDOPA5GT (GenBank accession AB182643.1), BvDODA1 (accession HQ656027.1), CYP76AD1 (HQ656023.1). CYP76AD6 (KT962274), AroGl75 (JC233128.1), AAH (HQ003815.1). CYP76AD15 sequence is provided herein. M. jalapa cDOPA5GT, CYP76AD15 and B. vulgaris CYP76AD1, BvDODA1, and CYP76AD6 transcripts were amplified from M. jalapa red petal and B. vulgaris red hypocotyl cDNA libraries. DNA constructs used for N. benthamiana agroinfiltration and for agrobacteria-mediated plant transformation were constructed with Goldenbraid cloning (Sarrion-Perdigones et al., 2013; GoldenBraid 2.0: A Comprehensive DNA Assembly Framework for Plant Synthetic Biology. Plant Physiology 162: 1618-1631). BvDODA1, CYP76AD1, CYP76AD6, CYP76AD15, cDOPA5GL AroGl75 and AAH were initially cloned into a pUPD vector. pX11, pX11(E8), pX11(CHS), pX13, pDOPA3 and pDOPA4 are 3al vectors. pX12, pDOPA1 and pDOPA2 are 3f1 vectors. All vectors are based on a pCAMBIA backbone (Roberts et al., 1997; A Comprehensive Set of Modular Vectors for Advanced Manipulations and Efficient Transformation of Plants. In pCAMBIA Vector Release Manual Rockefeller Foundation Meeting of the International Program on Rice Biotechnology, September 15-19, Malacca, Malaysia).

Plant Transformation and Regeneration

Agrobacteria-mediated plant transformation and regeneration was done according to the following methods;

tobacco leaf discs (Horsch et al., 1985; Science 227: 1229-1231), eggplant (Van Eck and Snyder, 2006; Eggplant (*Solanum melongena* L.). In K Wang, ed, *Agrobacterium* Protocols. Springer, pp 439-448), tomato (McCormick, 1997; Transformation of tomato with *Agrobacterium tumefaciens*. In K Lindsey, ed, Plant tissue culture manual. Springer, pp 311-319), potato (Perl et al., 1992; Plant Molecular Biology 19: 815-823), and *Petunia* (Conner et al., 2009; Transformation and regeneration of *Petunia*. In T Gerats, J Strommer, eds, *Petunia*. Springer, pp 395-409). Transformation and cultivation of BY2 was done according to An, 1985 (Plant Physiology 79: 568-570). All plant species were transformed using agrobacteria GV3101 strain. Plant tissue culture was carried out in a climate rooms (22° C.; 70% humidity; 16/8 hours of light/dark, 2500 Lux light intensity).

Transient Expression in *Nicotiana benthamiana*

Transient gene expression assays in *N. benthamiana* for the BvDODA1 and CYP76AD15 genes and subsequent sampling for LC-MS analysis were performed as described hereinabove.

Metabolite Extraction and Analysis

For LC-MS analyses, extraction of plant tissue from tomato fruit (flesh and peel), eggplant fruit (flesh), potato tuber (flesh), *N. tabacum* petals and *N. benthamiana* leaf was performed as previously described (Polturak et al., 2016). For extraction of BY2 cells, calli sampled from petri dishes (approx. 500 mg) were lysed by two freeze-thaw cycles with liquid nitrogen followed by disruption with metal beads. Cell-extract was centrifuged to remove cell debris and supernatant collected and filtered through 0.22 μm PVDF filters (Millipore) before analysis. LC-MS Analysis of L-DOPA and betalains was performed as previously described (Polturak et al., 2016). Relative quantification of L-DOPA in BY2 cells was determined by peak area, based on transition 198→152.

Seed Germination Assays

Seeds of pX11 and wildtype (WT) tobacco plants were sown on petri dishes containing full Murashige-Skoog (MS) media (4.4 gr/liter) and 1% agar. For stress condition assays, the MS media additionally contained either 150 mM NaCl or 400 mM mannitol. Seeds were sown in three petri dishes, each containing 50 seeds per genotype. Sealed plates were kept in dark for 1 week and then moved to climate rooms (22° C.; 70% humidity; 16/8 hours of light/dark, 2500 Lux light intensity). Seed germination rates were examined for a period of 26 days.

Plant Material and Growth Conditions

*Mirabilis jalapa, N. tabacum, S. tuberosum, S. melongena* and *S. lycopersicum* plants were soil-grown in a greenhouse with long-day light conditions (25° C.). *Beta vulgaris* and *Nicotiana benthamiana* plants were soil-grown in climate rooms (22° C.; 70% humidity; 18/6 hours of light/dark).

Example 11 pX11 Expression in Tomato, Potato and Eggplant Results in Red-Pigmented Plants

Figure 14A:
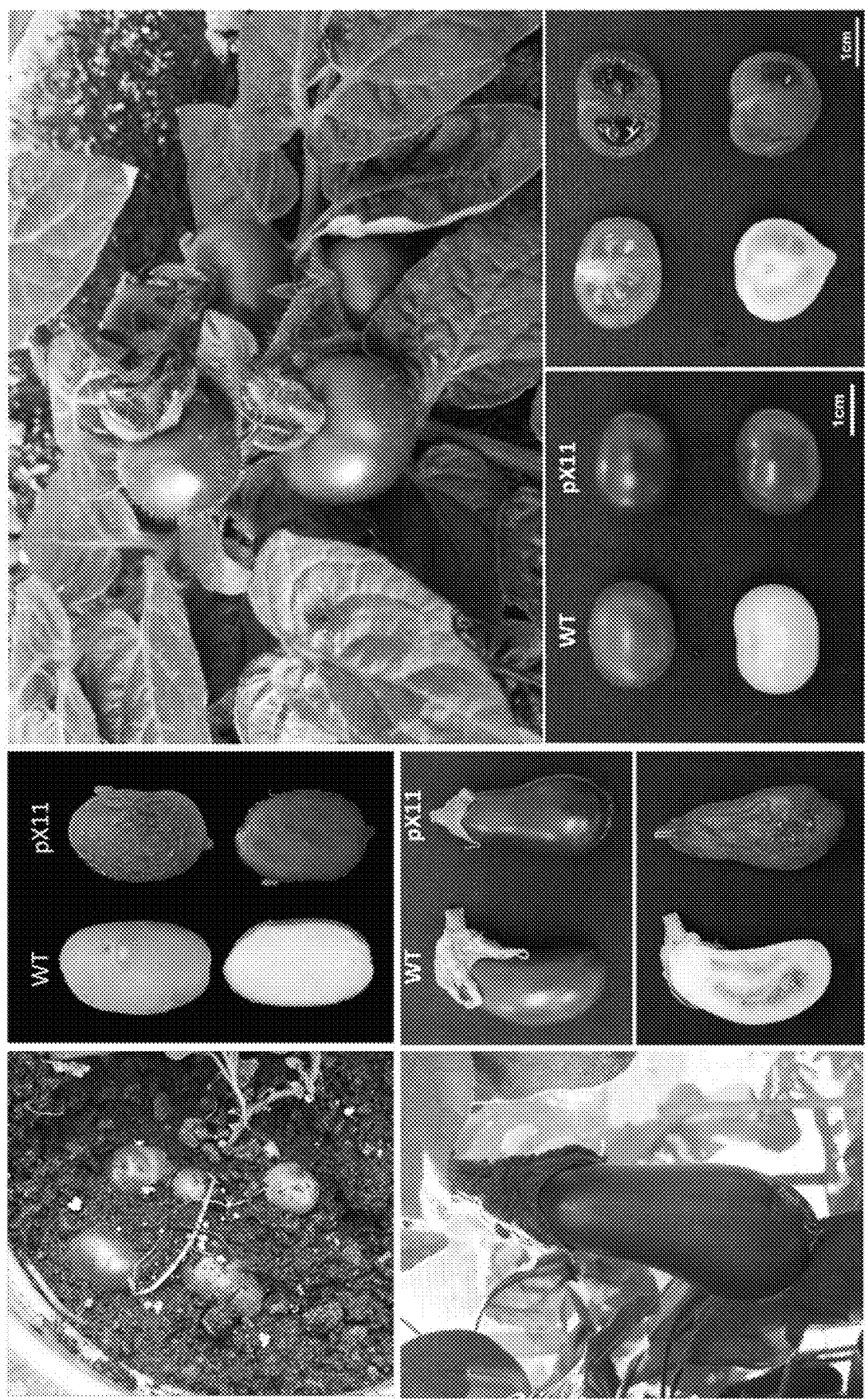
FIGS. 14A-14B. Betalain production in food crops tomato, potato and eggplant.
Figure 14B:
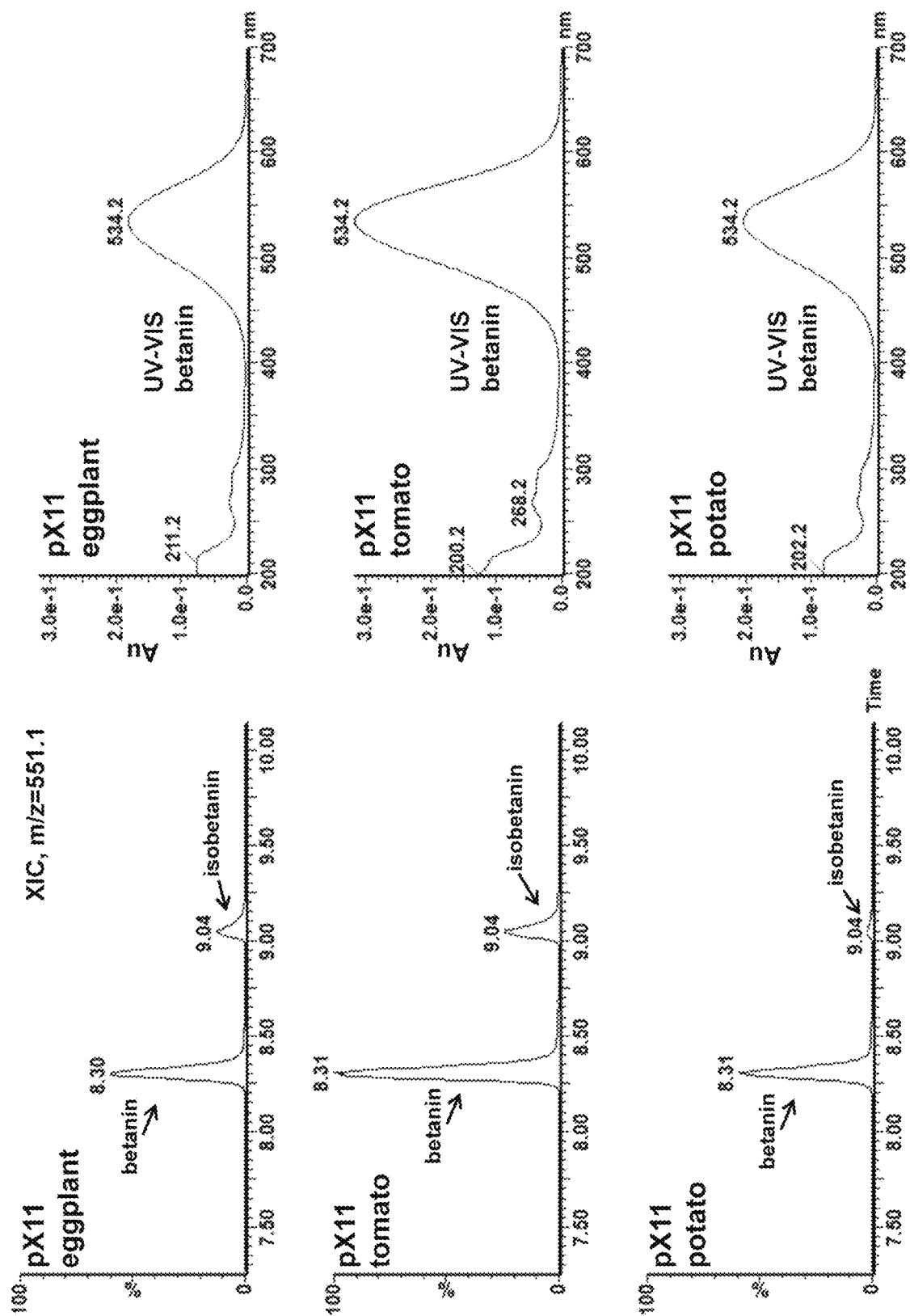

To inspect the feasibility of heterologous betalain production in food crops, the pX11 vector was introduced into tomato (*Solanum lycopersicum* var. MicroTom), potato (*Solanum tuberosum* var. Désirée) and eggplant (*Solanum melongena* line DR2) via agrobacteria-mediated stable transformation. Signs of red-violet pigmentation in transformed explants of all three species were observed within several days after co-cultivation with agrobacteria. As previously observed with pX11-expressing tobacco plants, transformed explants eventually evolved into entirely red-pigmented plants. Tomato and eggplant fruits, as well as potato tubers exhibited strong red-violet coloration (FIG. 14). LC-MS analysis of tomato fruit, eggplant fruit and potato tubers verified the occurrence of betalains, with betanin and isobetanin identified as the major occurring betacyanins (FIG. 14).

Example 12

Fruit-Specific Accumulation of Betalains in Tomato Plants

In all pX11-expressing plant species, betalain accumulation was visible in virtually all plant tissues and organs, owing to the constitutively-expressing promoter sequences used for gene expression, namely CaMV 35S for the BvDODA1 and CYP76AD1 genes, and the *Arabidopsis* Ubiquitin-10 promoter for cDOPA5GT. We initially hypothesized that constitutive production of nitrogen-containing compounds may lead to a significant metabolic burden on the transgenic plants. We therefore constructed a binary vector to be expressed in tomato, which would result in the restriction of pigment accumulation to ripening and ripe fruit. To this end, pX11 was modified to have CYP76AD1 driven by the fruit specific E8 promoter instead of CaMV 35S (FIG. 15). Transformation of the pX11(E8) vector to tomato var. M-82 indeed resulted in generation of plants which have betalain-pigmentation limited to ripe fruit (FIG. 16) albeit with lower betalain concentration than fruit of the pX11-expressing MicroTom tomatoes. Notably, pX11-expressing tomato, potato and eggplant plants did not eventually exhibit any apparent developmental phenotype or growth retardation.

Example 13

Flower-Specific Accumulation of Betalains in Petunias

In a similar approach, an additional version of the pX11 vector was constructed, in which CYP76AD1 is driven by the flower-specific *Petunia* x *hybrida* CHALCONE SYNTHASE (CHS) promoter instead of CaMV 35S (FIG. 15). Transformation of pX11(CHS) into *Petunia* x *hybrida* plants is expected to result in generation of plants that accumulate betalains only in petals, during flower maturation.

Example 14

Figure 17A:
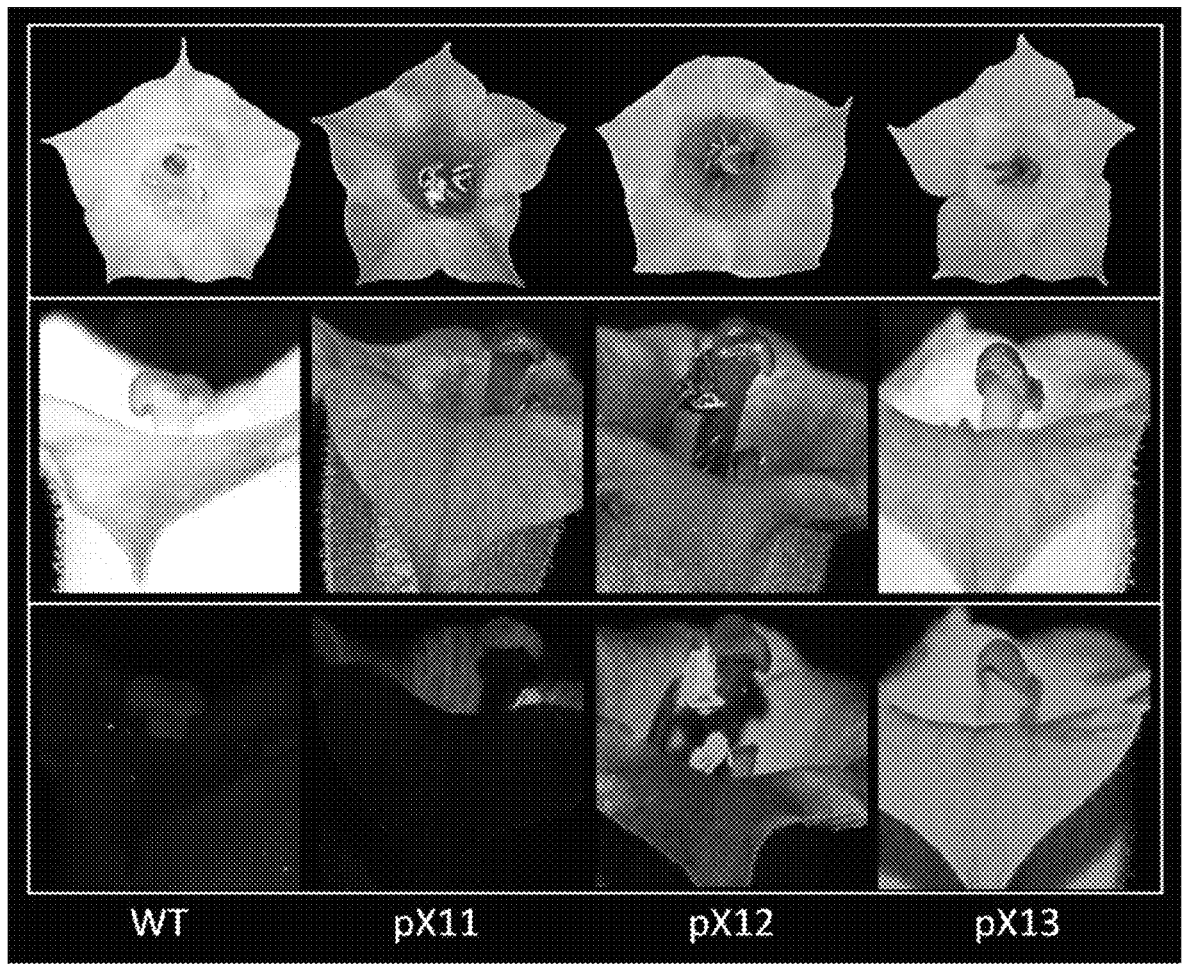
FIGS. 17A-17B. Color variation in flowers of transgenic betalain-producing tobacco is determined by varying betacyanin/betaxanthin ratios.
Figure 17B:
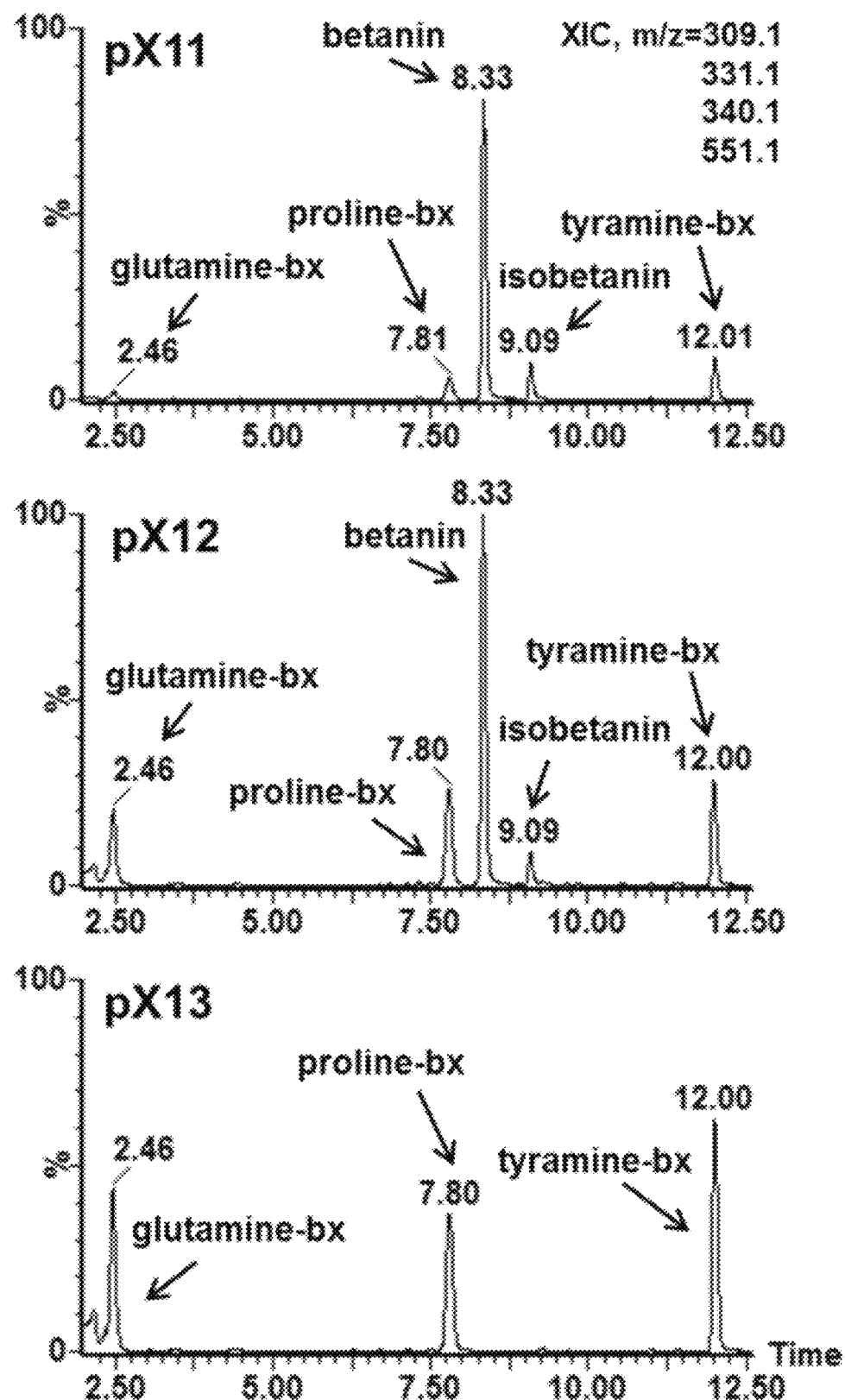

Expression of pX11, pX12 and pX13 in Tobacco Results in Differently-Colored Flowers pX11-expressing plants displayed a predominantly red-violet color due to the accumulation of high amounts of betacyanins versus betaxanthins. pX11 incorporates the expression of CYP76AD1 that encodes an enzyme with dual-activity in betalain biosynthesis, catalyzing both hydroxylation of tyrosine to L-DOPA and conversion of L-DOPA to cyclo-DOPA. As described hereinabove and in Polturak et al. 2016 (New Phytol. 2016 April; 210(1):269-83, which is incorporated herein by reference in its entirety), a related enzyme in red beet, CYP76AD6, uniquely exhibits tyrosine 3-hydroxylation activity, to form L-DOPA. Since cyclo-DOPA derivatives are required for the formation of betacyanins, in-planta expression of CYP76AD6 instead of CYP76AD1 results in the formation of betaxanthins but not betacyanins, as was previously observed by transient expression in *Nicotiana benthamiana*. To explore the possibility of generating transgenic plants that accumulate only betaxanthin-type betalains, a binary vector was constructed for expression of BvDODA1 and CYP76AD6, hereinafter named pX13. An additional vector, pX12, was designed for expression of both cytochrome P450 genes CYP76AD1 and CYP76AD6, alongside BvDODA1 and cDOPA5GT (FIG. 15). pX12 and pX13 were next introduced into tobacco by stable transformation. While pX13-expressing tobacco plants produced only betaxanthins, resulting in formation of yellow-pigmented flowers, expression of pX12 in tobacco plants generated plants with flowers of an orange-pink hue (FIG. 17). LC-MS analysis of petals from pX11, pX12 and pX13 plants verified that the different colors observed in flowers of the three lines are the result of varying betacyanin/betaxanthin ratios; pX11 flower extracts predominantly contained betacyanins, pX13 extracts contained betaxanthins only, while pX12 extracts contained both groups of betalains, with a lower betacyanin/betaxanthin ratio than pX11 (FIG. 17). Differences in betaxanthin versus betacyanin accumulation could also be observed by blue light imaging, under which betaxanthins have a typical strong fluorescence (Gandia-Herrero et al., 2005). Thus, the flux towards biosynthesis of red-violet betacyanins or yellow betaxanthins can be manipulated via expression of CYP76AD1, CYP76AD6 or a combination of both.

Example 15 pX11 and pX13 Expression in BY2 Cells

Biotechnological production of betalain pigments may provide new viable sources for their use as natural colorants for food, pharma and cosmetics industries. To date, most research has mainly been focused on development of *Beta vulgaris* hairy root culture or cell culture for betalain production.

Genetic engineering for heterologous betalain production enables the development of numerous new sources for these pigments. One viable source may be the culture of well-studied plant cell lines such as the tobacco BY2 or *arabidopsis* T87 lines. A previously reported attempt to use these lines for betalain production involved the expression of the *Mirabilis jalapa* DOD gene MjDOD together with a Shiitake mushroom tyrosinase gene. Production of betaxanthins in BY2 and T87 cells was demonstrated. However, within several weeks the cultured cells turned brown and stunted, most likely due to the toxic accumulation of dopaquinone and its derivatives, as a result of activity of the exogenous tyrosinase (Nakatsuka et al., 2013).

Figure 18A:
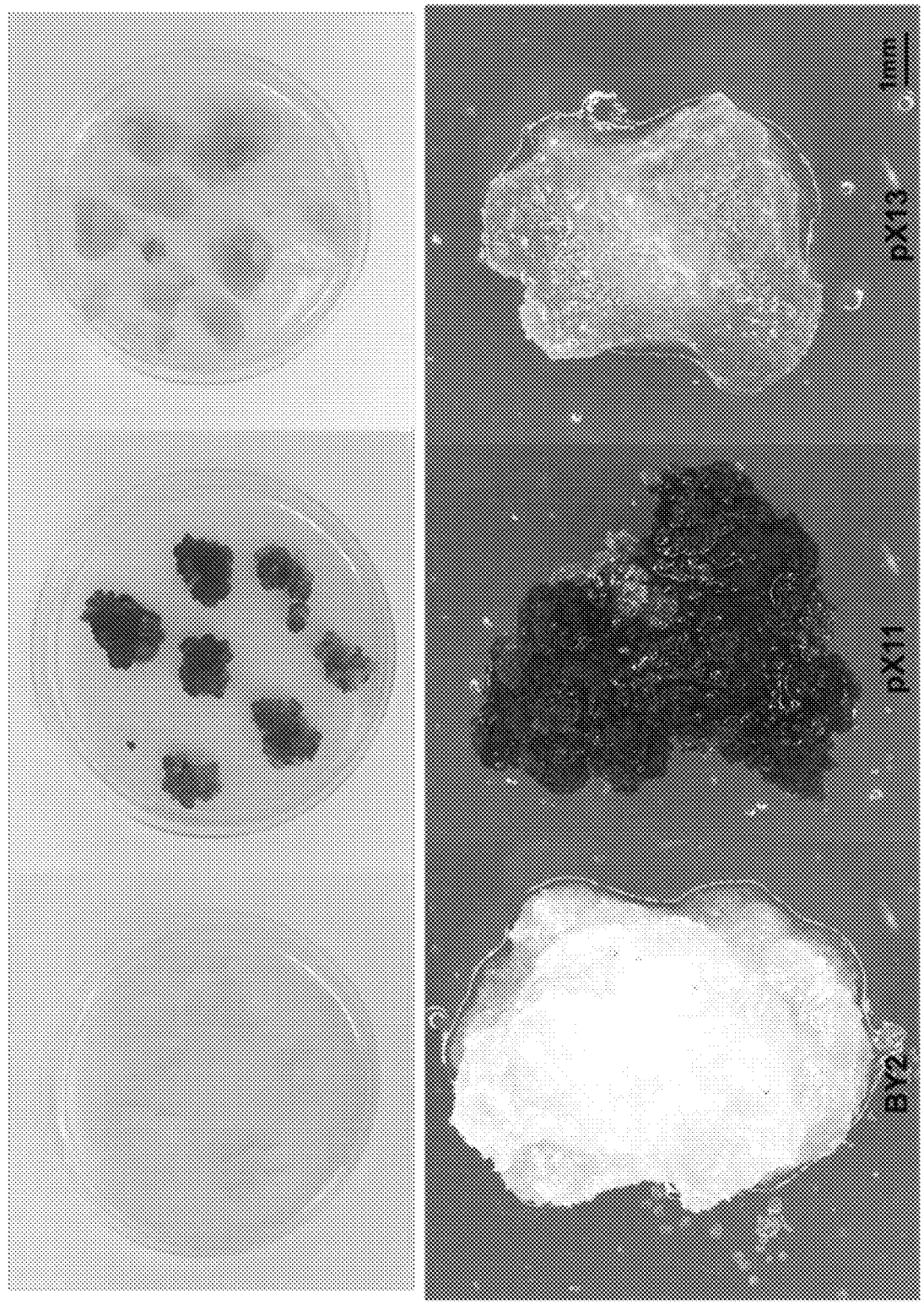
FIGS. 18A-18B. Production of betalains in tobacco BY2 cells.
Figure 18B:
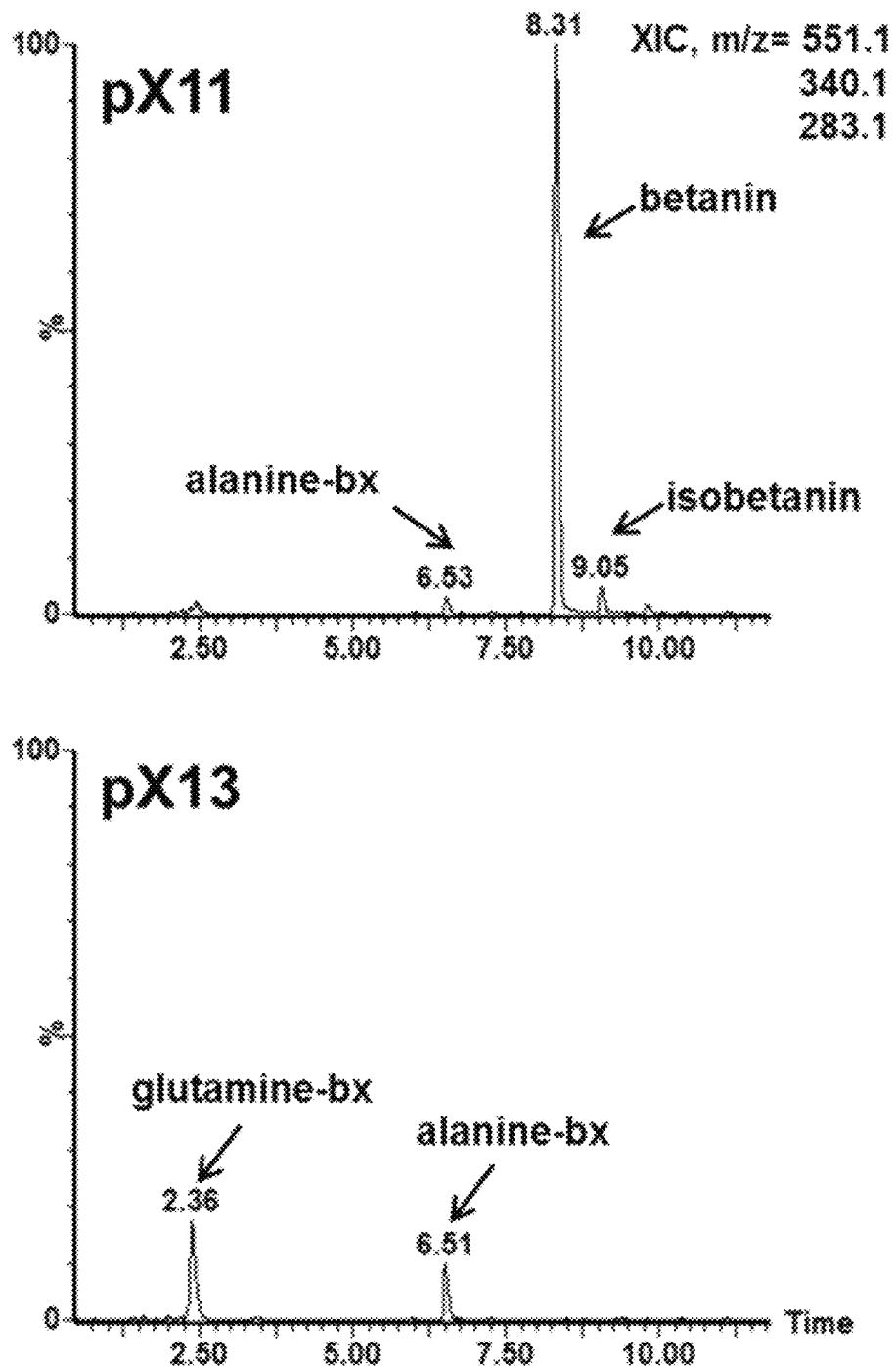

To explore the potential use of plant cell culture for betalain production through expression of betalain-related genes only, we expressed the pX11 and pX13 vectors in tobacco cell line BY2, resulting in generation of red-violet or yellow cells, respectively (FIG. 18). LC-MS analysis of cell extract of the pX11-expressing cells showed betanin and iso-betanin as the major betacyanins. Several betaxanthins were identified in both pX11 and pX13 cell lines, including glutamine-betaxanthin and alanine-betaxanthin (FIG. 18). Notably, pX11 and pX13 cell lines did not exhibit signs of browning or stunted growth as was previously reported for tyrosinase expressing calli (Nakatsuka et al., 2013).

Example 16

L-DOPA Production in Tobacco and BY2 Cells by Expression of CYP76AD6

Figure 20A:
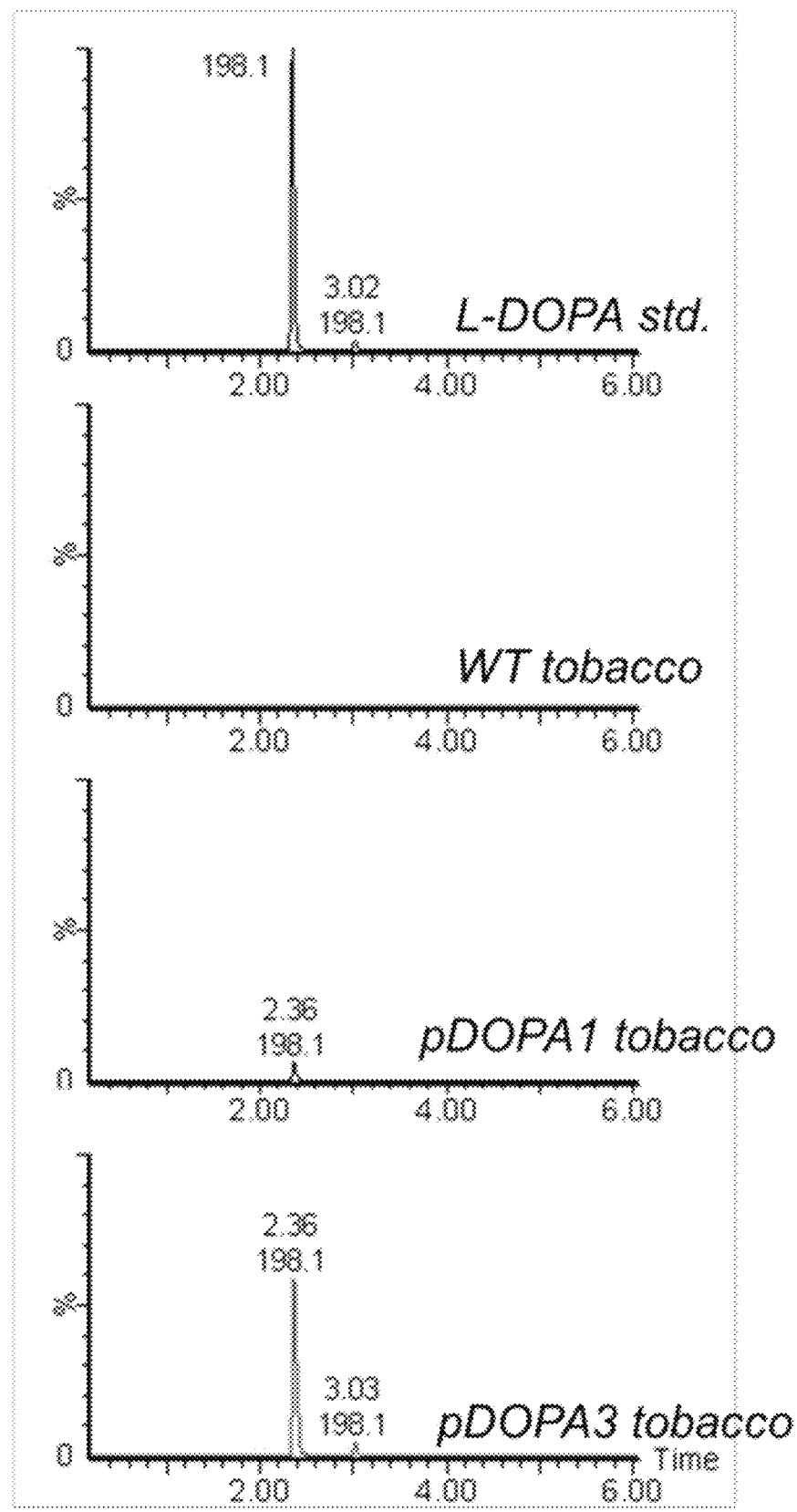
FIGS. 20A-20C. Production of L-DOPA in tobacco plants and BY2 cells.
Figure 20B:
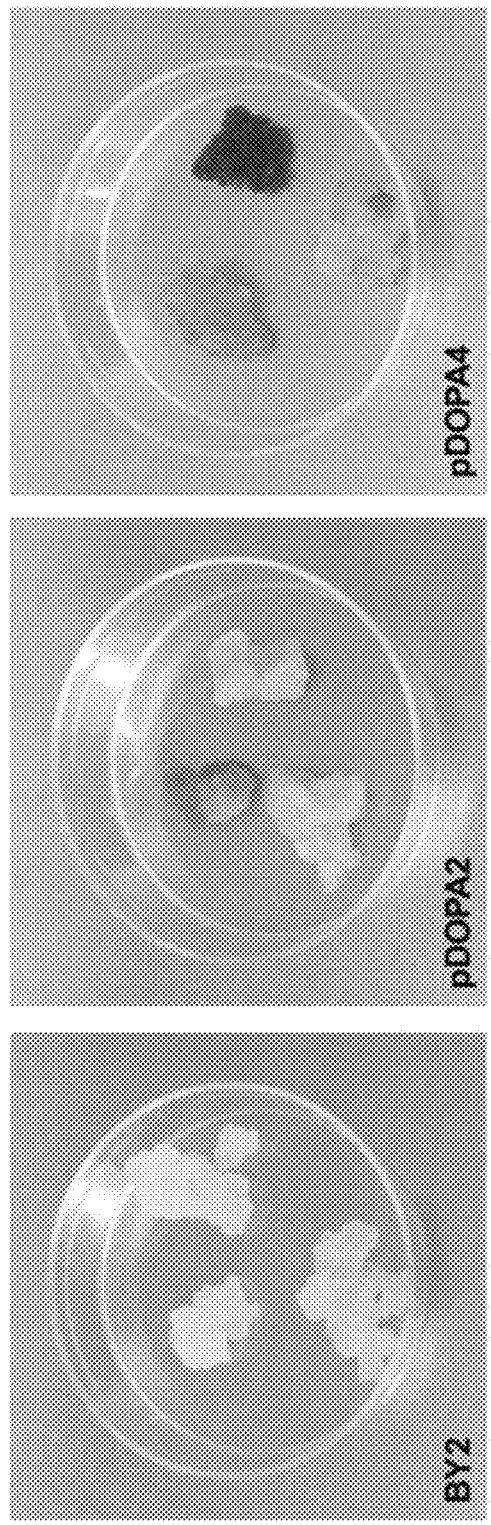
Figure 20C:
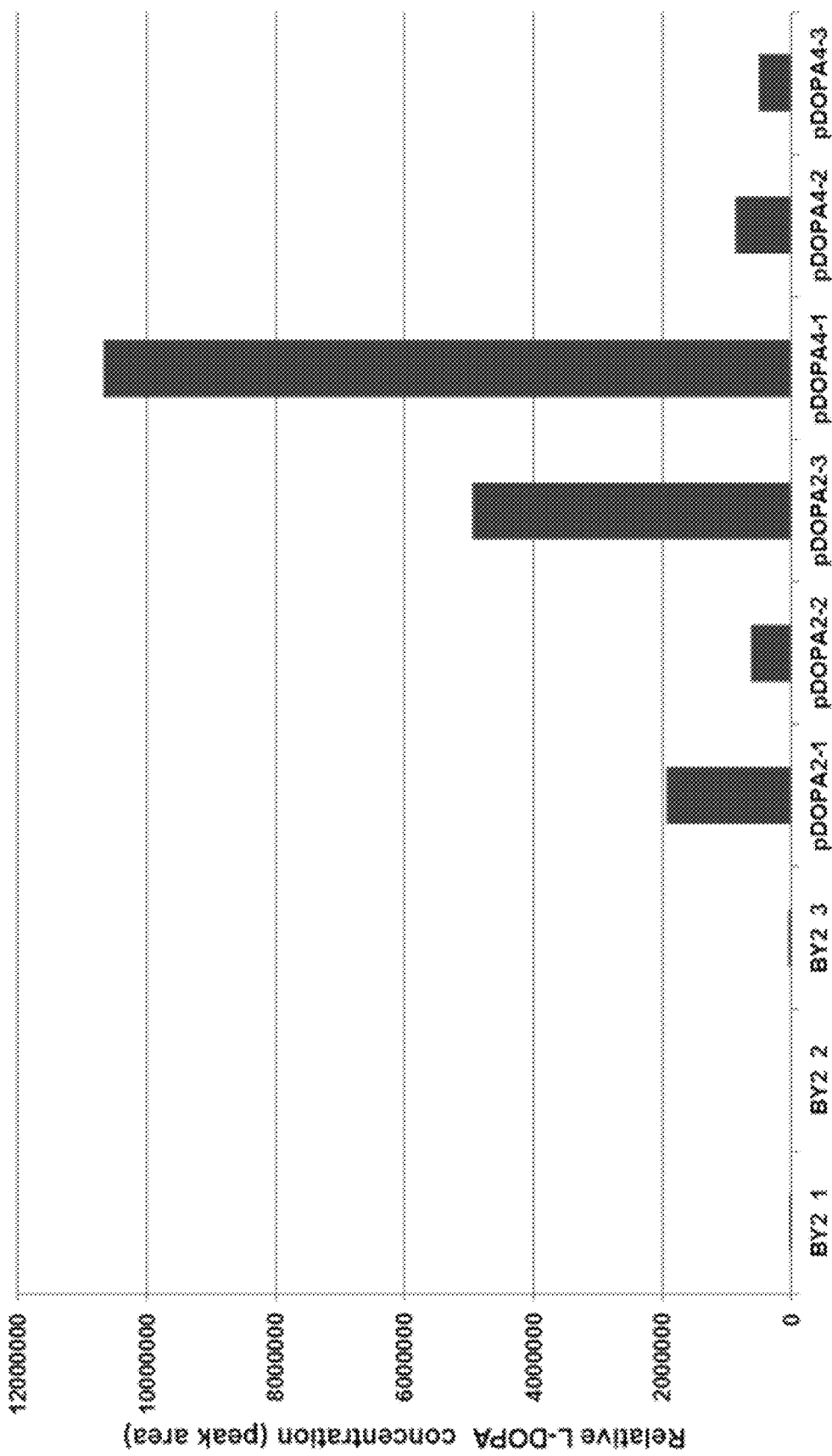

L-DOPA is an economically important compound that has been used for treatment of Parkinson's disease and is a precursor of high-value metabolites, including among others catecholeamines, benzilisoquinoline alkaloids and betalains. Current methods for industrial-scale production of L-DOPA show critical limitations. The tyrosine 3-hydroxylase activity of the CYP76AD6 enzyme may be implemented for production of L-DOPA that is advantageous compared to current production methods, by which L-DOPA would be directly formed from tyrosine. We explored the implementation of CYP76AD6 for L-DOPA production via expression in tobacco plants and in tobacco cell line BY2. To this end, four different vectors for expression of CYP76AD6 were constructed (FIG. 19); in one vector, CYP76AD6 is driven by the CaMV 35S promoter (hereinafter named pDOPA1). In another vector, pDOPA2, CYP76AD6 is driven by the *Solanum lycopersicum* ubiquitin 10 promoter (SlUb10). In vector pDOPA3, CYP76AD6 under 35S promoter is expressed together with two additional genes, AroG175 (Tzin et al., 2012) and aromatic amino acidhydroxylase (AAH) (Pribat et al., 2010), both of which are used in means of increasing tyrosine availability. In vector pDOPA4, CYP76AD6 under SlUb10 promoter is expressed together with AroG175 and AAH. All four vectors additionally express the neomycin phosphotransferase II (nptII) gene to confer kanamycin resistance for transformant selection. pDOPA1, pDOPA2, pDOPA3 and pDOPA4 were introduced into tobacco plants by agrobacteria-mediated stable transformation. LC-MS analysis of first generation (t0) plants confirmed that L-DOPA is produced in lines expressing the four different vectors. Analysis of pDOPA1 and pDOPA3 tobacco plants is presented in FIG. 20. The four pDOPA vectors were also introduced into BY2 cells lines. BY2 cells expressing pDOPA2 or pDOPA4 vectors exhibited varying degrees of gray to black pigmentation after several weeks of cultivation, likely due to formation of L-DOPA derivatives, possibly resulting from enzymatic or non-enzymatic oxidation of L-DOPA. LC-MS analysis of extracts obtained from pDOPA2 and pDOPA4-expressing calli showed occurrence of L-DOPA in varying concentrations (FIG. 20).

Example 17

Figure 21A:
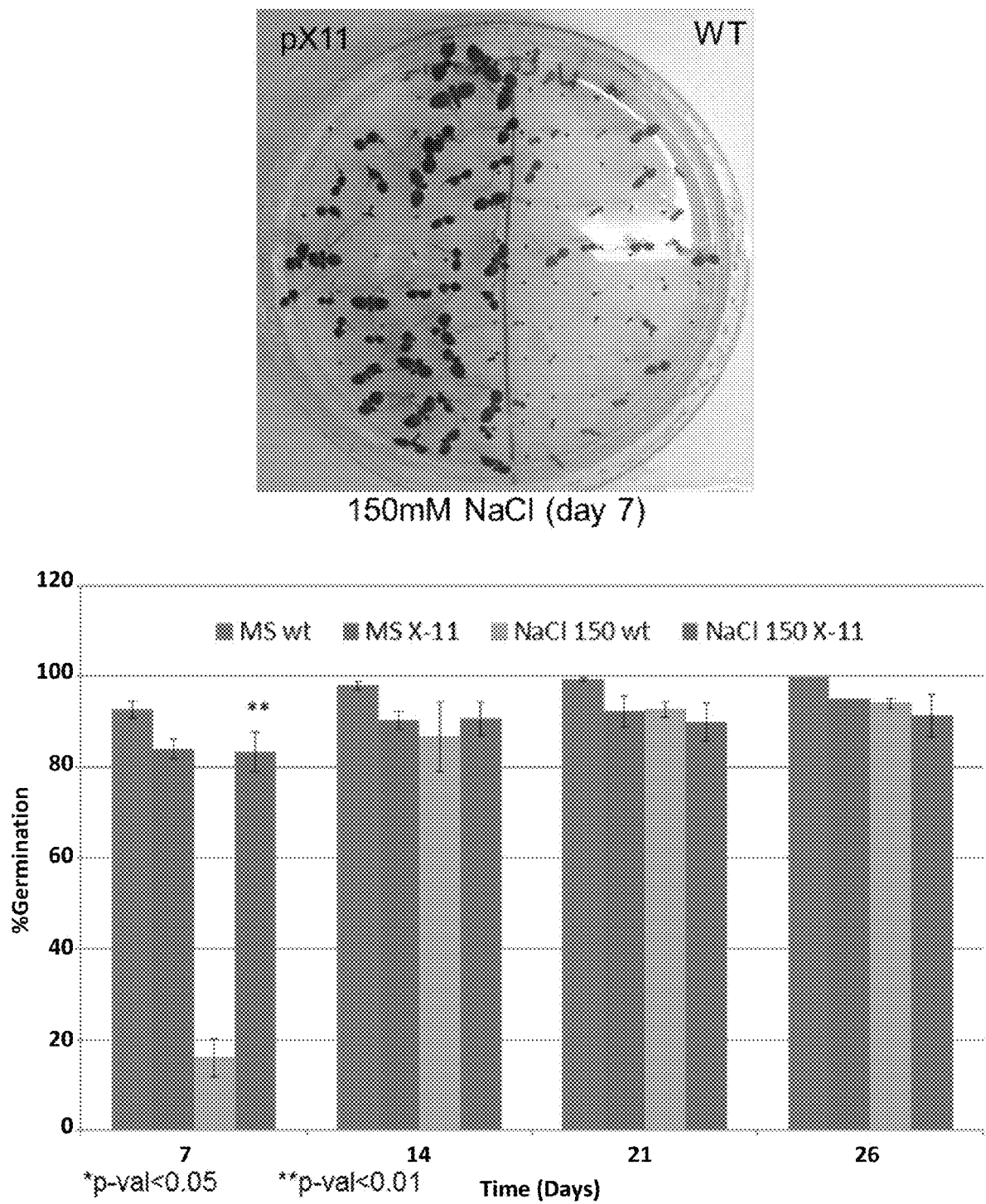
FIGS. 21A-21B. Seed germination assays of betalain-producing tobacco under osmotic and salinity stress conditions.
Figure 21B:
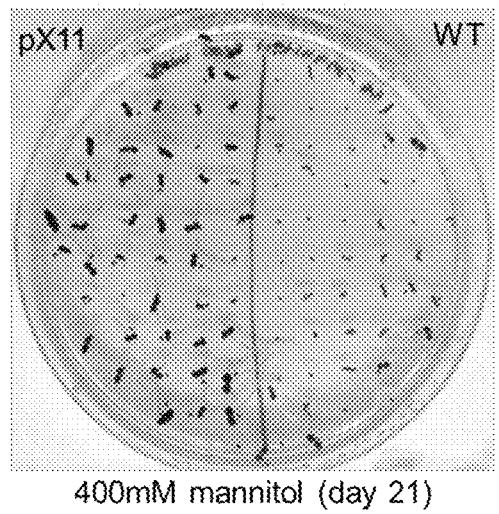
Figure 21B:
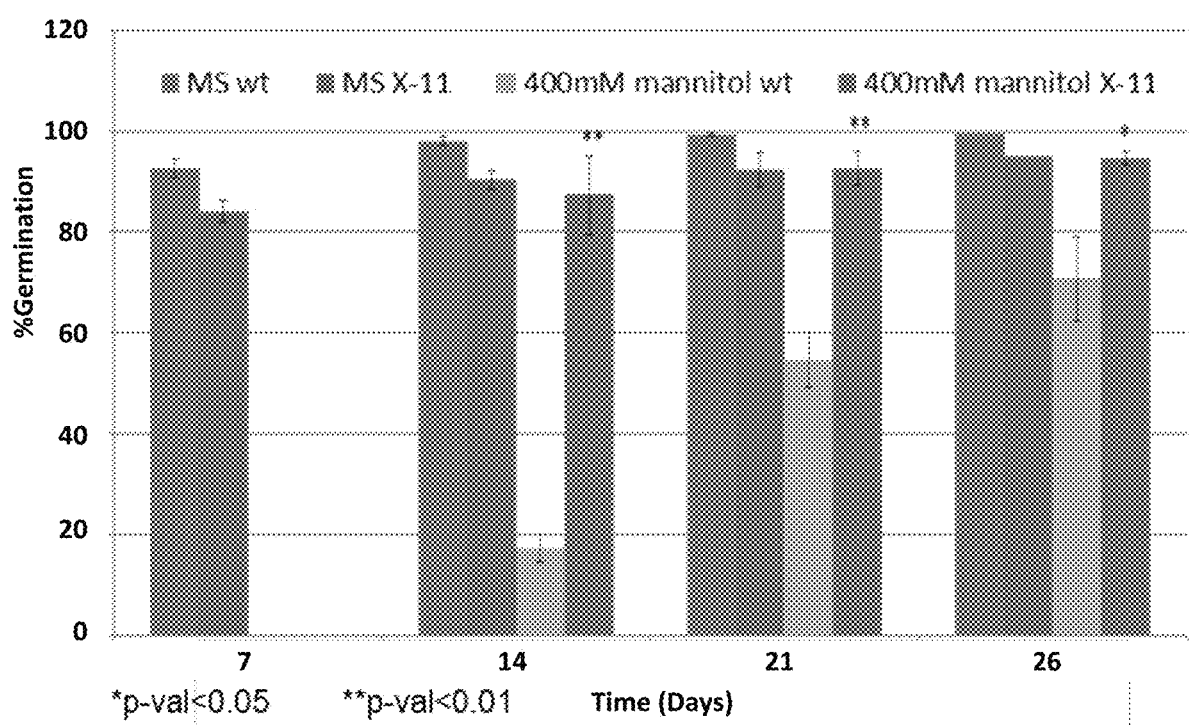

Betalains Confer Plant Resistance to High Osmotic and High Salinity Stress Conditions Considering the suggested roles of betalains in conferring resistance in plants to various abiotic stress factors such as drought, high salinity and excess light, enabling production of betalains in naturally non-producing plants may serve to increase their tolerance to abiotic stress factors. We therefore proceeded to examine this assumption via seed germination assays of betalain-producing tobacco plants. Seeds of pX11 and wildtype (WT) tobacco were placed on petri dishes containing Murashige-Skoog (MS) media supplemented with 400 mM mannitol or 150 mM NaCl, to mimic conditions of high osmotic stress or high salinity stress, respectively. Petri dishes containing MS media without additional supplementation were used as control. Germination rates of seeds sown on all plates were determined over a period of 26 days. While pX11 and WT tobacco seeds exhibited similar germination rates in the control MS media, pX11 seeds exhibited significantly higher germination versus WT seeds in plates containing 400 mM mannitol throughout the experiment time period. In plates containing 150 mM NaCl, pX11 seeds showed significantly higher germination rates after one week of incubation, but WT seeds obtained similar germination rates within two weeks and onwards (FIG. 21). Betalain-producing tobacco plants therefore exhibit increased tolerance to high osmotic and high salinity conditions compared with wildtype plants, having a higher germination rate in high osmotic stress conditions and faster germination in high salinity conditions.

Example 18

Betalains Confer Resistance to *Botrytis Cinerea* Infection in Tobacco Leaves

Figure 22A:
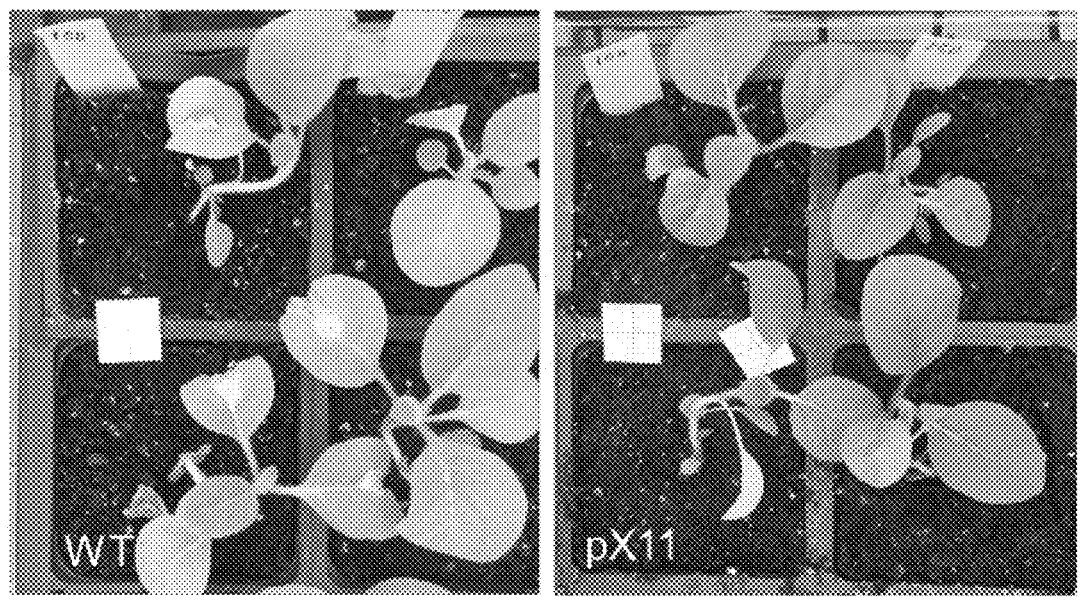
FIGS. 22A-22C. *Botrytis cinerea* resistance assays of betalain-producing tobacco plants.
Figure 22B:
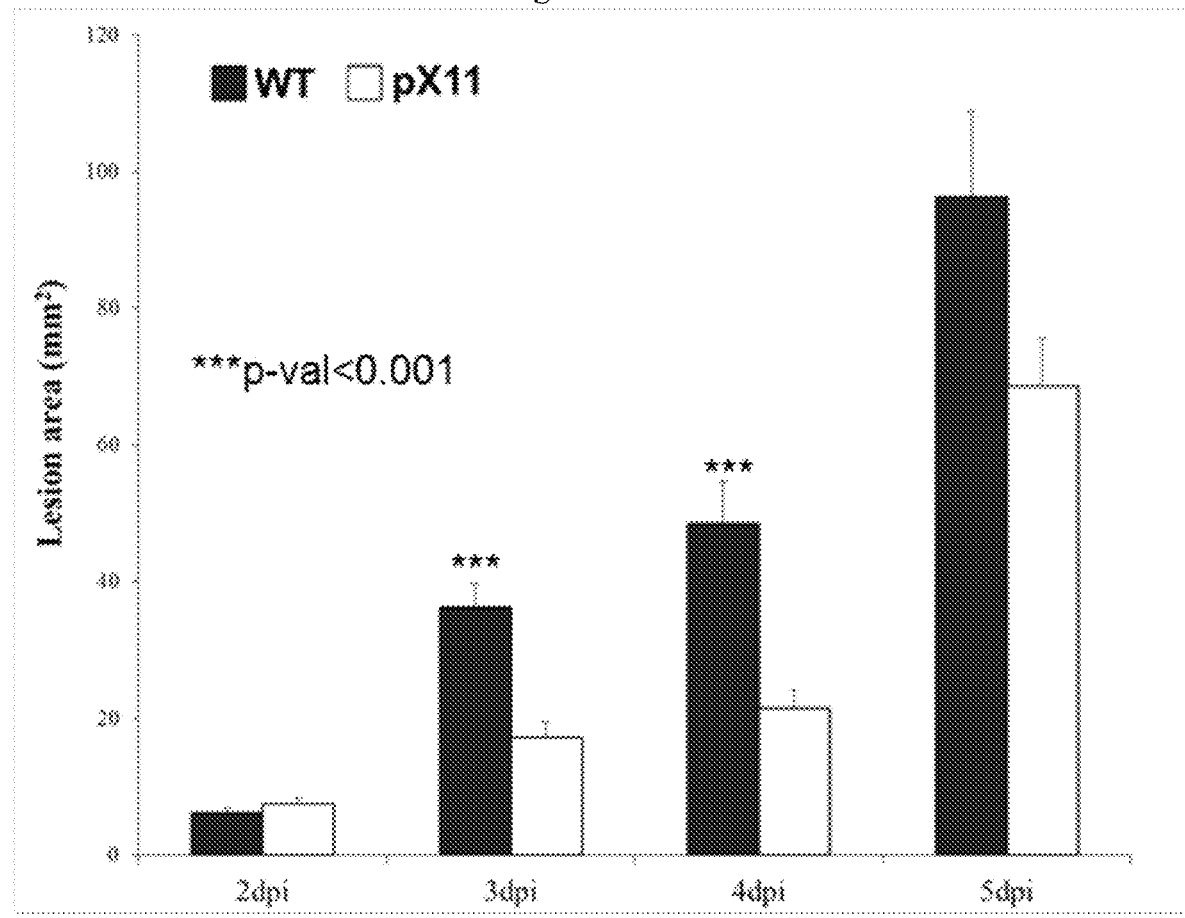
Figure 22C:
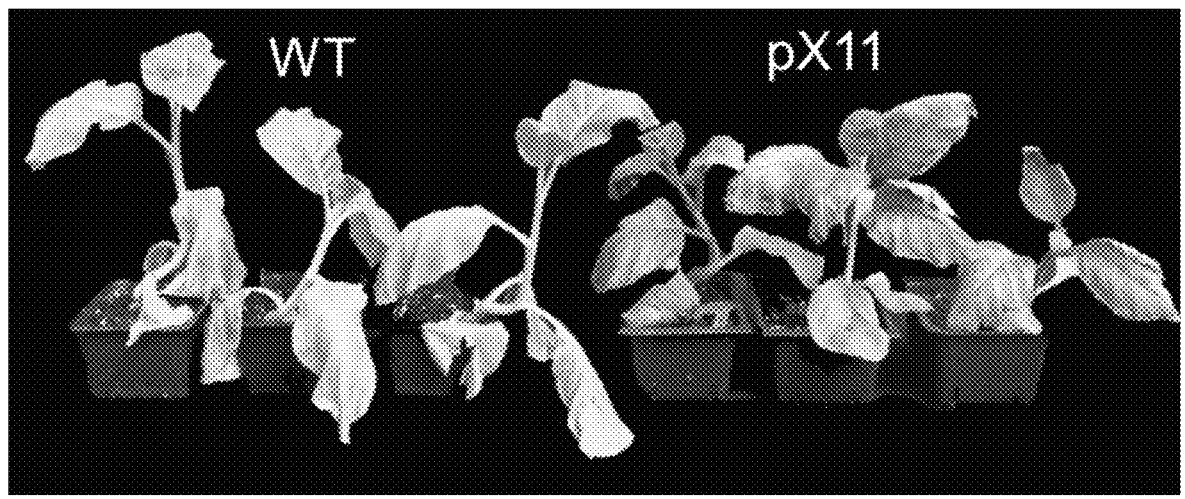
Figure 23A:
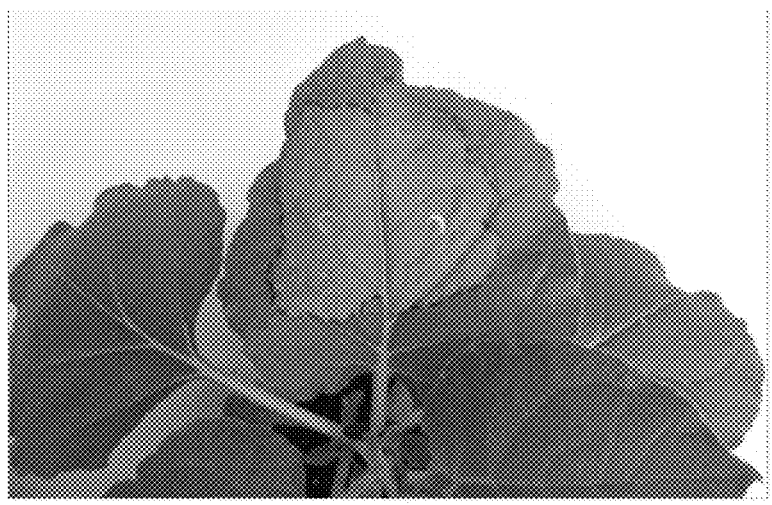
FIGS. 23A-23D. Recombinant expression of CYP76AD15 in *Nicotiana benthamiana* enables betaxanthin and L-DOPA production.
Figure 23B:
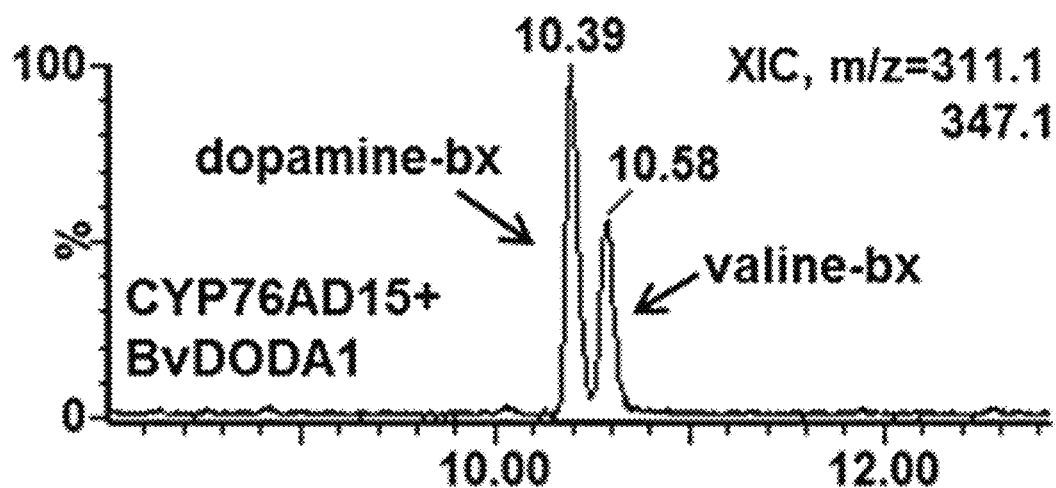
Figure 23B:
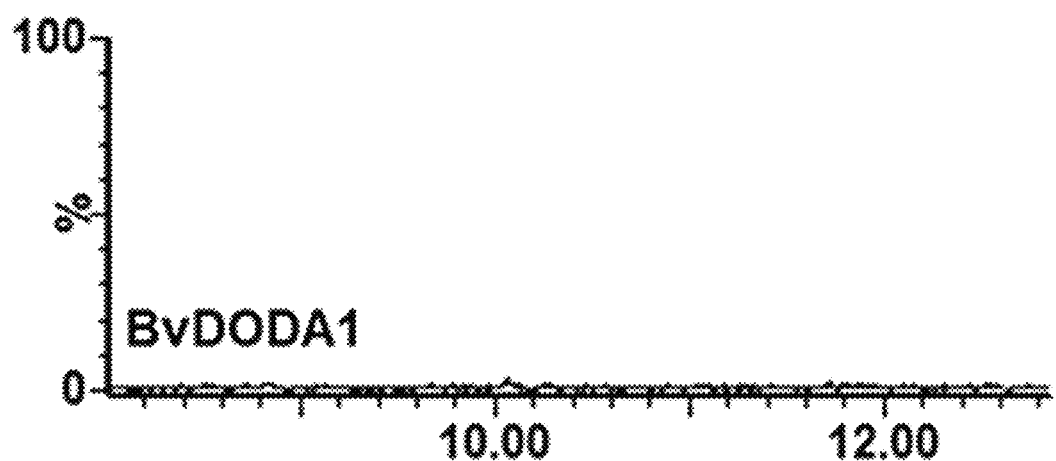
Figure 23B:
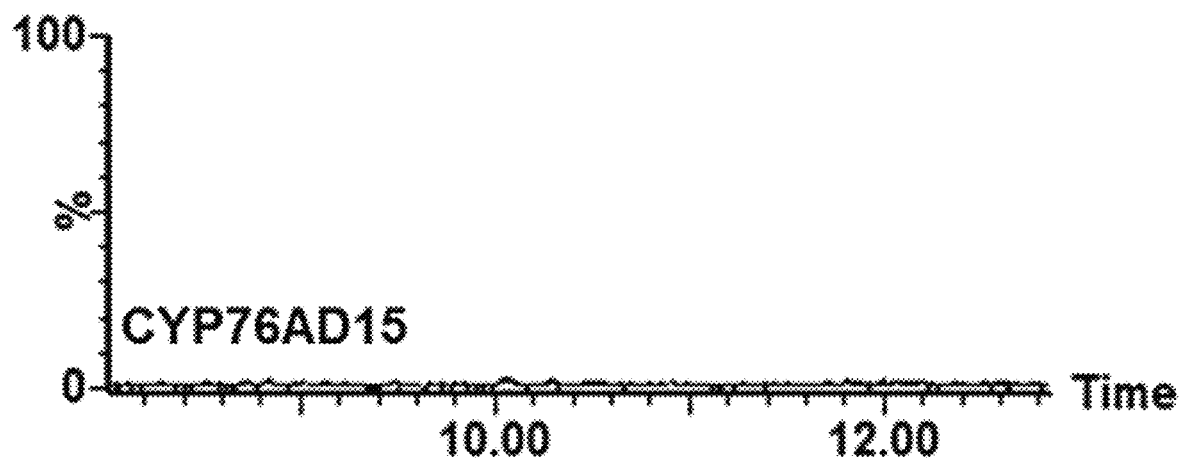
Figure 23C:
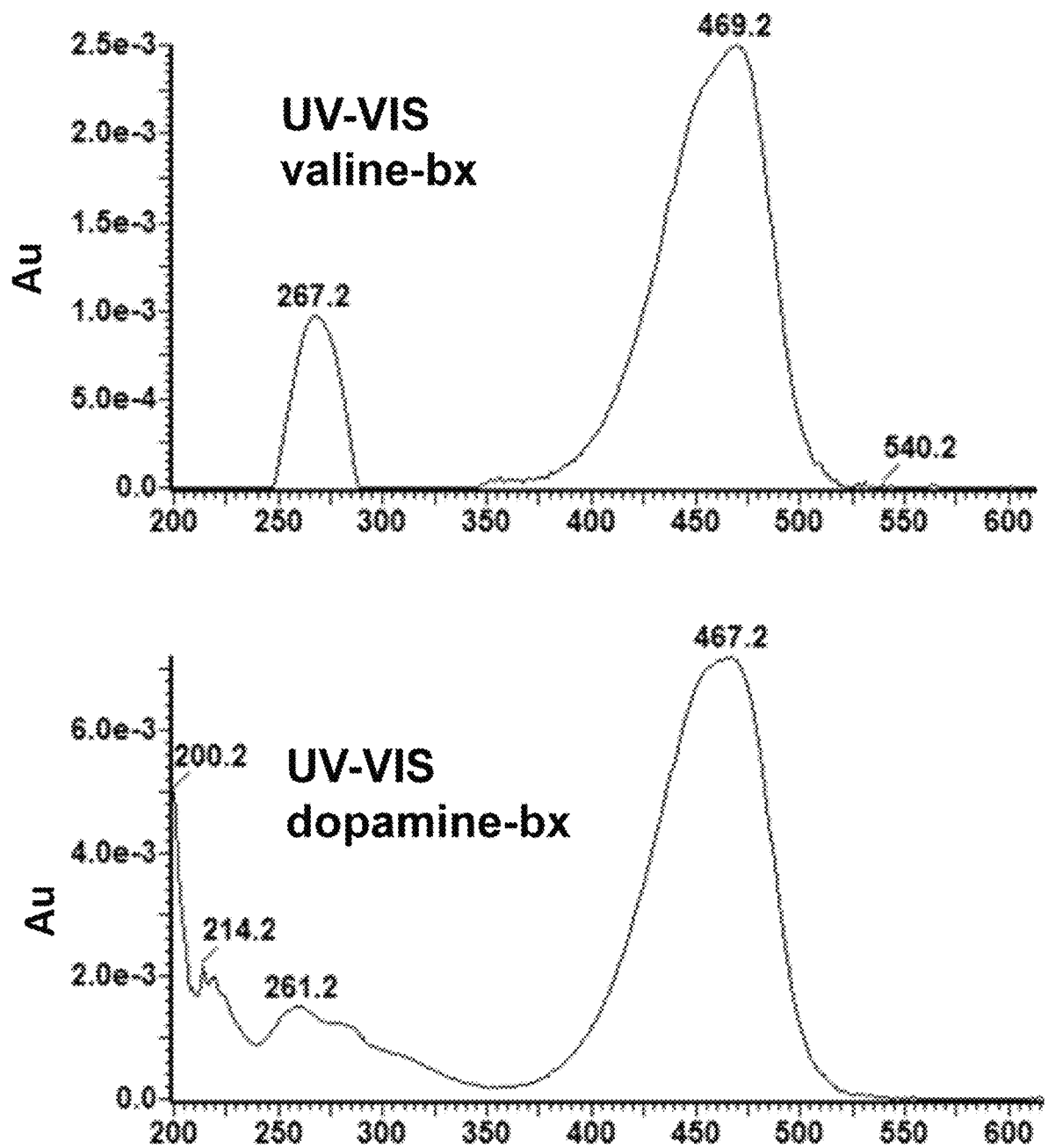
Figure 23D:
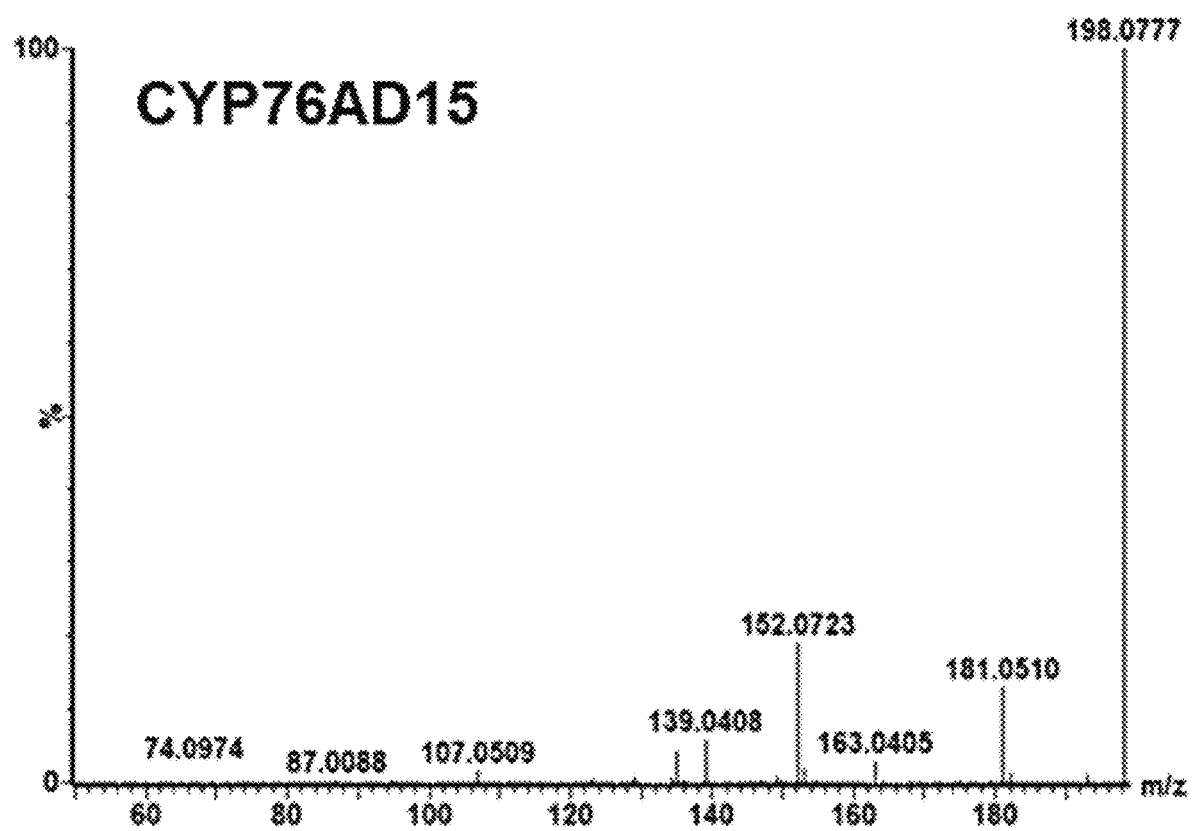

Betalains have previously been suggested to play a role in defense against pathogenic fungi, but evidence for antifungal activity of betalains in scientific literature is scarce. Heterologous betalain production in plants provides an excellent platform for studying antifungal activities of betalains in-planta, and may also be implemented for conferring resistance to phytopathogenic fungi in target crop species. To examine possible antifungal effects of betalains, wildtype and pX11 tobacco plants were subjected to leaf infection by gray mold fungus (*Botrytis cinerea*), a necrotrophic plant pathogen that is responsible for major losses in agricultural produce in both pre-harvest and post-harvest stages. Droplets of *B. cinerea* spore suspension in different concentration were applied on plant leaves, totaling approximately 100, 250 or 500 spores per plant. The degree of *B. cinerea* infection was then estimated by daily measurements of lesion size around the infection points. Leaves of pX11 tobacco exhibited significantly smaller lesion area upon infection compared to wildtype tobacco leaves (FIG. 22). Infected wildtype tobacco leaves also exhibited increased signs of necrosis compared to pX11 leaves within several days post infection (FIG. 22). Together, these results indicate increased resistance towards *B. cinerea* infection of betalain-producing plants.

Example 19

CYP76AD15 is a Functional Ortholog of CYP76AD6 in *Mirabilis jalapa*

Considering the natural occurrence of additional betalain-producing plant species that consist of red or yellow-colored varieties, it is plausible that these species have a molecular mechanism similar to the one observed in red beet, where one cytochrome P450 enzyme catalyzes only tyrosine hydroxylation, while another catalyzes both tyrosine hydroxylation and cyclo-DOPA formation. It is also possible that the functional orthologs of CYP76AD1 and CYP76AD6 are found in the CYP76AD1-α and the CYP76AD1-3 subclades, respectively. However, functional analyses of corresponding genes from additional betalain-producing species are needed to support this hypothesis.

Functional orthologs of CYP76AD1 have previously been identified in several plants, including *Mirabilis jalapa*, where CYP76AD3 was identified based on sequence similarity to CYP76AD1 (Hatlestad et al., 2012). However, CYP76AD6 orthologs were not previously described. In order to assess the occurrence of a CYP76AD6 ortholog in *M. jalapa*, a tBLASTx query was performed in a previously obtained *M. jalapa* transcriptome dataset (Polturak et al., 2016), using the CYP76AD1 nucleotide sequence. This search resulted in the identification of several interrelated genes, including one gene with the highest sequence similarity to CYP76AD6, hereinafter named CYP76AD15. Interestingly, according to the data obtained in the *M. jalapa* transcriptome analysis, CYP76AD15 does not exhibit an expression pattern that parallels betalain accumulation. Instead, a generally constitutive expression pattern was observed for this gene. CYP76AD15 activity was tested by agroinfiltration assays in *N. benthamiana*. Similarly to CYP76AD6, CYP76AD15 was found to allow betaxanthin production in *N. benthamiana* leaves when co-infiltrated with BvDODA1, and L-DOPA production when infiltrated alone (FIG. 23). Occurrence of several betaxanthins was verified by LC-MS analysis, including dopamine-betaxanthin and valine-betaxanthin that were identified based on typical absorption patterns and MS/MS fragmentation. CYP76AD15 was therefore identified as a functional ortholog of CYP76AD6, catalyzing the formation of L-DOPA from tyrosine. Sequence analysis indicates that CYP76AD15 belongs to the CYP76AD1-0 subclade together with CYP76AD6, while CYP76AD3 belongs in the CYP76AD1-α clade with CYP76AD1, thereby confirming the association of each of the subclades with a specific catalytic activity.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of producing L-DOPA from tyrosine, comprising: introducing into a cell a recombinant polynucleotide that encodes CYP76AD6, wherein said recombinant polynucleotide is under the control of a heterologous promoter active in said cell, wherein said CYP76AD6 is a tyrosine hydroxylase that converts tyrosine to L-DOPA and comprises the amino acid sequence set forth in SEQ ID NO: 18 and wherein said cell is selected from a plant cell, a bacterial cell and a yeast cell, thereby producing L-DOPA from tyrosine.

2. The method of claim 1, wherein said method is performed without provision of L-DOPA.

3. The method of claim 1, wherein said cell is a yeast cell.

4. The method of claim 1, wherein said cell is a bacterial cell.

5. The method of claim 1, further comprising introducing into the cell a nucleic acid that increases tyrosine availability in said cell.

6. The method of claim 1, wherein said cell is a plant cell.

7. The method of claim 1, wherein said method is performed in culture.

8. The method of claim 1, wherein said cell is within an organism.

* * * * *

SEQUENCE LISTING

<160> NUMBER OF SEQ ID NOS: 86

<210> SEQ ID NO 1
<211> LENGTH: 1901
<212> TYPE: DNA
<213> ORGANISM: Mirabilis jalapa

<400> SEQUENCE: 1

```
cttcaaatcc tcccacgtat atatcaacaa aaaccaaaaa catcatctca ttacaataat      60
ggagtatcat cttctcttcc ttctcctcct gccgatcatc cttatcttcg tgttcctcaa     120
tcacaagccc aagcaaacca aactcgaacc accaggacca cgtccatggc ccatcatagg     180
ccacaccaac ctcgtcggct ccaaacctca tcagtccatt gccaaactag ctcatattta     240
cggtcccata atgtcactta agctagggag aatcactact attgtcatat cttcccctga     300
agcagccaaa gacttgttcc tgaaacatga ccttactttc tcaagtaggc aagttcctca     360
```

-continued

```
cgcttcaacc gctacaaacc atgacaaact atccatggtt tggctccctg tatgtcccaa      420
atggcgctat cttagaaaga tcgcggccat ccaactattc accaaccaac aacttgatgg      480
tggtcaggta ctaaggcgta agaaagtgga cgagttgatc caatttgtga ctcgttgtag      540
taaacaaggg caagtcattg atattggaga ggctgttttt attactactc ttaacttaat      600
gtcaaatacc tttttttcca aggatttgtg tagttatggt ttggccgaat cacgagagtt      660
taaggatcta ttttgggagt tcatgaaagt gctagcgagt cctaatgttt ctgattattt      720
tccatggtta agatggttgg atttgcaagg catcaagaga agaagcgagg gttgttatcg      780
caagatgttg ggttttttg gggagattat tgatcagaga ttgagagatc caatgtcatg      840
taagaacgat gtattggaca ctctactcaa acttgtcgac caaaagagt tgagctttga      900 ggatgtcaaa catatgcttg tggatttgtt tgttgcaggg acggatacaa cttcgaacac      960
attggaatgg acaatggtag aactttacg ccaccctaac atattgacta agcacaaac      1020 tgaactcagc caagtcatag gcaaggacaa gttagtccaa gaatcatgta tcaccaagtt      1080
gccatatctt caatcaatat tgaaagaaac attcaggttg cacccaccga ctccttttt      1140 acttccacac aaagcaatcg agaacgttga actatgcaac tatcacatac ctaaaggtgc      1200
tcaagtttgg gtgaatgtgt ggtctattgg ccgcgatccc aacatttggt caagcccgga      1260
cttattttcc ccagagagat ttttaggtac cgacattgat ataaaaggta accatttcga      1320
gctcatacca ttcggagcag aagaaggat ttgccccggg ttgtcactag cttacaggat      1380
gcttcatttg attttggcca ctctccttca ttcattcaat tggaaccttc ctaatgacgt      1440
atgtccggaa aatatggata ttgaagaaaa atttgggatt acacttcaaa agatcatgcc      1500
actcaaagtc ataccaagct ctaggtgtct ggatcacgac aactaactgg tgttaatctt      1560
ttacaacata ttgaatgata tatatcacgt taaggtacat gcgtctagat gcagaaactt      1620
gcatacgttt ccttttcaat aaagtcttgc atatgtatgg tttataggt gatgtaattt      1680 cttgtttgtt tttacttaag tttataagac attttttttt tttttttatc gatgctctta      1740
ctcattaaaa tattggaaca tatacaaaat tttatatgtt ttagataaaa ttatacaggt      1800
tttaatttta ggaacttacc acttgttcac actgcgagac ttaaatagtc aaaatagaaa      1860
atacacacta ttaaaaagta ctcactattt atcaaattta t                         1901
```

<210> SEQ ID NO 2  
<211> LENGTH: 1663  
<212> TYPE: DNA  
<213> ORGANISM: Mirabilis jalapa

<400> SEQUENCE: 2

```
cctcacctcc ataacaaaga atgaccgcc attaaaatga acaccaatgg tgaaggtgaa        60
acacaacata tactaatgat accttcatg gcgcaagggc atttacgtcc tttccttgag      120
cttgctatgt ttctatataa acgaagtcat gttatcatta ctcttcttac taccccgctc      180
aatgcgggtt tcctacgaca tctccttcac caccatagct attctagctc ggggatcaga      240
attgtcgagt tacctttcaa ctcaaccaat catggtcttc cacctggcat tgaaaacact      300
gataaactta cactcccact tgtagtatca cttttttcatt caaccatttc tcttgaccct      360
caccttagag attatattc ccgccatttc tcccctgcgc gccctcctct gtgtgtcata      420
catgatgtgt tccttggttg ggttgatcaa gttgctaaag acgtgggctc aactggtgtt      480
gttttactta cgggtggcgc gtatggtaca agcgcatatg tgtccatttg gaatgatctg      540
```

```
cctcaccaga attactctga tgatcaagag tttccgcttc ctggtttccc ggagaatcat      600
aaattccgac gttctcaact tcatcggttt ctgaggtatg ccgatggatc agatgattgg      660
tcgaaatatt tccaaccgca attgaggcaa tcaatgaaga gttttggatg gctatgtaat      720
tcagttgagg aaatcgaaac acttgggttt agtatcctca ggaactacac taaactaccc      780
atttggggta ttggaccgtt gatagcttca cctgtacaac attcatcatc tgataataac      840
agtactggtg ccgagtttgt tcaatggttg agcttgaaag aaccagattc tgtattatac      900
atctcatttg gatcacagaa cacaatttca ccaacccaga tgatggaact agcagccggt      960
ttggagtcaa gtgagaagcc gttttttgtgg gtgattcgag caccatttgg gttcgatatc     1020
aatgaggaaa tgagaccaga atggctacca gagggattcg aggagcgaat gaaggtgaaa     1080
aaacaaggaa agttggtgta taagttggga ccacagttgg agatacttaa ccatgagtca     1140
atcggagggt tcttaactca ttgtgggtgg aattcgatcc ttgagtcact tcgagaaggt     1200
gtgcctatgt tagggtggcc attggcagcc gaacaagctt ataatttgaa gtatttggag     1260
gacgaaatgg gggttgcagt cgagttagcg agggattgg aaggagagat aagtaaagag       1320
aaagtgaaga gaattgtgga gatgattta gagagaaatg aaggaagtaa aggatgggaa       1380
atgaaaaata gagcagtaga aatggggaag aaacttaaag acgctgtcaa tgaggagaag     1440
gaactgaagg gttcttctgt taaggcaata gatgatttct tagatgcggt catgcaagct     1500
aagttggaac cttctcttca ataataagat cgatagttta tctcgtctca gagactcaaa     1560
caattgacta ctaggatgat cagaaagaga gttatgttca gtgttctgtt attatgcaag     1620
acttcaataa taacagaaaa attcgtgatt agattcataa ctt                       1663

<210> SEQ ID NO 3
<211> LENGTH: 1005
<212> TYPE: DNA
<213> ORGANISM: Mirabilis jalapa

<400> SEQUENCE: 3
atgaaaggaa catactatat aaatcatggt gatccactaa tgtacttaaa aaaacatata       60
aaactaaggc aattcttaga aggatggcaa gaaaatgttg ttattgaaaa accaaagagt      120
atacttatca tttctgctca ttgggatact aatgtaccta ctgtcaactt tgttgaacat      180
tgtgatacta ttcatgattt tgatgactat cctgatcctt gtaccagat acaatatcga       240 gcaccgggag caccaaattt agcaaaaaag gtggaagagt tactaaaaga gtcaggaatg     300
gaatgtgaga tagatacaaa gagaggactc gatcatgcag catggtttcc actaatgttt     360
atgtatcctg aagctaatat tcctatttgt gagctctcag tccaaccaag caaagatggg     420
atccaccact ataatgttgg gaaagctctt tctcctcttt tgcaacaagg tgttctcatc     480
attggctctg gtggtactgt tcatccttct gatgatactc ctcattgtcc caatggtgtt     540
gctccttggg ctattgagtt tgataactgg cttgaagatg ctcttcttag tggaaggtat      600
gaagatgtga acaacttcaa gaaattggca ccaaattggg agatatctca tccaggacaa     660
gaacatttgt accctttgca tgtggcatta ggggctgctg gcaaaaatcc aaagacacaa     720
cttattcatc gaagctgggc tgccaatggt gtctttggat attccaccta caacttcact     780
cccaccactc aaaaaactga ttaaaacttc ttttatatat ctcctattct tgctttattt      840
cttccttgtt caattgtttt atttatgttg taatattatg taaatttgc ctaaattggg      900 ctaccggtgt attatactat gactaacatt tgatatagtt gctccgacta ctatgtcaaa     960
gctgtaaggt gtttgatcat tgtgtaatcg aaaaatgttg gattc                     1005
```

<210> SEQ ID NO 4
<211> LENGTH: 1680
<212> TYPE: DNA
<213> ORGANISM: Mirabilis jalapa

<400> SEQUENCE: 4

| | | | | | | |
|---|---|---|---|---|---|---|
| aaagcataca | atgaccacca | gcaatcatta | aacaagagtt | aacactgtca | ctcatctaat | 60 |
| tttcttcaaa | acactatttc | ttctctcatc | tctttaagta | gttatttatt | taattttgat | 120 |
| catcataata | tggatttctt | aacccttgtc | atgatattat | ctattatctt | cttcttttac | 180 |
| aatctattaa | aaatgaaatt | cactacccat | tcagatgccc | aacttcctcc | aggacctaaa | 240 |
| ccaatgccaa | tattcggtaa | tatcttcgaa | ctaggtgaaa | aacctcaccg | atcatttgct | 300 |
| aacttagcaa | aaacacacgg | accactaatg | tcgttaaggt | taggaagtgt | caccaccatt | 360 |
| gtcgtctcct | cggcagaggt | tgctaaagaa | atgttcctta | aaaatgacca | gtcccttgca | 420 |
| gatagaagtg | tccctaattc | tgtaacggca | ggtgaccatc | acaagctaac | catgtcatgg | 480 |
| ttgcctgtct | ctccaaaatg | gaaaaatttc | cgaaaaatca | cagccgttca | tttgctttct | 540 |
| cctcaaaggc | ttgatgcttg | ccatgcactt | agacatgcca | aggtcaaaca | actctatgaa | 600 |
| tatgttcaag | agtgtgccct | aaaaggagaa | gcagttgata | ttggcaaggc | cgcatttacc | 660 |
| acttcactta | atctattatc | caatttgttc | ttttcggttg | agttagctaa | tcatacttct | 720 |
| aatacttccc | aagagtttaa | acaacttata | tgggatataa | tggaagatat | tggaaagcct | 780 |
| aactatgctg | attatttttcc | tttacttaaa | tatgttgatc | cctctggcat | acgacgtcgt | 840 |
| ttagcggcta | attttgataa | acttattgat | gtatttcaaa | gctttatctc | caaaaggtta | 900 |
| tcatctgctt | attctagtgc | aacaagtctc | gatgatgtgc | ttgatgttct | tctcaaactc | 960 |
| ctcaaggaaa | aggagcttaa | tatgggtgag | attaatcatc | ttcttgtgga | catatttgat | 1020 |
| gcaggtacag | acacaacatc | aaatacattc | gaatgggcaa | tggcagaact | aatgaggaac | 1080 |
| ccaataatga | tgaaaagagc | tcaaaatgag | atagcattag | tattaggcaa | agataatgcc | 1140 |
| actattcaag | aatctgatat | agcaaacatg | ccttatctac | aagcaattat | caaagaaaca | 1200 |
| ttacgtttac | atcctccaac | tgtctttcta | ttgccacgaa | aagccattac | taatgttaag | 1260 |
| ctatatggtt | atattgtccc | aaaaaatgca | cagatacttg | ttaacttgtg | ggccattggt | 1320 |
| cgcgacccca | aggtctggaa | gaaccctaat | gagttcttac | ctgataggtt | tttgaattct | 1380 |
| gatattgatg | tcaaaggtcg | agattttggg | ttgttgcctt | ttggtgcagg | gagaaggata | 1440 |
| tgtcctggta | tgaacttggc | ttataggatg | ttaactttga | tgttggcaac | tcttcttcaa | 1500 |
| tcttttgatt | ggaagcttcc | tcatcggaat | agtcctctgg | atttggatat | ggatgagaaa | 1560 |
| tttggtatcg | ctttacaaaa | gactaaacca | cttgagatta | ttcctcttat | taaatattga | 1620 |
| tgttttatat | gttgtattat | tattgcaatt | gtttaaacat | cttctttatt | attttggttg | 1680 |

<210> SEQ ID NO 5
<211> LENGTH: 749
<212> TYPE: DNA
<213> ORGANISM: Mirabilis jalapa

<400> SEQUENCE: 5

| | | | | | | |
|---|---|---|---|---|---|---|
| tcgatgtcac | caatttcccc | tatggacgtc | caaaccacat | tcccaaagca | actagactca | 60 |
| gtgattcgaa | ccaaggtggc | aaggccagca | aaaaaaagga | accaagaaga | gaagaagaaa | 120 |
| gaagaagaga | tacttgtgat | agagttagaa | gagctaaaac | aaaacgagta | cgtcaaattt | 180 |

| | |
|---|---|
| gatgtgtaca taaatgatga ttatgattac gagaataaga atgacggcgt gacgaggcca | 240 |
| acggaaaaat atgcagggag tttcgtgagt ttggcatcat cgggacaggg aatggagagc | 300 |
| aagaagagtg ggttgagatt ggcgttgacc aagttgatcg atgaaattgg tgctgatggt | 360 |
| gatgacttct tagatgtggt gctagtggct aaagctggga aaggtggtgt tgttataaat | 420 |
| gacgtcaaga ttgagttcct tgcttgattt agttaagtat tagtatggta gtggttgatg | 480 |
| tattgccttt taatttgtgt acaagttaca actttatttg caattcacca cttgttttta | 540 |
| tttgtatatg agtttctggt ttatctcaat atttagtcat ggtgttactg ttttatggtg | 600 |
| tttcctcacg tatctaagaa aaaataacaa tagatattgg aattatcatg aattgtgcgc | 660 |
| ccatcactgg tggtttgaaa aagaaagaca ataaaaataa gaaaaaatta taaaaaaaat | 720 |
| tctataatat atttattttt ttaaaaaaa | 749 |

<210> SEQ ID NO 6
<211> LENGTH: 2176
<212> TYPE: DNA
<213> ORGANISM: Mirabilis jalapa

<400> SEQUENCE: 6

| | |
|---|---|
| catcccactt ccattccgac aaccaactca accaccatca tcaaccctcc tcacaacaac | 60 |
| cccttctct ctcacctttc tccgatcaat cgccgccgtt cattccgcca cctttcaccc | 120 |
| aaactctcca tccgaaacaa ccaacaatcc accaacaacg accctctttt cgacccatca | 180 |
| aaactcgacc gaagaaacat ccttatcggg agtggtctcg ccggcatcta cggcggagcc | 240 |
| accactctcg gaggtaaccc cgccctagct gctcccccgc tccctgacgt caaaacatgc | 300 |
| aacctcacgt ccacctccgg tggggccct gaggggctcg aatgttgccc accctcattc | 360 |
| agaaacatcg tagatttcaa ccctcgaaac tacgccggcc cggcactccg ggtcagacgt | 420 |
| ccggctcatg aagtcgcgaa tgacccggag tacatggcta aatttaaaga agcaataaga | 480 |
| agaatgagag cacttcctag atctgatcca agaaactttg taacaagcc taatgttcat | 540 |
| tgtgcttatt gtgatggctc ataccgtcaa gataaacaca gtgacgtcga ttacacggtt | 600 |
| cattttctt ggttattctt cccattccat agagtttacc tctatttctt cgaacgtatc | 660 |
| ttggggaaat tgatcgatga tccaactttc gcaatcccat actggaactg ggatcatcca | 720 |
| gatggtatga aatgccaac tatttacacg aacccagatt caccattgtt tgatgctctt | 780 |
| agagatccgg ctcatcagcc gcctagagtt gcagatctta actacaatga tgttgatact | 840 |
| gatataagtc cagagttgca gattgagtat aacttaagag tgatgaatta tcaaatgaca | 900 |
| aggaataata aacctgagtt gtttatgggt gcacctttgt accctggtaa tgctgctgaa | 960 |
| gagaagggta ctggtgcact tgaaaatgtt cctcataatt tgcttcatgt ttgggttggt | 1020 |
| gatcgtaatg acgatccatt tcacaggaac atgggatcct tcttctcggc tggaagagac | 1080 |
| ccaatattct acggtcacca tgcaaacgta gacagaatgt ggtacatttg gaataccaag | 1140 |
| cttagccatc aaaatttcac tacaaaagat tggctagaca cttactttgt tctctacgac | 1200 |
| gagaacaaac aagctgtcag gattcgaact tcagactgtc tggatgttga aaaacaactc | 1260 |
| ggctacacct attcgaacca agacttaccc tggttagact caacgactgg aggaggagcc | 1320 |
| attgaaccaa ccccaccccc accatctggt gtggccgagt tcccacaagt tctagacaag | 1380 |
| gttatcagaa ccagggtggc tcgacccaag acctcaaggt cacaacagga aaaggaagtt | 1440 |
| gctacagaag tgctgaaagt gtctgtcaac attgataaag aagataatta cattaagttt | 1500 |
| gatgttttta tcaatgatgg tcaggatttt gagaccggtg gtcagactga tatcggtaag | 1560 |

| | |
|---|---|
| tcttatgcag gaagctttac tagcgtccct cataagacta gaaaaggtgc taggatggat | 1620 |
| atgaaccgcc gggtttcact tcccttgact gagattttgg agaatttggg tgctgatggt | 1680 |
| gatgattata ttgatgttgc tattgttcct aaggctggtt taggtaatgt caccattact | 1740 |
| gctgttaagg ttgattatat tatttgatta gtcactaatc aagtaattaa taaattaaaa | 1800 |
| ttactaccat atataataat tagttatgat gagtgtgtta atgtagtaag tggtattatt | 1860 |
| attaagtgag taaaataaaa agcgaccatg cattatgatt catgattgtg ggagtcgtgt | 1920 |
| ttcatgcatg gtagtgatgg gatgttatcg tatcttttgg tgcgctttaa atctgtttcc | 1980 |
| actttattat tttttttttt tccaagtatt tccactttat tgttatgact tgtcaaaagt | 2040 |
| tggtattata taagtttgtc gttctatatt aaaattattt tttaatgttt tttttattt | 2100 |
| ttacttttag taaagttgtt atcaaggaca tgatattttt gaaggaatga agacaaacat | 2160 |
| taatataact gtaagg | 2176 |

<210> SEQ ID NO 7
<211> LENGTH: 282
<212> TYPE: DNA
<213> ORGANISM: Mirabilis jalapa

<400> SEQUENCE: 7

| | |
|---|---|
| caaacaagct gtcaggattc gaacctctga ttgcctcgat gttgaaaacc aactcggcta | 60 |
| cacctatgag gaccaagatt tgccatggtt agactcatct gtcggaaaag acgcccctat | 120 |
| acccaccaaa ccccaaccat ctgatgtggc cgagttccca caagtcctag acaaagttat | 180 |
| ccgtactaga gtggctcgac ccaaggccac aaggtccgag caagaaaagc aggttgctgc | 240 |
| agaagccctg aaagtatccg tcaacattga taaagaagat aa | 282 |

<210> SEQ ID NO 8
<211> LENGTH: 1016
<212> TYPE: DNA
<213> ORGANISM: Mirabilis jalapa

<400> SEQUENCE: 8

| | |
|---|---|
| acggaggcgc ataaaaaaat ggttgtatta ttttgctatt gatatctgct gggaaaacaa | 60 |
| ggagtagtgt attcggattc tcacatcccc gaaatcgatc aacgtcttta tttgggcggt | 120 |
| ttaaagcaag gaatatctga ggaattgcta tcagtgactc atttgtgtgt caagcatat | 180 |
| caaccagcta taggaggtgc taccgtgggt aacttgaatt ctttaggccc cttttgaatg | 240 |
| tcacgaaaga gatgtgtcct tattggtaaa ctgtttgatt tctattgttg agaagtcaaa | 300 |
| acctggacat tagacaacca cttgtattat ttgactgttt ccgattaatc ctactaatga | 360 |
| cggtctctct cccttctcct ataacgacca tcaacattcc cgttgccact agaaacacta | 420 |
| aaccactccc taagccattg atgctttatc aatcctgcca ccctaccttg aaaatttcat | 480 |
| gccaagcctc ccacaacctc aaggtgaatc acaacgccg agatctccta attgggctag | 540 |
| ccacccctatg tgggacccccc accttgtgtg tcccactagt ctcagcagca ccagcagcag | 600 |
| caacccctttt tccacagctg ttggactccg tggttcggac cagggtggca aggccagcaa | 660 |
| aagaaagaag ccaaagagag aaggatgatg aagaggaggt gcttgtggtt agcttggagc | 720 |
| aactaaggga agatgaatat gtcaaatttg atgtgtacat caatgatgat tatgactttg | 780 |
| agaataagaa tgatgggctg acaaggccaa caaaagaata tgcggggagt tattctagcc | 840 |
| tgccatctcc aaggcgactc atggagagca agaagattgc gttgaagctg gcgttgacac | 900 |

```
agctgattga tgacattggt gccgatagcg atgactatat tgacgtggtg ctggtgccta    960
aagcaggaaa aggtgctctt gttgtaaaaa atgtcaagat tgagttcctt gcttga       1016

<210> SEQ ID NO 9
<211> LENGTH: 1922
<212> TYPE: DNA
<213> ORGANISM: Beta vulgaris

<400> SEQUENCE: 9
cagtcattta aaatcctgta aattactcac atacataacc aaattaaagt tgccgccgta     60
ctgatttcca aaggtcctac atctatcaat ggagtattac accataacgc tattattcat    120
catcttcaca atatcaatat tcggtacaaa aattttgagc aagtccaaac ttcctccagg    180
accaacacca tggcctatca taggcaacat cctcgagcta ggcaagttac ctcatcaggc    240
agttgacaag ctctcaaaaa cctatggccc tatattatct ctcaaactcg gaagcatcac    300
tacaatagta atatcatccc ctgaaatcgt taaagaaatg ttcctcgagc acgacttagc    360
cctttctagt aggccttccc cggatgcttc gagggtggga aaccataaca aattttccat    420
tgtttggctc ccagtgtccc ccaaatggcg ggaccttaga aaaattgcta ctatccaatt    480
gtttactact caacgcctag attctagcca agaactacgg cagatcaagg tgaacgagct    540
ggttgattat gtacgacagt gttgtgaaaa gggtctacct gttgatgttg gtaaagccgg    600
gtttactacc acgttaaata tgttgtctaa cacgttttttc tccatggatt tggctagcca    660
tgcttcttcg aattcgcaag agttcaagga tcttgtttgg agtctttttgg aagagggtgc    720 aaagcctaat gtgtcggatt ttttcccgat agttagagaa ttggatttgc agggagtatc    780
gaaaaataga agggtgcaca tgaagaagct aatgggaatt tcgaggaaa tcattgatgg    840 aaggttgaca aagttaaagg atgtgaagga tgatgttcta agtactttac tcaaacttgt    900
taaggatgaa gaattgaacc ttgacgacgt caaacatatg ctcatggatt tatttttagc    960
gggaacagat acaacctcta tcacattgga gtgggcgatg acagaattac ttcgcaatcc   1020
agaaaagatg gaaaaggttc aaattgagtt ggacaaagta cttggcaagg atagttctct   1080
gcaagagtca atgatctcaa aattaccata tattcaagca atagtgaaag aaacattaag   1140
attacaccca ccaactcctt tcttgattcc tcacaaagca gaaaaagatg tattgttatg   1200
caactattta gtgcccaaaa actcaattat ttgggttaat ttatggtcga tcgctcgtag   1260
tccaagtgtg tggccaaatc cagaatcatt ttctcctgaa aggttttttgg agatggaaat   1320 tgatattaaa ggacgagatt tcaaactcat acccttttgga tcaggaagaa gaatgtgtcc   1380
tggaatgcca cttgcttata ggatgacaca tatgttgttg gctactcttc ttcattcatt   1440
taactggaag tatggtgagg caagtccaaa agatatagac atgaaagaaa agtttgggtt   1500
gacgttgcaa aaggctcagc cacttcaagc aattccaatt cccagatgat caatctcttt   1560
tgaggagtta gacgatttct ttgtgtcaac caactagtac ttatcggaac atttattgtt   1620
aaatgtgtct gttagatgta catatgatgt tgttatacta agaataacg gtgtttaagt   1680 gcaacatggg acaagaggat tatgtaaagt atcctagatt ttattaggtg ctcctacacc   1740
tatgtattgg tgcatttgca ccaagtcgtc tgtagaaaac ttgagacttg ggaggcaaga   1800
actttacctc tgtaaaaaaaa acgcgttttt tgcattctcc ttgtatcttt tgcaagagat   1860
tgtacgcatt cacaaaacat caaatacatt tgtgtttaca caataagaat cgccaacact   1920
ga                                                                  1922
```

```
<210> SEQ ID NO 10
<211> LENGTH: 495
<212> TYPE: PRT
<213> ORGANISM: Beta vulgaris

<400> SEQUENCE: 10

Met Asp Asn Ala Thr Leu Ala Val Ile Leu Ser Ile Leu Phe Val Phe
1               5                   10                  15

Tyr His Ile Phe Lys Ser Phe Phe Thr Asn Ser Ser Arg Arg Leu
            20                  25                  30

Pro Pro Gly Pro Lys Pro Val Pro Ile Phe Gly Asn Ile Phe Asp Leu
            35                  40                  45

Gly Glu Lys Pro His Arg Ser Phe Ala Asn Leu Ser Lys Ile His Gly
    50                  55                  60

Pro Leu Ile Ser Leu Lys Leu Gly Ser Val Thr Thr Ile Val Val Ser
65                  70                  75                  80

Ser Ala Ser Val Ala Glu Glu Met Phe Leu Lys Asn Asp Gln Ala Leu
                85                  90                  95

Ala Asn Arg Thr Ile Pro Asp Ser Val Arg Ala Gly Asp His Asp Lys
            100                 105                 110

Leu Ser Met Ser Trp Leu Pro Val Ser Gln Lys Trp Arg Asn Met Arg
            115                 120                 125

Lys Ile Ser Ala Val Gln Leu Leu Ser Asn Gln Lys Leu Asp Ala Ser
130                 135                 140

Gln Pro Leu Arg Gln Ala Lys Val Lys Gln Leu Leu Ser Tyr Val Gln
145                 150                 155                 160

Asp Cys Ser Lys Lys Met Gln Pro Val Asp Ile Gly Arg Ala Ala Phe
                165                 170                 175

Thr Thr Ser Leu Leu Leu Ser Asn Thr Phe Phe Ser Ile Glu Leu Ala
            180                 185                 190

Ser His Glu Ser Ser Ala Ser Gln Glu Phe Lys Gln Leu Met Trp Asn
            195                 200                 205

Ile Met Glu Glu Ile Gly Arg Pro Asn Tyr Ala Asp Phe Phe Pro Ile
210                 215                 220

Leu Gly Tyr Ile Asp Pro Phe Gly Ile Arg Arg Arg Leu Ala Gly Tyr
225                 230                 235                 240

Phe Asp Lys Leu Ile Asp Val Phe Gln Asp Ile Ile Arg Glu Arg Gln
                245                 250                 255

Lys Leu Arg Ser Ser Asn Ser Ser Gly Ala Lys Gln Thr Asn Asp Ile
            260                 265                 270

Leu Asp Thr Leu Leu Lys Leu His Glu Asp Asn Glu Leu Ser Met Pro
            275                 280                 285

Glu Ile Asn His Leu Leu Val Asp Ile Phe Asp Ala Gly Thr Asp Thr
290                 295                 300

Thr Ala Ser Thr Leu Glu Trp Ala Met Ala Glu Leu Val Lys Asn Pro
305                 310                 315                 320

Glu Met Met Thr Lys Val Gln Asn Glu Ile Glu Ala Leu Gly Lys
                325                 330                 335

Asp Cys Leu Asp Ile Gln Glu Ser Asp Ile Ser Lys Leu Pro Tyr Leu
            340                 345                 350

Gln Ala Ile Ile Lys Glu Thr Leu Arg Leu His Pro Pro Thr Val Phe
            355                 360                 365

Leu Leu Pro Arg Lys Ala Asp Asn Asp Val Glu Leu Tyr Gly Tyr Val
370                 375                 380
```

```
Val Pro Lys Asn Ala Gln Val Leu Val Asn Leu Trp Ala Ile Gly Arg
385                 390                 395                 400

Asp Pro Lys Val Trp Lys Asn Pro Glu Val Phe Ser Pro Glu Arg Phe
                405                 410                 415

Leu Asp Cys Asn Ile Asp Tyr Lys Gly Arg Asp Phe Glu Leu Leu Pro
            420                 425                 430

Phe Gly Ala Gly Arg Arg Ile Cys Pro Gly Leu Thr Leu Ala Tyr Arg
        435                 440                 445

Met Leu Asn Leu Met Leu Ala Thr Leu Leu Gln Asn Tyr Asn Trp Lys
    450                 455                 460

Leu Glu Asp Gly Ile Asn Pro Lys Asp Leu Asp Met Asp Glu Lys Phe
465                 470                 475                 480

Gly Ile Thr Leu Gln Lys Ile Lys Pro Leu Gln Val Ile Pro Val
                485                 490                 495

<210> SEQ ID NO 11
<211> LENGTH: 499
<212> TYPE: PRT
<213> ORGANISM: Froelichia latifolia

<400> SEQUENCE: 11

Met Asp Asn Thr Thr Leu Ala Val Val Leu Ser Val Met Phe Val Leu
1               5                   10                  15

Phe His Leu Leu Lys Thr Ile Phe Thr Asn Ser Ser Asn Asn Lys Leu
            20                  25                  30

Pro Pro Gly Pro Lys Arg Met Pro Ile Phe Gly Asn Ile Phe Asp Leu
        35                  40                  45

Gly Glu Lys Pro His Arg Ser Phe Ala Asn Phe Ala Lys Ile His Gly
    50                  55                  60

Pro Leu Ile Ser Leu Lys Leu Gly Ser Val Thr Thr Ile Val Val Ser
65                  70                  75                  80

Ser Ala Ser Val Ala Glu Glu Met Phe Leu Lys Asn Asp Gln Ala Leu
                85                  90                  95

Ala Asn Arg Thr Ile Pro Asp Ser Val Arg Ala Gly Asp His Asp Lys
            100                 105                 110

Leu Ser Met Ser Trp Leu Pro Val Ser Ala Lys Trp Arg Asn Leu Arg
        115                 120                 125

Lys Ile Ser Ala Val Gln Leu Leu Ser Asn Gln Arg Leu Asp Ala Ser
    130                 135                 140

Gln Pro Leu Arg Gln Ala Lys Val Lys Gln Leu Leu Ala Tyr Val Gln
145                 150                 155                 160

Asn Cys Ser Glu Lys Asn Gln Ala Val Asp Ile Gly Arg Ala Ala Phe
                165                 170                 175

Thr Thr Ser Leu Asn Leu Leu Ser Asn Thr Phe Phe Ser Met Glu Leu
            180                 185                 190

Ala Ser His Glu Ser Ser Ala Ser Gln Glu Phe Lys Gln Leu Met Trp
        195                 200                 205

Asn Ile Met Glu Glu Ile Gly Arg Pro Asn Tyr Ala Asp Phe Phe Pro
    210                 215                 220

Ile Leu Gly Tyr Ile Asp Pro Phe Gly Ile Arg Arg Leu Ala Gly
225                 230                 235                 240

Tyr Phe Asp Lys Leu Ile Asp Val Phe Gln Asp Ile Ile Arg Glu Arg
                245                 250                 255

Gln Lys Ile Arg Ala Ser Asn Ala Asn Gly Thr Lys Gln Thr Ser Asp
            260                 265                 270
```

```
Ile Leu Asp Thr Leu Leu Lys Leu Tyr Glu Asp Asn Glu Leu Ser Met
            275                 280                 285
Gly Glu Ile Asn His Leu Leu Val Asp Ile Phe Asp Ala Gly Thr Asp
        290                 295                 300
Thr Thr Ala Ser Thr Leu Glu Trp Ala Met Ala Glu Leu Val Lys Asn
305                 310                 315                 320
Pro Glu Met Met Val Arg Ala Gln Asn Glu Ile Glu Glu Val Leu Gly
                325                 330                 335
Lys Asp Cys Ser Asn Ile Gln Glu Ser Asp Ile Ser Lys Leu Pro Tyr
            340                 345                 350
Leu Gln Ala Ile Ile Lys Glu Ser Leu Arg Leu His Pro Pro Thr Val
        355                 360                 365
Phe Leu Leu Pro Arg Lys Ala Asp Val Asp Val Glu Leu Tyr Gly Tyr
    370                 375                 380
Val Val Pro Lys Asn Ala Gln Val Leu Val Asn Leu Trp Ala Ile Gly
385                 390                 395                 400
Arg Asp Pro Lys Val Trp Lys Asn Pro Glu Val Phe Ser Pro Glu Arg
                405                 410                 415
Phe Leu Glu Cys Asp Ile Asp Tyr Lys Gly Arg Asp Phe Glu Leu Leu
            420                 425                 430
Pro Phe Gly Ala Gly Arg Arg Ile Cys Pro Gly Leu Thr Leu Ala Tyr
        435                 440                 445
Arg Met Leu Asn Leu Met Leu Ala Thr Leu Leu His Asn Tyr Asn Trp
    450                 455                 460
Lys Leu Gly Asp Asp Met Asp Pro Lys Asp Leu Asp Met Glu Glu Lys
465                 470                 475                 480
Phe Gly Ile Thr Leu Gln Lys Ile Lys Pro Leu Gln Val Ile Pro Val
                485                 490                 495
Ala Arg Lys

<210> SEQ ID NO 12
<211> LENGTH: 495
<212> TYPE: PRT
<213> ORGANISM: Alternanthera caracasana

<400> SEQUENCE: 12

Met Asp Asn Thr Thr Leu Ala Val Val Leu Ser Ile Met Phe Ala Cys
1               5                   10                  15
Phe His Leu Ile Lys Thr Ile Phe Ser Asn Ser Ser Asn Ser Lys Leu
            20                  25                  30
Pro Pro Gly Pro Lys Arg Leu Pro Ile Phe Gly Asn Ile Phe Asp Leu
        35                  40                  45
Gly Glu Lys Pro His Arg Ser Phe Ala Asn Tyr Ala Lys Leu His Gly
    50                  55                  60
Pro Leu Ile Ser Leu Gln Leu Gly Ser Val Met Thr Val Ile Val Ser
65                  70                  75                  80
Ser Ala Ser Val Ala Glu Glu Met Phe Leu Lys Asn Asp Gln Ala Leu
                85                  90                  95
Ala Asn Arg Thr Ile Pro Asp Ser Val Arg Ala Gly Asp His Asp Lys
            100                 105                 110
Leu Ser Met Ser Trp Leu Pro Val Ser Pro Lys Trp Arg Asn Leu Arg
        115                 120                 125
Lys Ile Ser Ala Val Gln Leu Leu Ser Thr Gln Arg Leu Asp Ala Ser
    130                 135                 140
```

Gln Pro Leu Arg Gln Ala Lys Val Gln Leu Leu Ala Tyr Val Gln
145                 150                 155                 160

Asp Cys Ser Lys Lys Gly Gln Pro Val Asp Ile Gly Arg Ala Ala Phe
                165                 170                 175

Thr Thr Ser Leu Asn Leu Leu Ser Asn Thr Phe Phe Ser Met Glu Leu
            180                 185                 190

Ala Ser His Glu Ser Ser Ala Ser Gln Glu Phe Lys Gln Leu Met Trp
        195                 200                 205

Asn Ile Met Glu Glu Ile Gly Arg Pro Asn Tyr Ala Asp Phe Phe Pro
    210                 215                 220

Ile Leu Gly Tyr Ile Asp Pro Phe Gly Ile Arg Arg Leu Ala Ser
225                 230                 235                 240

Tyr Phe Asp Lys Leu Ile Ala Val Phe Gln Asp Ile Ile Arg Glu Arg
                245                 250                 255

Gln Lys Ile Arg Ser Ser Asn Val Ser Gly Thr Lys Gln Thr Asn Asp
                260                 265                 270

Ile Leu Asp Thr Leu Leu Lys Leu His Glu Glu Asn Glu Leu Ser Met
            275                 280                 285

Gly Glu Ile Asn His Leu Leu Val Asp Ile Phe Asp Ala Gly Thr Asp
        290                 295                 300

Thr Thr Ala Ser Thr Leu Glu Trp Ala Met Ala Glu Leu Val Lys Asn
305                 310                 315                 320

Pro Tyr Met Met Val Lys Ala Gln Asn Glu Ile Glu Ala Leu Gly
                325                 330                 335

Lys Asp Cys Ser Asn Ile Gln Glu Ser Asp Ile Ser Lys Leu Pro Tyr
                340                 345                 350

Leu Gln Ala Ile Ile Lys Glu Ser Leu Arg Leu His Pro Pro Thr Val
            355                 360                 365

Phe Leu Leu Pro Arg Lys Ala Asp His Asp Val Glu Leu Tyr Gly Tyr
        370                 375                 380

Val Val Pro Lys Asn Ala Gln Val Leu Val Asn Leu Trp Ala Ile Gly
385                 390                 395                 400

Arg Asp Pro Lys Val Trp Lys Asn Pro Glu Val Phe Phe Pro Glu Arg
                405                 410                 415

Phe Leu Gly Cys Asp Ile Asp Tyr Lys Gly Arg Asp Phe Glu Leu Leu
                420                 425                 430

Pro Phe Gly Ala Gly Arg Arg Ile Cys Pro Gly Leu Thr Leu Ala Tyr
            435                 440                 445

Arg Met Leu Asn Leu Met Leu Ala Thr Leu Leu His Asn Tyr Asn Trp
        450                 455                 460

Lys Leu Gly Asp Gly Met Asn Pro Lys Asp Met Asp Met Glu Glu Lys
465                 470                 475                 480

Phe Gly Ile Thr Leu Gln Lys Ile Lys Pro Leu Gln Val Ile Pro
                485                 490                 495

<210> SEQ ID NO 13
<211> LENGTH: 493
<212> TYPE: PRT
<213> ORGANISM: Alternanthera ficoidea

<400> SEQUENCE: 13

Met Asp Asn Thr Thr Leu Ala Leu Leu Leu Ser Gly Leu Phe Val Phe
1               5                   10                  15

Phe His Leu Ile Arg Ser Leu Val Ser His Ser Ser Lys Ser Ser Lys

```
                    20                  25                  30
Leu Pro Pro Gly Pro Lys Arg Met Pro Ile Phe Gly Asn Ile Phe Asp
                35                  40                  45

Leu Gly Glu Lys Pro His Arg Ser Phe Ala Asn Phe Ser Lys Ile Tyr
        50                  55                  60

Gly Pro Leu Ile Ser Leu Lys Leu Gly Ser Val Thr Thr Val Val Val
 65                  70                  75                  80

Ser Ser Ala Glu Val Ala Lys Glu Met Phe Leu Lys Asn Asp Gln Ala
                    85                  90                  95

Leu Ala Asn Arg Thr Ile Pro Asp Ser Val Arg Ala Gly Asp His Asp
                100                 105                 110

Lys Leu Ser Met Ser Trp Leu Pro Val Ser Asn Lys Trp Arg Asn Leu
                115                 120                 125

Arg Lys Ile Ser Ala Val Gln Leu Leu Ser Thr Gln Arg Leu Asp Ala
                130                 135                 140

Ser Gln Ala Asn Arg Gln Ala Lys Val Gln Gln Leu Leu Ala Tyr Val
145                 150                 155                 160

Gln Asp Cys Ser Lys Lys Gly Gln Pro Val Asp Ile Gly Arg Ala Ala
                165                 170                 175

Phe Thr Thr Ser Leu Asn Leu Leu Ser Asn Thr Phe Phe Ser Ile Glu
                180                 185                 190

Leu Ala Ser His Glu Ser Ser Ala Ser Gln Glu Phe Lys Gln Leu Met
                195                 200                 205

Trp Asn Ile Met Glu Glu Ile Gly Arg Pro Asn Tyr Ala Asp Phe Phe
                210                 215                 220

Pro Ile Leu Gly Tyr Ile Asp Pro Phe Gly Ile Arg Arg Arg Leu Ala
225                 230                 235                 240

Ala Tyr Phe Asp Lys Leu Ile Ala Val Phe Gln Asp Ile Ile Gln Glu
                245                 250                 255

Arg Gln Lys Ile Arg Ser Ser Gly Thr Lys Gln Thr Asn Asp Ile Leu
                260                 265                 270

Asp Thr Leu Leu Asn Leu Tyr Glu Glu Asn Glu Leu Ser Met Gly Glu
                275                 280                 285

Ile Asn His Leu Leu Val Asp Ile Phe Asp Ala Gly Thr Asp Thr Thr
                290                 295                 300

Ala Ser Thr Leu Glu Trp Ala Met Ala Glu Leu Val Lys Asn Pro Glu
305                 310                 315                 320

Met Met Ile Arg Val Gln Asn Glu Ile Glu Gln Ala Val Gly Lys Asp
                325                 330                 335

Cys Pro Met Ile Gln Glu Ser Asp Ile Ser Lys Leu Pro Tyr Leu Gln
                340                 345                 350

Ala Ile Ile Lys Glu Thr Leu Arg Leu His Pro Thr Val Phe Leu
                355                 360                 365

Leu Pro Arg Lys Ala Asp Val Asp Val Glu Leu Tyr Gly Tyr Thr Val
                370                 375                 380

Pro Lys Asp Ala Gln Val Leu Val Asn Leu Trp Ala Ile Gly Arg Asp
385                 390                 395                 400

Pro Lys Val Trp Lys Asn Ser Glu Val Phe Ser Pro Glu Arg Phe Leu
                405                 410                 415

Glu Cys Asp Ile Asp Tyr Lys Gly Arg Asp Phe Glu Leu Leu Pro Phe
                420                 425                 430

Gly Ala Gly Arg Arg Ile Cys Pro Gly Leu Thr Leu Ala Tyr Arg Met
                435                 440                 445
```

```
Leu Asn Leu Met Met Ala Asn Phe Leu Tyr Ser Phe Asp Trp Lys Leu
    450                 455                 460

Glu Gly Gly Met His Pro Lys Asp Leu Asp Met Asp Glu Lys Phe Gly
465                 470                 475                 480

Ile Thr Leu Gln Lys Val Lys Pro Leu Gln Val Ile Pro
                485                 490
```

<210> SEQ ID NO 14
<211> LENGTH: 497
<212> TYPE: PRT
<213> ORGANISM: Beta vulgaris

<400> SEQUENCE: 14

```
Met Asp His Ala Thr Leu Ala Met Ile Leu Ala Ile Trp Phe Ile Ser
1               5                   10                  15

Phe His Phe Ile Lys Leu Leu Phe Ser Gln Gln Thr Thr Lys Leu Leu
                20                  25                  30

Pro Pro Gly Pro Lys Pro Leu Pro Ile Ile Gly Asn Ile Leu Glu Val
            35                  40                  45

Gly Lys Lys Pro His Arg Ser Phe Ala Asn Leu Ala Lys Ile His Gly
50                  55                  60

Pro Leu Ile Ser Leu Arg Leu Gly Ser Val Thr Thr Ile Val Val Ser
65                  70                  75                  80

Ser Ala Asp Val Ala Lys Glu Met Phe Leu Lys Lys Asp His Pro Leu
                85                  90                  95

Ser Asn Arg Thr Ile Pro Asn Ser Val Thr Ala Gly Asp His His Lys
                100                 105                 110

Leu Thr Met Ser Trp Leu Pro Val Ser Pro Lys Trp Arg Asn Phe Arg
            115                 120                 125

Lys Ile Thr Ala Val His Leu Leu Ser Pro Gln Arg Leu Asp Ala Cys
130                 135                 140

Gln Thr Phe Arg His Ala Lys Val Gln Gln Leu Tyr Glu Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Val Glu Leu
            180                 185                 190

Ala His His Lys Ser His Thr Ser Gln Glu Phe Lys Glu Leu Ile Trp
        195                 200                 205

Asn Ile Met Glu Asp Ile Gly Lys Pro Asn Tyr Ala Asp Tyr Phe Pro
210                 215                 220

Ile Leu Gly Cys Val Asp Pro Ser Gly Ile Arg Arg Arg Leu Ala Cys
225                 230                 235                 240

Ser Phe Asp Lys Leu Ile Ala Val Phe Gln Gly Ile Ile Cys Glu Arg
                245                 250                 255

Leu Ala Pro Asp Ser Ser Thr Thr Thr Thr Thr Thr Asp Asp Val
            260                 265                 270

Leu Asp Val Leu Leu Gln Leu Phe Lys Gln Asn Glu Leu Thr Met Gly
            275                 280                 285

Glu Ile Asn His Leu Leu Val Asp Ile Phe Asp Ala Gly Thr Asp Thr
290                 295                 300

Thr Ser Ser Thr Phe Glu Trp Val Met Thr Glu Leu Ile Arg Asn Pro
305                 310                 315                 320

Glu Met Met Glu Lys Ala Gln Glu Glu Ile Lys Gln Val Leu Gly Lys
```

```
                    325                 330                 335
Asp Lys Gln Ile Gln Glu Ser Asp Ile Ile Asn Leu Pro Tyr Leu Gln
                340                 345                 350

Ala Ile Ile Lys Glu Thr Leu Arg Leu His Pro Pro Thr Val Phe Leu
                355                 360                 365

Leu Pro Arg Lys Ala Asp Thr Asp Val Glu Leu Tyr Gly Tyr Ile Val
            370                 375                 380

Pro Lys Asp Ala Gln Ile Leu Val Asn Leu Trp Ala Ile Gly Arg Asp
385                 390                 395                 400

Pro Asn Ala Trp Gln Asn Ala Asp Ile Phe Ser Pro Glu Arg Phe Ile
                405                 410                 415

Gly Cys Glu Ile Asp Val Lys Gly Arg Asp Phe Gly Leu Leu Pro Phe
                420                 425                 430

Gly Ala Gly Arg Arg Ile Cys Pro Gly Met Asn Leu Ala Ile Arg Met
            435                 440                 445

Leu Thr Leu Met Leu Ala Thr Leu Leu Gln Phe Phe Asn Trp Lys Leu
        450                 455                 460

Glu Gly Asp Ile Ser Pro Lys Asp Leu Asp Met Asp Glu Lys Phe Gly
465                 470                 475                 480

Ile Ala Leu Gln Lys Thr Lys Pro Leu Lys Leu Ile Pro Ile Pro Arg
                485                 490                 495

Tyr

<210> SEQ ID NO 15
<211> LENGTH: 496
<212> TYPE: PRT
<213> ORGANISM: Amaranthus hybridus subsp. cruentus

<400> SEQUENCE: 15

Met Asp Asn Ala Thr Leu Ala Met Ile Leu Thr Ile Trp Phe Ile Ser
1               5                   10                  15

Ile Asn Phe Ile Lys Met Phe Phe Tyr His Gln Asn Thr Lys Leu Ser
                20                  25                  30

Leu Pro Pro Gly Pro Lys Pro Leu Pro Ile Ile Gly Asn Ile Leu Glu
            35                  40                  45

Val Gly Lys Lys Pro His Arg Ser Phe Ala Asn Leu Ala Lys Ile His
        50                  55                  60

Gly Pro Leu Ile Ser Leu Arg Leu Gly Ser Val Thr Thr Ile Val Val
65                  70                  75                  80

Ser Ser Ala Glu Val Ala Lys Glu Met Phe Leu Lys Lys Asp Gln Pro
                85                  90                  95

Leu Ser Asn Arg Asn Val Pro Asn Ser Val Thr Ala Gly Asp His His
            100                 105                 110

Lys Leu Thr Met Ser Trp Leu Pro Val Ser Pro Lys Trp Arg Asn Phe
        115                 120                 125

Arg Lys Ile Thr Ala Val His Leu Leu Ser Pro Leu Arg Leu Asp Ala
    130                 135                 140

Cys Gln Ser Leu Arg His Ala Lys Val Gln Gln Leu Tyr Gln Tyr Val
145                 150                 155                 160

Gln Glu Cys Ala Leu Lys Gly Gln Ser Val Asp Ile Gly Lys Ala Ala
                165                 170                 175

Phe Thr Thr Ser Leu Asn Leu Leu Ser Lys Leu Phe Phe Ser Lys Glu
            180                 185                 190

Leu Ala Cys His Lys Ser His Glu Ser Gln Glu Leu Lys Gln Leu Ile
```

```
            195                 200                 205

Trp Asn Ile Met Glu Asp Ile Gly Lys Pro Asn Tyr Ala Asp Tyr Phe
    210                 215                 220

Pro Ile Leu Gly Cys Ile Asp Pro Leu Gly Ile Arg Arg Arg Leu Ala
225                 230                 235                 240

Ala Asn Phe Asp Lys Leu Ile Ser Val Phe Gln Thr Ile Ile Ser Glu
            245                 250                 255

Arg Leu Glu Asn Asp Ile Asn Ser Asn Ala Thr Thr Asn Asp Val Leu
                260                 265                 270

Asp Val Leu Leu Gln Leu Tyr Lys Gln Lys Glu Leu Ser Met Gly Glu
            275                 280                 285

Ile Asn His Leu Leu Val Asp Ile Phe Asp Ala Gly Thr Asp Thr Thr
        290                 295                 300

Ser Ser Thr Phe Glu Trp Val Met Ala Glu Leu Ile Arg Asn Pro Lys
305                 310                 315                 320

Met Met Glu Lys Ala Gln Gln Glu Ile His Glu Val Leu Gly Lys Asp
                325                 330                 335

Arg Gln Ile Gln Glu Ser Asp Ile Ile Lys Leu Pro Tyr Leu Gln Ala
            340                 345                 350

Leu Ile Lys Glu Thr Leu Arg Leu His Pro Pro Thr Val Phe Leu Leu
        355                 360                 365

Pro Arg Lys Ala Asp Met Asp Val Glu Leu Tyr Gly Tyr Val Val Pro
370                 375                 380

Lys Asp Ala Gln Ile Leu Val Asn Leu Trp Ala Ile Gly Arg Asp Ser
385                 390                 395                 400

Gln Val Trp Glu Lys Pro Asn Val Phe Leu Pro Glu Arg Phe Leu Gly
                405                 410                 415

Ser Asp Val Asp Val Lys Gly Arg Asp Phe Gly Leu Leu Pro Phe Gly
            420                 425                 430

Ala Gly Lys Arg Ile Cys Pro Gly Met Asn Leu Ala Ile Arg Met Leu
        435                 440                 445

Thr Leu Met Leu Ala Thr Leu Leu Gln Phe Phe Asn Trp Lys Leu Glu
450                 455                 460

Asp Gly Met Asn Pro Gln Asp Leu Asp Met Asp Glu Lys Phe Gly Ile
465                 470                 475                 480

Ala Leu Gln Lys Asn Lys Pro Leu Glu Ile Ile Pro Ser Leu Arg His
            485                 490                 495

<210> SEQ ID NO 16
<211> LENGTH: 496
<212> TYPE: PRT
<213> ORGANISM: Mirabilis jalapa

<400> SEQUENCE: 16

Met Asp Phe Leu Thr Leu Val Met Ile Leu Ser Ile Ile Phe Phe Phe
1               5                   10                  15

Tyr Asn Leu Leu Lys Met Lys Phe Thr Thr His Ser Asp Ala Gln Leu
            20                  25                  30

Pro Pro Gly Pro Lys Pro Met Pro Ile Phe Gly Asn Ile Phe Glu Leu
        35                  40                  45

Gly Glu Lys Pro His Arg Ser Phe Ala Asn Leu Ala Lys Thr His Gly
    50                  55                  60

Pro Leu Met Ser Leu Arg Leu Gly Ser Val Thr Thr Ile Val Val Ser
65                  70                  75                  80
```

```
Ser Ala Glu Val Ala Lys Glu Met Phe Leu Lys Asn Asp Gln Ser Leu
             85                  90                  95
Ala Asp Arg Ser Val Pro Asn Ser Val Thr Ala Gly Asp His His Lys
            100                 105                 110
Leu Thr Met Ser Trp Leu Pro Val Ser Pro Lys Trp Lys Asn Phe Arg
            115                 120                 125
Lys Ile Thr Ala Val His Leu Leu Ser Pro Gln Arg Leu Asp Ala Cys
130                 135                 140
His Ala Leu Arg His Ala Lys Val Lys Gln Leu Tyr Glu Tyr Val Gln
145                 150                 155                 160
Glu Cys Ala Leu Lys Gly Glu Ala Val Asp Ile Gly Lys Ala Ala Phe
                165                 170                 175
Thr Thr Ser Leu Asn Leu Leu Ser Asn Leu Phe Phe Ser Val Glu Leu
            180                 185                 190
Ala Asn His Thr Ser Asn Thr Ser Gln Glu Phe Lys Gln Leu Ile Trp
            195                 200                 205
Asp Ile Met Glu Asp Ile Gly Lys Pro Asn Tyr Ala Asp Tyr Phe Pro
            210                 215                 220
Leu Leu Lys Tyr Val Asp Pro Ser Gly Ile Arg Arg Arg Leu Ala Ala
225                 230                 235                 240
Asn Phe Asp Lys Leu Ile Asp Val Phe Gln Ser Phe Ile Ser Lys Arg
                245                 250                 255
Leu Ser Ser Ala Tyr Ser Ser Ala Thr Ser Leu Asp Asp Val Leu Asp
            260                 265                 270
Val Leu Leu Lys Leu Leu Lys Glu Lys Glu Leu Asn Met Gly Glu Ile
            275                 280                 285
Asn His Leu Leu Val Asp Ile Phe Asp Ala Gly Thr Asp Thr Thr Ser
290                 295                 300
Asn Thr Phe Glu Trp Ala Met Ala Glu Leu Met Arg Asn Pro Ile Met
305                 310                 315                 320
Met Lys Arg Ala Gln Asn Glu Ile Ala Leu Val Leu Gly Lys Asp Asn
                325                 330                 335
Ala Thr Ile Gln Glu Ser Asp Ile Ala Asn Met Pro Tyr Leu Gln Ala
            340                 345                 350
Ile Ile Lys Glu Thr Leu Arg Leu His Pro Pro Thr Val Phe Leu Leu
            355                 360                 365
Pro Arg Lys Ala Ile Thr Asn Val Lys Leu Tyr Gly Tyr Ile Val Pro
            370                 375                 380
Lys Asn Ala Gln Ile Leu Val Asn Leu Trp Ala Ile Gly Arg Asp Pro
385                 390                 395                 400
Lys Val Trp Lys Asn Pro Asn Glu Phe Leu Pro Asp Arg Phe Leu Asn
                405                 410                 415
Ser Asp Ile Asp Val Lys Gly Arg Asp Phe Gly Leu Leu Pro Phe Gly
            420                 425                 430
Ala Gly Arg Arg Ile Cys Pro Gly Met Asn Leu Ala Tyr Arg Met Leu
            435                 440                 445
Thr Leu Met Leu Ala Thr Leu Leu Gln Ser Phe Asp Trp Lys Leu Pro
            450                 455                 460
His Arg Asn Ser Pro Leu Asp Leu Asp Met Asp Glu Lys Phe Gly Ile
465                 470                 475                 480
Ala Leu Gln Lys Thr Lys Pro Leu Glu Ile Ile Pro Leu Ile Lys Tyr
                485                 490                 495
```

```
<210> SEQ ID NO 17
<211> LENGTH: 494
<212> TYPE: PRT
<213> ORGANISM: Celosia cristata

<400> SEQUENCE: 17

Met Asp Asn Ala Thr Leu Ala Met Leu Leu Ala Ile Trp Phe Ile Ser
1               5                   10                  15

Phe His Phe Ile Lys Met Leu Phe Thr Asn Gln Ser Thr Lys Leu Leu
            20                  25                  30

Pro Pro Gly Pro Lys Pro Leu Pro Ile Ile Gly Asn Ile Leu Glu Val
        35                  40                  45

Gly Lys Lys Pro His Arg Ser Phe Ala Asn Leu Ala Lys Ile His Gly
    50                  55                  60

Pro Leu Ile Ser Leu Lys Leu Gly Ser Val Thr Thr Ile Val Val Ser
65                  70                  75                  80

Ser Ala Glu Val Ala Lys Glu Met Phe Leu Lys Lys Asp Gln Pro Leu
                85                  90                  95

Ser Asn Arg Thr Val Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125

Lys Ile Thr Ala Val His Leu Leu Ser Pro Leu Arg Leu Asp Ala Cys
130                 135                 140

Gln Ser Leu Arg His Ala Lys Val Gln Gln Leu Phe Gln Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Lys Glu Leu
            180                 185                 190

Ala Ser His Lys Ser Arg Glu Ser Gln Glu Phe Lys Gln Leu Ile Trp
        195                 200                 205

Asn Ile Met Glu Asp Ile Gly Lys Pro Asn Tyr Ala Asp Tyr Phe Pro
210                 215                 220

Ile Leu Gly Cys Val Asp Pro Ser Gly Ile Arg Arg Arg Leu Ala Ser
225                 230                 235                 240

Asn Phe Asp Lys Leu Ile Glu Val Phe Gln Cys Ile Ile Arg Gln Arg
                245                 250                 255

Leu Glu Arg Asn Pro Ser Thr Pro Thr Asn Asp Val Leu Asp Val
            260                 265                 270

Leu Leu Glu Leu Tyr Lys Gln Asn Glu Leu Ser Met Gly Glu Ile Asn
        275                 280                 285

His Leu Leu Val Asp Ile Phe Asp Ala Gly Thr Asp Thr Thr Ser Ser
    290                 295                 300

Thr Phe Glu Trp Val Met Ala Glu Leu Ile Arg Asn Pro Glu Met Met
305                 310                 315                 320

Ala Lys Ala Gln Asp Glu Ile Glu Gln Val Leu Gly Lys Asp Arg Gln
                325                 330                 335

Ile Gln Glu Ser Asp Ile Ile Lys Leu Pro Tyr Leu Gln Ala Ile Ile
            340                 345                 350

Lys Glu Thr Leu Arg Leu His Pro Pro Thr Val Phe Leu Leu Pro Arg
        355                 360                 365

Lys Ala Asp Thr Asp Val Glu Leu Tyr Gly Tyr Ile Val Pro Lys Asp
    370                 375                 380
```

```
Ala Gln Ile Leu Val Asn Leu Trp Ala Ile Gly Arg Asp Ser Gln Ala
385                 390                 395                 400

Trp Glu Asn Pro Lys Val Phe Ser Pro Asp Arg Phe Leu Gly Cys Glu
            405                 410                 415

Ile Asp Val Lys Gly Arg Asp Phe Gly Leu Leu Pro Phe Gly Ala Gly
            420                 425                 430

Lys Arg Ile Cys Pro Gly Met Asn Leu Ala Ile Arg Met Leu Thr Leu
            435                 440                 445

Met Leu Ala Thr Leu Leu Gln Phe Phe Asn Trp Lys Leu Gln Asp Gly
450                 455                 460

Met Ser Leu Glu Asp Leu Asp Met Glu Glu Lys Phe Gly Ile Ala Leu
465                 470                 475                 480

Gln Lys Thr Lys Pro Leu Arg Ile Ile Pro Val Ser Arg Tyr
                485                 490

<210> SEQ ID NO 18
<211> LENGTH: 499
<212> TYPE: PRT
<213> ORGANISM: Beta vulgaris

<400> SEQUENCE: 18

Met Asp Asn Ala Thr Leu Ala Val Ile Leu Ser Ile Leu Phe Val Phe
1               5                   10                  15

Tyr His Ile Phe Lys Ser Phe Phe Thr Asn Ser Ser Ser Arg Arg Leu
            20                  25                  30

Pro Pro Gly Pro Lys Pro Val Pro Ile Phe Gly Asn Ile Phe Asp Leu
            35                  40                  45

Gly Glu Lys Pro His Arg Ser Phe Ala Asn Leu Ser Lys Ile His Gly
50                  55                  60

Pro Leu Ile Ser Leu Lys Leu Gly Ser Val Thr Thr Ile Val Val Ser
65                  70                  75                  80

Ser Ala Ser Val Ala Glu Glu Met Phe Leu Lys Asn Asp Gln Ala Leu
            85                  90                  95

Ala Asn Arg Thr Ile Pro Asp Ser Val Arg Ala Gly Asp His Asp Lys
            100                 105                 110

Leu Ser Met Ser Trp Leu Pro Val Ser Gln Lys Trp Arg Asn Met Arg
            115                 120                 125

Lys Ile Ser Ala Val Gln Leu Leu Ser Asn Gln Lys Leu Asp Ala Ser
130                 135                 140

Gln Pro Leu Arg Gln Ala Lys Val Lys Gln Leu Leu Ser Tyr Val Gln
145                 150                 155                 160

Val Cys Ser Glu Lys Met Gln Pro Val Asp Ile Gly Arg Ala Ala Phe
            165                 170                 175

Thr Thr Ser Leu Asn Leu Leu Ser Asn Thr Phe Phe Ser Ile Glu Leu
            180                 185                 190

Ala Ser His Glu Ser Ser Ala Ser Gln Glu Phe Lys Gln Leu Met Trp
            195                 200                 205

Asn Ile Met Glu Glu Ile Gly Arg Pro Asn Tyr Ala Asp Phe Phe Pro
210                 215                 220

Ile Leu Gly Tyr Ile Asp Pro Phe Gly Ile Arg Arg Arg Leu Ala Gly
225                 230                 235                 240

Tyr Phe Asp Lys Leu Ile Asp Val Phe Gln Asp Ile Ile Arg Glu Arg
            245                 250                 255

Gln Lys Leu Arg Ser Ser Asn Ser Ser Gly Ala Lys Gln Thr Asn Asp
            260                 265                 270
```

```
Ile Leu Asp Thr Leu Leu Lys Leu His Glu Asp Asn Glu Leu Ser Met
            275                 280                 285

Pro Glu Ile Asn His Leu Leu Val Asp Ile Phe Asp Ala Gly Thr Asp
            290                 295                 300

Thr Thr Ala Ser Thr Leu Glu Trp Ala Met Ala Glu Leu Val Lys Asn
305                 310                 315                 320

Pro Glu Met Met Thr Lys Val Gln Ile Glu Ile Glu Gln Ala Leu Gly
                325                 330                 335

Lys Asp Cys Leu Asp Ile Gln Glu Ser Asp Ile Ser Lys Leu Pro Tyr
            340                 345                 350

Leu Gln Ala Ile Ile Lys Glu Thr Leu Arg Leu His Pro Pro Thr Val
            355                 360                 365

Phe Leu Leu Pro Arg Lys Ala Asp Asn Asp Val Glu Leu Tyr Gly Tyr
            370                 375                 380

Val Val Pro Lys Asn Ala Gln Val Leu Val Asn Leu Trp Ala Ile Gly
385                 390                 395                 400

Arg Asp Pro Lys Val Trp Lys Asn Pro Glu Val Phe Ser Pro Glu Arg
                405                 410                 415

Phe Leu Asp Cys Asn Ile Asp Tyr Lys Gly Arg Asp Phe Glu Leu Leu
            420                 425                 430

Pro Phe Gly Ala Gly Arg Arg Ile Cys Pro Gly Leu Thr Leu Ala Tyr
            435                 440                 445

Arg Met Leu Asn Leu Met Leu Ala Thr Leu Leu Gln Asn Tyr Asn Trp
450                 455                 460

Lys Leu Glu Asp Gly Ile Asn Pro Lys Asp Leu Asp Met Asp Glu Lys
465                 470                 475                 480

Phe Gly Ile Thr Leu Gln Lys Val Lys Pro Leu Gln Val Ile Pro Val
                485                 490                 495

Pro Arg Asn

<210> SEQ ID NO 19
<211> LENGTH: 16212
<212> TYPE: DNA
<213> ORGANISM: Artificial Sequence
<220> FEATURE:
<223> OTHER INFORMATION: pX11 overexpression vector

<400> SEQUENCE: 19
cgctgtcatg agacgaattc tgacaggata tattggcggg taaacctaag agaaaagagc      60
gtttattaga ataatcggat atttaaaagg gcgtgaaaag gtttatccgt tcgtccattt     120
gtatgtgcat gccaaccaca gggttcccct cgggatcaaa gtactttgat ccaacccctc     180
cgctgctata gtgcagtcgg cttctgacgt tcagtgcagc cgtcatctga aaacgacatg     240
tcgcacaagt cctaagttac gcgacaggct gccgccctgc ccttttcctg gcgttttctt     300
gtcgcgtgtt ttagtcgcat aaagtagaat acttgcgact agaaccggag acattacgcc     360
atgaacaaga gcgccgccgc tggcctgctg gctatgccc gcgtcagcac cgacgaccag     420
gacttgacca accaacgggc cgaactgcac gcggccggct gcaccaagct gttttccgag     480
aagatcaccg gcaccaggcg cgaccgcccg gagctggcca ggatgcttga ccacctacgc     540
cctggcgacg ttgtgacagt gaccaggcta gaccgcctgg cccgcagcac ccgcgaccta     600
ctggacattg ccgagcgcat ccaggaggcc ggcgcgggcc tgcgtagcct ggcagagccg     660
tgggccgaca ccaccacgcc ggccggccgc atggtgttga ccgtgttcgc cggcattgcc     720
```

```
gagttcgagc gttccctaat catcgaccgc acccggagcg ggcgcgaggc cgccaaggcc    780
cgaggcgtga agtttggccc ccgccctacc ctcaccccgg cacagatcgc gcacgcccgc    840
gagctgatcg accaggaagg ccgcaccgtg aaagaggcgg ctgcactgct tggcgtgcat    900
cgctcgaccc tgtaccgcgc acttgagcgc agcgaggaag tgacgcccac cgaggccagg    960
cggcgcggtg ccttccgtga ggacgcattg accgaggccg acgccctggc ggccgccgag   1020
aatgaacgcc aagaggaaca agcatgaaac cgcaccagga cggccaggac gaaccgtttt   1080
tcattaccga agagatcgag gcggagatga tcgcggccgg gtacgtgttc gagccgcccg   1140
cgcacctctc aaccgtgcgg ctgcatgaaa tcctggccgg tttgtctgat gccaagctgg   1200
cggcctggcc ggccagcttg gccgctgaag aaaccgagcg ccgccgtcta aaaaggtgat   1260
gtgtatttga gtaaaacagc ttgcgtcatg cggtcgctgc gtatatgatc cgatgagtaa   1320
ataaacaaat acgcaagggg aacgcatgaa ggttatcgct gtacttaacc agaaaggcgg   1380
gtcaggcaag acgaccatcg gaacccatct agcccgcgcc ctgcaactcg ccggggccga   1440
tgttctgtta gtcgattccg atccccaggg cagtgcccgc gattgggcgg ccgtgcggga   1500
agatcaaccg ctaaccgttg tcggcatcga ccgcccgacg attgaccgcg acgtgaaggc   1560
catcggccgg cgcgacttcg tagtgatcga cggagcgccc caggcggcgg acttggctgt   1620
gtccgcgatc aaggcagccg acttcgtgct gattccggtg cagccaagcc cttacgacat   1680
atgggccacc gccgacctgg tggagctggt taagcagcgc attgaggtca cggatggaag   1740
gctacaagcg gcctttgtcg tgtcgcgggc gatcaaaggc acgcgcatcg gcggtgaggt   1800
tgccgaggcg ctggccgggt acgagctgcc cattcttgag tcccgtatca cgcagcgcgt   1860
gagctaccca ggcactgccg ccgccggcac aaccgttctt gaatcagaac ccgagggcga   1920
cgctgcccgc gaggtccagg cgctggccgc tgaaattaaa tcaaaactca tttgagttaa   1980
tgaggtaaag agaaaatgag caaaagcaca acacgctaag tgccggccg tccgagcgca   2040
cgcagcagca aggctgcaac gttggccagc ctggcagaca cgccagccat gaagcgggtc   2100
aactttcagt tgccggcgga ggatcacacc aagctgaaga tgtacgcggt acgccaaggc   2160
aagaccatta ccgagctgct atctgaatag atcgcgcagc taccagagta atgagcaaa   2220
tgaataaatg agtagatgaa ttttagcggc taaaggaggc ggcatggaaa atcaagaaca   2280
accaggcacc gacgccgtgg aatgccccat gtgtggagga cgggcggtt ggccaggcgt   2340
aagcggctgg gttgtctgcc ggccctgcaa tggcactgga accccaagc ccgaggaatc   2400
ggcgtgacgg tcgcaaacca tccggcccgg tacaaatcgg cgcggcgctg ggtgatgacc   2460
tggtggagaa gttgaaggcc gcgcaggccg cccagcggca acgcatcgag gcagaagcac   2520
gccccggtga atcgtggcaa gcggccgctg atcgaatccg caaagaatcc ggcaaccgc   2580
cggcagccgg tgcgccgtcg attaggaagc cgcccaaggg cgacgagcaa ccagattttt   2640
tcgttccgat gctctatgac gtgggcaccc gcgatagtcg cagcatcatg gacgtggccg   2700
ttttccgtct gtcgaagcgt gaccgacgag ctggcgaggt gatccgctac gagcttccag   2760
acgggcacgt agaggtttcc gcagggccgg ccggcatggc cagtgtgtgg gattacgacc   2820
tggtactgat ggcggtttcc catctaaccg aatccatgaa ccgataccgg aagggaagg   2880
gagacaagcc cggccgcgtg ttccgtccac acgttgcgga cgtactcaag ttctgccggc   2940
gagccgatgg cggaaagcag aaagacgacc tggtagaaac ctgcattcgg ttaaacacca   3000
cgcacgttgc catgcagcgt acgaagaagg ccaagaacgg ccgcctggtg acggtatccg   3060
agggtgaagc cttgattagc cgctacaaga tcgtaaagag cgaaaccggg cggccggagt   3120
```

```
acatcgagat cgagctagct gattggatgt accgcgagat cacagaaggc aagaacccgg    3180
acgtgctgac ggttcacccc gattactttt tgatcgatcc cggcatcggc cgttttctct    3240
accgcctggc acgccgcgcc gcaggcaagg cagaagccag atggttgttc aagacgatct    3300
acgaacgcag tggcagcgcc ggagagttca agaagttctg tttcaccgtg cgcaagctga    3360
tcgggtcaaa tgacctgccg gagtacgatt tgaaggagga ggcggggcag gctggcccga    3420
tcctagtcat gcgctaccgc aacctgatcg agggcgaagc atccgccggt tcctaatgta    3480
cggagcagat gctagggcaa attgccctag caggggaaaa aggtcgaaaa ggactctttc    3540
ctgtggatag cacgtacatt gggaacccaa agccgtacat tgggaaccgg aacccgtaca    3600
ttgggaaccc aaagccgtac attgggaacc ggtcacacat gtaagtgact gatataaaag    3660
agaaaaaagg cgattttttcc gcctaaaaact ctttaaaact tattaaaact cttaaaccc     3720 gcctggcctg tgcataactg tctggccagc gcacagccga agagctgcaa aaagcgccta    3780
cccttcggtc gctgcgctcc ctacgccccg ccgcttcgcg tcggcctatc gcggccgctg    3840
gccgctcaaa atggctggc ctacggccag gcaatctacc agggcgcgga caagccgcgc    3900
cgtcgccact cgaccgccgg cgcccacatc aaggcaccct gcctcgcgcg tttcggtgat    3960
gacggtgaaa acctctgaca catgcagctc ccggtgacgg tcacagcttg tctgtaagcg    4020
gatgccggga gcagacaagc ccgtcagggc gcgtcagcgg gtgttggcgg gtgtcggggc    4080
gcagccatga cccagtcacg tagcgatagc ggagtgtata ctggcttaac tatgcggcat    4140
cagagcagat tgtactgaga gtgcaccata tgcggtgtga ataccgcac agatgcgtaa     4200 ggagaaaata ccgcatcagg cgctcttccg cttcctcgct cactgactcg ctgcgctcgg    4260
tcgttcggct gcggcgagcg gtatcagctc actcaaaggc ggtaatacgg ttatccacag    4320
aatcagggga taacgcagga aagaacatgt gagcaaaagg ccagcaaaag gccaggaacc    4380
gtaaaaaggc cgcgttgctg gcgttttttcc ataggctccg ccccccctgac gagcatcaca    4440 aaaatcgacg ctcaagtcag aggtggcgaa acccgacagg actataaaga taccaggcgt    4500
ttccccctgg aagctccctc gtgcgctctc ctgttccgac cctgccgctt accggatacc    4560
tgtccgcctt tctcccttcg ggaagcgtgg cgctttctca tagctcacgc tgtaggtatc    4620
tcagttcggt gtaggtcgtt cgctccaagc tgggctgtgt gcacgaaccc cccgttcagc    4680
ccgaccgctg cgccttatcc ggtaactatc gtcttgagtc aacccggta agacacgact    4740 tatcgccact ggcagcagcc actggtaaca ggattagcag agcgaggtat gtaggcggtg    4800
ctacagagtt cttgaagtgg tggcctaact acggctacac tagaaggaca gtatttggta    4860
tctgcgctct gctgaagcca gttaccttcg gaaaaagagt tggtagctct tgatccggca    4920
aacaaaccac cgctggtagc ggtggttttt tgtttgcaa gcagcagatt acgcgcagaa    4980 aaaaggatc tcaagaagat cctttgatct tttctacggg gtctgacgct cagtggaacg    5040
aaaactcacg ttaagggatt ttggtcatgc attctaggtg attagaaaaa ctcatcgagc    5100
atcaaatgaa actgcaattt attcatatca ggattatcaa taccatattt ttgaaaaagc    5160
cgtttctgta atgaaggaga aaactcaccg aggcagttcc ataggatggc aagatcctgg    5220
tatcggtctg cgattccgac tcgtccaaca tcaatacaac ctattaattt cccctcgtca    5280
aaaataaggt tatcaagtga aaatcacca tgagtgacga ctgaatccgg tgagaatggc     5340
aaaagtttat gcatttcttt ccagacttgt tcaacaggcc agccattacg ctcgtcatca    5400
aaatcactcg catcaaccaa accgttattc attcgtgatt gcgcctgagc gagtcgaaat    5460
```

```
acgcgatcgc tgttaaaagg acaattacaa acaggaatcg aatgcaaccg gcgcaggaac    5520
actgccagcg catcaacaat attttcacct gaatcaggat attcttctaa tacctggaat    5580
gctgttttcc ctgggatcgc agtggtgagt aaccatgcat catcaggagt acggataaaa    5640
tgcttgatgg tcggaagagg cataaattcc gtcagccagt ttagtctgac catctcatct    5700
gtaacatcat tggcaacgct acctttgcca tgtttcagaa acaactctgg cgcatcgggc    5760
ttcccataca atcggtagat tgtcgcacct gattgcccga cattatcgcg agcccattta    5820
tacccatata aatcagcatc catgttggaa tttaatcgcg gccttgagca agacgtttcc    5880
cgttgaatat ggctcataac agaacttatt atttccttcc tcttttctac agtatttaaa    5940
gatacoccaa gaagctaatt ataacaagac gaactccaat tcactgttcc ttgcattcta    6000
aaaccttaaa taccagaaaa cagcttttc aaagttgttt tcaaagttgg cgtataacat     6060
agtatcgacg gagccgattt tgaaaccgcg gtgatcacag gcagcaacgc tctgtcatcg    6120
ttacaatcaa catgctaccc tccgcgagat catccgtgtt tcaaaccgg cagcttagtt     6180
gccgttcttc cgaatagcat cggtaacatg agcaaagtct gccgccttac aacggctctc    6240
ccgctgacgc cgtcccggac tgatgggctg cctgtatcga gtggtgattt tgtgccgagc    6300
tgccggtcgg ggagctgttg gctggctggt ggcaggatat attgtggtgt aaacataacg    6360
aattcgtctc aggagagcgt cgatctagta acatagatga caccgcgcgc gataatttat    6420
cctagtttgc gcgctatatt ttgttttcta tcgcgtatta aatgtataat tgcgggactc    6480
taatcataaa aacccatctc ataaataacg tcatgcatta catgttaatt attacatgct    6540
taacgtaatt caacagaaat tatatgataa tcatcgcaag accggcaaca ggattcaatc    6600
ttaagaaact ttattgccaa atgtttgaac gatctgcttc gacgcactcc ttctttactc    6660
caccatctcg tccttattga aaacgtgggt agcaccaaaa cgaatcaagt cgctggaact    6720
gaagttacca atcacgctgg atgatttgcc agttggatta atcttgcctt tccccgcatg    6780
aataatattg atgaatgcat gcgtgagggg tagttcgatg ttggcaatag ctgcaattgc    6840
cgcgacatcc tccaacgagc ataattcttc agaaaaatag cgatgttcca tgttgtcagg    6900
gcatgcatga tgcacgttat gaggtgacgg tgctaggcag tattccctca aagtttcata    6960
gtcagtatca tattcatcat tgcattcctg caagagagaa ttgagacgca atccacacgc    7020
tgcggcaacc ttccggcgtt cgtggtctat ttgctcttgg acgttgcaaa cgtaagtgtt    7080
ggatcggggt gggcgaagaa ctccagcatg agatccccgc gctggaggat catccagccg    7140
gcgtcccgga aaacgattcc gaagcccaac ctttcataga aggcggcggt ggaatcgaaa    7200
tctcgtgatg gcaggttggg cgtcgcttgg tcggtcattt cgaaccccag agtccgctc    7260
agaagaactc gtcaagaagg cgatagaagg cgatgcgctg cgaatcggga gcggcgatac    7320
cgtaaagcac gaggaagcgg tcagcccatt cgccgccaag ctcttcagca atatcacggg    7380
tagccaacgc tatgtcctga tagcggtccg ccacacccag ccggccacag tcgatgaatc    7440
cagaaaagcg gccattttcc accatgatat tcggcaagca ggcatcgcca tgggtcacga    7500
cgagatcctc gccgtcgggc atgcgcgcct tgagcctggc gaacagttcg gctggcgcga    7560
gcccctgatg ctcttcgtcc agatcatcct gatcgacaag accggcttcc atccgagtac    7620
gtgctcgctc gatgcgatgt ttcgcttggt ggtcgaatgg gcaggtagcc ggatcaagcg    7680
tatgcagccg ccgcattgca tcagccatga tggatacttt ctcggcagga gcaaggtgag    7740
atgacaggag atcctgcccc ggcacttcgc ccaatagcag ccagtccctt cccgcttcag    7800
tgacaacgtc gagcacagct gcgcaaggaa cgcccgtcgt ggccagccac gatagccgcg    7860
```

```
ctgcctcgtc ctgcagttca ttcagggcac cggacaggtc ggtcttgaca aaaagaaccg   7920
ggcgcccctg cgctgacagc cggaacacgg cggcatcaga gcagccgatt gtctgttgtg   7980
cccagtcata gccgaatagc ctctccaccc aagcggccgg agaacctgcc cggatccggg   8040
cggaaatagg taaagaagtt gcggataagg taattgccat tgcagattat ttggattgag   8100
agtgaatatg agactctaat tggataccga ggggaattta tggaacgtca gtggagcatt   8160
tttgacaaga aatatttgct agctgatagt gaccttaggc gacttttgaa cgcgcaataa   8220
tggtttctga cgtatgtgct tagctcatta aactccagaa acccctccgt caggagacta   8280
gagccaagct gatctccttt gccccggaga tcaccatgga cgactttctc tatctctacg   8340
atctaggaag aaagttcgac ggagaaggtg acgataccat gttcaccacc gataatgaga   8400
agattagcct cttcaatttc agaaagaatg ctgacccaca gatggttaga gaggcctacg   8460
cggcaggtct gatcaagacg atctacccga gtaataatct ccaggagatc aaataccttc   8520
ccaagaaggt taaagatgca gtcaaaagat tcaggactaa ctgcatcaag aacacagaga   8580
aagatatatt tctcaagatc agaagtacta ttccagtatg gacgattcaa ggcttgcttc   8640
ataaaccaag gcaagtaata gagattggag tctctaagaa agtagttcct actgaatcaa   8700
aggccatgga gtcaaaaatt cagatcgagg atctaacaga actcgccgtg aagactggcg   8760
aacagttcat acagagtctt ttacgactca atgacaagaa gaaaatcttc gtcaacatgg   8820
tggagcacga cactctcgtc tactccaaga atatcaaaga tacagtctca gaagaccaaa   8880
gggctattga gacttttcaa caaagggtaa tatcggaaaa cctcctcgga ttccattgcc   8940
cagctatctg tcacttcatc aaaaggacag tagaaaagga aggtggcacc tacaaatgcc   9000
atcattgcga taaggaaaag gctatcgttc aagatgcctc tgccgacagt ggtcccaaag   9060
atggaccccc acccacgagg agcatcgtgg aaaaagaaga cgttccaacc acgtcttcaa   9120
agcaagtgga ttgatgtgat atctccactg acgtaaggga tgacgcacaa tcccactatc   9180
cttcgcaaga cccttcctct atataaggaa gttcatttca tttggagagg actccggtat   9240
ttttacaaca ataccacaac aaaacaaaca acaaacaaca ttacaattta ctattctagt   9300
cgaaatgaaa atgatgaatg gtgaagatgc taatgatcaa atgatcaaag aaagcttctt   9360
cataacacat ggaaacccaa tattaacagt agaagacaca catccattaa gacctttctt   9420
tgaaacttgg agagagaaaa tcttttctaa gaaacctaag gcaattctta ttatttctgg   9480
tcattgggaa actgttaaac ctactgttaa tgctgtccat atcaatgata ctatccatga   9540
ttttgatgac tatcctgctg ctatgtacca gttcaagtat ccagctcctg gggaaccaga   9600
attggcaaga aaagtagagg aaattctgaa aaaatcgggt ttcgaaacgg cggaaactga   9660
tcaaaaacgt gggcttgatc atggtgcatg ggtacctcta atgctaatgt atcctgaggc   9720
tgatatacca gtatgtcagc tctcagttca gccgcattta gatggaacat accattacaa   9780
cttaggacga gcattggctc ccttgaaaaa cgacggcgta ttaatcattg gttcaggaag   9840
tgcaactcac cctttggatg aaactcctca ttattttgat ggagttgcac cttgggcagc   9900
tgcctttgat tcatggcttc gtaaagctct cattaatgga aggtttgaag aagtgaatat   9960
atatgaaagc aaagcaccaa attggaaatt agcacatcct ttcccagaac atttttatcc  10020
attgcatgtt gttcttggcg ctgctggtga aaaatggaag gcagagctta ttcatagcag  10080
ttgggatcat ggcaccttgt gtcatggctc ctacaagttc acttcagcct aggcttggaa  10140
tggatcttcg atcccgatcg ttcaaacatt tggcaataaa gtttcttaag attgaatcct  10200
```

```
gttgccggtc ttgcgacgat tatcatataa tttctgttga attacgttaa gcatgtaata    10260
attaacatgt aatgcatgac gttatttatg agatgggttt ttatgattag agtcccgcaa    10320
ttatacattt aatacgcgat agaaaacaaa atatagcgcg caaactagga taaattatcg    10380
cgcdcggtgt catctatgtt actagatcgg gaattgccaa gctaattctt gaagacgaaa    10440
gggcctcgtg atacgcctat ttttataggt taatgtcatg ataataatgg tttcttagac    10500
gtcaggtggc acttttcggg gaaatgtgcg cggaacccct atttgtttat ttttctaaat    10560
acattcaaat atgtatccgc tcatgagaca ataaccctga taaatgcttc aataatggga    10620
ccgactcgcg ctgtcaggag actagagcca agctgatctc ctttgccccg gagatcacca    10680
tggacgactt tctctatctc tacgatctag gaagaaagtt cgacggagaa ggtgacgata    10740
ccatgttcac caccgataat gagaagatta gcctcttcaa tttcagaaag aatgctgacc    10800
cacagatggt tagagaggcc tacgcggcag gtctgatcaa gacgatctac ccgagtaata    10860
atctccagga gatcaaatac cttcccaaga aggttaaaga tgcagtcaaa agattcagga    10920
ctaactgcat caagaacaca gagaaagata tatttctcaa gatcagaagt actattccag    10980
tatggacgat tcaaggcttg cttcataaac caaggcaagt aatagagatt ggagtctcta    11040
agaaagtagt tcctactgaa tcaaaggcca tggagtcaaa aattcagatc gaggatctaa    11100
cagaactcgc cgtgaagact ggcgaacagt tcatacagag tcttttacga ctcaatgaca    11160
agaagaaaat cttcgtcaac atggtggagc acgacactct cgtctactcc aagaatatca    11220
aagatacagt ctcagaagac caaagggcta ttgagacttt tcaacaaagg gtaatatcgg    11280
gaaacctcct cggattccat tgcccagcta tctgtcactt catcaaaagg acagtagaaa    11340
aggaaggtgg cacctacaaa tgccatcatt gcgataaagg aaaggctatc gttcaagatg    11400
cctctgccga cagtggtccc aaagatggac ccccacccac gaggagcatc gtggaaaaag    11460
aagacgttcc aaccacgtct tcaaagcaag tggattgatg tgatatctcc actgacgtaa    11520
gggatgacgc acaatcccac tatccttcgc aagacccttc ctctatataa ggaagttcat    11580
ttcatttgga gaggactccg gtattttac aacaatacca caacaaaaca acaacaaac    11640 aacattacaa tttactattc tagtcgaaat ggatcatgca acattagcaa tgatactagc    11700
catttggttc atttctttc atttcataaa attactttt agccaacaaa ctaccaaact    11760
tcttcctcct ggtccaaaac cattgccaat aattggtaac atcttagaag ttggtaaaaa    11820
accccatcgt tcatttgcta atcttgctaa aattcacggc cctttaatat cgttacgtct    11880
aggaagtgta acaactattg ttgtatcatc agcagatgta gctaaagaaa tgttcttaaa    11940
aaaagaccac cctctttcta accgtactat tcctaattct gtcacggccg gtgaccacca    12000
taaactcacc atgtcgtggt tgcccgtttc gccgaaatgg cggaattttc gtaagattac    12060
agccgtccat ttgctttctc ctcaaagact tgatgcttgc caaacctttc gccatgccaa    12120
ggtgcaacag ctttatgaat atgtacaaga atgtgcacaa aaaggccaag ctgttgatat    12180
tggcaaagct gcatttacta cctcccttaa tttgttatct aaactattct tttcagtgga    12240
attagcccac cataaatcac acacttctca agagtttaag gaactaatat ggaacattat    12300
ggaagatatt gggaaaccta attatgctga ttattttcct attttaggct gtgttgatcc    12360
atcaggtatt cgtcgaagat tagcatgtag ttttgacaag ttgattgcag tttttcaggg    12420
tataatatgt gaaaggcttg cgcctgattc ttcaactaca acaacaacga cgactgatga    12480
tgtgctagac gttcttcttc agctcttcaa acaaaatgag ctcactatgg gcgagattaa    12540
ccatttgctc gtcgacattt ttgatgctgg aacagacact acatcaagta cttttgagtg    12600
```

```
ggtcatgaca gagttaatta ggaatcctga aatgatggaa aaggctcaag aagaaattaa   12660
gcaagtattg ggcaaagata acaaattca ggaatcagac attattaacc taccttactt   12720
acaagccatt atcaaagaaa ctttgcgact acatccacca actgtatttc ttttgcctcg   12780
taaagccgac actgatgttg aactatatgg ttatattgtg cctaaagatg cacaaatact   12840
tgttaactta tgggctattg aagagatcc taatgcatgg caaaatgctg atattttttc   12900
gcccgaaaga tttatagggt gtgaaaytga tgtcaaagga agagattttg gactcttacc   12960
ttttggagcc ggaagaagga tatgtcctgg gatgaatttg gccattagaa tgttaacttt   13020
gatgctagct actttacttc aattcttcaa ttggaagctt gaaggagaca taagtccaaa   13080
agacttagac atggatgaga aatttgggat tgcgttacaa aagacaaagc ctttaaaact   13140
tattccaata cctaggtatt gataataagc ttgctctcaa gatcaaaggc ttaaaaagct   13200
ggggttttat gaatgggatc aaagtttctt ttttttcttt atatttgctt ctccatttgt   13260
ttgtttcatt tcccttttg ttttcgtttc tatgatgcac ttgtgtgtga caaactctct   13320 gggttttttac ttacgtctgc gtttcaaaaa aaaaaaccgc tttcgttttg cgttttagtc   13380
ccattgtttt gtagctctga gtgatcgaat tgatgcctct ttattccttt tgttccctat   13440
aatttctttc aaaactcaga agaaaaacct tgaaactctt tgcaatgtta atataagtat   13500
tgtataagat ttttattgat ttggttatta gtcttacttt tgctacctcc atcttcactt   13560
ggaactgata ttctgaatag ttaaagcgtt acatgtcttc cattcacaaa tgaacttaaa   13620
ctagcacaaa gtcagatatt ttaagatcgc accattttat ataaccccaa tcgtcaattc   13680
tactgtttca agttttacac caaaacaatt acgaggtgta tctattcgtt actcttttcg   13740
cttattaatc cttttacatg atgcaaaata taacaaatta atttcaaatt gtcctgcaca   13800
tttggtttat acatcttgat tccaaaaagt cgctgtcagg aggtcgacga gtcagtaata   13860
aacggcgtca aagtggttgc agccggcaca cacgagtcgt gtttatcaac tcaaagcaca   13920 aatactttc ctcaacctaa aaataaggca attagccaaa acaactttg cgtgtaaaca   13980 acgctcaata cacgtgtcat tttattatta gctattgctt caccgcctta gctttctcgt   14040
gacctagtcg tcctcgtctt ttcttcttct tcttctataa acaatacccc aaagagctct   14100
tcttcttcac aattcagatt tcaatttctc aaaatcttaa aaactttctc tcaattctct   14160
ctaccgtgat caaggtaaat ttctgtgttc cttattctct caaaatcttc gattttgttt   14220
tcgttcgatc ccaatttcgt atatgttctt tggtttagat tctgttaatc ttagatcgaa   14280
gacgattttc tgggtttgat cgttagatat catcttaatt ctcgattagg gtttcataga   14340
tatcatccga tttgttcaaa taatttgagt tttgtcgaat aattactctt cgatttgtga   14400
tttctatcta gatctggtgt tagttttctag tttgtgcgat cgaatttgtc gattaatctg   14460 agttttctg attaacagaa tgaccgccat taaaatgaac accaatggtg aaggtgaaac   14520
acaacatata ctaatgatac ctttcatggc gcaagggcat ttacgtcctt tccttgagct   14580
tgctatgttt ctatataaac gaagtcattt tatcattact cttcttacta ccccgctcaa   14640
tgcgggtttc ctacgacatc tccttcacca ccatagctat tctagctcgg ggatcagaat   14700
tgtcgagtta ccttttcaact caaccaatca tggtcttcca cctggcattg aaaacactga   14760
taaacttaca ctcccacttg tagtatcact ttttcattca accatttctc ttgaccctca   14820
ccttagagat tatatttccc gccatttctc ccctgcgcgc cctcctctgt gtgtcataca   14880
tgatgtgttc cttggttggg ttgatcaagt tgctaaagac gtgggctcaa ctggtgttgt   14940
```

```
ttttactacg gtggcgcgt atggtacaag cgcatatgtg tccatttgga atgatctgcc    15000
tcaccagaat tactctgatg atcaagagtt tccgcttcct ggtttccgg agaatcataa    15060 attccgacgt tctcaacttc atcggtttct gaggtatgcc gatggatcag atgattggtc    15120
gaaatatttc caaccgcaat tgaggcaatc aatgaagagt tttggatggc tatgtaattc    15180
agttgaggaa atcgaaacac ttgggtttag tatcctcagg aactcacta aactacccat     15240 ttggggtatt ggaccgttga tagcttcacc tgtacaacat tcatcatctg ataataacag    15300
tactggtgcc gagtttgttc aatggttgag cttgaaagaa ccagattctg tattatacat    15360
ctcatttgga tcacagaaca caatttcacc aacccagatg atggaactag cagccggttt    15420
ggagtcaagt gagaagccgt ttttgtgggt gattcgagca ccatttgggt tcgatatcaa    15480
tgaggaaatg agrccagaat ggctaccaga gggattcgag gagcgaatga aggtgaaaaa    15540
acaaggaaag ttggtgtata agttgggacc acagttggag atacttaacc atgagtcaat    15600
cggagggttc ttaactcatt gtgggtggaa ttcgatcctt gagtcacttc gagaaggtgt    15660
gcctatgtta gggtggccat ggcagccga acaagcttat aatttgaagt atttggagga    15720
cgaaatgggg gttgcagtcg agttagcgag gggattggaa ggagagataa gtaaagagaa    15780
agtgaagaga attgtggaga tgattttaga gagaaatgaa ggaagtaaag gatgggaaat    15840
gaaaaataga gcagtagaaa tggggaagaa acttaaagac gctgtcaatg aggagaagga    15900
actgaagggt tcttctgtta aggcaataga tgatttctta gatgcggtca tgcaagctaa    15960
gttggaacct tctcttcaat aagcttcggc catgctagag tccgcaaaaa tcaccagtct    16020
ctctctacaa atctatctct ctctattttt ctccagaata atgtgtgagt agttcccaga    16080
taagggaatt agggttctta tagggtttcg ctcatgtgtt gagcatataa gaaaccctta    16140
gtatgtattt gtatttgtaa aatacttcta tcaataaaat ttctaattcc taaaaccaaa    16200
atccagtgac ct                                                        16212

<210> SEQ ID NO 20
<211> LENGTH: 16919
<212> TYPE: DNA
<213> ORGANISM: Artificial Sequence
<220> FEATURE:
<223> OTHER INFORMATION: pX11(E8)

<400> SEQUENCE: 20
ggagggtttt ctggagttta atgagctaag cacatacgtc agaaaccatt attgcgcgtt      60
caaaagtcgc ctaaggtcac tatcagctag caaatatttc ttgtcaaaaa tgctccactg     120
acgttccata aattcccctc ggtatccaat tagagtctca tattcactct caatccaaat     180
aatctgcaat ggcaattacc ttatccgcaa cttctttacc tatttccgcc cggatccggg     240
caggttctcc ggccgcttgg gtggagaggc tattcggcta tgactgggca acagacaa       300 tcggctgctc tgatgccgcc gtgttccggc tgtcagcgca ggggcgcccg gttcttttttg    360 tcaagaccga cctgtccggt gccctgaatg aactgcagga cgaggcagcg cggctatcgt     420
ggctggccac gacgggcgtt ccttgcgcag ctgtgctcga cgttgtcact gaagcgggaa     480
gggactggct gctattgggc gaagtgccgg gcaggatct cctgtcatct caccttgctc      540
ctgccgagaa agtatccatc atggctgatg caatgcggcg gctgcatacg cttgatccgg     600
ctacctgccc attcgaccac caagcgaaac atcgcatcga gcgagcacgt actcggatgg     660
aagccggtct tgtcgatcag gatgatctgg acgaagagca tcaggggctc gcgccagccg     720
aactgttcgc caggctcaag gcgcgcatgc ccgacggcga ggatctcgtc gtgacccatg     780
```

```
gcgatgcctg cttgccgaat atcatggtgg aaaatggccg cttttctgga ttcatcgact    840
gtggccggct gggtgtggcg gaccgctatc aggacatagc gttggctacc cgtgatattg    900
ctgaagagct tggcggcgaa tgggctgacc gcttcctcgt gctttacggt atcgccgctc    960
ccgattcgca gcgcatcgcc ttctatcgcc ttcttgacga gttcttctga gcgggactct   1020
ggggttcgaa atgaccgacc aagcgacgcc caacctgcca tcacgagatt tcgattccac   1080
cgccgccttc tatgaaaggt tgggcttcgg aatcgttttc cgggacgccg gctggatgat   1140
cctccagcgc ggggatctca tgctggagtt cttcgcccac cccgatccaa cacttacgtt   1200
tgcaacgtcc aagagcaaat agaccacgaa cgccggaagg ttgccgcagc gtgtggattg   1260
cgtctcaatt ctctcttgca ggaatgcaat gatgaatatg atactgacta tgaaactttg   1320
agggaatact gcctagcacc gtcacctcat aacgtgcatc atgcatgccc tgacaacatg   1380
gaacatcgct attttctga agaattatgc tcgttggagg atgtcgcggc aattgcagct    1440
attgccaaca tcgaactacc cctcacgcat gcattcatca atattattca tgcggggaaa   1500
ggcaagatta atccaactgg caaatcatcc agcgtgattg gtaacttcag ttccagcgac   1560
ttgattcgtt ttggtgctac ccacgttttc aataaggacg agatggtgga gtaaagaagg   1620
agtgcgtcga agcagatcgt tcaaacattt ggcaataaag tttcttaaga ttgaatcctg   1680
ttgccggtct tgcgatgatt atcatataat ttctgttgaa ttacgttaag catgtaataa   1740
ttaacatgta atgcatgacg ttatttatga gatgggtttt tatgattaga gtcccgcaat   1800
tatacattta atacgcgata gaaaacaaaa tatagcgcgc aaactaggat aaattatcgc   1860
gcgcggtgtc atctatgtta ctagatcgac gctgtcagga gactagagcc aagctgatct   1920
cctttgcccc ggagatcacc atggacgact ttctctatct ctacgatcta ggaagaaagt   1980
tcgacggaga aggtgacgat accatgttca ccaccgataa tgagaagatt agcctcttca   2040
atttcagaaa gaatgctgac ccacagatgg ttagagaggc ctacgcggca ggtctgatca   2100
agacgatcta cccgagtaat aatctccagg agatcaaata ccttcccaag aaggttaaag   2160
atgcagtcaa aagattcagg actaactgca tcaagaacac agagaaagat atatttctca   2220
agatcagaag tactattcca gtatggacga ttcaaggctt gcttcataaa ccaaggcaag   2280
taatagagat tggagtctct aagaaagtag ttcctactga atcaaaggcc atggagtcaa   2340
aaattcagat cgaggatcta acagaactcg ccgtgaagac tggcgaacag ttcatacaga   2400
gtcttttacg actcaatgac aagaagaaaa tcttcgtcaa catggtggag cacgacactc   2460
tcgtctactc caagaatatc aaagatacag tctcagaaga ccaaagggct attgagactt   2520
ttcaacaaag ggtaatatcg ggaaacctcc tcggattcca ttgcccagct atctgtcact   2580
tcatcaaaag acagtagaa aaggaaggtg gcacctacaa atgccatcat tgcgataaag    2640
gaaaggctat cgttcaagat gcctctgccg acagtggtcc caaagatgga cccccaccca   2700
cgaggagcat cgtggaaaaa gaagacgttc caaccacgtc ttcaaagcaa gtggattgat   2760
gtgatatctc cactgacgta agggatgacg cacaatccca ctatccttcg caagacccct   2820
cctctatata aggaagttca tttcatttgg agaggactcc ggtattttta caacaatacc   2880
acaacaaaac aaacaacaaa caacattaca atttactatt ctagtcgaaa tgaaaatgat   2940
gaatggtgaa gatgctaatg atcaaatgat caaagaaagc ttcttcataa cacatggaaa   3000
cccaatatta acagtagaag acacacatcc attaagacct ttctttgaaa cttggagaga   3060
gaaaatcttt tctaagaaac ctaaggcaat tcttattatt tctggtcatt gggaaactgt   3120
```

```
taaacctact gttaatgctg tccatatcaa tgatactatc catgattttg atgactatcc    3180
tgctgctatg taccagttca agtatccagc tcctggggaa ccagaattgg caagaaaagt    3240
agaggaaatt ctgaaaaaat cgggtttcga acggcggaa  actgatcaaa acgtgggct    3300 tgatcatggt gcatgggtac ctctaatgct aatgtatcct gaggctgata taccagtatg    3360
tcagctctca gttcagccgc atttagatgg aacataccat tacaacttag gacgagcatt    3420
ggctcccttg aaaacgacg  gcgtattaat cattggttca ggaagtgcaa ctcacccttt    3480
ggatgaaact cctcattatt ttgatggagt tgcaccttgg gcagctgcct ttgattcatg    3540
gcttcgtaaa gctctcatta atggaaggtt tgaagaagtg aatatatatg aaagcaaagc    3600
accaaattgg aaattagcac atcctttccc agaacatttt tatccattgc atgttgttct    3660
tggcgctgct ggtgaaaaat ggaaggcaga gcttattcat agcagttggg atcatggcac    3720
cttgtgtcat ggctcctaca agttcacttc agcctaggct tggaatggat cttcgatccc    3780
gatcgttcaa acatttggca ataaagtttc ttaagattga atcctgttgc cggtcttgcg    3840
acgattatca tataatttct gttgaattac gttaagcatg taataattaa catgtaatgc    3900
atgacgttat ttatgagatg ggttttatg  attagagtcc cgcaattata catttaatac    3960
gcgatagaaa acaaaatata gcgcgcaaac taggataaat tatcgcgcdc ggtgtcatct    4020
atgttactag atcgggaatt gccaagctaa ttcttgaaga cgaaagggcc tcgtgatacg    4080 cctatttta  taggttaatg tcatgataat aatggtttct tagacgtcag gtggcacttt    4140
tcggggaaat gtgcgcggaa cccctatttg tttattttc  taaatacatt caaatatgta    4200
tccgctcatg agacaataac cctgataaat gcttcaataa tgggaccgac tcgcgctgtc    4260
aggaggaatt cattttttgac atccctaatg atattgttca cgtaattaag ttttgtggaa    4320
gtgagagagt ccaattttga taagaaaaga gtcagaaaac gtaatatttt aaaagtctaa    4380
atctttctac aaataagagc aaatttattt attttttaat ccaataaata ttaatggagg    4440
acaaattcaa ttcacttggt tgtaaaataa acttaaacca ataaccaaag aactaataaa    4500
tctgaagtgg aattattaag gataatgtac atagacaatg aagaaataat aggttcgatg    4560
aattaataat aattaaggat gttacaatca tcatgtgcca agtatataca caatattcta    4620
tgggatttat aatttcgtta cttcacttaa cttttgcgta aataaaacga attatctgat    4680
attttataat aaaacagtta attaagaacc atcatttta  acaacataga tatattattt    4740
ctaatagttt aatgatactt ttaaatcttt taaatttat  gtttcttta  gaaaataaaa    4800 attcaaaaaa attaaatata tttacaaaaa ctacaatcaa acacaacttc atatattaaa    4860
agcaaaatat attttgaaaa tttcaagtgt cctaacaaat aagacaagag gaaaatgtac    4920
gatgagagac ataagagaa  ctaataattg aggagtccta taatatataa taaagtttat    4980
tagtaaactt aattattaag gactcctaaa atatatgata ggagaaaatg aatggtgaga    5040
gatattggaa aacttaataa ttaaggatat taaaatatat ggtaaaagat aggcaaagta    5100
tccattatcc cctttaact  tgaagtctac ctaggcgcat gtgaaaggtt gatttttgt     5160 cacgtcatat agctataacg taaaaaaaga aagtaaaatt tttaattttt tttaatatat    5220
gacatatttt aaacgaaata taggacaaaa tgtaaatgaa tagtaaagga aacaaagatt    5280
aatacttact ttgtaagaat ttaagataaa tttaaaattt aatagatcaa ctttacgtct    5340
agaaagaccc atatctagaa ggaatttcac gaaatcggcc cttattcaaa ataactttt     5400 aaataatgaa ttttaaattt taagaaataa tatccaatga ataaatgaca tgtagcattt    5460
tacctaaata tttcaactat tttaatccaa tattaatttg ttttattccc aacaatagaa    5520
```

```
agtcttgtgc agacatttaa tctgactttt ccagtactaa atattaattt tctgaagatt    5580
ttcgggttta gtccacaagt tttagtgaga agttttgctc aaaattttag gtgagaaggt    5640
ttgatattta tcttttgtta aattaattta tctaggtgac tattatttat ttaagtagaa    5700
attcatatca ttacttttgc caacttgtag tcataatagg agtaggtgta tatgatgaag    5760
gaataaacaa gttcagtgaa gtgattaaaa taaaatataa tttaggtgta catcaaataa    5820
aaaccttaaa gtttagaaag gcaccgaata attttgcata gaagatatta gtaaatttat    5880
aaaaataaaa gaaatgtagt tgtcaagttg tcttcttttt tttggataaa aatagcagtt    5940
ggcttatgtc attcttttac aacctccatg ccacttgtcc aattgttgac acttaactaa    6000
ttagtttgat tcatgtatga atactaaata attttttagg actgactcaa atattttat     6060 attatcatag taatatttat ctaattttta ggaccactta ttactaaata ataaattaac    6120
tactactata ttattgttgt gaaacaacaa cgttttggtt gttatgatga acactatatc    6180
agtatgaaaa attcaaaacg attagtataa attatattga aaatttgata tttttctatt    6240
cttaatcaga cgtattgggt ttcatatttt aaaaagggac taaacttaga agagaagttt    6300
gtttgaaact acttttgtct cttcttgtt cccatttctc tcttagattt caaaaagtga    6360
actactttat ctctttcttt gttcacattt tattttattc tattataaat atggcatcct    6420
catattgaga tttttaatgg atcatgcaac attagcaatg atactagcca tttggttcat    6480 ttctttcat ttcataaaat tacttttag ccaacaaact accaaacttc ttcctcctgg     6540
tccaaaacca ttgccaataa ttggtaacat cttagaagtt ggtaaaaaac cccatcgttc    6600
atttgctaat cttgctaaaa ttcacggccc tttaatatcg ttacgtctag gaagtgtaac    6660
aactattgtt gtatcatcag cagatgtagc taaagaaatg ttcttaaaaa aagaccaccc    6720
tctttctaac cgtactattc ctaattctgt cacggccggt gaccaccata aactcaccat    6780
gtcgtggttg cccgtttcgc cgaaatggcg gaattttcgt aagattacag ccgtccattt    6840
gctttctcct caaagacttg atgcttgcca aacctttcgc catgccaagg tgcaacagct    6900
ttatgaatat gtacaagaat gtgcacaaaa aggccaagct gttgatattg gcaaagctgc    6960
atttactacc tcccttaatt tgttatctaa actattcttt tcagtggaat tagcccacca    7020
taaatcacac acttctcaag agtttaagga actaatatgg aacattatgg aagatattgg    7080
gaaacctaat tatgctgatt atttttcctat tttaggctgt gttgatccat caggtattcg    7140
tcgaagatta gcatgtagtt ttgacaagtt gattgcagtt tttcagggta taatatgtga    7200
aaggcttgcg cctgattctt caactacaac aacaacgacg actgatgatg tgctagacgt    7260
tcttcttcag ctcttcaaac aaaatgagct cactatgggc gagattaacc atttgctcgt    7320
cgacattttt gatgctggaa cagacactac atcaagtact tttgagtggg tcatgacaga    7380
gttaattagg aatcctgaaa tgatggaaaa ggctcaagaa gaaattaagc aagtattggg    7440
caaagataaa caaattcagg aatcagacat tattaaccta ccttacttac aagccattat    7500
caaagaaact ttgcgactac atccaccaac tgtatttctt ttgcctcgta aagccgacac    7560
tgatgttgaa ctatatggtt atattgtgcc taaagatgca caaatacttg ttaacttatg    7620
ggctattgga agagatccta atgcatgca aatgctgat atttttcgc ccgaaagatt      7680 tatagggtgt gaaaytgatg tcaaaggaag agattttgga ctcttacctt ttggagccgg    7740
aagaaggata tgtcctggga tgaatttggc cattagaatg ttaactttga tgctagctac    7800
tttacttcaa ttcttcaatt ggaagcttga aggagacata agtccaaaag acttagacat    7860
```

```
ggatgagaaa tttgggattg cgttacaaaa gacaaagcct ttaaaactta ttccaatacc   7920
taggtattga taataagctt cggccatgct agagtccgca aaaatcacca gtctctctct   7980
acaaatctat ctctctctat ttttctccag aataatgtgt gagtagttcc cagataaggg   8040
aattagggtt cttataggg ttcgctcatg tgttgagcat ataagaaacc cttagtatgt    8100
atttgtattt gtaaaatact tctatcaata aaatttctaa ttcctaaaac caaaatccag   8160
tgacctcgct gtcaggaggt cgacgagtca gtaataaacg gcgtcaaagt ggttgcagcc   8220
ggcacacacg agtcgtgttt atcaactcaa agcacaaata cttttcctca acctaaaaat   8280
aaggcaatta gccaaaaaca actttgcgtg taaacaacgc tcaatacacg tgtcattta    8340 ttattagcta ttgcttcacc gccttagctt tctcgtgacc tagtcgtcct cgtcttttct   8400
tcttcttctt ctataaaaca atacccaaag agctcttctt cttcacaatt cagatttcaa   8460
tttctcaaaa tcttaaaaac tttctctcaa ttctctctac cgtgatcaag gtaaatttct   8520
gtgttcctta ttctctcaaa atcttcgatt ttgttttcgt tcgatcccaa tttcgtatat   8580
gttctttggt ttagattctg ttaatcttag atcgaagacg attttctggg tttgatcgtt   8640
agatatcatc ttaattctcg attagggttt catagatatc atccgatttg ttcaaataat   8700
ttgagttttg tcgaataatt actcttcgat ttgtgatttc tatctagatc tggtgttagt   8760
ttctagtttg tgcgatcgaa tttgtcgatt aatctgagtt tttctgatta acagaatgac   8820
cgccattaaa atgaacacca atggtgaagg tgaaacacaa catatactaa tgatacctt    8880 catggcgcaa gggcatttac gtcctttcct tgagcttgct atgtttctat ataaacgaag   8940
tcattttatc attactcttc ttactacccc gctcaatgcg ggtttcctac gacatctcct   9000
tcaccaccat agctattcta gctcggggat cagaattgtc gagttacctt tcaactcaac   9060
caatcatggt cttccacctg gcattgaaaa cactgataaa cttacactcc cacttgtagt   9120 atcactttt cattcaacca tttctcttga ccctcacctt agagattata tttcccgcca    9180
tttctcccct gcgcgccctc ctctgtgtgt catacatgat gtgttccttg gttgggttga   9240
tcaagttgct aaagacgtgg gctcaactgg tgttgttttt actacggtg gcgcgtatgg    9300 tacaagcgca tatgtgtcca tttggaatga tctgcctcac cagaattact ctgatgatca   9360
agagtttccg cttcctggtt tcccggagaa tcataaattc cgacgttctc aacttcatcg   9420
gtttctgagg tatgccgatg gatcagatga ttggtcgaaa tatttccaac cgcaattgag   9480
gcaatcaatg aagagttttg gatggctatg taattcagtt gaggaaatcg aaacacttgg   9540
gtttagtatc ctcaggaact acactaaact acccatttgg ggtattggac cgttgatagc   9600
ttcacctgta caacattcat catctgataa taacagtact ggtgccgagt ttgttcaatg   9660
gttgagcttg aaagaaccag attctgtatt atacatctca tttggatcac agaacacaat   9720
ttcaccaacc cagatgatgg aactagcagc cggtttggag tcaagtgaga agccgttttt   9780
gtgggtgatt cgagcaccat ttgggttcga tatcaatgag gaaatgagrc cagaatggct   9840
accagaggga ttcgaggagc gaatgaaggt gaaaaaacaa ggaaagttgg tgtataagtt   9900
gggaccacag ttggagatac ttaaccatga gtcaatcgga gggttcttaa ctcattgtgg   9960
gtggaattcg atccttgagt cacttcgaga aggtgtgcct atgttagggt ggccattggc  10020
agccgaacaa gcttataatt tgaagtattt ggaggacgaa atgggggttg cagtcgagtt  10080
agcgagggga ttgaaggag agataagtaa agagaaagtg aagagaattg tggagatgat   10140
tttagagaga aatgaaggaa gtaaaggatg ggaaatgaaa aatagagcag tagaaatggg   10200
gaagaaactt aaagacgctg tcaatgagga gaaggaactg aagggttctt ctgttaaggc   10260
```

```
aatagatgat ttcttagatg cggtcatgca agctaagttg gaaccttctc ttcaataagc    10320
ttcggccatg ctagagtccg caaaaatcac cagtctctct ctacaaatct atctctctct    10380 attttttctcc agaataatgt gtgagtagtt cccagataag ggaattaggg ttcttatagg   10440
gtttcgctca tgtgttgagc atataagaaa cccttagtat gtatttgtat ttgtaaaata   10500
cttctatcaa taaaatttct aattcctaaa accaaaatcc agtgacctcg ctgtcatgag    10560
acgaattctg acaggatata ttggcgggta aacctaagag aaaagagcgt ttattagaat   10620
aatcggatat ttaaaagggc gtgaaaaggt ttatccgttc gtccatttgt atgtgcatgc   10680
caaccacagg gttcccctcg ggatcaaagt actttgatcc aacccctccg ctgctatagt   10740
gcagtcggct tctgacgttc agtgcagccg tcatctgaaa cgacatgtc gcacaagtcc    10800 taagttacgc gacaggctgc cgccctgccc ttttcctggc gttttcttgt cgcgtgtttt    10860
agtcgcataa agtagaatac ttgcgactag aaccggagac attacgccat gaacaagagc    10920
gccgccgctg gcctgctggg ctatgcccgc gtcagcaccg acgaccagga cttgaccaac    10980
caacgggccg aactgcacgc ggccggctgc accaagctgt tttccgagaa gatcaccggc   11040
accaggcgcg accgcccgga gctggccagg atgcttgacc acctacgccc tggcgacgtt   11100
gtgacagtga ccaggctaga ccgcctggcc cgcagcaccc gcgacctact ggacattgcc   11160
gagcgcatcc aggaggccgg cgcgggcctg cgtagcctgg cagagccgtg ggccgacacc    11220
accacgccgg ccggccgcat ggtgttgacc gtgttcgccg gcattgccga gttcgagcgt    11280
tccctaatca tcgaccgcac ccggagcggg cgcgaggccg ccaaggcccg aggcgtgaag   11340
tttggccccc gccctaccct caccccggca cagatcgcgc acgcccgcga gctgatcgac    11400
caggaaggcc gcaccgtgaa agaggcggct gcactgcttg gcgtgcatcg ctcgaccctg    11460
taccgcgcac ttgagcgcag cgaggaagtg acgcccaccg aggccaggcg gcgcggtgcc   11520
ttccgtgagg acgcattgac cgaggccgac gccctggcgg ccgccgagaa tgaacgccaa    11580
gaggaacaag catgaaaccg caccaggacg gccaggacga accgttttc attaccgaag    11640 agatcgaggc ggagatgatc gcggccgggt acgtgttcga gccgcccgcg cacctctcaa    11700
ccgtgcggct gcatgaaatc ctggccggtt tgtctgatgc caagctggcg gcctggccgg    11760
ccagcttggc cgctgaagaa accgagcgcc gccgtctaaa aaggtgatgt gtatttgagt    11820
aaaacagctt gcgtcatgcg gtcgctgcgt atatgatccg atgagtaaat aaacaaatac   11880
gcaaggggaa cgcatgaagg ttatcgctgt acttaaccag aaaggcgggt caggcaagac    11940
gaccatcgga acccatctag cccgcgccct gcaactcgcc ggggccgatg ttctgttagt   12000
cgattccgat ccccagggca gtgcccgcga ttgggcggcc gtgcgggaag atcaaccgct   12060
aaccgttgtc ggcatcgacc gcccgacgat tgaccgcgac gtgaaggcca tcggccggcg    12120
cgacttcgta gtgatcgacg gagcgcccca ggcggcggac ttggctgtgt ccgcgatcaa    12180
ggcagccgac ttcgtgctga ttccggtgca gccaagccct tacgacatat gggccaccgc    12240
cgacctggtg gagctggtta agcagcgcat tgaggtcacg gatggaaggc tacaagcggc   12300
ctttgtcgtg tcgcgggcga tcaaaggcac gcgcatcggc ggtgaggttg ccgaggcgct    12360
ggccgggtac gagctgccca ttcttgagtc ccgtatcacg cagcgcgtga gctacccagg    12420
cactgccgcc gccggcacaa ccgttcttga atcagaaccc gagggcgacg ctgcccgcga    12480
ggtccaggcg ctggccgctg aaattaaatc aaaactcatt tgagttaatg aggtaaagag   12540
aaaatgagca aaagcacaaa cacgctaagt gccggccgtc cgagcgcacg cagcagcaag    12600
```

```
gctgcaacgt tggccagcct ggcagacacg ccagccatga agcgggtcaa ctttcagttg    12660
ccggcggagg atcacaccaa gctgaagatg tacgcggtac gccaaggcaa gaccattacc    12720
gagctgctat ctgaatagat cgcgcagcta ccagagtaaa tgagcaaatg aataaatgag    12780
tagatgaatt ttagcggcta aaggaggcgg catggaaaat caagaacaac caggcaccga    12840
cgccgtggaa tgccccatgt gtggaggaac gggcggttgg ccaggcgtaa gcggctgggt    12900
tgtctgccgg ccctgcaatg gcactggaac ccccaagccc gaggaatcgg cgtgacggtc    12960
gcaaaccatc cggcccggta caaatcggcg cggcgctggg tgatgacctg gtggagaagt    13020
tgaaggccgc gcaggccgcc cagcggcaac gcatcgaggc agaagcacgc cccggtgaat    13080
cgtggcaagc ggccgctgat cgaatccgca aagaatcccg gcaaccgccg gcagccggtg    13140
cgccgtcgat taggaagccg cccaaggggc acgagcaacc agatttttttc gttccgatgc    13200 tctatgacgt gggcacccgc gatagtcgca gcatcatgga cgtggccgtt ttccgtctgt    13260
cgaagcgtga ccgacgagct ggcgaggtga tccgctacga gcttccagac gggcacgtag    13320
aggtttccgc agggccggcc ggcatggcca gtgtgtggga ttacgacctg gtactgatgg    13380
cggtttccca tctaaccgaa tccatgaacc gataccggga agggaaggga gacaagcccg    13440
gccgcgtgtt ccgtccacac gttgcggacg tactcaagtt ctgccggcga gccgatggcg    13500
gaaagcagaa agacgacctg gtagaaacct gcattcggtt aaacaccacg cacgttgcca    13560
tgcagcgtac gaagaaggcc aagaacggcc gcctggtgac ggtatccgag ggtgaagcct    13620
tgattagccg ctacaagatc gtaaagagcg aaaccgggcg gccggagtac atcgagatcg    13680
agctagctga ttggatgtac cgcgagatca cagaaggcaa gaacccggac gtgctgacgg    13740
ttcaccccga ttacttttttg atcgatcccg gcatcggccg ttttctctac cgcctggcac    13800
gccgcgccgc aggcaaggca gaagccagat ggttgttcaa gacgatctac gaacgcagtg    13860
gcagcgccgg agagttcaag aagttctgtt tcaccgtgcg caagctgatc gggtcaaatg    13920
acctgccgga gtacgatttg aaggaggagg cggggcaggc tggcccgatc ctagtcatgc    13980
gctaccgcaa cctgatcgag ggcgaagcat ccgccggttc ctaatgtacg gagcagatgc    14040
tagggcaaat tgccctagca ggggaaaaag gtcgaaaagg actctttcct gtggatagca    14100
cgtacattgg gaacccaaag ccgtacattg ggaaccggaa cccgtacatt gggaacccaa    14160
agccgtacat tgggaaccgg tcacacatgt aagtgactga tataaaagag aaaaaaggcg    14220 attttttccgc ctaaaactct ttaaaactta ttaaaactct taaaaccgc ctggcctgtg    14280 cataactgtc tggccagcgc acagccgaag agctgcaaaa agcgcctacc cttcggtcgc    14340
tgcgctccct acgcccgcc gcttcgcgtc ggcctatcgc ggccgctggc cgctcaaaaa    14400
tggctggcct acggccaggc aatctaccag ggcgcggaca agccgcgccg tcgccactcg    14460
accgccggcg cccacatcaa ggcaccctgc ctcgcgcgtt tcggtgatga cggtgaaaac    14520
ctctgacaca tgcagctccc ggtgacggtc acagcttgtc tgtaagcgga tgccgggagc    14580
agacaagccc gtcagggcgc gtcagcgggt gttggcgggt gtcggggcgc agccatgacc    14640
cagtcacgta gcgatagcgg agtgtatact ggcttaacta tgcggcatca gagcagattg    14700
tactgagagt gcaccatatg cggtgtgaaa taccgcacag atgcgtaagg agaaaatacc    14760
gcatcaggcg ctcttccgct tcctcgctca ctgactcgct gcgctcggtc gttcggctgc    14820
ggcgagcggt atcagctcac tcaaaggcgg taatacggtt atccacagaa tcaggggata    14880
acgcaggaaa gaacatgtga gcaaaaggcc agcaaaaggc caggaaccgt aaaaaggccg    14940
cgttgctggc gttttttccat aggctccgcc cccctgacga gcatcacaaa aatcgacgct    15000
```

```
caagtcagag gtggcgaaac ccgacaggac tataaagata ccaggcgttt ccccctggaa   15060
gctccctcgt gcgctctcct gttccgaccc tgccgcttac cggatacctg tccgcctttc   15120
tcccttcggg aagcgtggcg ctttctcata gctcacgctg taggtatctc agttcggtgt   15180
aggtcgttcg ctccaagctg gctgtgtgc acgaaccccc cgttcagccc gaccgctgcg    15240
ccttatccgg taactatcgt cttgagtcca acccggtaag acacgactta tcgccactgg   15300
cagcagccac tggtaacagg attagcagag cgaggtatgt aggcggtgct acagagttct   15360
tgaagtggtg gcctaactac ggctacacta aaggacagt attggtatc tgcgctctgc     15420 tgaagccagt taccttcgga aaagagttg gtagctcttg atccggcaaa caaccaccg    15480 ctggtagcgg tggttttttt gtttgcaagc agcagattac gcgcagaaaa aaggatctc    15540 aagaagatcc tttgatcttt tctacggggt ctgacgctca gtggaacgaa actcacgtt    15600 aagggatttt ggtcatgcat tctaggtgat tagaaaaact catcgagcat caaatgaaac   15660
tgcaatttat tcatatcagg attatcaata ccatattttt gaaaaagccg tttctgtaat   15720
gaaggagaaa actcaccgag gcagttccat aggatggcaa gatcctggta tcggtctgcg   15780
attccgactc gtccaacatc aatacaacct attaatttcc cctcgtcaaa ataaggtta    15840 tcaagtgaga atcaccatg agtgacgact gaatccggtg agaatggcaa agtttatgc    15900 atttctttcc agacttgttc aacaggccag ccattacgct cgtcatcaaa atcactcgca   15960
tcaaccaaac cgttattcat tcgtgattgc gcctgagcga gtcgaaatac gcgatcgctg   16020
ttaaaaggac aattacaaac aggaatcgaa tgcaaccggc gcaggaacac tgccagcgca   16080
tcaacaatat tttcacctga atcaggatat tcttctaata cctggaatgc tgttttccct   16140
gggatcgcag tggtgagtaa ccatgcatca tcaggagtac ggataaaatg cttgatggtc   16200
ggaagaggca taaattccgt cagccagttt agtctgacca tctcatctgt aacatcattg   16260
gcaacgctac ctttgccatg tttcagaaac aactctggcg catcgggctt cccatacaat   16320
cggtagattg tcgcacctga ttgcccgaca ttatcgcgag cccatttata cccatataaa   16380
tcagcatcca tgttggaatt taatcgcggc cttgagcaag acgtttcccg ttgaatatgg   16440
ctcataacag aacttattat ttccttcctc ttttctacag tatttaaaga tacccccaaga  16500 agctaattat aacaagacga actccaattc actgttcctt gcattctaaa accttaaata   16560
ccagaaaaca gcttttttcaa agttgttttc aaagttggcg tataacatag tatcgacgga   16620
gccgattttg aaaccgcggt gatcacaggc agcaacgctc tgtcatcgtt acaatcaaca   16680
tgctaccctc cgcgagatca tccgtgtttc aaacccggca gcttagttgc cgttcttccg   16740
aatagcatcg gtaacatgag caaagtctgc cgccttacaa cggctctccc gctgacgccg   16800
tcccggactg atgggctgcc tgtatcgagt ggtgattttg tgccgagctg ccggtcgggg   16860
agctgttggc tggctggtgg caggatatat tgtggtgtaa acataacgaa ttcgtctca   16919
```

<210> SEQ ID NO 21
<211> LENGTH: 15191
<212> TYPE: DNA
<213> ORGANISM: Artificial Sequence
<220> FEATURE:
<223> OTHER INFORMATION: pX11(CHS)

<400> SEQUENCE: 21

```
cgctgtcatg agacgaattc tgacaggata tattggcggg taaacctaag agaaaagagc    60
gtttattaga ataatcggat atttaaaagg gcgtgaaaag gtttatccgt tcgtccattt    120
```

| | |
|---|---|
| gtatgtgcat gccaaccaca gggttcccct cgggatcaaa gtactttgat ccaccccctc | 180 |
| cgctgctata gtgcagtcgg cttctgacgt tcagtgcagc cgtcatctga aaacgacatg | 240 |
| tcgcacaagt cctaagttac gcgacaggct gccgccctgc ccttttcctg gcgttttctt | 300 |
| gtcgcgtgtt ttagtcgcat aaagtagaat acttgcgact agaaccggag acattacgcc | 360 |
| atgaacaaga gcgccgccgc tggcctgctg ggctatgccc gcgtcagcac cgacgaccag | 420 |
| gacttgacca accaacgggc cgaactgcac gcggccggct gcaccaagct gttttccgag | 480 |
| aagatcaccg gcaccaggcg cgaccgcccg gagctggcca ggatgcttga ccacctacgc | 540 |
| cctggcgacg ttgtgacagt gaccaggcta gaccgcctgg cccgcagcac ccgcgaccta | 600 |
| ctggacattg ccgagcgcat ccaggaggcc ggcgcgggcc tgcgtagcct ggcagagccg | 660 |
| tgggccgaca ccaccacgcc ggccggccgc atggtgttga ccgtgttcgc cggcattgcc | 720 |
| gagttcgagc gttccctaat catcgaccgc acccggagcg ggcgcgaggc cgccaaggcc | 780 |
| cgaggcgtga agtttggccc ccgccctacc ctcaccccgg cacagatcgc gcacgcccgc | 840 |
| gagctgatcg accaggaagg ccgcaccgtg aaagaggcgc tgcactgct tggcgtgcat | 900 |
| cgctcgaccc tgtaccgcgc acttgagcgc agcgaggaag tgacgcccac cgaggccagg | 960 |
| cggcgcggtg ccttccgtga ggacgcattg accgaggccg acgccctggc ggccgccgag | 1020 |
| aatgaacgcc aagaggaaca agcatgaaac cgcaccagga cggccaggac gaaccgtttt | 1080 |
| tcattaccga agagatcgag gcggagatga tcgcggccgg gtacgtgttc gagccgcccg | 1140 |
| cgcacctctc aaccgtgcgg ctgcatgaaa tcctggccgg tttgtctgat gccaagctgg | 1200 |
| cggcctggcc ggccagcttg gccgctgaag aaaccgagcg ccgccgtcta aaaggtgat | 1260 |
| gtgtatttga gtaaaacagc ttgcgtcatg cggtcgctgc gtatatgatc cgatgagtaa | 1320 |
| ataaacaaat acgcaagggg aacgcatgaa ggttatcgct gtacttaacc agaaaggcgg | 1380 |
| gtcaggcaag acgaccatcg gaacccatct agcccgcgcc ctgcaactcg ccggggccga | 1440 |
| tgttctgtta gtcgattccg atccccaggg cagtgcccgc gattgggcgg ccgtgcggga | 1500 |
| agatcaaccg ctaaccgttg tcggcatcga ccgcccgacg attgaccgcg acgtgaaggc | 1560 |
| catcggccgg cgcgacttcg tagtgatcga cggagcgccc caggcggcgg acttggctgt | 1620 |
| gtccgcgatc aaggcagccg acttcgtgct gattccggtg cagccaagcc cttacgacat | 1680 |
| atgggccacc gccgacctgg tggagctggt taagcagcgc attgaggtca cggatggaag | 1740 |
| gctacaagcg gcctttgtcg tgtcgcgggc gatcaaaggc acgcgcatcg gcggtgaggt | 1800 |
| tgccgaggc ctgccgggt acgagctgcc cattcttgag tcccgtatca cgcagcgcgt | 1860 |
| gagctaccca ggcactgccg ccgccggcac aaccgttctt gaatcagaac ccgagggcga | 1920 |
| cgctgcccgc gaggtccagg cgctggccgc tgaaattaaa tcaaaactca tttgagttaa | 1980 |
| tgaggtaaag agaaaatgag caaaagcaca aacacgctaa gtgccggccg tccgagcgca | 2040 |
| cgcagcagca aggctgcaac gttggccagc ctggcagaca cgccagccat gaagcgggtc | 2100 |
| aactttcagt tgccggcgga ggatcacacc aagctgaaga tgtacgcggt acgccaaggc | 2160 |
| aagaccatta ccgagctgct atctgaatag atcgcgcagc taccagagta aatgagcaaa | 2220 |
| tgaataaatg agtagatgaa ttttagcggc taaaggaggc ggcatggaaa atcaagaaca | 2280 |
| accaggcacc gacgccgtgg aatgccccat gtgtggagga acgggcggtt ggccaggcgt | 2340 |
| aagcggctgg gttgtctgcc ggccctgcaa tggcactgga accccaagc ccgaggaatc | 2400 |
| ggcgtgacgg tcgcaaacca tccgcccgg tacaaatcgg cgcggcgctg ggtgatgacc | 2460 |
| tggtggagaa gttgaaggcc gcgcaggccg cccagcggca acgcatcgag gcagaagcac | 2520 |

```
gccccggtga atcgtggcaa gcggccgctg atcgaatccg caaagaatcc cggcaaccgc    2580
cggcagccgg tgcgccgtcg attaggaagc cgcccaaggg cgacgagcaa ccagattttt    2640
tcgttccgat gctctatgac gtgggcaccc gcgatagtcg cagcatcatg acgtggccg     2700 ttttccgtct gtcgaagcgt gaccgacgag ctggcgaggt gatccgctac gagcttccag    2760
acgggcacgt agaggtttcc gcagggccgg ccggcatggc cagtgtgtgg gattacgacc    2820
tggtactgat ggcggtttcc catctaaccg aatccatgaa ccgataccgg aagggaagg     2880 gagacaagcc cggccgcgtg ttccgtccac acgttgcgga cgtactcaag ttctgccggc    2940
gagccgatgg cggaaagcag aaagacgacc tggtagaaac ctgcattcgg ttaaacacca    3000
cgcacgttgc catgcagcgt acgaagaagg ccaagaacgg ccgcctggtg acggtatccg    3060
agggtgaagc cttgattagc cgctacaaga tcgtaaagag cgaaaccggg cggccggagt    3120
acatcgagat cgagctagct gattggatgt accgcgagat cacagaaggc aagaacccgg    3180
acgtgctgac ggttcacccc gattactttt tgatcgatcc cggcatcggc cgttttctct    3240
accgcctggc acgccgcgcc gcaggcaagg cagaagccag atggttgttc aagacgatct    3300
acgaacgcag tggcagcgcc ggagagttca agaagttctg tttcaccgtg cgcaagctga    3360
tcgggtcaaa tgacctgccg gagtacgatt tgaaggagga ggcggggcag gctggcccga    3420
tcctagtcat gcgctaccgc aacctgatcg agggcgaagc atccgccggt tcctaatgta    3480
cggagcagat gctagggcaa attgccctag caggggaaaa aggtcgaaaa ggactctttc    3540
ctgtggatag cacgtacatt gggaacccaa agccgtacat tgggaaccgg aacccgtaca    3600
ttgggaaccc aaagccgtac attgggaacc ggtcacacat gtaagtgact gatataaaag    3660
agaaaaaagg cgattttcc gcctaaaact ctttaaaact tattaaaact cttaaaaccc     3720
gcctggcctg tgcataactg tctggccagc gcacagccga agagctgcaa aaagcgccta    3780
cccttcggtc gctgcgctcc ctacgccccg ccgcttcgcg tcggcctatc gcggccgctg    3840
gccgctcaaa aatggctggc ctacggccag gcaatctacc agggcgcgga caagccgcgc    3900
cgtcgccact cgaccgccgg cgcccacatc aaggcaccct gcctcgcgcg tttcggtgat    3960
gacggtgaaa acctctgaca catgcagctc ccggtgacgg tcacagcttg tctgtaagcg    4020
gatgccggga gcagacaagc ccgtcagggc gcgtcagcgg gtgttggcgg gtgtcggggc    4080
gcagccatga cccagtcacg tagcgatagc ggagtgtata ctggcttaac tatgcggcat    4140
cagagcagat tgtactgaga gtgcaccata tgcggtgtga ataccgcac agatgcgtaa     4200 ggagaaaata ccgcatcagg cgctcttccg cttcctcgct cactgactcg ctgcgctcgg    4260
tcgttcggct gcggcgagcg gtatcagctc actcaaaggc ggtaatacgg ttatccacag    4320
aatcagggga taacgcagga agaacatgt gagcaaaagg ccagcaaaag gccaggaacc     4380
gtaaaaaggc cgcgttgctg gcgttttcc ataggctccg ccccctgac gagcatcaca     4440 aaaatcgacg ctcaagtcag aggtggcgaa acccgacagg actataaaga taccaggcgt    4500
ttccccctgg aagctccctc gtgcgctctc ctgttccgac cctgccgctt accggatacc    4560
tgtccgcctt tctcccttcg ggaagcgtgg cgctttctca tagctcacgc tgtaggtatc    4620
tcagttcggt gtaggtcgtt cgctccaagc tgggctgtgt gcacgaaccc ccgttcagc    4680 ccgaccgctg cgccttatcc ggtaactatc gtcttgagtc aacccggta agacacgact     4740 tatcgccact ggcagcagcc actggtaaca ggattagcag agcgaggtat gtaggcggtg    4800
ctacagagtt cttgaagtgg tggcctaact acggctacac tagaaggaca gtatttggta    4860
```

```
tctgcgctct gctgaagcca gttaccttcg gaaaagagt tggtagctct tgatccggca   4920
aacaaaccac cgctggtagc ggtggttttt ttgtttgcaa gcagcagatt acgcgcagaa   4980
aaaaaggatc tcaagaagat cctttgatct tttctacggg gtctgacgct cagtggaacg   5040
aaaactcacg ttaagggatt ttggtcatgc attctaggtg attagaaaaa ctcatcgagc   5100
atcaaatgaa actgcaattt attcatatca ggattatcaa taccatattt tgaaaaagc   5160
cgtttctgta atgaaggaga aaactcaccg aggcagttcc ataggatggc aagatcctgg   5220
tatcggtctg cgattccgac tcgtccaaca tcaatacaac ctattaattt ccctcgtca   5280
aaaataaggt tatcaagtga gaaatcacca tgagtgacga ctgaatccgg tgagaatggc   5340
aaaagtttat gcatttcttt ccagacttgt tcaacaggcc agccattacg ctcgtcatca   5400
aaatcactcg catcaaccaa accgttattc attcgtgatt gcgcctgagc gagtcgaaat   5460
acgcgatcgc tgttaaaagg acaattacaa acaggaatcg aatgcaaccg gcgcaggaac   5520
actgccagcg catcaacaat attttcacct gaatcaggat attcttctaa tacctggaat   5580
gctgttttcc ctgggatcgc agtggtgagt aaccatgcat catcaggagt acggataaaa   5640
tgcttgatgg tcggaagagg cataaattcc gtcagccagt ttagtctgac catctcatct   5700
gtaacatcat tggcaacgct acctttgcca tgtttcagaa acaactctgg cgcatcgggc   5760
ttcccataca atcggtagat tgtcgcacct gattgcccga cattatcgcg agcccattta   5820
tacccatata aatcagcatc catgttggaa tttaatcgcg gccttgagca agacgtttcc   5880
cgttgaatat ggctcataac agaacttatt atttccttcc tcttttctac agtatttaaa   5940
gataccccaa gaagctaatt ataacaagac gaactccaat tcactgttcc ttgcattcta   6000
aaaccttaaa taccagaaaa cagctttttc aaagttgttt tcaaagttgg cgtataacat   6060
agtatcgacg gagccgattt tgaaaccgcg gtgatcacag gcagcaacgc tctgtcatcg   6120
ttacaatcaa catgctaccc tccgcgagat catccgtgtt tcaaacccgg cagcttagtt   6180
gccgttcttc cgaatagcat cggtaacatg agcaaagtct gccgccttac aacggctctc   6240
ccgctgacgc cgtcccggac tgatgggctg cctgtatcga gtggtgattt tgtgccgagc   6300
tgccggtcgg ggagctgttg gctggctggt ggcaggatat attgtggtgt aaacataacg   6360
aattcgtctc aggagggggtt tctggagttt aatgagctaa gcacatacgt cagaaaccat   6420
tattgcgcgt tcaaaagtcg cctaaggtca ctatcagcta gcaaatattt cttgtcaaaa   6480
atgctccact gacgttccat aaaattcccct cggtatccaa ttagagtctc atattcactc   6540
tcaatccaaa taatctgcaa tggcaattac cttatccgca acttctttac ctatttccgc   6600
ccggatccgg gcaggttctc cggccgcttg ggtggagagg ctattcggct atgactgggc   6660
acaacagaca atcggctgct ctgatgccgc cgtgttccgg ctgtcagcgc aggggcgccc   6720
ggttcttttt gtcaagaccg acctgtccgg tgccctgaat gaactgcagg acgaggcagc   6780
gcggctatcg tggctggcca cgacgggcgt tccttgcgca gctgtgctcg acgttgtcac   6840
tgaagcggga agggactggc tgctattggg cgaagtgccg gggcaggatc tcctgtcatc   6900
tcaccttgct cctgccgaga agtatccat catggctgat gcaatgcggc ggctgcatac   6960
gcttgatccg gctacctgcc cattcgacca ccaagcgaaa catcgcatcg agcgagcacg   7020
tactcggatg gaagccggtc ttgtcgatca ggatgatctg gacgaagagc atcaggggct   7080
cgcgccagcc gaactgttcg ccaggctcaa ggcgcgcatg cccgacggcg aggatctcgt   7140
cgtgacccat ggcgatgcct gcttgccgaa tatcatggtg aaaatggcc gcttttctgg   7200
attcatcgac tgtggccggc tgggtgtggc ggaccgctat caggacatag cgttggctac   7260
```

```
ccgtgatatt gctgaagagc ttggcggcga atgggctgac cgcttcctcg tgctttacgg   7320
tatcgccgct cccgattcgc agcgcatcgc cttctatcgc cttcttgacg agttcttctg   7380
agcgggactc tggggttcga atgaccgac caagcgacgc ccaacctgcc atcacgagat    7440
ttcgattcca ccgccgcctt ctatgaaagg ttgggcttcg gaatcgtttt ccgggacgcc   7500
ggctggatga tcctccagcg cggggatctc atgctggagt tcttcgccca ccccgatcca   7560
acacttacgt ttgcaacgtc caagagcaaa tagaccacga acgccggaag gttgccgcag   7620
cgtgtggatt gcgtctcaat tctctcttgc aggaatgcaa tgatgaatat gatactgact   7680
atgaaacttt gagggaatac tgcctagcac cgtcacctca taacgtgcat catgcatgcc   7740
ctgacaacat ggaacatcgc tattttctg aagaattatg ctcgttggag gatgtcgcgg    7800
caattgcagc tattgccaac atcgaactac ccctcacgca tgcattcatc aatattattc   7860
atgcggggaa aggcaagatt aatccaactg gcaaatcatc cagcgtgatt ggtaacttca   7920
gttccagcga cttgattcgt tttggtgcta cccacgtttt caataaggac gagatggtgg   7980
agtaaagaag gagtgcgtcg aagcagatcg ttcaaacatt tggcaataaa gtttcttaag   8040
attgaatcct gttgccggtc ttgcgatgat tatcatataa tttctgttga attacgttaa   8100
gcatgtaata attaacatgt aatgcatgac gttatttatg agatgggttt ttatgattag   8160
agtcccgcaa ttatacattt aatacgcgat agaaaacaaa atatagcgcg caaactagga   8220
taaattatcg cgcgcggtgt catctatgtt actagatcga cgctgtcagg agactagagc   8280
caagctgatc tcctttgccc cggagatcac catggacgac tttctctatc tctacgatct   8340
aggaagaaag ttcgacggag aaggtgacga taccatgttc accaccgata atgagaagat   8400
tagcctcttc aatttcagaa agaatgctga cccacagatg gttagagagg cctacgcggc   8460
aggtctgatc aagacgatct acccgagtaa taatctccag gagatcaaat accttcccaa   8520
gaaggttaaa gatgcagtca aaagattcag gactaactgc atcaagaaca cagagaaaga   8580
tatatttctc aagatcagaa gtactattcc agtatggacg attcaaggct tgcttcataa   8640
accaaggcaa gtaatagaga ttggagtctc taagaaagta gttcctactg aatcaaaggc   8700
catggagtca aaaattcaga tcgaggatct aacagaactc gccgtgaaga ctggcgaaca   8760
gttcatacag agtctttac gactcaatga caagaagaaa atcttcgtca acatggtgga    8820
gcacgacact ctcgtctact ccaagaatat caaagataca gtctcagaag accaaagggc   8880
tattgagact tttcaacaaa gggtaatatc gggaaacctc ctcggattcc attgcccagc   8940
tatctgtcac ttcatcaaaa ggacagtaga aaaggaaggt ggcacctaca aatgccatca   9000
ttgcgataaa ggaaaggcta tcgttcaaga tgcctctgcc gacagtggtc ccaaagatgg   9060
accccacccc acgaggagca tcgtggaaaa agaagacgtt ccaaccacgt cttcaaagca   9120
agtggattga tgtgatatct ccactgacgt aagggatgac gcacaatccc actatccttc   9180
gcaagaccct tcctctatat aaggaagttc atttcatttg gagaggactc cggtattttt   9240
acaacaatac cacaacaaaa caaacaacaa acaacattac aatttactat tctagtcgaa   9300
atgaaaatga tgaatggtga agatgctaat gatcaaatga tcaaagaaag cttcttcata   9360
acacatggaa acccaatatt aacagtagaa gacacacatc cattaagacc tttctttgaa   9420
acttggagag agaaaatctt ttctaagaaa cctaaggcaa ttcttattat ttctggtcat   9480
tgggaaactg ttaaacctac tgttaatgct gtccatatca atgatactat ccatgatttt   9540
gatgactatc ctgctgctat gtaccagttc aagtatccag ctcctgggga accagaattg   9600
```

```
gcaagaaaag tagaggaaat tctgaaaaaa tcgggtttcg aaacggcgga aactgatcaa   9660
aaacgtgggc ttgatcatgg tgcatgggta cctctaatgc taatgtatcc tgaggctgat   9720
ataccagtat gtcagctctc agttcagccg catttagatg aacatacca ttacaactta   9780 ggacgagcat tggctcccctt gaaaaacgac ggcgtattaa tcattggttc aggaagtgca   9840 actcacccctt tggatgaaac tcctcattat tttgatggag ttgcaccttg ggcagctgcc   9900
tttgattcat ggcttcgtaa agctctcatt aatggaaggt ttgaagaagt gaatatatat   9960
gaaagcaaag caccaaattg gaaattagca catcctttcc cagaacattt ttatccattg  10020
catgttgttc ttggcgctgc tggtgaaaaa tggaaggcag agcttattca tagcagttgg  10080
gatcatggca ccttgtgtca tggctcctac aagttcactt cagcctaggc ttggaatgga  10140
tcttcgatcc cgatcgttca aacatttggc aataaagttt cttaagattg aatcctgttg  10200
ccggtcttgc gacgattatc atataatttc tgttgaatta cgttaagcat gtaataatta  10260
acatgtaatg catgacgtta tttatgagat gggtttttat gattagagtc ccgcaattat  10320
acatttaata cgcgatagaa aacaaaatat agcgcgcaaa ctaggataaa ttatcgcgcd  10380
cggtgtcatc tatgttacta gatcgggaat tgccaagcta attcttgaag acgaaagggc  10440
ctcgtgatac gcctattttt ataggttaat gtcatgataa taatggtttc ttagacgtca  10500
ggtggcactt tcggggaaa tgtgcgcgga acccctattt gtttattttt ctaaatacat  10560
tcaaatatgt atccgctcat gagacaataa ccctgataaa tgcttcaata atgggaccga  10620
ctcgcgctgt caggaggtgc actgtcaaat tatgtcataa attctaatga gatgagttta  10680
tatagcattt acaaattcaa atacttaaaa aggatactac aatttggtat tacgtgtcaa  10740
attcctgttc aaagctgatg ctagaggtga cagaaatcat atgcaagaac gtcaaggcca  10800
ttcattttgg ttcaacagat tgatgaaaaa tctaagagcc tttgatcttg agaagtaggt  10860
aaccattaat ttgtgttgaa ggtttgctac gaaaataaaa aggatgtcac gtgccatcaa  10920
gttatagcta cacgtgatta ctatctacca ttctccttta gggttctcgt ataaatactc  10980
tacaatcccc atgcaaacca taacacaata taaaagatac ttacacttgt cacgtactac  11040
ataaaaaaaa aaaatacca aactttttc aagcaaaaaa tggatcatgc aacattagca  11100
atgatactag ccatttggtt catttctttt catttcataa aattacttt tagccaacaa  11160 actaccaaac ttcttcctcc tggtccaaaa ccattgccaa taattggtaa catcttagaa  11220
gttggtaaaa aaccccatcg ttcatttgct aatcttgcta aaattcacgg ccctttaata  11280
tcgttacgtc taggaagtgt aacaactatt gttgtatcat cagcagatgt agctaaagaa  11340
atgttcttaa aaaaagacca ccctctttct aaccgtacta ttcctaattc tgtcacggcc  11400
ggtgaccacc ataaactcac catgtcgtgg ttgcccgttt cgccgaaatg gcggaatttt  11460
cgtaagatta cagccgtcca tttgctttct cctcaaagac ttgatgcttg ccaaaccttt  11520
cgccatgcca aggtgcaaca gctttatgaa tatgtacaag aatgtgcaca aaaaggccaa  11580
gctgttgata ttgcaaagc tgcatttact acctccctta atttgttatc taaactattc  11640
ttttcagtgg aattagccca ccataaatca cacacttctc aagagtttaa ggaactaata  11700
tggaacatta tggaagatat tgggaaacct aattatgctg attattttcc tatttttaggc  11760 tgtgttgatc catcaggtat tcgtcgaaga ttagcatgta gttttgacaa gttgattgca  11820 gttttcagg gtataaatatg tgaaaggctt gcgcctgatt cttcaactac aacaacaacg  11880
acgactgatg atgtgctaga cgttcttctt cagctcttca aacaaaatga gctcactatg  11940
ggcgagatta accatttgct cgtcgacatt tttgatgctg gaacagacac tacatcaagt  12000
```

```
acttttgagt gggtcatgac agagttaatt aggaatcctg aaatgatgga aaaggctcaa   12060
gaagaaatta agcaagtatt gggcaaagat aaacaaattc aggaatcaga cattattaac   12120
ctaccttact tacaagccat tatcaaagaa actttgcgac tacatccacc aactgtattt   12180
cttttgcctc gtaaagccga cactgatgtt gaactatatg gttatattgt gcctaaagat   12240
gcacaaatac ttgttaactt atgggctatt ggaagagatc taatgcatg gcaaaatgct    12300 gatattttt cgcccgaaag atttataggg tgtgaaaytg atgtcaaagg aagagatttt    12360
ggactcttac cttttggagc cggaagaagg atatgtcctg ggatgaattt ggccattaga   12420
atgttaactt tgatgctagc tactttactt caattcttca attggaagct tgaaggagac   12480
ataagtccaa aagacttaga catggatgag aaatttggga ttgcgttaca aaagacaaag   12540
cctttaaaac ttattccaat acctaggtat tgataataag cttcggccat gctagagtcc   12600
gcaaaaatca ccagtctctc tctacaaatc tatctctctc tattttctc cagaataatg    12660 tgtgagtagt tcccagataa gggaattagg gttcttatag ggtttcgctc atgtgttgag   12720
catataagaa acccttagta tgtatttgta tttgtaaaat acttctatca ataaaatttc   12780
taattcctaa aaccaaaatc cagtgacctc gctgtcagga ggtcgacgag tcagtaataa   12840
acggcgtcaa agtggttgca gccggcacac acgagtcgtg tttatcaact caaagcacaa   12900
atacttttcc tcaacctaaa aataaggcaa ttagccaaaa acaactttgc gtgtaaacaa   12960
cgctcaatac acgtgtcatt ttattattag ctattgcttc accgccttag ctttctcgtg   13020
acctagtcgt cctcgtcttt tcttcttctt cttctataaa acaatacccca aagagctctt   13080 cttcttcaca attcagattt caatttctca aaatcttaaa aactttctct caattctctc   13140
taccgtgatc aaggtaaatt tctgtgttcc ttattctctc aaaatcttcg attttgtttt   13200
cgttcgatcc caatttcgta tatgttcttt ggtttagatt ctgttaatct tagatcgaag   13260
acgattttct gggtttgatc gttagatatc atcttaattc tcgattaggg tttcatagat   13320
atcatccgat ttgttcaaat aatttgagtt ttgtcgaata attactcttc gatttgtgat   13380
ttctatctag atctggtgtt agtttctagt ttgtgcgatc gaatttgtcg attaatctga   13440
gtttttctga ttaacagaat gaccgccatt aaaatgaaca ccaatggtga aggtgaaaca   13500
caacatatac taatgatacc tttcatggcg caagggcatt tacgtccttt ccttgagctt   13560
gctatgtttc tatataaacg aagtcatttt atcattactc ttcttactac cccgctcaat   13620
gcgggtttcc tacgacatct ccttcaccac catagctatt ctagctcggg gatcagaatt   13680
gtcgagttac ctttcaactc aaccaatcat ggtcttccac ctggcattga aaacactgat   13740
aaacttacac tcccacttgt agtatcactt tttcattcaa ccatttctct tgaccctcac   13800
cttagagatt atatttcccg ccatttctcc cctgcgcgcc ctcctctgtg tgtcatacat   13860
gatgtgttcc ttggttgggt tgatcaagtt gctaaagacg tgggctcaac tggtgttgtt   13920
tttactacgg gtggcgcgta tggtacaagc gcatatgtgt ccatttggaa tgatctgcct   13980
caccagaatt actctgatga tcaagagttt ccgcttcctg gtttcccgga gaatcataaa   14040
ttccgacgtt ctcaacttca tcggtttctg aggtatgccg atggatcaga tgattggtcg   14100
aaatatttcc aaccgcaatt gaggcaatca atgaagagtt ttggatggct atgtaattca   14160
gttgaggaaa tcgaaacact tgggtttagt atcctcagga actacactaa actacccatt   14220
tggggtattg gaccgttgat agcttcacct gtacaacatt catcatctga taataacagt   14280
actggtgccg agtttgttca atggttgagc ttgaaagaac cagattctgt attatacatc   14340
```

| | |
|---|---:|
| tcatttggat cacagaacac aatttcacca acccagatga tggaactagc agccggtttg | 14400 |
| gagtcaagtg agaagccgtt tttgtgggtg attcgagcac catttgggtt cgatatcaat | 14460 |
| gaggaaatga grccagaatg gctaccagag ggattcgagg agcgaatgaa ggtgaaaaaa | 14520 |
| caaggaaagt tggtgtataa gttgggacca cagttggaga tacttaacca tgagtcaatc | 14580 |
| ggagggttct taactcattg tgggtggaat tcgatccttg agtcacttcg agaaggtgtg | 14640 |
| cctatgttag ggtggccatt ggcagccgaa caagcttata atttgaagta tttggaggac | 14700 |
| gaaatggggg ttgcagtcga gttagcgagg ggattggaag agagataag taaagagaaa | 14760 |
| gtgaagagaa ttgtggagat gattttagag agaaatgaag gaagtaaagg atgggaaatg | 14820 |
| aaaaatagag cagtagaaat ggggaagaaa cttaaagacg ctgtcaatga ggagaaggaa | 14880 |
| ctgaagggtt cttctgttaa ggcaatagat gatttcttag atgcggtcat gcaagctaag | 14940 |
| ttggaacctt ctcttcaata agcttcggcc atgctagagt ccgcaaaaat caccagtctc | 15000 |
| tctctacaaa tctatctctc tctattttc tccagaataa tgtgtgagta gttcccagat | 15060 |
| aagggaatta gggttcttat aggtttcgc tcatgtgttg agcatataag aaacccttag | 15120 |
| tatgtatttg tatttgtaaa atacttctat caataaaatt tctaattcct aaaaccaaaa | 15180 |
| tccagtgacc t | 15191 |

<210> SEQ ID NO 22
<211> LENGTH: 19745
<212> TYPE: DNA
<213> ORGANISM: Artificial Sequence
<220> FEATURE:
<223> OTHER INFORMATION: pX12

<400> SEQUENCE: 22

| | |
|---|---:|
| cgctgtcatg agaccggatc ctgacaggat atattggcgg gtaaacctaa gagaaaagag | 60 |
| cgtttattag aataatcgga tatttaaaag ggcgtgaaaa ggtttatccg ttcgtccatt | 120 |
| tgtatgtgca tgccaaccac agggttcccc tcgggatcaa agtactttga tccaacccct | 180 |
| ccgctgctat agtgcagtcg gcttctgacg ttcagtgcag ccgtcatctg aaaacgacat | 240 |
| gtcgcacaag tcctaagtta cgcgacaggc tgccgccctg cccttttcct ggcgttttct | 300 |
| tgtcgcgtgt tttagtcgca taaagtagaa tacttgcgac tagaaccgga gacattacgc | 360 |
| catgaacaag agcgccgccg ctggcctgct gggctatgcc cgcgtcagca ccgacgacca | 420 |
| ggacttgacc aaccaacggg ccgaactgca cgcggccggc tgcaccaagc tgttttccga | 480 |
| gaagatcacc ggcaccaggc gcgaccgccc ggagctggcc aggatgcttg accacctacg | 540 |
| ccctggcgac gttgtgacag tgaccaggct agaccgcctg gcccgcagca cccgcgacct | 600 |
| actggacatt gccgagcgca tccaggaggc cggcgcgggc ctgcgtagcc tggcagagcc | 660 |
| gtgggccgac accaccacgc cggccggccg catggtgttg accgtgttcg ccggcattgc | 720 |
| cgagttcgag cgttccctaa tcatcgaccg cacccgagc gggcgcgagg ccgccaaggc | 780 |
| ccgaggcgtg aagtttggcc cccgccctac cctcaccccg gcacagatcg cgcacgcccg | 840 |
| cgagctgatc gaccaggaag gccgcaccgt gaaagaggcg gctgcactgc ttggcgtgca | 900 |
| tcgctcgacc ctgtaccgcg cacttgagcg cagcgaggaa gtgacgccca ccgaggccag | 960 |
| gcggcgcggt gccttccgtg aggacgcatt gaccgaggcc gacgccctgg cggccgccga | 1020 |
| gaatgaacgc caagaggaac aagcatgaaa ccgcaccagg acggccagga cgaaccgttt | 1080 |
| ttcattaccg aagagatcga ggcggagatg atcgcggccg ggtacgtgtt cgagccgccc | 1140 |
| gcgcacctct caaccgtgcg gctgcatgaa atcctggccg gtttgtctga tgccaagctg | 1200 |

```
gcggcctggc cggccagctt ggccgctgaa gaaaccgagc gccgccgtct aaaaaggtga    1260
tgtgtatttg agtaaaacag cttgcgtcat gcggtcgctg cgtatatgat ccgatgagta    1320
aataaacaaa tacgcaaggg gaacgcatga aggttatcgc tgtacttaac cagaaaggcg    1380
ggtcaggcaa gacgaccatc ggaacccatc tagcccgcgc cctgcaactc gccggggccg    1440
atgttctgtt agtcgattcc gatcccagg gcagtgcccg cgattgggcg gccgtgcggg     1500
aagatcaacc gctaaccgtt gtcggcatcg accgccgac gattgaccgc gacgtgaagg     1560
ccatcggccg gcgcgacttc gtagtgatcg acggagcgcc ccaggcggcg gacttggctg    1620
tgtccgcgat caaggcagcc gacttcgtgc tgattccggt gcagccaagc ccttacgaca    1680
tatgggccac cgccgacctg gtggagctgg ttaagcagcg cattgaggtc acggatggaa    1740
ggctacaagc ggccttttgtc gtgtcgcggg cgatcaaagg cacgcgcatc ggcggtgagg   1800
ttgccgaggc gctggccggg tacgagctgc ccattcttga gtcccgtatc acgcagcgcg   1860
tgagctaccc aggcactgcc gccgccggca caaccgttct tgaatcagaa cccgagggcg    1920
acgctgcccg cgaggtccag gcgctggccg ctgaaattaa atcaaaactc atttgagtta    1980
atgaggtaaa gagaaaatga gcaaaagcac aaacacgcta agtgccggcc gtccgagcgc    2040
acgcagcagc aaggctgcaa cgttggccag cctggcagac acgccagcca tgaagcgggt    2100
caactttcag ttgccggcgg aggatcacac caagctgaag atgtacgcgg tacgccaagg    2160
caagaccatt accgagctgc tatctgaata gatcgcgcag ctaccagagt aaatgagcaa    2220
atgaataaat gagtagatga attttagcgg ctaaaggagg cggcatggaa aatcaagaac    2280
aaccaggcac cgacgccgtg gaatgcccca tgtgtggagg aacgggcggt tggccaggcg    2340
taagcggctg ggttgtctgc cggccctgca atggcactgg aacccccaag cccgaggaat    2400
cggcgtgacg gtcgcaaacc atccggcccg gtacaaatcg cgcggcgct gggtgatgac     2460 ctggtggaga agttgaaggc cgcgcaggcc gcccagcggc aacgcatcga ggcagaagca    2520
cgccccggtg aatcgtggca agcggccgct gatcgaatcc gcaaagaatc ccggcaaccg    2580
ccggcagccg gtgcgccgtc gattaggaag ccgcccaagg gcgacgagca accagatttt    2640
ttcgttccga tgctctatga cgtgggcacc cgcgatagtc gcagcatcat ggacgtggcc    2700
gttttccgtc tgtcgaagcg tgaccgacga gctggcgagg tgatccgcta cgagcttcca    2760
gacgggcacg tagaggtttc cgcagggccg gccggcatgg ccagtgtgtg ggattacgac    2820
ctggtactga tggcggtttc ccatctaacc gaatccatga accgataccg ggaagggaag    2880
ggagacaagc ccgccgcgt gttccgtcca cacgttgcgg acgtactcaa gttctgccgg    2940
cgagccgatg gcggaaagca gaaagacgac ctggtagaaa cctgcattcg gttaaacacc    3000
acgcacgttg ccatgcagcg tacgaagaag gccaagaacg gccgcctggt gacggtatcc    3060
gagggtgaag ccttgattag ccgctacaag atcgtaaaga gcgaaaccgg gcggccggag    3120
tacatcgaga tcgagctagc tgattggatg taccgcgaga tcacagaagg caagaacccg    3180
gacgtgctga cggttcaccc cgattacttt ttgatcgatc ccggcatcgg ccgttttctc    3240
taccgcctgg cacgccgcgc cgcaggcaag gcagaagcca gatggttgtt caagacgatc    3300
tacgaacgca gtggcagcgc cggagagttc aagaagttct gtttcaccgt gcgcaagctg    3360
atcgggtcaa atgacctgcc ggagtacgat ttgaaggagg aggcggggca ggctggcccg    3420
atcctagtca tgcgctaccg caacctgatc gagggcgaag catccgccgg ttcctaatgt    3480
acggagcaga tgctagggca aattgcccta gcaggggaaa aaggtcgaaa aggactcttt    3540
```

```
cctgtggata gcacgtacat tgggaaccca aagccgtaca ttgggaaccg gaacccgtac    3600
attgggaacc caaagccgta cattgggaac cggtcacaca tgtaagtgac tgatataaaa    3660
gagaaaaaag gcgattttc cgcctaaaac tctttaaaac ttattaaaac tcttaaaacc    3720
cgcctggcct gtgcataact gtctggccag cgcacagccg aagagctgca aaaagcgcct    3780
acccttcggt cgctgcgctc cctacgcccc gccgcttcgc gtcggcctat cgcggccgct    3840
ggccgctcaa aaatggctgg cctacggcca ggcaatctac cagggcgcgg acaagccgcg    3900
ccgtcgccac tcgaccgccg cgcccacat caaggcaccc tgcctcgcgc gtttcggtga    3960
tgacggtgaa aacctctgac acatgcagct cccggtgacg gtcacagctt gtctgtaagc    4020
ggatgccggg agcagacaag cccgtcaggg cgcgtcagcg ggtgttggcg ggtgtcgggg    4080
cgcagccatg acccagtcac gtagcgatag cggagtgtat actggcttaa ctatgcggca    4140
tcagagcaga ttgtactgag agtgcaccat atgcggtgtg aaataccgca cagatgcgta    4200
aggagaaaat accgcatcag gcgctcttcc gcttcctcgc tcactgactc gctgcgctcg    4260
gtcgttcggc tgcggcgagc ggtatcagct cactcaaagg cggtaatacg ttatccaca    4320 gaatcagggg ataacgcagg aaagaacatg tgagcaaaag gccagcaaaa ggccaggaac    4380
cgtaaaaagg ccgcgttgct ggcgttttc cataggctcc gcccccctga cgagcatcac    4440
aaaaatcgac gctcaagtca ggtggcga acccgacag gactataaag ataccaggcg    4500
tttccccctg gaagctccct cgtgcgctct cctgttccga ccctgccgct taccggatac    4560
ctgtccgcct ttctcccttc gggaagcgtg gcgctttctc atagctcacg ctgtaggtat    4620
ctcagttcgg tgtaggtcgt tcgctccaag ctgggctgtg tgcacgaacc ccccgttcag    4680
cccgaccgct gcgccttatc cggtaactat cgtcttgagt ccaacccggt aagacacgac    4740
ttatcgccac tggcagcagc cactggtaac aggattagca gagcgaggta tgtaggcggt    4800
gctacagagt tcttgaagtg gtggcctaac tacggctaca ctagaaggac agtatttggt    4860
atctgcgctc tgctgaagcc agttaccttc ggaaaaagag ttggtagctc ttgatccggc    4920
aaacaaacca ccgctggtag cggtggtttt tttgtttgca agcagcagat tacgcgcaga    4980
aaaaaaggat ctcaagaaga tcctttgatc ttttctacgg ggtctgacgc tcagtggaac    5040
gaaaactcac gttaagggat tttggtcatg cattctaggt gattatttgc cgactacctt    5100
ggtgatctcg cctttcacgt agtggacaaa ttcttccaac tgatctgcgc gcgaggccaa    5160
gcgatcttct tcttgtccaa gataagcctg tctagcttca agtatgacgg gctgatactg    5220
ggccggcagg cgctccattg cccagtcggc agcgacatcc ttcggcgcga ttttgccggt    5280
tactgcgctg taccaaatgc gggacaacgt aagcactaca tttcgctcat caccagccca    5340
gtcgggcggc gagttccata gcgttaaggt ttcatttagc gcctcaaata gatcctgttc    5400
aggaaccgga tcaaagagtt cctccgccgc tggacctacc aaggcaacgc tatgttctct    5460
tgcttttgtc agcaagatag ccagatcaat gtcgatcgtg gctggctcga agatacctgc    5520
aagaatgtca ttgcgctgcc attctccaaa ttgcagttcg cgcttagctg gataacgcca    5580
cggaatgatg tcgtcgtgca caacaatggt gacttctaca gcgcggagaa tctcgctctc    5640 tccagggga gccgaagttt ccaaaaggtc gttgatcaaa gctcgccgcg ttgtttcatc    5700
aagccttacg gtcaccgtaa ccagcaaatc aatatcactg tgtggcttca ggccgccatc    5760
cactgcggag ccgtacaaat gtacggccag caacgtcggt tcgagatggc gctcgatgac    5820
gccaactacc tctgatagtt gagtcgatac ttcggcgatc accgcttccc tcataatgtt    5880
taactttgtt ttagggcgac tgccctgctg cgtaacatcg ttgctgctcc ataacatcaa    5940
```

```
acatcgaccc acggcgtaac gcgcttgctg cttggatgcc cgaggcatag actgtacccc    6000
aaaaaaacag tcataacaag ccatgaaaac cgccactgcg ccgttaccac cgctgcgttc    6060
ggtcaaggtt ctggaccagt tgcgtgagcg catacgctac ttgcattaca gcttacgaac    6120
cgaacaggct tatgtccact ggggttcgtgc cttcatccgt ttccacggtg tgcgtcaccc    6180
ggcaaccttg ggtagcagcg aagtcgaggc atttctgtcc tggctggaac agaacttatt    6240
atttccttcc tcttttctac agtatttaaa gatacccccaa gaagctaatt ataacaagac    6300
gaactccaat tcactgttcc ttgcattcta aaaccttaaa taccagaaaa cagctttttc    6360
aaagttgttt tcaaagttgg cgtataacat agtatcgacg gagccgattt tgaaaccgcg    6420
gtgatcacag gcagcaacgc tctgtcatcg ttacaatcaa catgctaccc tccgcgagat    6480
catccgtgtt tcaaacccgg cagcttagtt gccgttcttc gaatagcat cggtaacatg    6540 agcaaagtct gccgccttac aacggctctc ccgctgacgc cgtcccggac tgatgggctg    6600
cctgtatcga gtggtgattt tgtgccgagc tgccggtcgg ggagctgttg gctggctggt    6660
ggcaggatat attgtggtgt aaacataacg gatccggtct caggagagcg tcgatctagt    6720
aacatagatg acaccgcgcg cgataattta tcctagtttg cgcgctatat tttgttttct    6780
atcgcgtatt aaatgtataa ttgcgggact ctaatcataa aaacccatct cataaataac    6840
gtcatgcatt acatgttaat tattacatgc ttaacgtaat tcaacagaaa ttatatgata    6900
atcatcgcaa gaccggcaac aggattcaat cttaagaaac tttattgcca aatgtttgaa    6960
cgatctgctt cgacgcactc cttctttact ccaccatctc gtccttattg aaaacgtggg    7020
tagcaccaaa acgaatcaag tcgctggaac tgaagttacc aatcacgctg gatgatttgc    7080
cagttggatt aatcttgcct ttccccgcat gaataatatt gatgaatgca tgcgtgaggg    7140
gtagttcgat gttggcaata gctgcaattg ccgcgacatc ctccaacgag cataattctt    7200
cagaaaaata gcgatgttcc atgttgtcag ggcatgcatg atgcacgtta tgaggtgacg    7260
gtgctaggca gtattccctc aaagtttcat agtcagtatc atattcatca ttgcattcct    7320
gcaagagaga attgagacgc aatccacacg ctgcggcaac cttccggcgt tcgtggtcta    7380
tttgctcttg gacgttgcaa acgtaagtgt tggatcgggg tgggcgaaga actccagcat    7440
gagatccccg cgctggagga tcatccagcc ggcgtcccgg aaaacgattc cgaagcccaa    7500
cctttcatag aaggcggcgg tggaatcgaa atctcgtgat ggcaggttgg gcgtcgcttg    7560
gtcggtcatt tcgaacccca gagtcccgct cagaagaact cgtcaagaag gcgatagaag    7620
gcgatgcgct gcgaatcggg agcggcgata ccgtaaagca cgaggaagcg gtcagcccat    7680
tcgccgccaa gctcttcagc aatatcacgg gtagccaacg ctatgtcctg atagcggtcc    7740
gccacaccca gccggccaca gtcgatgaat ccagaaaagc ggccattttc caccatgata    7800
ttcggcaagc aggcatcgcc atgggtcacg acgagatcct cgccgtcggg catgcgcgcc    7860
ttgagcctgg cgaacagttc ggctggcgcg agccctgat gctcttcgtc cagatcatcc    7920
tgatcgacaa gaccggcttc catccgagta cgtgctcgct cgatgcgatg tttcgcttgg    7980
tggtcgaatg ggcaggtagc cggatcaagc gtatgcagcc gccgcattgc atcagccatg    8040
atggatactt tctcggcagg agcaaggtga gatgacagga gatcctgccc cggcacttcg    8100
cccaatagca gccagtccct tcccgcttca gtgacaacgt cgagcacagc tgcgcaagga    8160
acgcccgtcg tggccagcca cgatagccgc gctgcctcgt cctgcagttc attcagggca    8220
ccggacaggt cggtcttgac aaaaagaacc gggcgcccct gcgctgacag ccggaacacg    8280
```

```
gcggcatcag agcagccgat tgtctgttgt gcccagtcat agccgaatag cctctccacc    8340
caagcggccg gagaacctgc ccggatccgg gcggaaatag gtaaagaagt tgcggataag    8400
gtaattgcca ttgcagatta tttggattga gagtgaatat gagactctaa ttggataccg    8460
aggggaattt atggaacgtc agtggagcat ttttgacaag aaatatttgc tagctgatag    8520
tgaccttagg cgacttttga acgcgcaata atggtttctg acgtatgtgc ttagctcatt    8580
aaactccaga aaccoctccg tcaggagact agagccaagc tgatctcctt tgccccggag    8640
atcaccatgg acgactttct ctatctctac gatctaggaa gaaagttcga cggagaaggt    8700
gacgatacca tgttcaccac cgataatgag aagattagcc tcttcaattt cagaaagaat    8760
gctgacccac agatggttag agaggcctac gcggcaggtc tgatcaagac gatctacccg    8820
agtaataatc tccaggagat caaatacctt cccaagaagg ttaaagatgc agtcaaaaga    8880
ttcaggacta actgcatcaa gaacacagag aaagatatat ttctcaagat cagaagtact    8940
attccagtat ggacgattca aggcttgctt cataaaccaa ggcaagtaat agagattgga    9000
gtctctaaga aagtagttcc tactgaatca aaggccatgg agtcaaaaat tcagatcgag    9060
gatctaacag aactcgccgt gaagactggc gaacagttca tacagagtct tttacgactc    9120
aatgacaaga agaaaatctt cgtcaacatg gtggagcacg acactctcgt ctactccaag    9180
aatatcaaag atacagtctc agaagaccaa agggctattg agacttttca acaaagggta    9240
atatcgggaa acctcctcgg attccattgc ccagctatct gtcacttcat caaaaggaca    9300
gtagaaaagg aaggtggcac ctacaaatgc catcattgcg ataaaggaaa ggctatcgtt    9360
caagatgcct ctgccgacag tggtcccaaa gatggacccc cacccacgag gagcatcgtg    9420
gaaaaagaag acgttccaac cacgtcttca aagcaagtgg attgatgtga tatctccact    9480
gacgtaaggg atgacgcaca atcccactat ccttcgcaag acccttcctc tatataagga    9540
agttcatttc atttggagag gactccggta ttttttacaac aataccacaa caaaacaaac    9600
aacaaacaac attacaattt actattctag tcgaaatgaa aatgatgaat ggtgaagatg    9660
ctaatgatca aatgatcaaa gaaagcttct tcataacaca tggaaaccca atattaacag    9720
tagaagacac acatccatta agacctttct ttgaaacttg gagagagaaa atcttttcta    9780
agaaacctaa ggcaattctt attatttctg gtcattggga aactgttaaa cctactgtta    9840
atgctgtcca tatcaatgat actatccatg attttgatga ctatcctgct gctatgtacc    9900
agttcaagta tccagctcct ggggaaccag aattggcaag aaaagtagag gaaattctga    9960
aaaaatcggg tttcgaaacg gcggaaactg atcaaaaacg tgggcttgat catggtgcat    10020
gggtacctct aatgctaatg tatcctgagg ctgatatacc agtatgtcag ctctcagttc    10080
agccgcattt agatgaaaca taccattaca acttaggacg agcattggct cccttgaaaa    10140
acgacggcgt attaatcatt ggttcaggaa gtgcaactca ccctttggat gaaactcctc    10200
attattttga tggagttgca ccttgggcag ctgcctttga ttcatggctt cgtaaagctc    10260
tcattaatgg aaggtttgaa gaagtgaata tatatgaaag caaagcacca aattggaaat    10320
tagcacatcc tttcccagaa catttttatc cattgcatgt tgttcttggc gctgctggtg    10380
aaaaatggaa ggcagagctt attcatagca gttgggatca tggcaccttg tgtcatggct    10440
cctacaagtt cacttcagcc taggcttgga atggatcttc gatcccgatc gttcaaacat    10500
ttggcaataa agtttcttaa gattgaatcc tgttgccggt cttgcgacga ttatcatata    10560
atttctgttg aattacgtta agcatgtaat aattaacatg taatgcatga cgttatttat    10620
gagatgggtt tttatgatta gagtcccgca attatacatt taatacgcga tagaaaacaa    10680
```

```
aatatagcgc gcaaactagg ataaattatc gcgcdcggtg tcatctatgt tactagatcg   10740
ggaattgcca agctaattct tgaagacgaa agggcctcgt gatacgccta tttttatagg   10800
ttaatgtcat gataataatg gtttcttaga cgtcaggtgg cacttttcgg ggaaatgtgc   10860
gcggaacccc tatttgttta tttttctaaa tacattcaaa tatgtatccg ctcatgagac   10920
aataaccctg ataaatgctt caataatggg accgactcgc gctgtcagga gactagagcc   10980
aagctgatct cctttgcccc ggagatcacc atggacgact ttctctatct ctacgatcta   11040
ggaagaaagt tcgacggaga aggtgacgat accatgttca ccaccgataa tgagaagatt   11100
agcctcttca atttcagaaa gaatgctgac ccacagatgg ttagagaggc ctacgcggca   11160
ggtctgatca agacgatcta cccgagtaat aatctccagg agatcaaata ccttcccaag   11220
aaggttaaag atgcagtcaa aagattcagg actaactgca tcaagaacac agagaaagat   11280
atatttctca agatcagaag tactattcca gtatggacga ttcaaggctt gcttcataaa   11340
ccaaggcaag taatagagat tggagtctct aagaaagtag ttcctactga atcaaaggcc   11400
atggagtcaa aaattcagat cgaggatcta acagaactcg ccgtgaagac tggcgaacag   11460
ttcatacaga gtcttttacg actcaatgac aagaagaaaa tcttcgtcaa catggtggag   11520
cacgacactc tcgtctactc caagaatatc aaagatacag tctcagaaga ccaaagggct   11580
attgagactt tcaacaaagg gtaatatcg ggaaacctcc tcggattcca ttgcccagct   11640
atctgtcact tcatcaaaag gacagtagaa aaggaaggtg gcacctacaa atgccatcat   11700
tgcgataaag gaaaggctat cgttcaagat gcctctgccg acagtggtcc caaagatgga   11760
cccccaccca cgaggagcat cgtggaaaaa gaagacgttc caaccacgtc ttcaaagcaa   11820
gtggattgat gtgatatctc cactgacgta agggatgacg cacaatccca ctatccttcg   11880
caagacccct cctctatata aggaagttca tttcatttgg agaggactcc ggtatttta   11940
caacaatacc acaacaaaac aaacaacaaa caacattaca atttactatt ctagtcgaaa   12000
tggatcatgc aacattagca atgatactag ccatttggtt catttctttt catttcataa   12060
aattactttt tagccaacaa actaccaaac ttcttcctcc tggtccaaaa ccattgccaa   12120
taattggtaa catcttagaa gttggtaaaa aaccccatcg ttcatttgct aatcttgcta   12180
aaattcacgg ccctttaata tcgttacgtc taggaagtgt aacaactatt gttgtatcat   12240
cagcagatgt agctaaagaa atgttcttaa aaaaagacca ccctctttct aaccgtacta   12300
ttcctaattc tgtcacggcc ggtgaccacc ataaactcac catgtcgtgg ttgcccgttt   12360
cgccgaaatg gcggaatttt cgtaagatta cagccgtcca tttgctttct cctcaaagac   12420
ttgatgcttg ccaaaccttt cgccatgcca aggtgcaaca gctttatgaa tatgtacaag   12480
aatgtgcaca aaaaggccaa gctgttgata ttggcaaagc tgcatttact acctcccttta   12540
atttgttatc taaactattc ttttcagtgg aattagccca ccataaatca cacacttctc   12600
aagagtttaa ggaactaata tggaacatta tggaagatat tgggaaacct aattatgctg   12660
attattttcc tattttaggc tgtgttgatc catcaggtat tcgtcgaaga ttagcatgta   12720
gttttgacaa gttgattgca gttttttcagg gtataatatg tgaaaggctt gcgcctgatt   12780
cttcaactac aacaacaacg acgactgatg atgtgctaga cgttcttctt cagctcttca   12840
aacaaaatga gctcactatg ggcgagatta accatttgct cgtcgacatt tttgatgctg   12900
gaacagacac tacatcaagt acttttgagt gggtcatgac agagttaatt aggaatcctg   12960
aaatgatgga aaaggctcaa gaagaaatta agcaagtatt gggcaaagat aaacaaattc   13020
```

```
aggaatcaga cattattaac ctaccttact tacaagccat tatcaaagaa actttgcgac   13080
tacatccacc aactgtattt cttttgcctc gtaaagccga cactgatgtt gaactatatg   13140
gttatattgt gcctaaagat gcacaaatac ttgttaactt atgggctatt ggaagagatc   13200
ctaatgcatg gcaaaatgct gatatttttt cgcccgaaag atttataggg tgtgaaaytg   13260
atgtcaaagg aagagatttt ggactcttac cttttggagc cggaagaagg atatgtcctg   13320
ggatgaattt ggccattaga atgttaactt tgatgctagc tactttactt caattcttca   13380
attggaagct tgaaggagac ataagtccaa aagacttaga catggatgag aaatttggga   13440
ttgcgttaca aaagacaaag cctttaaaac ttattccaat acctaggtat tgataataag   13500
cttgctctca agatcaaagg cttaaaaagc tggggtttta tgaatgggat caaagtttct   13560
ttttttcttt tatatttgct tctccatttg tttgtttcat ttcccttttt gttttcgttt   13620
ctatgatgca cttgtgtgtg acaaactctc tgggttttta cttacgtctg cgtttcaaaa   13680
aaaaaaaccg ctttcgtttt gcgttttagt cccattgttt tgtagctctg agtgatcgaa   13740
ttgatgcctc tttattcctt ttgttcccta taatttcttt caaaactcag aagaaaaacc   13800
ttgaaactct ttgcaatgtt aatataagta ttgtataaga ttttattga tttggttatt   13860 agtcttactt ttgctacctc catcttcact tggaactgat attctgaata gttaaagcgt   13920
tacatgtctt ccattcacaa atgaacttaa actagcacaa agtcagatat tttaagatcg   13980
caccatttta tataacccca atcgtcaatt ctactgtttc aagttttaca ccaaaacaat   14040
tacgaggtgt atctattcgt tactcttttc gcttattaat ccttttacat gatgcaaaat   14100
ataacaaatt aatttcaaat tgtcctgcac atttggttta tacatcttga ttccaaaaag   14160
tcgctgtcag gaggtcgacg agtcagtaat aaacggcgtc aaagtggttg cagccggcac   14220
acacgagtcg tgtttatcaa ctcaaagcac aaatactttt cctcaaccta aaataaggc   14280 aattagccaa aaacaacttt gcgtgtaaac aacgctcaat acacgtgtca ttttattatt   14340
agctattgct tcaccgcctt agctttctcg tgacctagtc gtcctcgtct tttcttcttc   14400
ttcttctata aaacaatacc caaagagctc ttcttcttca caattcagat ttcaatttct   14460
caaaatctta aaaactttct ctcaattctc tctaccgtga tcaaggtaaa tttctgtgtt   14520
ccttattctc tcaaaatctt cgattttgtt ttcgttcgat cccaatttcg tatatgttct   14580
ttggtttaga ttctgttaat cttagatcga agacgatttt ctgggtttga tcgttagata   14640
tcatcttaat tctcgattag ggtttcatag atatcatccg atttgttcaa ataatttgag   14700
ttttgtcgaa taattactct tcgatttgtg atttctatct agatctggtg ttagtttcta   14760
gtttgtgcga tcgaatttgt cgattaatct gagttttttct gattaacaga atgaccgcca   14820
ttaaaatgaa caccaatggt gaaggtgaaa cacaacatat actaatgata cctttcatgg   14880
cgcaagggca tttacgtcct ttccttgagc ttgctatgtt tctatataaa cgaagtcatt   14940
ttatcattac tcttcttact accccgctca atgcgggttt cctacgacat ctccttcacc   15000
accatagcta ttctagctcg gggatcagaa ttgtcgagtt accttcaac tcaaccaatc   15060 atggtcttcc acctggcatt gaaaacactg ataaacttac actcccactt gtagtatcac   15120
tttttcattc aaccatttct cttgacccte accttagaga ttatatttcc cgccatttct   15180
cccctgcgcg ccctcctctg tgtgtcatac atgatgtgtt ccttggttgg gttgatcaag   15240
ttgctaaaga cgtgggctca actggtgttg ttttttactac gggtggcgcg tatggtacaa   15300
gcgcatatgt gtccatttgg aatgatctgc ctcaccagaa ttactctgat gatcaagagt   15360
ttccgcttcc tggtttcccg gagaatcata aattccgacg ttctcaactt catcggtttc   15420
```

```
tgaggtatgc cgatggatca gatgattggt cgaaatattt ccaaccgcaa ttgaggcaat    15480
caatgaagag ttttggatgg ctatgtaatt cagttgagga aatcgaaaca cttgggttta    15540
gtatcctcag gaactacact aaactaccca tttggggtat tggaccgttg atagcttcac    15600
ctgtacaaca ttcatcatct gataataaca gtactggtgc cgagtttgtt caatggttga    15660
gcttgaaaga accagattct gtattataca tctcatttgg atcacagaac acaatttcac    15720
caacccagat gatggaacta gcagccggtt tggagtcaag tgagaagccg ttttgtggg     15780 tgattcgagc accatttggg ttcgatatca atgaggaaat gagrccagaa tggctaccag    15840
agggattcga ggagcgaatg aaggtgaaaa aacaaggaaa gttggtgtat aagttgggac    15900
cacagttgga gatacttaac catgagtcaa tcggagggtt cttaactcat tgtgggtgga    15960
attcgatcct tgagtcactt cgagaaggtg tgcctatgtt agggtggcca ttggcagccg    16020
aacaagctta taatttgaag tatttggagg acgaaatggg ggttgcagtc gagttagcga    16080
ggggattgga aggagagata agtaaagaga aagtgaagag aattgtggag atgattttag    16140
agagaaatga aggaagtaaa ggatgggaaa tgaaaaatag agcagtagaa atggggaaga    16200
aacttaaaga cgctgtcaat gaggagaagg aactgaaggg ttcttctgtt aaggcaatag    16260
atgatttctt agatgcggtc atgcaagcta agttggaacc ttctcttcaa taagcttcgg    16320
ccatgctaga gtccgcaaaa atcaccagtc tctctctaca aatctatctc tctctatttt    16380
tctccagaat aatgtgtgag tagttcccag ataagggaat tagggttctt ataggggtttc   16440 gctcatgtgt tgagcatata agaaacccct agtatgtatt tgtatttgta aaatacttct    16500
atcaataaaa tttctaattc ctaaaaccaa aatccagtga cctcgctgtc aggagactag    16560
agccaagctg atctcctttg ccccggagat caccatggac gactttctct atctctacga    16620
tctaggaaga aagttcgacg gagaaggtga cgataccatg ttcaccaccg ataatgagaa    16680
gattagcctc ttcaatttca gaaagaatgc tgacccacag atggttagag aggcctacgc    16740
ggcaggtctg atcaagacga tctacccgag taataatctc caggagatca aatacttcc    16800 caagaaggtt aaagatgcag tcaaaagatt caggactaac tgcatcaaga acacagagaa    16860
agatatattt ctcaagatca gaagtactat tccagtatgg acgattcaag gcttgcttca    16920
taaaccaagg caagtaatag agattggagt ctctaagaaa gtagttccta ctgaatcaaa    16980
ggccatggag tcaaaaattc agatcgagga tctaacagaa ctcgccgtga agactggcga    17040
acagttcata cagagtcttt tacgactcaa tgacaagaag aaaatcttcg tcaacatggt    17100
ggagcacgac actctcgtct actccaagaa tatcaaagat acagtctcag aagaccaaag    17160
ggctattgag acttttcaac aaagggtaat atcgggaaac ctcctcggat tccattgccc    17220
agctatctgt cacttcatca aaaggacagt agaaaaggaa ggtggcacct acaaatgcca    17280
tcattgcgat aaaggaaagg ctatcgttca agatgcctct gccgacagtg gtcccaaaga    17340
tggaccccca cccacgagga gcatcgtgga aaaagaagac gttccaacca cgtcttcaaa    17400
gcaagtggat tgatgtgata tctccactga cgtaagggat gacgcacaat cccactatcc    17460
ttcgcaagac ccttcctcta tataaggaag ttcatttcat ttggagagga ctccggtatt    17520
tttacaacaa taccacaaca aaacaaacaa caaacaacat tacaatttac tattctagtc    17580
gaaatggata acgcaacact tgctgtgatc cttttccattt tgtttgtgtt ttaccacatt    17640
ttcaaatcct ttttcaccaa ttcttcatct cgtaggcttc ctcctggtcc caacccgtg    17700 ccaattttg gcaacatttt cgatcttggc gaaaagcctc atcgatcttt tgccaatcta   17760
```

```
tctaaaattc acggcccttt gattagccta aagttaggaa gtgtaacaac tattgttgtt    17820
tcctcggcct ctgtggccga ggaaatgttc cttaaaaatg accaagcact tgctaaccga    17880
accattcctg actcggttag ggctggtgac cacgacaaat tatccatgtc gtggttgcct    17940
gtttcccaaa aatggagaaa tatgagaaaa atctccgctg tccaattact ctccaaccaa    18000
aaacttgatg ctagtcaacc tcttagacaa gctaaggtga acaacttttt atcatacgta    18060
caagtttgtt ccgaaaaaat gcaacccgtc gatattggac gggccgcatt tacaacgtca    18120
cttaatttat tatcaaacac attttttctca atcgaattag caagtcatga atctagtgct    18180
tcccaagagt ttaaacaact catgtggaat attatggagg aaattggaag gcctaattat    18240
gctgattttt tccctattct tggttacatt gatccctttg gtataagacg tcgtttggct    18300
ggttactttg ataaactcat tgatgttttc caagacatta ttcgtgaaag acaaaagctt    18360
cgatcttcta attcttccgg cgcaaaacaa acaaatgaca ttcttgatac tcttcttaaa    18420
ctccatgaag ataatgagtt gagtatgcct gaaattaatc accttctcgt ggatatcttt    18480
gacgccggaa cagacacaac agcaagcaca ttagaatggg caatggccga acttgtgaaa    18540
aacccggaaa tgatgactaa agttcaaatt gaaatcgaac aagctcttgg aaaagattgc    18600
ttagacatac aagaatccga catctcaaaa ctaccttatt tacaagccat tataaaagaa    18660
acgttacgtt tacaccctcc tactgtgttt ttgctgcctc gaaaggcaga caatgacgta    18720
gagttatatg gctacgttgt accaagaaat gctcaagtcc ttgtcaatct ttgggcaatt    18780
ggtcgtgatc caaaggtatg gaaaaatccg gaagtatttt ctcctgaaag gttttttagat    18840
tgcaatatcg attataaagg acgagatttc gaacttttac cctttggtgc tggtagaagg    18900
atatgccctg gacttacttt ggcatataga atgttgaact tgatgttggc tactcttctt    18960
caaaactaca attggaaact tgaagatggt atcaatccta aggatttaga catggatgag    19020
aaatttggga ttacattgca aaaggttaaa cctcttcaag ttattccagt tcccagaaac    19080
taggcttgct ctcaagatca aaggcttaaa aagctgggt ttatgaatg ggatcaaagt    19140
ttctttttt cttttatatt tgcttctcca tttgttgtt tcattccct ttttgttttc    19200
gtttctatga tgcacttgtg tgtgacaaac tctctgggtt tttacttacg tctgcgttttc    19260
aaaaaaaaaa accgctttcg ttttgcgttt tagtcccatt gttttgtagc tctgagtgat    19320
cgaattgatg cctctttatt cctttttgttc cctataattt ctttcaaaac tcagaagaaa    19380
aaccttgaaa ctctttgcaa tgttaatata agtattgtat aagatttta ttgatttggt    19440
tattagtctt acttttgcta cctccatctt cacttggaac tgatattctg aatagttaaa    19500
gcgttacatg tcttccattc acaaatgaac ttaaactagc acaaagtcag atatttaag    19560
atcgcaccat tttatataac cccaatcgtc aattctactg tttcaagttt tacaccaaaa    19620
caattacgag gtgtatctat tcgttactct tttcgcttat taatccttt acatgatgca    19680
aaatataaca aattaatttc aaattgtcct gcacatttgg tttatacatc ttgattccaa    19740
aaagt                                                                19745
```

<210> SEQ ID NO 23
<211> LENGTH: 13992
<212> TYPE: DNA
<213> ORGANISM: Artificial Sequence
<220> FEATURE:
<223> OTHER INFORMATION: pX13

<400> SEQUENCE: 23

```
cgctgtcatg agacgaattc tgacaggata tattggcggg taaacctaag agaaaagagc    60
```

```
gtttattaga ataatcggat atttaaaagg gcgtgaaaag gtttatccgt tcgtccattt    120
gtatgtgcat gccaaccaca gggttcccct cgggatcaaa gtactttgat ccaacccctc    180
cgctgctata gtgcagtcgg cttctgacgt tcagtgcagc cgtcatctga aaacgacatg    240
tcgcacaagt cctaagttac gcgacaggct gccgccctgc ccttttcctg gcgttttctt    300
gtcgcgtgtt ttagtcgcat aaagtagaat acttgcgact agaaccggag acattacgcc    360
atgaacaaga gcgccgccgc tggcctgctg ggctatgccc gcgtcagcac cgacgaccag    420
gacttgacca accaacgggc cgaactgcac gcggccggct gcaccaagct gttttccgag    480
aagatcaccg gcaccaggcg cgaccgcccg gagctggcca ggatgcttga ccacctacgc    540
cctggcgacg ttgtgacagt gaccaggcta gaccgcctgg cccgcagcac ccgcgaccta    600
ctggacattg ccgagcgcat ccaggaggcc ggcgcgggcc tgcgtagcct ggcagagccg    660
tgggccgaca ccaccacgcc ggccggccgc atggtgttga ccgtgttcgc cggcattgcc    720
gagttcgagc gttccctaat catcgaccgc acccggagcg ggcgcgaggc cgccaaggcc    780
cgaggcgtga agtttggccc ccgccctacc ctcaccccgg cacagatcgc gcacgcccgc    840
gagctgatcg accaggaagg ccgcaccgtg aaagaggcgg ctgcactgct ggcgtgcat     900 cgctcgaccc tgtaccgcgc acttgagcgc agcgaggaag tgacgcccac cgaggccagg    960
cggcgcggtg ccttccgtga ggacgcattg accgaggccg acgccctggc ggccgccgag   1020
aatgaacgcc aagaggaaca agcatgaaac cgcaccagga cggccaggac gaaccgtttt   1080
tcattaccga agagatcgag gcggagatga tcgcggccgg gtacgtgttc gagccgcccg   1140
cgcacctctc aaccgtgcgg ctgcatgaaa tcctggccgg tttgtctgat gccaagctgg   1200
cggcctggcc ggccagcttg gccgctgaag aaaccgagcg ccgccgtcta aaaaggtgat   1260
gtgtatttga gtaaaacagc ttgcgtcatg cggtcgctgc gtatatgatc cgatgagtaa   1320
ataaacaaat acgcaagggg aacgcatgaa ggttatcgct gtacttaacc agaaaggcgg   1380
gtcaggcaag acgaccatcg gaacccatct agcccgcgcc ctgcaactcg ccggggccga   1440
tgttctgtta gtcgattccg atcccccaggg cagtgcccgc gattgggcgg ccgtgcggga   1500
agatcaaccg ctaaccgttg tcggcatcga ccgcccgacg attgaccgcg acgtgaaggc   1560
catcggccgg cgcgacttcg tagtgatcga cggagcgccc caggcggcgg acttggctgt   1620
gtccgcgatc aaggcagccg acttcgtgct gattccggtg cagccaagcc cttacgacat   1680
atgggccacc gccgacctgg tggagctggt taagcagcgc attgaggtca cggatggaag   1740
gctacaagcg gcctttgtcg tgtcgcgggc gatcaaaggc acgcgcatcg gcggtgaggt   1800
tgccgaggcg ctggccgggt acgagctgcc cattcttgag tcccgtatca cgcagcgcgt   1860
gagctaccca ggcactgccg ccgccggcac aaccgttctt gaatcagaac ccgagggcga   1920
cgctgcccgc gaggtccagg cgctggccgc tgaaattaaa tcaaaactca tttgagttaa   1980
tgaggtaaag agaaaatgag caaaagcaca aacacgctaa gtgccggccg tccgagcgca   2040
cgcagcagca aggctgcaac gttggccagc ctggcagaca cgccagccat gaagcgggtc   2100
aactttcagt tgccggcgga ggatcacacc aagctgaaga tgtacgcggt acgccaaggc   2160
aagaccatta ccgagctgct atctgaatag atcgcgcagc taccagagta atgagcaaa    2220 tgaataaatg agtagatgaa ttttagcggc taaaggaggc ggcatggaaa atcaagaaca   2280
accaggcacc gacgccgtgg aatgccccat gtgtggagga acgggcggtt ggccaggcgt   2340
aagcggctgg gttgtctgcc ggccctgcaa tggcactgga accccaagc ccgaggaatc    2400
```

```
ggcgtgacgg tcgcaaacca tccggcccgg tacaaatcgg cgcggcgctg ggtgatgacc    2460
tggtggagaa gttgaaggcc gcgcaggccg cccagcggca acgcatcgag gcagaagcac    2520
gccccggtga atcgtggcaa gcggccgctg atcgaatccg caaagaatcc cggcaaccgc    2580
cggcagccgg tgcgccgtcg attaggaagc cgcccaaggg cgacgagcaa ccagattttt    2640
tcgttccgat gctctatgac gtgggcaccc gcgatagtcg cagcatcatg gacgtggccg    2700
ttttccgtct gtcgaagcgt gaccgacgag ctggcgaggt gatccgctac gagcttccag    2760
acgggcacgt agaggtttcc gcagggccgg ccggcatggc cagtgtgtgg gattacgacc    2820
tggtactgat ggcggttttcc catctaaccg aatccatgaa ccgataccgg gaagggaagg    2880
gagacaagcc cggccgcgtg ttccgtccac acgttgcgga cgtactcaag ttctgccggc    2940
gagccgatgg cggaaagcag aaagacgacc tggtagaaac ctgcattcgg ttaaacacca    3000
cgcacgttgc catgcagcgt acgaagaagg ccaagaacgg ccgcctggtg acggtatccg    3060
agggtgaagc cttgattagc cgctacaaga tcgtaaagag cgaaaccggg cggccggagt    3120
acatcgagat cgagctagct gattggatgt accgcgagat cacagaaggc aagaacccgg    3180
acgtgctgac ggttcacccc gattacttttt tgatcgatcc cggcatcggc cgttttctct    3240
accgcctggc acgccgcgcc gcaggcaagg cagaagccag atggttgttc aagacgatct    3300
acgaacgcag tggcagcgcc ggagagttca agaagttctg tttcaccgtg cgcaagctga    3360
tcgggtcaaa tgacctgccg gagtacgatt tgaaggagga ggcggggcag gctggcccga    3420
tcctagtcat gcgctaccgc aacctgatcg agggcgaagc atccgccggt tcctaatgta    3480
cggagcagat gctagggcaa attgccctag caggggaaaa aggtcgaaaa ggactcttttc    3540 ctgtggatag cacgtacatt gggaacccaa agccgtacat tgggaaccgg aacccgtaca    3600
ttgggaaccc aaagccgtac attgggaacc ggtcacacat gtaagtgact gatataaaag    3660 agaaaaagg cgattttttcc gcctaaaact cttttaaaact tattaaaact cttaaaaccc    3720
gcctggcctg tgcataactg tctgccagc gcacagccga agagctgcaa aaagcgccta    3780
cccttcggtc gctgcgctcc ctacgccccg ccgcttcgcg tcggcctatc gcggccgctg    3840
gccgctcaaa aatggctggc ctacggccag gcaatctacc agggcgcgga caagccgcgc    3900
cgtcgccact cgaccgccgg cgcccacatc aaggcaccct gcctcgcgcg tttcggtgat    3960
gacggtgaaa acctctgaca catgcagctc ccggtgacgg tcacagcttg tctgtaagcg    4020
gatgccggga gcagacaagc ccgtcagggc gcgtcagcgg gtgttggcgg gtgtcggggc    4080
gcagccatga cccagtcacg tagcgatagc ggagtgtata ctggcttaac tatgcggcat    4140
cagagcagat tgtactgaga gtgcaccata tgcggtgtga ataccgcac agatgcgtaa    4200 ggagaaaata ccgcatcagg cgctcttccg cttcctcgct cactgactcg ctgcgctcgg    4260
tcgttcggct gcggcgagcg gtatcagctc actcaaaggc ggtaatacgg ttatccacag    4320
aatcagggga taacgcagga agaacatgt gagcaaaagg ccagcaaaag gccaggaacc    4380
gtaaaaaggc cgcgttgctg gcgttttttcc ataggctccg ccccctgac gagcatcaca    4440 aaaatcgacg ctcaagtcag aggtggcgaa acccgacagg actataaaga taccaggcgt    4500
ttccccctgg aagctccctc gtgcgctctc ctgttccgac cctgccgctt accggatacc    4560
tgtccgcctt tctcccttcg ggaagcgtgg cgctttctca gctcacgc tgtaggtatc    4620 tcagttcggt gtaggtcgtt cgctccaagc tgggctgtgt gcacgaaccc ccgttcagc    4680 ccgaccgctg cgccttatcc ggtaactatc gtcttgagtc caacccggta agacacgact    4740
tatcgccact ggcagcagcc actggtaaca ggattagcag agcgaggtat gtaggcggtg    4800
```

```
ctacagagtt cttgaagtgg tggcctaact acggctacac tagaaggaca gtatttggta    4860
tctgcgctct gctgaagcca gttaccttcg gaaaaagagt tggtagctct tgatccggca    4920
aacaaaccac cgctggtagc ggtggttttt ttgtttgcaa gcagcagatt acgcgcagaa    4980
aaaaaggatc tcaagaagat cctttgatct tttctacggg gtctgacgct cagtggaacg    5040
aaaactcacg ttaagggatt ttggtcatgc attctaggtg attagaaaaa ctcatcgagc    5100
atcaaatgaa actgcaattt attcatatca ggattatcaa taccatattt ttgaaaaagc    5160
cgtttctgta atgaaggaga aaactcaccg aggcagttcc ataggatggc aagatcctgg    5220
tatcggtctg cgattccgac tcgtccaaca tcaatacaac ctattaattt ccctcgtca    5280 aaaataaggt tatcaagtga gaaatcacca tgagtgacga ctgaatccgg tgagaatggc    5340
aaaagtttat gcatttcttt ccagacttgt tcaacaggcc agccattacg ctcgtcatca    5400
aaatcactcg catcaaccaa accgttattc attcgtgatt gcgcctgagc gagtcgaaat    5460
acgcgatcgc tgttaaaagg acaattacaa acaggaatcg aatgcaaccg gcgcaggaac    5520
actgccagcg catcaacaat attttcacct gaatcaggat attcttctaa tacctggaat    5580
gctgttttcc ctgggatcgc agtggtgagt aaccatgcat catcaggagt acggataaaa    5640
tgcttgatgg tcggaagagg cataaattcc gtcagccagt ttagtctgac catctcatct    5700
gtaacatcat tggcaacgct acctttgcca tgtttcagaa acaactctgg cgcatcgggc    5760
ttcccataca atcggtagat tgtcgcacct gattgcccga cattatcgcg agcccattta    5820
tacccatata aatcagcatc catgttggaa tttaatcgcg gccttgagca agacgtttcc    5880
cgttgaatat ggctcataac agaacttatt atttccttcc tcttttctac agtatttaaa    5940
gataccccaa gaagctaatt ataacaagac gaactccaat tcactgttcc ttgcattcta    6000
aaaccttaaa taccagaaaa cagcttttc aaagttgttt tcaaagttgg cgtataacat    6060
agtatcgacg gagccgattt tgaaaccgcg gtgatcacag gcagcaacgc tctgtcatcg    6120
ttacaatcaa catgctaccc tccgcgagat catccgtgtt tcaaacccgg cagcttagtt    6180
gccgttcttc cgaatagcat cggtaacatg agcaaagtct gccgccttac aacggctctc    6240
ccgctgacgc cgtcccggac tgatgggctg cctgtatcga gtggtgattt tgtgccgagc    6300
tgccggtcgg ggagctgttg gctggctggt ggcaggatat attgtggtgt aaacataacg    6360
aattcgtctc aggagagcgt cgatctagta acatagatga caccgcgcgc gataatttat    6420
cctagtttgc gcgctatatt ttgttttcta tcgcgtatta aatgtataat gcgggactc    6480 taatcataaa aacccatctc ataaataacg tcatgcatta catgttaatt attacatgct    6540
taacgtaatt caacagaaat tatatgataa tcatcgcaag accggcaaca ggattcaatc    6600
ttaagaaact ttattgccaa atgtttgaac gatctgcttc gacgcactcc ttctttactc    6660
caccatctcg tccttattga aaacgtgggt agcaccaaaa cgaatcaagt cgctggaact    6720
gaagttacca atcacgctgg atgatttgcc agttggatta atcttgcctt tccccgcatg    6780
aataatattg atgaatgcat gcgtgagggg tagttcgatg ttggcaatag ctgcaattgc    6840
cgcgacatcc tccaacgagc ataattcttc agaaaaatag cgatgttcca tgttgtcagg    6900
gcatgcatga tgcacgttat gaggtgacgg tgctaggcag tattccctca agtttcata    6960 gtcagtatca tattcatcat tgcattcctg caagagagaa ttgagacgca atccacacgc    7020
tgcggcaacc ttccggcgtt cgtggtctat ttgctcttgg acgttgcaaa cgtaagtgtt    7080
ggatcggggt gggcgaagaa ctccagcatg agatcccgc gctggaggat catccagccg    7140
```

```
gcgtcccgga aaacgattcc gaagcccaac ctttcataga aggcggcggt ggaatcgaaa    7200
tctcgtgatg gcaggttggg cgtcgcttgg tcggtcattt cgaacccag agtcccgctc     7260 agaagaactc gtcaagaagg cgatagaagg cgatgcgctg cgaatcggga gcggcgatac    7320
cgtaaagcac gaggaagcgg tcagcccatt cgccgccaag ctcttcagca atatcacggg    7380
tagccaacgc tatgtcctga tagcggtccg ccacacccag ccggccacag tcgatgaatc    7440
cagaaaagcg gccattttcc accatgatat tcggcaagca ggcatcgcca tgggtcacga    7500
cgagatcctc gccgtcgggc atgcgcgcct tgagcctggc gaacagttcg gctggcgcga    7560 gccctgatg ctcttcgtcc agatcatcct gatcgacaag accggcttcc atccgagtac    7620
gtgctcgctc gatgcgatgt ttcgcttggt ggtcgaatgg gcaggtagcc ggatcaagcg    7680
tatgcagccg ccgcattgca tcagccatga tggatacttt ctcggcagga gcaaggtgag    7740
atgacaggag atcctgcccc ggcacttcgc ccaatagcag ccagtccctt cccgcttcag    7800
tgacaacgtc gagcacagct gcgcaaggaa cgcccgtcgt ggccagccac gatagccgcg    7860
ctgcctcgtc ctgcagttca ttcagggcac cggacaggtc ggtcttgaca aaagaaccg     7920 ggcgccctg cgctgacagc cggaacacgg cggcatcaga gcagccgatt gtctgttgtg    7980
cccagtcata gccgaatagc ctctccaccc aagcggccgg agaacctgcc cggatccggg    8040
cggaaatagg taaagaagtt gcggataagg taattgccat tgcagattat ttggattgag    8100
agtgaatatg agactctaat tggataccga ggggaattta tggaacgtca gtggagcatt    8160
tttgacaaga aatatttgct agctgatagt gaccttaggc gactttgaa cgcgcaataa     8220 tggtttctga cgtatgtgct tagctcatta aactccagaa accctccgt caggagacta     8280 gagccaagct gatctccttt gccccggaga tcaccatgga cgactttctc tatctctacg    8340
atctaggaag aaagttcgac ggagaaggtg acgataccat gttcaccacc gataatgaga    8400
agattagcct cttcaatttc agaaagaatg ctgacccaca gatggttaga gaggcctacg    8460
cggcaggtct gatcaagacg atctacccga gtaataatct ccaggagatc aaataccttc    8520
ccaagaaggt taaagatgca gtcaaaagat tcaggactaa ctgcatcaag aacacagaga    8580
aagatatatt tctcaagatc agaagtacta ttccagtatg gacgattcaa ggcttgcttc    8640
ataaaccaag gcaagtaata gagattggag tctctaagaa agtagttcct actgaatcaa    8700
aggccatgga gtcaaaaatt cagatcgagg atctaacaga actcgccgtg aagactggcg    8760
aacagttcat acagagtctt ttacgactca atgacaagaa gaaaatcttc gtcaacatgg    8820
tggagcacga cactctcgtc tactccaaga atatcaaaga tacagtctca gaagaccaaa    8880
gggctattga cttttcaa caaagggtaa tatcgggaaa cctcctcgga ttccattgcc      8940
cagctatctg tcacttcatc aaaaggacag tagaaaagga aggtggcacc tacaaatgcc    9000
atcattgcga taaggaaag gctatcgttc aagatgcctc tgccgacagt ggtcccaaag     9060
atggaccccc acccacgagg agcatcgtgg aaaaagaaga cgttccaacc acgtcttcaa    9120
agcaagtgga ttgatgtgat atctccactg acgtaaggga tgacgcacaa tcccactatc    9180
cttcgcaaga cccttcctct atataaggaa gttcatttca tttggagagg actccggtat    9240
ttttacaaca ataccacaac aaaacaaaca acaaacaaca ttacaattta ctattctagt    9300
cgaaatgaaa atgatgaatg gtgaagatgc taatgatcaa atgatcaaag aaagcttctt    9360
cataacacat ggaaacccaa tattaacagt agaagacaca catccattaa gacctttctt    9420
tgaaacttgg agagagaaaa tcttttctaa gaaacctaag gcaattctta ttatttctgg    9480
tcattgggaa actgttaaac ctactgttaa tgctgtccat atcaatgata ctatccatga    9540
```

```
ttttgatgac tatcctgctg ctatgtacca gttcaagtat ccagctcctg gggaaccaga    9600
attggcaaga aaagtagagg aaattctgaa aaaatcgggt ttcgaaacgg cggaaactga    9660
tcaaaaacgt gggcttgatc atggtgcatg ggtacctcta atgctaatgt atcctgaggc    9720
tgatatacca gtatgtcagc tctcagttca gccgcattta gatggaacat accattacaa    9780
cttaggacga gcattggctc ccttgaaaaa cgacggcgta ttaatcattg gttcaggaag    9840
tgcaactcac cctttggatg aaactcctca ttattttgat ggagttgcac cttgggcagc    9900
tgcctttgat tcatggcttc gtaaagctct cattaatgga aggtttgaag aagtgaatat    9960
atatgaaagc aaagcaccaa attggaaatt agcacatcct ttcccagaac atttttatcc   10020
attgcatgtt gttcttggcg ctgctggtga aaaatggaag gcagagctta ttcatagcag   10080
ttgggatcat ggcaccttgt gtcatggctc ctacaagttc acttcagcct aggcttggaa   10140
tggatcttcg atcccgatcg ttcaaacatt tggcaataaa gtttcttaag attgaatcct   10200
gttgccggtc ttgcgacgat tatcatataa tttctgttga attacgttaa gcatgtaata   10260
attaacatgt aatgcatgac gttatttatg agatgggttt ttatgattag agtcccgcaa   10320
ttatacattt aatacgcgat agaaaacaaa atatagcgcg caaactagga taaattatcg   10380
cgcdcggtgt catctatgtt actagatcgg gaattgccaa gctaattctt gaagacgaaa   10440
gggcctcgtg atacgcctat ttttataggt taatgtcatg ataataatgg tttcttagac   10500
gtcaggtggc acttttcggg gaaatgtgcg cggaacccct atttgtttat ttttctaaat   10560
acattcaaat atgtatccgc tcatgagaca ataaccctga taaatgcttc aataatggga   10620
ccgactcgcg ctgtcaggag actagagcca agctgatctc ctttgccccg gagatcacca   10680
tggacgactt tctctatctc tacgatctag gaagaaagtt cgacggagaa ggtgacgata   10740
ccatgttcac caccgataat gagaagatta gcctcttcaa tttcagaaag aatgctgacc   10800
cacagatggt tagagaggcc tacgcggcag gtctgatcaa gacgatctac ccgagtaata   10860
atctccagga gatcaaatac cttcccaaga aggttaaaga tgcagtcaaa agattcagga   10920
ctaactgcat caagaacaca gagaaagata tatttctcaa gatcagaagt actattccag   10980
tatggacgat tcaaggcttg cttcataaac caaggcaagt aatagagatt ggagtctcta   11040
agaaagtagt tcctactgaa tcaaaggcca tggagtcaaa aattcagatc gaggatctaa   11100
cagaactcgc cgtgaagact ggcgaacagt tcatacagag tcttttacga ctcaatgaca   11160
agaagaaaat cttcgtcaac atggtggagc acgacactct cgtctactcc aagaatatca   11220
aagatacagt ctcagaagac caaagggcta ttgagacttt tcaacaaagg gtaatatcgg   11280
gaaacctcct cggattccat tgcccagcta tctgtcactt catcaaaagg acagtagaaa   11340
aggaaggtgg cacctacaaa tgccatcatt gcgataaagg aaaggctatc gttcaagatg   11400
cctctgccga cagtggtccc aaagatggac ccccacccac gaggagcatc gtggaaaaag   11460
aagacgttcc aaccacgtct tcaaagcaag tggattgatg tgatatctcc actgacgtaa   11520
gggatgacgc acaatcccac tatccttcgc aagacccttc ctctatataa ggaagttcat   11580
ttcatttgga gaggactccg gtattttac aacaatacca caacaaaaca acaacaaac    11640 aacattacaa tttactattc tagtcgaaat ggataacgca acacttgctg tgatcctttc   11700
catttgtttt gtgttttacc acattttcaa atccttttc accaattctt catctcgtag    11760
gcttcctcct ggtcccaaac ccgtgccaat ttttggcaac attttcgatc ttggcgaaaa   11820
gcctcatcga tcttttgcca atctatctaa aattcacggc cctttgatta gcctaaagtt   11880
```

```
aggaagtgta acaactattg ttgtttcctc ggcctctgtg gccgaggaaa tgttccttaa    11940
aaatgaccaa gcacttgcta accgaaccat tcctgactcg gttagggctg gtgaccacga    12000
caaattatcc atgtcgtggt tgcctgtttc ccaaaaatgg agaaatatga gaaaaatctc    12060
cgctgtccaa ttactctcca accaaaaact tgatgctagt caacctctta gacaagctaa    12120
ggtgaaacaa cttttatcat acgtacaagt tgttccgaa aaaatgcaac ccgtcgatat     12180
tggacgggcc gcatttacaa cgtcacttaa tttattatca aacacatttt tctcaatcga    12240
attagcaagt catgaatcta gtgcttccca agagtttaaa caactcatgt ggaatattat    12300
ggaggaaatt ggaaggccta attatgctga tttttttccct attcttggtt acattgatcc   12360
ctttggtata agacgtcgtt tggctggtta ctttgataaa ctcattgatg ttttccaaga    12420
cattattcgt gaaagacaaa agcttcgatc ttctaattct tccggcgcaa aacaaacaaa    12480
tgacattctt gatactcttc ttaaactcca tgaagataat gagttgagta tgcctgaaat    12540
taatcacctt ctcgtggata tctttgacgc cggaacagac acaacagcaa gcacattaga    12600
atgggcaatg gccgaacttg tgaaaaaccc ggaaatgatg actaaagttc aaattgaaat    12660
cgaacaagct cttggaaaag attgcttaga catacaagaa tccgacatct caaaactacc    12720
ttatttacaa gccattataa agaaacgtt acgtttacac cctcctactg tgttttgct     12780 gcctcgaaag gcagacaatg acgtagagtt atatggctac gttgtaccaa agaatgctca    12840
agtccttgtc aatctttggg caattggtcg tgatccaaag gtatggaaaa atccggaagt    12900
attttctcct gaaaggtttt tagattgcaa tatcgattat aaaggacgag atttcgaact    12960 tttaccctt ggtgctggta gaaggatatg ccctggactt actttggcat atagaatgtt     13020
gaacttgatg ttggctactc ttcttcaaaa ctacaattgg aaacttgaag atggtatcaa    13080
tcctaaggat ttagacatgg atgagaaatt tgggattaca ttgcaaaagg ttaaacctct    13140
tcaagttatt ccagttccca gaaactaggc ttgctctcaa gatcaaaggc ttaaaaagct    13200
ggggttttat gaatgggatc aaagtttctt ttttttcttttt atatttgctt ctccatttgt  13260
ttgtttcatt tccctttttg ttttcgtttc tatgatgcac ttgtgtgtga caaactctct    13320 gggttttac ttacgtctgc gtttcaaaaa aaaaaaccgc tttcgttttg cgttttagtc     13380
ccattgtttt gtagctctga gtgatcgaat tgatgcctct ttattccttt tgttccctat    13440
aatttctttc aaaactcaga agaaaaacct tgaaactctt tgcaatgtta atataagtat    13500
tgtataagat ttttattgat ttggttatta gtcttacttt tgctacctcc atcttcactt    13560
ggaactgata ttctgaatag ttaaagcgtt acatgtcttc cattcacaaa tgaacttaaa    13620
ctagcacaaa gtcagatatt ttaagatcgc accattttat ataaccccaa tcgtcaattc    13680
tactgtttca agttttacac caaaacaatt acgaggtgta tctattcgtt actcttttcg    13740
cttattaatc cttttacatg atgcaaaata taacaaatta atttcaaatt gtcctgcaca    13800
tttggtttat acatcttgat tccaaaaagt cgctgtcagg agtctcaatg gtaactttac    13860 tctttatta accatacatt ttttttatt ttttcactt tgttcttcat ccactattgt       13920
tctttgttca tcttgaacaa aagctccctc cttctttgtt cttcatccac cattgttctt    13980
catcaatcat tt                                                        13992
```

<210> SEQ ID NO 24
<211> LENGTH: 11797
<212> TYPE: DNA
<213> ORGANISM: Artificial Sequence
<220> FEATURE:
<223> OTHER INFORMATION: pDOPA1 overexpression vector

<400> SEQUENCE: 24

```
cgctgtcatg agaccggatc ctgacaggat atattggcgg gtaaacctaa gagaaaagag      60
cgtttattag aataatcgga tatttaaaag ggcgtgaaaa ggtttatccg ttcgtccatt     120
tgtatgtgca tgccaaccac agggttcccc tcgggatcaa agtactttga tccaacccct    180
ccgctgctat agtgcagtcg gcttctgacg ttcagtgcag ccgtcatctg aaaacgacat    240
gtcgcacaag tcctaagtta cgcgacaggc tgccgccctg cccttttcct ggcgttttct    300
tgtcgcgtgt tttagtcgca taaagtagaa tacttgcgac tagaaccgga gacattacgc    360
catgaacaag agcgccgccg ctggcctgct gggctatgcc cgcgtcagca ccgacgacca    420
ggacttgacc aaccaacggg ccgaactgca cgcggccggc tgcaccaagc tgttttccga    480
gaagatcacc ggcaccaggc gcgaccgccc ggagctggcc aggatgcttg accacctacg    540
ccctggcgac gttgtgacag tgaccaggct agaccgcctg gcccgcagca ccgcgaccct    600
actggacatt gccgagcgca tccaggaggc cggcgcgggc ctgcgtagcc tggcagagcc    660
gtgggccgac accaccacgc cggccggccg catggtgttg accgtgttcg ccggcattgc    720
cgagttcgag cgttccctaa tcatcgaccg cacccgagc gggcgcgagg ccgccaaggc    780
ccgaggcgtg aagtttggcc cccgccctac cctcaccccg gcacagatcg cgcacgcccg    840
cgagctgatc gaccaggaag gccgcaccgt gaaagaggcg gctgcactgc ttggcgtgca    900
tcgctcgacc ctgtaccgcg cacttgagcg cagcgaggaa gtgacgccca ccgaggccag    960
gcggcgcggt gccttccgtg aggacgcatt gaccgaggcc gacgccctgg cggccgccga   1020
gaatgaacgc caagaggaac aagcatgaaa ccgcaccagg acggccagga cgaaccgttt   1080
ttcattaccg aagagatcga ggcggagatg atcgcggccg ggtacgtgtt cgagccgccc   1140
gcgcacctct caaccgtgcg gctgcatgaa atcctggccg gtttgtctga tgccaagctg   1200
gcggcctggc cggccagctt ggccgctgaa gaaaccgagc gccgccgtct aaaaaggtga   1260
tgtgtatttg agtaaaacag cttgcgtcat gcggtcgctg cgtatatgat ccgatgagta   1320
aataaacaaa tacgcaaggg gaacgcatga aggttatcgc tgtacttaac cagaaaggcg   1380
ggtcaggcaa gacgaccatc ggaacccatc tagcccgcgc cctgcaactc gccggggccg   1440
atgttctgtt agtcgattcc gatcccagg gcagtgcccg cgattgggcg gccgtgcggg   1500
aagatcaacc gctaaccgtt gtcggcatcg accgccgac gattgaccgc gacgtgaagg   1560
ccatcggccg gcgcgacttc gtagtgatcg acggagcgcc ccaggcggcg gacttggctg   1620
tgtccgcgat caaggcagcc gacttcgtgc tgattccggt gcagccaagc ccttacgaca   1680
tatgggccac cgccgacctg gtggagctgg ttaagcagcg cattgaggtc acggatggaa   1740
ggctacaagc ggcctttgtc gtgtcgcggg cgatcaaagg cacgcgcatc ggcggtgagg   1800
ttgccgaggc gctggccggg tacgagctgc ccattcttga gtcccgtatc acgcagcgcg   1860
tgagctaccc aggcactgcc gccgccggca caaccgttct tgaatcagaa cccgagggcg   1920
acgctgcccg cgaggtccag cgctggccg ctgaaattaa atcaaaactc atttgagtta   1980
atgaggtaaa gagaaaatga gcaaaagcac aaacacgcta agtgccggcc gtccgagcgc   2040
acgcagcagc aaggctgcaa cgttggccag cctggcagac acgccagcca tgaagcgggt   2100
caactttcag ttgccggcgg aggatcacac caagctgaag atgtacgcgg tacgccaagg   2160
caagaccatt accgagctgc tatctgaata gatcgcgcag ctaccagagt aaatgagcaa   2220
atgaataaat gagtagatga attttagcgg ctaaaggagg cggcatggaa aatcaagaac   2280
```

-continued

```
aaccaggcac cgacgccgtg gaatgcccca tgtgtggagg aacgggcggt tggccaggcg    2340
taagcggctg ggttgtctgc cggccctgca atggcactgg aaccccaag cccgaggaat    2400 cggcgtgacg gtcgcaaacc atccggcccg gtacaaatcg gcgcggcgct gggtgatgac    2460
ctggtggaga agttgaaggc cgcgcaggcc gcccagcggc aacgcatcga ggcagaagca    2520
cgccccggtg aatcgtggca agcggccgct gatcgaatcc gcaaagaatc ccggcaaccg    2580
ccggcagccg gtgcgccgtc gattaggaag ccgcccaagg gcgacgagca accagatttt    2640
ttcgttccga tgctctatga cgtgggcacc cgcgatagtc gcagcatcat ggacgtggcc    2700
gttttccgtc tgtcgaagcg tgaccgacga gctggcgagg tgatccgcta cgagcttcca    2760
gacgggcacg tagaggtttc cgcagggccg gccggcatgg ccagtgtgtg ggattacgac    2820
ctggtactga tggcggtttc ccatctaacc gaatccatga accgataccg ggaagggaag    2880
ggagacaagc ccggccgcgt gttccgtcca cacgttgcgg acgtactcaa gttctgccgg    2940
cgagccgatg gcggaaagca gaaagacgac ctggtagaaa cctgcattcg gttaaacacc    3000
acgcacgttg ccatgcagcg tacgaagaag gccaagaacg gccgcctggt gacggtatcc    3060
gagggtgaag ccttgattag ccgctacaag atcgtaaaga gcgaaaccgg gcggccggag    3120
tacatcgaga tcgagctagc tgattggatg taccgcgaga tcacagaagg caagaacccg    3180
gacgtgctga cggttcaccc cgattacttt ttgatcgatc ccggcatcgg ccgttttctc    3240
taccgcctgg cacgccgcgc cgcaggcaag gcagaagcca gatggttgtt caagacgatc    3300
tacgaacgca gtggcagcgc cggagagttc aagaagttct gtttcaccgt gcgcaagctg    3360
atcgggtcaa atgacctgcc ggagtacgat ttgaaggagg aggcggggca ggctggcccg    3420
atcctagtca tgcgctaccg caacctgatc gagggcgaag catccgccgg ttcctaatgt    3480
acggagcaga tgctagggca aattgcccta gcaggggaaa aaggtcgaaa aggactcttt    3540
cctgtggata gcacgtacat tgggaaccca agccgtaca ttgggaaccg gaacccgtac    3600
attgggaacc caaagccgta cattgggaac cggtcacaca tgtaagtgac tgatataaaa    3660
gagaaaaaag gcgattttc cgcctaaaac tctttaaaac ttattaaaac tcttaaaacc    3720
cgcctggcct gtgcataact gtctggccag cgcacagccg aagagctgca aaaagcgcct    3780
acccttcggt cgctgcgctc cctacgcccc gccgcttcgc gtcggcctat cgcggccgct    3840
ggccgctcaa aaatggctgg cctacggcca ggcaatctac cagggcgcgg acaagccgcg    3900
ccgtcgccac tcgaccgccg gcgcccacat caaggcaccc tgcctcgcgc gtttcggtga    3960
tgacggtgaa aacctctgac acatgcagct cccggtgacg gtcacagctt gtctgtaagc    4020
ggatgccggg agcagacaag cccgtcaggg cgcgtcagcg ggtgttggcg ggtgtcgggg    4080
cgcagccatg acccagtcac gtagcgatag cggagtgtat actggcttaa ctatgcggca    4140
tcagagcaga ttgtactgag agtgcaccat atgcggtgtg aaataccgca cagatgcgta    4200
aggagaaaat accgcatcag gcgctcttcc gcttcctcgc tcactgactc gctgcgctcg    4260
gtcgttcggc tgcggcgagc ggtatcagct cactcaaagg cggtaatacg gttatccaca    4320
gaatcagggg ataacgcagg aaagaacatg tgagcaaaag gccagcaaaa ggccaggaac    4380
cgtaaaaagg ccgcgttgct ggcgtttttc cataggctcc gcccccctga cgagcatcac    4440
aaaaatcgac gctcaagtca gaggtggcga aacccgacag gactataaag ataccaggcg    4500
tttccccctg gaagctccct cgtgcgctct cctgttccga ccctgccgct taccggatac    4560
ctgtccgcct ttctcccttc gggaagcgtg gcgctttctc atagctcacg ctgtaggtat    4620
ctcagttcgg tgtaggtcgt tcgctccaag ctgggctgtg tgcacgaacc ccccgttcag    4680
```

```
cccgaccgct gcgccttatc cggtaactat cgtcttgagt ccaacccggt aagacacgac    4740
ttatcgccac tggcagcagc cactggtaac aggattagca gagcgaggta tgtaggcggt    4800
gctacagagt tcttgaagtg gtggcctaac tacggctaca ctagaaggac agtatttggt    4860
atctgcgctc tgctgaagcc agttaccttc ggaaaaagag ttggtagctc ttgatccggc    4920
aaacaaacca ccgctggtag cggtggtttt tttgtttgca agcagcagat tacgcgcaga    4980
aaaaaaggat ctcaagaaga tcctttgatc ttttctacgg ggtctgacgc tcagtggaac    5040
gaaaactcac gttaagggat tttggtcatg cattctaggt gattatttgc cgactacctt    5100
ggtgatctcg cctttcacgt agtggacaaa ttcttccaac tgatctgcgc gcgaggccaa    5160
gcgatcttct tcttgtccaa gataagcctg tctagcttca agtatgacgg gctgatactg    5220
ggccggcagg cgctccattg cccagtcggc agcgacatcc ttcggcgcga ttttgccggt    5280
tactgcgctg taccaaatgc gggacaacgt aagcactaca tttcgctcat caccagccca    5340
gtcgggcggc gagttccata gcgttaaggt ttcatttagc gcctcaaata gatcctgttc    5400
aggaaccgga tcaaagagtt cctccgccgc tggacctacc aaggcaacgc tatgttctct    5460
tgcttttgtc agcaagatag ccagatcaat gtcgatcgtg gctggctcga agatacctgc    5520
aagaatgtca ttgcgctgcc attctccaaa ttgcagttcg cgcttagctg gataacgcca    5580
cggaatgatg tcgtcgtgca caacaatggt gacttctaca gcgcggagaa tctcgctctc    5640 tccagggga gccgaagttt ccaaaaggtc gttgatcaaa gctcgccgcg ttgtttcatc    5700
aagccttacg gtcaccgtaa ccagcaaatc aatatcactg tgtggcttca ggccgccatc    5760
cactgcggag ccgtacaaat gtacggccag caacgtcggt tcgagatggc gctcgatgac    5820
gccaactacc tctgatagtt gagtcgatac ttcggcgatc accgcttccc tcataatgtt    5880
taactttgtt ttagggcgac tgccctgctg cgtaacatcg ttgctgctcc ataacatcaa    5940
acatcgaccc acggcgtaac gcgcttgctg cttggatgcc cgaggcatag actgtacccc    6000
aaaaaaacag tcataacaag ccatgaaaac cgccactgcg ccgttaccac cgctgcgttc    6060
ggtcaaggtt ctggaccagt tgcgtgagcg catacgctac ttgcattaca gcttacgaac    6120
cgaacaggct tatgtccact gggttcgtgc cttcatccgt ttccacggtg tgcgtcaccc    6180
ggcaaccttg ggtagcagcg aagtcgaggc atttctgtcc tggctggaac agaacttatt    6240
atttccttcc tcttttctac agtatttaaa gataccccaa gaagctaatt ataacaagac    6300
gaactccaat tcactgttcc ttgcattcta aaaccttaaa taccagaaaa cagctttttc    6360
aaagttgttt tcaaagttgg cgtataacat agtatcgacg gagccgattt tgaaaccgcg    6420
gtgatcacag gcagcaacgc tctgtcatcg ttacaatcaa catgctaccc tccgcgagat    6480
catccgtgtt tcaaacccgg cagcttagtt gccgttcttc cgaatagcat cggtaacatg    6540
agcaaagtct gccgccttac aacggctctc ccgctgacgc cgtcccggac tgatgggctg    6600
cctgtatcga gtggtgattt tgtgccgagc tgccggtcgg ggagctgttg gctggctggt    6660
ggcaggatat attgtggtgt aaacataacg gatccggtct caggagagcg tcgatctagt    6720
aacatagatg acaccgcgcg cgataattta tcctagtttg cgcgctatat tttgttttct    6780
atcgcgtatt aaatgtataa ttgcgggact ctaatcataa aaacccatct cataaataac    6840
gtcatgcatt acatgttaat tattacatgc ttaacgtaat tcaacagaaa ttatatgata    6900
atcatcgcaa gaccggcaac aggattcaat cttaagaaac tttattgcca atgtttgaa    6960 cgatctgctt cgacgcactc cttctttact ccaccatctc gtccttattg aaaacgtggg    7020
```

```
tagcaccaaa acgaatcaag tcgctggaac tgaagttacc aatcacgctg gatgatttgc    7080
cagttggatt aatcttgcct ttccccgcat gaataatatt gatgaatgca tgcgtgaggg    7140
gtagttcgat gttggcaata gctgcaattg ccgcgacatc ctccaacgag cataattctt    7200
cagaaaaata gcgatgttcc atgttgtcag ggcatgcatg atgcacgtta tgaggtgacg    7260
gtgctaggca gtattccctc aaagtttcat agtcagtatc atattcatca ttgcattcct    7320
gcaagagaga attgagacgc aatccacacg ctgcggcaac cttccggcgt tcgtggtcta    7380
tttgctcttg gacgttgcaa acgtaagtgt tggatcgggg tgggcgaaga actccagcat    7440
gagatcccg cgctggagga tcatccagcc ggcgtcccgg aaaacgattc cgaagcccaa    7500
cctttcatag aaggcggcgg tggaatcgaa atctcgtgat ggcaggttgg gcgtcgcttg    7560
gtcggtcatt tcgaacccca gagtcccgct cagaagaact cgtcaagaag gcgatagaag    7620
gcgatgcgct gcgaatcggg agcggcgata ccgtaaagca cgaggaagcg gtcagcccat    7680
tcgccgccaa gctcttcagc aatatcacgg gtagccaacg ctatgtcctg atagcggtcc    7740
gccacaccca gccggccaca gtcgatgaat ccagaaaagc ggccattttc caccatgata    7800
ttcggcaagc aggcatcgcc atgggtcacg acgagatcct cgccgtcggg catgcgcgcc    7860
ttgagcctgg cgaacagttc ggctggcgcg agccctgat gctcttcgtc cagatcatcc    7920
tgatcgacaa gaccggcttc catccgagta cgtgctcgct cgatgcgatg tttcgcttgg    7980
tggtcgaatg ggcaggtagc cggatcaagc gtatgcagcc gccgcattgc atcagccatg    8040
atggatactt tctcggcagg agcaaggtga gatgacagga gatcctgccc cggcacttcg    8100
cccaatagca gccagtccct tcccgcttca gtgacaacgt cgagcacagc tgcgcaagga    8160
acgcccgtcg tggccagcca cgatagccgc gctgcctcgt cctgcagttc attcagggca    8220
ccggacaggt cggtcttgac aaaaagaacc gggcgcccct cgctgacag ccggaacacg    8280
gcggcatcag agcagccgat tgtctgttgt gcccagtcat agccgaatag cctctccacc    8340
caagcggccg gagaacctgc ccggatccgg gcggaaatag gtaaagaagt tgcggataag    8400
gtaattgcca ttgcagatta tttggattga gagtgaatat gagactctaa ttggataccg    8460
aggggaattt atggaacgtc agtggagcat ttttgacaag aaatatttgc tagctgatag    8520
tgaccttagg cgacttttga acgcgcaata atggtttctg acgtatgtgc ttagctcatt    8580
aaactccaga aaccctccg tcaggagact agagccaagc tgatctcctt tgccccggag    8640
atcaccatgg acgactttct ctatctctac gatctaggaa gaaagttcga cggagaaggt    8700
gacgatacca tgttcaccac cgataatgag aagattagcc tcttcaattt cagaaagaat    8760
gctgacccac agatggttag agaggcctac gcggcaggtc tgatcaagac gatctacccg    8820
agtaataatc tccaggagat caaataccct cccaagaagg ttaaagatgc agtcaaaaga    8880
ttcaggacta actgcatcaa gaacacagag aaagatatat ttctcaagat cagaagtact    8940
attccagtat ggacgattca aggcttgctt cataaaccaa ggcaagtaat agagattgga    9000
gtctctaaga aagtagttcc tactgaatca aaggccatgg agtcaaaaat tcagatcgag    9060
gatctaacag aactcgccgt gaagactggc gaacagttca tacagagtct tttacgactc    9120
aatgacaaga agaaaatctt cgtcaacatg gtggagcacg acactctcgt ctactccaag    9180
aatatcaaag atacagtctc agaagaccaa agggctattg agacttttca acaaagggta    9240
atatcgggaa acctcctcgg attccattgc ccagctatct gtcacttcat caaaaggaca    9300
gtagaaaagg aaggtggcac ctacaaatgc catcattgcg ataaaggaaa ggctatcgtt    9360
caagatgcct ctgccgacag tggtcccaaa gatggacccc cacccacgag gagcatcgtg    9420
```

```
gaaaaagaag acgttccaac cacgtcttca aagcaagtgg attgatgtga tatctccact    9480
gacgtaaggg atgacgcaca atcccactat ccttcgcaag acccttcctc tatataagga    9540
agttcatttc atttggagag gactccggta tttttacaac aataccacaa caaaacaaac    9600
aacaaacaac attacaattt actattctag tcgaaatgga taacgcaaca cttgctgtga    9660
tcctttccat tttgtttgtg ttttaccaca ttttcaaatc cttttcacc aattcttcat     9720
ctcgtaggct tcctcctggt cccaaacccg tgccaatttt tggcaacatt ttcgatcttg    9780
gcgaaaagcc tcatcgatct tttgccaatc tatctaaaat tcacggccct ttgattagcc    9840
taaagttagg aagtgtaaca actattgttg tttcctcggc ctctgtggcc gaggaaatgt    9900
tccttaaaaa tgaccaagca cttgctaacc gaaccattcc tgactcggtt agggctggtg    9960
accacgacaa attatccatg tcgtggttgc ctgtttccca aaaatggaga aatatgagaa   10020
aaatctccgc tgtccaatta ctctccaacc aaaaacttga tgctagtcaa cctcttagac   10080
aagctaaggt gaaacaactt ttatcatacg tacaagtttg ttccgaaaaa atgcaacccg   10140
tcgatattgg acgggccgca tttacaacgt cacttaattt attatcaaac acattttct   10200
caatcgaatt agcaagtcat gaatctagtg cttcccaaga gtttaaacaa ctcatgtgga   10260
atattatgga ggaaattgga aggcctaatt atgctgattt tttcccctatt cttggttaca  10320
ttgatccctt tggtataaga cgtcgtttgg ctggttactt tgataaactc attgatgttt   10380
tccaagacat tattcgtgaa agacaaaagc ttcgatcttc taattcttcc ggcgcaaaac   10440
aaacaaatga cattcttgat actcttctta aactccatga agataatgag ttgagtatgc   10500
ctgaaattaa tcaccttctc gtggatatct ttgacgccgg aacagacaca acagcaagca   10560
cattagaatg ggcaatggcc gaacttgtga aaaacccgga aatgatgact aaagttcaaa   10620
ttgaaatcga acaagctctt ggaaaagatt gcttagacat acaagaatcc gacatctcaa   10680
aactacctta tttacaagcc attataaaag aaacgttacg tttacaccct cctactgtgt   10740
ttttgctgcc tcgaaaggca gacaatgacg tagagttata tggctacgtt gtaccaaaga   10800
atgctcaagt ccttgtcaat ctttgggcaa ttggtcgtga tccaaaggta tggaaaaatc   10860
cggaagtatt ttctcctgaa aggtttttag attgcaatat cgattataaa ggacgagatt   10920
tcgaactttt accctttggt gctggtagaa ggatatgccc tggacttact ttggcatata   10980
gaatgttgaa cttgatgttg gctactcttc ttcaaaacta caattggaaa cttgaagatg   11040
gtatcaatcc taaggattta gacatggatg agaaatttgg gattacattg caaaaggtta   11100
aacctcttca agttattcca gttcccagaa actaggcttg ctctcaagat caaaggctta   11160
aaaagctggg gttttatgaa tgggatcaaa gtttcttttt ttcttttata tttgcttctc   11220
catttgtttg tttcatttcc cttttttgttt tcgtttctat gatgcacttg tgtgtgacaa   11280
actctctggg tttttactta cgtctgcgtt tcaaaaaaaa aaaccgcttt cgttttgcgt   11340
tttagtccca ttgttttgta gctctgagtg atcgaattga tgcctcttta ttcctttgt   11400
tccctataat ttctttcaaa actcagaaga aaaaccttga aactctttgc aatgttaata   11460
taagtattgt ataagatttt tattgatttg gttattagtc ttacttttgc tacctccatc   11520
ttcacttgga actgatattc tgaatagtta aagcgttaca tgtcttccat tcacaaatga   11580
acttaaacta gcacaaagtc agatatttta agatcgcacc attttatata accccaatcg   11640
tcaattctac tgtttcaagt tttacaccaa aacaattacg aggtgtatct attcgttact   11700
cttttcgctt attaatcctt ttacatgatg caaaatataa caaattaatt tcaaattgtc   11760
```
ctgcacattt ggtttataca tcttgattcc aaaaagt                           11797

<210> SEQ ID NO 25
<211> LENGTH: 13626
<212> TYPE: DNA
<213> ORGANISM: Artificial Sequence
<220> FEATURE:
<223> OTHER INFORMATION: pDOPA2 overexpression vector

<400> SEQUENCE: 25

```
cgctgtcatg agaccggatc ctgacaggat atattggcgg gtaaacctaa gagaaaagag      60
cgtttattag aataatcgga tatttaaaag ggcgtgaaaa ggtttatccg ttcgtccatt     120
tgtatgtgca tgccaaccac agggttcccc tcgggatcaa agtactttga tccaacccct     180
ccgctgctat agtgcagtcg gcttctgacg ttcagtgcag ccgtcatctg aaaacgacat     240
gtcgcacaag tcctaagtta cgcgacaggc tgccgccctg cccttttcct ggcgttttct     300
tgtcgcgtgt tttagtcgca taaagtagaa tacttgcgac tagaaccgga gacattacgc     360
catgaacaag agcgccgccg ctggcctgct gggctatgcc cgcgtcagca ccgacgacca     420
ggacttgacc aaccaacggg ccgaactgca cgcggccggc tgcaccaagc tgttttccga     480
gaagatcacc ggcaccaggc gcgaccgccc ggagctggcc aggatgcttg accacctacg     540
ccctggcgac gttgtgacag tgaccaggct agaccgcctg gcccgcagca cccgcgacct     600
actggacatt gccgagcgca tccaggaggc cggcgcgggc ctgcgtagcc tggcagagcc     660
gtgggccgac accaccacgc cggccggccg catggtgttg accgtgttcg ccggcattgc     720
cgagttcgag cgttccctaa tcatcgaccg cacccgagc gggcgcgagg ccgccaaggc     780
ccgaggcgtg aagtttggcc cccgccctac cctcaccccg gcacagatcg cgcacgcccg     840
cgagctgatc gaccaggaag gccgcaccgt gaaagaggcg gctgcactgc ttggcgtgca     900
tcgctcgacc ctgtaccgcg cacttgagcg cagcgaggaa gtgacgccca ccgaggccag     960
gcggcgcggt gccttccgtg aggacgcatt gaccgaggcc gacgccctgg cggccgccga    1020
gaatgaacgc caagaggaac aagcatgaaa ccgcaccagg acggccagga cgaaccgttt    1080
ttcattaccg aagagatcga ggcggagatg atcgcggccg ggtacgtgtt cgagccgccc    1140
gcgcacctct caaccgtgcg gctgcatgaa atcctggccg gtttgtctga tgccaagctg    1200
gcggcctggc cggccagctt ggccgctgaa gaaaccgagc gccgccgtct aaaaaggtga    1260
tgtgtatttg agtaaaacag cttgcgtcat gcggtcgctg cgtatatgat ccgatgagta    1320
aataaacaaa tacgcaaggg gaacgcatga aggttatcgc tgtacttaac cagaaaggcg    1380
ggtcaggcaa gacgaccatc ggaacccatc tagcccgcgc cctgcaactc gccggggccg    1440
atgttctgtt agtcgattcc gatccccagg gcagtgcccg cgattgggcg ccgtgcggg    1500
aagatcaacc gctaaccgtt gtcggcatcg accgccgac gattgaccgc gacgtgaagg    1560
ccatcggccg gcgcgacttc gtagtgatcg acggagcgcc caggcggcg gacttggctg    1620
tgtccgcgat caaggcagcc gacttcgtgc tgattccggt gcagccaagc ccttacgaca    1680
tatgggccac cgccgacctg gtggagctgg ttaagcagcg cattgaggtc acggatggaa    1740
ggctacaagc ggcctttgtc gtgtcgcggg cgatcaaagg cacgcgcatc ggcggtgagg    1800
ttgccgaggc gctggccggg tacgagctgc ccattcttga gtcccgtatc acgcagcgcg    1860
tgagctaccc aggcactgcc gccgccggca caaccgttct tgaatcagaa cccgagggcg    1920
acgctgcccg cgaggtccag gcgctggccg ctgaaattaa atcaaactc atttgagtta    1980
atgaggtaaa gagaaaatga gcaaaagcac aaacacgcta agtgccggcc gtccgagcgc    2040
```

| | |
|---|---|
| acgcagcagc aaggctgcaa cgttggccag cctggcagac acgccagcca tgaagcgggt | 2100 |
| caactttcag ttgccggcgg aggatcacac caagctgaag atgtacgcgg tacgccaagg | 2160 |
| caagaccatt accgagctgc tatctgaata gatcgcgcag ctaccagagt aaatgagcaa | 2220 |
| atgaataaat gagtagatga atttttagcgg ctaaaggagg cggcatggaa aatcaagaac | 2280 |
| aaccaggcac cgacgccgtg gaatgcccca tgtgtggagg aacgggcggt tggccaggcg | 2340 |
| taagcggctg ggttgtctgc cggccctgca atggcactgg aaccccccaag cccgaggaat | 2400 |
| cggcgtgacg gtcgcaaacc atccggcccg gtacaaatcg gcgcggcgct gggtgatgac | 2460 |
| ctggtggaga agttgaaggc cgcgcaggcc gcccagcggc aacgcatcga ggcagaagca | 2520 |
| cgccccggtg aatcgtggca agcggccgct gatcgaatcc gcaaagaatc ccggcaaccg | 2580 |
| ccggcagccg gtgcgccgtc gattaggaag ccgcccaagg gcgacgagca accagatttt | 2640 |
| ttcgttccga tgctctatga cgtgggcacc cgcgatagtc gcagcatcat ggacgtggcc | 2700 |
| gttttccgtc tgtcgaagcg tgaccgacga gctggcgagg tgatccgcta cgagcttcca | 2760 |
| gacgggcacg tagaggtttc cgcagggccg gccggcatgg ccagtgtgtg ggattacgac | 2820 |
| ctggtactga tggcggtttc ccatctaacc gaatccatga accgataccg ggaagggaag | 2880 |
| ggagacaagc ccggccgcgt gttccgtcca cacgttgcgg acgtactcaa gttctgccgg | 2940 |
| cgagccgatg gcgaaagca gaaagacgac ctggtagaaa cctgcattcg gttaaacacc | 3000 |
| acgcacgttg ccatgcagcg tacgaagaag gccaagaacg gccgcctggt gacggtatcc | 3060 |
| gagggtgaag ccttgattag ccgctacaag atcgtaaaga gcgaaaccgg gcggccggag | 3120 |
| tacatcgaga tcgagctagc tgattggatg taccgcgaga tcacagaagg caagaacccg | 3180 |
| gacgtgctga cggttcaccc cgattacttt ttgatcgatc ccggcatcgg ccgttttctc | 3240 |
| taccgcctgg cacgccgcgc cgcaggcaag gcagaagcca gatggttgtt caagacgatc | 3300 |
| tacgaacgca gtggcagcgc cggagagttc aagaagttct gtttcaccgt gcgcaagctg | 3360 |
| atcgggtcaa atgacctgcc ggagtacgat ttgaaggagg aggcggggca ggctggcccg | 3420 |
| atcctagtca tgcgctaccg caacctgatc gagggcgaag catccgccgg ttcctaatgt | 3480 |
| acggagcaga tgctagggca aattgcccta gcaggggaaa aaggtcgaaa aggactcttt | 3540 |
| cctgtggata gcacgtacat tgggaaccca aagccgtaca ttgggaaccg gaacccgtac | 3600 |
| attgggaacc caaagccgta cattgggaac cggtcacaca tgtaagtgac tgatataaaa | 3660 |
| gagaaaaaag gcgattttc cgcctaaaac tctttaaaac ttattaaaac tcttaaaacc | 3720 |
| cgcctggcct gtgcataact gtctggccag cgcacagccg aagagctgca aaaagcgcct | 3780 |
| acccttcggt cgctgcgctc cctacgcccc gccgcttcgc gtcggcctat cgcggccgct | 3840 |
| ggccgctcaa aaatgctggg cctacggcca ggcaatctac cagggcgcgg acaagccgcg | 3900 |
| ccgtcgccac tcgaccgccg gcgcccacat caaggcaccc tgcctcgcgc gtttcggtga | 3960 |
| tgacggtgaa aacctctgac acatgcagct cccggtgacg gtcacagctt gtctgtaagc | 4020 |
| ggatgccggg agcagacaag cccgtcaggg cgcgtcagcg ggtgttggcg ggtgtcgggg | 4080 |
| cgcagccatg acccagtcac gtagcgatag cggagtgtat actggcttaa ctatgcggca | 4140 |
| tcagagcaga ttgtactgag agtgcaccat atgcggtgtg aaataccgca cagatgcgta | 4200 |
| aggagaaaat accgcatcag gcgctcttcc gcttcctcgc tcactgactc gctgcgctcg | 4260 |
| gtcgttcggc tgcggcgagc ggtatcagct cactcaaagg cggtaatacg gttatccaca | 4320 |
| gaatcagggg ataacgcagg aaagaacatg tgagcaaaag gccagcaaaa ggccaggaac | 4380 |

```
cgtaaaaagg ccgcgttgct ggcgttttc cataggctcc gccccctga cgagcatcac    4440 aaaaatcgac gctcaagtca gaggtggcga aacccgacag gactataaag ataccaggcg    4500
tttccccctg gaagctccct cgtgcgctct cctgttccga ccctgccgct taccggatac    4560
ctgtccgcct ttctcccttc gggaagcgtg gcgctttctc atagctcacg ctgtaggtat    4620
ctcagttcgg tgtaggtcgt tcgctccaag ctgggctgtg tgcacgaacc ccccgttcag    4680
cccgaccgct gcgccttatc cggtaactat cgtcttgagt ccaacccggt aagcacgac     4740 ttatcgccac tggcagcagc cactggtaac aggattagca gagcgaggta tgtaggcggt    4800
gctacagagt tcttgaagtg gtggcctaac tacggctaca ctagaaggac agtatttggt    4860
atctgcgctc tgctgaagcc agttaccttc ggaaaaagag ttggtagctc ttgatccggc    4920
aaacaaacca ccgctggtag cggtggtttt tttgtttgca agcagcagat tacgcgcaga    4980 aaaaaggat ctcaagaaga tcctttgatc ttttctacgg ggtctgacgc tcagtggaac     5040
gaaaactcac gttaagggat tttggtcatg cattctaggt gattatttgc cgactacctt    5100
ggtgatctcg cctttcacgt agtggacaaa ttcttccaac tgatctgcgc gcgaggccaa    5160
gcgatcttct tcttgtccaa gataagcctg tctagcttca agtatgacgg gctgatactg    5220
ggccggcagg cgctccattg cccagtcggc agcgacatcc ttcggcgcga ttttgccggt    5280
tactgcgctg taccaaatgc gggacaacgt aagcactaca tttcgctcat caccagccca    5340
gtcgggcggc gagttccata gcgttaaggt ttcatttagc gcctcaaata gatcctgttc    5400
aggaaccgga tcaaagagtt cctccgccgc tggacctacc aaggcaacgc tatgttctct    5460
tgcttttgtc agcaagatag ccagatcaat gtcgatcgtg gctggctcga agatacctgc    5520
aagaatgtca ttgcgctgcc attctccaaa ttgcagttcg cgcttagctg gataacgcca    5580
cggaatgatg tcgtcgtgca caacaatggt gacttctaca gcgcggagaa tctcgctctc    5640 tccagggaa gccgaagttt ccaaaaggtc gttgatcaaa gctcgccgcg ttgtttcatc     5700
aagccttacg gtcaccgtaa ccagcaaatc aatatcactg tgtggcttca ggccgccatc    5760
cactgcggag ccgtacaaat gtacggccag caacgtcggt tcgagatggc gctcgatgac    5820
gccaactacc tctgatagtt gagtcgatac ttcggcgatc accgcttccc tcataatgtt    5880
taactttgtt ttagggcgac tgccctgctg cgtaacatcg ttgctgctcc ataacatcaa    5940
acatcgaccc acggcgtaac gcgcttgctg cttggatgcc cgaggcatag actgtacccc    6000
aaaaaaacag tcataacaag ccatgaaaac cgccactgcg ccgttaccac cgctgcgttc    6060
ggtcaaggtt ctggaccagt tgcgtgagcg catacgctac ttgcattaca gcttacgaac    6120
cgaacaggct tatgtccact gggttcgtgc cttcatccgt ttccacggtg tgcgtcaccc    6180
ggcaaccttg ggtagcagcg aagtcgaggc atttctgtcc tggctggaac agaacttatt    6240
atttccttcc tcttttctac agtatttaaa gataccccaa gaagctaatt ataacaagac    6300
gaactccaat tcactgttcc ttgcattcta aaaccttaaa taccagaaaa cagcttttc     6360 aaagttgttt tcaaagttgg cgtataacat agtatcgacg gagccgattt tgaaaccgcg    6420
gtgatcacag gcagcaacgc tctgtcatcg ttacaatcaa catgctaccc tccgcgagat    6480
catccgtgtt tcaaacccgg cagcttagtt gccgttcttc cgaatagcat cggtaacatg    6540
agcaaagtct gccgccttac aacggctctc ccgctgacgc cgtcccggac tgatgggctg    6600
cctgtatcga gtggtgattt tgtgccgagc tgccggtcgg ggagctgttg gctggctggt    6660
ggcaggatat attgtggtgt aaacataacg gatccggtct caggagagcg tcgatctagt    6720
aacatagatg acaccgcgcg cgataattta tcctagtttg cgcgctatat tttgttttct    6780
```

```
atcgcgtatt aaatgtataa ttgcgggact ctaatcataa aaacccatct cataaataac    6840
gtcatgcatt acatgttaat tattacatgc ttaacgtaat tcaacagaaa ttatatgata    6900
atcatcgcaa gaccggcaac aggattcaat cttaagaaac tttattgcca aatgtttgaa    6960
cgatctgctt cgacgcactc cttctttact ccaccatctc gtccttattg aaaacgtggg    7020
tagcaccaaa acgaatcaag tcgctggaac tgaagttacc aatcacgctg atgatttgc     7080 cagttggatt aatcttgcct ttccccgcat gaataatatt tgatgaatgca tgcgtgaggg   7140 gtagttcgat gttggcaata gctgcaattg ccgcgacatc ctccaacgag cataattctt    7200
cagaaaaata gcgatgttcc atgttgtcag ggcatgcatg atgcacgtta tgaggtgacg    7260
gtgctaggca gtattccctc aaagtttcat agtcagtatc atattcatca ttgcattcct    7320
gcaagagaga attgagacgc aatccacacg ctgcggcaac cttccggcgt tcgtggtcta    7380
tttgctcttg gacgttgcaa acgtaagtgt tggatcgggg tgggcgaaga actccagcat    7440
gagatccccg cgctggagga tcatccagcc ggcgtcccgg aaaacgattc cgaagcccaa    7500
cctttcatag aaggcggcgg tggaatcgaa atctcgtgat ggcaggttgg gcgtcgcttg    7560
gtcggtcatt tcgaacccca gagtcccgct cagaagaact cgtcaagaag gcgatagaag    7620
gcgatgcgct gcgaatcggg agcggcgata ccgtaaagca cgaggaagcg gtcagcccat    7680
tcgccgccaa gctcttcagc aatatcacgg gtagccaacg ctatgtcctg atagcggtcc    7740
gccacaccca gccggccaca gtcgatgaat ccagaaaagc ggccattttc caccatgata    7800
ttcggcaagc aggcatcgcc atgggtcacg acgagatcct cgccgtcggg catgcgcgcc    7860
ttgagcctgg cgaacagttc ggctggcgcg agcccctgat gctcttcgtc cagatcatcc    7920
tgatcgacaa gaccggcttc catccgagta cgtgctcgct cgatgcgatg tttcgcttgg    7980
tggtcgaatg ggcaggtagc cggatcaagc gtatgcagcc gccgcattgc atcagccatg    8040
atggatactt tctcggcagg agcaaggtga gatgacagga gatcctgccc cggcacttcg    8100
cccaatagca gccagtccct tcccgcttca gtgacaacgt cgagcacagc tgcgcaagga    8160
acgcccgtcg tggccagcca cgatagccgc gctgcctcgt cctgcagttc attcagggca    8220
ccggacaggt cggtcttgac aaaaagaacc gggcgcccct gcgctgacag ccggaacacg    8280
gcggcatcag agcagccgat tgtctgttgt gcccagtcat agccgaatag cctctccacc    8340
caagcggccg gagaacctgc ccggatccgg gcggaaatag gtaaagaagt tgcggataag    8400
gtaattgcca ttgcagatta tttggattga gagtgaatat gagactctaa ttggataccg    8460
aggggaattt atgaacgtc agtggagcat ttttgacaag aaatatttgc tagctgatag     8520
tgaccttagg cgacttttga acgcgcaata atggtttctg acgtatgtgc ttagctcatt    8580
aaactccaga aaccccctccg tcaggaggtc aactacccca atttaaattt tatttgatta   8640
agatattttt atggacctac tttataatta aaaatatttt ctatttgaaa aggaaggaca    8700
aaaatcatac aattttggtc caactactcc tctcttttt tttttggctt tataaaaaag     8760
gaaagtgatt agtaataaat aattaaataa tgaaaaaagg aggaaataaa attttcgaat    8820
taaaatgtaa aagagaaaaa ggagagggag taatcattgt ttaactttat ctaaagtacc    8880
ccaattcgat tttacatgta tatcaaatta tacaaatatt ttattaaaat atagatattg    8940
aataatttta ttattcttga acatgtaaat aaaaattatc tattatttca attttatat     9000 aaactattat ttgaaatctc aattatgatt ttttaatatc actttctatc catgataatt    9060
tcagcttaaa aagttttgtc aataattaca ttaattttgt tgatgaggat gacaagattt    9120
```

```
cggtcatcaa ttacatatac acaaattgaa atagtaagca acttgatttt ttttctcata    9180
atgataatga caaagacacg aaaagacaat tcaatattca cattgattta tttttatatg    9240
ataataatta caataataat attcttataa agaaagagat caattttgac tgatccaaaa    9300
atttatttat ttttactata ccaacgtcac taattatatc taataatgta aaacaattca    9360
atcttactta aatattaatt tgaaataaac tattttata acgaaattac taaatttatc     9420
caataacaaa aaggtcttaa gaagacataa attctttttt tgtaatgctc aaataaattt    9480
gagtaaaaaa gaatgaaatt gagtgatttt tttttaatca taagaaaata aataattaat    9540
ttcaatataa taaacagta atataaattc ataaatggaa ttcaatactt acctcttaga     9600
tataaaaaat aaatataaaa ataagtgtt tctaataaac ccgcaattta aataaaatat     9660
ttaatatttt caatcaaatt taaataatta tattaaaata tcgtagaaaa agagcaatat    9720
ataatacaag aaagaagatt taagtacaat tatcaactat tattatactc taattttgtt    9780
atatttaatt tcttacggtt aaggtcatgt tcacgataaa ctcaaaatac gctgtatgag    9840
gacatatttt aaattttaac caataataaa actaagttat tttagtata tttttttgtt     9900
taacgtgact taattttct tttctagagg agcgtgtaag tgtcaacctc attctcctaa     9960
ttttcccaac cacataaaaa aaaaataaag gtagcttttg cgtgttgatt tggtacacta   10020
cacgtcatta ttacacgtgt tttcgtatga ttggttaatc catgaggcgg tttcctctag   10080
agtcggccat accatctata aaataaagct ttctgcagct catttttca tcttctatct    10140
gatttctatt ataatttctc tgaattgcct tcaaatttct ctttcaaggt tagaattttt   10200
ctctattttt tggttttgt ttgtttagat tctgagttta gttaatcagg tgctgttaaa    10260
gccctaaatt ttgagttttt ttcggttgtt ttgatggaaa atacctaaca attgagtttt   10320
ttcatgttgt tttgtcggag aatgcctaca attggagttc ctttcgttgt tttgatgaga   10380
aagcccctaa tttgagtgtt tttccgtcga tttgatttta aaggtttata ttcgagtttt   10440
tttcgtcggt ttaatgagaa ggcctaaaat aggagttttt ctggttgatt tgactaaaaa   10500
agccatggaa ttttgtgttt ttgatgtcgc tttggttctc aaggcctaag atctgagttt   10560
ctccggttgt tttgatgaaa aagccctaaa attggagttt ttatcttgtg ttttaggttg   10620
ttttaatcct tataatttga gttttttcgt tgttctgatt gttgttttta tgaattttgc   10680
agaatggata acgcaacact tgctgtgatc ctttccattt tgtttgtgtt ttaccacatt   10740
ttcaaatcct ttttcaccaa ttcttcatct cgtaggcttc ctcctggtcc caaacccgtg   10800
ccaattttg gcaacatttt cgatcttggc gaaaagcctc atcgatcttt tgccaatcta    10860
tctaaaattc acggcccttt gattagccta aagttaggaa gtgtaacaac tattgttgtt   10920
tcctcggcct ctgtggccga ggaaatgttc cttaaaaatg accaagcact tgctaaccga   10980
accattcctg actcggttag ggctggtgac cacgacaaat tatccatgtc gtggttgcct   11040
gtttcccaaa aatggagaaa tatgagaaaa atccgctg tccaattact ctccaaccaa     11100
aaacttgatg ctagtcaacc tcttagacaa gctaaggtga aacaactttt atcatacgta   11160
caagtttgtt ccgaaaaaat gcaacccgtc gatattggac gggccgcatt tacaacgtca   11220
cttaatttat tatcaacac attttttctca atcgaattag caagtcatga atctagtgct   11280
tcccaagagt ttaaacaact catgtggaat attatggagg aaattggaag gcctaattat   11340
gctgattttt tccctattct tggttacatt gatccctttg gtataagacg tcgtttggct   11400
ggttactttg ataaactcat tgatgttttc caagacatta ttcgtgaaag acaaaagctt   11460
cgatcttcta attcttccgg cgcaaaacaa acaaatgaca ttcttgatac tcttcttaaa   11520
```

```
ctccatgaag ataatgagtt gagtatgcct gaaattaatc accttctcgt ggatatcttt    11580
gacgccggaa cagacacaac agcaagcaca ttagaatggg caatggccga acttgtgaaa    11640
aacccggaaa tgatgactaa agttcaaatt gaaatcgaac aagctcttgg aaaagattgc    11700
ttagacatac aagaatccga catctcaaaa ctaccttatt tacaagccat tataaaagaa    11760
acgttacgtt tacaccctcc tactgtgttt ttgctgcctc gaaaggcaga caatgacgta    11820
gagttatatg gctacgttgt accaaagaat gctcaagtcc ttgtcaatct ttgggcaatt    11880
ggtcgtgatc caaggtatg gaaaaatccg gaagtatttt ctcctgaaag gttttttagat    11940 tgcaatatcg attataaagg acgagatttc gaacttttac cctttggtgc tggtagaagg    12000
atatgccctg gacttacttt ggcatataga atgttgaact tgatgttggc tactcttctt    12060
caaaactaca attggaaact tgaagatggt atcaatccta aggatttaga catggatgag    12120
aaatttggga ttacattgca aaaggttaaa cctcttcaag ttattccagt tcccagaaac    12180
taggcttgtt gtggttgtct ggttgcgtct gttgcccgtt gtctgttgcc cattgtggtg    12240
gttgtgtttg tatgatggtc gttaaggatc atcaatgtgt tttcgctttt tgttccattc    12300
tgtttctcat ttgtgaataa taatggtatc tttatgaata tgcagtttgt ggtttctttt    12360
ctgattgcag ttctgagcat tttgtttttg cttccgttta ctataccact tacagtttgc    12420
actaatttag ttgatatgcg agccatctga tgtttgatga ttcaaatggc gtttatgtaa    12480
ctcgtacccg agtggatgga gaagagctcc attgccggtt tgtttcatgg gtggcggagg    12540
gcaactcctg ggaaggaaca aaagaaaaac cgtgatacga gttcatgggt gagagctcca    12600
gcttgatccc ttctctgtcg atcaaatttg aattttggga tcacggcagg ctcacaagat    12660
aatccaaagt aaaacataat gaatagtact tctcaatgat cacttatttt tagcaaatca    12720
gcaattgtgc atgtcaaatg atttcggtgt aagagaaaga gttgatgaat caaaatatct    12780
gtagctggat caagaatctg aggcagttgt atgtatcaat gatctttccg ctacaatgat    12840
gttagctatc cgagtcaaat tgttgtagaa ttgcatactt cggcatcaca ttctggatga    12900
cataataaat aggaagtctt cagatcccta aaaaattgag agctaataac attagtccta    12960
gatgtaactg ggtgacaacc aagaaagaga catgcaaata ctactttgt ttgaaggagc    13020 atccctggtt tgacatattt tttctgaata tcaaactttg aaactctacc tagtctaatg    13080
tctaacgaca gatcttactg gtttaactgc agtgatatct actatctttt ggaatgtttt    13140
ctccttcagt tatacatcaa gttccaagat gcaggtgtgc ttgattgatg tacatggctg    13200
tgagaagtgc atcctgatgt tcagatgatg gttcattcta atgtcttttc cttcaatcag    13260
ttttctcagt ctgacttagc ttgtttcatc tgcatgtttg aatgttcgtt tactcatagt    13320
aattgcattt ttgtagcaga acatatcatt ggtcatggtt tcaactgtgc gcgagtctta    13380
tgcttattca aactaggaaa gcctccgtct agagggtaca cgagttgttg ctctgtgtgc    13440
gtcagtccat agtattaatc ttgctagttg tagtatattg tttatgtgga ctcggaattc    13500
atcatatgct ccttctttgc atcaagtaag gcaaggtaat gtatagaagc ttttttaactc    13560 tttcatggaa gctggccttt gccagcatac catccagaag atatcaaccc tgcatcttgg    13620
ctgccg                                                               13626
```

<210> SEQ ID NO 26
<211> LENGTH: 16818
<212> TYPE: DNA
<213> ORGANISM: Artificial Sequence
<220> FEATURE:

<223> OTHER INFORMATION: pDOPA3 overexpression vector

<400> SEQUENCE: 26

```
cgctgtcatg agacgaattc tgacaggata tattggcggg taaacctaag agaaaagagc      60
gtttattaga ataatcggat atttaaaagg gcgtgaaaag gtttatccgt tcgtccattt     120
gtatgtgcat gccaaccaca gggttcccct cgggatcaaa gtactttgat ccaacccctc    180
cgctgctata gtgcagtcgg cttctgacgt tcagtcagc cgtcatctga aaacgacatg     240
tcgcacaagt cctaagttac gcgacaggct gccgccctgc ccttttcctg gcgttttctt    300
gtcgcgtgtt ttagtcgcat aaagtagaat acttgcgact agaaccgag acattacgcc     360
atgaacaaga gcgccgccgc tggcctgctg ggctatgccc gcgtcagcac cgacgaccag    420
gacttgacca accaacgggc cgaactgcac gcggccggct gcaccaagct gttttccgag    480
aagatcaccg gcaccaggcg cgaccgcccg gagctggcca ggatgcttga ccacctacgc    540
cctggcgacg ttgtgacagt gaccaggcta gaccgcctgg cccgcagcac ccgcgaccta    600
ctggacattg ccgagcgcat ccaggaggcc ggcgcgggcc tgcgtagcct ggcagagccg    660
tgggccgaca ccaccacgcc ggccggccgc atggtgttga ccgtgttcgc cggcattgcc    720
gagttcgagc gttccctaat catcgaccgc acccggagcg ggcgcgaggc cgccaaggcc    780
cgaggcgtga agtttggccc ccgccctacc ctcaccccgg cacagatcgc gcacgcccgc    840
gagctgatcg accaggaagg ccgcaccgtg aaagaggcgg ctgcactgct ggcgtgcat    900
cgctcgaccc tgtaccgcgc acttgagcgc agcgaggaag tgacgcccac cgaggccagg    960
cggcgcggtg ccttccgtga ggacgcattg accgaggccg acgccctggc ggccgccgag   1020
aatgaacgcc aagaggaaca agcatgaaac cgcaccagga cggccaggac gaaccgtttt   1080
tcattaccga agagatcgag gcggagatga tcgcggccgg gtacgtgttc gagccgcccg   1140
cgcacctctc aaccgtgcgg ctgcatgaaa tcctggccgg tttgtctgat gccaagctgg   1200
cggcctggcc ggccagcttg gccgctgaag aaaccgagcg ccgccgtcta aaaaggtgat   1260
gtgtatttga gtaaaacagc ttgcgtcatg cggtcgctgc gtatatgatc cgatgagtaa   1320
ataaacaaat acgcaagggg aacgcatgaa ggttatcgct gtacttaacc agaaaggcgg   1380
gtcaggcaag acgaccatcg gaacccatct agcccgcgcc ctgcaactcg ccggggccga   1440
tgttctgtta gtcgattccg atcccagg cagtgcccgc gattgggcgg ccgtgcggga    1500
agatcaaccg ctaaccgttg tcggcatcga ccgcccgacg attgaccgcg acgtgaaggc   1560
catcggccgg cgcgacttcg tagtgatcga cggagcgccc caggcggcgg acttggctgt   1620
gtccgcgatc aaggcagccg acttcgtgct gattccggtg cagccaagcc cttacgacat   1680
atgggccacc gccgacctgg tggagctggt taagcagcgc attgaggtca cggatggaag   1740
gctacaagcg gcctttgtcg tgtcgcgggc gatcaaaggc acgcgcatcg gcggtgaggt   1800
tgccgaggcg ctggccgggt acgagctgcc cattcttgag tcccgtatca cgcagcgcgt   1860
gagctaccca ggcactgccg ccgccggcac aaccgttctt gaatcagaac ccgagggcga   1920
cgctgcccgc gaggtccagg cgctggccgc tgaaattaaa tcaaaactca tttgagttaa   1980
tgaggtaaag agaaaatgag caaaagcaca aacacgctaa gtgccggccg tccgagcgca   2040
cgcagcagca aggctgcaac gttggccagc ctggcagaca cgccagccat gaagcgggtc   2100
aactttcagt tgccggcgga ggatcacacc aagctgaaga tgtacgcggt acgccaaggc   2160
aagaccatta ccgagctgct atctgaatag atcgcgcagc taccagagta atgagcaaa    2220
tgaataaatg agtagatgaa ttttagcggc taaaggaggc ggcatggaaa atcaagaaca   2280
```

```
accaggcacc gacgccgtgg aatgcccat gtgtggagga acgggcggtt ggccaggcgt    2340
aagcggctgg gttgtctgcc ggccctgcaa tggcactgga accccaagc ccgaggaatc    2400 ggcgtgacgg tcgcaaacca tccggcccgg tacaaatcgg cgcggcgctg ggtgatgacc   2460
tggtggagaa gttgaaggcc gcgcaggccg cccagcggca acgcatcgag gcagaagcac   2520
gccccggtga atcgtggcaa gcggccgctg atcgaatccg caaagaatcc cggcaaccgc   2580
cggcagccgg tgcgccgtcg attaggaagc cgcccaaggg cgacgagcaa ccagattttt   2640
tcgttccgat gctctatgac gtgggcaccc gcgatagtcg cagcatcatg acgtggccg    2700 tttccgtct gtcgaagcgt gaccgacgag ctggcgaggt gatccgctac gagcttccag    2760
acgggcacgt agaggtttcc gcagggccgg ccggcatggc cagtgtgtgg gattacgacc   2820
tggtactgat ggcggtttcc catctaaccg aatccatgaa ccgataccgg aagggaagg    2880 gagacaagcc cggccgcgtg ttccgtccac acgttgcgga cgtactcaag ttctgccggc   2940
gagccgatgg cggaaagcag aaagacgacc tggtagaaac ctgcattcgg ttaaacacca   3000
cgcacgttgc catgcagcgt acgaagaagg ccaagaacgg ccgcctggtg acggtatccg   3060
agggtgaagc cttgattagc cgctacaaga tcgtaaagag cgaaaccggg cggccggagt   3120
acatcgagat cgagctagct gattggatgt accgcgagat cacagaaggc aagaacccgg   3180
acgtgctgac ggttcacccc gattacttt tgatcgatcc cggcatcggc cgttttctct    3240
accgcctggc acgccgcgcc gcaggcaagg cagaagccag atggttgttc aagacgatct   3300
acgaacgcag tggcagcgcc ggagagttca agaagttctg tttcaccgtg cgcaagctga   3360
tcgggtcaaa tgacctgccg gagtacgatt tgaaggagga ggcggggcag gctggcccga   3420
tcctagtcat gcgctaccgc aacctgatcg agggcgaagc atccgccggt tcctaatgta   3480
cggagcagat gctagggcaa attgccctag caggggaaaa aggtcgaaaa ggactctttc   3540
ctgtggatag cacgtacatt gggaacccaa agccgtacat tgggaaccgg aacccgtaca   3600
ttgggaaccc aaagccgtac attgggaacc ggtcacacat gtaagtgact gatataaaag   3660
agaaaaaagg cgattttcc gcctaaaact ctttaaaact tattaaaact cttaaaaccc     3720
gcctggcctg tgcataactg tctggccagc gcacagccga agagctgcaa aaagcgccta   3780
cccttcggtc gctgcgctcc ctacgccccg ccgcttcgcg tcggcctatc gcggccgctg   3840
gccgctcaaa aatggctggc ctacggccag gcaatctacc agggcgcgga caagccgcgc   3900
cgtcgccact cgaccgccgg cgcccacatc aaggcaccct gcctcgcgcg tttcggtgat   3960
gacggtgaaa acctctgaca catgcagctc ccggtgacgg tcacagcttg tctgtaagcg   4020
gatgccggga gcagacaagc ccgtcagggc gcgtcagcgg gtgttggcgg gtgtcgggc    4080 gcagccatga cccagtcacg tagcgatagc ggagtgtata ctggcttaac tatgcggcat   4140
cagagcagat tgtactgaga gtgcaccata tgcggtgtga ataccgcac agatgcgtaa    4200 ggagaaaata ccgcatcagg cgctcttccg cttcctcgct cactgactcg ctgcgctcgg   4260
tcgttcggct gcggcgagcg gtatcagctc actcaaaggc ggtaatacgg ttatccacag   4320
aatcagggga taacgcagga agaacatgt gagcaaaagg ccagcaaaag gccaggaacc    4380
gtaaaaaggc cgcgttgctg gcgtttttcc ataggctccg ccccccctgac gagcatcaca   4440 aaaatcgacg ctcaagtcag aggtggcgaa acccgacagg actataaaga taccaggcgt   4500
ttccccctgg aagctccctc gtgcgctctc ctgttccgac cctgccgctt accggatacc   4560
tgtccgcctt tctcccttcg ggaagcgtgg cgctttctca tagctcacgc tgtaggtatc   4620
```

```
tcagttcggt gtaggtcgtt cgctccaagc tgggctgtgt gcacgaaccc cccgttcagc    4680
ccgaccgctg cgccttatcc ggtaactatc gtcttgagtc caacccggta agacacgact    4740
tatcgccact ggcagcagcc actggtaaca ggattagcag agcgaggtat gtaggcggtg    4800
ctacagagtt cttgaagtgg tggcctaact acggctacac tagaaggaca gtatttggta    4860
tctgcgctct gctgaagcca gttaccttcg gaaaagagt tggtagctct tgatccggca     4920
aacaaaccac cgctggtagc ggtggttttt ttgtttgcaa gcagcagatt acgcgcagaa    4980
aaaaggatc tcaagaagat cctttgatct tttctacggg gtctgacgct cagtggaacg    5040
aaaactcacg ttaagggatt ttggtcatgc attctaggtg attagaaaaa ctcatcgagc    5100
atcaaatgaa actgcaattt attcatatca ggattatcaa taccatattt ttgaaaaagc    5160
cgtttctgta atgaaggaga aaactcaccg aggcagttcc ataggatggc aagatcctgg    5220
tatcggtctg cgattccgac tcgtccaaca tcaatacaac ctattaattt ccctcgtca    5280
aaaataaggt tatcaagtga gaaatcacca tgagtgacga ctgaatccgg tgagaatggc    5340
aaaagtttat gcatttcttt ccagacttgt tcaacaggcc agccattacg ctcgtcatca    5400
aaatcactcg catcaaccaa accgttattc attcgtgatt gcgcctgagc gagtcgaaat    5460
acgcgatcgc tgttaaaagg acaattacaa acaggaatcg aatgcaaccg gcgcaggaac    5520
actgccagcg catcaacaat attttcacct gaatcaggat attcttctaa tacctggaat    5580
gctgttttcc ctgggatcgc agtggtgagt aaccatgcat catcaggagt acggataaaa    5640
tgcttgatgg tcggaagagg cataaattcc gtcagccagt ttagtctgac catctcatct    5700
gtaacatcat tggcaacgct acctttgcca tgtttcagaa acaactctgg cgcatcgggc    5760
ttcccataca atcggtagat tgtcgcacct gattgcccga cattatcgcg agcccattta    5820
tacccatata aatcagcatc catgttggaa tttaatcgcg gccttgagca agacgtttcc    5880
cgttgaatat ggctcataac agaacttatt atttccttcc tcttttctac agtatttaaa    5940
gataccccaa gaagctaatt ataacaagac gaactccaat tcactgttcc ttgcattcta    6000
aaaccttaaa taccagaaaa cagctttttc aaagttgttt tcaaagttgg cgtataacat    6060
agtatcgacg gagccgattt tgaaaccgcg gtgatcacag gcagcaacgc tctgtcatcg    6120
ttacaatcaa catgctaccc tccgcgagat catccgtgtt caaacccgg cagcttagtt     6180
gccgttcttc cgaatagcat cggtaacatg agcaaagtct gccgccttac aacggctctc    6240
ccgctgacgc cgtcccggac tgatgggctg cctgtatcga gtggtgattt tgtgccgagc    6300
tgccggtcgg ggagctgttg gctggctggt ggcaggatat attgtggtgt aaacataacg    6360
aattcgtctc aggagagcgt cgatctagta acatagatga caccgcgcgc gataatttat    6420
cctagtttgc gcgctatatt ttgttttcta tcgcgtatta aatgtataat tgcgggactc    6480
taatcataaa aacccatctc ataaataacg tcatgcatta catgttaatt attacatgct    6540
taacgtaatt caacagaaat tatatgataa tcatcgcaag accggcaaca ggattcaatc    6600
ttaagaaact ttattgccaa atgtttgaac gatctgcttc gacgcactcc ttctttactc    6660
caccatctcg tccttattga aaacgtgggt agcaccaaaa cgaatcaagt cgctggaact    6720
gaagttacca atcacgctgg atgatttgcc agttggatta atcttgcctt tccccgcatg    6780
aataatattg atgaatgcat gcgtgagggg tagttcgatg ttggcaatag ctgcaattgc    6840
cgcgacatcc tccaacgagc ataattcttc agaaaatag cgatgttcca tgttgtcagg    6900
gcatgcatga tgcacgttat gaggtgacgg tgctaggcag tattccctca agtttcata    6960
gtcagtatca tattcatcat tgcattcctg caagagagaa ttgagacgca atccacacgc    7020
```

```
tgcggcaacc ttccggcgtt cgtggtctat ttgctcttgg acgttgcaaa cgtaagtgtt    7080
ggatcggggt gggcgaagaa ctccagcatg agatccccgc gctggaggat catccagccg    7140
gcgtcccgga aaacgattcc gaagcccaac ctttcataga aggcggcggt ggaatcgaaa    7200
tctcgtgatg gcaggttggg cgtcgcttgg tcggtcattt cgaacccag agtcccgctc    7260 agaagaactc gtcaagaagg cgatagaagg cgatgcgctg cgaatcggga gcggcgatac    7320
cgtaaagcac gaggaagcgg tcagcccatt cgccgccaag ctcttcagca atatcacggg    7380
tagccaacgc tatgtcctga tagcggtccg ccacacccag ccggccacag tcgatgaatc    7440
cagaaaagcg gccattttcc accatgatat tcggcaagca ggcatcgcca tgggtcacga    7500
cgagatcctc gccgtcgggc atgcgcgcct tgagcctggc gaacagttcg gctggcgcga    7560 gccctgatg ctcttcgtcc agatcatcct gatcgacaag accggcttcc atccgagtac    7620
gtgctcgctc gatgcgatgt ttcgcttggt ggtcgaatgg gcaggtagcc ggatcaagcg    7680
tatgcagccg ccgcattgca tcagccatga tggatacttt ctcggcagga gcaaggtgag    7740
atgacaggag atcctgcccc ggcacttcgc ccaatagcag ccagtcccctt cccgcttcag    7800 tgacaacgtc gagcacagct gcgcaaggaa cgcccgtcgt ggccagccac gatagccgcg    7860
ctgcctcgtc ctgcagttca ttcagggcac cggacaggtc ggtcttgaca aaaagaaccg    7920 ggcgccctg cgctgacagc cggaacacgg cggcatcaga gcagccgatt gtctgttgtg    7980
cccagtcata gccgaatagc ctctccaccc aagcggccgg agaacctgcc cggatccggg    8040
cggaaatagg taaagaagtt gcggataagg taattgccat tgcagattat ttggattgag    8100
agtgaatatg agactctaat tggataccga ggggaattta tggaacgtca gtggagcatt    8160
tttgacaaga aatatttgct agctgatagt gaccttaggc gacttttgaa cgcgcaataa    8220
tggtttctga cgtatgtgct tagctcatta aactccagaa acccctccgt caggagacta    8280
gagccaagct gatctccttt gccccggaga tcaccatgga cgactttctc tatctctacg    8340
atctaggaag aaagttcgac ggagaaggtg acgataccat gttcaccacc gataatgaga    8400
agattagcct cttcaatttc agaaagaatg ctgacccaca gatggttaga gaggcctacg    8460
cggcaggtct gatcaagacg atctaccccga gtaataatct ccaggagatc aaataccttc    8520
ccaagaaggt taaagatgca gtcaaaagat tcaggactaa ctgcatcaag aacacagaga    8580
aagatatatt tctcaagatc agaagtacta ttccagtatg gacgattcaa ggcttgcttc    8640
ataaaccaag gcaagtaata gagattggag tctctaagaa agtagttcct actgaatcaa    8700
aggccatgga gtcaaaaatt cagatcgagg atctaacaga actcgccgtg aagactggcg    8760
aacagttcat acagagtctt ttacgactca atgacaagaa gaaaatcttc gtcaacatgg    8820
tggagcacga cactctcgtc tactccaaga atatcaaaga tacagtctca gaagaccaaa    8880
gggctattga cttttcaa caaagggtaa tatcgggaaa cctcctcgga ttccattgcc    8940
cagctatctg tcacttcatc aaaaggacag tagaaaagga aggtggcacc tacaaatgcc    9000
atcattgcga taaaggaaag gctatcgttc aagatgcctc tgccgacagt ggtcccaaag    9060
atggaccccc acccacgagg agcatcgtgg aaaaagaaga cgttccaacc acgtcttcaa    9120
agcaagtgga ttgatgtgat atctccactg acgtaaggga tgacgcacaa tcccactatc    9180
cttcgcaaga cccttcctct atataaggaa gttcatttca tttggagagg actccggtat    9240
ttttacaaca ataccacaac aaaacaaaca acaaacaaca ttacaattta ctattctagt    9300
cgaaatggat aacgcaacac ttgctgtgat cctttccatt ttgtttgtgt tttaccacat    9360
```

```
tttcaaatcc ttttttcacca attcttcatc tcgtaggctt cctcctggtc ccaaacccgt    9420
gccaattttt ggcaacattt tcgatcttgg cgaaaagcct catcgatctt ttgccaatct    9480
atctaaaatt cacggcccct tgattagcct aaagttagga agtgtaacaa ctattgttgt    9540
ttcctcggcc tctgtggccg aggaaatgtt ccttaaaaat gaccaagcac ttgctaaccg    9600
aaccattcct gactcggtta gggctggtga ccacgacaaa ttatccatgt cgtggttgcc    9660
tgtttcccaa aaatggagaa atatgagaaa aatctccgct gtccaattac tctccaacca    9720
aaaacttgat gctagtcaac ctcttagaca agctaaggtg aaacaacttt tatcatacgt    9780
acaagtttgt tccgaaaaaa tgcaacccgt cgatattgga cgggccgcat ttacaacgtc    9840
acttaattta ttatcaaaca catttttctc aatcgaatta gcaagtcatg aatctagtgc    9900
ttcccaagag tttaaacaac tcatgtgaaa tattatggag gaaattggaa ggcctaatta    9960
tgctgatttt ttccctattc ttggttacat tgatcccttt ggtataagac gtcgtttggc    10020
tggttacttt gataaactca ttgatgtttt ccaagacatt attcgtgaaa gacaaaagct    10080
tcgatcttct aattcttccg gcgcaaaaca aacaaatgac attcttgata ctcttcttaa    10140
actccatgaa gataatgagt tgagtatgcc tgaaattaat caccttctcg tggatatctt    10200
tgacgccgga acagacacaa cagcaagcac attagaatgg gcaatggccg aacttgtgaa    10260
aaacccggaa atgatgacta aagttcaaat tgaaatcgaa caagctcttg gaaaagattg    10320
cttagacata caagaatccg acatctcaaa actaccttat ttacaagcca ttataaaaga    10380
aacgttacgt ttacaccctc ctactgtgtt tttgctgcct cgaaaggcag acaatgacgt    10440
agagttatat ggctacgttg taccaaagaa tgctcaagtc cttgtcaatc tttgggcaat    10500
tggtcgtgat ccaaaggtat ggaaaaatcc ggaagtattt tctcctgaaa ggttttaga    10560
ttgcaatatc gattataaag gacgagattt cgaactttta ccctttggtg ctggtagaag    10620
gatatgccct ggacttactt tggcatatag aatgttgaac ttgatgttgg ctactcttct    10680
tcaaaactac aattggaaac ttgaagatgg tatcaatcct aaggatttag acatggatga    10740
gaaatttggg attacattgc aaaaggttaa acctcttcaa gttattccag ttcccagaaa    10800
ctaggcttgc tctcaagatc aaaggcttaa aaagctgggg ttttatgaat gggatcaaag    10860
tttctttttt tcttttatat ttgcttctcc atttgtttgt ttcatttccc ttttttgtttt    10920
cgtttctatg atgcacttgt gtgtgacaaa ctctctgggt ttttacttac gtctgcgttt    10980
caaaaaaaaa aaccgctttc gttttgcgtt ttagtcccat tgttttgtag ctctgagtga    11040
tcgaattgat gcctctttat tccttttgtt ccctataatt tctttcaaaa ctcagaagaa    11100
aaaccttgaa actctttgca atgttaatat aagtattgta taagattttt attgatttgg    11160
ttattagtct tactttttgct acctccatct tcacttggaa ctgatattct gaatagttaa    11220
agcgttacat gtcttccatt cacaaatgaa cttaaactag cacaaagtca gatattttaa    11280
gatcgcacca ttttatataa ccccaatcgt caattctact gtttcaagtt ttacaccaaa    11340
acaattacga ggtgtatcta ttcgttactc ttttcgctta ttaatccttt tacatgatgc    11400
aaaatataac aaattaattt caaattgtcc tgcacatttg gtttatacat cttgattcca    11460
aaaagtcgct gtcaggagat acatgagaat taagggagtc acggtatgac ccccgccgat    11520
gacgcgggac aagccgtttt acgtttggaa ctgacagaac cgcaacgttg aaggagccac    11580
tgagccgcgg gttctggag tttaatgagc taagcacata cgtcagaaac cattattgcg    11640
cgttcaaaag tcgcctaagg tcactatcag ctagcaaata tttcttgtca aaaatgctcc    11700
actgacgttc cataaattcc cctcggtatc caattagagt ctcatattca ctctcaactc    11760
```

```
gatcgaggca atgatggcta tggaagtggg ttatcttcgg cactcgacaa cgatcaccaa  11820
cggactgtgt tgtaactgtg atccgaagcc ccgaggagca cgtcgtgtac agactaggct  11880
gcctggcacc ctgtgtctcg tcaaggatac ctttacctct agcaaagcta aactaaaaaa  11940
gccgtcgcag agagaaatct ttctaacaag taggaagagg ctgaatcaga tacaagctgt  12000
ttcaacggct gaaaggaga gagaggcaga caaaacatcc actccaccta ttcccagtag  12060
catccacgat atttcaaatg gagatcacat tcttggcttc ggagccgatt tgaccgaaga  12120
tcatcctggc taccatgatc ttgaatataa gaggaggcgt agtcgtattg ctgaccttgc  12180
gaagatacat aaaataggtg aacccattcc ttgcgtggac tacacatcgg aagagattcg  12240
tgtgtggggt catgtgttag atactctagt ggacctctac ccaactcatg cttgtaagga  12300
atacctgaat tgctacgagc tgtttaactt caagccaaac tatattccac agctgcaaga  12360
actttcggag gtcctggaac ggagcacagg atggcacatc cgcccagtag ctggactcct  12420
ccaccctcgt gacttcctaa acggtctagc cttccgcact ttccattcaa cccagtatgt  12480
tcggcatggc agcaatccca tgtacacccc cgagccagac atttgtcacg aggttttagg  12540
ccacgtcccc attctggctg atccggagtt tgctgactta gcttgggcca ttggccaagc  12600
ttctctgggt gcttcagaga aggatatctg gcaccttacg aagctctact ggtacactgt  12660
ggagtttggc acagtaaagg aaggtaacga gattaaagcg ttcggtgcag gccttctgtc  12720
tagttttggg gagctgaagc acatgcgggt ggggacggat ggattcatgc ctgagttcgt  12780
ggagcttgac ccgtttaaga agatgcccaa gatgagctac aaagacgggt accagaagag  12840
gtattttcta tgcgagagct ttgcagatgc agcggcaaag cttagggcgt attccagaag  12900
cattctgaag cctgaggtgc agtccatcaa gtttggagat acgccaatcc ggctctaagc  12960
ttatatgaag atgaagatga aatatttggt gtgtcaaata aaaagcttgt gtgcttaagt  13020
ttgtgttttt ttcttggctt gttgtgttat gaatttgtgg cttttttctaa tattaaatga  13080 atgtaagatc tcattataat gaataaacaa atgtttctat aatccattgt gaatgttttg  13140
ttggatctct tctgcagcat ataactactg tatgtgctat ggtatggact atggaatatg  13200
attaaagata agcgctgtca ggagccgtac aaaattgatt attgatgtca caaatcaatc  13260
agagctaaat tccaaaaaaa atatgatctt tgaaacttgc atcaataact aacgattcta  13320
ggaagagccc atttcgattt caacaaaaag atgagagctt gattacatat aaaatcaaga  13380
gaaattaacg acattgaaga gaattcgatc tcgaaaccgg aaacaaagac ttataagtcg  13440
attagtctaa ttcaatgcag aagaaagaat accaggtttg gccttcacga tggaaagctt  13500
cggatttgga gccaagtctc ataaacgcca ttgtggaaga agtcttgag ttggtggtaa  13560 tgtaacagag tagtaagaac agagaagaga gagtgtga atacatgaa ttgtcgggca  13620 acaaaaatcc tgaacatctt attttagcaa agagaaagag ttccgagtct gtagcagaag  13680
agtgaggaga aatttaagct cttggacttg tgaattgttc cgcctcttga atacttcttc  13740
aatcctcata tattcttctt ctatgttacc tgaaaaccgg catttaatct cgcgggttta  13800
ttccggttca acattttttt tgttttgagt tattatctgg gcttaataac gcaggcctga  13860
aataaattca aggcccaact gtttttttttt ttaagaagtt gctgttaaaa aaaaaaaag  13920 ggaattaaca acaacaacaa aaaagataa agaaaataat aacaattact ttaattgtag  13980
actaaaaaaa catagatttt atcatgaaaa aagagaaaa gaaataaaaa cttggatcaa  14040
aaaaaaaaac atacagatct tctaattatt aacttttctt aaaaattagg tcctttttcc  14100
```

```
caacaattag gtttagagtt ttggaattaa accaaaaaga ttgttctaaa aaatactcaa    14160
atttggtaga taagtttcct tattttaatt agtcaatggt agatactttt ttttcttttc    14220
tttattagag tagattagaa tcttttatgc caagtattga taaattaaat caagaagata    14280
aactatcata atcaacatga aattaaaaga aaaatctcat atatagtatt agtattctct    14340
atatatatta tgattgctta ttcttaatgg gttgggttaa ccaagacata gtcttaatgg    14400
aaagaatctt ttttgaactt tttccttatt gattaaattc ttctatagaa aagaaagaaa    14460
ttatttgagg aaaagtatat acaaaaagaa aaatagaaaa atgtcagtga agcagatgta    14520
atggatgacc taatccaacc accaccatag gatgtttcta cttgagtcgg tcttttaaaa    14580
acgcacggtg gaaaatatga cacgtatcat atgattcctt cctttagttt cgtgataata    14640
atcctcaact gatatcttcc ttttttttgtt ttggctaaag atattttatt ctcattaata    14700
gaaaagacgg ttttgggctt ttggtttgcg atataaagaa gaccttcgtg tggaagataa    14760
taattcatcc tttcgtcttt ttctgactct tcaatctctc ccaaagccta aagcgatctc    14820
tgcaaatctc tcgcgactct ctcttttcaag gtatattttc tgattctttt tgttttttgat    14880 tcgtatctga tctccaattt ttgttatgtg gattattgaa tcttttgtat aaattgcttt    14940
tgacaatatt gttcgtttcg tcaatccagc ttctaaattt tgtcctgatt actaagatat    15000
cgattcgtag tgtttacatc tgtgtaattt cttgcttgat tgtgaaatta ggattttcaa    15060
ggacgatcta ttcaattttt gtgttttctt tgttcgattc tctctgtttt aggtttctta    15120
tgtttagatc cgtttctctt tggtgttgtt ttgatttctc ttacggcttt tgatttggta    15180
tatgttcgct gattggtttc tacttgttct attgttttat ttcagaatgg cttctatgat    15240
atcctcttca gctgtgacta cagtcagccg tgcttctacg gtgcaatcgg ccgcggtggc    15300
tccattcggc ggcctcaaat ccatgactgg attcccagtt aagaaggtca acactgacat    15360
tacttccatt acaagcaatg gtggaagagt aaagtgcatg ctgatgaatt atcagaacga    15420
cgatttacgc atcaaagaaa tcaaagagtt acttcctcct gtcgcattgc tggaaaaatt    15480
ccccgctact gaaaatgccg cgaatacggt tgcccatgcc cgaaaagcga tccataagat    15540
cctgaaaggt aatgatgatc gcctgttggt tgtgattggc ccatgctcaa ttcatgatcc    15600
tgtcgcggca aaagagtatg ccactcgctt gctggcgctg cgtgaagagc tgaaagatga    15660
gctggaaatc gtaatgcgcg tctatttga aaagccgcgt accacggtgg gctgaaaagg    15720
gctgattaac gatccgcata tggataatag cttccagatc aacgacggtc tgcgtatagc    15780
ccgtaaattg ctgcttgata ttaacgacag cggtctgcca gcggcaggtg agtttctcga    15840
tatgatcacc ccacaatatc tcgctgacct gatgagctgg ggcgcaattg gcgcacgtac    15900
caccgaatcg caggtgcacc gcgaacaggc atcagggctt tcttgtccgg tcggcttcaa    15960
aaatggcacc gacggtacga ttaaagtggc tatcgatgcc attaatgccg ccggtgcgcc    16020
gcactgcttc ctgtccgtaa cgaaatgggg cattcggcg attgtgaata ccagcggtaa    16080
cggcgattgc catatcattc tgcgcggcgg taaagagcct aactacagcg cgaagcacgt    16140
tgctgaagtg aaagaagggc tgaacaaagc aggcctgcca gcacaggtga tgatcgattt    16200
cagccatgct aactcgtcca aacaattcaa aaagcagatg gatgtttgtg ctgacgtttg    16260
ccagcagatt gccggtggcg aaaaggccat tattggcgtg atggtggaaa gccatctggt    16320
ggaaggcaat cagagcctcg agagcgggga gccgctggcc tacggtaaga gcatcaccga    16380
tgcctgcatc ggctgggaag ataccgatgc tctgttacgt caactggcga atgcagtaaa    16440
agcgcgtcgc ggggaattca tcttttaccc atacgatgtt cctgactatg cgggctatcc    16500
```

```
ctatgacgtc ccggactatg caggatccta tccatatgac gttccagatt acgctgctca    16560
gtaggcttat atgaagatga agatgaaata tttggtgtgt caaataaaaa gcttgtgtgc    16620
ttaagtttgt gttttttct tggcttgttg tgttatgaat ttgtggcttt ttctaatatt     16680
aaatgaatgt aagatctcat tataatgaat aaacaaatgt ttctataatc cattgtgaat    16740
gttttgttgg atctcttctg cagcatataa ctactgtatg tgctatggta tggactatgg    16800
aatatgatta aagataag                                                   16818

<210> SEQ ID NO 27
<211> LENGTH: 18647
<212> TYPE: DNA
<213> ORGANISM: Artificial Sequence
<220> FEATURE:
<223> OTHER INFORMATION: pDOPA4 overexpression vector

<400> SEQUENCE: 27
cgctgtcatg agacgaattc tgacaggata tattggcggg taaacctaag agaaaagagc       60
gtttattaga ataatcggat atttaaaagg gcgtgaaaag gtttatccgt tcgtccattt      120
gtatgtgcat gccaaccaca gggttcccct cgggatcaaa gtactttgat ccaacccctc      180
cgctgctata gtgcagtcgg cttctgacgt tcagtgcagc cgtcatctga aaacgacatg      240
tcgcacaagt cctaagttac gcgacaggct gccgccctgc cctttcctg gcgttttctt       300 gtcgcgtgtt ttagtcgcat aaagtagaat acttgcgact agaaccggag acattacgcc      360
atgaacaaga gcgccgccgc tggcctgctg ggctatgccc gcgtcagcac cgacgaccag      420
gacttgacca ccaacgggc gaactgcac gcggccggct gcaccaagct gttttccgag        480
aagatcaccg gcaccaggcg cgaccgcccg gagctggcca ggatgcttga ccacctacgc      540
cctggcgacg ttgtgacagt gaccaggcta gaccgcctgg cccgcagcac ccgcgaccta     600
ctggacattg ccgagcgcat ccaggaggcc ggcgcgggcc tgcgtagcct ggcagagccg      660
tgggccgaca ccaccacgcc ggccggccgc atggtgttga ccgtgttcgc cggcattgcc     720
gagttcgagc gttccctaat catcgaccgc acccggagcg ggcgcgaggc cgccaaggcc     780
cgaggcgtga agtttggccc ccgccctacc ctcaccccgg cacagatcgc gcacgcccgc      840
gagctgatcg accaggaagg ccgcaccgtg aaagaggcgg ctgcactgct ggcgtgcat       900 cgctcgaccc tgtaccgcgc acttgagcgc agcgaggaag tgacgcccac cgaggccagg     960
cggcgcggtg ccttccgtga ggacgcattg accgaggccg acgccctggc ggccgccgag    1020
aatgaacgcc aagaggaaca agcatgaaac cgcaccagga cggccaggac gaaccgtttt    1080
tcattaccga agagatcgag gcggagatga tcgcggccgg gtacgtgttc gagccgcccg    1140
cgcacctctc aaccgtgcgg ctgcatgaaa tcctggccgg tttgtctgat gccaagctgg    1200
cggcctggcc ggccagcttg gccgctgaag aaaccgagcg ccgccgtcta aaaaggtgat    1260
gtgtatttga gtaaaacagc ttgcgtcatg cggtcgctgc gtatatgatc cgatgagtaa    1320
ataaacaaat acgcaagggg aacgcatgaa ggttatcgct gtacttaacc agaaaggcgg    1380
gtcaggcaag acgaccatcg gaacccatct agcccgcgcc ctgcaactcg ccggggccga    1440
tgttctgtta gtcgattccg atccccaggg cagtgcccgc gattgggcgg ccgtgcggga    1500
agatcaaccg ctaaccgttg tcggcatcga ccgcccgacg attgaccgcg acgtgaaggc    1560
catcggccgg cgcgacttcg tagtgatcga cggagcgccc caggcggcgg acttggctgt    1620
gtccgcgatc aaggcagccg acttcgtgct gattccggtg cagccaagcc cttacgacat    1680
```

```
atgggccacc gccgacctgg tggagctggt taagcagcgc attgaggtca cggatggaag    1740
gctacaagcg gcctttgtcg tgtcgcgggc gatcaaaggc acgcgcatcg gcggtgaggt    1800
tgccgaggcg ctggccgggt acgagctgcc cattcttgag tcccgtatca cgcagcgcgt    1860
gagctaccca ggcactgccg ccgccggcac aaccgttctt gaatcagaac ccagggggcga   1920 cgctgcccgc gaggtccagg cgctggccgc tgaaattaaa tcaaaactca tttgagttaa    1980
tgaggtaaag agaaaatgag caaaagcaca aacacgctaa gtgccggccg tccgagcgca    2040
cgcagcagca aggctgcaac gttggccagc ctggcagaca cgccagccat gaagcgggtc    2100
aactttcagt tgccggcgga ggatcacacc aagctgaaga tgtacgcggt acgccaaggc    2160
aagaccatta ccgagctgct atctgaatag atcgcgcagc taccagagta aatgagcaaa    2220
tgaataaatg agtagatgaa ttttagcggc taaaggaggc ggcatggaaa atcaagaaca    2280
accaggcacc gacgccgtgg aatgccccat gtgtggagga acgggcggtt ggccaggcgt    2340
aagcggctgg gttgtctgcc ggccctgcaa tggcactgga accccaagcc cgaggaatc    2400 ggcgtgacgg tcgcaaacca tccggcccgg tacaaatcgg cgcggcgctg ggtgatgacc    2460
tggtggagaa gttgaaggcc gcgcaggccg cccagcggca acgcatcgag gcagaagcac    2520
gccccggtga atcgtggcaa gcggccgctg atcgaatccg caaagaatcc cggcaaccgc    2580
cggcagccgg tgcgccgtcg attaggaagc cgcccaaggg cgacgagcaa ccagatttt    2640 tcgttccgat gctctatgac gtgggcaccc gcgatagtcg cagcatcatg gacgtggccg    2700
ttttccgtct gtcgaagcgt gaccgacgag ctggcgaggt gatccgctac gagcttccag    2760
acgggcacgt agaggtttcc gcagggccgg ccggcatggc cagtgtgtgg gattacgacc    2820
tggtactgat ggcggtttcc catctaaccg aatccatgaa ccgataccgg aagggaagg    2880 gagacaagcc cggccgcgtg ttccgtccac acgttgcgga cgtactcaag ttctgccggc    2940
gagccgatgg cggaaagcag aaagacgacc tggtagaaac ctgcattcgg ttaaacacca    3000
cgcacgttgc catgcagcgt acgaagaagg ccaagaacgg ccgcctggtg acggtatccg    3060
agggtgaagc cttgattagc cgctacaaga tcgtaaagag cgaaaccggg cggccggagt    3120
acatcgagat cgagctagct gattggatgt accgcgagat cacagaaggc aagaacccgg    3180
acgtgctgac ggttcacccc gattactttt tgatcgatcc cggcatcggc cgttttctct    3240
accgcctggc acgccgcgcc gcaggcaagg cagaagccag atggttgttc aagacgatct    3300
acgaacgcag tggcagcgcc ggagagttca agaagttctg tttcaccgtg cgcaagctga    3360
tcgggtcaaa tgacctgccg gagtacgatt tgaaggagga ggcggggcag gctggcccga    3420
tcctagtcat gcgctaccgc aacctgatcg agggcgaagc atccgccggt tcctaatgta    3480
cggagcagat gctagggcaa attgccctag caggggaaaa aggtcgaaaa ggactctttc    3540
ctgtggatag cacgtacatt gggaacccaa agccgtacat tgggaaccgg aacccgtaca    3600
ttgggaaccc aaagccgtac attgggaacc ggtcacacat gtaagtgact gatataaaag    3660
agaaaaaagg cgattttcc gcctaaaact ctttaaaact tattaaaact cttaaaaccc    3720
gcctggcctg tgcataactg tctggccagc gcacagccga agagctgcaa aaagcgccta    3780
cccttcggtc gctgcgctcc ctacgcccg ccgcttcgcg tcggcctatc gcggccgctg    3840
gccgctcaaa aatggctggc ctacggccag gcaatctacc agggcgcgga caagccgcgc    3900
cgtcgccact cgaccgccgg cgcccacatc aaggcaccct gcctcgcgcg tttcggtgat    3960
gacggtgaaa acctctgaca catgcagctc ccggtgacgg tcacagcttg tctgtaagcg    4020
gatgccggga gcagacaagc ccgtcagggc gcgtcagcgg gtgttggcgg gtgtcgggc    4080
```

```
gcagccatga cccagtcacg tagcgatagc ggagtgtata ctggcttaac tatgcggcat   4140
cagagcagat tgtactgaga gtgcaccata tgcggtgtga ataccgcac agatgcgtaa    4200 ggagaaaata ccgcatcagg cgctcttccg cttcctcgct cactgactcg ctgcgctcgg   4260
tcgttcggct gcggcgagcg gtatcagctc actcaaaggc ggtaatacgg ttatccacag   4320
aatcagggga taacgcagga agaacatgt gagcaaaagg ccagcaaaag gccaggaacc    4380
gtaaaaaggc cgcgttgctg gcgttttcc ataggctccg ccccctgac gagcatcaca    4440 aaaatcgacg ctcaagtcag aggtggcgaa acccgacagg actataaaga taccaggcgt   4500
ttccccctgg aagctccctc gtgcgctctc ctgttccgac cctgccgctt accggatacc   4560
tgtccgcctt tctcccttcg ggaagcgtgg cgctttctca tagctcacgc tgtaggtatc   4620
tcagttcggt gtaggtcgtt cgctccaagc tgggctgtgt gcacgaaccc cccgttcagc   4680
ccgaccgctg cgccttatcc ggtaactatc gtcttgagtc caacccggta agacacgact   4740
tatcgccact ggcagcagcc actggtaaca ggattagcag agcgaggtat gtaggcggtg   4800
ctacagagtt cttgaagtgg tggcctaact acggctacac tagaaggaca gtatttggta   4860
tctgcgctct gctgaagcca gttaccttcg gaaaaagagt tggtagctct tgatccggca   4920
aacaaaccac cgctggtagc ggtggttttt tgtttgcaa gcagcagatt acgcgcagaa    4980
aaaaaggatc tcaagaagat cctttgatct tttctacggg gtctgacgct cagtggaacg   5040
aaaactcacg ttaagggatt ttggtcatgc attctaggtg attagaaaaa ctcatcgagc   5100
atcaaatgaa actgcaattt attcatatca ggattatcaa taccatattt ttgaaaaagc   5160
cgtttctgta atgaaggaga aaactcaccg aggcagttcc ataggatggc aagatcctgg   5220
tatcggtctg cgattccgac tcgtccaaca tcaatacaac ctattaattt ccctcgtca    5280 aaaataaggt tatcaagtga gaaatcacca tgagtgacga ctgaatccgg tgagaatggc   5340
aaaagtttat gcatttcttt ccagacttgt tcaacaggcc agccattacg ctcgtcatca   5400
aaatcactcg catcaaccaa accgttattc attcgtgatt gcgcctgagc gagtcgaaat   5460
acgcgatcgc tgttaaaagg acaattacaa acaggaatcg aatgcaaccg gcgcaggaac   5520
actgccagcg catcaacaat attttcacct gaatcaggat attcttctaa tacctggaat   5580
gctgttttcc ctgggatcgc agtggtgagt aaccatgcat catcaggagt acggataaaa   5640
tgcttgatgg tcgaagagg cataaattcc gtcagccagt ttagtctgac catctcatct    5700
gtaacatcat tggcaacgct acctttgcca tgtttcagaa acaactctgg cgcatcgggc   5760
ttcccataca atcggtagat tgtcgcacct gattgcccga cattatcgcg agcccattta   5820
tacccatata atcagcatc catgttggaa tttaatcgcg gcttgagca agacgtttcc    5880 cgttgaatat ggctcataac agaacttatt atttccttcc tcttttctac agtatttaaa   5940 gatacccaa gaagctaatt ataacaagac gaactccaat tcactgttcc ttgcattcta    6000
aaaccttaaa taccagaaaa cagcttttc aaagttgttt tcaaagttgg cgtataacat    6060
agtatcgacg gagccgattt tgaaaccgcg gtgatcacag gcagcaacgc tctgtcatcg   6120
ttacaatcaa catgctaccc tccgcgagat catccgtgtt tcaaacccgg cagcttagtt   6180
gccgttcttc cgaatagcat cggtaacatg agcaaagtct gccgccttac aacggctctc   6240
ccgctgacgc cgtcccggac tgatgggctg cctgtatcga gtggtgattt tgtgccgagc   6300
tgccggtcgg ggagctgttg gctggctggt ggcaggatat attgtggtgt aaacataacg   6360
aattcgtctc aggagagcgt cgatctagta acatagatga caccgcgcgc gataatttat   6420
```

```
cctagtttgc gcgctatatt ttgttttcta tcgcgtatta aatgtataat tgcgggactc    6480
taatcataaa aacccatctc ataaataacg tcatgcatta catgttaatt attacatgct    6540
taacgtaatt caacagaaat tatatgataa tcatcgcaag accggcaaca ggattcaatc    6600
ttaagaaact ttattgccaa atgtttgaac gatctgcttc gacgcactcc ttctttactc    6660
caccatctcg tccttattga aaacgtgggt agcaccaaaa cgaatcaagt cgctggaact    6720
gaagttacca atcacgctgg atgatttgcc agttggatta tcttgcctt tccccgcatg     6780 aataatattg atgaatgcat gcgtgagggg tagttcgatg ttggcaatag ctgcaattgc    6840
cgcgacatcc tccaacgagc ataattcttc agaaaaatag cgatgttcca tgttgtcagg    6900
gcatgcatga tgcacgttat gaggtgacgg tgctaggcag tattccctca aagtttcata    6960
gtcagtatca tattcatcat tgcattcctg caagagagaa ttgagacgca atccacacgc    7020
tgcggcaacc ttccggcgtt cgtggtctat ttgctcttgg acgttgcaaa cgtaagtgtt    7080 ggatcgggt gggcgaagaa ctccagcatg agatccccgc gctggaggat catccagccg     7140
gcgtcccgga aaacgattcc gaagcccaac ctttcataga aggcggcggt ggaatcgaaa    7200
tctcgtgatg gcaggttggg cgtcgcttgg tcggtcattt cgaaccccag agtcccgctc    7260
agaagaactc gtcaagaagg cgatagaagg cgatgcgctg cgaatcggga gcggcgatac    7320
cgtaaagcac gaggaagcgg tcagcccatt cgccgccaag ctcttcagca atatcacggg    7380
tagccaacgc tatgtcctga tagcggtccg ccacacccag ccggccacag tcgatgaatc    7440
cagaaaagcg gccattttcc accatgatat tcggcaagca ggcatcgcca tgggtcacga    7500
cgagatcctc gccgtcgggc atgcgcgcct tgagcctggc gaacagttcg gctggcgcga    7560
gcccctgatg ctcttcgtcc agatcatcct gatcgacaag accggcttcc atccgagtac    7620
gtgctcgctc gatgcgatgt ttcgcttggt ggtcgaatgg gcaggtagcc ggatcaagcg    7680
tatgcagccg ccgcattgca tcagccatga tggatacttt ctcggcagga gcaaggtgag    7740
atgacaggag atcctgcccc ggcacttcgc ccaatagcag ccagtcccct cccgcttcag    7800
tgacaacgtc gagcacagct gcgcaaggaa cgcccgtcgt ggccagccac gatagccgcg    7860
ctgcctcgtc ctgcagttca ttcagggcac cggacaggtc ggtcttgaca aaaagaaccg    7920
ggcgcccctg cgctgacagc cggaacacgg cggcatcaga gcagccgatt gtctgttgtg    7980
cccagtcata gccgaatagc ctctccaccc aagcggccgg agaacctgcc cggatccggg    8040
cggaaatagg taaagaagtt gcggataagg taattgccat tgcagattat ttggattgag    8100
agtgaatatg agactctaat tggataccga ggggaattta tggaacgtca gtggagcatt    8160
tttgacaaga aatatttgct agctgatagt gaccttaggc gacttttgaa cgcgcaataa    8220
tggtttctga cgtatgtgct tagctcatta aactccagaa accctccgt caggaggtca     8280 actacccca tttaaatttt atttgattaa gatattttta tggacctact ttataattaa     8340 aaatatttc tatttgaaaa ggaaggacaa aaatcataca attttggtcc aactactcct     8400 ctctttttt ttttggcttt ataaaaagg aaagtgatta gtaataaata attaaataat       8460 gaaaaagga ggaaataaaa ttttcgaatt aaaatgtaaa agagaaaaag gagagggagt      8520
aatcattgtt taactttatc taaagtaccc caattcgatt ttacatgtat atcaaattat    8580
acaaatattt tattaaaata tagatattga ataattttat tattcttgaa catgtaaata    8640
aaaattatct attatttcaa ttttatata aactattatt tgaaatctca attatgattt      8700
tttaatatca ctttctatcc atgataattt cagcttaaaa agtttgtca ataattacat      8760 taattttgtt gatgaggatg acaagatttc ggtcatcaat tacatataca caaattgaaa    8820
```

| | |
|---|---|
| tagtaagcaa cttgattttt ttctcataa tgataatgac aaagacacga aaagacaatt | 8880 |
| caatattcac attgatttat ttttatatga taataattac aataataata ttcttataaa | 8940 |
| gaaagagatc aattttgact gatccaaaaa tttatttatt tttactatac caacgtcact | 9000 |
| aattatatct aataatgtaa aacaattcaa tcttacttaa atattaattt gaaataaact | 9060 |
| atttttataa cgaaattact aaatttatcc aataacaaaa aggtcttaag aagacataaa | 9120 |
| ttcttttttt gtaatgctca aataaatttg agtaaaaaag aatgaaattg agtgattttt | 9180 |
| ttttaatcat aagaaaataa ataattaatt tcaatataat aaaacagtaa tataatttca | 9240 |
| taaatggaat tcaatactta cctcttagat ataaaaaata aatataaaaa taaagtgttt | 9300 |
| ctaataaacc cgcaatttaa ataaaatatt taatattttc aatcaatttt aaataattat | 9360 |
| attaaaatat cgtagaaaaa gagcaatata taatacaaga aagaagattt aagtacaatt | 9420 |
| atcaactatt attatactct aattttgtta tatttaattt cttacggtta aggtcatgtt | 9480 |
| cacgataaac tcaaaatacg ctgtatgagg acatatttta aattttaacc aataataaaa | 9540 |
| ctaagttatt tttagtatat ttttttgttt aacgtgactt aattttttctt ttctagagga | 9600 |
| gcgtgtaagt gtcaacctca ttctcctaat tttcccaacc acataaaaaa aaaataaagg | 9660 |
| tagcttttgc gtgttgattt ggtacactac acgtcattat tacacgtgtt ttcgtatgat | 9720 |
| tggttaatcc atgaggcggt ttcctctaga gtcggccata ccatctataa aataaagctt | 9780 |
| tctgcagctc atttttttcat cttctatctg atttctatta taatttctct gaattgcctt | 9840 |
| caaatttctc tttcaaggtt agaatttttc tctattttt ggttttgtt tgtttagatt | 9900 |
| ctgagtttag ttaatcaggt gctgttaaag ccctaaattt tgagtttttt tcggttgttt | 9960 |
| tgatggaaaa tacctaacaa ttgagttttt tcatgttgtt ttgtcggaga atgcctacaa | 10020 |
| ttggagttcc tttcgttgtt ttgatgagaa agcccctaat ttgagtgttt ttccgtcgat | 10080 |
| ttgattttaa aggtttatat tcgagttttt ttcgtcggtt taatgagaag gcctaaaata | 10140 |
| ggagttttc tggttgattt gactaaaaaa gccatggaat tttgtgtttt tgatgtcgct | 10200 |
| ttggttctca aggcctaaga tctgagtttc tccggttgtt ttgatgaaaa agccctaaaa | 10260 |
| ttggagtttt tatcttgtgt tttaggttgt tttaatcctt ataatttgag tttttcgtt | 10320 |
| gttctgattg ttgtttttat gaattttgca gaatggataa cgcaacactt gctgtgatcc | 10380 |
| tttccatttt gtttgtgttt taccacattt tcaaatcctt tttcaccaat tcttcatctc | 10440 |
| gtaggcttcc tcctggtccc aaacccgtgc caatttttgg caacattttc gatcttggcg | 10500 |
| aaaagcctca tcgatctttt gccaatctat ctaaaattca cggccctttg attagcctaa | 10560 |
| agttaggaag tgtaacaact attgttgttt cctcggcctc tgtggccgag gaaatgttcc | 10620 |
| ttaaaaatga ccaagcactt gctaaccgaa ccattcctga ctcggttagg gctggtgacc | 10680 |
| acgacaaatt atccatgtcg tggttgcctg tttcccaaaa atggagaaat atgagaaaaa | 10740 |
| tctccgctgt ccaattactc tccaaccaaa aacttgatgc tagtcaacct cttagacaag | 10800 |
| ctaaggtgaa acaacttta tcatacgtac aagtttgttc cgaaaaatg caacccgtcg | 10860 |
| atattggacg ggccgcattt acaacgtcac ttaatttatt atcaaacaca tttttctcaa | 10920 |
| tcgaattagc aagtcatgaa tctagtgctt cccaagagtt taaacaactc atgtggaata | 10980 |
| ttatggagga aattggaagg cctaattatg ctgattttt ccctattctt ggttacattg | 11040 |
| atcccttggg tataagacgt cgtttggctg gttactttga taaactcatt gatgttttcc | 11100 |
| aagacattat tcgtgaaaga caaaagcttc gatcttctaa ttcttccggc gcaaaacaaa | 11160 |

```
caaatgacat tcttgatact cttcttaaac tccatgaaga taatgagttg agtatgcctg   11220
aaattaatca ccttctcgtg gatatctttg acgccggaac agacacaaca gcaagcacat   11280
tagaatgggc aatggccgaa cttgtgaaaa acccggaaat gatgactaaa gttcaaattg   11340
aaatcgaaca agctcttgga aaagattgct tagacataca agaatccgac atctcaaaac   11400
taccttattt acaagccatt ataaaagaaa cgttacgttt acaccctcct actgtgtttt   11460
tgctgcctcg aaaggcagac aatgacgtag agttatatgg ctacgttgta ccaaagaatg   11520
ctcaagtcct tgtcaatctt tgggcaattg gtcgtgatcc aaaggtatgg aaaaatccgg   11580
aagtattttc tcctgaaagg ttttttagatt gcaatatcga ttataaagga cgagatttcg   11640
aactttttacc ctttggtgct ggtagaagga tatgccctgg acttactttg gcatatagaa   11700
tgttgaactt gatgttggct actcttcttc aaaactacaa ttggaaactt gaagatggta   11760
tcaatcctaa ggatttagac atggatgaga aatttgggat tacattgcaa aaggttaaac   11820
ctcttcaagt tattccagtt cccagaaact aggcttgttg tggttgtctg gttgcgtctg   11880
ttgcccgttg tctgttgccc attgtggtgg ttgtgtttgt atgatggtcg ttaaggatca   11940
tcaatgtgtt ttcgcttttt gttccattct gtttctcatt tgtgaataat aatggtatct   12000
ttatgaatat gcagttgtg gtttcttttc tgattgcagt tctgagcatt ttgttttttgc   12060
ttccgtttac tataccactt acagtttgca ctaatttagt tgatatgcga gccatctgat   12120
gtttgatgat tcaaatggcg tttatgtaac tcgtacccga gtggatggag aagagctcca   12180
ttgccggttt gtttcatggg tggcggaggg caactcctgg gaaggaacaa aagaaaaacc   12240
gtgatacgag ttcatgggtg agagctccag cttgatccct tctctgtcga tcaaatttga   12300
attttttggat cacggcaggc tcacaagata atccaaagta aaacataatg aatagtactt   12360
ctcaatgatc acttatttt agcaaatcag caattgtgca tgtcaaatga tttcggtgta   12420
agagaaagag ttgatgaatc aaaatatctg tagctggatc aagaatctga ggcagttgta   12480
tgtatcaatg atctttccgc tacaatgatg ttagctatcc gagtcaaatt gttgtagaat   12540
tgcatacttc ggcatcacat tctggatgac ataataaata ggaagtcttc agatccctaa   12600
aaaattgaga gctaataaca ttagtcctag atgtaactgg gtgacaacca agaaagagac   12660
atgcaaatac tacttttgtt tgaaggagca tccctggttt gacatatttt ttctgaatat   12720
caaactttga aactctacct agtctaatgt ctaacgacag atcttactgg tttaactgca   12780
gtgatatcta ctatcttttg gaatgttttc tccttcagtt atacatcaag ttccaagatg   12840
caggtgtgct tgattgatgt acatggctgt gagaagtgca tcctgatgtt cagatgatgg   12900
ttcattctaa tgtctttcc ttcaatcagt tttctcagtc tgacttagct tgtttcatct   12960
gcatgtttga atgttcgttt actcatagta attgcatttt tgtagcagaa catatcattg   13020
gtcatggttt caactgtgcg cgagtcttat gcttattcaa actaggaaag cctccgtcta   13080
gagggtacac gagttgttgc tctgtgtgcg tcagtccata gtattaatct tgctagttgt   13140
agtatattgt ttatgtggac tcggaattca tcatatgctc cttctttgca tcaagtaagg   13200
caaggtaatg tatagaagct ttttaactct ttcatggaag ctggcctttg ccagcatacc   13260
atccagaaga tatcaaccct gcatcttggc tgccgcgctg tcaggagata catgagaatt   13320
aagggagtca cggtatgacc cccgccgatg acgcgggaca agccgtttta cgtttggaac   13380
tgacagaacc gcaacgttga aggagccact gagccgcggg tttctggagt taatgagct   13440
aagcacatac gtcagaaacc attattgcgc gttcaaaagt cgcctaaggt cactatcagc   13500
tagcaaatat ttcttgtcaa aaatgctcca ctgacgttcc ataaattccc ctcggtatcc   13560
```

```
aattagagtc tcatattcac tctcaactcg atcgaggcaa tgatggctat ggaagtgggt   13620
tatcttcggc actcgacaac gatcaccaac ggactgtgtt gtaactgtga tccgaagccc   13680
cgaggagcac gtcgtgtaca gactaggctg cctggcaccc tgtgtctcgt caaggatacc   13740
tttacctcta gcaaagctaa actaaaaaag ccgtcgcaga gagaaatctt tctaacaagt   13800
aggaagaggc tgaatcagat acaagctgtt tcaacggctg aaaaggagag agaggcagac   13860
aaaacatcca ctccacctat tcccagtagc atccacgata tttcaaatgg agatcacatt   13920
cttggcttcg gagccgattt gaccgaagat catcctggct accatgatct tgaatataag   13980
aggaggcgta gtcgtattgc tgaccttgcg aagatacata aaataggtga acccattcct   14040
tgcgtggact acacatcgga agagattcgt gtgtgggtc atgtgttaga tactctagtg    14100
gacctctacc caactcatgc ttgtaaggaa tacctgaatt gctacgagct gtttaacttc   14160
aagccaaact atattccaca gctgcaagaa cttcggagg tcctggaacg gagcacagga    14220
tggcacatcc gcccagtagc tggactcctc caccctcgtg acttcctaaa cggtctagcc   14280
ttccgcactt tccattcaac ccagtatgtt cggcatggca gcaatcccat gtacaccccc   14340
gagccagaca tttgtcacga ggttttaggc cacgtcccca ttctggctga tccggagttt   14400
gctgacttag cttgggccat tggccaagct tctctgggtg cttcagagaa ggatatctgg   14460
caccttacga agctctactg gtacactgtg gagtttggca cagtaaagga aggtaacgag   14520
attaaagcgt tcggtgcagg ccttctgtct agttttgggg agctgaagca catgcgggtg   14580
gggacggatg gattcatgcc tgagttcgtg gagcttgacc cgtttaagaa gatgcccaag   14640
atgagctaca aagacgggta ccagaagagg tattttctat gcgagagctt tgcagatgca   14700
gcggcaaagc ttagggcgta ttccagaagc attctgaagc tgaggtgca gtccatcaag    14760 tttggagata cgccaatccg gctctaagct tatatgaaga tgaagatgaa atatttggtg   14820
tgtcaaataa aaagcttgtg tgcttaagtt tgtgtttttt tcttggcttg ttgtgttatg   14880
aatttgtggc tttttctaat attaaatgaa tgtaagatct cattataatg aataaacaaa   14940
tgtttctata atccattgtg aatgttttgt tggatctctt ctgcagcata taactactgt   15000
atgtgctatg gtatggacta tggaatatga ttaaagataa gcgctgtcag gagccgtaca   15060
aaattgatta ttgatgtcac aaatcaatca gagctaaatt ccaaaaaaaa tatgatcttt   15120
gaaacttgca tcaataacta acgattctag gaagagccca tttcgatttc aacaaaaaga   15180
tgagagcttg attacatata aaatcaagag aaattaacga cattgaagag aattcgatct   15240
cgaaaccgga aacaaagact tataagtcga ttagtctaat tcaatgcaga agaaagaata   15300
ccaggtttgg ccttcacgat ggaaagcttc ggatttggag ccaagtctca taaacgccat   15360
tgtggaagaa agtcttgagt tggtggtaat gtaacagagt agtaagaaca gagaagagag   15420
agagtgtgag atacatgaat tgtcgggcaa caaaaatcct gaacatctta ttttagcaaa   15480
gagaaagagt tccgagtctg tagcagaaga gtgaggagaa atttaagctc ttggacttgt   15540
gaattgttcc gcctcttgaa tacttcttca atcctcatat attcttcttc tatgttacct   15600
gaaaaccggc atttaatctc gcgggtttat tccggttcaa catttttttt gttttgagtt   15660
attatctggg cttaataacg caggcctgaa ataaattcaa ggcccaactg tttttttttt   15720
taagaagttg ctgttaaaaa aaaaaaagg gaattaacaa caacaacaaa aaaagataaa    15780
gaaaataata acaattactt taattgtaga ctaaaaaaac atagatttta tcatgaaaaa   15840
aagagaaaag aaataaaaac ttggatcaaa aaaaaaaaca tacagatctt ctaattatta   15900
```

```
acttttctta aaaattaggt ccttttccc aacaattagg tttagagttt tggaattaaa   15960
ccaaaaagat tgttctaaaa aatactcaaa tttggtagat aagtttcctt attttaatta   16020
gtcaatggta gatacttttt tttcttttct ttattagagt agattagaat cttttatgcc   16080
aagtattgat aaattaaatc aagaagataa actatcataa tcaacatgaa attaaaagaa   16140
aaatctcata tatagtatta gtattctcta tatatattat gattgcttat tcttaatggg   16200
ttgggttaac caagacatag tcttaatgga aagaatcttt tttgaacttt ttccttattg   16260
attaaattct tctatagaaa agaaagaaat tatttgagga aaagtatata caaaaagaaa   16320
aatagaaaaa tgtcagtgaa gcagatgtaa tggatgacct aatccaacca ccaccatagg   16380
atgtttctac ttgagtcggt cttttaaaaa cgcacggtgg aaaatatgac acgtatcata   16440
tgattccttc ctttagtttc gtgataataa tcctcaactg atatcttcct tttttgttt   16500
tggctaaaga tattttattc tcattaatag aaaagacggt tttgggcttt tggtttgcga   16560
tataagaag accttcgtgt ggaagataat aattcatcct ttcgtctttt tctgactctt   16620
caatctctcc caaagcctaa agcgatctct gcaaatctct cgcgactctc tctttcaagg   16680
tatattttct gattctttt gttttgatt cgtatctgat ctccaatttt tgttatgtgg   16740
attattgaat cttttgtata aattgctttt gacaatattg ttcgtttcgt caatccagct   16800
tctaaatttt gtcctgatta ctaagatatc gattcgtagt gtttacatct gtgtaattc   16860
ttgcttgatt gtgaaattag gatttcaag gacgatctat tcaattttg tgttttcttt    16920
gttcgattct ctctgtttta ggtttcttat gtttagatcc gtttctcttt ggtgttgttt   16980
tgatttctct tacggctttt gatttggtat atgttcgctg attggtttct acttgttcta   17040
ttgtttatt tcagaatggc ttctatgata tcctcttcag ctgtgactac agtcagccgt     17100
gcttctacgg tgcaatcggc cgcggtggct ccattcggcg gcctcaaatc catgactgga   17160
ttcccagtta agaaggtcaa cactgacatt acttccatta caagcaatgg tggaagagta   17220
aagtgcatgc tgatgaatta tcagaacgac gatttacgca tcaaagaaat caaagagtta   17280
cttcctcctg tcgcattgct ggaaaaattc cccgctactg aaaatgccgc gaatacggtt   17340
gcccatgccc gaaaagcgat ccataagatc ctgaaggta atgatgatcg cctgttggtt    17400
gtgattggcc catgctcaat tcatgatcct gtcgcggcaa aagagtatgc cactcgcttg   17460
ctggcgctgc gtgaagagct gaaagatgag ctggaaatcg taatgcgcgt ctatttgaa    17520
aagccgcgta ccacggtggg ctggaagg ctgattaacg atccgcatat ggataatagc     17580
ttccagatca acgacggtct gcgtatagcc cgtaaattgc tgcttgatat taacgacagc   17640
ggtctgccag cggcaggtga gtttctcgat atgatcaccc cacaatatct cgctgacctg   17700
atgagctggg gcgcaattgg cgcacgtacc accgaatcgc aggtgcaccg cgaacaggca   17760
tcagggcttt cttgtccggt cggcttcaaa aatggcaccg acggtacgat taaagtggct   17820
atcgatgcca ttaatgccgc cggtgcgccg cactgcttcc tgtccgtaac gaatgggggg   17880
cattcggcga ttgtgaatac cagcggtaac ggcgattgcc atatcattct gcgcggcggt   17940
aaagagccta actacagcgc gaagcacgtt gctgaagtga agaagggct gaacaaagca    18000
ggcctgccag cacaggtgat gatcgatttc agccatgcta actcgtccaa acaattcaaa   18060
aagcagatgg atgtttgtgc tgacgtttgc cagcagattg ccggtggcga aaaggccatt   18120
attggcgtga tggtggaaag ccatctggtg gaaggcaatc agagcctcga gagcggggag   18180
ccgctggcct acggtaagag catcaccgat gcctgcatcg gctgggaaga taccgatgct   18240
ctgttacgtc aactggcgaa tgcagtaaaa gcgcgtcgcg gggaattcat cttttaccca   18300
```

```
tacgatgttc ctgactatgc gggctatccc tatgacgtcc cggactatgc aggatcctat    18360
ccatatgacg ttccagatta cgctgctcag taggcttata tgaagatgaa gatgaaatat    18420
ttggtgtgtc aaataaaaag cttgtgtgct taagtttgtg ttttttttctt ggcttgttgt   18480 gttatgaatt tgtggctttt tctaatatta atgaatgta agatctcatt ataatgaata    18540
aacaaatgtt tctataatcc attgtgaatg ttttgttgga tctcttctgc agcatataac    18600
tactgtatgt gctatggtat ggactatgga atatgattaa agataag                  18647

<210> SEQ ID NO 28
<211> LENGTH: 1050
<212> TYPE: DNA
<213> ORGANISM: Artificial Sequence
<220> FEATURE:
<223> OTHER INFORMATION: Polynucleotide encoding E Coli AroG175 mutant

<400> SEQUENCE: 28
atgaattatc agaacgacga tttacgcatc aaagaaatca agagttact tcctcctgtc     60 gcattgctgg aaaaattccc cgctactgaa atgccgcga atacggttgc ccatgcccga    120
aaagcgatcc ataagatcct gaaaggtaat gatgatcgcc tgttggttgt gattggccca    180
tgctcaattc atgatcctgt cgcggcaaaa gagtatgcca ctcgcttgct ggcgctgcgt    240
gaagagctga agatgagct ggaaatcgta atgcgcgtct attttgaaaa gccgcgtacc    300
acggtgggct ggaaagggct gattaacgat ccgcatatgg ataatagctt ccagatcaac    360
gacggtctgc gtatagcccg taaattgctg cttgatatta cgacagcgg tctgccagcg    420 gcaggtgagt ttctcgatat gatcacccca caatatctcg ctgacctgat gagctggggc    480
gcaattggcg cacgtaccac cgaatcgcag gtgcaccgcg aacaggcatc agggctttct    540
tgtccggtcg gcttcaaaaa tggcaccgac ggtacgatta agtggctat cgatgccatt    600 aatgccgccg gtgcgccgca ctgcttcctg tccgtaacga aatgggggca ttcggcgatt    660
gtgaatacca gcggtaacgg cgattgccat atcattctgc gcggcggtaa agagcctaac    720
tacagcgcga agcacgttgc tgaagtgaaa gaagggctga acaaagcagg cctgccagca    780
caggtgatga tcgatttcag ccatgctaac tcgtccaaac aattcaaaaa gcagatggat    840
gtttgtgctg acgtttgcca gcagattgcc ggtggcgaaa aggccattat tggcgtgatg    900
gtggaaagcc atctggtgga aggcaatcag agcctcgaga gcggggagcc gctgcctac     960 ggtaagagca tcaccgatgc ctgcatcggc tgggaagata ccgatgctct gttacgtcaa   1020
ctggcgaatg cagtaaaagc gcgtcgcggg                                     1050

<210> SEQ ID NO 29
<211> LENGTH: 1185
<212> TYPE: DNA
<213> ORGANISM: Physcomitrella patens

<400> SEQUENCE: 29
atggctatgg aagtgggtta tcttcggcac tcgacaacga tcaccaacgg actgtgttgt     60
aactgtgatc cgaagccccg aggagcacgt cgtgtacaga ctaggctgcc tggcaccctg    120
tgtctcgtca aggatacctt tacctctagc aaagctaaac taaaaaagcc gtctcagaga    180
gaaatctttc taacaagtag gaagaggctg aatcagatac aagctgtttc aacggctgaa    240
aaggagagag aggcagacaa acatccact ccacctattc ccagtagcat ccacgatatt     300
tcaaatggag accacattct tggcttcgga gccgatttga ccgaagatca tcctggctac    360
```

| | |
|---|---|
| catgatcttg aaatataagag gaggcgtagt cgtattgctg accttgcgaa gatacataaa | 420 |
| ataggtgaac ccattccttg cgtggactac acatcggaag agattcgtgt gtggggtcat | 480 |
| gtgttagata ctctagtgga cctctaccca actcatgctt gtaaggaata cctgaattgc | 540 |
| tacgagctgt ttaacttcaa gccaaactat attccacagc tgcaagaact ttcggaggtc | 600 |
| ctggaacgga gcacaggatg gcacatccgc ccagtagctg gactcctcca ccctcgtgac | 660 |
| ttcctaaacg gtctagcctt ccgcactttc cattcaaccc agtatgttcg gcatggcagc | 720 |
| aatcccatgt acacccccga gccagacatt tgtcacgagg ttttaggcca cgtccccatt | 780 |
| ctggctgatc cggagtttgc tgacttagct tgggccattg gccaagcttc tctgggtgct | 840 |
| tcagagaagg atatctggca ccttacgaag ctctactggt acactgtgga gtttggcaca | 900 |
| gtaaaggaag gtaacgagat taaagcgttc ggtgcaggcc ttctgtctag ttttggggag | 960 |
| ctgaagcaca tgcgggtggg gacggatgga ttcatgcctg agttcgtgga gcttgacccg | 1020 |
| tttaagaaga tgcccaagat gagctacaaa gacgggtacc agaagaggta ttttctatgc | 1080 |
| gagagctttg cagatgcagc ggcaaagctt agggcgtatt ccagaagcat tctgaagcct | 1140 |
| gaggtgcagt ccatcaagtt tggagatacg ccaatccggc tctaa | 1185 |

<210> SEQ ID NO 30
<211> LENGTH: 1988
<212> TYPE: DNA
<213> ORGANISM: Beta vulgaris

<400> SEQUENCE: 30

| | |
|---|---|
| tcgatgtgtt ttcaagaaga gcttgagcct acattctaca acaatatatt gttcctctct | 60 |
| tgcgcaatta agcccttaaa cctgcaatta tcttagaatt tttgggtttc taatttattc | 120 |
| tctcctttaa ttagctagct tcttagatta ttcatatttt tccagcattt tcaaacaatg | 180 |
| gataacgcaa cacttgctgt gatccttttcc attttgtttg tgttttacca cattttcaaa | 240 |
| tccttttttca ccaattcttc atctcgtagg cttcctcctg gtcccaaacc cgtgccaatt | 300 |
| tttggcaaca ttttcgatct tggcgaaaag cctcatcgat cttttgccaa tctatctaaa | 360 |
| attcacggcc ctttgattag cctaaagtta ggaagtgtaa caactattgt tgtttcctcg | 420 |
| gcctctgtgg ccgaggaaat gttccttaaa aatgaccaag cacttgctaa ccgaaccatt | 480 |
| cctgactcgg ttagggctgg tgaccacgac aaattatcca tgtcgtggtt gcctgtttcc | 540 |
| caaaaatgga gaaatatgag aaaaatctcc gctgtccaat tactctccaa ccaaaaactt | 600 |
| gatgctagtc aacctcttag acaagctaag gtgaaacaac ttttatcata cgtacaagtt | 660 |
| tgttccgaaa aaatgcaacc cgtcgatatt ggacgggccg catttacaac gtcacttaat | 720 |
| ttattatcaa acacattttt ctcaatcgaa ttagcaagtc atgaatctag tgcttcccaa | 780 |
| gagtttaaac aactcatgtg gaatattatg gaggaaattg gaaggcctaa ttatgctgat | 840 |
| ttttccccta ttcttggtta cattgatccc tttggtataa gacgtcgttt ggctggttac | 900 |
| tttgataaac tcattgatgt tttccaagac attattcgtg aaagacaaaa gcttcgatct | 960 |
| tctaattctt ccggcgcaaa acaaacaaat gacattcttg atactcttct taaactccat | 1020 |
| gaagataatg agttgagtat gcctgaaatt aatcaccttc tcgtggatat ctttgacgcc | 1080 |
| ggaacagaca caacagcaag cacattagaa tgggcgatgg ccgaacttgt gaaaaacccg | 1140 |
| gaaatgatga ctaaagttca aattgaaatc gaacaagctc ttggaaaaga ttgcttagac | 1200 |
| atacaagaat ccgacatctc aaaactacct tatttacaag ccattataaa agaaacgtta | 1260 |
| cgtttacacc ctcctactgt gttttttgctg cctcgaaagg cagacaatga cgtagagtta | 1320 |

| | |
|---|---|
| tatggctacg ttgtaccaaa gaatgctcaa gtccttgtca atctttgggc aattggtcgt | 1380 |
| gatccaaagg tatggaaaaa tccggaagta ttttctcctg aaaggttttt agattgcaat | 1440 |
| atcgattata aaggacgaga tttcgaactt ttacccttg gtgctggtag aaggatatgc | 1500 |
| cctggactta ctttggcata tagaatgttg aacttgatgt tggctactct tcttcaaaac | 1560 |
| tacaattgga aacttgaaga tggtatcaat cctaaggatt tagacatgga tgagaaattt | 1620 |
| gggattacat tgcaaaaggt taaacctctt caagttattc cagttccag aaactagcta | 1680 |
| gtgggttgtg ccgttgtggg ctgtgggctg attgtgcact tttgtttcct ctaattgttg | 1740 |
| ttgcaaactt ctctagaagg gtattatctt ttgtataaat aaagcgaaag ctacatgtcc | 1800 |
| tattattaaa ttagtgtata ctatattaag taagtatgag catatagtat ccattattgt | 1860 |
| ttttggttga atcgtattaa actgataaat caagtaaatg tctccaacct aagcattcaa | 1920 |
| ttattctgtt agtcataaca tatgtagagg gtaagtatga agaattaata acggcgtgat | 1980 |
| catcctta | 1988 |

<210> SEQ ID NO 31
<211> LENGTH: 1500
<212> TYPE: DNA
<213> ORGANISM: Beta vulgaris

<400> SEQUENCE: 31

| | |
|---|---|
| atggataacg caacacttgc tgtgatcctt tccattttgt ttgtgtttta ccacattttc | 60 |
| aaatcctttt tcaccaattc ttcatctcgt aggcttcctc ctggtcccaa acccgtgcca | 120 |
| attttggca acattttcga tcttggcgaa aagcctcatc gatcttttgc caatctatct | 180 |
| aaaattcacg gcccttttgat tagcctaaag ttaggaagtg taacaactat tgttgtttcc | 240 |
| tcggcctctg tggccgagga atgttccttt aaaaatgacc aagcacttgc taaccgaacc | 300 |
| attcctgact cggttagggc tggtgaccac gacaaattat ccatgtcgtg gttgcctgtt | 360 |
| tcccaaaaat ggagaaatat gagaaaaatc tccgctgtcc aattactctc caaccaaaaa | 420 |
| cttgatgcta gtcaacctct tagacaagct aaggtgaaac aactttatc atacgtacaa | 480 |
| gtttgttccg aaaaaatgca acccgtcgat attggacggg ccgcatttac aacgtcactt | 540 |
| aatttattat caaacacatt tttctcaatc gaattagcaa gtcatgaatc tagtgcttcc | 600 |
| caagagttta acaactcat gtggaatatt atggaggaaa ttggaaggcc taattatgct | 660 |
| gatttttcc ctattcttgg ttacattgat ccctttggta taagacgtcg tttggctggt | 720 |
| tactttgata aactcattga tgttttccaa gacattattc gtgaaagaca aaagcttcga | 780 |
| tcttctaatt cttccggcgc aaaacaaaca aatgacattc ttgatactct tcttaaactc | 840 |
| catgaagata atgagttgag tatgcctgaa attaatcacc ttctcgtgga tatctttgac | 900 |
| gccggaacag acacaacagc aagcacatta gaatgggcaa tggccgaact tgtgaaaaac | 960 |
| ccggaaatga tgactaaagt tcaaattgaa atcgaacaag ctcttggaaa agattgctta | 1020 |
| gacatacaag aatccgacat ctcaaaacta cctattttac aagccattat aaaagaaacg | 1080 |
| ttacgtttac accctcctac tgtgtttttg ctgcctcgaa aggcagacaa tgacgtagag | 1140 |
| ttatatggct acgttgtacc aaagaatgct caagtccttg tcaatctttg ggcaattggt | 1200 |
| cgtgatccaa aggtatggaa aaatccggaa gtattttctc ctgaaaggtt tttagattgc | 1260 |
| aatatcgatt ataaaggacg agatttcgaa cttttacccct tggtgctgg tagaaggata | 1320 |
| tgccctggac ttactttggc atatagaatg ttgaacttga tgttggctac tcttcttcaa | 1380 |

```
aactacaatt ggaaacttga agatggtatc aatcctaagg atttagacat ggatgagaaa      1440
tttgggatta cattgcaaaa ggttaaacct cttcaagtta ttccagttcc cagaaactag      1500

<210> SEQ ID NO 32
<211> LENGTH: 2200
<212> TYPE: DNA
<213> ORGANISM: Beta vulgaris

<400> SEQUENCE: 32
tactaatgtg caaatgcata aatttaattt cagatactct ttttttataaa tattattata     60 ctgtgcattc ttttaaccca aaaaaaaaac tgtcttaata caccatttaa ttcctttctc     120
taggatccac tatcacatgt agtatataaa tataatccta tacagttcac gttatcaaac     180
accaaagcat caaagccctt ccacacttgt attattttgg ggtagttgat ttgttagcgt     240
gttatttgtg agatcatcat ggatcatgca acattagcaa tgatactagc catttggttc     300
atttcttttc atttcataaa attacttttt agccaacaaa ctaccaaact tcttcctcct     360
ggtccaaaac cattgccaat aattggtaac atcttagaag ttggtaaaaa accccatcgt     420
tcatttgcta atcttgctaa aattcacggc cctttaatat cgttacgtct aggaagtgta     480
acaactattg ttgtatcatc agcagatgta gctaaagaaa tgttcttaaa aaaagaccac     540
cctctttcta accgtactat tcctaattct gtcacggccg gtgaccacca taaactcacc     600
atgtcgtggt tgcccgtttc gccgaaatgg cggaattttc gtaagattac agccgtccat     660
ttgctttctc ctcaaagact tgatgcttgc caaaccttc gccatgccaa ggtgcaacag     720
ctttatgaat atgtacaaga atgtgcacaa aaaggccaag ctgttgatat tggcaaagct     780
gcatttacta cctcccttaa tttgttatct aaactattct tttcagtgga attagcccac     840
cataaatcac acacttctca agagtttaag gaactaaatt ggaacattat ggaagatatt     900
gggaaaccta attatgctga ttattttcct attttaggct gtgttgatcc atcaggtatt     960
cgtcgaagat tagcatgtag ttttgacaag ttgattgcag ttttttcaggg tataatatgt    1020 gaaaggcttg cgcctgattc ttcaactaca acaacaacga cgactgatga tgtgctagac    1080
gttcttcttc agctcttcaa acaaaatgag ctcactatgg gcgagattaa ccatttgctc    1140
gtcgacattt ttgatgctgg aacagacact acatcaagta cttttgagtg ggtcatgaca    1200
gagttaatta ggaatcctga aatgatggaa aaggctcaag aagaaattaa gcaagtattg    1260
ggcaaagata aacaaattca ggaatcagac attattaacc taccttactt acaagccatt    1320
atcaaagaaa ctttgcgact acatccacca actgtatttc ttttgcctcg taaagccgac    1380
actgatgttg aactatatgg ttatattgtg cctaaagatg cacaaatact tgttaactta    1440
tgggctattg gaagagatcc taatgcatgg caaaatgctg atattttttc gcccgaaaga    1500 tttataggggt gtgaaattga tgtcaaagga agagattttg gactcttacc ttttggagcc    1560
ggaagaagga tatgtcctgg gatgaatttg gccattagaa tgttaacttt gatgctagct    1620
actttacttc aattcttcaa ttggaagctt gaaggagaca taagtccaaa agacttagac    1680
atggatgaga aatttgggat tgcgttacaa aagacaaagc ctttaaaact tattccaata    1740
cctaggtatt gaaatttgtt agacttacgt acaacaatta ttattgtttg tggttggttt    1800
tgggttagct tcctgttcat gtttgtttga tgtgctcgat tgaatttact acaaatcaac    1860
gaactccaat tatatcttgt caacttggag taatggcttg ggtttctcat ctgtcatctc    1920
ttttggttgg ctgtgcaagg gagtgagctt gcagcttagc atccttcaag aagatttaat    1980
taataatatg tgtatgtgta tgtgtatgtg tggattgtat ctcgtcattc atttttgcttg    2040
```

```
ttgtaatgat tttagttaat tattgtaatt ataaaggatt tgatcctcct ttgtgttgaa      2100
attatatata taatgtgtag cacgacaata aagtgacaga taacttatat aatcttattt      2160
tctatgaaat gttacagact tgctttgtgt tttaaaaaaa                            2200
```

<210> SEQ ID NO 33
<211> LENGTH: 1161
<212> TYPE: DNA
<213> ORGANISM: Beta vulgaris

<400> SEQUENCE: 33

```
aaaacaagaa gaaacaaaa caaccttta tataactaga aagcaacaaa aaaaaagaa          60 tgaaatgat gaatggtgaa gatgctaatg atcaaatgat caagaaagc ttcttcataa        120 cacatggaaa cccaatatta acagtagaag acacacatcc attaagacct ttctttgaaa      180
cttggagaga gaaaatcttt tctaagaaac ctaaggcaat tcttattatt tctggtcatt      240
gggaaactgt taaacctact gttaatgctg tccatatcaa tgatactatc catgattttg      300
atgactatcc tgctgctatg taccagttca agtatccagc tcctggggaa ccagaattgg      360
caagaaaagt agaggaaatt ctgaaaaaat cgggttttcga aacggcggaa actgatcaaa    420
aacgtgggct tgatcatggt gcatgggtac ctctaatgct aatgtatcct gaggctgata      480
taccagtatg tcagctctca gttcagccgc atttagatgg aacataccat acaacttag       540 gacgagcatt ggctcccttg aaaaacgacg gcgtattaat cattggttca ggaagtgcaa      600
ctcacccttt ggatgaaact cctcattatt ttgatggagt tgcaccttgg gcagctgcct      660
ttgattcatg gcttcgtaaa gctctcatta atggaaggtt tgaagaagtg aatatatatg      720
aaagcaaagc accaaattgg aaattagcac atcctttccc agaacatttt tatccattgc      780
atgttgttct tggcgctgct ggtgaaaaat ggaaggcaga gcttattcat agcagttggg      840
atcatggcac cttgtgtcat ggctcctaca agttcacttc agcctagttt tactttaaa      900 cactatgtct acagtctatg ttattgtatt tggtaatttg gtatgtggtg ttgttttgt      960 tttattcttt tgagttattg tacttggtat ttggtgttgt tttcatttgg tgcataattc     1020
ttttagtcta tatattgcta ttcttttgaa tgaggaataa atcgcgagct cgatgtaata     1080
gtttgtttta ttgttccaa tctatcatta tatatatata tatattatta aaaaaaatt      1140 attgtgttac tcgcaaaaaa a                                              1161
```

<210> SEQ ID NO 34
<211> LENGTH: 499
<212> TYPE: PRT
<213> ORGANISM: Beta vulgaris

<400> SEQUENCE: 34

```
Met Asp Asn Ala Thr Leu Ala Val Ile Leu Ser Ile Leu Phe Val Phe
1               5                   10                  15

Tyr His Ile Phe Lys Ser Phe Phe Thr Asn Ser Ser Arg Arg Leu
            20                  25                  30

Pro Pro Gly Pro Lys Pro Val Pro Ile Phe Gly Asn Ile Phe Asp Leu
        35                  40                  45

Gly Glu Lys Pro His Arg Ser Phe Ala Asn Leu Ser Lys Ile His Gly
    50                  55                  60

Pro Leu Ile Ser Leu Lys Leu Gly Ser Val Thr Thr Ile Val Val Ser
65                  70                  75                  80

Ser Ala Ser Val Ala Glu Glu Met Phe Leu Lys Asn Asp Gln Ala Leu
```

```
                    85                  90                  95
Ala Asn Arg Thr Ile Pro Asp Ser Val Arg Ala Gly Asp His Asp Lys
                100                 105                 110
Leu Ser Met Ser Trp Leu Pro Val Ser Gln Lys Trp Arg Asn Met Arg
                115                 120                 125
Lys Ile Ser Ala Val Gln Leu Leu Ser Asn Gln Lys Leu Asp Ala Ser
            130                 135                 140
Gln Pro Leu Arg Gln Thr Lys Val Lys Gln Leu Leu Ser Tyr Val Gln
145                 150                 155                 160
Asp Cys Ser Lys Lys Met Gln Pro Val Asp Ile Gly Arg Ala Ala Phe
                165                 170                 175
Thr Thr Ser Leu Asn Leu Leu Ser Asn Thr Phe Phe Ser Ile Glu Leu
                180                 185                 190
Ala Ser His Glu Ser Ser Ala Ser Gln Glu Phe Lys Gln Leu Met Trp
            195                 200                 205
Asn Ile Met Glu Glu Ile Gly Arg Pro Asn Tyr Ala Asp Phe Phe Pro
            210                 215                 220
Ile Leu Gly Tyr Ile Asp Pro Phe Gly Ile Arg Arg Arg Leu Ala Gly
225                 230                 235                 240
Tyr Phe Asp Lys Leu Ile Asp Val Phe Gln Asp Ile Ile Arg Glu Arg
                245                 250                 255
Gln Lys Leu Arg Ser Ser Asn Ser Ser Gly Ala Lys Gln Thr Asn Asp
                260                 265                 270
Ile Leu Asp Thr Leu Leu Lys Leu His Glu Asp Asn Glu Leu Ser Met
            275                 280                 285
Pro Glu Ile Asn His Leu Leu Val Asp Ile Phe Asp Ala Gly Thr Asp
290                 295                 300
Thr Thr Ala Ser Thr Leu Glu Trp Ala Met Ala Glu Leu Val Lys Asn
305                 310                 315                 320
Pro Glu Met Met Thr Lys Val Gln Ile Glu Ile Glu Gln Ala Leu Gly
                325                 330                 335
Lys Asp Cys Leu Asp Ile Gln Glu Ser Asp Ile Ser Lys Leu Pro Tyr
            340                 345                 350
Leu Gln Gly Ile Ile Lys Glu Thr Leu Arg Leu His Pro Pro Thr Val
            355                 360                 365
Phe Leu Leu Pro Arg Lys Ala Asp Asn Asp Val Glu Leu Tyr Gly Tyr
        370                 375                 380
Val Val Pro Lys Asn Ala Gln Val Leu Val Asn Leu Trp Ala Ile Gly
385                 390                 395                 400
Arg Asp Pro Lys Val Trp Lys Asn Pro Glu Val Phe Ser Pro Glu Arg
                405                 410                 415
Phe Leu Asp Cys Asn Ile Asp Tyr Lys Gly Arg Asp Phe Glu Leu Leu
            420                 425                 430
Pro Phe Gly Ala Gly Arg Arg Ile Cys Pro Gly Leu Thr Leu Ala Tyr
            435                 440                 445
Arg Met Leu Asn Leu Met Leu Ala Thr Leu Leu Gln Asn Tyr Asn Trp
        450                 455                 460
Lys Leu Glu Asp Gly Ile Asn Pro Lys Asp Leu Asp Met Asp Glu Lys
465                 470                 475                 480
Phe Gly Ile Thr Leu Gln Lys Val Lys Pro Leu Gln Val Ile Pro Val
            485                 490                 495

Pro Arg Asn
```

<210> SEQ ID NO 35
<211> LENGTH: 1799
<212> TYPE: DNA
<213> ORGANISM: Mirabilis jalapa

<400> SEQUENCE: 35

| | | | | | |
|---|---|---|---|---|---|
| tttgtctatt | attggctcaa | aatccctctc | tctatctttt | tgtaaaagaa | aatagttgtt | 60 |
| caacttaggg | aattattgat | atttcattat | ggaaaacaca | atgttaggtg | ttatcctagc | 120 |
| aaccattttc | ctcacttttc | acataatgaa | gatgttattt | agtccttcca | aggttaaact | 180 |
| accccccgggt | ccgagaccat | tgccaattat | tggtaatatt | ctcgagcttg | gggataaacc | 240 |
| acatcgttct | tttgcaaacc | ttgcgaaaat | tcacggtcct | ttagttactt | tgaaactcgg | 300 |
| gagtgtaacc | actattgtgg | tttcctcttc | tgaagttgct | aaagaaatgt | ttttgaaaaa | 360 |
| tgaccaacct | ttggcaaatc | gtaccatacc | tgactcagta | agagcaggta | accatgacaa | 420 |
| actatcaatg | tcgtggttgc | ctgtatcacc | caaatggcga | atcttagaa | agatttcagc | 480 |
| cgtccaattg | ctctcaactc | aacgacttga | tgcaagtcaa | gctcatagac | aagctaaaat | 540 |
| caaacaactt | attgagtacg | taaaaaaatg | cagtaaaatc | ggccaatacg | tcgatattgg | 600 |
| ccaagttgca | ttcactacat | cacttaattt | actatcaaac | acattctttt | caaaagaact | 660 |
| agcatcattt | gattcagata | atgcacaaga | gttcaaacaa | ctaatgtggt | gcattatgga | 720 |
| agaaattggt | aggcctaatt | atgccgatta | ttttcctatc | ttgggttatg | tcgatccatt | 780 |
| cggtgctaga | cgtcgacttt | ctcgttactt | cgatcaacta | attgaagtat | ttcaagtgat | 840 |
| tattcgtgag | agacttacac | atgataataa | tattgtgggt | aataacaatg | atgttttagc | 900 |
| tacgttgctc | gatctttata | aacaaaacga | gttaactatg | gatgaaatca | accatttact | 960 |
| agtggacatt | tttgatgctg | gtacggatac | aacagcaagt | acactagaat | gggcaatgtc | 1020 |
| agagctcata | aaaaatccac | acataatggc | caaagctcaa | gaggaggtcc | ggcgagccac | 1080 |
| catgtctcac | ggcggagcta | cggtggcgga | aatacaagaa | tcggatatca | ataatcttcc | 1140 |
| atacatacaa | tctattatta | aagaaacact | tcgtttacac | ccaccaactg | tgttttact | 1200 |
| tcctagaaaa | gctgacgtgg | atgtccaatt | attcggctat | gtggtcccca | aaaatgctca | 1260 |
| agtcctagtc | aatttatggg | ccattggtcg | tgacccaaat | gtgtggcccg | acccggaagt | 1320 |
| ttttagtccc | gaaagattta | tggattgtga | gattgatgtc | aagggtcgtg | attttgagct | 1380 |
| attgcctttc | ggggcgggtc | gtcggatttg | tccgggattg | tctttggctt | atcggatgct | 1440 |
| taatttgatg | ttggctaata | tggtacattc | ttttgattgg | aaattacccg | gtgttgaaaa | 1500 |
| tggatccggg | tcggaaatgg | atagtttgga | tatggatgag | aaatttggta | tcactttgca | 1560 |
| aaaggttcaa | cccccttaagg | ttattcctgt | ctcaaggaaa | tagattttg | gaagatcgat | 1620 |
| ggttgggaga | taatcatatt | gtttttaatt | attgttggtg | tatttattg | ttattattgg | 1680 |
| ggacaatttt | ataataaaag | atataaataa | gttcctaatt | gtgatttata | ttgtgaattt | 1740 |
| tctagttaat | ataaatacat | atgaatattt | atgatgaaaa | aaaaaaaaa | aaaaaagg | 1799 |

<210> SEQ ID NO 36
<211> LENGTH: 2130
<212> TYPE: DNA
<213> ORGANISM: Mirabilis jalapa

<400> SEQUENCE: 36

| | | | | | |
|---|---|---|---|---|---|
| tacgtctatt | cttgcctccc | atttcctccc | tgcaaaaagg | aagaaaatgg | aaatacccctt | 60 |
| taatttgcaa | cctatttttc | taattattgt | actatctacc | ttcattctaa | cccacctaat | 120 |

```
aacaaaaaac acaagaaagt tcaaccaatg caaatcaaaa accaagccaa taccaaaacc     180
acctggctca ctacccataa taggtcactt gcacctccta agaggtcatg gaaccaccct     240
aggtcgcacc ctcggagcca tggccgacaa gtccggaccc attttcggcc tcaagctagg     300
ccaacacaag gctatagtca ttagtaactg ggagatagtc aaggattgtt tcaccaataa     360
tgacatgaac cttgcaacta gacctagcat ggctattagc aaatatattg gttatgactt     420
tgcctctttc tctatctcac cttatggccg atattggcgt gagattcgta agatctctac     480
tgttgagctc ttgtcaaaca aacgccttga gaaaatgaag catgttcgaa cttttgaggt     540
gaactcttgc cttcaaatct tctatgaaaa atgtgtcaaa tcagaggata atgaaagtaa     600
taaagtagca aaatttgtc ttaaaaagtg gttagaatat attggtttta atatcgcact     660
atctatgata gttggcaaga gattctccta cgaccagtat tataaaaaaa atactgttgc     720
atcgagattt atgaaggcaa tagaaagagc aacccactta gcaggacttc ctatacccctc     780 ggatttttta ccatgggttg aatggatgga tttggtgggt tacattggtg ctatgaagga     840
aactcataag gaaattgatg tgattattgg acattggctt gatgagcata ttcaaaagag     900
gaaagagacg ttagaaaggc gaggtacaag cattgatgat agtgacttca tggatgtaat     960
gttatctaac attactgaac aatttgccaa gtcaacctac tctaaaaaca ccatcattaa     1020
agcaacagct ttgacactac ttctaacagg ttcagaaagc acctcaatca cactaacatg     1080
ggccatatca ctacttctaa caaccctac ggcccaaaat ttggcccaac aagaaatgga     1140
caaacaagtt ggtaaacaaa gatgggttga agaatctgac atcaccaatc taccatacct     1200
ccaagccatc ataaaggaaa ctttacgttt gtatccacca gcccattag caggcccaag     1260 agtggcccaa gaagactgcc aaatcaatgg acattgtatc acaaaaggaa cccgggtgat     1320
tgttaacata tggaagttgc atcgtgatcc gatggtttgg tccgacccag ataagttccg     1380
acccgaaagg tttattgggg agcataagga tattgatttt aagggtcaat actttgggta     1440
tatacctttt agcttgggta ggaggggttg tcctgggatg aattttgggc tacaagtggt     1500
ccatttgatg ttagctcgtt tggtccaagg gttcgatatt tgggctcaaa atggtggcct     1560
aattgatttg aaggaagggt tgggcttggc tttgcccaag gctggtccat tggatgtcat     1620
tcttgcacca cgtttgtcca gtgagcttta tggagcttta tcaaaggtga atgttactta     1680
tggtcgggca atgaatgaac tagctttgta tttataattt tacaaataat ttgtaagata     1740
tgaactgttt atctagtcac ttttccgcgt cttagaatat caataagcaa aaagttttat     1800
gtaataatat gtattagtgt gttattgtat catgattcgt cggtatactg aaaatatttt     1860
acgtctagga gaatgtgcac acatttaatc ttatttgctt ataagtatta tatacataaa     1920
attttctact ttataattta ggtatattga gctttcgacc aaaacccaaa aactaaagaa     1980 gttttttta aaacatacaa gttggtattg tttagatttt tatttatttt tattatctct     2040
tttatttgta cttagtgggt gtgttaataa tgtaaagaag tattaaatat ttatagagtt     2100
ggaaaaaccc aatattttac attggaaaaa                                     2130
```

<210> SEQ ID NO 37
<211> LENGTH: 1903
<212> TYPE: DNA
<213> ORGANISM: Mirabilis jalapa

<400> SEQUENCE: 37

```
tacgtctcta acctccttct cctcaccatc atcatcttat ttctctctct aacttcctat      60
```

| | |
|---|---|
| ttctctctct agaatggtct caactagtga ctcactctgg cttttcacct acttagcttc | 120 |
| aaaatatgat catttacga cccctaactt tatttattct ttgttttgtt tcgtaatatt | 180 |
| ttttattttg attcatctac tgtactggtc ccacccaggt ggtccggcat gggggaagta | 240 |
| ttcatggact catctctcgg gatgggccgg gaagcccatc ccgggcccaa gaagttggcc | 300 |
| cattataggt ggtttggacc tgaagatggg actggctcat cggaagttag ccacaatggc | 360 |
| tgagaaatac gggaccatgg ctaagaggct catggctttt agcctaggag aaacacgcgt | 420 |
| gattgtcacg tgcaatcccg acgtggcgaa agaaatacta aatagcccgg ttttcttgga | 480 |
| ccgacccgac caggagtcgg cttatgggtt gatgtttaac cggtctatag gttcgcacc | 540 |
| ctatgggacc tactggcgaa ccctaaggaa aataacatca acccatttat taagccctaa | 600 |
| acacgtaaaa gaatatgaga acctacgtag ggaaataatg gaacaaatgg ttgactcgat | 660 |
| atcgaaccaa gccggaccgg ttcgggtccg ggaaatacta aggagggctt cattggataa | 720 |
| tatgatgggg tcagtgtttg gtgggcccca caaggaggtc gttgaacagt tgatagaaat | 780 |
| ggttggtgaa gggtatgact tattgggtgt ccttaatttg ggggaccatc tatcttggct | 840 |
| agccgagttt gacttcaaa aggttcggtt caggtgctct caacttgttc caaaagtcaa | 900 |
| ccggttcgtt ggtgaaatta tcgatgaaca tcggtctagt tcgggtcaaa ttatgaaccg | 960 |
| ggactttgtt gatgttttgt tgactctacc acaacatgaa caactttctc attctgacat | 1020 |
| ggtcgctgtt ctttgggaga tgatatttag aggaacagat gcaacagcag tattaataga | 1080 |
| atggacatta gcacgattag taattcataa agatattcaa tcaaaggtcc aaaatgagtt | 1140 |
| agaccaagta gttggaacat cacgagccgt tgaagagtct gacctatcat cactgatata | 1200 |
| tctaacggct gtgattaaag aagtattgcg ggtccaccca cctgggcccc tcctatcgtg | 1260 |
| gtctcgcctt tcaattcaag atactactat agatggttgt catgtgccaa aaggtactac | 1320 |
| tgctatggtt aacatgtggg ctattgctag agatcctaat gtgtgggcca acccagatga | 1380 |
| atttgacccg gatagatttt taatcggtgg gtccgagttt gagttctctg ttcttgggtc | 1440 |
| ggatcttaga cttgccccctt tcgggtcggg tcgtaggtca tgtcctggga aggtcttagg | 1500 |
| tttgaccaca gtcagttttt gggttgcttc actcttgcat gagtttgagt gggtgacatc | 1560 |
| acctaacgct gacgtggatt tgagtgaagt gcttaagctt tcgtgtgaga tggctcatcc | 1620 |
| tcttaccgtg gaagctaggc cgcgacgtca ttaattttac aaaagacgat attctcatac | 1680 |
| acagattatt gtcaacttta tcaatatata cgggtgatag tttgacattg ttatagtatt | 1740 |
| cggaaaaata ttttctagag ataagtaaat ttataataat ctaaaaaact gaatgtataa | 1800 |
| ttatattaat taatgtacta atgttattat aatgtttata aatgattgtg aaatatatat | 1860 |
| ggttaacatt atatgtaatg agaaatggtt tgcttggcaa aaa | 1903 |

<210> SEQ ID NO 38
<211> LENGTH: 1915
<212> TYPE: DNA
<213> ORGANISM: Mirabilis jalapa

<400> SEQUENCE: 38

| | |
|---|---|
| gctagctgcc ttgttcattt caagaacaat atacactagt caatccattt caaatggcct | 60 |
| acttagaaat tgtcatattc ttcatttttc tcatcgtaat ttgttttct tttcgtgaca | 120 |
| aaaatggtct cccaacaaat tggccgattg ttgggatgct accagctgtt ctaatcaatc | 180 |
| ttcatagaat taatgactat tttgctgaac ttgttgctaa atcaaattta acattctcat | 240 |
| ttaagggtcc ttggtttagc aacatgcgaa ttttagcgac agttgatcca gcaaatgtgc | 300 |

| accatataat gagtaagaat tttaacaatt atcctaaggg tgctaagttt tacgacatct | 360 |
| ttgatatact tggagatggt atttttaaca ccgactttaa tatatggcaa taccatcgga | 420 |
| aaatggctca gtcatatatt ggtgactcaa gatttcaaca attttgttg aagaaagttg | 480 |
| gggaaaagat tgaaggtgga ttaattccta tccttgatca tgttgccatg caagggttac | 540 |
| aagttgattt acaagattta tttgaaaggt ttactttga tactatttgt tcacttatta | 600 |
| tgaactatga tcctatgtct ttgtccattg attttcctga tgttccatca tctaaggctc | 660 |
| tagatgttgc tgaagaagtc atacttcttc gtcatttagt acctacaagt gtttggaagt | 720 |
| ttcaaagatg gttaggtgta gggatggaaa agaagcataa gatagcttgg caagtacttg | 780 |
| atgatttcat ttatgagtgc atatcaagga aaagagaaga gatgagagat agtttgtcct | 840 |
| atgagaataa ggacaatgag atgggtgttg atttaatgac attgtatatg aatgaaatca | 900 |
| aaagtaatga acttgtcaag gatgatccta acaagttttt gagggatact attcttaact | 960 |
| tttttattgc aggtcgagat acaactagta ctgctttatc gtggttttc tatctactat | 1020 |
| ccaagaatcc acaagtggta gaaaagatta gacaagagtt atcttggatc gtttcacaag | 1080 |
| aaaaaactaa aaattatgct aatttgattg ataaacttgt ttatcttcat gccgcattat | 1140 |
| gtgaagcttt aagattatat cctccggtgg tatttgaagc aaagtctccg attgaatcgg | 1200 |
| acactttacc aagtggtcat aagattgatc ctgacacaca aataatctta aatatgtacg | 1260 |
| caatggcgag gatgaaaaca atatggggcg atgattgcga tcaatttaaa cctgagaggt | 1320 |
| ggatatcatc aacaacagga aagattaagc atgaaccttc gtacaagttc ttggcttttta | 1380 |
| atgcaggacc aagaacttgt gtaggaaaaa atatggcttt tactcaaatg aaagcaatag | 1440 |
| caatagctat attacaaaac tatcatatac atggtattga tggacaagtt attgaacctg | 1500 |
| atctatccat aattctccat atgaagaatg gattcagagt aactgtttca ccgtgtaacg | 1560 |
| tttctatata accatcgaga gaaccaagtt tcctcgatct cttttaaaca ttgtaatgtt | 1620 |
| taattatcaa ctaaaaaatc gtatattctc ttcgtttcat ttttttcttt ttcttttat | 1680 |
| caaagatcaa ggtaacgtcg gaaataacca tattgttttc tttggttaaa tgaaaagaca | 1740 |
| atgtaagttg taaaagtatg taagtgtaaa ataaaattta aaaaattgtg tgaaaataag | 1800 |
| ttgtaataaa taagaataa tgttggtatt ttattgttta ctattttgat aaacagaaaa | 1860 |
| aataaaaataa aactgtttaa aaataaaagt gagaagaaaa aaaataaaag aaaat | 1915 |

<210> SEQ ID NO 39
<211> LENGTH: 817
<212> TYPE: DNA
<213> ORGANISM: Portulaca grandiflora

<400> SEQUENCE: 39

| atgggtgttg ggaaggaagt gtcgtttaag gagagtttct tcttgtctca tgggaatcca | 60 |
| gccatgttgg cggatgaatc ctttatagcg aggaacttcc ttttgggatg gaaaaagaat | 120 |
| gtgtttcctg tgaaacccaa gtccatttta gtagtctctg ctcactggga gactgatgtc | 180 |
| ccttgtgtat ctgctggtca gtaccctaat gttatctacg atttcactga agtccctgct | 240 |
| tccatgtttc agatgaagta cccagctcca gggtgcccaa agctggcaaa agagtgcag | 300 |
| gaactgctga tagcgggagg tttcaagagc gcgaagctag atgaggagcg gggtttcgac | 360 |
| cacagctcat gggtgccact gagcatgatg tgcccggagg cggacatccc ggtgcccag | 420 |
| cttcggtgc agcctgggct tgacgcgacc caccacttca acgtggggcg agcgttggcc | 480 |

```
ccactcaaag gggaaggtgt cctcttcatt ggctccggtg gggctgtcca cccttctgat      540
gacacccctc attggttcga tggtgttgct ccctgggctg ctgagtttga tcaatggctt      600
gaggatgctc tcctagaagg aaggtacgaa gatgtgaata actatcaaac aaaagcacca      660
gaagggtgga agctagcaca tccaattcca gaacattttc taccattgca tgtagccatg      720
ggtgcaggtg gtgagaaatc aaaggcagag cttatttatc gtacttggga tcatggtact      780
cttggctacg cctcttacaa gttcacttcc atatgat                               817

<210> SEQ ID NO 40
<211> LENGTH: 1078
<212> TYPE: DNA
<213> ORGANISM: Bougainvillea glabra

<400> SEQUENCE: 40
atgggtgggg agaaaaaaat gaagggaaca tactatatag cacatggtga tccaattatg       60
tacatcaata atcaataaa acttaggcac tttttagaag agtggaaaga gaatgtggtt      120
atggagaaac ctatatgtat tcttgtgatt tcagctcatt gggatactga tgttcccact      180
gttaaccttg ttgaacattg tgataccatc catgattttg atgactatcc tgatcccttg      240
taccagataa agtatccagc tcctgggggct ccaaaattgg caatgaaagt gcaagagtta      300
ttgaaaggtg gaggattcaa atgtgaagtg gatacaaagc gtggacttga ccatgctgca      360
tggtttccac tcatgttgat gtatcctgaa gctgatattc caatttgtga gctctcagtt      420
caaaccaaca aggatgggac ccaccactac aaccttggaa aagcactttc tcctctcttg      480
aatgatgatg ttctcatcat tggctctggt ggagctgttc atccctcaga tgatactcct      540
cattgtccta atggtgttgc tccttgggct ttgcagtttg acaattggct tgaagatgct      600
cttctcagtg gaaggtatga agatgtgaaa gaattcaaaa aaatggcacc aaattgggag      660
atatcacatc cagggcaaga gcacttgtac cctttgcatg tggctcttgg ggctgcaggc      720
aacaacgtaa agacagagct tattcatcaa acttgggctg ccaatggcgt ctttggatat      780
tcctcctaca gttcacatc cacttgaaca ataaattaaa tattcatctt tacacatttc      840
aataattccc ttcttgtgtt tgcttttct ggtattaaat ttgtttgtca tttttttta      900
gagtcgacag ttgagggtct ttttaaaaca atttttttta tctttatggc gagagtgaca      960
tccttgtaaa attcatttat tatggtgtat ttggatacta gtatttcatt tgagatgcat     1020
gaattatgtt aaattcactg tttgaataac aataaattta taaatttgaa tttgactc      1078

<210> SEQ ID NO 41
<211> LENGTH: 228
<212> TYPE: PRT
<213> ORGANISM: Amanita muscaria

<400> SEQUENCE: 41

Met Val Pro Ser Phe Val Val Tyr Ser Ser Trp Val Asn Gly Arg Gln
1               5                  10                  15

Arg Tyr Ile Arg Gln Ala Phe Ala Ser Ile Leu Phe Tyr Ile Ile Arg
            20                  25                  30

Asp Thr Thr Leu Ser Phe Pro Ser His Thr Thr Met Ser Thr Lys Pro
        35                  40                  45

Glu Thr Asp Leu Gln Thr Val Leu Asp Ser Glu Ile Lys Glu Trp His
    50                  55                  60

Phe His Ile Tyr Phe His Gln Asn Asn Ala Ala Glu His Gln Ala Ala
65                  70                  75                  80
```

```
Leu Glu Leu Arg Asp Ala Val Leu Arg Leu Arg Gln Asp Gly Ala Phe
             85                  90                  95

Val Ala Val Pro Leu Phe Arg Val Asn Met Asp Pro Met Gly Pro His
            100                 105                 110

Pro Val Gly Ser Tyr Glu Ile Trp Val Pro Ser Glu Thr Phe Ala Ser
            115                 120                 125

Val Phe Ser Tyr Leu Cys Met Asn Arg Gly Arg Leu Ser Ile Leu Val
130                 135                 140

His Pro Leu Thr Arg Glu Leu Arg Asp His Glu Ile Arg Asn Ala
145                 150                 155                 160

Trp Ile Gly Pro Ser Phe Pro Leu Asn Leu Ala Asn Leu Pro Ile Lys
            165                 170                 175

Ser Asp Glu Ile Pro Leu Gln Tyr Pro Ser Leu Lys Leu Gly Tyr Ser
            180                 185                 190

Ser Thr Ala His Lys Met Ser Leu Glu Glu Arg Arg Lys Leu Gly Asp
            195                 200                 205

Asp Ile Glu Ala Val Leu Arg Gly Glu Lys Ala Ala Arg Ala Pro
210                 215                 220

His Arg Asp Ala
225

<210> SEQ ID NO 42
<211> LENGTH: 275
<212> TYPE: PRT
<213> ORGANISM: Beta vulgaris

<400> SEQUENCE: 42

Met Lys Met Met Asn Gly Glu Asp Ala Asn Asp Gln Met Ile Lys Glu
1               5                   10                  15

Ser Phe Phe Ile Thr His Gly Asn Pro Ile Leu Thr Val Glu Asp Thr
            20                  25                  30

His Pro Leu Arg Pro Phe Phe Glu Thr Trp Arg Glu Lys Ile Phe Ser
        35                  40                  45

Lys Lys Pro Lys Ala Ile Leu Ile Ser Gly His Trp Glu Thr Val
    50                  55                  60

Lys Pro Thr Val Asn Ala Val His Ile Asn Asp Thr Ile His Asp Phe
65                  70                  75                  80

Asp Asp Tyr Pro Ala Ala Met Tyr Gln Phe Lys Tyr Pro Ala Pro Gly
                85                  90                  95

Glu Pro Glu Leu Ala Arg Lys Val Glu Glu Ile Leu Lys Lys Ser Gly
            100                 105                 110

Phe Glu Thr Ala Glu Thr Asp Gln Lys Arg Gly Leu Asp His Gly Ala
        115                 120                 125

Trp Val Pro Leu Met Leu Met Tyr Pro Glu Ala Asp Ile Pro Val Cys
    130                 135                 140

Gln Leu Ser Val Gln Pro His Leu Asp Gly Thr Tyr His Tyr Asn Leu
145                 150                 155                 160

Gly Arg Ala Leu Ala Pro Leu Lys Asn Asp Gly Val Leu Ile Ile Gly
                165                 170                 175

Ser Gly Ser Ala Thr His Pro Leu Asp Glu Thr Pro His Tyr Phe Asp
            180                 185                 190

Gly Val Ala Pro Trp Ala Ala Ala Phe Asp Ser Trp Leu Arg Lys Ala
        195                 200                 205

Leu Ile Asn Gly Arg Phe Glu Glu Val Asn Ile Tyr Glu Ser Lys Ala
    210                 215                 220
```

```
Pro Asn Trp Lys Leu Ala His Pro Phe Pro Glu His Phe Tyr Pro Leu
225                 230                 235                 240

His Val Val Leu Gly Ala Ala Gly Glu Lys Trp Lys Ala Glu Leu Ile
                245                 250                 255

His Ser Ser Trp Asp His Gly Thr Leu Cys His Gly Ser Tyr Lys Phe
                260                 265                 270

Thr Ser Ala
        275

<210> SEQ ID NO 43
<211> LENGTH: 500
<212> TYPE: PRT
<213> ORGANISM: Mirabilis jalapa

<400> SEQUENCE: 43

Met Thr Ala Ile Lys Met Asn Thr Asn Gly Glu Gly Glu Thr Gln His
1               5                   10                  15

Ile Leu Met Ile Pro Phe Met Ala Gln Gly His Leu Arg Pro Phe Leu
                20                  25                  30

Glu Leu Ala Met Phe Leu Tyr Lys Arg Ser His Val Ile Ile Thr Leu
            35                  40                  45

Leu Thr Thr Pro Leu Asn Ala Gly Phe Leu Arg His Leu His His
    50                  55                  60

His Ser Tyr Ser Ser Ser Gly Ile Arg Ile Val Glu Leu Pro Phe Asn
65              70                  75                  80

Ser Thr Asn His Gly Leu Pro Pro Gly Ile Glu Asn Thr Asp Lys Leu
                85                  90                  95

Thr Leu Pro Leu Val Val Ser Leu Phe His Ser Thr Ile Ser Leu Asp
            100                 105                 110

Pro His Leu Arg Asp Tyr Ile Ser Arg His Phe Ser Pro Ala Arg Pro
        115                 120                 125

Pro Leu Cys Val Ile His Asp Val Phe Leu Gly Trp Val Asp Gln Val
    130                 135                 140

Ala Lys Asp Val Gly Ser Thr Gly Val Val Phe Thr Thr Gly Gly Ala
145                 150                 155                 160

Tyr Gly Thr Ser Ala Tyr Val Ser Ile Trp Asn Asp Leu Pro His Gln
                165                 170                 175

Asn Tyr Ser Asp Asp Gln Glu Phe Pro Leu Pro Gly Phe Pro Glu Asn
            180                 185                 190

His Lys Phe Arg Arg Ser Gln Leu His Arg Phe Leu Arg Tyr Ala Asp
        195                 200                 205

Gly Ser Asp Asp Trp Ser Lys Tyr Phe Gln Pro Gln Leu Arg Gln Ser
    210                 215                 220

Met Lys Ser Phe Gly Trp Leu Cys Asn Ser Val Glu Glu Ile Glu Thr
225                 230                 235                 240

Leu Gly Phe Ser Ile Leu Arg Asn Tyr Thr Lys Leu Pro Ile Trp Gly
                245                 250                 255

Ile Gly Pro Leu Ile Ala Ser Pro Val Gln His Ser Ser Ser Asp Asn
            260                 265                 270

Asn Ser Thr Gly Ala Glu Phe Val Gln Trp Leu Ser Leu Lys Glu Pro
        275                 280                 285

Asp Ser Val Leu Tyr Ile Ser Phe Gly Ser Gln Asn Thr Ile Ser Pro
    290                 295                 300

Thr Gln Met Met Glu Leu Ala Ala Gly Leu Glu Ser Ser Glu Lys Pro
```

```
            305                 310                 315                 320
        Phe Leu Trp Val Ile Arg Ala Pro Phe Gly Phe Asp Ile Asn Glu Glu
                        325                 330                 335

Met Arg Pro Glu Trp Leu Pro Glu Gly Phe Glu Arg Met Lys Val
                        340                 345                 350

Lys Lys Gln Gly Lys Leu Val Tyr Lys Leu Gly Pro Gln Leu Glu Ile
                        355                 360                 365

Leu Asn His Glu Ser Ile Gly Gly Phe Leu Thr His Cys Gly Trp Asn
                        370                 375                 380

Ser Ile Leu Glu Ser Leu Arg Glu Gly Val Pro Met Leu Gly Trp Pro
        385                 390                 395                 400

Leu Ala Ala Glu Gln Ala Tyr Asn Leu Lys Tyr Leu Glu Asp Glu Met
                        405                 410                 415

Gly Val Ala Val Glu Leu Ala Arg Gly Leu Gly Glu Ile Ser Lys
                        420                 425                 430

Glu Lys Val Lys Arg Ile Val Glu Met Ile Leu Glu Arg Asn Glu Gly
                        435                 440                 445

Ser Lys Gly Trp Glu Met Lys Asn Arg Ala Val Glu Met Gly Lys Lys
                        450                 455                 460

Leu Lys Asp Ala Val Asn Glu Glu Lys Glu Leu Lys Gly Ser Ser Val
        465                 470                 475                 480

Lys Ala Ile Asp Asp Phe Leu Asp Ala Val Met Gln Ala Lys Leu Glu
                        485                 490                 495

Pro Ser Leu Gln
                        500

<210> SEQ ID NO 44
<211> LENGTH: 504
<212> TYPE: PRT
<213> ORGANISM: Mirabilis jalapa

<400> SEQUENCE: 44

Met Glu Asn Thr Met Leu Gly Val Ile Leu Ala Thr Ile Phe Leu Thr
        1               5                   10                  15

Phe His Ile Met Lys Met Leu Phe Ser Pro Ser Lys Val Lys Leu Pro
                        20                  25                  30

Pro Gly Pro Arg Pro Leu Pro Ile Ile Gly Asn Ile Leu Glu Leu Gly
                        35                  40                  45

Asp Lys Pro His Arg Ser Phe Ala Asn Leu Ala Lys Ile His Gly Pro
                        50                  55                  60

Leu Val Thr Leu Lys Leu Gly Ser Val Thr Thr Ile Val Val Ser Ser
        65                  70                  75                  80

Ser Glu Val Ala Lys Glu Met Phe Leu Lys Asn Asp Gln Pro Leu Ala
                        85                  90                  95

Asn Arg Thr Ile Pro Asp Ser Val Arg Ala Gly Asn His Asp Lys Leu
                        100                 105                 110

Ser Met Ser Trp Leu Pro Val Ser Pro Lys Trp Arg Asn Leu Arg Lys
                        115                 120                 125

Ile Ser Ala Val Gln Leu Leu Ser Thr Gln Arg Leu Asp Ala Ser Gln
                        130                 135                 140

Ala His Arg Gln Ala Lys Ile Lys Gln Leu Ile Glu Tyr Val Lys Lys
        145                 150                 155                 160

Cys Ser Lys Ile Gly Gln Tyr Val Asp Ile Gly Gln Val Ala Phe Thr
                        165                 170                 175
```

Thr Ser Leu Asn Leu Leu Ser Asn Thr Phe Phe Ser Lys Glu Leu Ala
            180                 185                 190

Ser Phe Asp Ser Asp Asn Ala Gln Glu Phe Lys Gln Leu Met Trp Cys
        195                 200                 205

Ile Met Glu Glu Ile Gly Arg Pro Asn Tyr Ala Asp Tyr Phe Pro Ile
    210                 215                 220

Leu Gly Tyr Val Asp Pro Phe Gly Ala Arg Arg Leu Ser Arg Tyr
225                 230                 235                 240

Phe Asp Gln Leu Ile Glu Val Phe Gln Val Ile Arg Glu Arg Leu
                245                 250                 255

Thr His Asp Asn Asn Ile Val Gly Asn Asn Asp Val Leu Ala Thr
                260                 265                 270

Leu Leu Asp Leu Tyr Lys Gln Asn Glu Leu Thr Met Asp Glu Ile Asn
            275                 280                 285

His Leu Leu Val Asp Ile Phe Asp Ala Gly Thr Asp Thr Thr Ala Ser
        290                 295                 300

Thr Leu Glu Trp Ala Met Ser Glu Leu Ile Lys Asn Pro His Ile Met
305                 310                 315                 320

Ala Lys Ala Gln Glu Glu Val Arg Arg Ala Thr Met Ser His Gly Gly
                325                 330                 335

Ala Thr Val Ala Glu Ile Gln Glu Ser Asp Ile Asn Asn Leu Pro Tyr
            340                 345                 350

Ile Gln Ser Ile Ile Lys Glu Thr Leu Arg Leu His Pro Pro Thr Val
        355                 360                 365

Phe Leu Leu Pro Arg Lys Ala Asp Val Asp Val Gln Leu Phe Gly Tyr
    370                 375                 380

Val Val Pro Lys Asn Ala Gln Val Leu Val Asn Leu Trp Ala Ile Gly
385                 390                 395                 400

Arg Asp Pro Asn Val Trp Pro Asp Pro Glu Val Phe Ser Pro Glu Arg
                405                 410                 415

Phe Met Asp Cys Glu Ile Asp Val Lys Gly Arg Asp Phe Glu Leu Leu
            420                 425                 430

Pro Phe Gly Ala Gly Arg Arg Ile Cys Pro Gly Leu Ser Leu Ala Tyr
        435                 440                 445

Arg Met Leu Asn Leu Met Leu Ala Asn Met Val His Ser Phe Asp Trp
    450                 455                 460

Lys Leu Pro Gly Val Glu Asn Gly Ser Gly Glu Met Asp Ser Leu
465                 470                 475                 480

Asp Met Asp Glu Lys Phe Gly Ile Thr Leu Gln Lys Val Gln Pro Leu
                485                 490                 495

Lys Val Ile Pro Val Ser Arg Lys
            500

<210> SEQ ID NO 45
<211> LENGTH: 24
<212> TYPE: DNA
<213> ORGANISM: Artificial
<220> FEATURE:
<223> OTHER INFORMATION: BvDODA1 Fwd + XhoI

<400> SEQUENCE: 45
tgtgctagac gttcttcttc agct                                      24

<210> SEQ ID NO 46
<211> LENGTH: 20
<212> TYPE: DNA

```
<213> ORGANISM: Artificial
<220> FEATURE:
<223> OTHER INFORMATION: BvDODA1 Rev + SacI

<400> SEQUENCE: 46
aaaatgtcga cgagcaaatg                                              20

<210> SEQ ID NO 47
<211> LENGTH: 22
<212> TYPE: DNA
<213> ORGANISM: Artificial
<220> FEATURE:
<223> OTHER INFORMATION: CYP76AD1 Fwd + XhoI

<400> SEQUENCE: 47
cttcatctcg taggcttcct cc                                           22

<210> SEQ ID NO 48
<211> LENGTH: 20
<212> TYPE: DNA
<213> ORGANISM: Artificial
<220> FEATURE:
<223> OTHER INFORMATION: CYP76AD1 Rev + SacI

<400> SEQUENCE: 48
gatgaggctt ttcgccaaga                                              20

<210> SEQ ID NO 49
<211> LENGTH: 20
<212> TYPE: DNA
<213> ORGANISM: Artificial
<220> FEATURE:
<223> OTHER INFORMATION: CYP76AD1 Fwd + BamHI

<400> SEQUENCE: 49
cctgtatcgg ctaaatggcg                                              20

<210> SEQ ID NO 50
<211> LENGTH: 21
<212> TYPE: DNA
<213> ORGANISM: Artificial
<220> FEATURE:
<223> OTHER INFORMATION: CYP76AD1 Rev + EcoRI

<400> SEQUENCE: 50
caattgcaca gcggagattt t                                            21

<210> SEQ ID NO 51
<211> LENGTH: 20
<212> TYPE: DNA
<213> ORGANISM: Artificial
<220> FEATURE:
<223> OTHER INFORMATION: BvCYP76new Fwd + XhoI

<400> SEQUENCE: 51
ttgatgctgt ttgcgcagtc                                              20

<210> SEQ ID NO 52
<211> LENGTH: 20
<212> TYPE: DNA
<213> ORGANISM: Artificial
<220> FEATURE:
<223> OTHER INFORMATION: BvCYP76new Rev + SacI

<400> SEQUENCE: 52
tgcgaagatt tcgccatttt                                              20
```

<210> SEQ ID NO 53
<211> LENGTH: 23
<212> TYPE: DNA
<213> ORGANISM: Artificial
<220> FEATURE:
<223> OTHER INFORMATION: CYP76AD6 Fwd + XhoI

<400> SEQUENCE: 53
tggtgctgat tttcgtcgta gag                                    23

<210> SEQ ID NO 54
<211> LENGTH: 19
<212> TYPE: DNA
<213> ORGANISM: Artificial
<220> FEATURE:
<223> OTHER INFORMATION: CYP76AD6 Rev + SacI

<400> SEQUENCE: 54
tggcaccacc cttcaagtg                                         19

<210> SEQ ID NO 55
<211> LENGTH: 20
<212> TYPE: DNA
<213> ORGANISM: Artificial
<220> FEATURE:
<223> OTHER INFORMATION: BvDODA1 Fwd

<400> SEQUENCE: 55
taaagctccc tcctggtcca                                        20

<210> SEQ ID NO 56
<211> LENGTH: 20
<212> TYPE: DNA
<213> ORGANISM: Artificial
<220> FEATURE:
<223> OTHER INFORMATION: BvDODA1 Rev

<400> SEQUENCE: 56
ccgcagaacg atgaggtttg                                        20

<210> SEQ ID NO 57
<211> LENGTH: 23
<212> TYPE: DNA
<213> ORGANISM: Artificial
<220> FEATURE:
<223> OTHER INFORMATION: CYP76AD1 Fwd

<400> SEQUENCE: 57
tcaaactcgg aagcatcact aca                                    23

<210> SEQ ID NO 58
<211> LENGTH: 20
<212> TYPE: DNA
<213> ORGANISM: Artificial
<220> FEATURE:
<223> OTHER INFORMATION: CYP76AD1 Rev

<400> SEQUENCE: 58
gggctaagtc gtgctcgagg                                        20

<210> SEQ ID NO 59
<211> LENGTH: 35
<212> TYPE: DNA
<213> ORGANISM: Artificial
<220> FEATURE:

```
<223> OTHER INFORMATION: CYP76AD6 Fwd1

<400> SEQUENCE: 59
aaaaactcga ggttaaacct actgttaatg ctgtc                             35

<210> SEQ ID NO 60
<211> LENGTH: 31
<212> TYPE: DNA
<213> ORGANISM: Artificial
<220> FEATURE:
<223> OTHER INFORMATION: CYP76AD6 Rev1

<400> SEQUENCE: 60
aaaaagagct cgctgcccaa ggtgcaactc c                                 31

<210> SEQ ID NO 61
<211> LENGTH: 34
<212> TYPE: DNA
<213> ORGANISM: Artificial
<220> FEATURE:
<223> OTHER INFORMATION: CYP76AD6 Fwd2

<400> SEQUENCE: 61
aaaaactcga ggctaatctt gctaaaattc acgg                              34

<210> SEQ ID NO 62
<211> LENGTH: 33
<212> TYPE: DNA
<213> ORGANISM: Artificial
<220> FEATURE:
<223> OTHER INFORMATION: CYP76AD6 Rev2

<400> SEQUENCE: 62
aaaaagagct cttatggtgg gctaattcca ctg                               33

<210> SEQ ID NO 63
<211> LENGTH: 34
<212> TYPE: DNA
<213> ORGANISM: Artificial
<220> FEATURE:
<223> OTHER INFORMATION: cDOPA5GT Fwd1

<400> SEQUENCE: 63
aaaaaggatc cgctaatctt gctaaaattc acgg                              34

<210> SEQ ID NO 64
<211> LENGTH: 33
<212> TYPE: DNA
<213> ORGANISM: Artificial
<220> FEATURE:
<223> OTHER INFORMATION: cDOPA5GT Rev1

<400> SEQUENCE: 64
aaaaagaatt cttatggtgg gctaattcca ctg                               33

<210> SEQ ID NO 65
<211> LENGTH: 32
<212> TYPE: DNA
<213> ORGANISM: Artificial
<220> FEATURE:
<223> OTHER INFORMATION: cDOPA5GT Fwd2

<400> SEQUENCE: 65
aaaaactcga gctgcaagag tcaatgatct ca                                32
```

```
<210> SEQ ID NO 66
<211> LENGTH: 33
<212> TYPE: DNA
<213> ORGANISM: Artificial
<220> FEATURE:
<223> OTHER INFORMATION: cDOPA5GT Rev2

<400> SEQUENCE: 66
aaaaagagct ctcatctggg aattggaatt gct                               33

<210> SEQ ID NO 67
<211> LENGTH: 32
<212> TYPE: DNA
<213> ORGANISM: Artificial
<220> FEATURE:
<223> OTHER INFORMATION: BvDODA1 Fwd

<400> SEQUENCE: 67
aaaaactcga gcacaacagc aagcacatta ga                                32

<210> SEQ ID NO 68
<211> LENGTH: 33
<212> TYPE: DNA
<213> ORGANISM: Artificial
<220> FEATURE:
<223> OTHER INFORMATION: BvDODA1 Rev

<400> SEQUENCE: 68
aaaaagagct cagtccaggg catatccttc tac                               33

<210> SEQ ID NO 69
<211> LENGTH: 41
<212> TYPE: DNA
<213> ORGANISM: Artificial
<220> FEATURE:
<223> OTHER INFORMATION: CYP76AD1 Fwd

<400> SEQUENCE: 69
gcgccgtctc gctcgaatga aaatgatgaa tggtgaagat g                      41

<210> SEQ ID NO 70
<211> LENGTH: 40
<212> TYPE: DNA
<213> ORGANISM: Artificial
<220> FEATURE:
<223> OTHER INFORMATION: CYP76AD1 Rev

<400> SEQUENCE: 70
gcgccgtctc gctcgaagcc taggctgaag tgaacttgta                        40

<210> SEQ ID NO 71
<211> LENGTH: 40
<212> TYPE: DNA
<213> ORGANISM: Artificial
<220> FEATURE:
<223> OTHER INFORMATION: CYP76AD6 Fwd

<400> SEQUENCE: 71
gcgccgtctc gctcgaatgg atcatgcaac attagcaatg                        40

<210> SEQ ID NO 72
<211> LENGTH: 43
<212> TYPE: DNA
<213> ORGANISM: Artificial
<220> FEATURE:
<223> OTHER INFORMATION: CYP76AD6 Rev
```

<400> SEQUENCE: 72
gcgccgtctc gctcgaagct caatacctag gtattggaat aag        43

<210> SEQ ID NO 73
<211> LENGTH: 37
<212> TYPE: DNA
<213> ORGANISM: Artificial
<220> FEATURE:
<223> OTHER INFORMATION: Synthetic

<400> SEQUENCE: 73
gcgccgtctc gctcgaatgg ataacgcaac acttgct        37

<210> SEQ ID NO 74
<211> LENGTH: 32
<212> TYPE: DNA
<213> ORGANISM: Artificial
<220> FEATURE:
<223> OTHER INFORMATION: Synthetic

<400> SEQUENCE: 74
gcgccgtctc gttgcccatt ctaatgtgct tg        32

<210> SEQ ID NO 75
<211> LENGTH: 31
<212> TYPE: DNA
<213> ORGANISM: Artificial
<220> FEATURE:
<223> OTHER INFORMATION: Synthetic

<400> SEQUENCE: 75
gcgccgtctc ggcaatggcc gaacttgtga a        31

<210> SEQ ID NO 76
<211> LENGTH: 40
<212> TYPE: DNA
<213> ORGANISM: Artificial
<220> FEATURE:
<223> OTHER INFORMATION: Synthetic

<400> SEQUENCE: 76
gcgccgtctc gctcgaagcc tagtttctgg gaactggaat        40

<210> SEQ ID NO 77
<211> LENGTH: 39
<212> TYPE: DNA
<213> ORGANISM: Artificial
<220> FEATURE:
<223> OTHER INFORMATION: Synthetic

<400> SEQUENCE: 77
gcgccgtctc gctcgaatga ccgccattaa aatgaacac        39

<210> SEQ ID NO 78
<211> LENGTH: 33
<212> TYPE: DNA
<213> ORGANISM: Artificial
<220> FEATURE:
<223> OTHER INFORMATION: Synthetic

<400> SEQUENCE: 78
gcgccgtctc ggcctcattt cctcattgat atc        33

<210> SEQ ID NO 79
<211> LENGTH: 31

```
<212> TYPE: DNA
<213> ORGANISM: Artificial
<220> FEATURE:
<223> OTHER INFORMATION: Synthetic

<400> SEQUENCE: 79
gcgccgtctc gaggccagaa tggctaccag a                               31

<210> SEQ ID NO 80
<211> LENGTH: 43
<212> TYPE: DNA
<213> ORGANISM: Artificial
<220> FEATURE:
<223> OTHER INFORMATION: Synthetic

<400> SEQUENCE: 80
gcgccgtctc gctcgaagct tattgaagag aaggttccaa ctt                  43

<210> SEQ ID NO 81
<211> LENGTH: 55
<212> TYPE: DNA
<213> ORGANISM: Artificial
<220> FEATURE:
<223> OTHER INFORMATION: Synthetic

<400> SEQUENCE: 81
ggggacaagt ttgtacaaaa aagcaggctt catgaaaatg atgaatggtg aagat     55

<210> SEQ ID NO 82
<211> LENGTH: 55
<212> TYPE: DNA
<213> ORGANISM: Artificial
<220> FEATURE:
<223> OTHER INFORMATION: Synthetic

<400> SEQUENCE: 82
ggggaccact ttgtacaaga aagctgggtc ctaggctgaa gtgaacttgt aggag     55

<210> SEQ ID NO 83
<211> LENGTH: 53
<212> TYPE: DNA
<213> ORGANISM: Artificial
<220> FEATURE:
<223> OTHER INFORMATION: Synthetic

<400> SEQUENCE: 83
ggggacaagt ttgtacaaaa aagcaggctt catggatcat gcaacattag caa       53

<210> SEQ ID NO 84
<211> LENGTH: 57
<212> TYPE: DNA
<213> ORGANISM: Artificial
<220> FEATURE:
<223> OTHER INFORMATION: Synthetic

<400> SEQUENCE: 84
ggggaccact ttgtacaaga aagctgggtc tcaataccta ggtattggaa taagttt   57

<210> SEQ ID NO 85
<211> LENGTH: 59
<212> TYPE: DNA
<213> ORGANISM: Artificial
<220> FEATURE:
<223> OTHER INFORMATION: Synthetic

<400> SEQUENCE: 85
```

-continued

```
ggggacaagt tgtacaaaa aagcaggctt catggataac gcaacacttg ctgtgatcc    59
```

<210> SEQ ID NO 86
<211> LENGTH: 62
<212> TYPE: DNA
<213> ORGANISM: Artificial
<220> FEATURE:
<223> OTHER INFORMATION: Synthetic

<400> SEQUENCE: 86

```
ggggaccact tgtacaaga aagctgggtc ctagtttctg ggaactggaa taacttgaag    60
ag                                                                 62
```